United States Patent
Gege et al.

(10) Patent No.: US 10,301,272 B2
(45) Date of Patent: May 28, 2019

(54) CARBOXAMIDE OR SULFONAMIDE SUBSTITUTED THIAZOLES AND RELATED DERIVATIVES AS MODULATORS FOR THE ORPHAN NUCLEAR RECEPTOR ROR[γ]

(71) Applicant: Phenex Pharmaceuticals AG, Ludwigshafen (DE)

(72) Inventors: Christian Gege, Ehingen (DE); Christoph Steeneck, Dossenheim (DE); Olaf Kinzel, Heidelberg (DE); Gerald Kleymann, Bad Salzuflen (DE); Thomas Hoffmann, Viernheim (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 151 days.

(21) Appl. No.: 14/403,903

(22) PCT Filed: May 29, 2013

(86) PCT No.: PCT/EP2013/001593
§ 371 (c)(1),
(2) Date: Nov. 25, 2014

(87) PCT Pub. No.: WO2013/178362
PCT Pub. Date: Dec. 5, 2013

(65) Prior Publication Data
US 2015/0175562 A1 Jun. 25, 2015

Related U.S. Application Data

(60) Provisional application No. 61/653,556, filed on May 31, 2012.

(30) Foreign Application Priority Data

May 31, 2012 (EP) .................................... 12004186

(51) Int. Cl.
*C07D 333/38* (2006.01)
*C07D 493/10* (2006.01)
(Continued)

(52) U.S. Cl.
CPC ......... *C07D 277/56* (2013.01); *C07D 239/28* (2013.01); *C07D 263/34* (2013.01);
(Continued)

(58) Field of Classification Search
CPC .. C07D 333/38; C07D 493/10; C07D 405/12; C07D 413/12; C07D 417/04;
(Continued)

(56) References Cited
U.S. PATENT DOCUMENTS 5,571,810 A 11/1996 Matsuo et al.
5,668,161 A 9/1997 Talley et al.
(Continued)

FOREIGN PATENT DOCUMENTS

CN 1059142 A 3/1992
EP 0 199 968 A1 12/1986
(Continued)

OTHER PUBLICATIONS

Hashimoto et al., 1999, caplus an 1999:134371.*
(Continued)

*Primary Examiner* — Sun Jae Yoo
(74) *Attorney, Agent, or Firm* — Seed IP Law Group LLP

(57) ABSTRACT

The invention provides modulators for the orphan nuclear receptor RORγ and methods for treating RORγ mediated diseases by administering these novel RORγ modulators to a human or a mammal in need thereof. Specifically, the present invention provides carboxamide or sulfonamide containing cyclic compounds of Formula (1), (1'), (100), (100'), (200) and (200') and the enantiomers, diastereomers, tautomers, /V-oxides, solvates and pharmaceutically acceptable salts thereof.

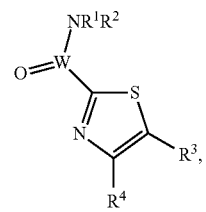

(1)

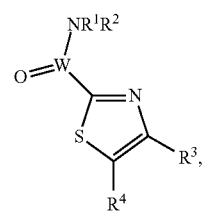

(1')

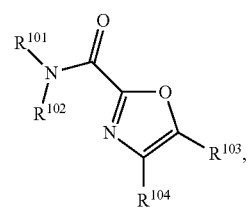

(100)

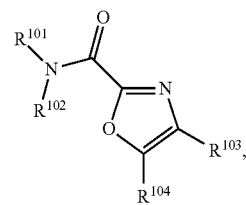

(100')

(Continued)

-continued

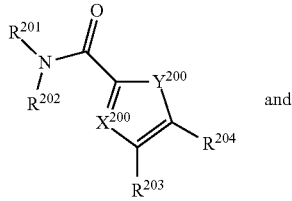

and

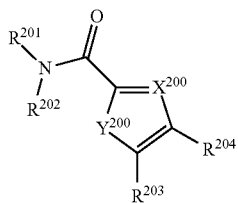

30 Claims, No Drawings

(51) Int. Cl.
| | |
|---|---|
| *C07D 405/12* | (2006.01) |
| *C07D 413/12* | (2006.01) |
| *C07D 417/04* | (2006.01) |
| *C07D 417/06* | (2006.01) |
| *C07D 417/12* | (2006.01) |
| *C07D 417/14* | (2006.01) |
| *C07D 453/02* | (2006.01) |
| *C07D 263/34* | (2006.01) |
| *C07D 487/08* | (2006.01) |
| *C07D 491/10* | (2006.01) |
| *C07D 495/10* | (2006.01) |
| *C07D 277/36* | (2006.01) |
| *C07D 498/08* | (2006.01) |
| *C07D 277/46* | (2006.01) |
| *C07D 277/52* | (2006.01) |
| *C07D 277/56* | (2006.01) |
| *C07D 307/08* | (2006.01) |
| *C07D 455/02* | (2006.01) |
| *C07D 493/08* | (2006.01) |
| *C07D 239/28* | (2006.01) |
| *C07D 307/68* | (2006.01) |

(52) U.S. Cl.
CPC ......... *C07D 277/36* (2013.01); *C07D 277/46* (2013.01); *C07D 277/52* (2013.01); *C07D 307/68* (2013.01); *C07D 333/38* (2013.01); *C07D 405/12* (2013.01); *C07D 413/12* (2013.01); *C07D 417/04* (2013.01); *C07D 417/06* (2013.01); *C07D 417/12* (2013.01); *C07D 417/14* (2013.01); *C07D 453/02* (2013.01); *C07D 455/02* (2013.01); *C07D 487/08* (2013.01); *C07D 491/10* (2013.01); *C07D 493/08* (2013.01); *C07D 493/10* (2013.01); *C07D 495/10* (2013.01); *C07D 498/08* (2013.01)

(58) Field of Classification Search
CPC .. C07D 417/06; C07D 417/12; C07D 417/14; C07D 453/02; C07D 263/34; C07D 487/08; C07D 491/10; C07D 495/10; C07D 277/36; C07D 498/08; C07D 277/45; C07D 277/52; C07D 277/56; C07D 307/08; C07D 455/02; C07D 493/08; C07D 239/28

See application file for complete search history.

(56) References Cited

U.S. PATENT DOCUMENTS

| | | | |
|---|---|---|---|
| 7,928,098 B2 | 4/2011 | Uesaka et al. | |
| 9,233,951 B2* | 1/2016 | Muhlthau | ............ C07D 401/04 |
| 2002/0022729 A1 | 2/2002 | Kawai et al. | |
| 2003/0236293 A1 | 12/2003 | Seibert | |
| 2005/0032859 A1 | 2/2005 | Chen | |
| 2005/0065189 A1 | 3/2005 | Lange et al. | |
| 2005/0113283 A1 | 5/2005 | Solow-Cordero et al. | |
| 2006/0094723 A1 | 5/2006 | Dunkern et al. | |
| 2006/0199817 A1 | 9/2006 | Tasker et al. | |
| 2009/0048258 A1 | 2/2009 | Ogino et al. | |
| 2009/0298832 A1 | 12/2009 | Li et al. | |
| 2010/0280023 A1 | 11/2010 | Sugawara et al. | |
| 2011/0224202 A1 | 9/2011 | Cutshall et al. | |
| 2012/0322837 A1 | 12/2012 | Maeba et al. | |
| 2014/0163001 A1 | 6/2014 | Yamamoto et al. | |
| 2014/0228409 A1 | 8/2014 | Yamamoto et al. | |

FOREIGN PATENT DOCUMENTS

| | | |
|---|---|---|
| EP | 0 388 909 A2 | 9/1990 |
| WO | WO 91/19708 A1 | 12/1991 |
| WO | WO 95/29904 A1 | 11/1995 |
| WO | WO 96/03392 A1 | 2/1996 |
| WO | WO 96/36617 A1 | 11/1996 |
| WO | WO 98/28282 A2 | 7/1998 |
| WO | WO 00/24739 A1 | 5/2000 |
| WO | WO 00/33836 A1 | 6/2000 |
| WO | WO 03/002567 A1 | 1/2003 |
| WO | WO 03/040147 A1 | 5/2003 |
| WO | WO 2004/094395 A2 | 11/2004 |
| WO | WO 2005/009539 A2 | 2/2005 |
| WO | WO 2005/009954 A2 | 2/2005 |
| WO | WO 2005/016929 A1 | 2/2005 |
| WO | WO 2005/028456 A1 | 3/2005 |
| WO | WO 2005/061510 A1 | 7/2005 |
| WO | WO 2005/074875 A2 | 8/2005 |
| WO | WO 2005/103022 A1 | 11/2005 |
| WO | WO 2005/103050 A2 | 11/2005 |
| WO | WO 2006/004984 A1 | 1/2006 |
| WO | WO 2006/023462 A1 | 3/2006 |
| WO | WO 2006/137527 A1 | 12/2006 |
| WO | WO 2007/015528 A1 | 2/2007 |
| WO | WO 2007/079186 A2 | 7/2007 |
| WO | WO 2007/087427 A2 | 8/2007 |
| WO | WO 2007/087429 A2 | 8/2007 |
| WO | WO 2007/125049 A1 | 11/2007 |
| WO | WO 2008/022281 A1 | 2/2008 |
| WO | WO 2008/083070 A1 | 7/2008 |
| WO | WO 2008/154601 A1 | 12/2008 |
| WO | WO 2009/037247 A1 | 3/2009 |
| WO | WO 2010/017046 A1 | 2/2010 |
| WO | WO 2010/075376 A2 | 7/2010 |
| WO | WO 2010/083145 A1 | 7/2010 |
| WO | WO 2010/111059 A1 | 9/2010 |
| WO | WO 2010/122504 A1 | 10/2010 |
| WO | WO 2011/107248 A1 | 9/2011 |
| WO | WO 2011/109059 A1 | 9/2011 |
| WO | WO 2011/112263 A1 | 9/2011 |
| WO | WO 2011/112264 A1 | 9/2011 |
| WO | WO 2011/115892 A1 | 9/2011 |
| WO | WO 2012/027965 A1 | 3/2012 |
| WO | WO 2012/028100 A1 | 3/2012 |
| WO | WO 2012/064744 A2 | 5/2012 |
| WO | WO 2012/074547 A2 | 6/2012 |
| WO | WO 2012/100732 A1 | 8/2012 |
| WO | WO 2012/100734 A1 | 8/2012 |
| WO | WO 2012/101261 A1 | 8/2012 |
| WO | WO 2012/101263 A1 | 8/2012 |
| WO | WO 2012/106995 A1 | 8/2012 |
| WO | WO 2012/139775 A1 | 10/2012 |

(56) References Cited

FOREIGN PATENT DOCUMENTS

| | | |
|---|---|---|
| WO | WO 2012/145254 A2 | 10/2012 |
| WO | WO 2012/147916 A1 | 11/2012 |
| WO | WO 2012/158784 A2 | 11/2012 |
| WO | WO 2013/000869 A1 | 1/2013 |
| WO | WO 2013/000871 A1 | 1/2013 |
| WO | WO 2013/014204 A2 | 1/2013 |
| WO | WO 2013/014205 A1 | 1/2013 |
| WO | WO 2013/018695 A1 | 2/2013 |
| WO | WO 2013/019621 A1 | 2/2013 |
| WO | WO 2013/019626 A1 | 2/2013 |
| WO | WO 2013/019635 A1 | 2/2013 |
| WO | WO 2013/019653 A1 | 2/2013 |
| WO | WO 2013/019682 A1 | 2/2013 |
| WO | WO 2013/029338 A1 | 3/2013 |
| WO | WO 2013/036912 A2 | 3/2013 |
| WO | WO 2013/041519 A1 | 3/2013 |
| WO | WO 2013/042782 A1 | 3/2013 |
| WO | WO 2013/045431 A1 | 4/2013 |
| WO | WO 2013/079223 A1 | 6/2013 |
| WO | WO 2013/132380 A1 | 9/2013 |

OTHER PUBLICATIONS

Katz et al., 2010, caplus an 2010:176204.*
Kang et al., 2009, caplus an 2009:603798.*
Reddy et al., 2009, caplus an 2009:553415.*
Smith et al., PLOS ONE, 2016, 18 pages.*
INV 17, 2018, https://globenewswire.conn/news-release/2014/01/15/602618/10063783/en/Innovimmune-s-Preclinical-Data-on-Highly-Selective-ROR-Gannnna-Inhibitor-Prevents-Multiple-Sclerosis-in-Mice.html.*
Xue et al., 2016, Scientific Reports, 17 pages, www.nature.com/scientificreports.*
Diabetes, 2015, https://diabetesnewsjournal.conn/2015/02/10/type-1-diabetes-inhibited-by-new-compound/.*
ROR, 2015, https://static1.squarespace.conn/static/577aff0015d5db17f97d2d57/t/584f44f9725e254d6b032644/1481590043630/150611_INV-17+Lupus+Thursday_EULAR_2015+small+size.pdf.*
Dai et al., abstract, 2017, J. Invest. Dermatol., 2017, 137(12), 2523-2531.*
Honnegowda et al., 2018, http://erj.ersjournals.com/content/46/suppl_59/PA4367.*
Crohns Disease, 2018, https://www.webmd.com/ibd-crohns-disease/crohns-disease/crohns-disease-treatment-common-medications-for-treating-crohns#1.*
Iizuka, 2015, J. Immunol, 194(1), 56-67.*
Kawasaki, 2018, https://www.webmd.com/drugs/condition-1662-Kawasaki+Disease.aspx?diseaseid=1662&diseasename=Kawasaki+Disease.*
Translation of Official Action from State Intellectual Property Office of China, dated Nov. 10, 2015, for Patent Application No. 201380028983.3, 12 pages.
Official Action from the Eurasian Patent Organization, dated May 31, 2016, for Patent Application No. 201491943/28, with translation, 8 pages.
Official Action from European Patent Office, dated Mar. 10, 2016, for Patent Application No. 13727805.7, 6 pages.
André et al., "A novel isoform of the orphan nuclear receptor RORβ is specifically expressed in pineal gland and retina," Gene 216: 277-283, 1998.
André et al., "Disruption of retinoid-related orphan receptor β changes circadian behavior, causes retinal degeneration and leads to vacillans phenotype in mice," The EMBO Journal 17(14): 3867-3877, 1998.
Awasthi et al., "$T_h17$ cells: from precursors to players in inflammation and infection," International Immunology 21(5): 489-498, 2009.
Ayesa et al., "Solid-phase parallel synthesis and SAR of 4-amidofuran-3-one inhibitors of cathepsin S: Effect of sulfonamides P3 substituents on potency and selectivity," Bioorganic & Medicinal Chemistry 17: 1307-1324, 2009.
Becker-André et al., "Identification of Nuclear Receptor mRNAs by RT-PCR Amplification of Conserved Zinc-Finger Motif Sequences," Biochemical and Biophysical Research Communications 194(3): 1371-1379, Aug. 16, 1993.
Crome et al., "Translational Mini-Review Series on Th17 Cells: Function and regulation of human T helper 17 cells in health and disease," Clinical and Experimental Immunology 159: 109-119, 2009.
Dyer et al., "A Noncommercial Dual Luciferase Enzyme Assay System for Reporter Gene Analysis," Analytical Biochemistry 282: 158-161, 2000.
Eberl et al., "The role of the nuclear hormone receptor RORγt in the development of lymph nodes and Peyer's patches," Immunological Reviews 195: 81-90, 2003.
Eberl et al., "Thymic Origin of Intestinal αβ T Cells Revealed by Fate Mapping of RORγt$^+$Cells," Science 305: 248-251, Jul. 9, 2004.
Evans, "The Steroid and Thyroid Hormone Receptor Superfamily," Science 240: 889-895, May 13, 1988.
Giguère et al., "The Orphan Nuclear Receptor RORα (RORA) Maps to a Conserved Region of Homology on Human Chromosome 15q21-q22 and Mouse Chromosome 9," Genomics 28: 596-598, 1995.
Gu et al., "Interleukin 10 suppresses Th17 cytokines secreted by macrophages and T cells," Eur. J. Immunol. 38: 1807-1813, 2008.
Hamilton et al., "Disruption of the nuclear hormone receptor RORα in staggerer mice," Nature 379: 736-739, Feb. 22, 1996.
He et al., "RORγt, a Novel Isoform of an Orphan Receptor, Negatively Regulates Fas Ligand Expression and IL-2 Production in T Cells," Immunity 9: 797-806, Dec. 1998.
He et al., "Down-Regulation of the Orphan Nuclear Receptor RORγt Is Essential for T Lymphocyte Maturation," The Journal of Immunology 164: 5668-5674, 2000.
Hopfer et al., "Characterization of the renal CD4+ T-cell response in experimental autoimmune glomerulonephritis," Kidney International 82: 60-71, 2012.
Houck et al., "T0901317 is a dual LXR/FXR agonist," Molecular Genetics and Metabolism 83: 184-187, 2004.
Ivanov et al., "The Orphan Nuclear Receptor RORγt Directs the Differentiation Program of Proinflammatory IL-17$^+$ T Helper Cells," Cell 126: 1121-1133, Sep. 22, 2006.
Kallen et al., "X-Ray Structure of the hRORα LBD at 1.63 Å: Structural and Functional Data that Cholesterol or a Cholesterol Derivative Is the Natural Ligand of RORα," Structure 10: 1697-1707, Dec. 2002.
Kumar et al., "The Benzenesulfoamide T0901317 [N-(2,2,2-Trifluoroethyl)-N-[4[2,2,2-trifluoro-1-hydroxy-1-(trifluoromethyl)ethyl]phenyl]-benzenesulfonamide] Is a Novel Retinoic Acid Receptor-Related Orphan Receptor-α/γ Inverse Agonist," Molecular Pharmacology 77(2): 228-236, 2010.
Lau et al., "The Orphan Nuclear Receptor, RORα, Regulates Gene Expression That Controls Lipid Metabolism," Journal of Biological Chemistry 283(26): 18411-18421, Jun. 27, 2008.
Mangelsdorf et al., "The Nuclear Receptor Superfamily: The Second Decade," Cell 83: 835-839, Dec. 15, 1995.
McKenna et al., "Nuclear Receptor Coregulators: Cellular and Molecular Biology," Endocrine Reviews 20(3): 321-344, 1999.
Missbach et al., "Thiazolidine Diones, Specific Ligands of the Nuclear Receptor Retinoid Z Receptor/Retinoid Acid Receptor-related Orphan Receptor α with Potent Antiarthritic Activity," The Journal of Biological Chemistry 271(23): 13515-13522, Jun. 7, 1996.
Paust et al., "Chemokines play a critical role in the cross-regulation of Th1 and Th17 immune responses in murine crescentic glomerulonephritis," Kidney International 82: 42-83, 2012.
Stehlin-Gaon et al., "All-trans retinoic acid is a ligand for the orphan nuclear receptor RORβ," Nature Structural Biology 10(10): 820-825, Oct. 2003.

(56) References Cited

OTHER PUBLICATIONS

Sun et al., "Requirement for RORγ in Thymocyte Survival and Lymphoid Organ Development," *Science* 288: 2369-2373, Jun. 30, 2000.
Tesmer et al., "Th17 cells in human disease," *Immunological Reviews* 223: 87-113, 2008.
Tilley et al., "Retinoid-Related Orphan Receptor γ Controls Immunoglobulin Production and Th1/Th2 Cytokine Balance in the Adaptive Immune Response to Allergen," *The Journal of Immunology* 178: 3208-3218, 2007.
Vanacker et al., "Transcriptional Activities of the Orphan Nuclear Receptor ERRα (Estrogen Receptor-Related Receptor-α)," *Molecular Endocrinology* 13: 764-773, 1999.
Velden et al., "Renal IL-17 expression in human ANCA associated glomerulonephritis," *Am. J. Physiol. Renal Physiol.* 302: F1663-F1673, 2012.
Villey et al., "RORγT, a thymus-specific isoform of the orphan nuclear receptor RORγ/TOR, is up-regulated by signaling through the pre-T cell receptor and binds to the TEA promoter," *Eur. J. Immunol.* 29: 4072-4080, 1999.
Wang et al., "Modulation of Retinoic Acid Receptor-related Orphan Receptor α and γ Activity by 7-Oxygenated Sterol Ligands," *Journal of Biological Chemistry* 285(7): 5013-5025, Feb. 12, 2010.
Wiesenberg et al., "Transcriptional activation of the nuclear receptor RZRα by the pineal gland hormone melatonin and identification of CGP 52608 as a synthetic ligand," *Nucleic Acids Research* 23(3): 327-333, 1995.
Wilson et al., "The Orphan Receptors NGFI-B and Steroidogenic Factor 1 Establish Monomer Binding as a Third Paradigm of Nuclear Receptor-DNA Interaction," *Molecular and Cellular Biology* 13(9): 5794-5804, Sep. 1993.
Xue et al., "Crystal structure of the PXR-T1317 complex provides a scaffold to examine the potential for receptor antagonism," *Bioorganic & Medcinal Chemistry* 15: 2156-2166, 2007.
Zhou et al., "Transcriptional regulatory networks in Th17 cell differentiation," *Curr. Opin. Immunol.* 21(2): 146-152, Apr. 2009.
Official Action from European Patent Office re extended European search report, dated Nov. 21, 2012, for Patent Application No. 12004186.8, 9 pages.
International Search Report dated Oct. 28, 2013, for PCTAN PCT/EP2013/001593, 8 pages.
International Preliminary Report on Patentability dated Dec. 2, 2014, for PCTAN PCT/EP2013/001593, 15 pages.
Translation of Official Action from Patent Office of Japan, dated Jan. 4, 2016, for Patent Application No. 2015-514380, 8 pages.
Official Action from New Zealand Intellectual Property Office, dated Oct. 12, 2015, for Patent Application No. 702539, 4 pages.
Official Action from the New Zealand Intellectual Property Office, dated Mar. 17, 2017, for Patent Application No. 723658, 7 pages.
Huang et al., "Retinoid-related orphan receptor γt is a potential therapeutic target for controlling inflammatory autoimmunity," *Expert Opin. Ther. Targets* 11(6): 737-743, 2007.
Korn et al., "IL-17 and Th17 Cells," *Annu. Rev. Immunol.* 27: 485-517, 2009.
Leonardi et al., "Anti-Interleukin-17 Monoclonal Antibody Ixekizumab in Chronic Plaque Psoriasis," *N. Engl. J. Med.* 366(13): 1190-1199, Mar. 29, 2012.
Papp et al., "Brodalumab, an Anti-Interleukin-17-Receptor Antibody for Psoriasis," *N. Engl. J. Med.* 366(13): 1181-1189, Mar. 29, 2012.

\* cited by examiner

CARBOXAMIDE OR SULFONAMIDE SUBSTITUTED THIAZOLES AND RELATED DERIVATIVES AS MODULATORS FOR THE ORPHAN NUCLEAR RECEPTOR ROR[γ]

The invention provides carboxamide or sulfonamide containing cyclic compounds, preferably thiazoles, as modulators for the orphan nuclear receptor RORγ and methods for treating RORγ mediated chronic inflammatory and autoimmune diseases by administering these novel RORγ modulators to a human or a mammal in need thereof.

The retinoid-receptor related orphan receptors consist of three family members, namely RORα (Beckerandre et al., *Biochem. Biophys. Res. Commun.* 1993, 194:1371), RORβ (Andre et al., *Gene* 1998, 516:277) and RORγ (He et al., *Immunity* 1998, 9:797) and constitute the NR1F (ROR/RZR) subgroup of the nuclear receptor superfamily (Mangelsdorf et al., *Cell* 1995, 83:835).

The nuclear receptor superfamily shares common modular structural domains consisting of a hypervariable N-terminal domain, a conserved DNA binding domain (DBD), a hinge region, and a conserved ligand-binding domain (LBD). The DBD targets the receptor to specific DNA sequences (nuclear hormone response elements or NREs), and the LBD functions in the recognition of endogenous or exogenous chemical ligands. A constitutive transcriptional activation domain is found at the N-terminus (AF1) and a ligand regulated transcriptional activation domain is embedded within the C-terminal LBD of typical NRs. The nuclear receptors can exist in a transcriptional activating or repressing state when bound to their target NREs. The basic mechanism of gene activation involves ligand dependent exchange of co-regulatory proteins, namely co-activators and co-repressors (McKenna et al., *Endocrine Rev.* 1999, 20:321). A NR in the repressing state is bound to its DNA recognition element and is associated with co-repressor proteins that recruit histone-deacetylases (HDACs). In the presence of an agonist, co-repressors are exchanged for coactivators that recruit transcription factors, which contribute to assembling of a chromatin-remodelling complex, which relieves transcriptional repression and stimulates transcriptional initiation via histone acetylation. The AF-2 domain of the LBD acts as a ligand dependant molecular switch presenting interaction surfaces for co-repressor or co-activator proteins and providing with a conserved mechanism for gene activation or repression that is shared by the members of the nuclear receptor superfamily.

The members of the NR1F family of nuclear receptors (such as RORγ) have been considered to be constitutively active transcription factors in the absence of known ligands, which is similar to the estrogen-related receptor alpha (Vanacker et al., *Mol. Endocrinol.* 1999, 13:764). Most recently, 7-oxygenated oxysterols were identified to be high affinity ligands for RORα and RORγ (Wang et al., *J. Biol. Chem.* 2010, 285:5013). 7-Hydroxycholesterol is a key metabolite during the conversion of cholesterol into bile acids, but to date it is not clear whether it is a true endogenous ligand for the RORs. In any case it can be expected that inverse agonists of RORγ should reduce the transcriptional activity of RORγ and influence the biological pathways controlled by RORγ.

The RORs are expressed as isoforms arising from differential splicing or alternative transcriptional start sites. So far, isoforms have been described that differ only in their N-terminal domain (A/B-domain). In humans, four different RORα isoforms have been identified (RORα 1-4) while only two isoforms are known for both RORβ (1 and 2) and RORγ (1 and 2) (Andre et al., *Gene* 1998, 216:277; Villey et al., *Eur. J. Immunol.* 1999, 29:4072). RORγ is used herein as a term describing both, RORγ1 and/or RORγ2 (also called RORγt).

The ROR isoforms show different tissue expression patterns and regulate different target genes and physiological pathways. For example, the RORγt is highly restricted to $CD4^+CD8^+$ thymocytes and to interleukin-17 (IL-17) producing T cells while other tissues express RORγ 1 (Eberl et al., *Science* 2004, 305:248, Zhou and Littmann, *Curr. Opin. Immunol.* 2009, 21:146).

RORs exhibit a structural architecture that is typical of nuclear receptors. RORs contain four major functional domains: an amino-terminal (A/B) domain, a DNA-binding domain, a hinge domain, and a ligand-binding domain (Evans et al., *Science* 1988, 240:889). The DBD consists of two highly conserved zinc finger motifs involved in the recognition of ROR response elements (ROREs) which consist of the consensus motif AGGTCA preceded by an AT-rich sequence (Andre et al., *Gene* 1998, 216:277) which is similar to that of the nuclear receptors Rev-ErbAα and Rev-Erbβ (NR1D1 and D2, respectively) (Giguere et al., *Genomics* 1995, 28:596). These recognition elements do also show high similarity to those identified for the estrogen related receptors and in particular ERRα (ERRs, NR3B1, -2, -3) (Vanacker et al., *Mol. Endocrinol.* 1999, 13:764), steroidogenic factor 1 (SF-1, NR5A) and NGFI-B (NR4A1, -2, -3) (Wilson et al., *Mol. Cell. Biol.* 1993, 13:5794).

RORα is highly expressed in different brain regions and most highly in cerebellum and thalamus. RORα knock-out mice show ataxia with strong cerebellar atrophy, highly similar to the symptoms displayed in the so-called staggerer mutant mouse ($ROR\alpha^{sg/sg}$). This mouse carries mutations in RORα that results in a truncated RORα which does not contain a LBD (Hamilton et al., *Nature* 1996, 379:736).

Analysis of $ROR\alpha^{sg/sg}$ staggerer-mice have revealed a strong impact on lipid metabolism beyond the CNS defects, namely significant decreases in serum and liver triglyceride, reduced serum HDL cholesterol levels and reduced adiposity. SREBP1c and the cholesterol transporters ABCA1 and ABCG1 are reduced in livers of staggerer mice and CHIP analysis suggest that RORα is directly recruited to and regulates the SREBP1c promoter. In addition, PGC1α, PGC1β, lipin1 and β2-adrenergic receptor were found to be increased in tissues such as liver or white and brown adipose tissue, which may help to explain the observed resistance to diet-induced obesity in staggerer mice (Lau et al., *J. Biol. Chem.* 2008, 283:18411). RORβ expression is mainly restricted to the brain and most abundantly found in the retina. RORβ knock-out mice display a duck-like gait and retinal degeneration which leads to blindness (Andre et al., *EMBO J.* 1998, 17:3867). The molecular mechanisms behind this retinal degeneration are still poorly understood.

RORγ (particularly RORγt) null-mutant mice lack lymph nodes and Peyer's patches (Eberl and Littmann, *Immunol. Rev.* 2003, 195:81) and lymphatic tissue inducer (LTi) cells are completely absent from spleen mesentery and intestine. In addition, the size of the thymus and the number of thymocytes is greatly reduced in RORγ null mice (Sun et al., *Science* 2000, 288:2369) due to a reduction in double-positive CD4+CD8+ and single positive $CD4^-CD8^-$ or $CD4^+CD8^-$ cells suggesting a very important role of RORγt in thymocyte development.

Thymocyte development follows a complex program involving coordinated cycles of proliferation, differentiation, cell death and gene recombination in cell populations dedicated by their microenvironment. Pluripotent lymphocyte progenitors migrating from fetal liver or adult bone marrow to the thymus are being committed to the T-cell lineage. They develop through a series of steps from CD4⁻CD8⁻ double negative cells to CD4⁺CD8⁺ cells and those with low affinity towards self-MHC peptides are eliminated by negative selection. These develop further into CD4⁻CD8⁺ (killer) or CD4⁺CD8⁻ (helper) T-cell lineages. RORγt is not expressed in double negative and little expressed in immature single negative thymocytes (He et al., *J. Immunol.* 2000, 164:5668), while highly upregulated in double-positive thymocytes and downregulated during differentiation in single-positive thymocytes. RORγ deficiency results in increased apoptosis in CD4⁺CD8⁺ cells and the number of peripheral blood thymocytes is decreased by 6-fold (10-fold CD4⁺ and 3-fold CD8⁺ thymocytes).

Recent experiments in a model of ovalbumin (OVA)-induced inflammation in mice, as a model for allergic airway disease, demonstrated a severe impairment of the development of the allergic phenotype in the RORγ KO mice with decreased numbers of CD4⁺ cells and lower Th2 cytokine/chemokine protein and mRNA expression in the lungs after challenge with OVA (Tilley et al., *J. Immunol.* 2007, 178: 3208). IFN-γ and IL-10 production were increased in splenocytes following re-stimulation with the OVA antigen compared to wt splenocytes suggesting a shift towards a Th1 type immune response on cost of a reduction of Th2 type response. This suggests that down-modulation of RORγ transcriptional activity with a ligand could result in a similar shift of the immune response towards a Th1 type response, which could be beneficial in the treatment of certain pulmonary diseases like asthma, chronic obstructive pulmonary disease (COPD) or allergic inflammatory conditions.

T-helper cells were previously considered to consist of Th1 and Th2 cells. However, a new class of Th cells, the Th17 cells, which produce IL-17, were also identified as a unique class of T-cells that are considered to be pro-inflammatory. They are recognized as key players in autoimmune and inflammatory diseases since IL-17 expression has been associated with many inflammatory diseases such as rheumatoid arthritis, systemic lupus erythematosus (SLE) and allograft rejection. (Tesmer et al., *Immunol. Rev.* 2008, 223:87).

RORγt is exclusively expressed in cells of the immune system and has been identified as a master regulator of Th17 cell differentiation. Expression of RORγt is induced by TGF-beta or IL-6 and overexpression of RORγt results in increased Th17 cell lineage and IL-17 expression. RORγt KO mice show very little Th17 cells in the intestinal lamina propria and demonstrate an attenuated response to challenges that usually lead to autoimmune disease (Ivanov et al., *Cell* 2006, 126:1121).

Inhibition of IL-17 production via inhibition of Th17 cell development may also be advantageous in atopic dermatitis and psoriasis where IL-17 is deeply involved. Interestingly, recent evidence was presented that IL-10 suppresses the expression of IL-17 secreted by both, macrophages and T-cells. In addition, the expression of the Th17 transcription factor RORγt was suppressed (Gu et al., *Eur. J. Immunol.* 2008, 38:1807). Moreover, IL-10 deficient mice provide a good model for inflammatory bowel disease (IBD) where a shift towards a Th1 type inflammatory response is frequently observed. Oral IL-10 delivery poses a potential treatment option for IBD.

The proinflammatory actions of IL-17 producing Th17 cells are counteracted by another T-helper cell type, so-called regulatory T-cells or Tregs. Naïve T-cells are differentiated into Tregs upon stimulation by TGFβ. This results in upregulation of the transcriptional modulator FoxP3 resulting in CD4⁺FoxP3⁺ Tregs. In case the naïve T-cells are co-stimulated by IL-6, FoxP3 expression is suppressed and RORγt expression is induced. These CD4⁺FoxP3⁻RORγt⁺ T-helper cells then differentiate into IL-17 producing Th17 cells. (reviewed in Awasthi and Kuchroo, *Int. Immunol.* 2009, 21:489, and Zhou and Littmann, *Curr. Opin. Immunol.* 2009, 21:146). Several lines of evidence suggest that these Th17 cells are responsible for the etiology of a whole range of autoimmune diseases such as multiple sclerosis, rheumatoid arthritis, ankylosing spondylitis, psoriasis, Crohn's disease and other types of inflammatory bowel disease, lupus erythematosus and asthma. The severity of disease seems to correlate with the presence of IL-17⁺ Th17 cells and it is believed that interception of RORγt by a small molecule inverse agonist or antagonist should result in a reduction of these IL-17⁺ Th17 cells ultimately leading to alleviation of disease symptoms and outcome (Crome et al., *Clin. Exp. Immunol.* 2010, 159:109).

Th1 and Th17 subtype effector CD4⁺ T cells are thought to play a critical role in the pathogenesis of human and experimental crescentic glomerulonephritis (Paust et al., *Kidney Int* 2012, doi: 10.1038/ki.2012.101). IL-17 modulators may thus be beneficial for treating acute glomerulonephritis (Velden et al., *Am. J. Physiol. Renal Physiol.* 2012, in press; Hopfer et al., *Kidney Int.* 2012, doi:10.1038/ki.2012.73).

Ligands for the RORs:

It was reported that cholesterol and its sulfated derivatives might function as RORα ligands and in particular cholesterol-sulfate could restore transcriptional activity of RORα in cholesterol-depleted cells (Kallen et al., *Structure* 2002, 10:1697). Previously, melatonin (Missbach et al., *J. Biol. Chem.* 1998, 271:13515) and thiazolidinediones were suggested to bind to RORα (Wiesenberg et al., *Nucleic Acid Res.* 1995, 23:327). However, none of these have been shown to be functional ligands of RORα or of any other of the RORs. Certain retinoids including all-trans retinoid acid have been demonstrated to bind to RORβ and function as partial antagonists for RORβ but not RORα (Stehlin-Gaon et al., *Nat. Struct. Biol.* 2003, 10:820).

Recently, 7-oxygenated sterols such as 7-hydroxy-cholesterol and 7-keto-cholesterol were identified as highly potent modulators of RORγ activity (Wang et al., *J. Biol. Chem.* 2010, 285:5013) in in vitro assays. The same group of investigators also found that a known LXR agonist, T0901317 ([N-(2,2,2-trifluoroethyl)-N-[4-[2,2,2-trifluoro-1-hydroxy-1-(trifluoromethyl)ethyl]phenyl]-benzenesulfonamide]) acts as a RORγ inverse agonist at submicromolar potency (Kumar et al., *Mol. Pharmacol.* 2010, 77:228). In neither case, however, in vivo data were obtained that demonstrate a beneficial impact of these RORγ modulating compounds. In case of the 7-oxysterols their endogenous presence as metabolites naturally produced by the body itself as well as their rapid turnover and their biological activities on many cellular proteins prevent a meaningful animal study that allows drawing conclusions on the role of RORγ. In case of the T0901317 its polypharmacodynamic properties, acting on at least six different nuclear receptors (LXRα/β, FXR, PXR, RORα/γ) prevents its usefulness as a drug candidate for the development in an autoimmune disease application (Houck et al., *Mol. Genet. Metab.* 2004, 83:184; Xue et al., *Bioorg. Med. Chem.* 2007, 15:2156).

WO2011/109059 (US2011/0257196) describes compounds with anti-cancer activity of general structure (A)

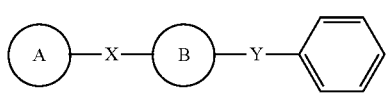

(A)

wherein cycle B can be selected from a large number of cyclic systems. However no thiazole, oxazole, thiophene or furan containing a carboxamide or sulfonamide in 2-position is described in the examples.

In WO2010/075376 compounds of general structure (B) for inhibiting replication of Hepatitis C virus are described. $A_1$ is defined to be a 3-14 membered carbo- or heterocycle, T can be e.g. $CONR^6$ and $SO_2NR^6$ while $A_2$ can be a carbo- or heterocycle. However, no thiazole, oxazole, thiophene or furan (representing $A_1$) is described in the examples—a typical example is e.g. B1.

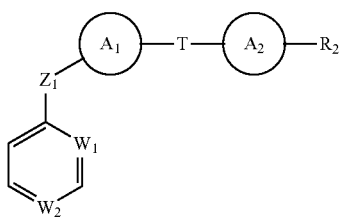

(B)

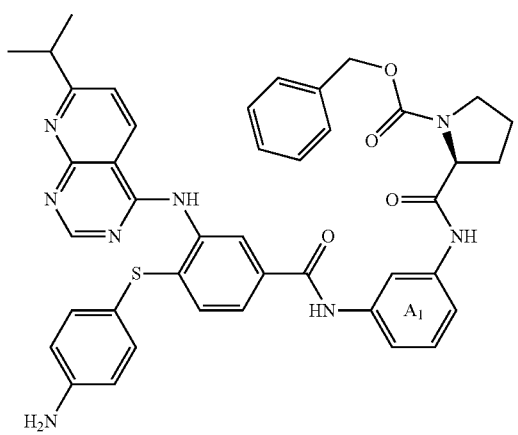

(B1)

WO2010/083145 and WO2010/017046 describe compounds of general structure (C) which selectively inhibit microtubule affinity regulating kinase (MARK). The heteroaryl substituent of the thiazole (Y=N) respectively thiophene (Y=CH) is limited to imidazo[1,2-b]pyridazin-3-yl (W=N) and imidazo[1,2-a]pyridin-3-yl (W=C), while $X_4$ can be $(CH_2)_{q=0\ to\ 3}$—$C_{3-6}$-cycloalkyl. No thiazole or thiophene examples with $X_4$ equals —Z—$C_{3-10}$-cycloalkyl (Z=optionally substituted carbon, oxygen, nitrogen or sulfur) are presented (in the closest structure $X_4$ equals benzyl).

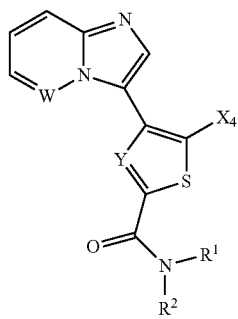

(C)

In WO2009/037247 pyrazine derivatives of general structure (D) as potassium channel modulating agents are described. 'Het' represents a heterocyclic group which can also be thiazolyl, which is optionally substituted e.g. with cycloalkyl-alkyl, amino-carbonyl and N,N-dialkyl-amino-carbonyl. No thiazole examples which are substituted with a carboxamide are presented.

(D)

WO2007/015528 (EP1921077) and WO2006/137527 (EP1894930) describe compounds of general structure (E) for treating and/or preventing sleep disorders. $R^1$ is defined to be a 5-membered aromatic heterocyclic group having at least one oxygen atom, while $R^2$ can be a optionally substituted lower alkyl, $NR^4R^5$ (with $R^4$ and $R^5$ e.g. cycloalkyl) or $COR^6$ ($R^6$ e.g. cycloalkyl). Five thiazole examples with a carboxamide moiety are mentioned, e.g. compound (E1) and (E2). However, in all of those examples the group $R^1$ is a 5-membered oxygen-containing ring.

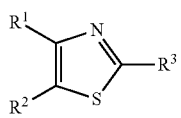

(E)

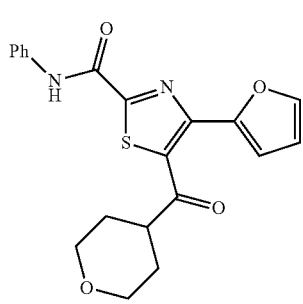

(E1)

-continued

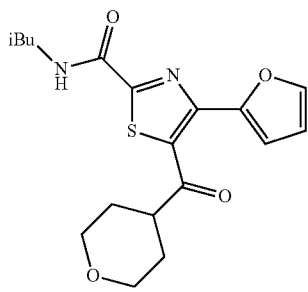

(E2)

In WO2005/103022 derivatives of general structure (F) as melanocortin receptor modulators are described, wherein W can be a sulfur atom, m e.g. zero and A can be for example a carbox- or sulfonamide. $R^6$ can be L-$D^2$-cycloalkyl (with L e.g. bond and $D^2$ e.g. nitrogen or alkylene) and $R^7$ can be L-$D^1$-aryl (with L and $D^1$ e.g. bond), therefor falling within the broadest scope of the present application. From the huge amount of examples, only two thiazoles with a directly linked carboxamide moiety are mentioned, e.g. (F1). However, those compounds do not have a substituent in position 4 of the thiazole ring.

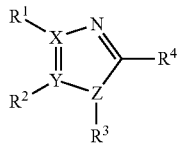

(F)

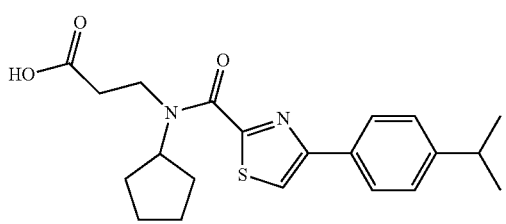

(F1)

WO2005/074875 describes a keratin dyeing composition comprising (a) a medium suitable for dyeing, and (b) one or more five-membered heteroaromatic dyeing compounds, e.g. structure (G) or (G') beside many other cyclic systems, wherein Y equals sulfur or oxygen and $R^1$, $R^2$ and $R^4$ can be alkyl, aryl, hetaryl, O-cycloalkyl and carboxamide. However no thiazole, oxazole, thiophene or furan examples which are substituted with a carboxamide or sulfonamide is presented.

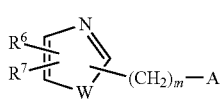

(G)

(G')

US2005/113283 claims a method of modulating an Edg-4-receptor mediated biological activity, wherein the modulator is a compound of structural formula (H) as presented in claim 40:

(H)

(H1)

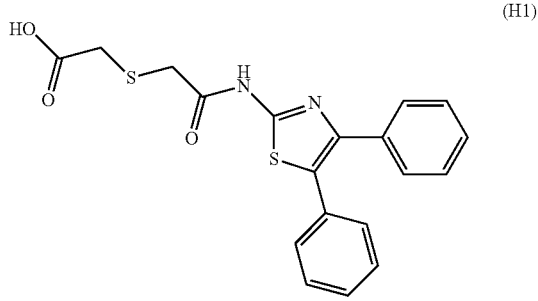

$R^1$ to $R^4$ is selected from CONHR, CONR$_2$, phenyl, $(CH_2)_{m=0\ to\ 8}$—$R^5$ ($R^5$ e.g. cycloalkyl) and others. However no thiazole or oxazole sulfon- or carboxamide is shown in the examples, only an inverse amide of structure (H1) is disclosed.

In US2005/065189 thiazoles of structure (J) as cannabinoid receptor modulators are described, wherein X can be a carboxamide moiety and $R^1$ can be a phenyl or pyridyl moiety optionally substituted with Me, Et, Pr, OMe, OEt, OH, hydroxymethyl, hydroxyethyl, halogen, $CF_3$, $OCF_3$, $SO_2Me$, SOMe, $SO_2CF_3$, phenyl or CN while R can be $R^1$ or alkyl-cycloalkyl. 21 thiazole examples are shown, the closest example is structure (J1) with an $CH_2$-phenyl moiety in position 4 of the thiazole ring.

(J)

(J1)

WO2005/016929 and WO2003/002567 describe compounds of general structure (K) and (K') as glutamate racemate inhibitors, wherein $R^4$ is broadly defined to be a monocyclic or bicyclic, saturated or unsaturated, ring system, which may contain from 5 to 12 ring atoms, 0 to 4 of which are heteroatoms independently selected from N, O or S and therefor also comprise thiazoles, oxazoles, thiophenes or furans. However no compounds were disclosed therein R⁴ is a thiazole, oxazole, thiophene or furan substituted with a carbox- or sulfonamide moiety.

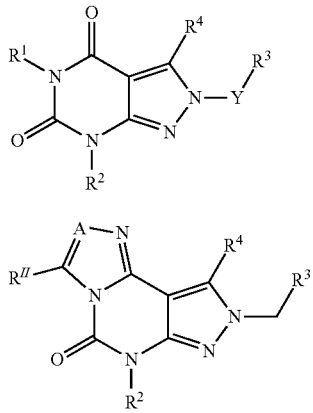

(K)

(K')

In WO2004/094395 biaryls of structure (L) as sodium channel blockers are described, wherein HET can be a thiazole, imidazole or oxazole moiety. The HET moiety can be substituted with sulfon- or carboxamides and alkyl-cycloalkyl. However, the thiazole or oxazole compounds disclosed therein all contain no cycloalkyl moiety.

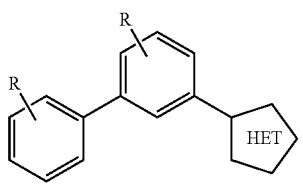

(L)

WO2000/024739 describes insecticides and acaricides of formula (M), wherein HET can be chosen from a large variety of heterocycles, however not thiophene or furan. However, no thiazole or oxazole carboxamide example is presented.

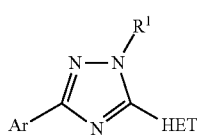

(M)

In WO1998/028282 factor Xa inhibitors of formula (N) are disclosed, wherein ring M may contain in addition to J other nitrogen atoms. However from the presented structures (>1000) no thiazole, oxazole, thiophene or furan at all is exemplified.

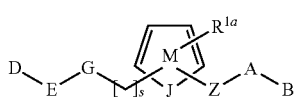

(N)

WO1995/029904 describes thiazoles of structure (P) as antiglaucoma agents. $R^1$ can be a primary sulfonamide, $R^2$ can be $OR^4$ (with $R^4$ as alicyclic residue), $R^3$ can be phenyl (optionally substituted with lower alkoxy, halogen or $C_{1-3}$ alkyl). The closest example to the compounds of the present invention is compound (P1).

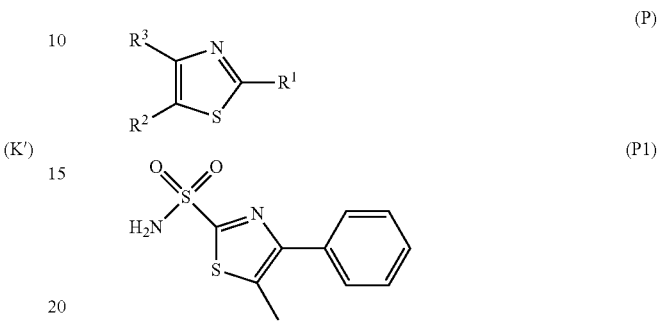

(P)

(P1)

WO2013/014205 describes thiazole-2-carboxamides of structure (Q) as inhibitors of the protease cathepsin A. All shown examples have an phenyl moiety in the amide residue and $R^1$ is always hydrogen. In WO2013/014204 the thiazole moiety is replaced by another 5-membered heterocycle, including oxazole. Again, all shown oxazole examples have an phenyl moiety in the amide residue and $R^1$ is always hydrogen.

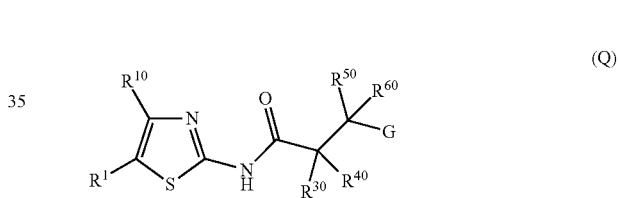

(Q)

WO2010/111059 describes P2x3 receptor antagonists for the treatment of pain of structure (R), wherein $R^2$ represents H, (halo)alkyl or OH; $R^3$ represents a broad range of optionally substituted alkyl substituents; B can be a oxazole cycle, $R^7$ represents for example an optionally substituted aryl moiety and with the rest W—Z—$R^6$ a X-cycloalkyl residue (X=$CR^2$, CO or $SO_2$) can be constructed. However no oxazole containing a carboxamide in 2-position is described in the examples nor an oxazole, having such a hypthetical X-cycloalkyl residue.

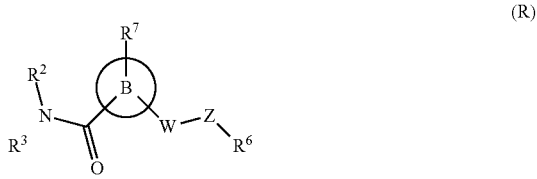

(R)

WO2006/023462 describes 1-(hetero)aroyl-2-(pyrrolidin-1-ylmethyl)pyrrolidine as histamine H3 receptor agents of structure (S), wherein $R^1$ selected from a broad variety of heterocycles, including oxazole. This heterocycle can be optionally substituted with, e.g. CO-cycloalkyl, $CONR^7R^8$. However no example is described, where $R^1$ is an oxazole.

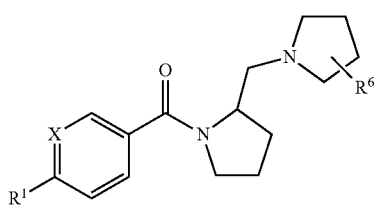

(S)

WO2003/040147 describes the preparation of N-(azabicyclyl)arylamides for therapeutic use as nicotinic acetylcholine receptor agonists of formula (T), wherein $R^1$ is hydrogen or optionally substituted alkyl, X is oxygen or sulfur and W is a cyclic heteroeromatic moiety, which can be substituted with e.g. CO-cycloalkyl or $SO_2$-cycloalkyl. From the presented oxazoles no compounds with two additional substituents are shown, only some of them contain a substituted aryl as substituent.

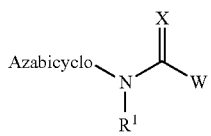

(T)

In WO2000/033836 selectin antagonists of formula (U) are disclosed, however no oxazole is presented.

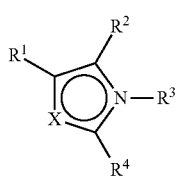

(U)

In WO1996/036617 substituted oxazoles of formula (V) as antiinflammatories are described. $R^5$ can be selected from a broad range of substitutents, including aminocarbonyl. $R^2$ is selected from amino and lower alkyl.

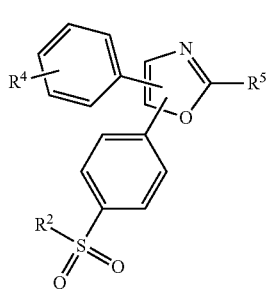

(V)

In WO1996/003392 substituted oxazoles of formula (W) for the treatment of inflammation are described. $R^6$ can be selected from a broad range of substitutents, including aminocarbonyl and alkylaminoarbonyl. $R^2$ is selected from amino and lower alkyl. No 2-carboxamide substituted oxazoles are shown.

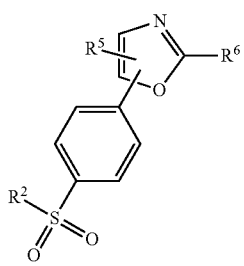

(W)

WO2008/154601 describes thiazole derivatives as antviral inhibitors of structure (X), wherein $L^2$-$R^2$ can be a substituted carboxamide, $R^5$ is selected from e.g. optionally substituted alkyl or cycloalkyl and $L^1$-$R^1$ can be a substituted sulfonamide. However, no compound is shown, wherein $L^1$-$R^1$ is a substituted sulfonamide.

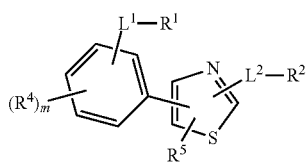

(X)

In WO2007/087429, phenyl and pyridyl compounds as $Ca^{2+}$ ion channel inhibitors with structure (Y) are described, wherein L is selected from various linker elements including $SO_2NR$ (R=H or alkyl) and $R^2$ can be an optionally substituted phenyl or heteroaryl. $R^3$ can be an optionally substituted 5-membered heteroaryl, however no 2-carboxamide substituted thiazole, oxazole, thiophene or furan is shown in the examples.

(Y)

WO2005/009954 and WO2005/009539 describe compounds of structure (Z), wherein A is selected from abroad range of substituents giving 5- or 6-membered aromatic cycles including thiophene and furan. L-Y can form a substituted carboxamide and X can be phenyl or pyridyl, which is optionally substituted with an alkylated sulfonamide, however such examples are not shown.

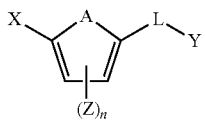

(Z)

In US2003/236293 tricyclic COX-2 selective inhibitors are claimed of structure (AA), wherein A can be a partially unsaturated or unsaturated heterocyclyl or carbocyclic ring. However no examples are shown, wherein A is a 2-carboxamide substituted thiazole, oxazole, thiophene or furan.

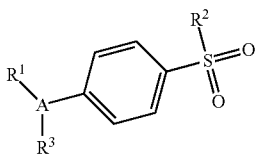

(AA)

WO2012/027965 and WO2012/028100 describe thiazole compounds of structure (AB) as RORγ receptor modulators, wherein $R^a$ represents a optionally substituted $C_{1-6}$-alkyl, $NH_2$ or $NHC_{1-3}$-alkyl; $R^b$ and $R^c$ represents H or $C_{1-6}$-alkyl; X is C=O and $R^d$ and $R^e$ are optional substituents. In WO2012/100734 compounds are described, wherein X represents O, NH, N—$C_{1-6}$-alkyl or $C_{1-3}$-alkyl, optionally substituted with OH. Similarly in WO2012/100732, the same derivatives with a thiophene core are described (structure AC).

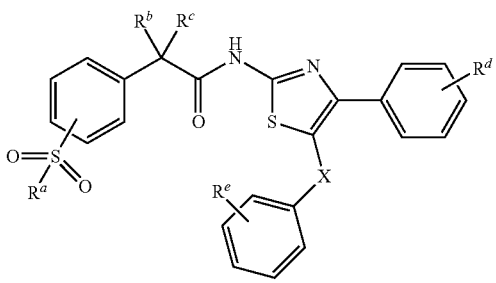

(AB)

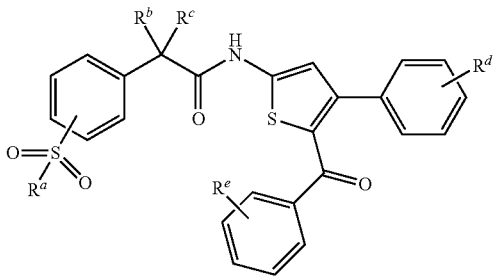

(AC)

In WO2013/029338 similar RORγ receptor modulators are described of structure (AD), wherein ring A, B and C is broadly defined as phenyl or heteroaryl and $R^2$ can be selected from e.g. $C_{1-6}$-alkylene-cycloalkyl, heterocycloalkyl, O-heteroaryl. In the examples ring B is limited to 6-membered (hetero)aryl.

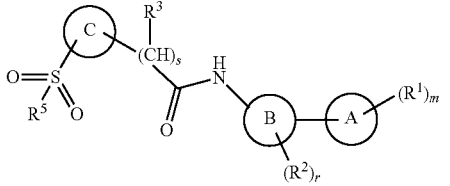

(AD)

Modulators of the RORγ receptor were recently disclosed in WO2011/107248, WO2011/112263, WO2011/112264, WO2011/115892, WO2012/027965, WO2012/028100, WO2012/064744, WO2012/074547, WO2012/100732, WO2012/100734, WO2012/101261, WO2012/101263, WO2012/106995, WO2012/139775, WO2012/145254, WO2012/147916, WO2012/158784, WO2013/000869, WO2013/000871, WO2013/018695, WO2013/019621, WO2013/019626, WO2013/019635, WO2013/019653, WO2013/019682, WO2013/036912, WO2013/041519, WO2013/042782, WO2013/045431 which are based upon other structural classes.

SUMMARY OF THE INVENTION

It is therefore the object of the present invention to provide compounds, which bind to the orphan nuclear receptors RORγ1 and/or RORγt and, thus, to open new methods for treating diseases associated with the modulation of RORγ, such as autoimmune diseases, inflammatory skin diseases or multiple sclerosis.

This object is solved by the appended claims.

Thus, the present invention provides carboxamide or sulfonamide containing cyclic compounds as RORγ modulators, which can be used for treating or preventing a disease or disorder associated with the inactivation or activation of the RORγ receptor.

The present invention relates to a RORγ modulator which is based on a cyclic scaffold for use in the treatment or prophylaxis of a disease or disorder associated with the inhibition or activation of RORγ.

When treating the disease or disorder associated with the modulation of the RORγ receptor, the activity of said receptor is preferably reduced.

Preferably, the disease or disorder is selected from the group consisting of autoimmune diseases. Autoimmune diseases comprise a group of diseases with a similar etiology of an overshooting immune response against endogenous targets resulting in chronic inflammation and physical disabilities or other severe symptoms. Autoimmune diseases comprise e.g. rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis.

The present invention provides novel compounds to be used in the treatment of diseases or disorders associated with the inactivation or activation of the RORγ receptor.

Further, the present invention relates to a method for treating autoimmune diseases comprising rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis, said method comprising administering a sufficient amount of a compound according to Formula (1), (1'), (2), (2'), (100), (100'), (200) or (200') as shown below to a mammal in need thereof.

DETAILED DESCRIPTION OF THE INVENTION

In a first alternative, the present invention provides a compound represented by Formula (200) and Formula (200')

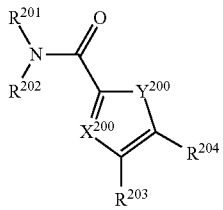

(200)

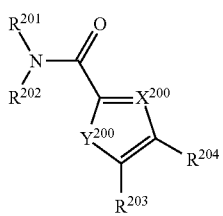

(200')

an enantiomer, diastereomer, tautomer, N-oxide, solvate, formulation and pharmaceutically acceptable salt thereof, wherein $R^{201}$ and $R^{202}$ are independently selected from H, $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl), $C_{1-10}$-alkylene-(6-membered heteroaryl), $SO_2$—$C_{1-10}$-alkyl, wherein alkyl, alkenyl, alkynyl, alkylene, cycloalkyl, heterocycloalkyl, aryl and heteroaryl is unsubstituted or substituted with 1 to 7 substituents independently selected from oxo, CN, $OR^{211}$, O—$C_{2-6}$-alkylene-$OR^{211}$, $C_{1-6}$-alkyl, halo-$C_{1-6}$-alkyl, halogen, $CO_2R^{211}$, $CONR^{211}R^{212}$, $CONR^{211}SO_2R^{211}$, $COR^{211}$, $SO_xR^{211}$, $SO_3H$, $SO_2NR^{211}R^{212}$, $NR^{211}COR^{211}$, $NR^{211}SO_2R^{211}$, $NR^{211}$—CO—$NR^{211}R^{212}$, $NR^{211}$—$SO_2$—$NR^{211}R^{212}$, $C_{3-10}$-cycloalkyl, O—$C_{3-10}$-cycloalkyl, $C_{3-10}$-heterocycloalkyl, O—$C_{3-10}$-heterocycloalkyl and $NR^{211}R^{212}$;

or $R^{201}$ and $R^{202}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{211}$, $SO_xR^{211}$, $SO_3H$, $NR^{211}SO_2R^{211}$, $SO_2NR^{211}R^{212}$, $C_{0-6}$-alkylene-$CO_2R^{211}$, $CONR^{211}R^{212}$, $CONR^{211}SO_2R^{211}$, $COR^{211}$, $NR^{211}$—CO—$R^{211}$, $NR^{211}$—CO—$NR^{211}R^{212}$, $NR^{211}$—$SO_2$—$NR^{211}R^{212}$, $NR^{211}R^{212}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$O_{3-8}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;

$R^{203}$ is selected from $C_{1-10}$-alkyl, fluoro-$C_{1-10}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(6- to 10-membered aryl), $C_{0-6}$-alkylene-(5- to 10-membered heteroaryl), wherein alkyl, alkylene, cycloalkyl, heterocycloalkyl, aryl and heteroaryl is unsubstituted or substituted with 1 to 6 substituents independently selected from oxo, halogen, CN, $C_{1-6}$-alkyl, halo-$C_{1-6}$-alkyl, $C_{3-6}$-cycloalkyl, $C_{3-6}$-heterocycloalkyl, $OR^{212}$, $CO_2R^{212}$, $CONR^{212}R^{212}$, $COR^{212}$; and wherein optionally one $CH_2$ unit in alkyl or alkylene can be replaced by O, $SO_x$, NH or $N(C_{1-3}$-alkyl);

$R^{204}$ is

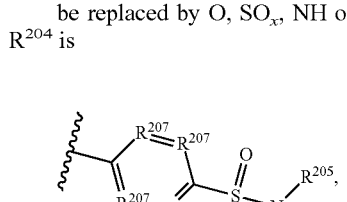

wherein $R^{205}$ and $R^{206}$ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cycloalkyl, heterocycloalkyl, aryl and heteroaryl are unsubstituted or substituted with 1 to 6 substituents independently selected from halogen, CN, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl, $NR^{211}R^{212}$, $CO_2R^{212}$ and $CONR^{211}R^{212}$;

and optionally wherein $R^{205}$ and $R^{206}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{207}$ is independently selected from N and $CR^{208}$; or two adjacent $R^{207}$ form a 5- or 6-membered unsaturated or partially saturated ring containing carbon atoms and optionally containing 1 or 2 heteroatoms selected from O, S or N, wherein the ring is unsubstituted or substituted with 1 to 4 substitutents independently selected from halogen, OH, oxo, $C_{1-4}$-alkyl and fluoro-$C_{1-4}$-alkyl;

$R^{208}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, $C_{3-10}$-cycloalkyl, wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;

$R^{209}$ is selected from H, halogen, CN, $C_{1-3}$-alkyl and fluoro-$C_{1-3}$-alkyl;

$R^{211}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, $NH(C_{1-3}$alkyl), $N(C_{1-3}$-alkyl$)_2$, $C_{3-6}$-heterocycloalkyl, $C_{3-6}$-cycloalkyl and $SO_2$—$C_{1-3}$-alkyl,
  wherein cycloalkyl and heterocycloalkyl is unsubstituted or substituted with 1 to 3 substituents independently selected from the group consisting of F, OH, oxo, Me and $CF_3$;

$R^{212}$ is independently selected from H, $C_{1-6}$-alkyl, halo-$C_{1-6}$-alkyl and $C_{3-6}$-cycloalkyl;

$X^{200}$ is selected from N and $CR^{209}$;

$Y^{200}$ is selected from O and S;

x is independently selected from 0, 1 and 2;

with the proviso, that 4-phenyl-5-(4-sulfamoylphenyl)oxazole-2-carboxamide is excluded.

In a preferred embodiment of the first alternative, the present invention provides a compound of Formula (200) and Formula (200'), wherein compounds with
$Y^{200}$ is S; $X^{200}$ is N;
$R^{203}$ is selected from $(CR^8R^9)R^{40}$; (C=O)$R^{40}$; $C_3$-cycloalkylene-$R^{40}$, $OR^{40}$, $NR^{41}R^{40}$ and $SO_y$—$R^7$, wherein $R^7$ is selected from $C_{3-10}$-cycloalkyl and $C_{3-10}$-heterocycloalkyl,
  wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;
$R^8$ and $R^9$ are independently selected from H, F, $C_{1-3}$-alkyl, halo-$C_{1-3}$-alkyl, OH, O—$C_{1-3}$-alkyl and O-halo-$C_{1-3}$-alkyl;
$R^{40}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl and halo-$C_{1-6}$-alkyl; and
y is selected from 0, 1 and 2;
are excluded.

In a further preferred embodiment in combination with any of the above or below embodiments of the first alternative $R^{201}$ is selected from H, $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl), $C_{1-10}$-alkylene-(6-membered heteroaryl), $SO_2$—$C_{1-10}$-alkyl, wherein alkyl, alkenyl, alkynyl, alkylene, cycloalkyl, heterocycloalkyl, aryl and heteroaryl is unsubstituted or substituted with 1 to 7 substituents independently selected from oxo, CN, $OR^{211}$, O—$C_{2-6}$-alkylene-$OR^{211}$, $C_{1-6}$-alkyl, halo-$C_{1-6}$-alkyl, halogen, $CO_2R^{211}$, $CONR^{211}R^{212}$, $CONR^{211}SO_2R^{211}$, $COR^{211}$, $SO_xR^{211}$, $SO_3H$, $SO_2NR^{211}R^{212}$, $NR^{211}COR^{211}$, $NR^{211}SO_2R^{211}$, $NR^{211}$—CO—$NR^{211}R^{212}$, $NR^{211}$—$SO_2$—$NR^{211}R^{212}$, $C_{3-10}$-cycloalkyl, O—$C_{3-10}$-cycloalkyl, $C_{3-10}$-heterocycloalkyl, O—$C_{3-10}$-heterocycloalkyl and $NR^{211}R^{112}$;

$R^{202}$ is selected from H, $C_{1-6}$-alkyl, halo-$C_{1-6}$-alkyl and hydroxy-$C_{1-6}$-alkyl, more preferably $R^{202}$ is hydrogen;
or $R^{201}$ and $R^{202}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{211}$, $SO_xR^{211}$, $SO_3H$, $NR^{211}SO_2R^{211}$, $SO_2NR^{211}R^{212}$, $C_{0-6}$-alkylene-$CO_2R^{211}$, $CONR^{211}R^{212}$, $CONR^{211}SO_2R^{211}$, $COR^{211}$, $NR^{211}$—CO—$R^{211}$, $NR^{211}$—CO—$NR^{211}R^{212}$, $NR^{211}$—$SO_2$—$NR^{211}R^{212}$, $NR^{211}R^{212}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl,
  wherein cycloalkyl and heterocycloalkyl are unsubstituted or substituted with 1 to 4 substituents independently selected from halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo.

More preferably, $R^{201}$ and $R^{202}$ when taken together with the nitrogen to which they are attached complete a 4- to 6-membered ring containing carbon atoms and optionally containing one additional nitrogen atom, wherein the ring is unsubstituted or substituted with 1 to 4 substituents independently selected from fluoro, oxo, $OR^{211}$, $SO_2R^{211}$, $NR^{211}SO_2R^{211}$, $SO_2NR^{211}R^{22}$, $C_{0-6}$-alkylene-$CO_2H$, $CONR^{211}R^{212}$, $COR^{211}$, $NR^{211}R^{212}$, $C_{1-6}$-alkyl, halo-$C_{1-6}$-alkyl, hydroxy-$C_{1-6}$-alkyl, $C_{3-8}$-cycloalkyl and $C_{3-8}$-heterocycloalkyl,
  wherein cycloalkyl and heterocycloalkyl are unsubstituted or substituted with 1 to 4 substituents independently selected from halogen, $C_{1-3}$-alkyl, halo-$C_{1-3}$-alkyl, $SO_2$—$C_{1-3}$-alkyl, COOH and oxo.

In a preferred embodiment in combination with any of the above or below embodiments of the first alternative $NR^{201}R^{202}$ is selected from NHMe, NHEt, $NH^iPr$, $NH^tBu$, $NHCH_2CONH_2$, $NHCH_2CONMe_2$, $NHCH_2CH_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CH(CF_3)OH$, $NHCH_2C(Me)(CF_3)OH$, $NHCH_2CMe_2OH$, $NHCH_2CH_2CMe_2OH$, $NHCH_2CMe_2NHCH_2CF_3$, $NHCH(Me)CMe_2OH$, $NHCH_2CMe_2OMe$, $NHCH_2CMe_2CO_2H$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_5SO_2NH_2NH(CH_2)_3NHSO_2Me$, $NH(CH_2)_2O(CH_2)_2OH$, $NHCH_2CHMeOH$, $NH(CH_2)_5SOMe$, $NH(CH_2)_3SO_2Me$, $NHC(CH_2OH)_3$, $NHCH_2CH(OH)CH_2OH$, $N(CH_2CH_2OH)_2$,

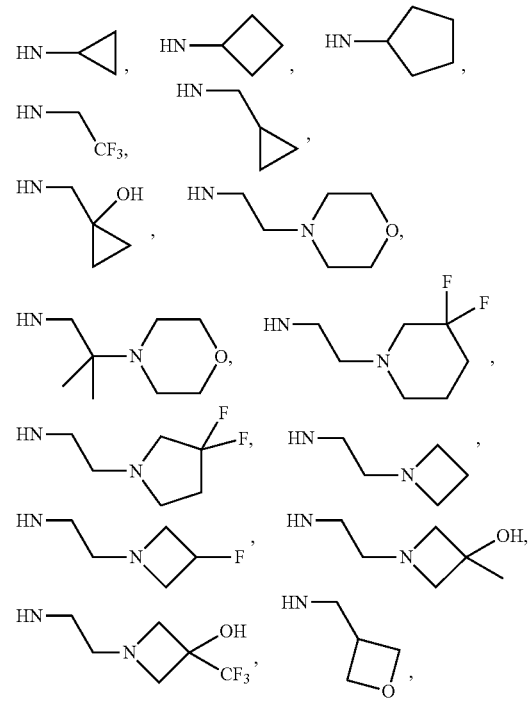

-continued
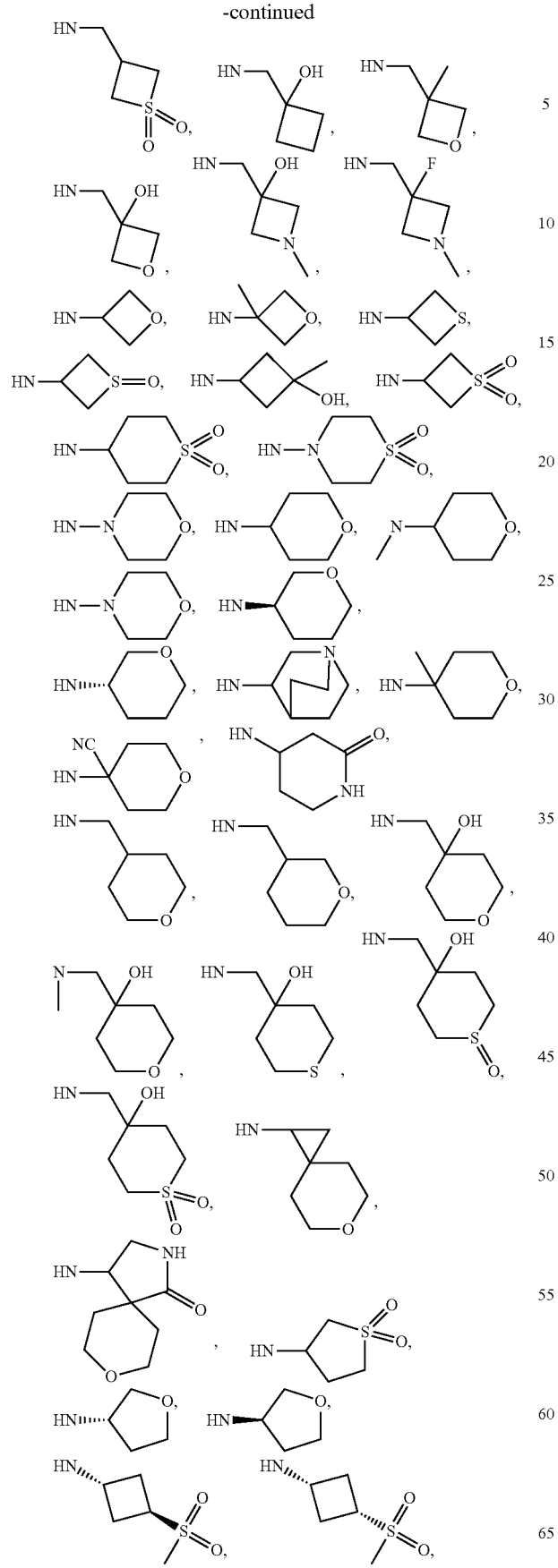
-continued
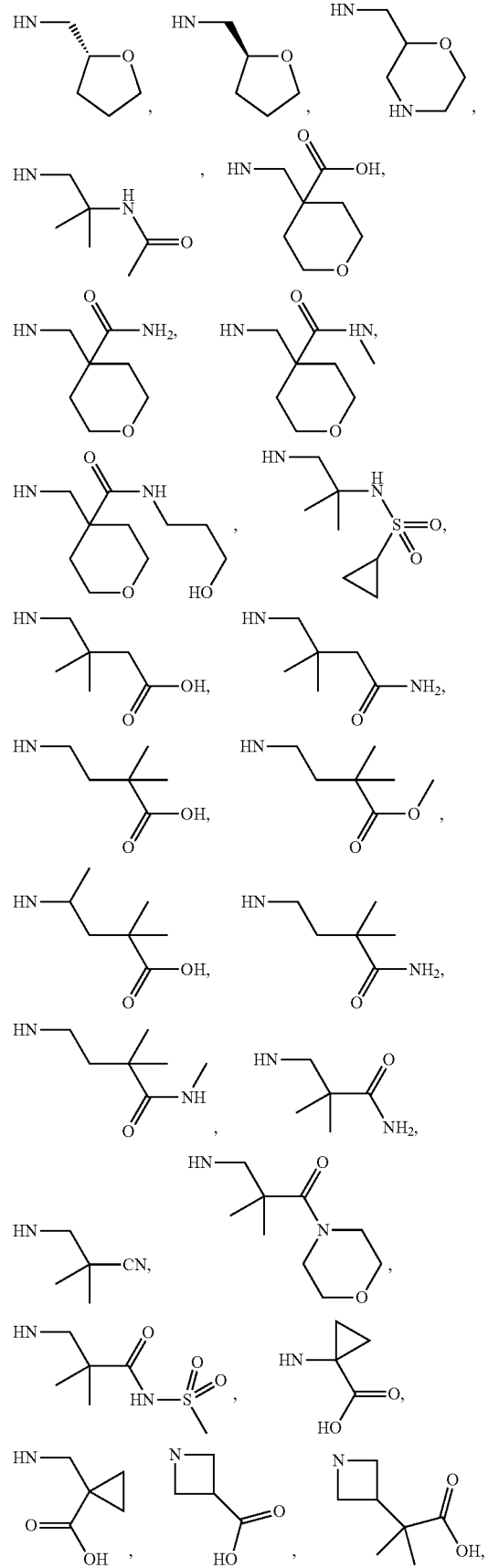

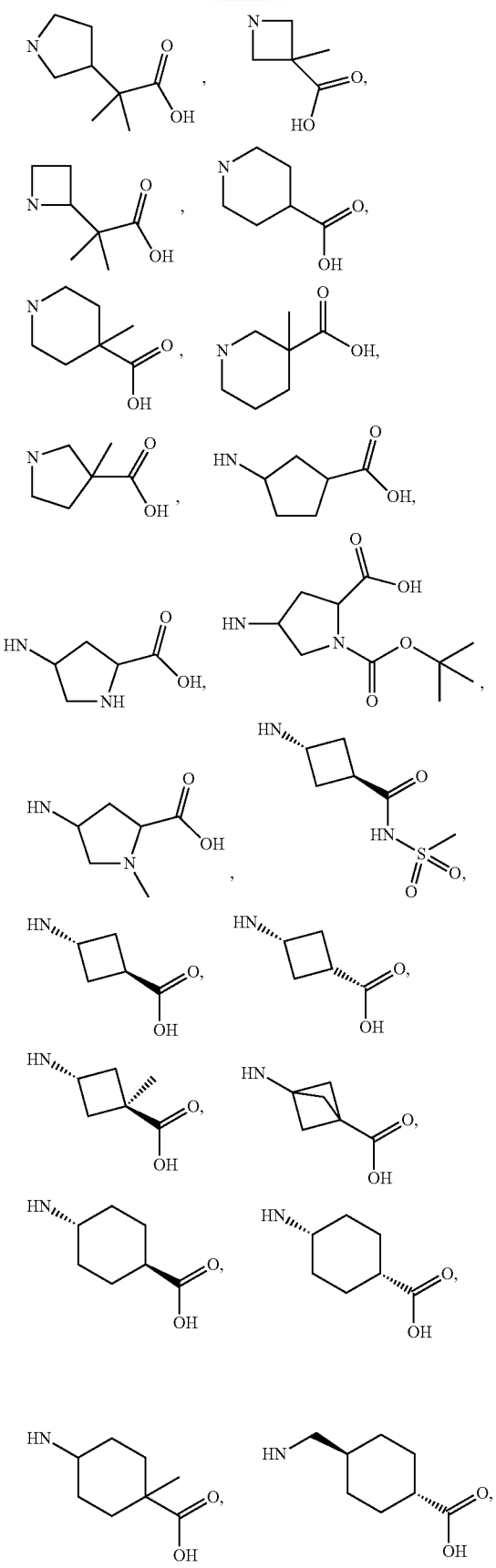
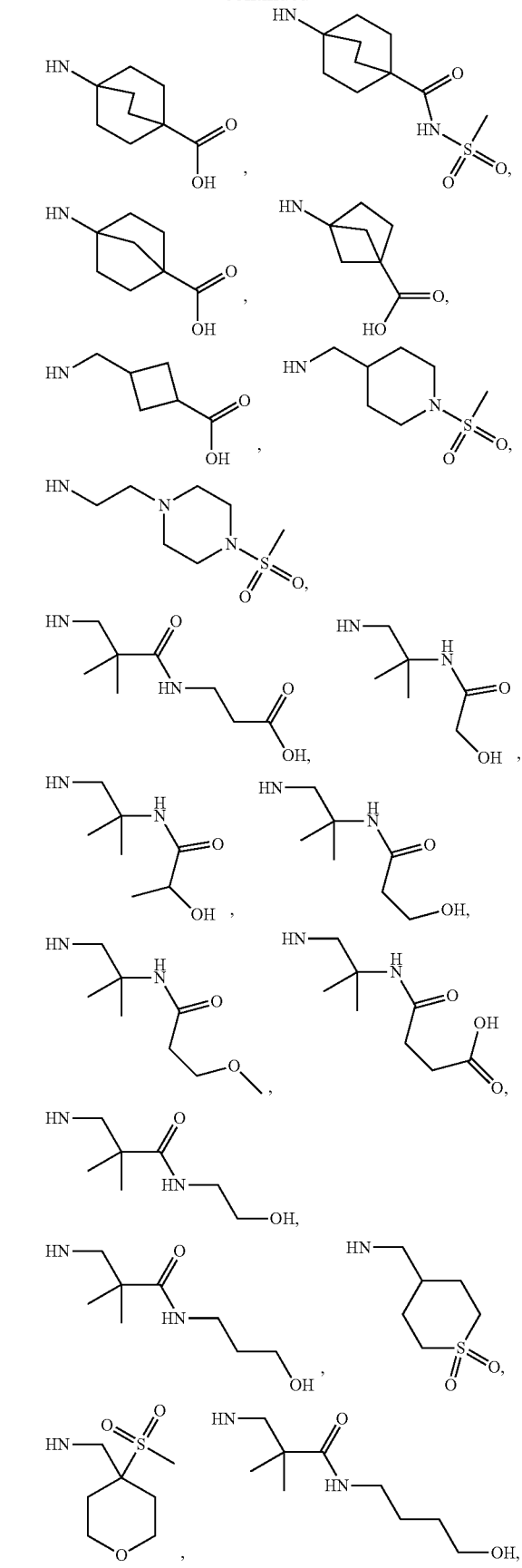

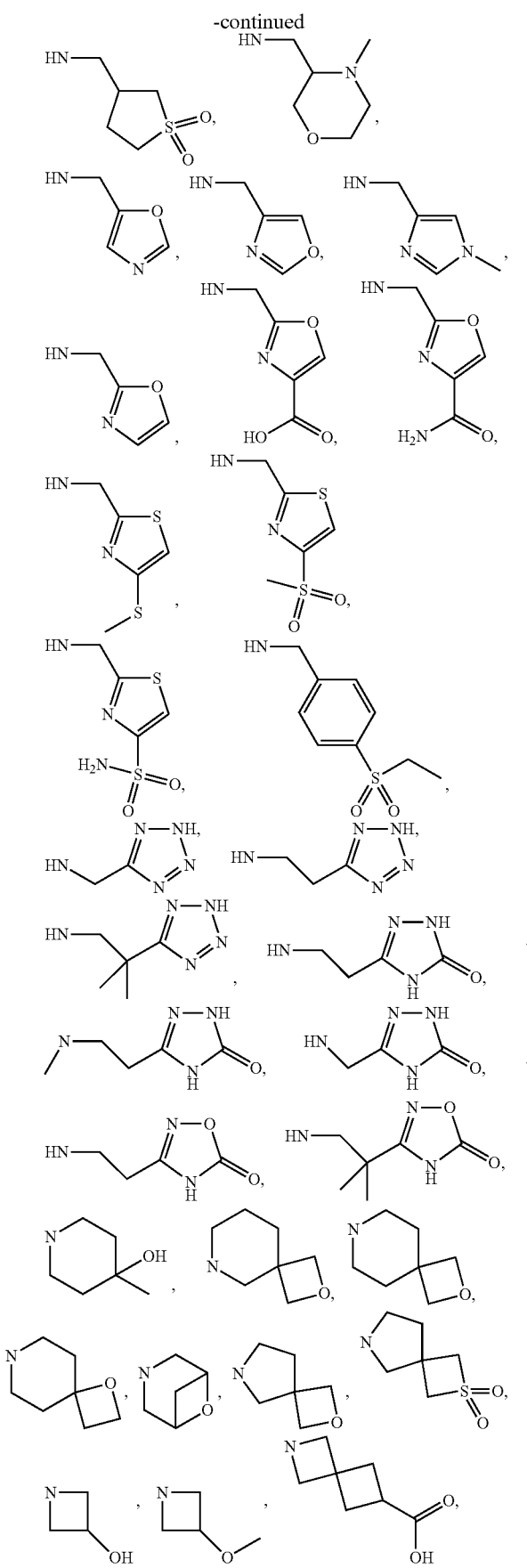

In a more preferred embodiment in combination with any of the above or below embodiments of the first alternative $NR^{201}R^{202}$ is selected from

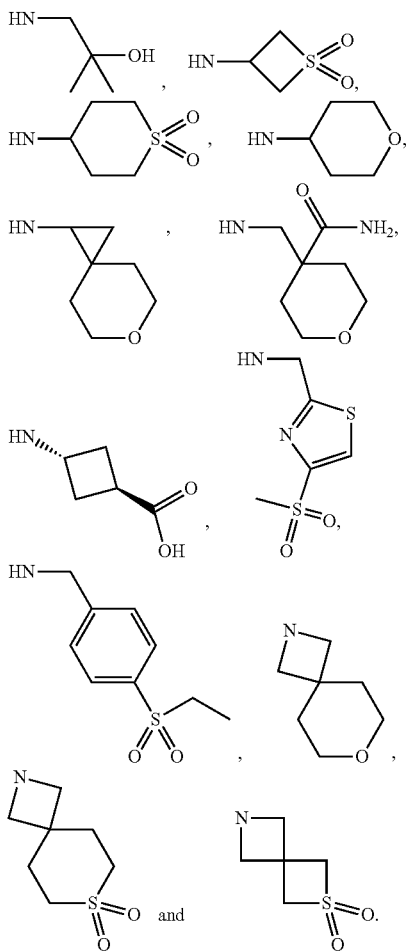

In an even more preferred embodiment in combination with any of the above or below embodiments of the first alternative $NR^{201}R^{202}$ is selected from

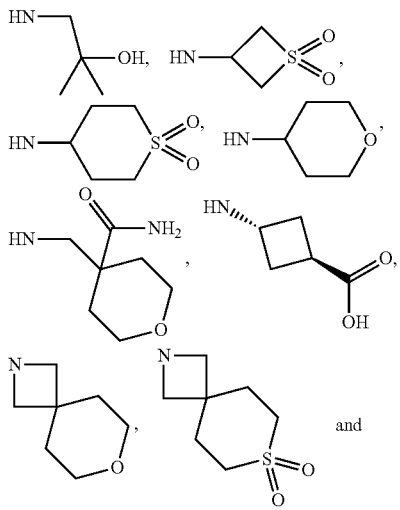

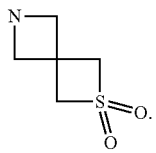

In another preferred embodiment in combination with any of the above or below embodiments of the first alternative $R^{204}$ is

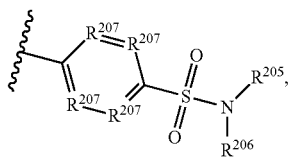

wherein
$R^{205}$ and $R^{206}$ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from halogen, CN, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl, $NR^{211}R^{212}$, $CO_2R^{212}$ and $CONR^{211}R^{212}$;
and optionally wherein $R^{205}$ and $R^{206}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;
$R^{207}$ is independently selected from N and $CR^{208}$; or
two adjacent $R^{207}$ form a 5- or 6-membered unsaturated or partially saturated ring containing carbon atoms and optionally containing 1 or 2 heteroatoms selected from O, S or N, wherein the ring is unsubstituted or substituted with 1 to 4 substitutents independently selected from halogen, OH, oxo, $C_{1-4}$-alkyl and fluoro-$C_{1-4}$-alkyl;
$R^{208}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, $C_{3-10}$-cycloalkyl,
wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl.

In a more preferred embodiment in combination with any of the above or below embodiments of the first alternative $R^{204}$ is

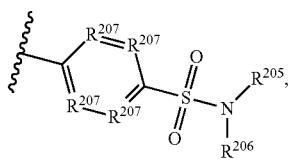

wherein all $R^{207}$ are $CR^{208}$ or one $R^{207}$ is N and the three other $R^{207}$ are $CR^{208}$; or wherein

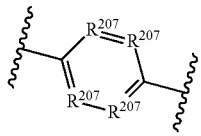

is selected from

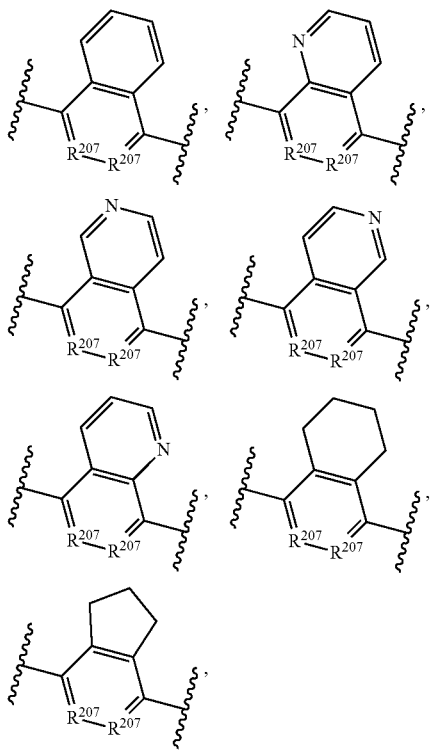

wherein the additional ring is unsubstituted or substituted with 1 to 4 substitutents independently selected from halogen, OH, oxo, $C_{1-4}$-alkyl and fluoro-$C_{1-4}$-alkyl.

In an even more preferred embodiment in combination with any of the above or below embodiments of the first alternative $R^{204}$ is

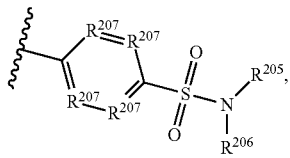

wherein all $R^{207}$ are $CR^{208}$ or one $R^{207}$ is N and the three other $R^{207}$ are $CR^{208}$; and
wherein one $R^{208}$ is independently selected from or two adjacent $R^{208}$ are independently selected from fluoro, chloro, methyl, $CHF_2$, $CF_3$, $CMe_2OH$, $OCHF_2$ and $OCF_3$ while the remaining $R^{208}$ residues are hydrogen; or wherein

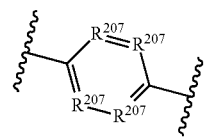

is selected from

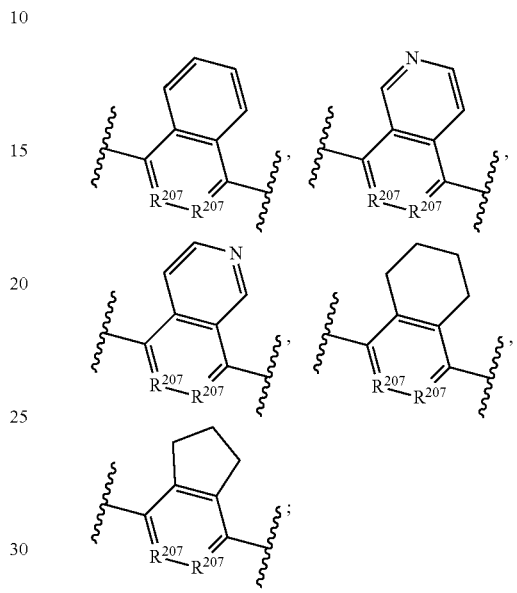

and
wherein both $R^{207}$ are $CR^{208}$ or one $R^{207}$ is N and the other is $CR^{208}$; and
$R^{208}$ is independently selected from H, fluoro, chloro, $CH_3$ and $CF_3$.

In an alternative preferred embodiment in combination with any of the above or below embodiments of the first alternative $R^{204}$ is selected from

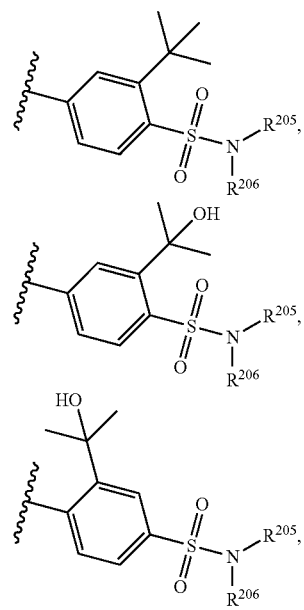

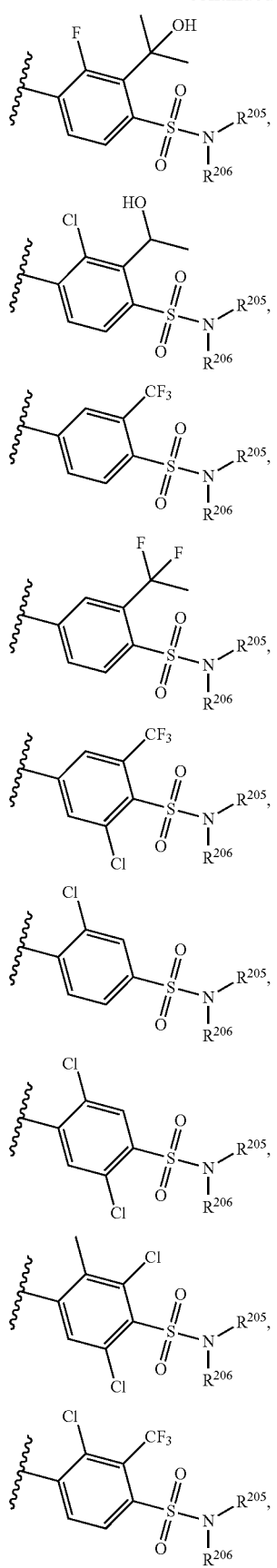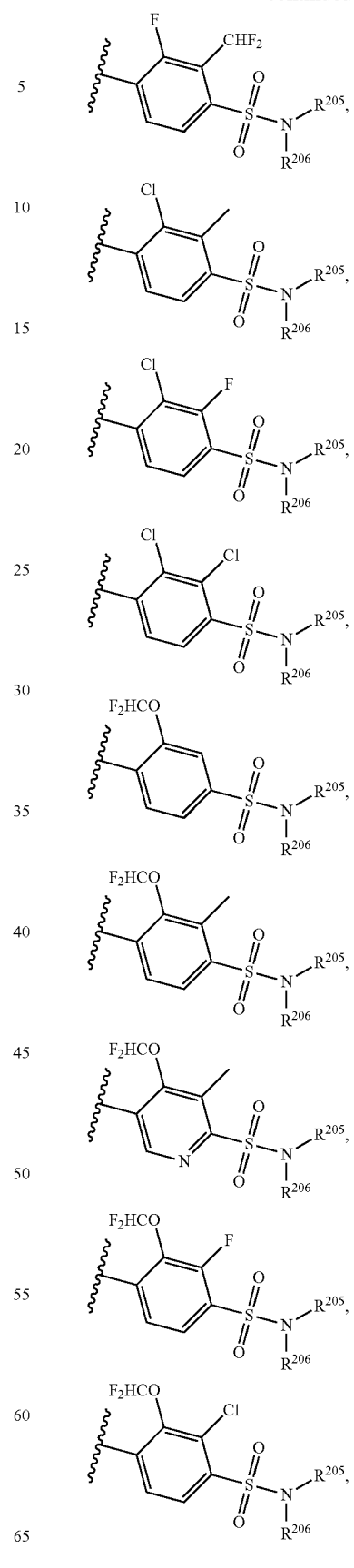

-continued
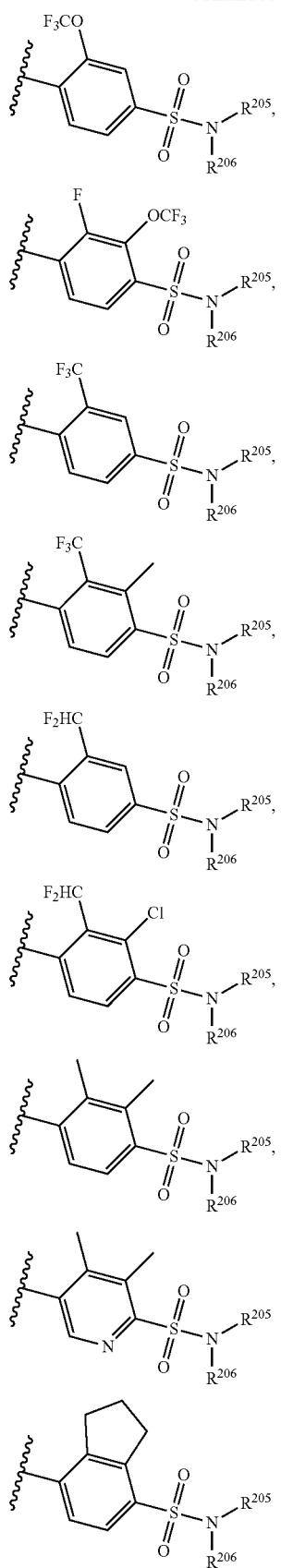
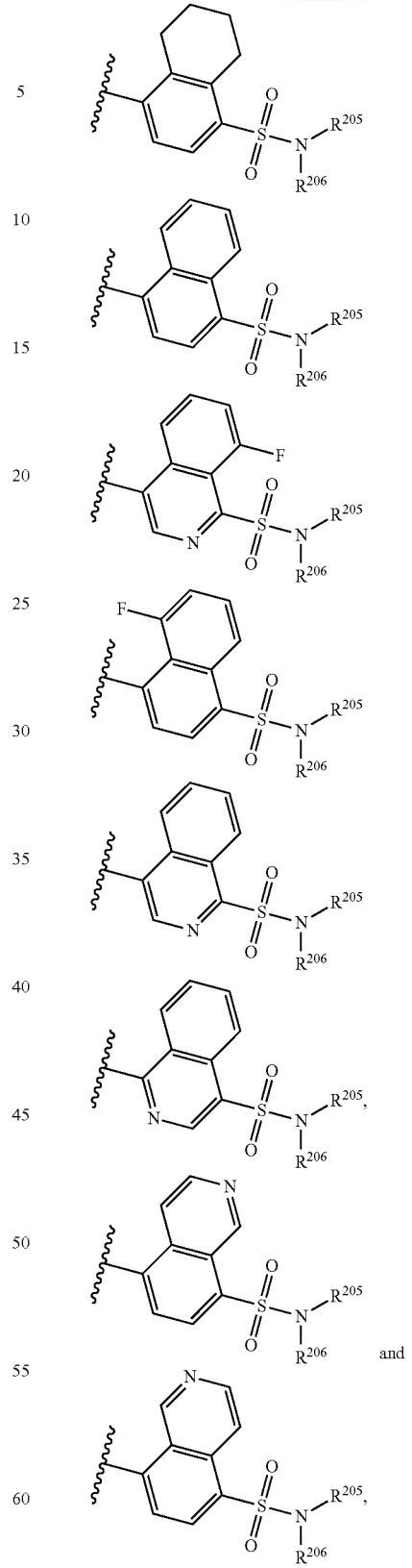
wherein
R²⁰⁵ and R²⁰⁶ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cycloalkyl, heterocycloalkyl, aryl and heteroaryl are unsubstituted or substituted with 1 to 6 substituents independently selected from halogen, CN, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl, $NR^{211}R^{212}$, $CO_2R^{212}$ and $CONR^{211}R^{212}$;

and optionally wherein $R^{205}$ and $R^{206}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl.

More preferably in combination with any of the above or below embodiments of the first alternative, $R^{204}$ is selected from

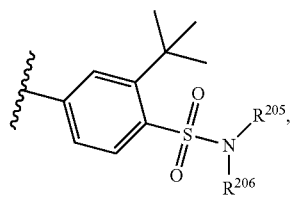

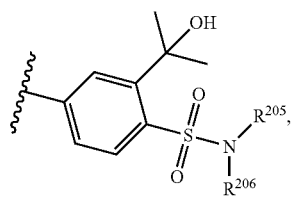

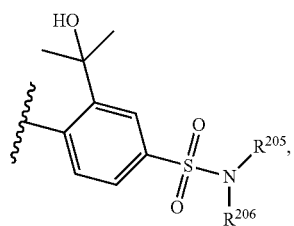

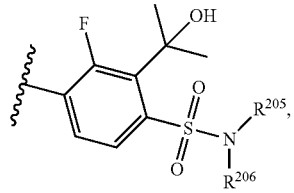

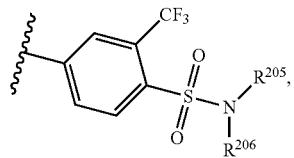

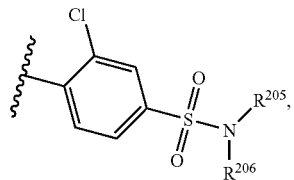

-continued

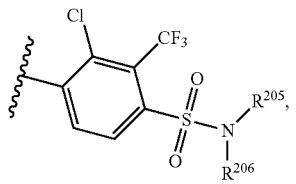

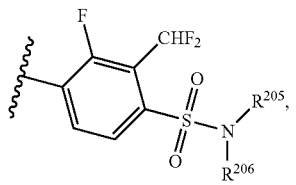

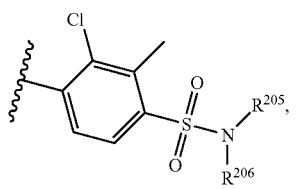

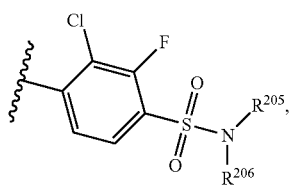

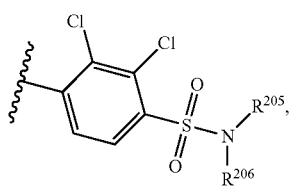

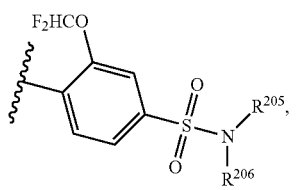

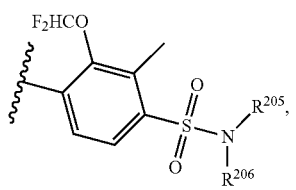

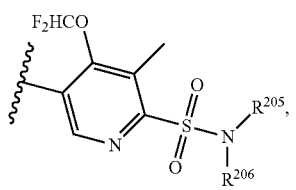

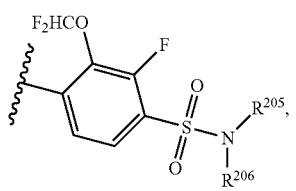

-continued
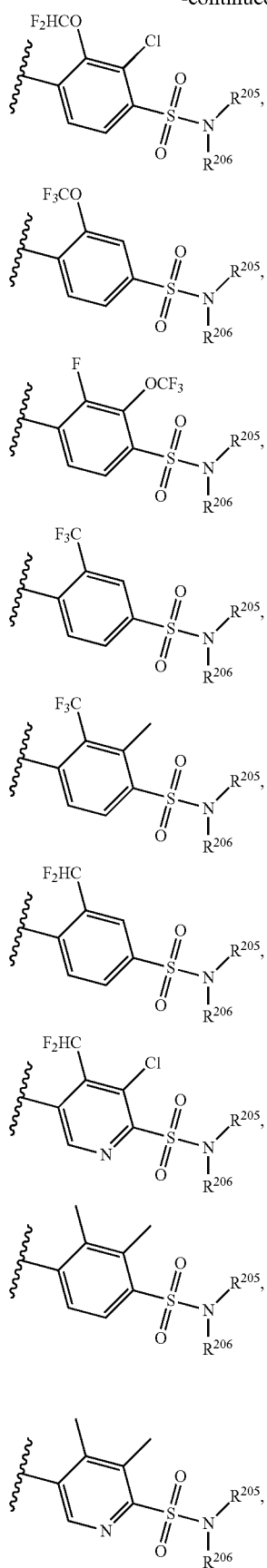
-continued
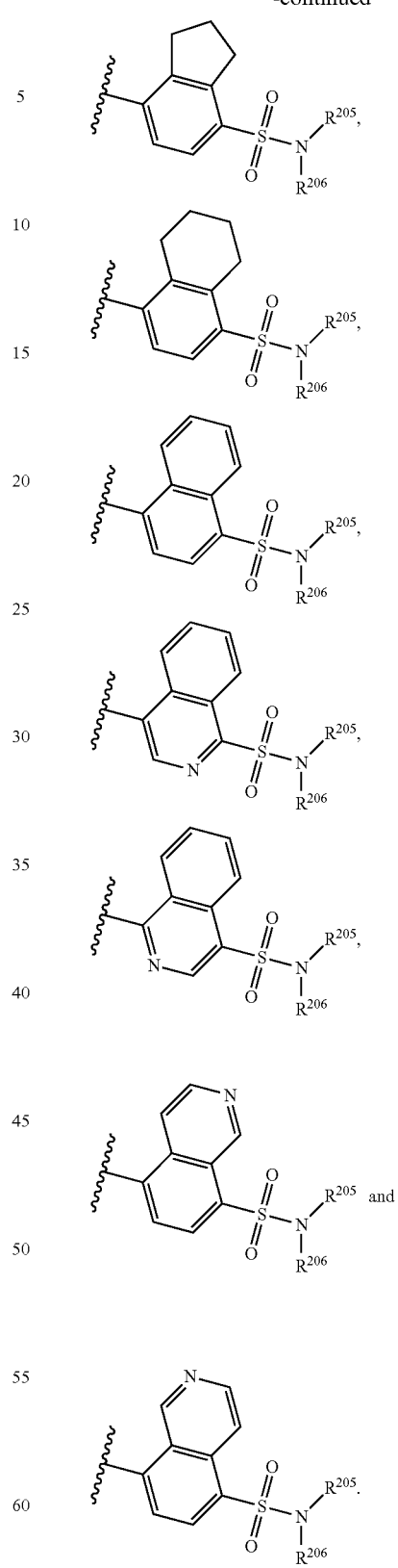
Even more preferably in combination with any of the above or below embodiments of the first alternative, $R^{204}$ is selected from

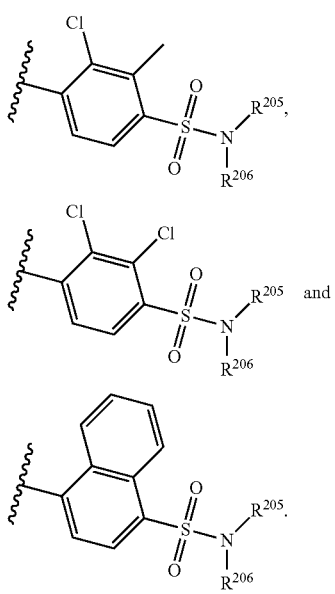

In another preferred embodiment in combination with any of the above or below embodiments of the first alternative $NR^{205}R^{206}$ is selected from

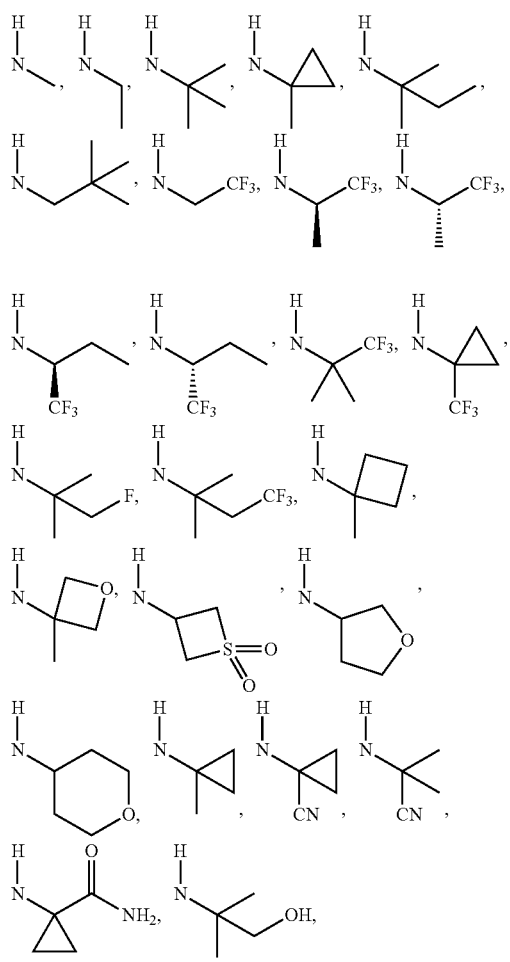

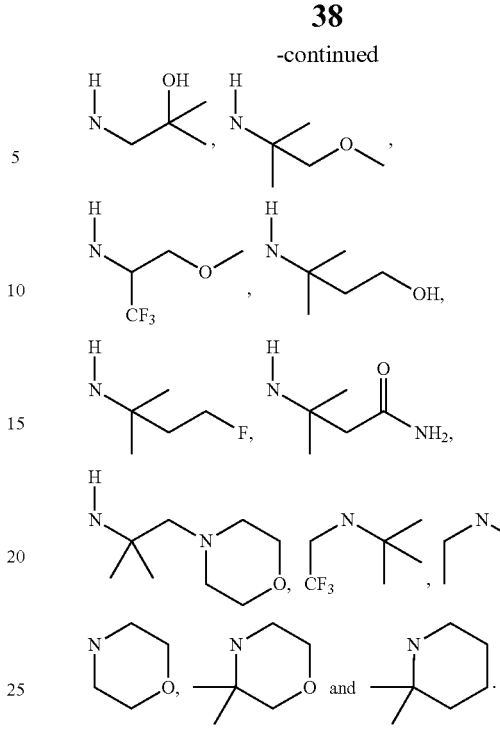

In a more preferred embodiment in combination with any of the above or below embodiments of the first alternative $NR^{205}R^{206}$ is preferably

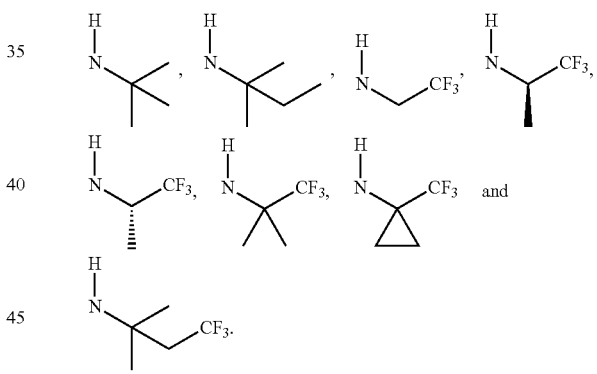

In another preferred embodiment in combination with any of the above or below embodiments of the first alternative $R^{204}$ is selected from

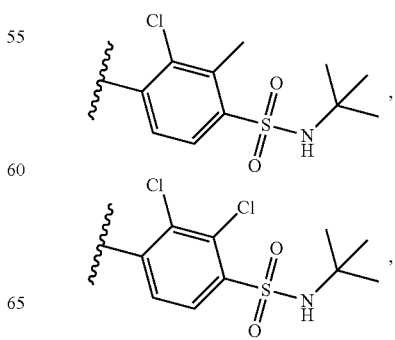

-continued

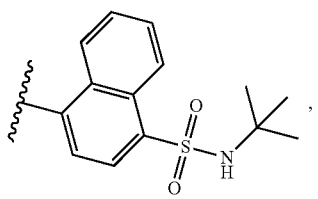
,

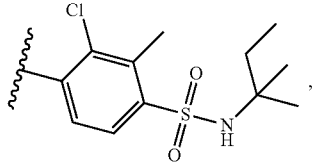
,

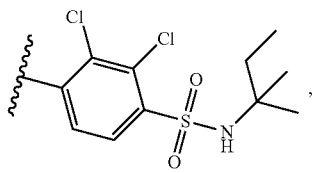
,

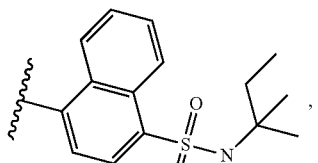
,

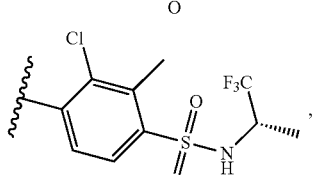
,

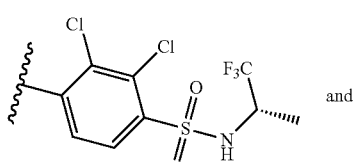 and

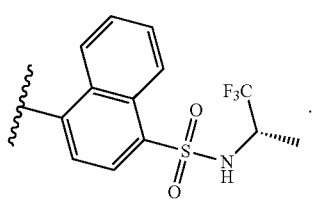
.

In a more preferred embodiment in combination with any of the above or below embodiments of the first alternative $R^{204}$ is selected from

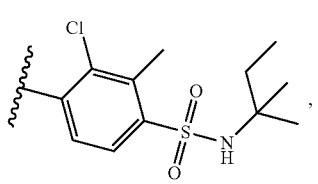
,

-continued

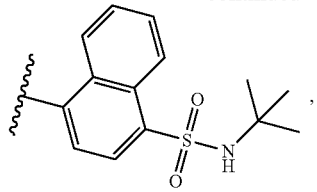
,

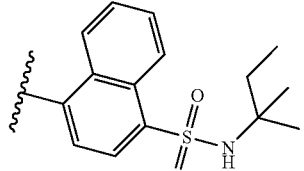 and

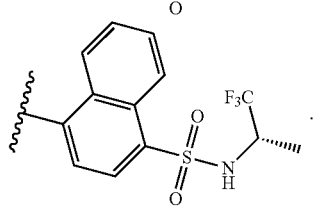
.

In another preferred embodiment in combination with any of the above or below embodiments of the first alternative $R^{203}$ is selected from $C_{1-10}$-alkyl, fluoro-$C_{1-10}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(6- to 10-membered aryl), $C_{0-6}$-alkylene-(5- to 10-membered heteroaryl), wherein alkyl, alkylene, cycloalkyl, heterocycloalkyl, aryl and heteroaryl is unsubstituted or substituted with 1 to 6 substituents independently selected from oxo, halogen, CN, $C_{1-6}$-alkyl, halo-$C_{1-6}$-alkyl, $C_{3-6}$-cycloalkyl, $C_{3-6}$-heterocycloalkyl, $OR^{212}$, $CO_2R^{212}$, $CONR^{212}R^{212}$, $COR^{212}$; and wherein optionally one $CH_2$ unit in alkyl or alkylene can be replaced by O, $SO_x$, NH or $N(C_{1-3}$-alkyl).

In an equally preferred embodiment in combination with any of the above or below embodiments of the first alternative, $R^{203}$ is selected from $C_{1-10}$-alkyl, fluoro-$C_{1-10}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(5- to 10-membered heteroaryl), wherein alkyl, alkylene, cycloalkyl, heterocycloalkyl and heteroaryl is unsubstituted or substituted with 1 to 6 substituents independently selected from oxo, halogen, CN, $C_{1-6}$-alkyl, halo-$C_{1-6}$-alkyl, $C_{3-6}$-cycloalkyl, $C_{3-6}$-heterocycloalkyl, $OR^{212}$, $CO_2R^{212}$, $CONR^{212}R^{212}$, $COR^{212}$; and wherein optionally one $CH_2$ unit in alkyl or alkylene can be replaced by O, $SO_x$, NH or $N(C_{1-3}$-alkyl).

In a more preferred embodiment in combination with any of the above or below embodiments of the first alternative, $R^{203}$ is selected from $C_{1-10}$-alkyl, fluoro-$C_{1-10}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents independently selected from oxo, halogen, CN, $C_{1-6}$-alkyl, halo-$C_{1-6}$-alkyl, $C_{3-6}$-cycloalkyl, $C_{3-6}$-heterocycloalkyl, $OR^{212}$, $CO_2R^{212}$, $CONR^{212}R^{212}$, $COR^{212}$; and wherein optionally one $CH_2$ unit in alkyl or alkylene can be replaced by O, $SO_x$, NH or $N(C_{1-3}$-alkyl).

In a more preferred embodiment in combination with any of the above or below embodiments of the first alternative $R^{203}$ is selected from $C_{1-8}$-alkyl, fluoro-$C_{1-8}$-alkyl, $C_{0-2}$- alkylene-$C_{3-8}$-cycloalkyl, $C_{0-2}$-alkylene-$C_{3-8}$-heterocycloalkyl, $C_{0-2}$-alkylene-(6- to 10-membered aryl), $C_{0-2}$-alkylene-(5- to 10-membered heteroaryl),
  wherein alkyl, alkylene, cycloalkyl, heterocycloalkyl, aryl and heteroaryl is unsubstituted or substituted with 1 to 6 substituents independently selected from oxo, fluoro, chloro, CN, $CONH_2$, $C_{1-3}$-alkyl, fluoro-$C_{1-3}$-alkyl, $C_{3-6}$-cycloalkyl, $C_{3-6}$-heterocycloalkyl and $OC_{1-4}$-alkyl.

In a more preferred embodiment in combination with any of the above or below embodiments of the first alternative $R^{203}$ is selected from $C_{1-6}$-alkyl, fluoro-$C_{1-6}$-alkyl, $C_{3-8}$-cycloalkyl, $C_{3-8}$-heterocycloalkyl, 6-membered aryl, 6-membered heteroaryl, $CH_2$-(6-membered aryl), $CH_2$-(6-membered heteroaryl), CO-(6-membered aryl), CO-(6-membered heteroaryl) and CO—$NR^aR^b$ (wherein $R^aR^b$ form a 4- to 8-membered saturated heterocycloalkyl),
  wherein cycloalkyl and heterocycloalkyl is unsubstituted or optionally substituted with 1 to 4 substituents independently selected from oxo, $C_{1-3}$-alkyl, fluoro-$C_{1-3}$-alkyl and $C_{3-8}$-cycloalkyl; and
  wherein aryl and heteroaryl is optionally substituted with 1 to 3 substituents independently selected from fluoro, chloro, CN, $C_{1-3}$-alkyl and fluoro-$C_{1-3}$-alkyl.

In a more preferred embodiment in combination with any of the above or below embodiments of the first alternative $R^{203}$ is selected from $CHF_2$, $CH_2CH_3$, $CH_2CH_2CH_3$, $CMe_3$, $CH_2OCMe_3$,

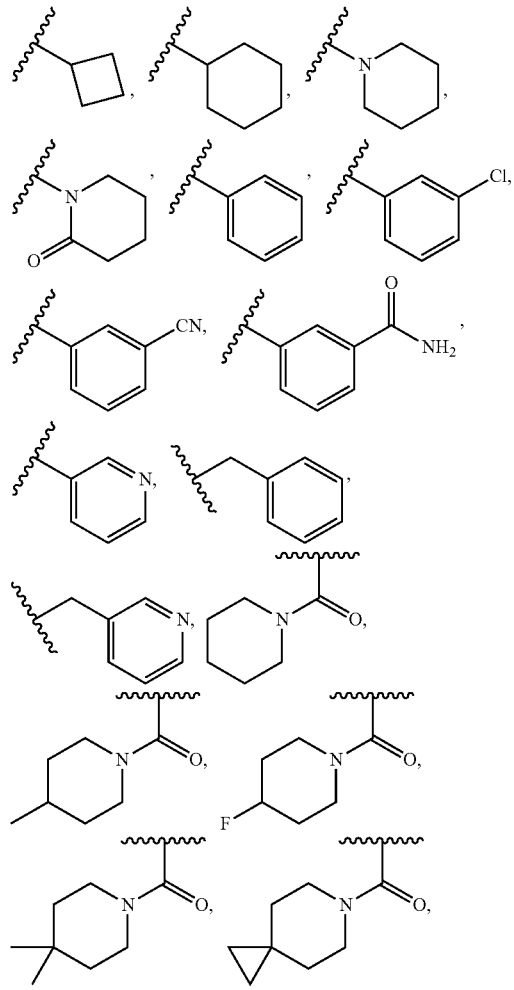

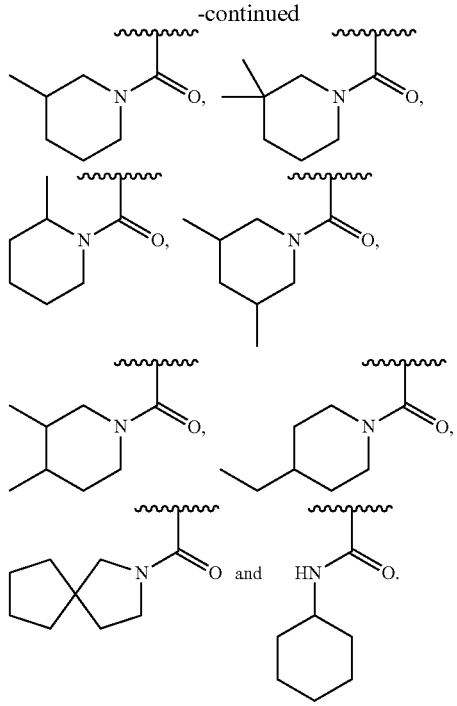

In another preferred embodiment in combination with any of the above or below embodiments of the first alternative the compound is represented by a Formula selected from

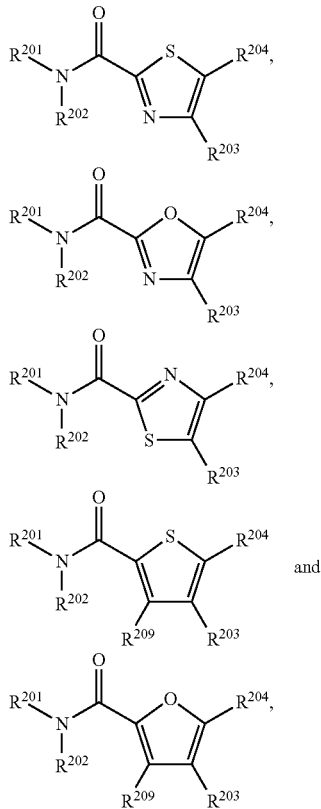

wherein $R^{209}$ is selected from H, fluoro, chloro and methyl.

In a more preferred embodiment in combination with any of the above or below embodiments of the first alternative the compound is represented by a Formula selected from

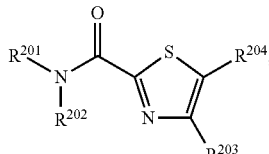

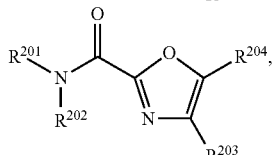

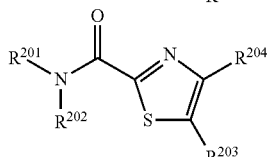 and

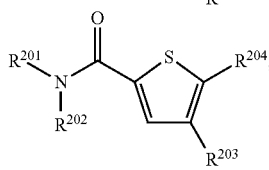

even more preferably by Formula

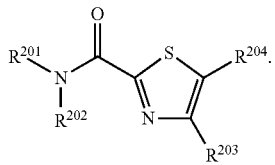

The invention also provides the compound of the first alternative of the invention for use as a medicament.

Also provided is the compound of the first alternative of the invention for use in the treatment or prophylaxis of a disease or disorder associated with the inhibition or activation of the RORγ receptor.

Also provided is the compound of the first alternative of the invention in treating RORγ mediated inflammatory and autoimmune diseases. Preferably, the disease is selected from the group consisting of rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis.

Also provided is a pharmaceutical composition comprising the compound of the first alternative of the invention and a pharmaceutically acceptable carrier.

In a second alternative, the present invention provides a compound represented by Formula (100) and Formula (100')

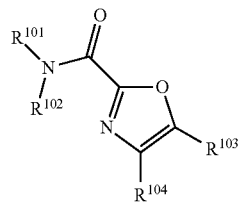

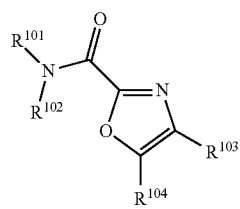

an enantiomer, diastereomer, tautomer, N-oxide, solvate, formulation and pharmaceutically acceptable salt thereof, wherein $R^{101}$ and $R^{102}$ are independently selected from H, $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl), $C_{1-10}$-alkylene-(6-membered heteroaryl), $SO_2$—$C_{1-10}$-alkyl, wherein alkyl, alkenyl, alkynyl, alkylene, cycloalkyl, heterocycloalkyl, aryl and heteroaryl is unsubstituted or substituted with 1 to 7 substituents independently selected from oxo, CN, $OR^{111}$, O—$C_{2-6}$-alkylene-$OR^{111}$, $C_{1-6}$-alkyl, halo-$C_{1-6}$-alkyl, halogen, $CO_2R^{111}$, $CONR^{111}R^{112}$, $CONR^{111}SO_2R^{111}$, $COR^{111}$, $SO_xR^{111}$, $SO_3H$, $SO_2NR^{111}R^{112}$, $NR^{111}COR^{111}$, $NR^{111}SO_2R^{111}$, $NR^{111}$—CO—$NR^{111}R^{112}$, $NR^{111}$—$SO_2$—$NR^{111}R^{112}$, $C_{3-10}$-cycloalkyl, O—$C_{3-10}$-cycloalkyl, $C_{3-10}$-heterocycloalkyl, O—$C_{3-10}$-heterocycloalkyl and $NR^{111}R^{112}$;

or $R^{101}$ and $R^{102}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{111}$, $SO_xR^{111}$, $SO_3H$, $NR^{111}SO_2R^{111}$, $SO_2NR^{111}R^{112}$, $C_{0-6}$-alkylene-$CO_2R^{111}$, $CONR^{111}R^{112}$, $CONR^{111}SO_2R^{111}$, $COR^{111}$, $NR^{111}$—CO—$R^{111}$, $NR^{111}$—CO—$NR^{111}R^{112}$, $NR^{111}$—$SO_2$—$NR^{111}R^{112}$, $NR^{111}R^{112}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substituents independently selected from halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;

$R^{103}$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl is optionally substituted with 1 to 5 substituents independently selected from halogen, $C_{1-6}$-alkyl, $C_{1-6}$-alkenyl, $C_{1-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered heteroaryl), $C_{1-6}$-alkylene-O—$R^{131}$, $C_{0-6}$-alkylene-CN, $C_{0-6}$-alkylene-$N(R^{131})_2$, O—$C_{3-10}$-cycloalkyl, O—$C_{1-6}$-alkylene-O—$R^{131}$, O—$C_{3-10}$-heterocycloalkyl, $C_{0-6}$-alkylene-$COOR^{131}$, $C_{0-6}$-alkylene-$C(O)R^{131}$, $C_{0-6}$-alkylene-$C(O)N(R^{131})_2$, $C_{0-6}$-alkylene-$N(R^{131})C(O)R^{131}$, $C_{0-6}$-alkylene-SO—$R^{131}$, $C_{0-6}$-alkylene-$SO_2$—$R^{131}$, $C_{0-6}$-alkylene-$SO_2$—$N(R^{131})_2$, $C_{0-6}$-alkylene-$N(R^{131})SO_2$—$R^{131}$, $C_{0-6}$-alkylene-$SO_2$—$C_{3-10}$-heterocycloalkyl and $C_{0-6}$-alkylene-$SO_2$—$C_{3-10}$-heterocycloalkyl, wherein alkylene, cycloalkyl, heterocycloalkyl and the 5- or 6-membered heteroaryl is optionally substituted by 1 to 4 substituents independently selected from the group consisting of halogen, CN, $C_{1-3}$-alkyl, halo-$C_{1-3}$-alkyl, OH, oxo, =N—$OR^{132}$, O—$C_{1-3}$-alkyl and O-halo-$C_{1-3}$-alkyl, or wherein two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 7 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{132}$, OH, O—$C_{1-6}$-alkyl and O-halo-$C_{1-6}$-alkyl;

$R^{104}$ is selected from $(CR^{108}R^{109})R^{140}$, $(C=O)R^{140}$, $OR^{140}$, $SO_y$—$R^{107}$ and $C_{3-6}$-cycloalkyl, which is spirocyclic fused with $R^{140}$, wherein cycloalkyl is unsubstituted or substituted with 1 to 4 substituents independently selected from the group consisting of F, methyl and $CF_3$;

$R^{107}$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^{108}$ is independently selected from H, F, $C_{1-3}$-alkyl, halo-$C_{1-3}$-alkyl, OH, O—$C_{1-3}$-alkyl and O-halo-$C_{1-3}$-alkyl;

$R^{109}$ is independently selected from H, F, $C_{1-3}$-alkyl and halo-$C_{1-3}$-alkyl;

$R^{111}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, $NH(C_{1-3}$-alkyl), $N(C_{1-3}$-alkyl)$_2$, $C_{3-6}$-heterocycloalkyl, $C_{3-6}$-cycloalkyl and $SO_2$—$C_{1-3}$-alkyl, wherein cycloalkyl and heterocycloalkyl is unsubstituted or substituted with 1 to 3 substituents independently selected from the group consisting of F, OH, oxo, Me and $CF_3$;

$R^{112}$ is independently selected from H, $C_{1-6}$-alkyl, halo-$C_{1-6}$-alkyl and $C_{3-6}$-cycloalkyl;

$R^{131}$ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from halogen, CN, OH, oxo, =N—$OR^{132}$, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

and optionally wherein two $R^{131}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{132}$ is independently selected from H, $C_{1-6}$-alkyl and halo-$C_{1-6}$-alkyl and $C_{3-6}$-cycloalkyl;

$R^{140}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-8}$-cycloalkyl and $C_{3-8}$-heterocycloalkyl;

x and y are independently selected from 0, 1 and 2.

In a further preferred embodiment in combination with any of the above or below embodiments of the second alternative $R^{101}$ is selected from H, $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl), $C_{1-10}$-alkylene-(6-membered heteroaryl), wherein alkyl, alkenyl, alkynyl, alkylene, cycloalkyl, heterocycloalkyl, aryl and heteroaryl is unsubstituted or substituted with 1 to 7 substituents independently selected from oxo, CN, $OR^{111}$, O—$C_{2-6}$-alkylene-$OR^{111}$, $C_{1-6}$-alkyl, halo-$C_{1-6}$-alkyl, halogen, $CO_2R^{111}$, $CONR^{111}R^{112}$, $CONR^{111}SO_2R^{111}$, $COR^{111}$, $SO_xR^{111}$, $SO_3H$, $SO_2NR^{111}R^{112}$, $NR^{1111}COR^{111}$, $NR^{111}SO_2R^{111}$, $NR^{111}$—CO—$NR^{111}R^{112}$, $NR^{111}$—$SO_2$—$NR^{111}R^{112}$, $C_{3-8}$-cycloalkyl, O—$C_{3-8}$-cycloalkyl, $C_{3-8}$-heterocycloalkyl, O—$C_{3-8}$-heterocycloalkyl and $NR^{111}R^{112}$;

$R^{102}$ are selected from the group consisting of H, $C_{1-3}$-alkyl, fluoro-$C_{1-3}$-alkyl and hydroxy-$C_{1-3}$-alkyl, more preferably $R^{102}$ is hydrogen;

or $R^{101}$ and $R^{102}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{111}$, $SO_xR^{111}$, $SO_3H$, $NR^{111}SO_2R^{111}$, $SO_2NR^{111}R^{112}$, $C_{0-6}$-alkylene-$CO_2R^{111}$, $CONR^{111}R^{112}$, $CONR^{111}SO_2R^{111}$, $COR^{111}$, $NR^{111}$—CO—$R^{111}$, $NR^{111}$—CO—$NR^{111}R^{112}$, $NR^{111}$—$SO_2$—$NR^{111}R^{112}$, $NR^{111}R^{112}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substituents independently selected from halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo.

More preferably, $R^{101}$ and $R^{102}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, oxo, $OR^{111}$, $SO_2R^{111}$, $NR^{111}SO_2R^{111}$, $SO_2NR^{111}R^{112}$, $C_{0-6}$-alkylene-$CO_2H$, $CONR^{111}R^{112}$, $COR^{111}$, $NR^{111}R^{112}$, $C_{1-6}$-alkyl, halo-$C_{1-6}$-alkyl, hydroxy-$C_{1-6}$-alkyl, $C_{3-8}$-cycloalkyl and $C_{3-8}$-heterocycloalkyl, wherein cycloalkyl and heterocycloalkyl are unsubstituted or substituted with 1 to 4 substituents independently selected from halogen, $C_{1-3}$-alkyl, halo-$C_{1-3}$-alkyl, $SO_2$—$C_{1-3}$-alkyl, COOH and oxo.

In a preferred embodiment in combination with any of the above or below embodiments of the second alternative $NR^{101}R^{102}$ is selected from NHMe, NHEt, $NH^iPr$, $NH^tBu$, $NHCH_2CONH_2$, $NHCH_2CONMe_2$, $NHCH_2CH_2OH$, NHCH$_2$CH$_2$OMe, NHCH$_2$CH$_2$SO$_2$Me, NHCH$_2$CH$_2$SO$_2$NH$_2$, NH(CH$_2$)$_3$OH, NH(CH$_2$)$_3$OMe, NH(CH$_2$)$_4$OH, NH(CH$_2$)$_4$OMe, NH(CH$_2$)$_5$OH, NH(CH$_2$)$_2$CO$_2$H, NH(CH$_2$)$_3$CO$_2$H, NH(CH$_2$)$_4$CO$_2$H, NH(CH$_2$)$_5$CO$_2$H, NHCH$_2$CH(CF$_3$)OH, NHCH$_2$C(Me)(CF$_3$)OH, NHCH$_2$CMe$_2$OH, NHCH$_2$CH$_2$CMe$_2$OH, NHCH$_2$CMe$_2$NHCH$_2$CF$_3$, NHCH(Me)CMe$_2$OH, NHCH$_2$CMe$_2$OMe, NHCH$_2$CMe$_2$CO$_2$H, NHCH$_2$CMe$_2$CONHMe, NHCH$_2$CMe$_2$CONMe$_2$, NHCH$_2$CMe$_2$NHSO$_2$Me, NH(CH$_2$)$_3$SOMe, NH(CH$_2$)$_5$SO$_2$Me, NH(CH$_2$)$_5$SO$_2$NH$_2$, NH(CH$_2$)$_3$NHSO$_2$Me, NH(CH$_2$)$_2$O(CH$_2$)$_2$OH, NHCH$_2$CHMeOH, NH(CH$_2$)$_5$SOMe, NH(CH$_2$)$_3$SO$_2$Me, NHC(CH$_2$OH)$_3$, NHCH$_2$CH(OH)CH$_2$OH, N(CH$_2$CH$_2$OH)$_2$,

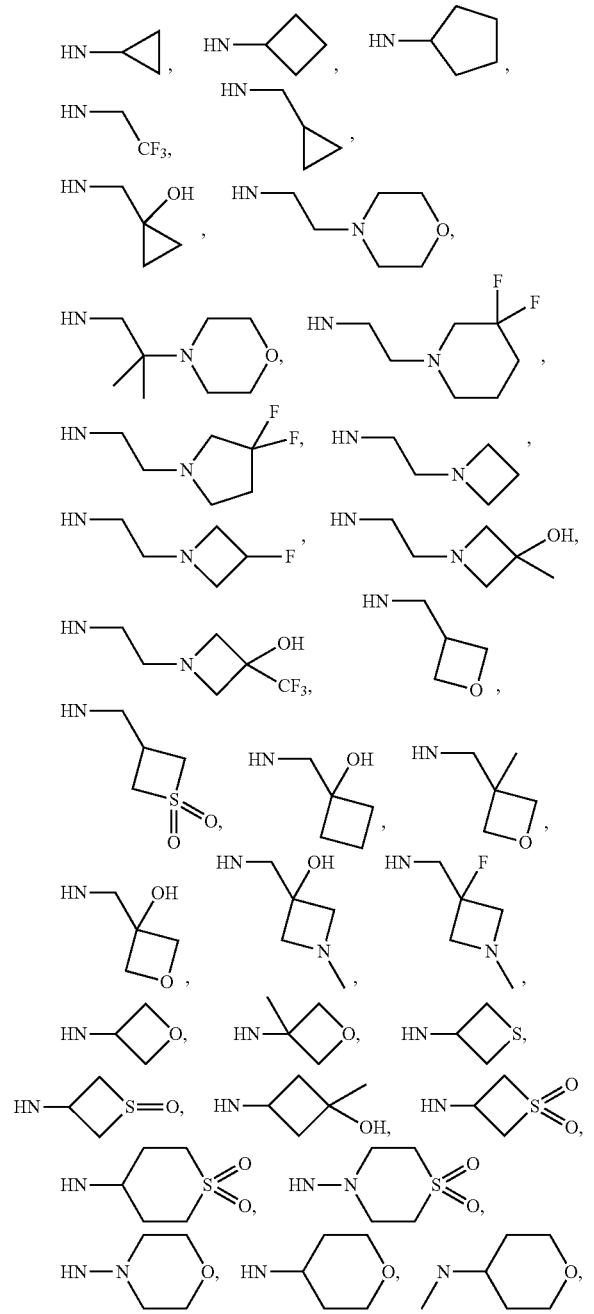

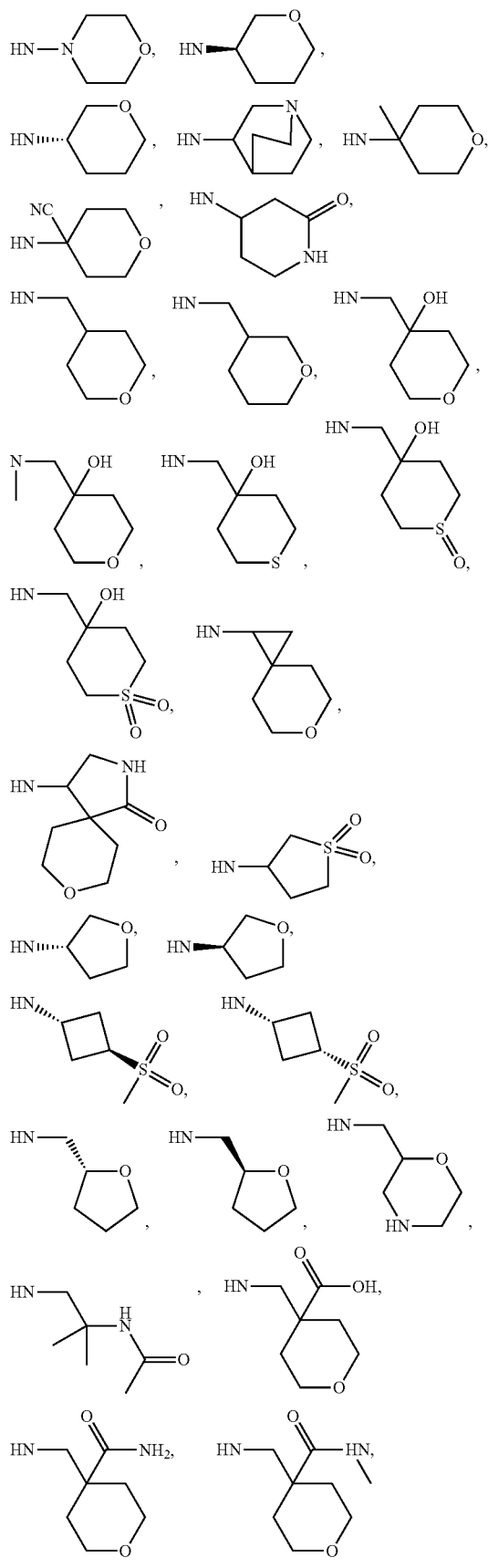

-continued

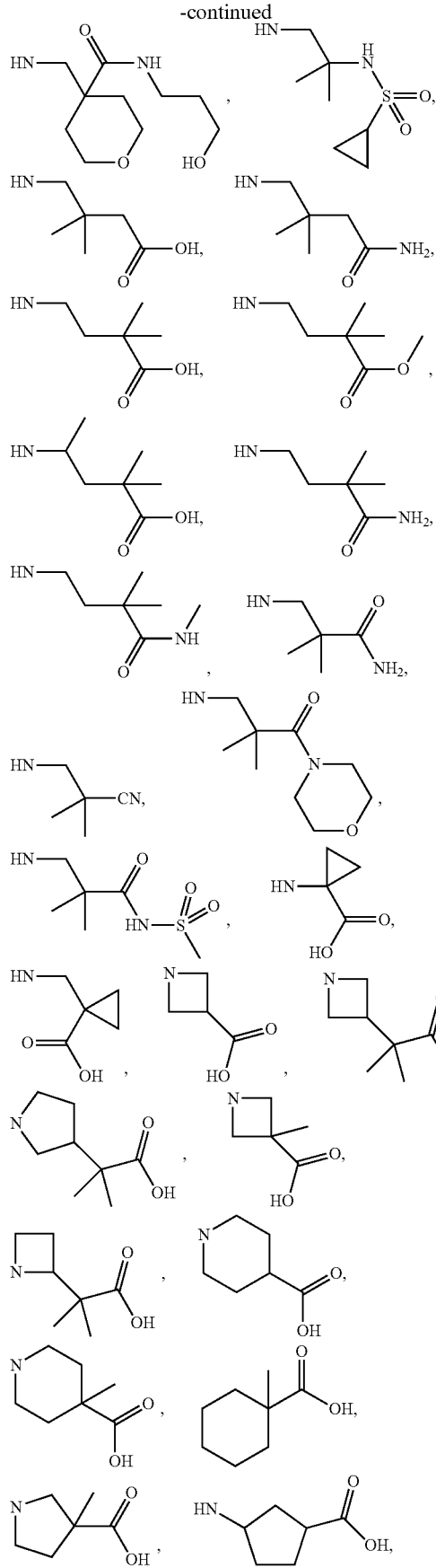
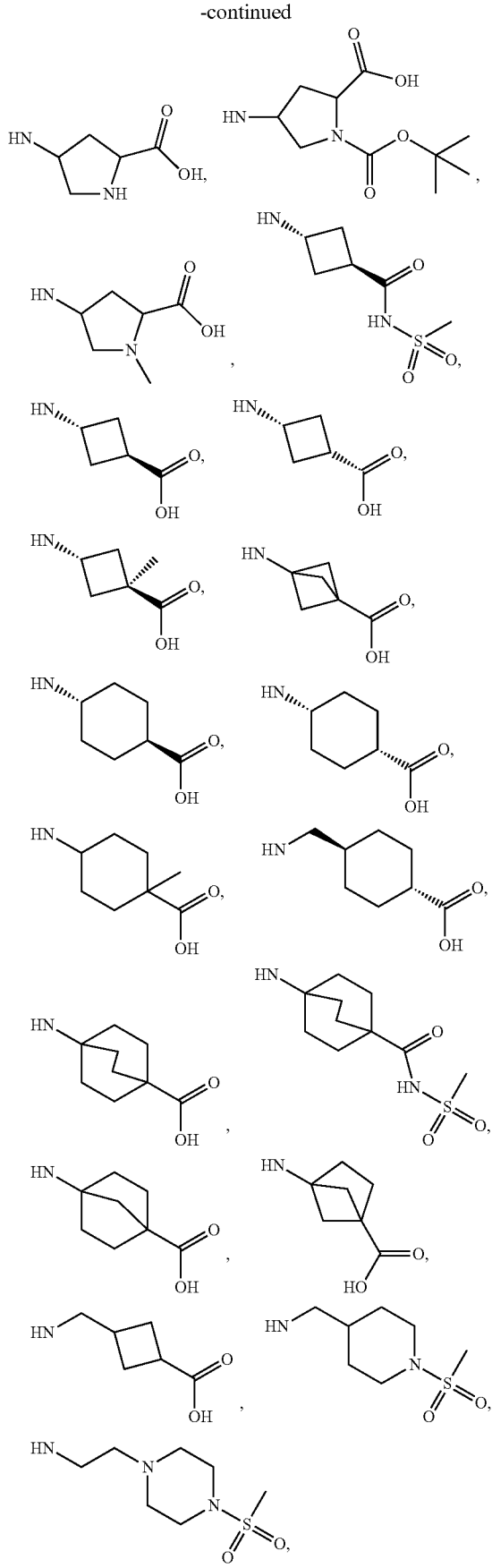

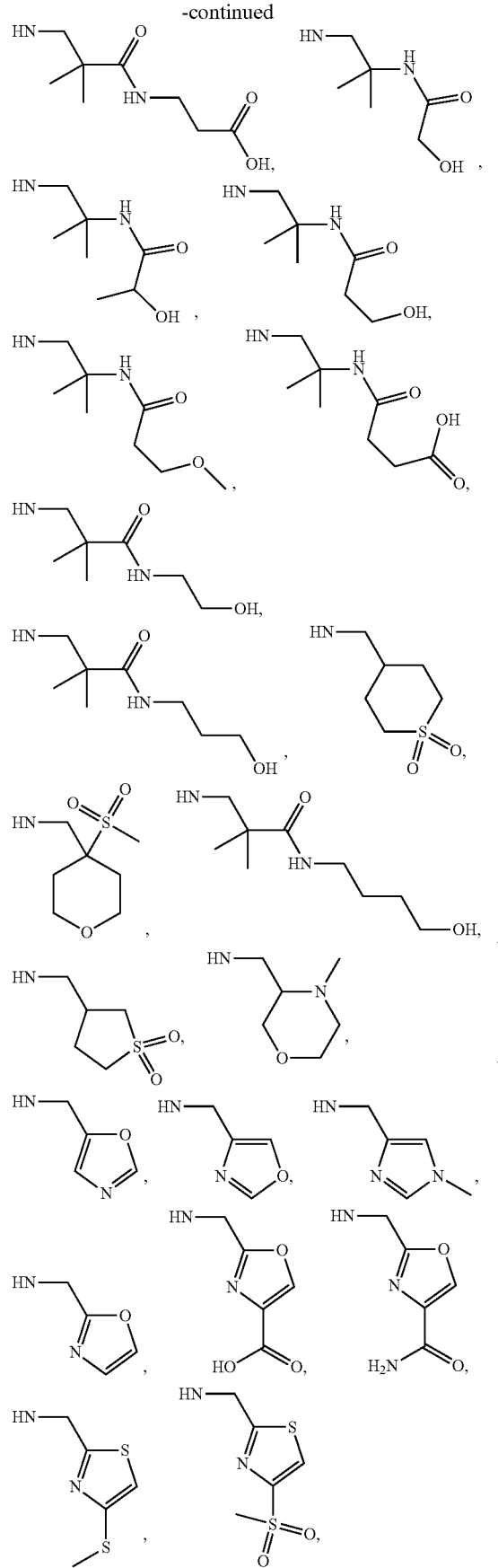
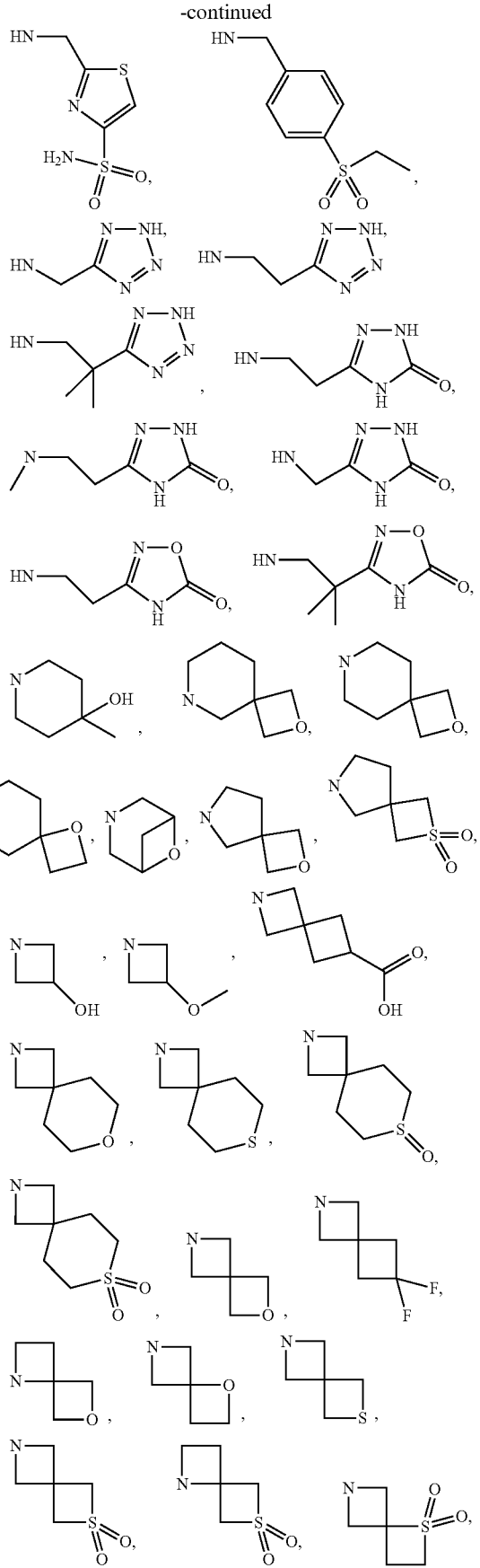

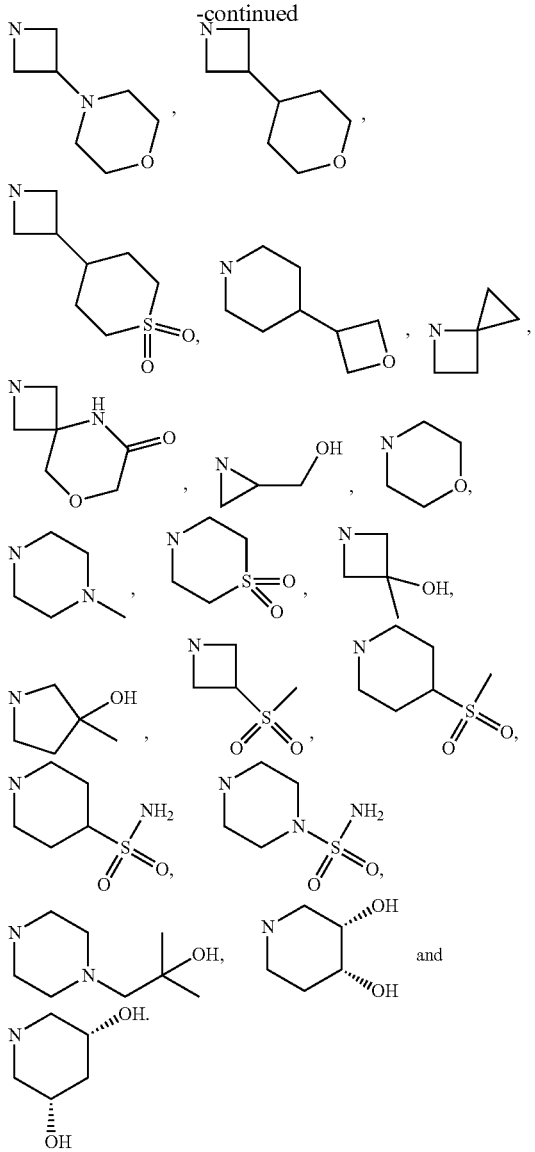
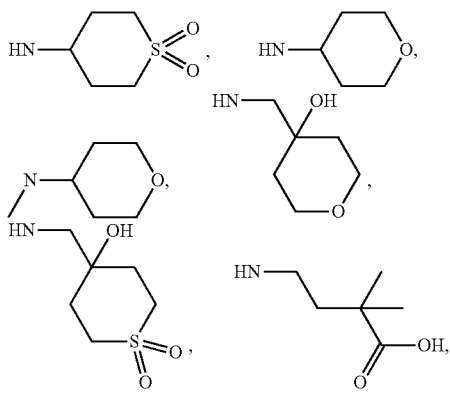
In a more preferred embodiment in combination with any of the above or below embodiments of the second alternative $NR^{101}R^{102}$ is selected from $NHCH_2CMe_2OH$, $NHCH_2CMe_2CO_2H$,
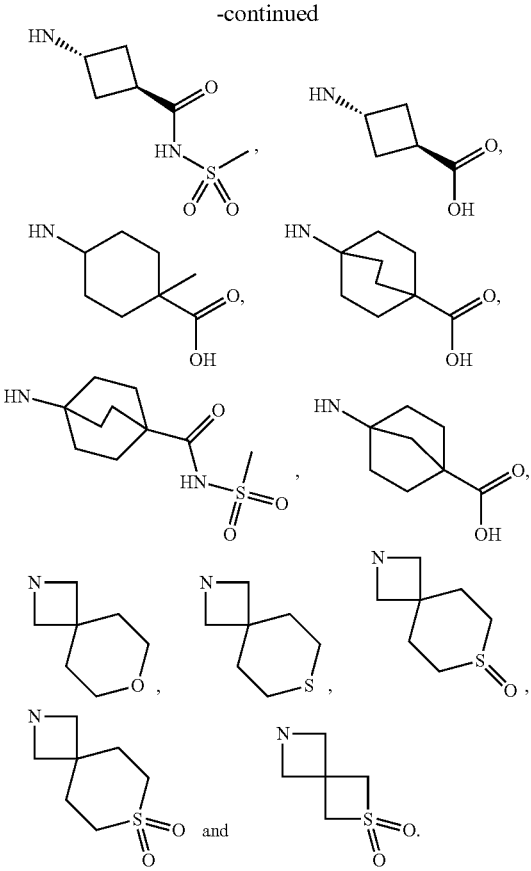
In another preferred embodiment in combination with any of the above or below embodiments of the second alternative $R^{103}$ is selected from
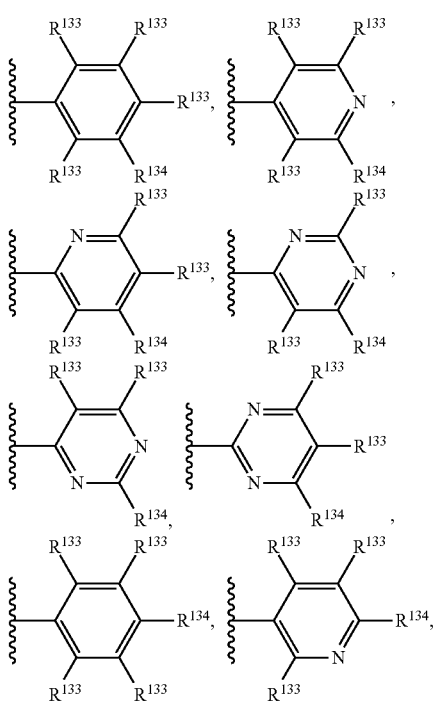

-continued

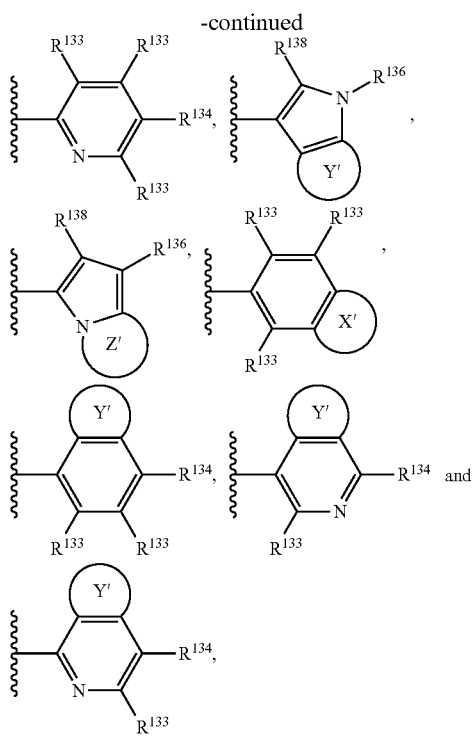

wherein
$R^{133}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl,
    wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;
$R^{134}$ are independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl, $C_{0-6}$-alkylene-$C_{3-10}$-heterocycloalkyl, 5-membered heteroaryl, 6-membered heteroaryl, $C(O)N(R^{137})_2$ and $SO_2N(R^{137})_2$,
    wherein alkylene is unsubstituted or substituted with 1 to 3 substituents selected from F and cycloalkyl, heterocycloalkyl and heteroaryl is unsubstituted or substituted with 1 to 3 substituents independently selected from F, $C_{1-3}$-alkyl, fluoro-$C_{1-3}$-alkyl, OH, O—$C_{1-3}$-alkyl, fluoro-O—$C_{1-3}$-alkyl;
$R^{135}$ is selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{132}$, OH, O—$C_{1-6}$-alkyl and O-halo-$C_{1-6}$-alkyl;
$R^{136}$ is selected from $C_{1-6}$-alkyl, fluoro-$C_{1-6}$-alkyl, $C(O)N(R^{137})_2$, $SO_2N(R^{137})_2$;
$R^{137}$ is independently selected from H, $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl, wherein alkyl and alkylene is unsubstituted or substituted with 1 to 4 substituents selected from halogen, OH, O—$C_{1-3}$-alkyl, CN; and cycloalkyl or heterocycloalkyl is unsubstituted or substituted with 1 to 3 substituents independently selected from F, CN, OH, oxo, $C_{1-3}$-alkyl and fluoro-$C_{1-3}$-alkyl;
or wherein two $R^{137}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, OH, oxo, $C_{1-4}$-alkyl and halo-$C_{1-4}$-alkyl;
$R^{138}$ is selected from H, $C_{1-3}$-alkyl and fluoro-$C_{1-3}$-alkyl;
X' is an annelated saturated heterocycle selected from the group consisting of

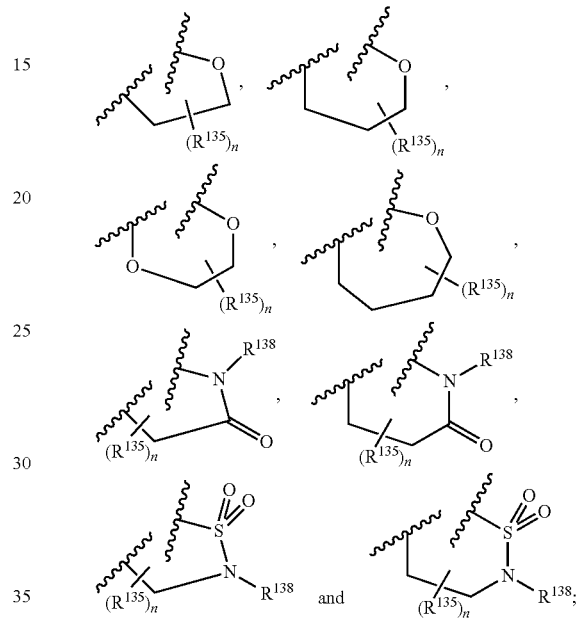

Y' is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, $C_{1-3}$-alkyl and fluoro-$C_{1-3}$-alkyl;
Z' is an annelated 6-membered cycle forming a heteroaryl containing 1 to 2 nitrogen atoms, wherein the heteroaryl is unsubstituted or substituted with 1 to 3 substituents selected from fluoro, $C_{1-3}$-alkyl and fluoro-$C_{1-3}$-alkyl;
n is selected from 1 to 4.

In a more preferred embodiment in combination with any of the above or below embodiments of the second alternative $R^{103}$ is selected from

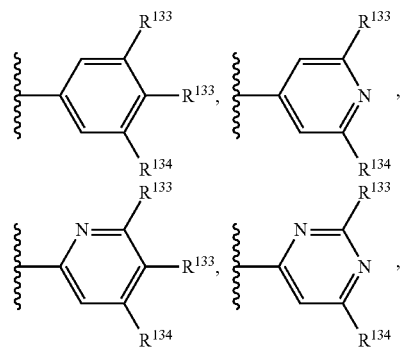

-continued

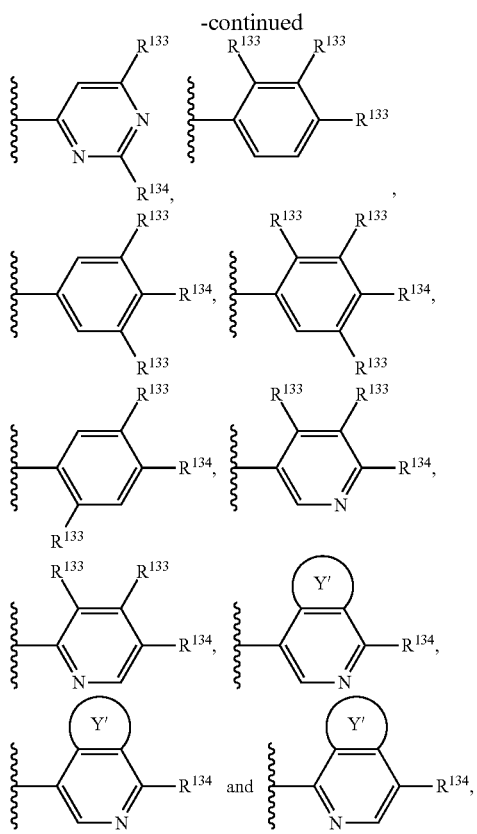

wherein
$R^{133}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl, $C(O)N(R^{137})_2$,
  wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;
$R^{134}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{137})_2$, $SO_2N(R^{137})_2$,
  wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;
$R^{137}$ is independently selected from H, $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl,
  wherein alkyl and alkylene is unsubstituted or substituted with 1 to 4 substituents selected from halogen, OH, O—$C_{1-3}$-alkyl, CN, $CONH_2$; and
  wherein cycloalkyl or heterocycloalkyl is unsubstituted or substituted with 1 to 3 substituents independently selected from F, CN, OH, oxo, O—$C_{1-3}$-alkyl, $C_{1-3}$-alkyl and fluoro-$C_{1-3}$-alkyl;
or wherein two $R^{137}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;
Y' is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl and $CF_3$.

In an even more preferred embodiment in combination with any of the above or below embodiments of the second alternative $R^{103}$ is selected from

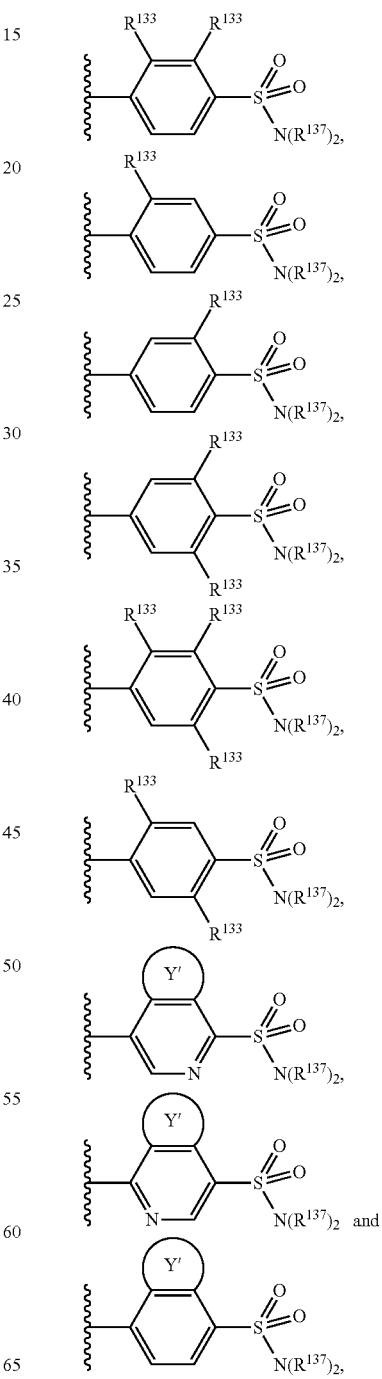

wherein R$^{133}$ is independently selected from H, halogen, C$_{1-6}$-alkyl, fluoro-C$_{1-6}$-alkyl, C$_{1-4}$-alkylene-OH, C$_{1-4}$-alkylene-O—C$_{1-3}$-alkyl, O—C$_{1-6}$-alkyl, and O-fluoro-C$_{1-6}$-alkyl, more preferably R$^{33}$ is independently selected from fluoro, chloro, CF$_3$, CHF$_2$, OCF$_3$, OCHF$_2$, methyl, $^t$butyl and CMe$_2$OH;

one R$^{137}$ is selected from H, C$_{1-6}$-alkyl, fluoro-C$_{1-6}$-alkyl and the other R$^{137}$ is selected from C$_{1-6}$-alkyl, fluoro-C$_{1-6}$-alkyl, C$_{0-4}$-alkylene-C$_{3-6}$-cycloalkyl, C$_{0-4}$-alkylene-C$_{3-6}$-heterocycloalkyl, wherein alkyl and alkylene is unsubstituted or substituted with a substituent selected from halogen, OH, O—C$_{1-3}$-alkyl, CN, CONH$_2$; and cycloalkyl or heterocycloalkyl is unsubstituted or substituted with 1 to 3 substituents independently selected from F, CN, CONH$_2$, OH, oxo, C$_{1-3}$-alkyl and fluoro-C$_{1-3}$-alkyl, or wherein two R$^{137}$ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, C$_{1-4}$-alkyl and halo-C$_{1-4}$-alkyl;

Y' is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl and CF$_3$.

In a most preferred embodiment in combination with any of the above or below embodiments of the second alternative R$^{103}$ is selected from

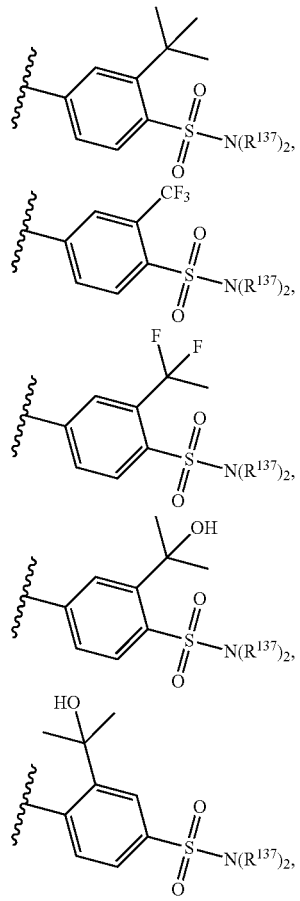

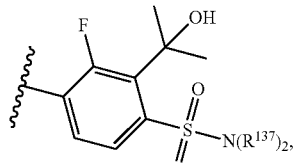

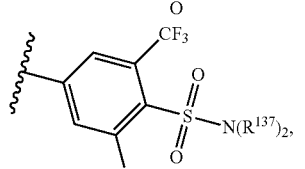

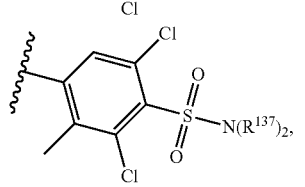

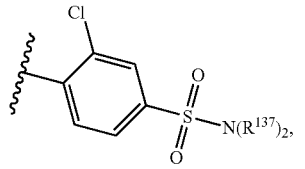

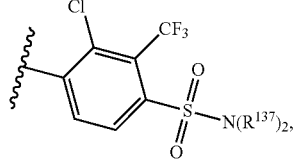

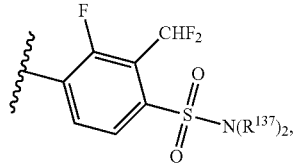

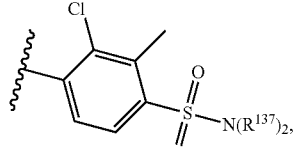

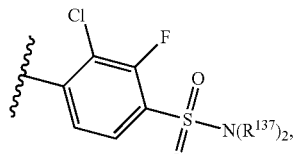

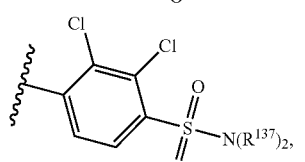

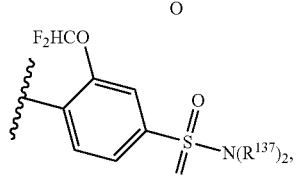

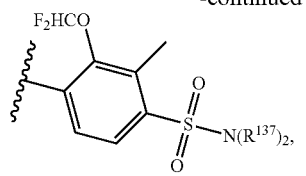
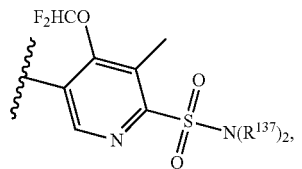
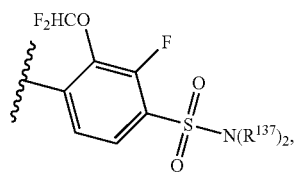
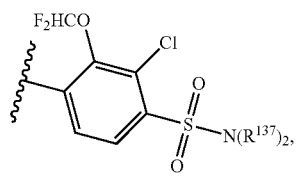
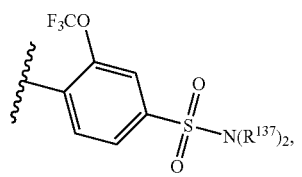
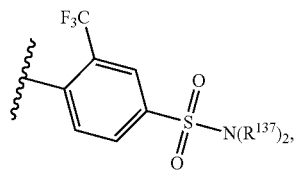
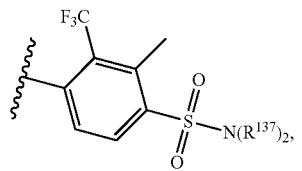
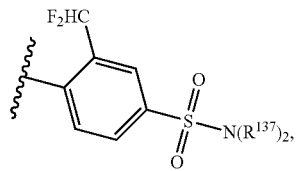
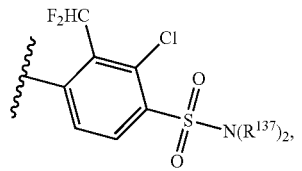
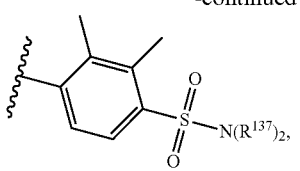
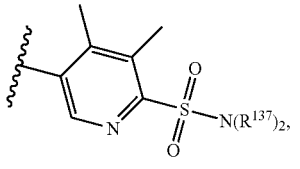
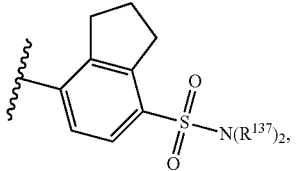
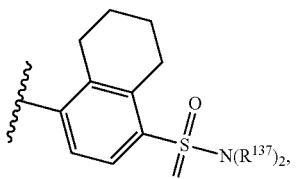
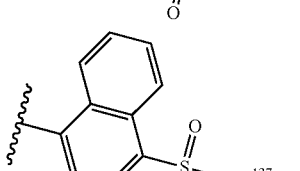
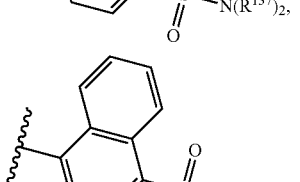
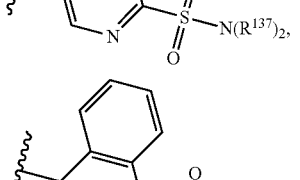
and
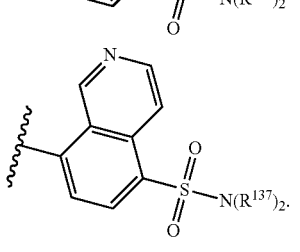

In another preferred embodiment in combination with any of the above or below embodiments of the second alternative $N(R^{137})_2$ is selected from

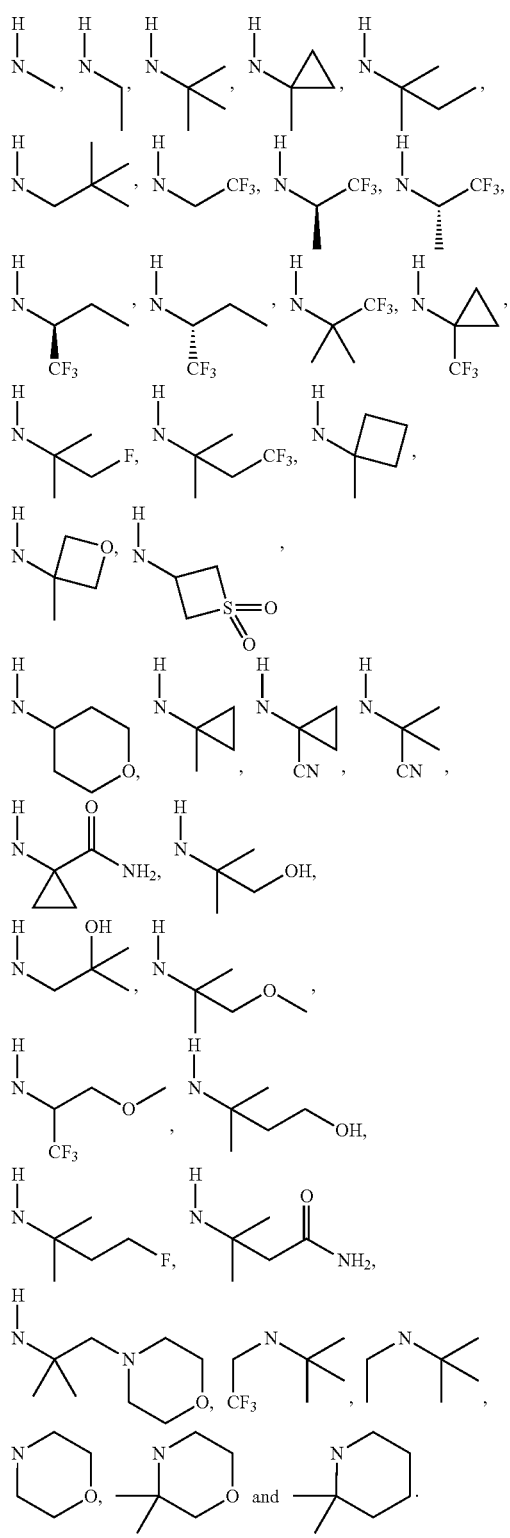

In a more preferred embodiment in combination with any of the above or below embodiments of the second alternative $N(R^{137})_2$ is selected from

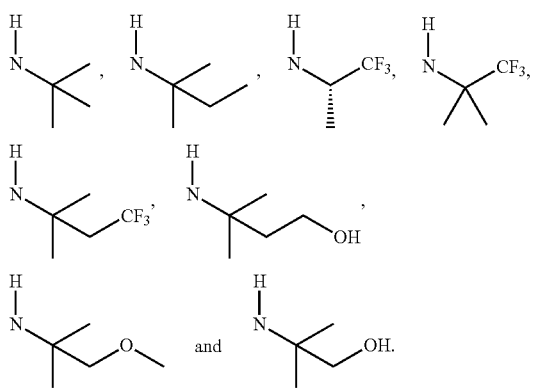

In another preferred embodiment in combination with any of the above or below embodiments of the second alternative $R^{13}$ is selected from

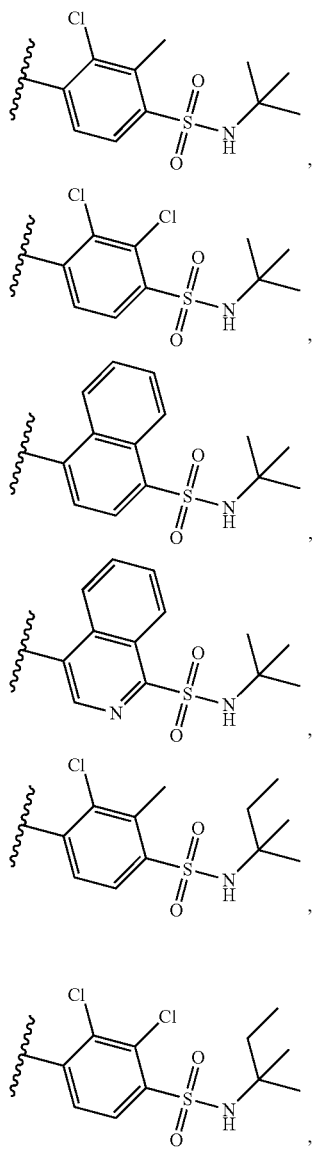

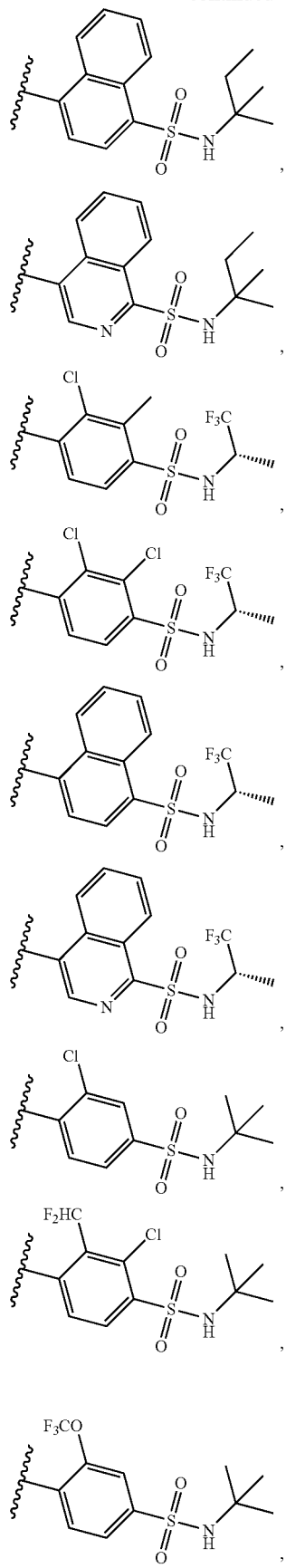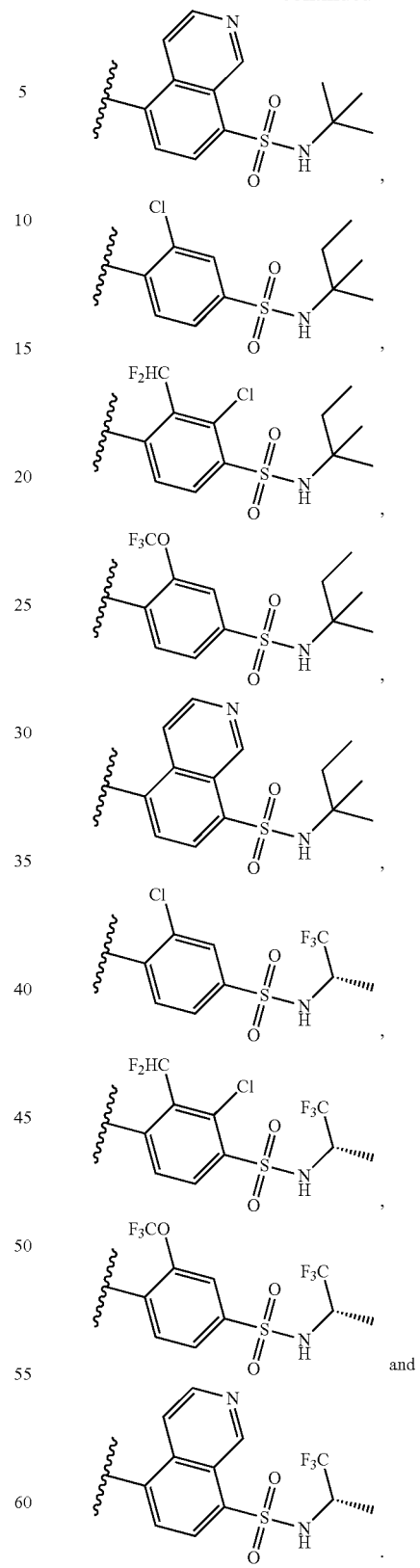
In an alternative preferred embodiment in combination with any of the above or below embodiments of the second alternative $R^{103}$ is selected from

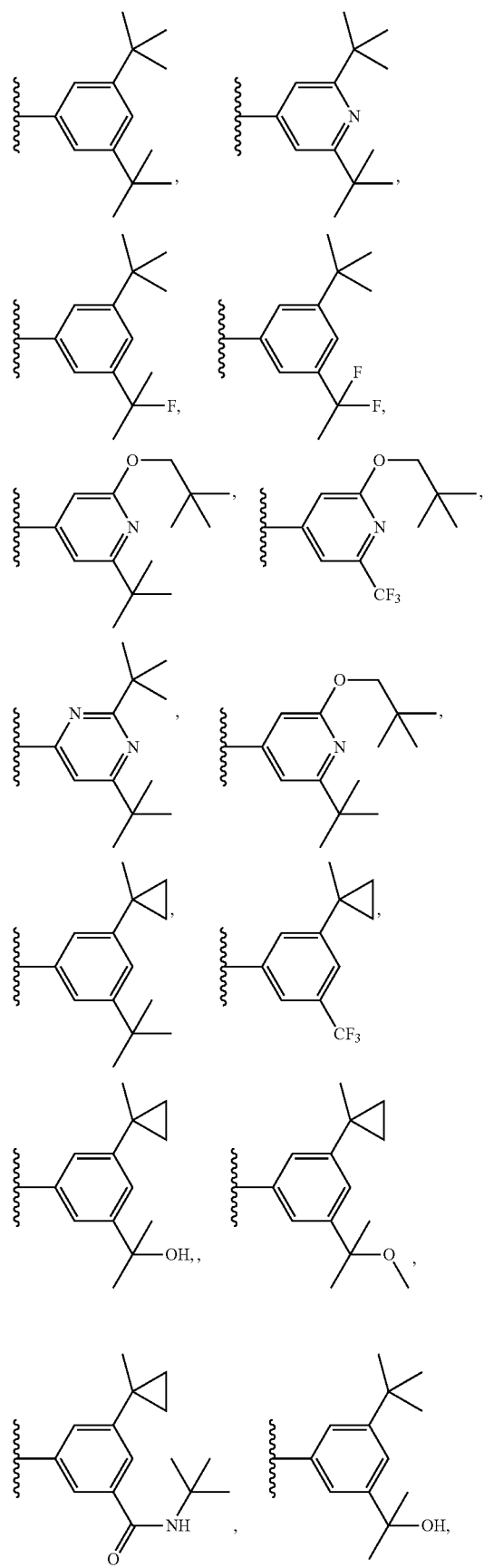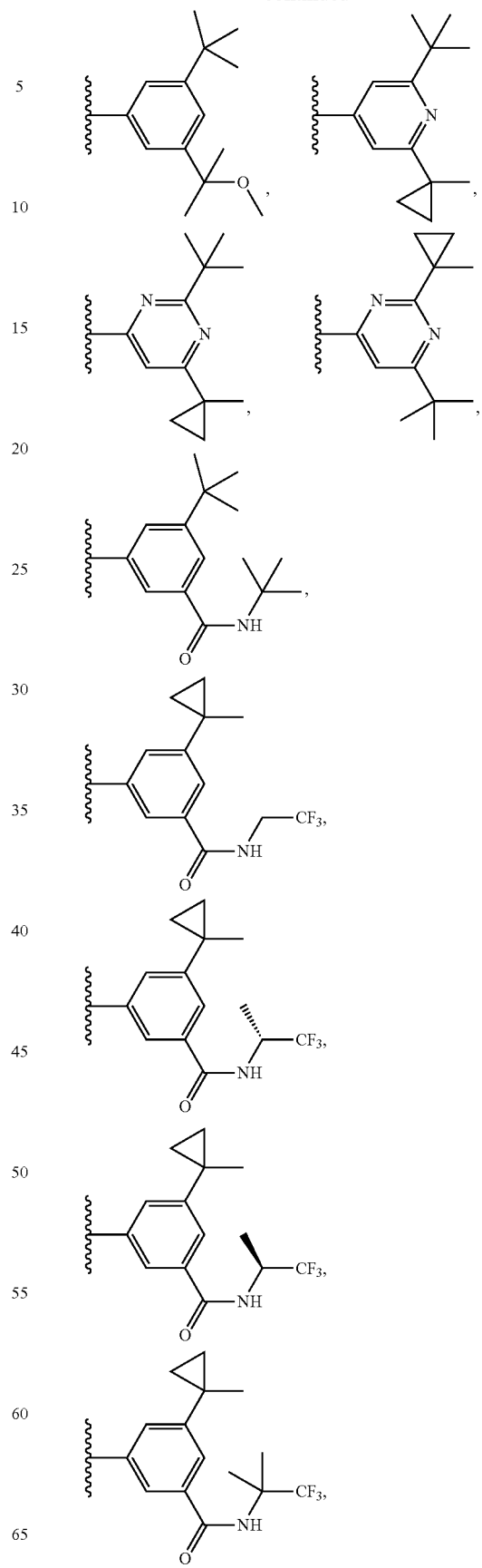

-continued
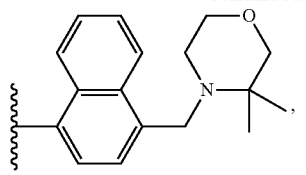
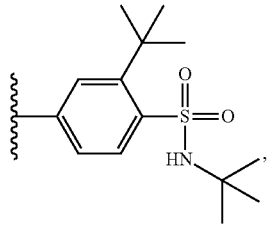
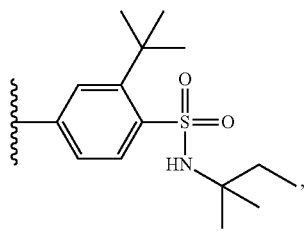
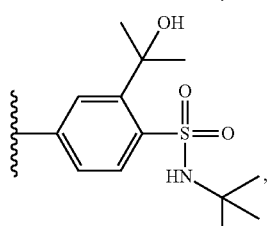
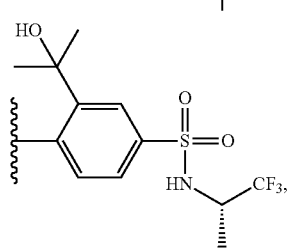
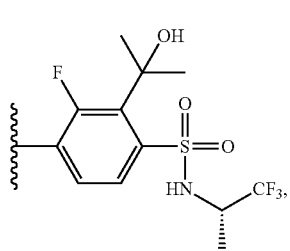
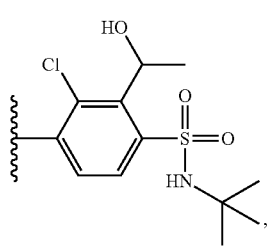
-continued
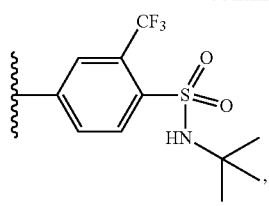
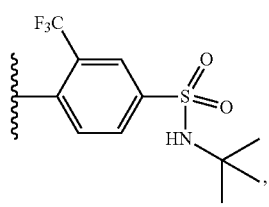
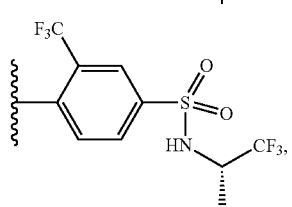
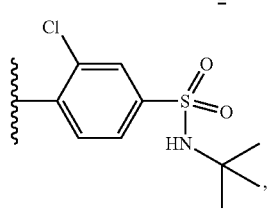
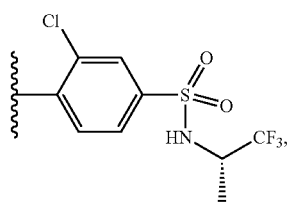
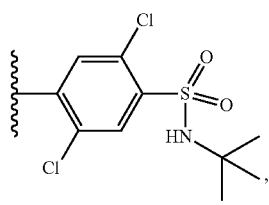
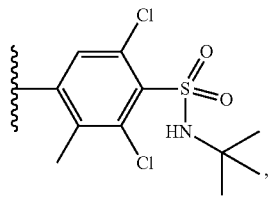
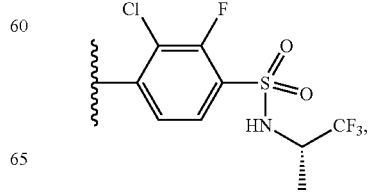

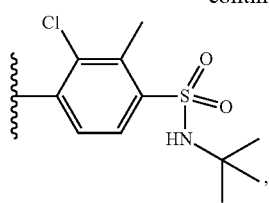
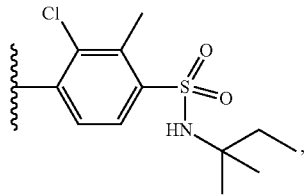
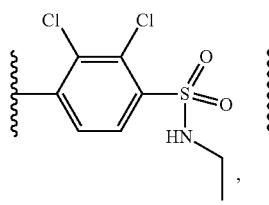
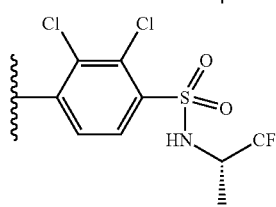
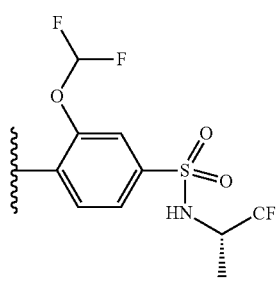
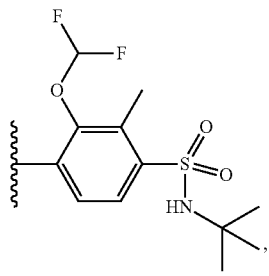
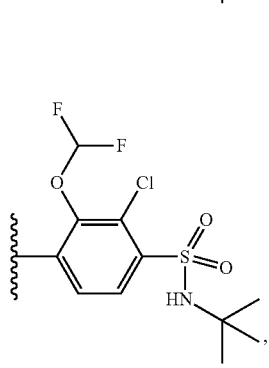
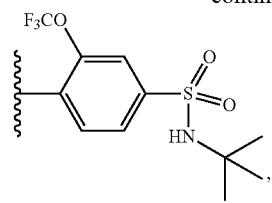
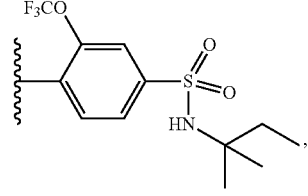
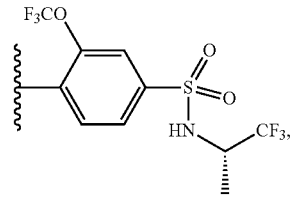
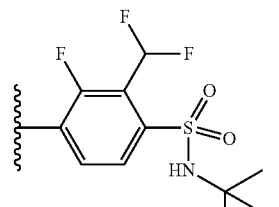
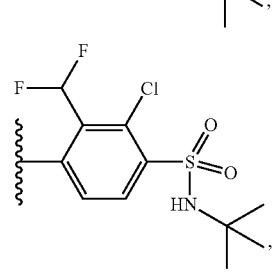
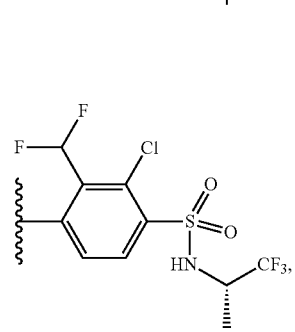
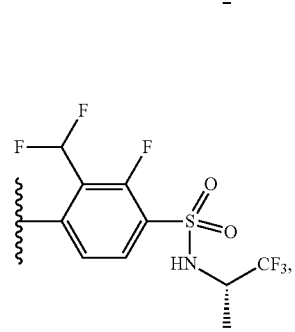

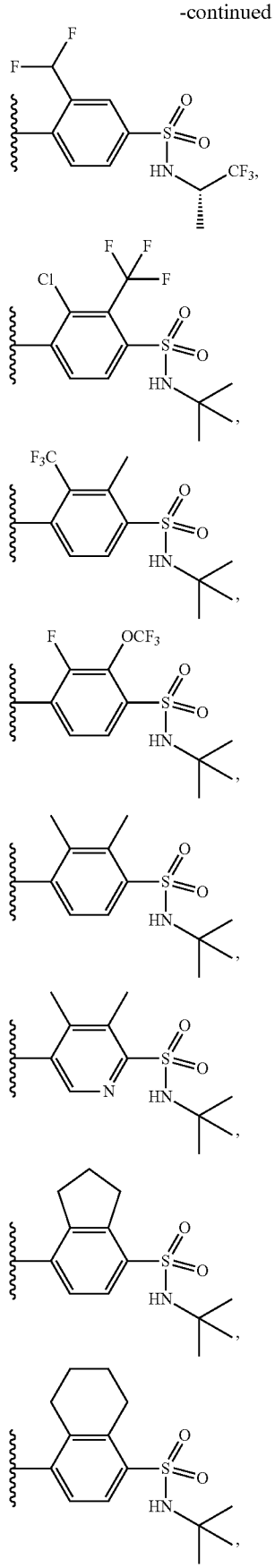
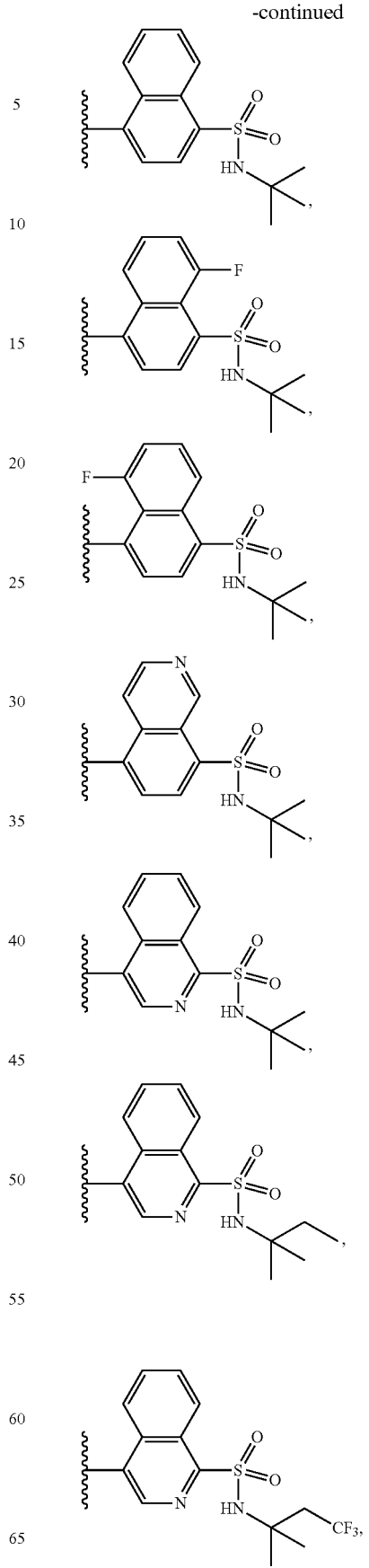

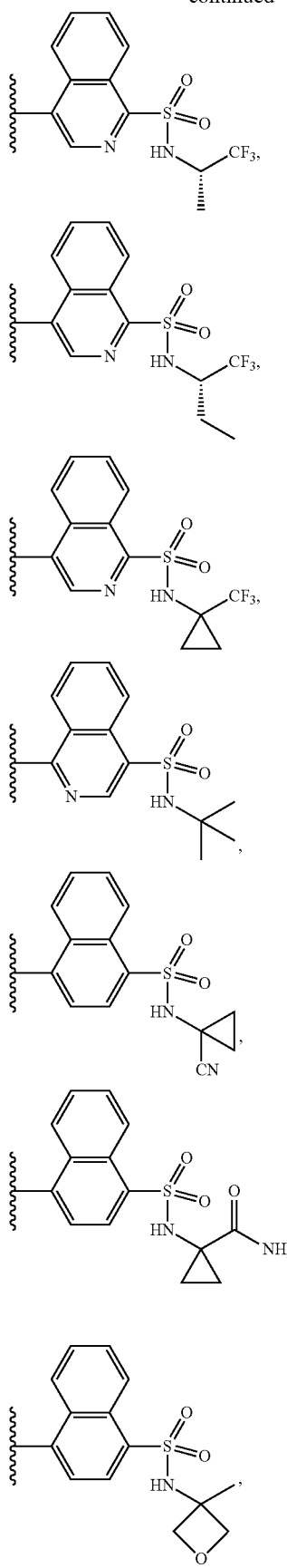
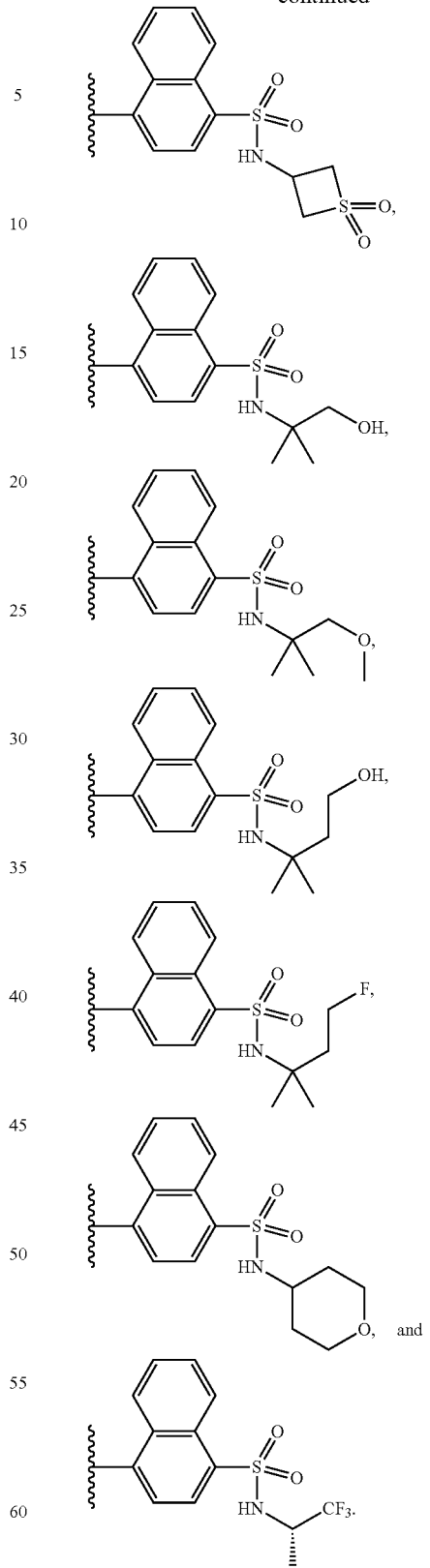
In a more preferred embodiment in combination with any of the above or below embodiments of the second alternative $R^{103}$ is selected from

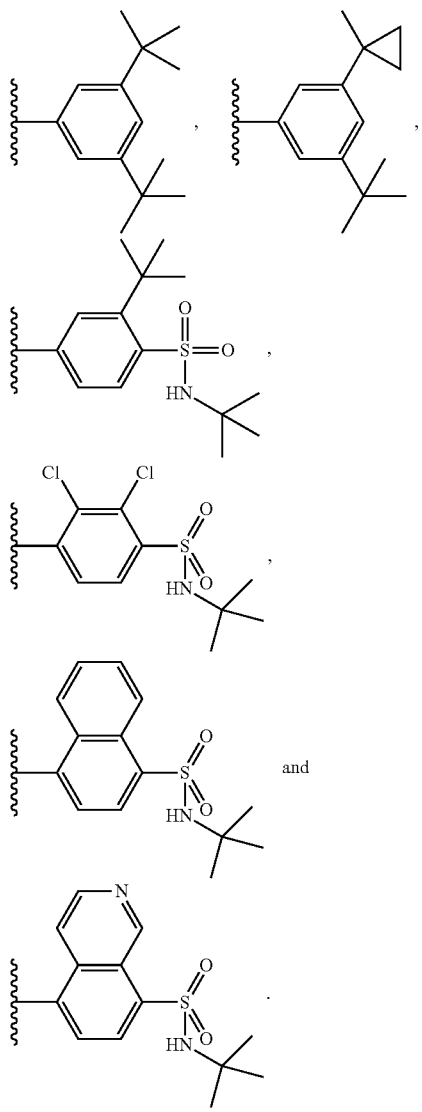

In another preferred embodiment in combination with any of the above or below embodiments of the third alternative $R^{103}$ is selected from

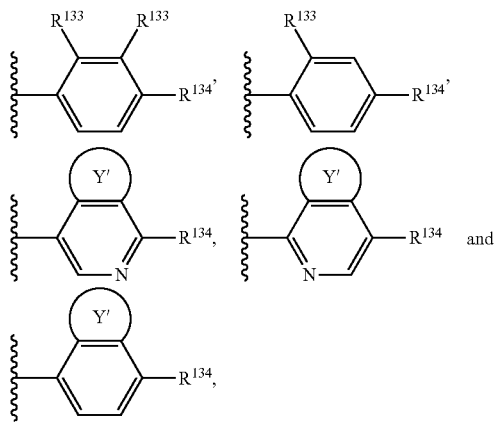

wherein $R^{133}$ is independently selected from H, halogen, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, and O-fluoro-$C_{1-6}$-alkyl, more preferably $R^{133}$ is independently selected from fluoro, chloro, $CF_3$, $CHF_2$, $OCF_3$, $OCHF_2$, methyl, $^t$butyl and $CMe_2OH$;

$R^{134}$ is selected from $C_{1-6}$-alkyl, halo-$C_{1-6}$-alkyl and $C_{0-6}$-alkylene-$C_{3-10}$-heterocycloalkyl, wherein alkyl, alkylene and heterocycloalkyl are unsubstituted or substituted by 1 to 3 substituents independently selected from the group consisting of halogen, $C_{1-6}$-alkyl, halo-$C_{1-6}$-alkyl, OH, oxo, $N(R^{131})_2$, O—$C_{1-6}$-alkyl, $C_{3-10}$-cycloalkyl, $C_{3-10}$-heterocycloalkyl; and Y' is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or $CF_3$.

In more preferred embodiment in combination with any of the above or below embodiments of the third alternative $R^{103}$ is selected from

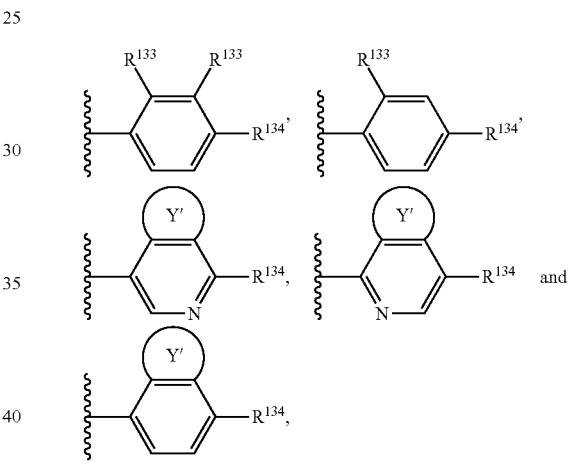

wherein $R^{133}$ is independently selected from H, halogen, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, and O-fluoro-$C_{1-6}$-alkyl, more preferably $R^{133}$ is independently selected from fluoro, chloro, $CF_3$, $CHF_2$, $OCF_3$, $OCHF_2$, methyl, $^t$butyl and $CMe_2OH$;

$R^{34}$ is selected from

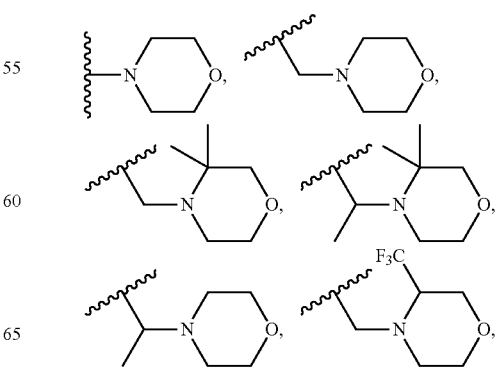

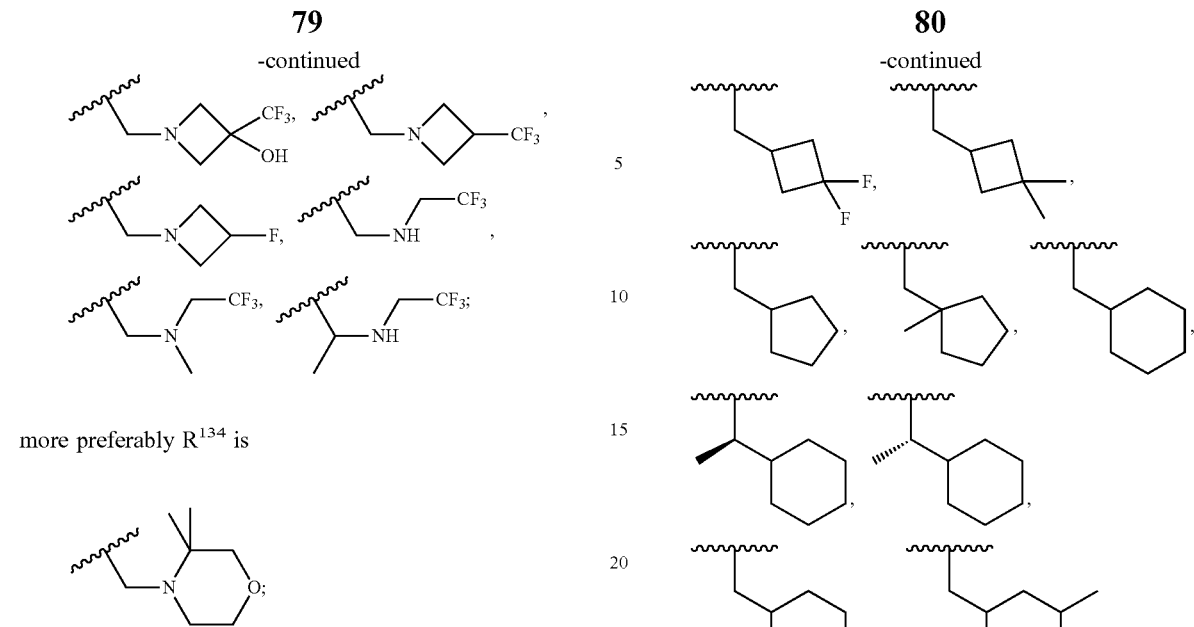

more preferably $R^{134}$ is

Y' is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or $CF_3$.

In another preferred embodiment in combination with any of the above or below embodiments of the second alternative $R^{104}$ is selected from $(CR^{108}R^{109})R^{140}$ and $(C=O)R^{140}$;

$R^{108}$ is independently selected from H, F, $C_{1-3}$-alkyl, halo-$C_{1-3}$-alkyl, OH, O—$C_{1-3}$-alkyl and O-halo-$C_{1-3}$-alkyl;

$R^{109}$ is selected from H, F and methyl;

$R^{140}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl.

In a more preferred embodiment in combination with any of the above or below embodiments of the second alternative, $R^{104}$ is $(CR^{108}R^{109})R^{140}$; $R^{108}$ is selected from H, F, methyl and O-methyl; $R^{109}$ is selected from H, F and methyl; and $R^{140}$ is $C_{3-8}$-cycloalkyl, which is unsubstituted or substituted with 1 to 3 substituents independently selected from the group consisting of F, methyl and $CF_3$.

In an even more preferred embodiment in combination with any of the above or below embodiments of the second alternative, $R^{104}$ is $(CH_2)R^{140}$, wherein $R^{140}$ is $C_{3-8}$-cycloalkyl, which is unsubstituted or substituted with 1 to 3 substituents independently selected from the group consisting of fluoro, methyl and $CF_3$.

In another preferred embodiment in combination with any of the above or below embodiments of the second alternative $R^{104}$ is selected from

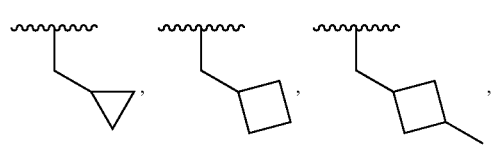

In a more preferred embodiment in combination with any of the above or below embodiments of the second alternative, $R^{104}$ is selected from

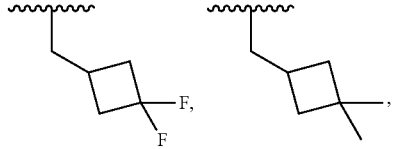

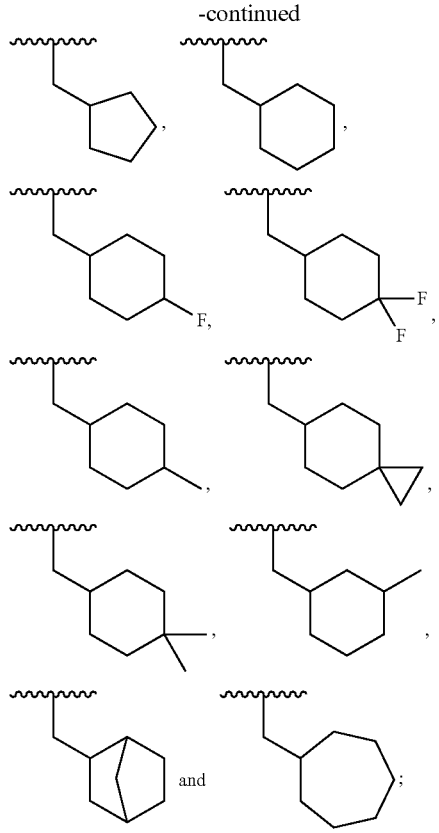

even more preferably, $R^{104}$ is selected from

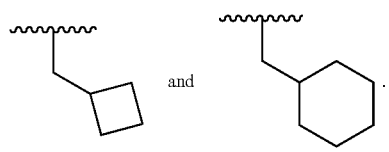 [SMILES: *CC1CCC1 ; *CC1CCCCC1]

In another preferred embodiment in combination with any of the above or below embodiments of the second alternative the compound is represented by Formula (100).

In yet another preferred embodiment in combination with any of the above or below embodiments of the second alternative, the compound of Formula (100) is selected from the group consisting of

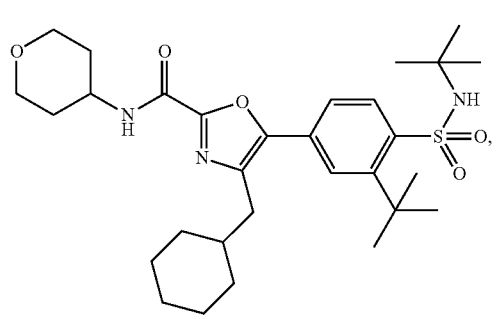

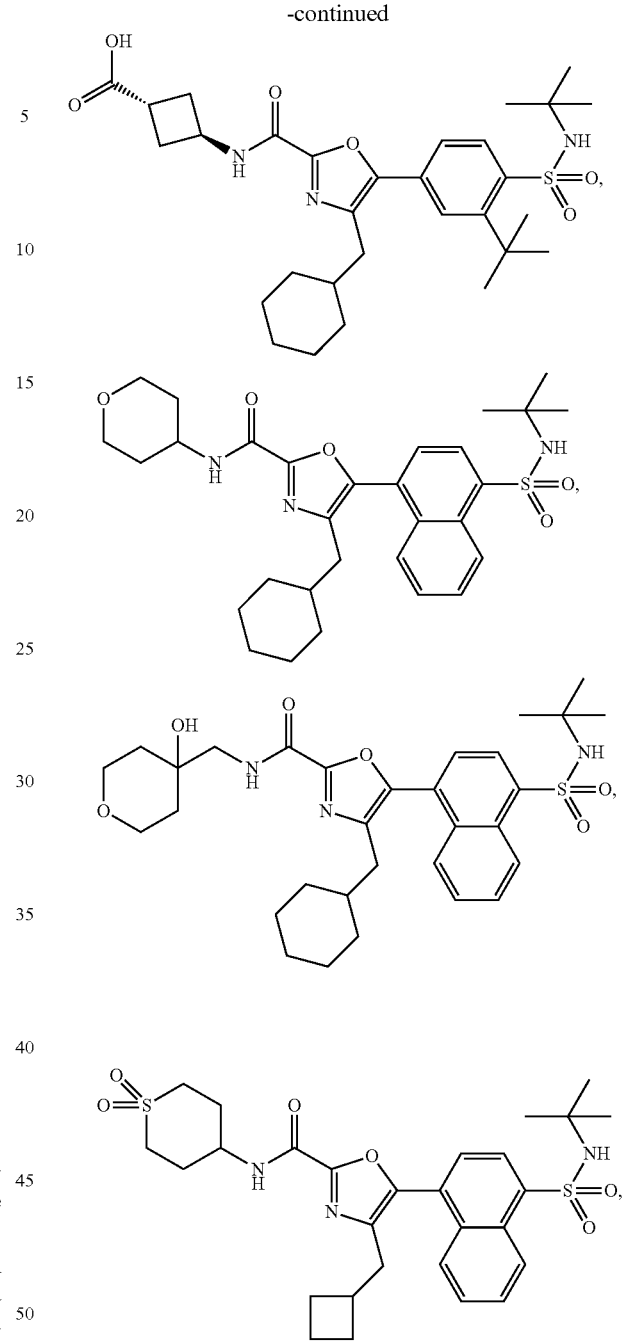

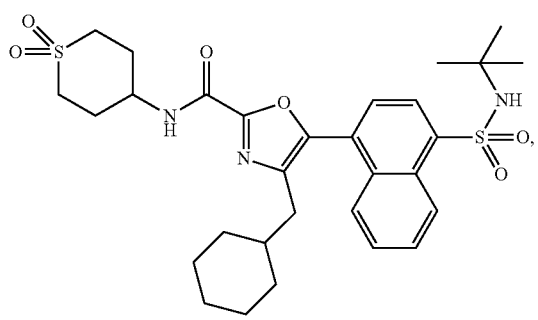

83
-continued
84
-continued
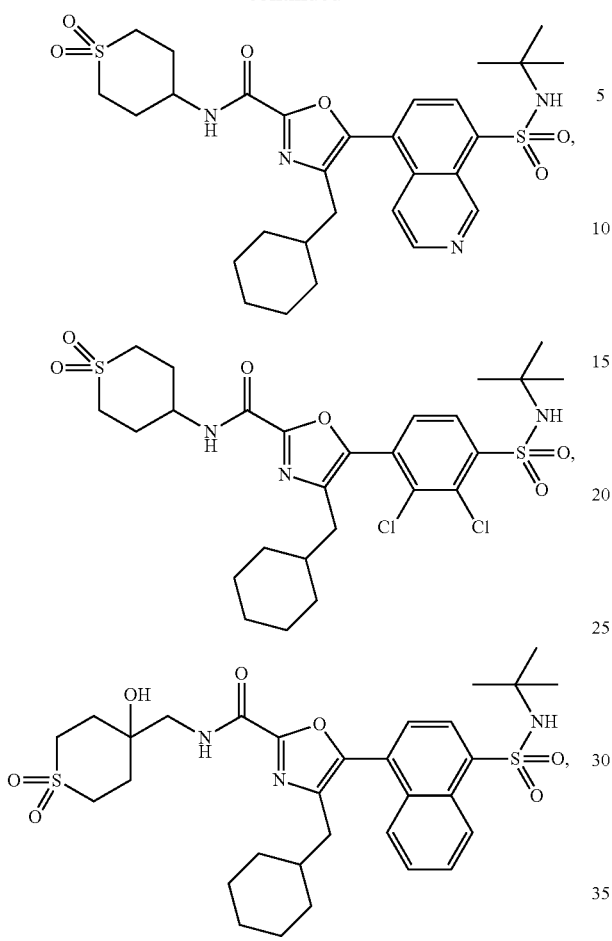
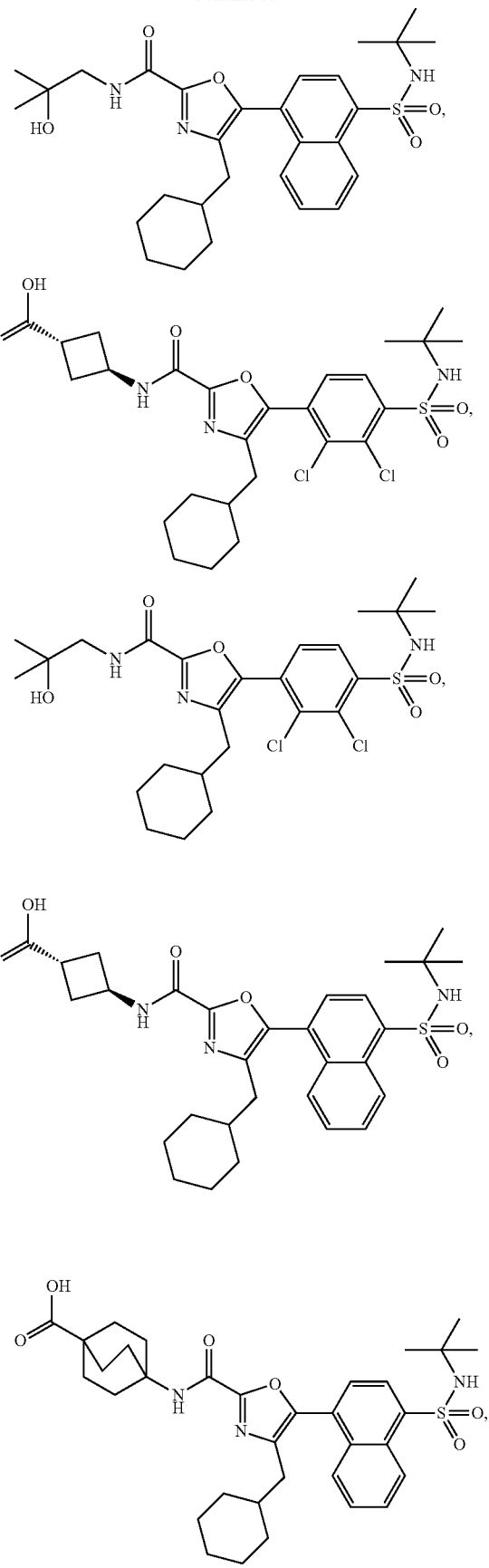

-continued

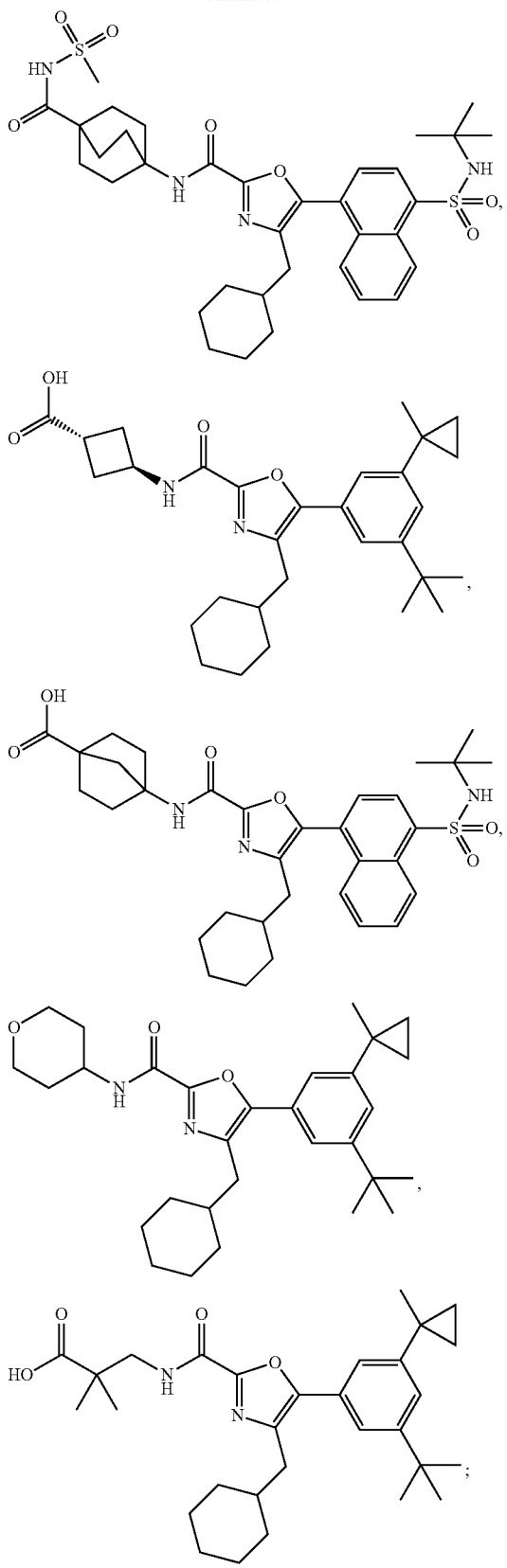

and an enantiomer, diastereomer, tautomer, N-oxide, solvate and pharmaceutically acceptable salt thereof.

The invention also provides the compound of the second alternative of the invention for use as a medicament.

Also provided is the compound of the second alternative of the invention for use in the treatment or prophylaxis of a disease or disorder associated with the inhibition or activation of the RORγ receptor.

Also provided is the compound of the second alternative of the invention in treating RORγ mediated inflammatory and autoimmune diseases. Preferably, the disease is selected from the group consisting of rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis.

Also provided is a pharmaceutical composition comprising the compound of the second alternative of the invention and a pharmaceutically acceptable carrier.

In a third alternative, the present invention provides a compound represented by Formula (1) or Formula (1')

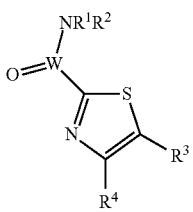
(1)

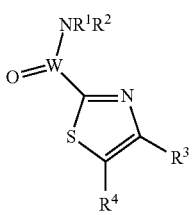
(1')

an enantiomer, diastereomer, tautomer, N-oxide, solvate, formulation and pharmaceutically acceptable salt thereof, $R^1$ and $R^2$ are independently selected from H, $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $CONR^{11}SO_2R^{11}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl,
wherein cycloalkyl and heterocycloalkyl are unsubstituted or substituted with 1 to 4 substituents independently selected from halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;

$R^3$ is a 6-10 membered mono- or bicyclic aryl or a 5-14 membered mono-, bi- or tricyclic heteroaryl containing 1 to 5 heteroatoms independently selected from the group consisting of N, O and S,
wherein aryl and heteroaryl is optionally substituted with 1 to 5 substituents independently selected from halogen, $C_{1-6}$-alkyl, $C_{1-6}$-alkenyl, $C_{1-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered heteroaryl), $C_{1-6}$-alkylene-O—$R^{31}$, $C_{0-6}$-alkylene-CN, $C_{0-6}$-alkylene-N$(R^{31})_2$, $C_{0-6}$-alkylene-O—$C_{3-10}$-cycloalkyl, O—$C_{1-6}$-alkylene-O—$R^{31}$, $C_{0-6}$-alkylene-O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N$(R^{31})_2$, $C_{0-6}$-alkylene-N$(R^{31})$C(O)$R^{31}$, $C_{0-6}$-alkylene-SO—$R^{31}$, $C_{0-6}$-alkylene-$SO_2$—$R^{31}$, $C_{0-6}$-alkylene-$SO_2$—N$(R^{31})_2$, $C_{0-6}$-alkylene-N$(R^{31})SO_2$—$R^{31}$, $C_{0-6}$-alkylene-$SO_2$—$C_{3-10}$-heterocycloalkyl and $C_{0-6}$-alkylene-$SO_2$—$C_{3-10}$-heterocycloalkyl,
wherein alkyl, alkenyl, alkynyl, alkylene, cycloalkyl, heterocycloalkyl and the 5- or 6-membered heteroaryl is optionally substituted by 1 to 4 substituents independently selected from the group consisting of halogen, CN, $C_{1-3}$-alkyl, halo-$C_{1-3}$-alkyl, OH, oxo, =N—$OR^{32}$, O—$C_{1-6}$-alkyl, O-halo-$C_{1-3}$-alkyl, N$(R^{31})_2$, COOH, CON$(R^{31})_2$, $NR^{31}$—$COR^{31}$, $C_{3-10}$-cycloalkyl, $C_{3-10}$-heterocycloalkyl, 6-10-membered mono- or bicyclic aryl and 6-10-membered mono- or bicyclic heteroaryl,
or wherein two adjacent substituents completing a 3- to 8-membered saturated or partially unsaturated ring containing carbon atoms and optionally containing 1 to 3 heteroatoms selected from O, S, N, SO, $SO_2$, or $NR^{31}$, wherein the ring is unsubstituted or substituted with 1 to 7 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl;

$R^4$ is selected from $(CR^8R^9)R^{40}$, (C=O)$R^{40}$, $OR^{40}$, $NR^{41}R^{40}$, $SO_y$—$R^7$ and $C_{3-6}$-cycloalkyl, which is spirocyclic fused with $R^{40}$
wherein cycloalkyl is unsubstituted or substituted with 1 to 4 substituents independently selected from the group consisting of F, methyl and $CF_3$;

$R^7$ is selected from $C_{3-10}$-cycloalkyl and $C_{3-10}$-heterocycloalkyl,
wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ and $R^9$ are independently selected from H, F, $C_{1-3}$-alkyl, halo-$C_{1-3}$-alkyl, OH, O—$C_{1-3}$-alkyl and O-halo-$C_{1-3}$-alkyl;

$R^{11}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl,
wherein alkyl, alkylene, cycloalkyl and heterocycloalkyl is unsubstituted or substituted with 1 to 6 substituents selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, NH($C_{1-3}$-alkyl), N($C_{1-3}$-alkyl)$_2$, $C_{3-6}$-heterocycloalkyl, $C_{3-6}$-cycloalkyl and $SO_2$—$C_{1-3}$-alkyl,
wherein cycloalkyl and heterocycloalkyl is unsubstituted or substituted with 1 to 3 substituents independently selected from the group consisting of F, OH, oxo, Me and $CF_3$;

$R^{12}$ is independently selected from H, $C_{1-6}$-alkyl, halo-$C_{1-6}$-alkyl and $C_{3-6}$-cycloalkyl;

$R^{31}$ is independently selected from H, $C_{1-6}$-alkyl, halo-$C_{1-6}$-alkyl, $C_{0-6}$alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from halogen, CN, OH, oxo, =N—$OR^{32}$, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;
and optionally wherein two $R^{31}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{32}$ is independently selected from H, $C_{1-6}$-alkyl and halo-$C_{1-6}$-alkyl and $C_{3-6}$-cycloalkyl;

$R^{40}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-8}$-cycloalkyl and $C_{3-8}$-heterocycloalkyl;

$R^{41}$ is selected from H, $C_{1-6}$-alkyl, $C_{3-6}$-cycloalkyl and $C_{3-6}$-heterocycloalkyl,
wherein alkyl, cycloalkyl and heterocycloalkyl is unsubstituted or substituted with 1 to 3 substituents selected from the group consisting of OH, oxo, CN, halogen, O—$C_{1-6}$-alkyl, O-halo-$C_{1-6}$-alkyl, $C_{3-6}$-heterocycloalkyl and $C_{3-6}$-cycloalkyl;

x and y are independently selected from 0, 1 and 2;
W is selected from C or S=O;
with the proviso that for $R^3$ the 5-14 membered mono-, bi- or tricyclic heteroaryl containing ring is not

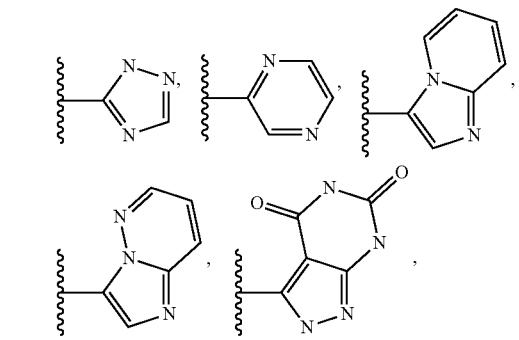

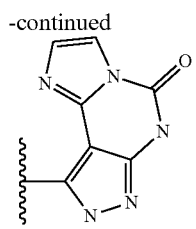

or a 5-membered aromatic heterocyclic group containing at least one oxygen atom.

In an alternative preferred embodiment of the third alternative the compound is represented by Formula (1) or Formula (1')

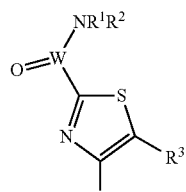

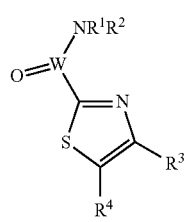

an enantiomer, diastereomer, tautomer, solvate, formulation and pharmaceutically acceptable salt thereof,
wherein
$R^1$ and $R^2$ are independently selected from H, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-(5-membered monocyclic heteroaryl), $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from oxo, CN, $OR^{11}$, $O$—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, $O$—$C_{3-6}$-cycloalkyl, $C_{3-6}$-heterocycloalkyl, $O$—$C_{3-6}$-heterocycloalkyl and $NR^{11}R^{12}$;
or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $CONR^{11}SO_2R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, $O$—$C_{3-6}$-cycloalkyl, $C_{3-6}$-heterocycloalkyl and $O$—$C_{3-6}$-heterocycloalkyl,
wherein cycloalkyl and heterocycloalkyl are unsubstituted or substituted with 1 to 3 substituents selected from oxo, OH, methyl, $CF_3$ and fluoro;

$R^3$ is a 6-10 membered mono- or bicyclic aryl or a 5-14 membered mono-, bi- or tricyclic heteroaryl containing 1 to 5 heteroatoms independently selected from the group consisting of N, O and S
wherein aryl and heteroaryl are unsubstituted or substituted with 1 to 5 substituents independently selected from halogen, CN, $C_{1-6}$-alkyl, $C_{1-6}$-alkenyl, $C_{1-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-$COOR^{31}$, $C_{0-6}$-alkylene-$C(O)R^{31}$, $C_{0-6}$-alkylene-$C(O)N(R^{31})_2$, $C_{0-6}$-alkylene-$SO_2$—$N(R^{31})_2$, $C_{0-6}$-alkylene-$SO_2$—$R^{31}$, $C_{0-6}$-alkylene-(5-membered heteroaryl), $C_{0-6}$-alkylene-(6-membered heteroaryl),
wherein alkyl, alkenyl, alkynyl, alkylene, cycloalkyl, heterocycloalkyl and heteroaryl are unsubstituted or substituted by 1 to 3 substituents independently selected from the group consisting of $C_{1-6}$-alkyl, halo-$C_{1-6}$-alkyl, halogen, OH, oxo, =N—$OR^{32}$, $N(R^{31})_2$, O—$C_{1-6}$-alkyl, O-halo-$C_{1-6}$-alkyl, COOH, $CON(R^{31})_2$, CN, $NR^{31}$—$COR^{31}$, $C_{3-10}$-cycloalkyl, $C_{3-10}$-heterocycloalkyl, 6-10-membered mono- or bicyclic aryl, 6-10-membered mono- or bicyclic heteroaryl,
or wherein two adjacent substituents may complete a 3- to 8-membered saturated or partially unsaturated ring containing carbon atoms and optionally containing 1 to 3 members selected from O, S, SO, $SO_2$ or $NR^{31}$, wherein the ring is unsubstituted or substituted with one to four substituents independently selected from halogen, oxo, =N—$OR^{32}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl;
$R^4$ is selected from $(CR^8R^9)R^{40}$, $(C=O)R^{40}$, $C_3$-cycloalkylene-$R^{40}$, $OR^{40}$, $NR^{41}R^{40}$ and $SO_y$—$R^7$;
$R^7$ is selected from $C_{3-10}$-cycloalkyl and $C_{3-10}$-heterocycloalkyl,
wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;
$R^8$ and $R^9$ are independently selected from H, F, $C_{1-3}$-alkyl, halo-$C_{1-3}$-alkyl, OH, O—$C_{1-3}$-alkyl and O-halo-$C_{1-3}$-alkyl,
$R^{11}$ and $R^{31}$ independently selected from H, $C_{1-6}$-alkyl, $C_{3-10}$-cycloalkyl, $C_{3-10}$-heterocycloalkyl, phenyl, 5-6-membered heteroaryl containing 1 to 4 heteroatoms independently selected from N, O and S
wherein alkyl, cycloalkyl and heterocycloalkyl is unsubstituted or substituted with 1 to 5 substituents selected from the group consisting of $C_{1-6}$-alkyl, halo-$C_{1-6}$-alkyl, OH, O—$C_{1-6}$-alkyl, O-halo-$C_{1-6}$-alkyl, phenyl, heteroaryl, halogen, $NH_2$, $NH(C_{1-6}$-alkyl), $N(C_{1-6}$-alkyl)$_2$, $C_{3-10}$-heterocycloalkyl and $C_{3-10}$-cycloalkyl, COOH, $SO_2$—$C_{1-3}$-alkyl, $SO_2$—$C_{1-3}$-fluoroalkyl, oxo and CN,
wherein cycloalkyl and heterocycloalkyl is unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, heteroaryl, halogen, $NH_2$, $NH(C_{1-6}$-alkyl), $N(C_{1-6}$-alkyl)$_2$ and $C_{3-10}$-cycloalkyl,
wherein phenyl and heteroaryl are unsubstituted or substituted with 1 to 4 substituents independently selected from the group consisting of OH, O—$C_{1-6}$-alkyl, O-halo-$C_{1-6}$-alkyl, halogen, $C_{1-6}$-alkyl, halo-$C_{1-6}$-alkyl, $NH_2$, $NH(C_{1-6}$-alkyl), $N(C_{1-6}$-alkyl)$_2$ and $C_{3-10}$-cycloalkyl;

$R^{12}$ and $R^{32}$ are independently selected from H, $C_{1-6}$-alkyl, halo-$C_{1-6}$-alkyl and $C_{3-10}$-cycloalkyl;

$R^{40}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl and halo-$C_{1-6}$-alkyl;

$R^{41}$ is selected from H, $C_{1-6}$-alkyl, $C_{3-6}$-cycloalkyl and $C_{3-6}$-heterocycloalkyl, wherein alkyl, cycloalkyl and heterocycloalkyl is unsubstituted or substituted with 1 to 3 substituents selected from the group consisting of OH, oxo, CN, halogen, O—$C_{1-6}$-alkyl, O-halo-$C_{1-6}$-alkyl, $C_{3-6}$-heterocycloalkyl and $C_{3-6}$-cycloalkyl;

y is independently selected from 0, 1 and 2;

W is selected from C or S=O;

with the proviso that for $R^3$ the 5-14 membered mono-, bi- or tricyclic heteroaryl containing ring is not

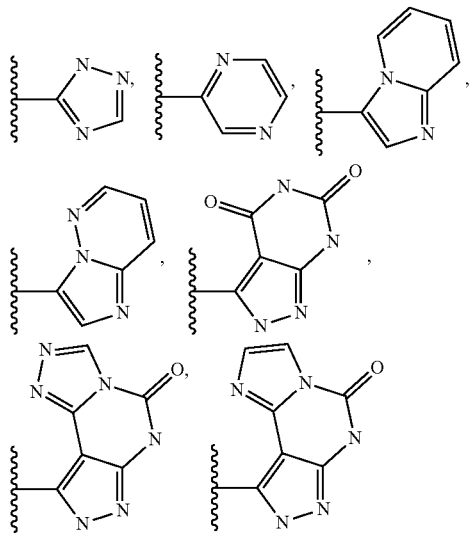

or a 5-membered aromatic heterocyclic group containing at least one oxygen atom.

In a preferred embodiment in combination with any of the above or below embodiments of the third alternative W is a carbon atom.

In a preferred embodiment in combination with any of the above or below embodiments of the third alternative $R^4$ is selected from $(CR^8R^9)R^{40}$, $(CO)R^{40}$ and $OR^{40}$;

$R^8$ is selected from H, F, methyl, trifluoromethyl and O-methyl;

$R^9$ is selected from H, F and methyl;

$R^{40}$ is $C_{3-8}$-cycloalkyl, which is unsubstituted or substituted with 1 to 3 substituents independently selected from the group consisting of fluoro, methyl and trifluoromethyl.

In a more preferred embodiment in combination with any of the above or below embodiments of the third alternative $R^4$ is selected from $(CR^8R^9)R^{40}$ and $OR^{40}$; $R^8$ is selected from H, F, methyl, $CF_3$ and OMe; $R^9$ is selected from H, F and methyl; and $R^{40}$ is $C_{3-8}$-cycloalkyl, which is unsubstituted or substituted with 1 to 3 substituents independently selected from the group consisting of fluoro, methyl and $CF_3$.

In an even more preferred embodiment in combination with any of the above or below embodiments of the third alternative $R^4$ is $(CR^8R^9)R^{40}$; $R^8$ is selected from H, F, methyl and O-methyl; $R^9$ is selected from H, F and methyl; and $R^{40}$ is $C_{3-8}$-cycloalkyl, which is unsubstituted or substituted with 1 to 3 substituents independently selected from the group consisting of fluoro, methyl and $CF_3$.

In a most preferred embodiment in combination with any of the above or below embodiments of the third alternative $R^4$ is $(CH_2)R^{40}$, wherein $R^{40}$ is $C_{3-8}$-cycloalkyl, which is unsubstituted or substituted with 1 to 3 substituents independently selected from the group consisting of fluoro, methyl and $CF_3$.

In an alternative preferred embodiment in combination with any of the above or below embodiments of the third alternative $R^4$ is selected from

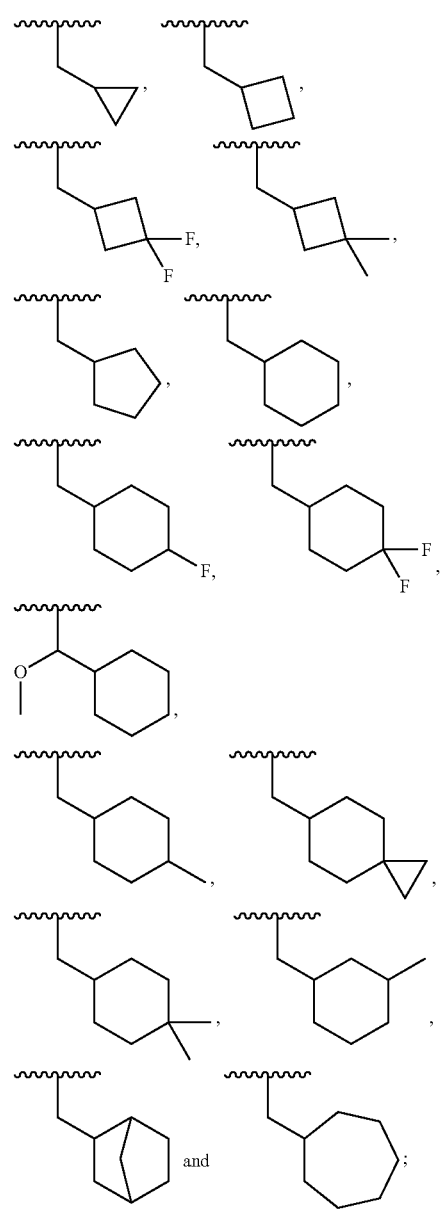

more preferably, $R^4$ is selected from

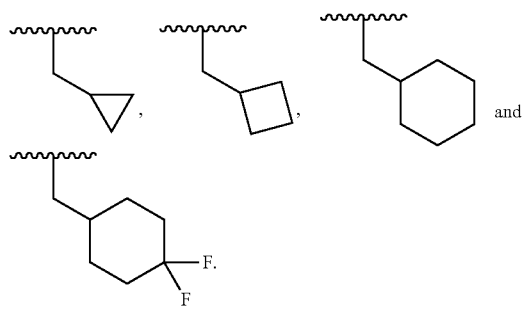

In a preferred embodiment in combination with any of the above or below embodiments of the third alternative $R^1$ is selected from H, $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), wherein alkyl, alkenyl, alkynyl, alkylene, cycloalkyl and heterocycloalkyl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$;
$R^2$ is selected from H, $C_{1-6}$-alkyl, halo-$C_{1-6}$-alkyl and hydroxy-$C_{1-6}$-alkyl;
or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $CONR^{11}SO_2R^{11}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl,
wherein cycloalkyl and heterocycloalkyl are unsubstituted or substituted with 1 to 4 substitutents independently selected from halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo.

In an alternative preferred embodiment in combination with any of the above or below embodiments of the third alternative $R^1$ is selected from H, $C_{1-10}$-alkyl, $C_{0-10}$-alkylene-$C_{3-10}$-cycloalkyl, and $C_{0-10}$-alkylene-$C_{3-10}$-heterocycloalkyl, wherein alkyl, alkylene, cycloalkyl and heterocycloalkyl is unsubstituted or substituted with 1 to 7 substituents independently selected from oxo, $OR^{11}$, $C_{1-6}$-alkyl, halo-$C_{1-6}$-alkyl, halogen, $CO_2R^{11}$, $CONR^{11}R^{12}$, $CONR^{11}SO_2R^{12}$, $COR^{11}$, $NR^{11}COR^{11}$, $NR^{11}SO_2R^{11}$, $NR^{11}$—CO—$NR^{11}R^{12}$, $NR^1$—$SO_2$—$NR^{11}R^{12}$, $C_{3-6}$-cycloalkyl, O—$C_{3-6}$-cycloalkyl, $C_{3-6}$-heterocycloalkyl and O—$C_{3-6}$-heterocycloalkyl;
$R^2$ is selected from the group consisting of H, $C_{1-6}$ alkyl and halo-$C_{1-6}$alkyl;
or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, oxo, $C_{1-6}$-alkyl.

In a preferred embodiment in combination with any of the above or below embodiments of the third alternative $NR^1R^2$ is selected from NHMe, NHEt, $NH^iPr$, $NH^tBu$, $NHCH_2CONH_2$, $NHCH_2CONMe_2$, $NHCH_2CH_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CH(CF_3)OH$, $NHCH_2C(Me)(CF_3)OH$, $NHCH_2CMe_2OH$, $NHCH_2CH_2CMe_2OH$, $NHCH_2CMe_2NHCH_2CF_3$, $NHCH(Me)CMe_2OH$, $NHCH_2CMe_2OMe$, $NHCH_2CMe_2CO_2H$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_5SO_2NH_2$, $NH(CH_2)_3NHSO_2Me$, $NH(CH_2)_2O(CH_2)_2OH$, $NHCH_2CHMeOH$, $NH(CH_2)_5SOMe$, $NH(CH_2)_3SO_2Me$, $NHC(CH_2OH)_3$, $NHCH_2CH(OH)CH_2OH$, $N(CH_2CH_2OH)_2$,

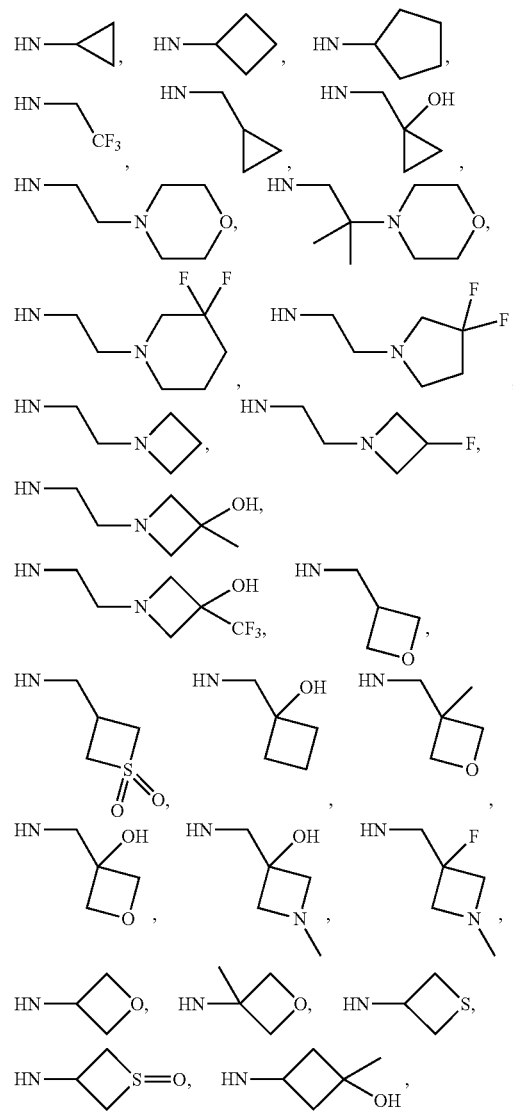

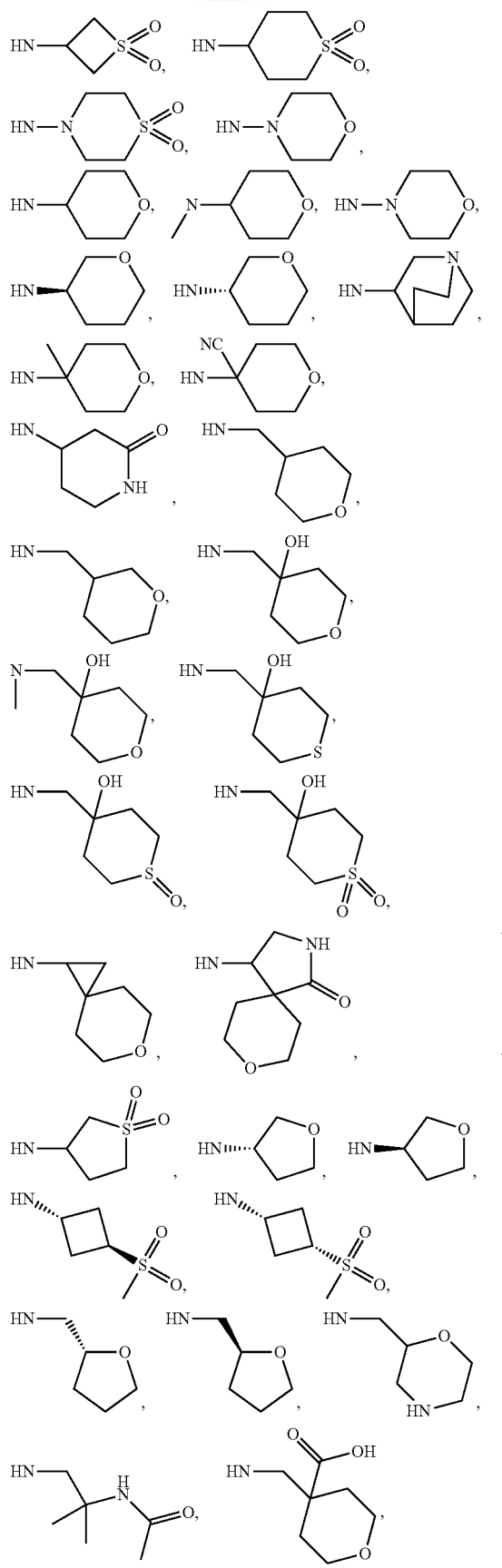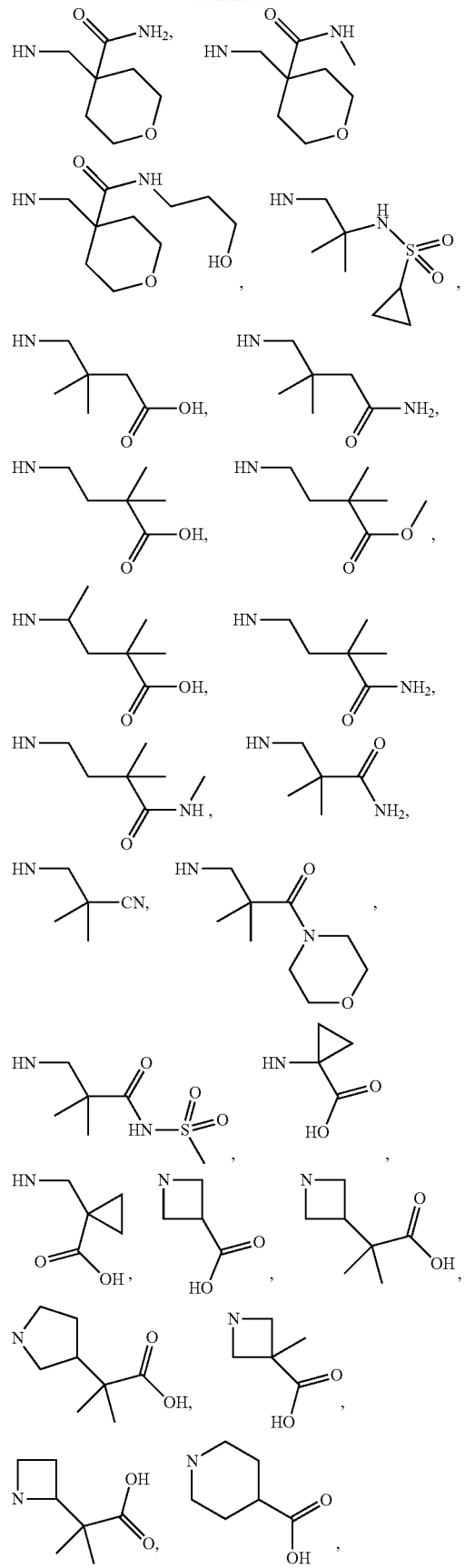

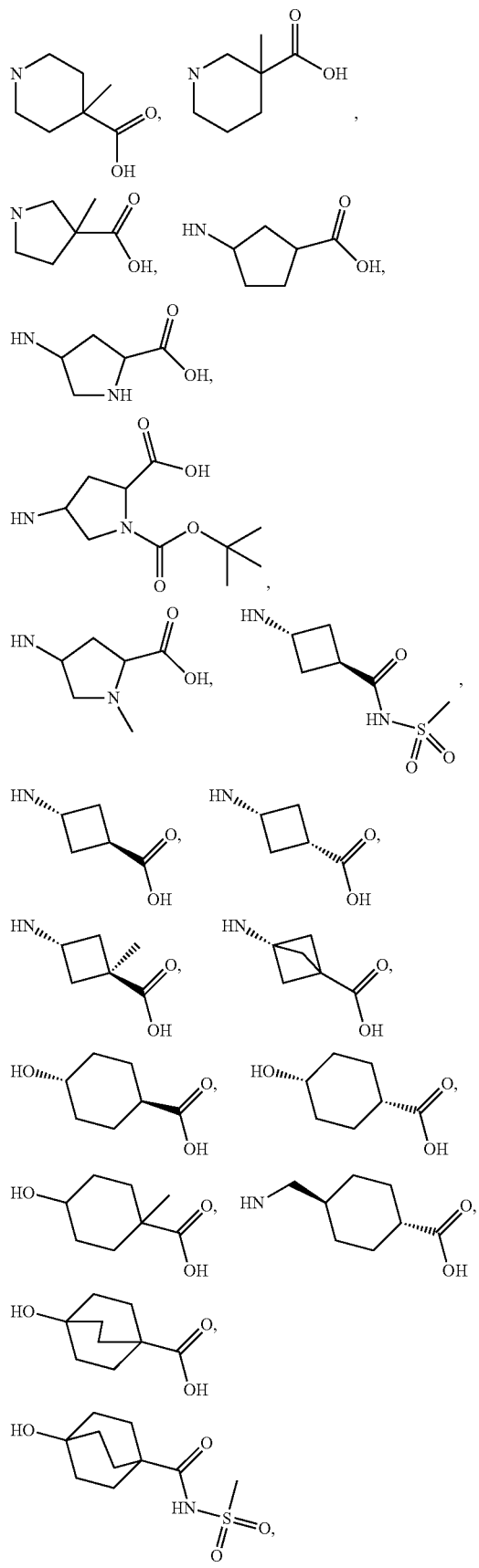
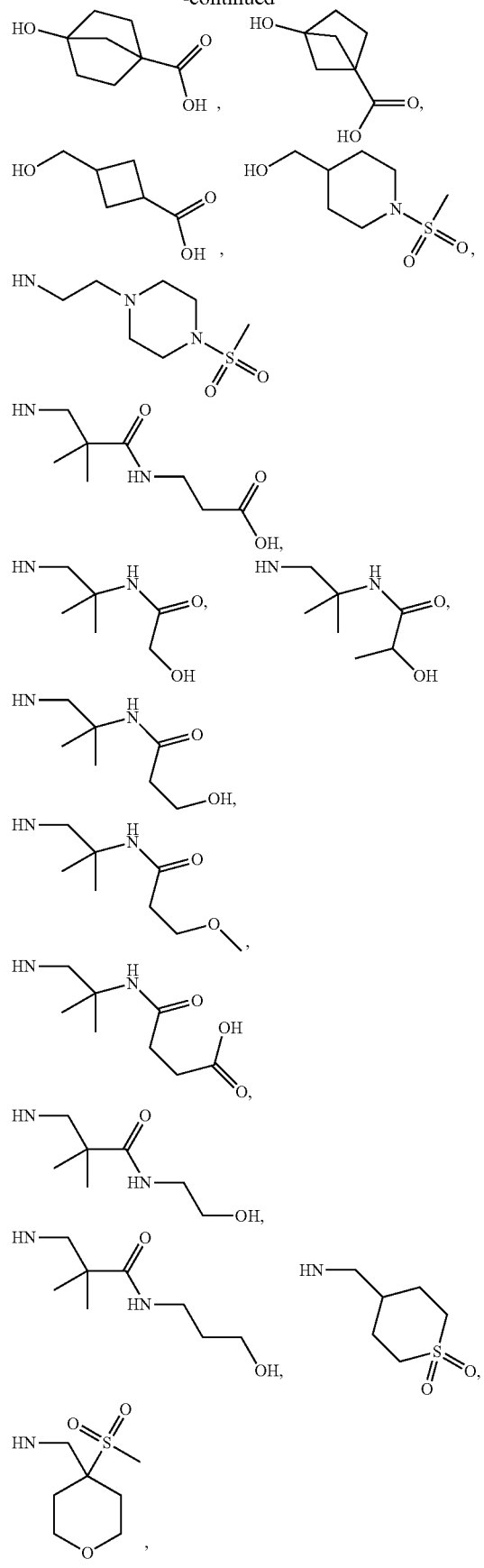

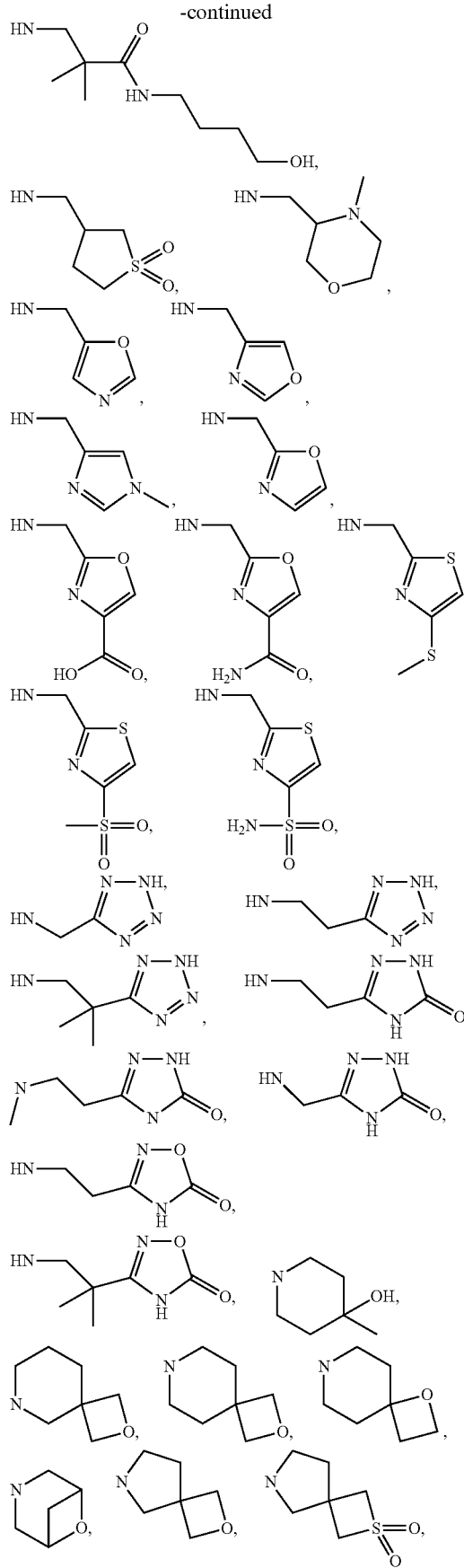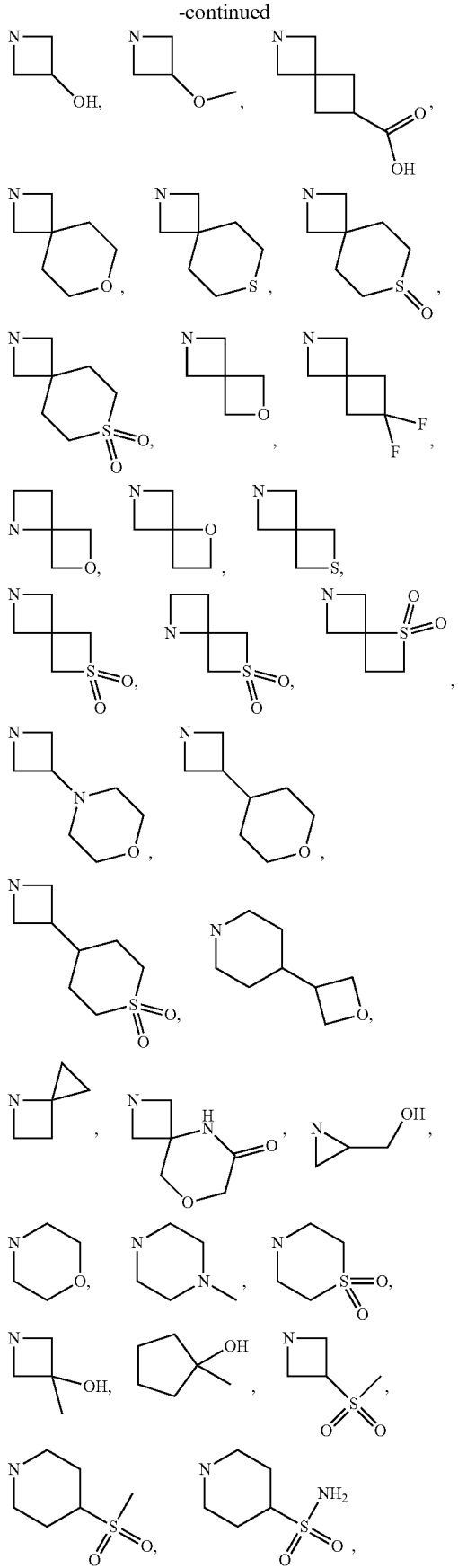

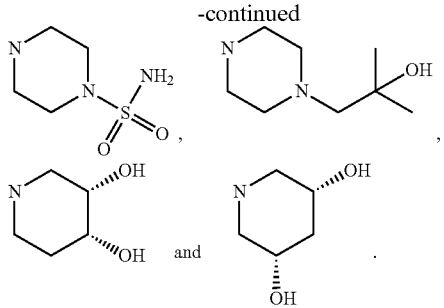

In an alternative preferred embodiment in combination with any of the above or below embodiments of the third alternative $NR^1R^2$ selected from $NH_2$, NHMe, NHEt, $NH^iPr$, $NH^tBu$, $NHCH_2CONH_2$, $NHCH_2CONMe_2$, $NHCH_2CH_2$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH(Me)CMe_2OH$, $NHCH_2CMe_2OH$, $NHCH_2CMe_2OMe$, $NHCH_2CMe_2CO_2H$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_3NHSO_2Me$, $NH(CH_2)_2O(CH_2)_2OH$, $NHCH_2CHMeOH$,

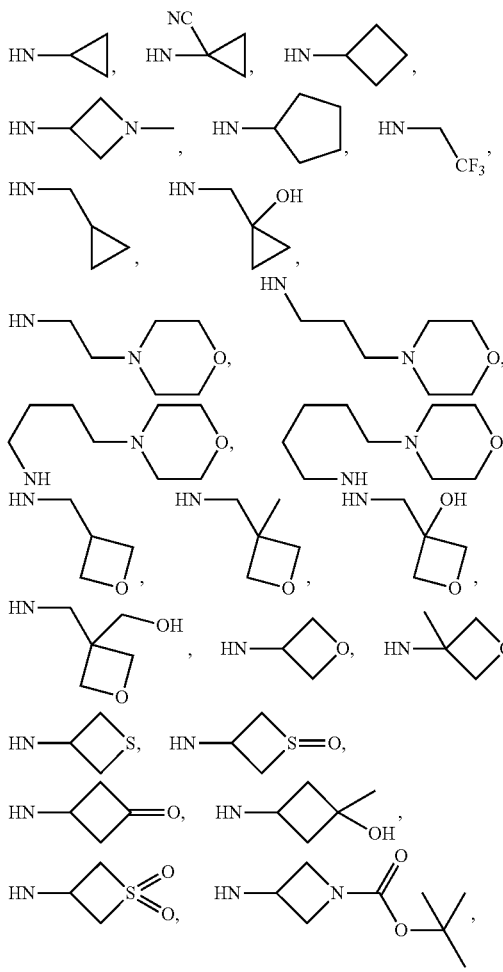

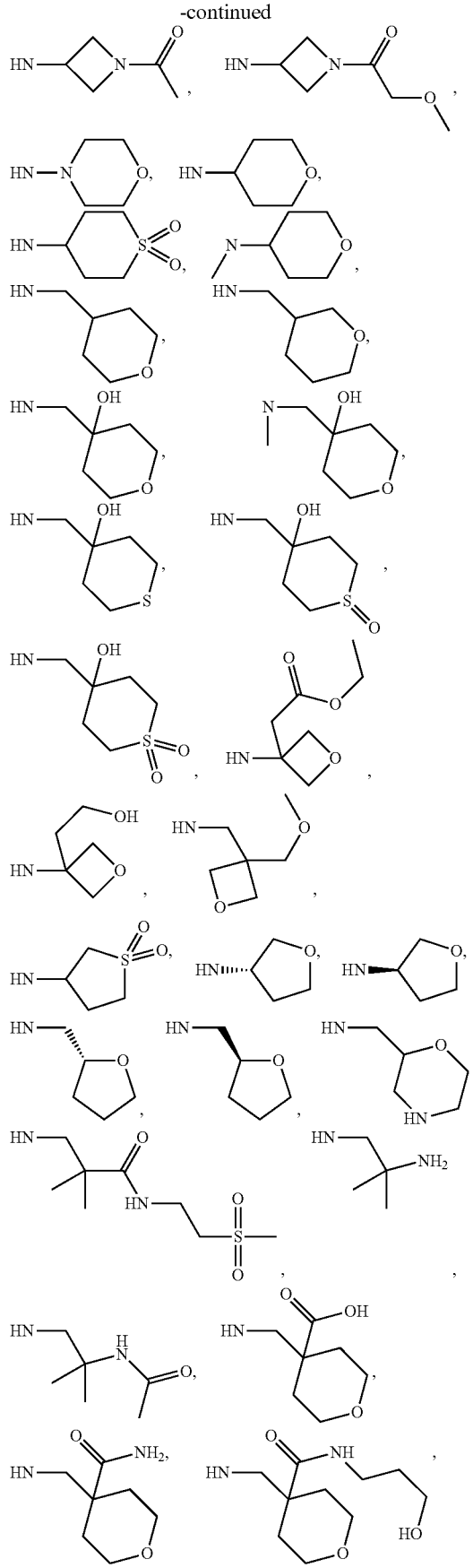

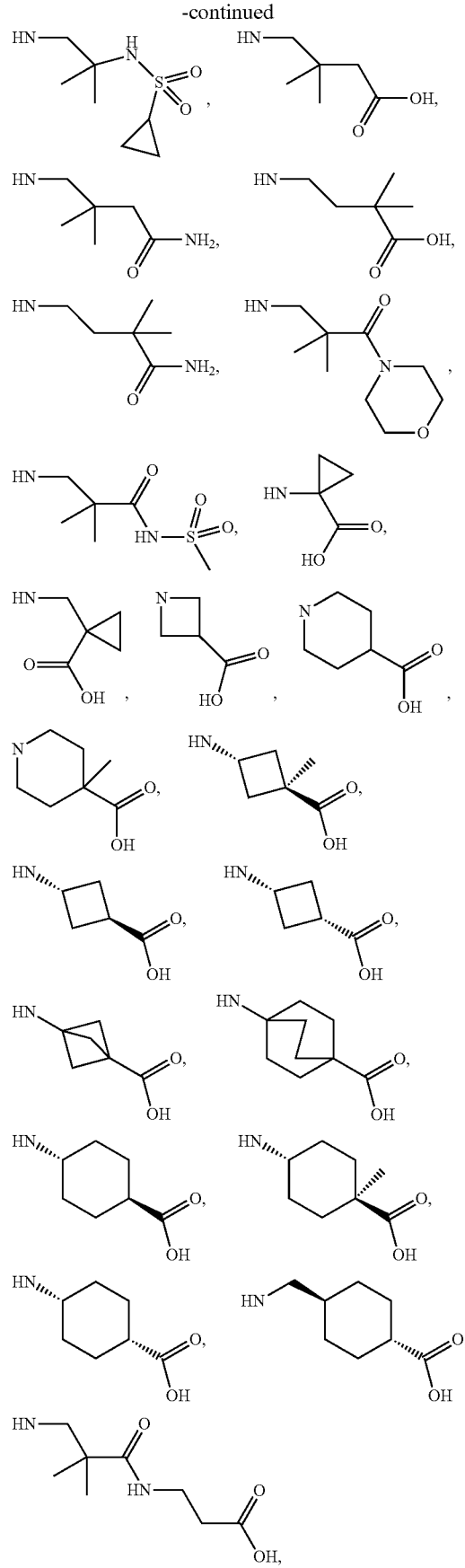
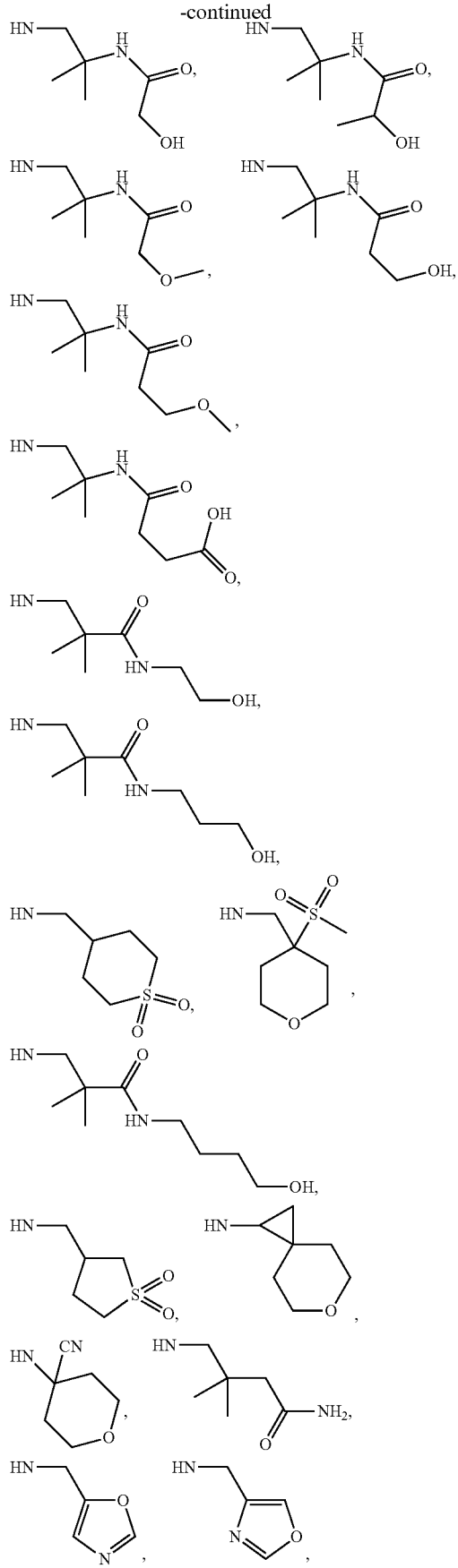

-continued
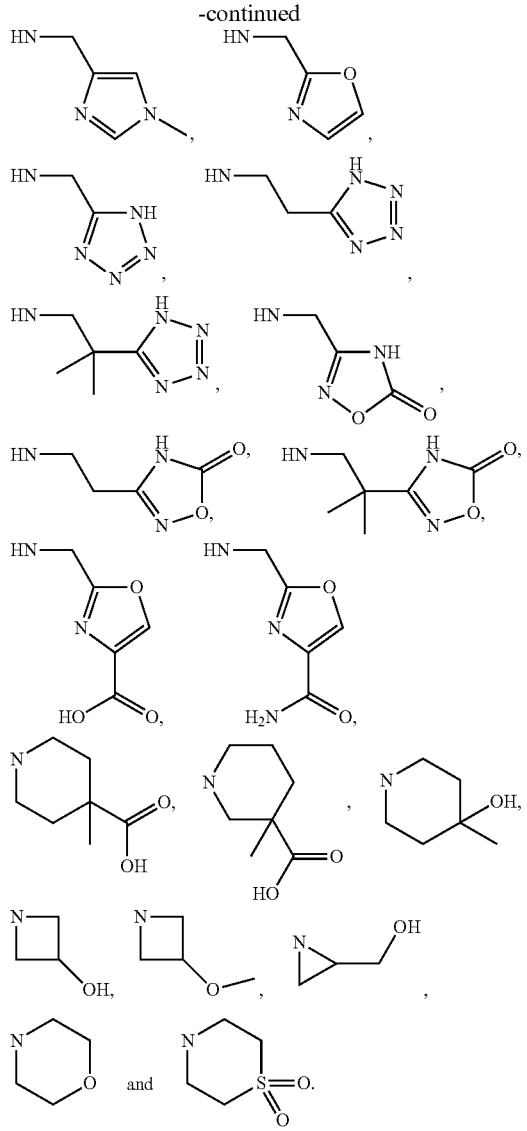
In a more preferred embodiment in combination with any of the above or below embodiments of the third alternative NR$^1$R$^2$ is selected from NHCH$_2$CH(CF$_3$)OH, NHCH$_2$C(Me)(CF$_3$)OH, NHCH$_2$CMe$_2$OH, NHCH$_2$CH$_2$CMe$_2$OH, NHCH$_2$CMe$_2$NHCH$_2$CF$_3$, NHC(CH$_2$OH)$_3$, NHCH$_2$CH(OH)CH$_2$OH, N(CH$_2$CH$_2$OH)$_2$,
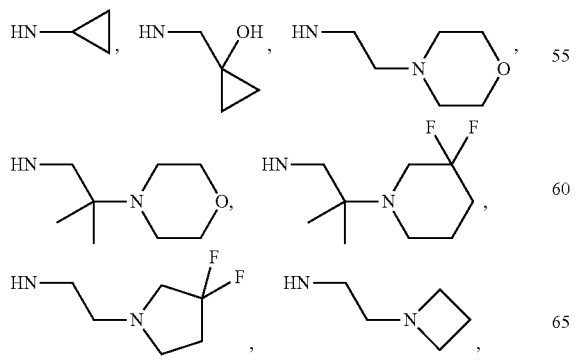
-continued
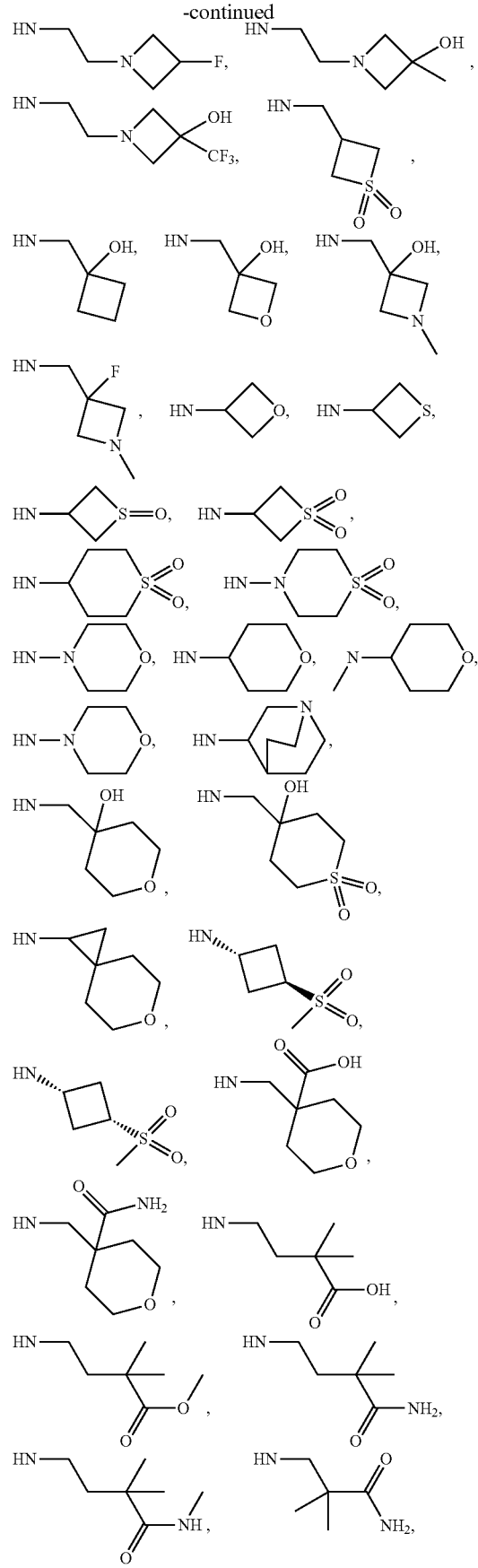

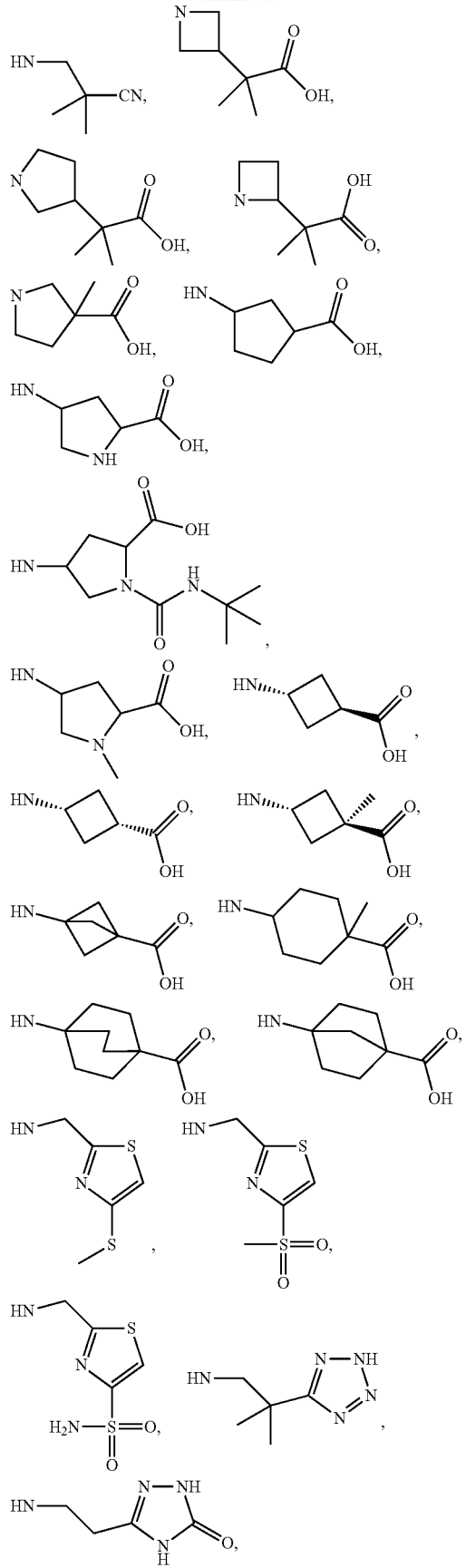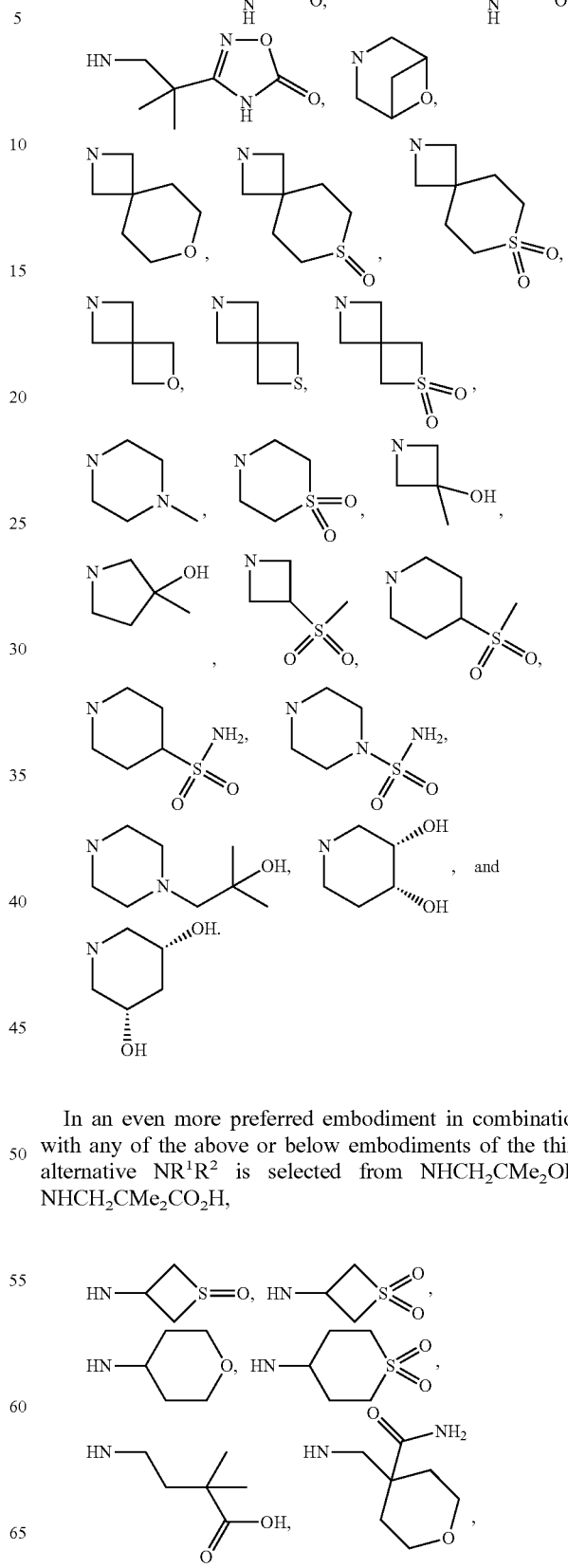
In an even more preferred embodiment in combination with any of the above or below embodiments of the third alternative $NR^1R^2$ is selected from $NHCH_2CMe_2OH$, $NHCH_2CMe_2CO_2H$,

109

-continued

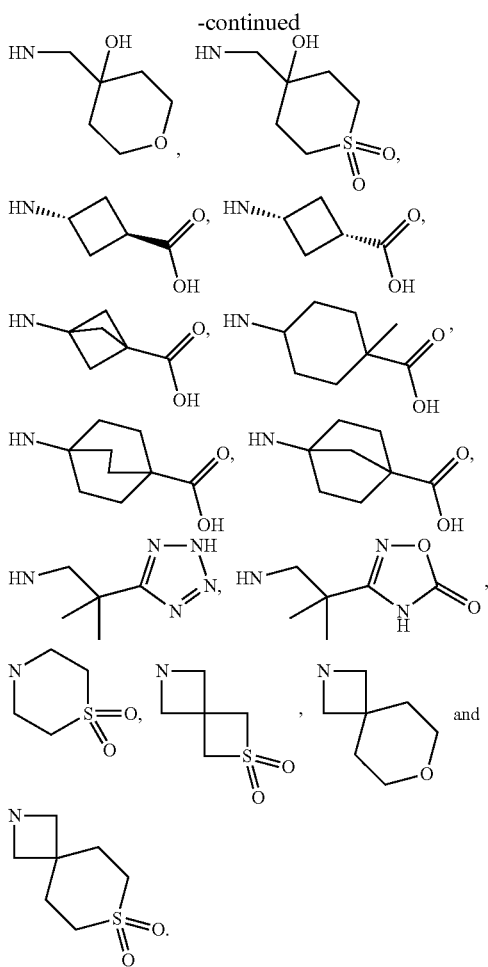

In a most preferred embodiment in combination with any of the above or below embodiments of the third alternative NR¹R² is selected from NHCH$_2$CMe$_2$OH, NHCH$_2$CMe$_2$CO$_2$H,

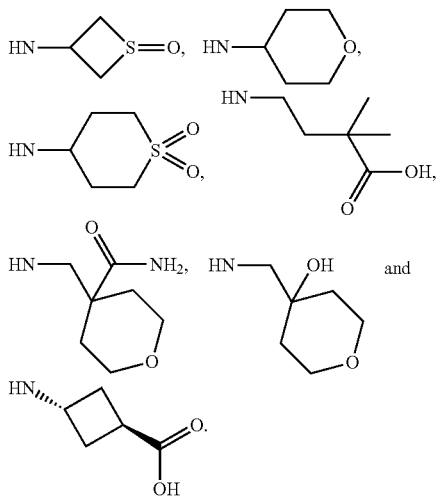

In another preferred embodiment in combination with any of the above or below embodiments of the third alternative R³ is a 6-10 membered mono- or bicyclic aryl or a 5-10

110 membered mono- or bicyclic heteroaryl containing 1 to 4 heteroatoms independently selected from the group consisting of N, O and S wherein aryl and heteroaryl are unsubstituted or substituted with 1 to 5 substituents independently selected from halogen, CN, $C_{1-6}$-alkyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-COOR$^{31}$, $C_{0-6}$-alkylene-C(O)R$^{31}$, $C_{0-6}$-alkylene-C(O)N(R$^{31}$)$_2$, $C_{0-6}$-alkylene-SO$_2$—N(R$^{31}$)$_2$, $C_{0-6}$-alkylene-SO$_2$—R$^{31}$, $C_{0-6}$-alkylene-(5-membered heteroaryl), $C_{0-6}$-alkylene-(6-membered heteroaryl), wherein alkyl, alkylene, cycloalkyl, heterocycloalkyl and heteroaryl are unsubstituted or substituted by 1 to 3 substituents independently selected from the group consisting of halogen, OH, oxo, =N—OR$^{32}$, N(R$^{31}$)$_2$, O—$C_{1-6}$-alkyl; COOH, CON(R$^{31}$)$_2$, CN, NR$^{31}$—COR$^{31}$, $C_{3-10}$-cycloalkyl, $C_{3-10}$-heterocycloalkyl, 6-10-membered mono- or bicyclic aryl, 6-10-membered mono- or bicyclic heteroaryl, or wherein two adjacent substituents may complete a 3- to 8-membered saturated or partially unsaturated ring containing carbon atoms and optionally containing 1 to 3 members selected from O, S, SO, SO$_2$ or NR$^{31}$, wherein the ring is unsubstituted or substituted with 1 to 4 substituents independently selected from halogen, oxo, =N—OR$^{32}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl.

In a more preferred embodiment in combination with any of the above or below embodiments of the third alternative R³ is a 6-membered aryl, a 10-membered bicyclic aryl, a 6-membered heteroaryl or 10-membered bicyclic heteroaryl containing 1 or 2 nitrogen atom wherein aryl and heteroaryl may be unsubstituted or substituted as above.

In another preferred embodiment in combination with any of the above or below embodiments of the third alternative R³ is selected from

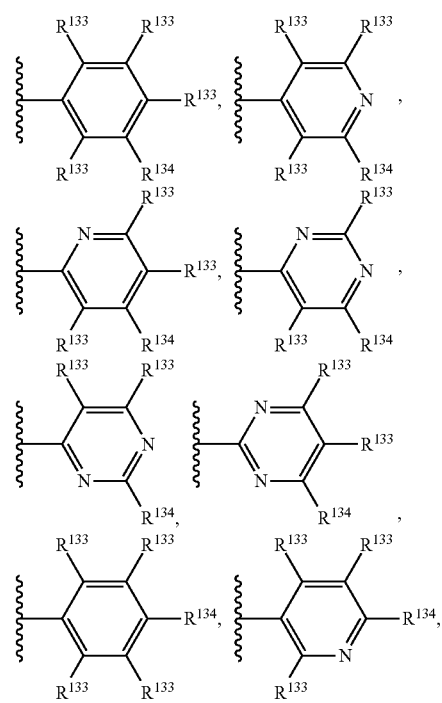

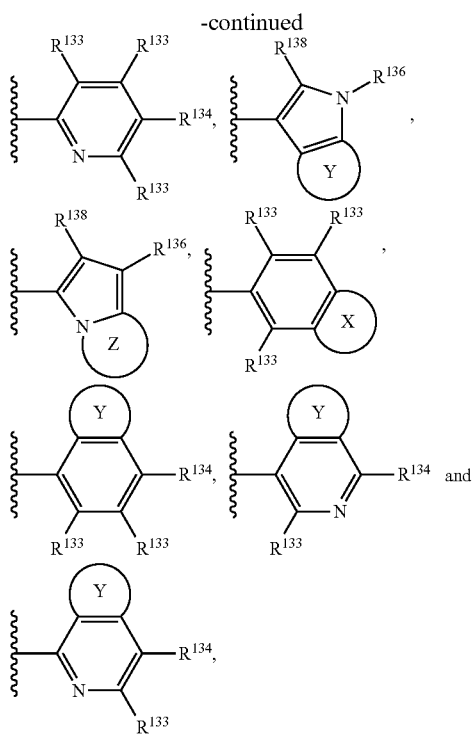

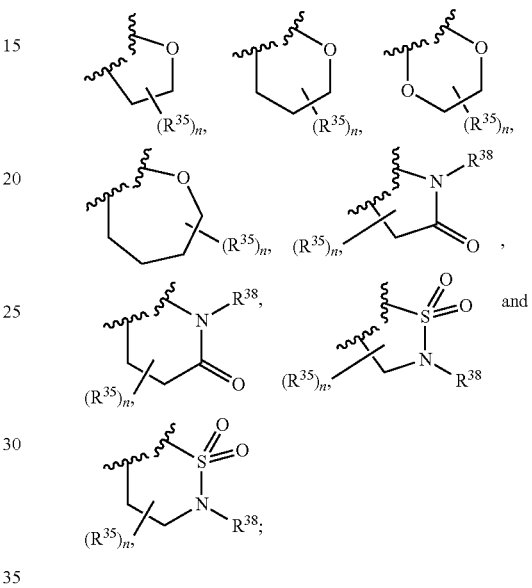

wherein
R$^{33}$ is independently selected from H, halogen, CN, C$_{1-6}$-alkyl, fluoro-C$_{1-6}$-alkyl, C$_{1-4}$-alkylene-OH, C$_{1-4}$-alkylene-O—C$_{1-3}$-alkyl, C$_{1-4}$-alkylene-O-fluoro-C$_{1-3}$-alkyl, OH, O—C$_{1-6}$-alkyl, O-fluoro-C$_{1-6}$-alkyl, NH—C$_{1-6}$-alkyl, NH-fluoro-C$_{1-6}$-alkyl, C$_{3-10}$-cycloalkyl,
  wherein alkylene is unsubstituted or substituted with 1 to 3 substituents selected from F and cycloalkyl is unsubstituted or substituted with 1 to 3 substituents independently selected from F, C$_{1-3}$-alkyl and fluoro-C$_{1-3}$-alkyl;
R$^{34}$ are independently selected from H, halogen, CN, C$_{1-6}$-alkyl, fluoro-C$_{1-6}$-alkyl, C$_{1-4}$-alkylene-OH, C$_{1-4}$-alkylene-O—C$_{1-3}$-alkyl, C$_{1-4}$-alkylene-O-fluoro-C$_{1-3}$-alkyl, OH, O—C$_{1-6}$-alkyl, O-fluoro-C$_{1-6}$-alkyl, NH—C$_{1-6}$-alkyl, NH-fluoro-C$_{1-6}$-alkyl, C$_{3-10}$-cycloalkyl, C$_{0-6}$-alkylene-C$_{3-10}$-heterocycloalkyl, 5-membered heteroaryl, 6-membered heteroaryl, C(O)N(R$^{37}$)$_2$ and SO$_2$N(R$^{37}$)$_2$,
  wherein alkylene is unsubstituted or substituted with 1 to 3 substituents selected from F and cycloalkyl, heterocycloalkyl and heteroaryl is unsubstituted or substituted with 1 to 3 substituents independently selected from F, C$_{1-3}$-alkyl, fluoro-C$_{1-3}$-alkyl, OH, O—C$_{1-3}$-alkyl, fluoro-O—C$_{1-3}$-alkyl;
R$^{35}$ is selected from halogen, C$_{1-6}$-alkyl, halo-C$_{1-6}$-alkyl, C$_{3-6}$-cycloalkyl, C$_{3-6}$-heterocycloalkyl, oxo, OH, O—C$_{1-6}$-alkyl and O-halo-C$_{1-6}$-alkyl;
R$^{36}$ is selected from C$_{1-6}$-alkyl, fluoro-C$_{1-6}$-alkyl, C(O)N(R$^{37}$)$_2$, SO$_2$N(R$^{37}$)$_2$;
R$^{37}$ is independently selected from H, C$_{1-6}$-alkyl, halo-C$_{1-6}$-alkyl, C$_{0-4}$-alkylene-C$_{3-6}$-cycloalkyl, C$_{0-4}$-alkylene-C$_{3-6}$-heterocycloalkyl, wherein alkyl and alkylene is unsubstituted or substituted with 1 to 4 substituents selected from halogen, OH, O—C$_{1-3}$-alkyl, CN, CONH$_2$; and cycloalkyl or heterocycloalkyl is unsubstituted or substituted with 1 to 3 substituents independently selected from F, CN, OH, oxo, C$_{1-3}$-alkyl and fluoro-C$_{1-3}$-alkyl;

or wherein two R$^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, C$_{1-4}$-alkyl and halo-C$_{1-4}$-alkyl;

R$^{38}$ is selected from H, C$_{1-3}$-alkyl and fluoro-C$_{1-3}$-alkyl;

X is an annelated saturated heterocycle selected from the group consisting of

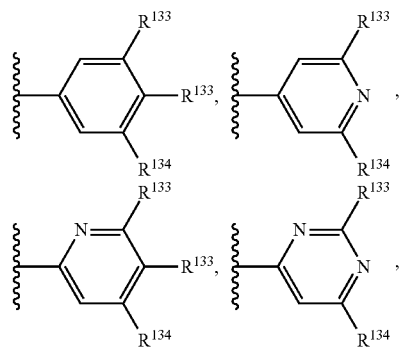

Y is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from halogen, C$_{1-3}$-alkyl and fluoro-C$_{1-3}$-alkyl;

Z is an annelated 6-membered cycle forming a heteroaryl containing 1 to 2 nitrogen atoms, wherein the heteroaryl is unsubstituted or substituted with 1 to 3 substituents selected from fluoro, C$_{1-3}$-alkyl and fluoro-C$_{1-3}$-alkyl;

n is selected from 1 to 4.

In a more preferred embodiment in combination with any of the above or below embodiments of the third alternative R$^3$ is selected from -continued

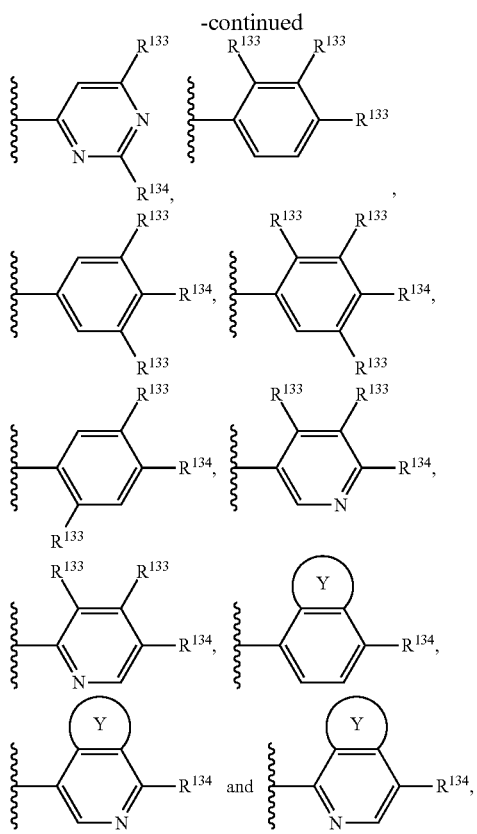

wherein
$R^{33}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl, $C(O)N(R^{37})_2$,
  wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;
$R^{34}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{37})_2$, $SO_2N(R^{37})_2$,
  wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;
$R^{37}$ is independently selected from H, $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl,
  wherein alkyl and alkylene is unsubstituted or substituted with 1 to 4 substituents selected from halogen, OH, O—$C_{1-3}$-alkyl, CN, $CONH_2$; and
  wherein cycloalkyl or heterocycloalkyl is unsubstituted or substituted with 1 to 3 substituents independently selected from F, CN, OH, oxo, O—$C_{1-3}$-alkyl, $C_{1-3}$-alkyl and fluoro-$C_{1-3}$-alkyl;
or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;
Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or $CF_3$.

In an even more preferred embodiment in combination with any of the above or below embodiments of the third alternative $R^3$ is selected from

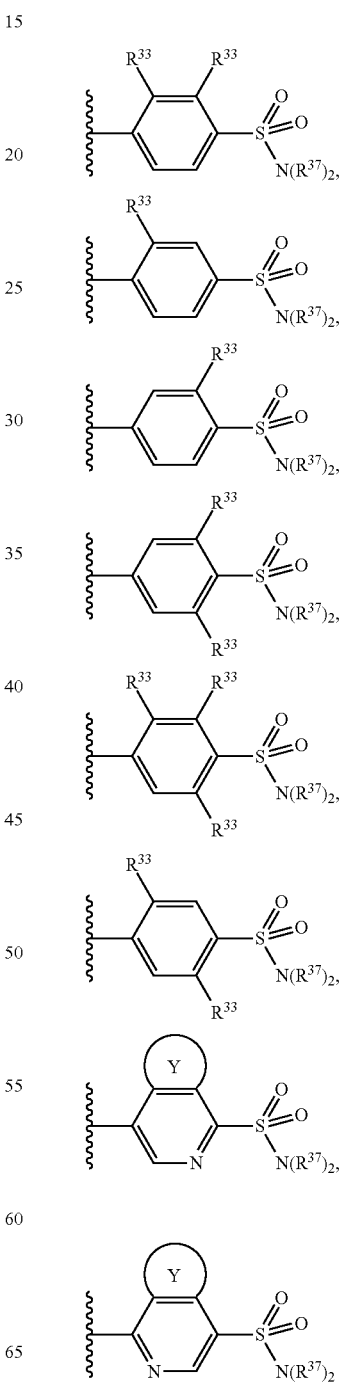

-continued

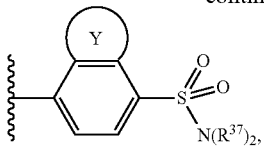

wherein R³³ is independently selected from H, halogen, C₁₋₆-alkyl, fluoro-C₁₋₆-alkyl, C₁₋₄-alkylene-OH, C₁₋₄-alkylene-O—C₁₋₃-alkyl, O—C₁₋₆-alkyl, and O-fluoro-C₁₋₆-alkyl, more preferably R³³ is independently selected from fluoro, chloro, CF₃, CHF₂, OCF₃, OCHF₂, methyl, ᵗbutyl and CMe₂OH;
one R³⁷ is selected from H, C₁₋₆-alkyl, fluoro-C₁₋₆-alkyl and the other R³⁷ is selected from C₁₋₆-alkyl, fluoro-C₁₋₆-alkyl, C₀₋₄-alkylene-C₃₋₆-cycloalkyl, C₀₋₄-alkylene-C₃₋₆-heterocycloalkyl, wherein alkyl and alkylene is unsubstituted or substituted with a substituent selected from halogen, OH, O—C₁₋₃-alkyl, CN, CONH₂; and cycloalkyl or heterocycloalkyl is unsubstituted or substituted with 1 to 3 substituents independently selected from F, CN, CONH₂, OH, oxo, C₁₋₃-alkyl and fluoro-C₁₋₃-alkyl,
or wherein two R³⁷ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, C₁₋₄-alkyl and halo-C₁₋₄-alkyl;
Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or CF₃.

In a most preferred embodiment in combination with any of the above or below embodiments of the third alternative R³ is selected from

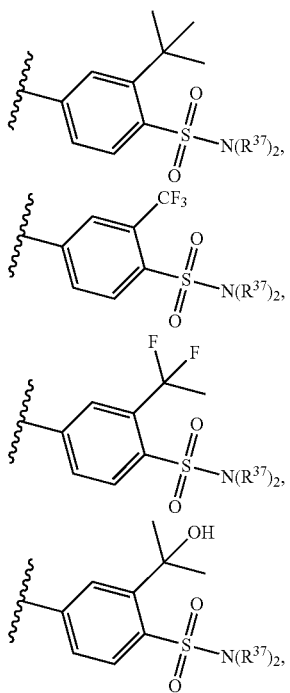

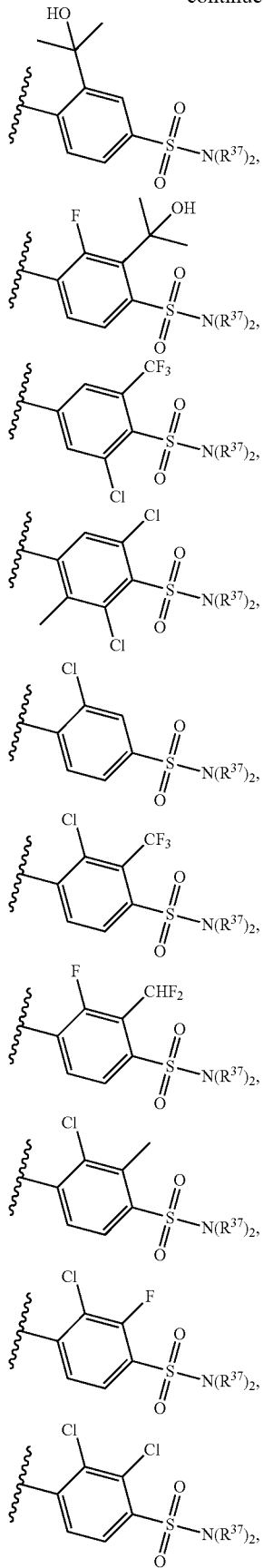

-continued
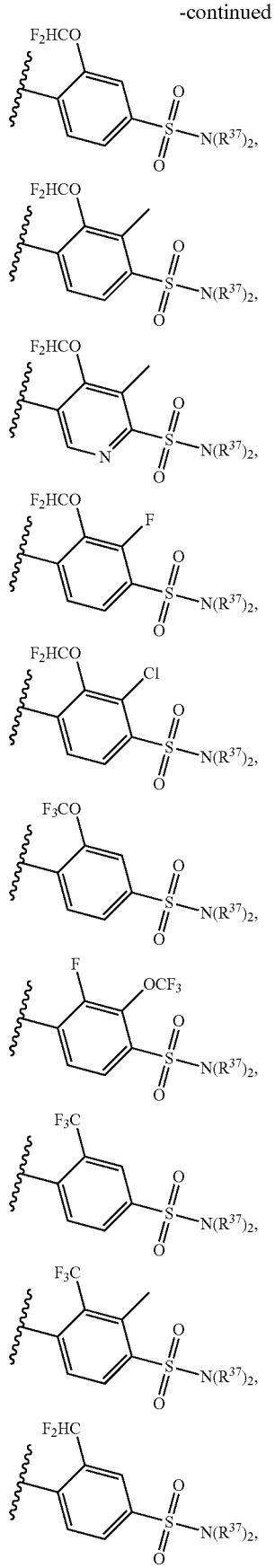
-continued
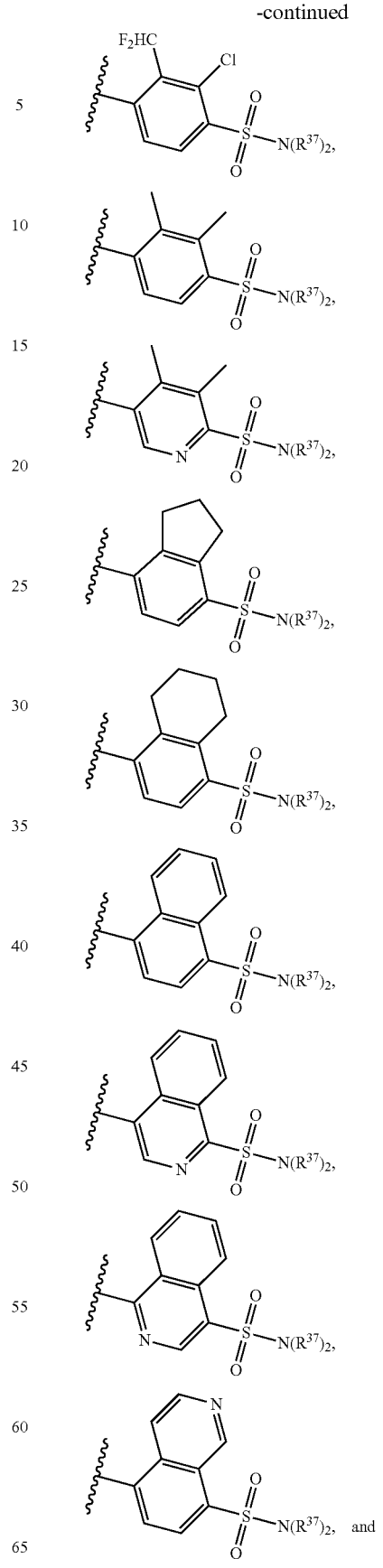

-continued

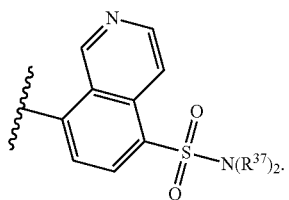

In another preferred embodiment in combination with any of the above or below embodiments of the third alternative $N(R^{37})_2$ is selected from

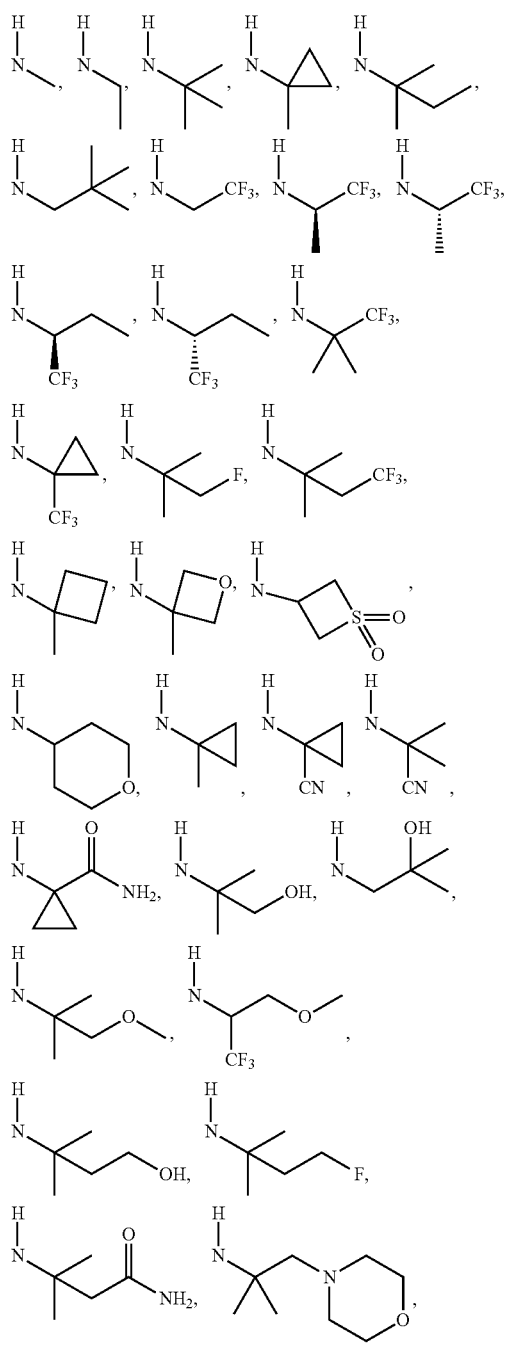

-continued

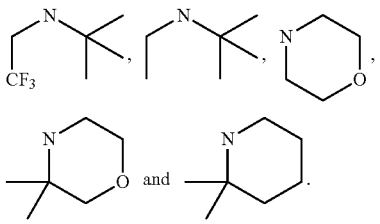

In a more preferred embodiment in combination with any of the above or below embodiments of the third alternative $N(R^{37})_2$ is selected from

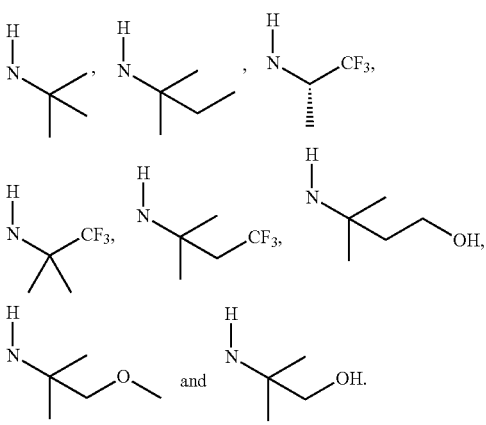

In another preferred embodiment in combination with any of the above or below embodiments of the third alternative $R^3$ is selected from

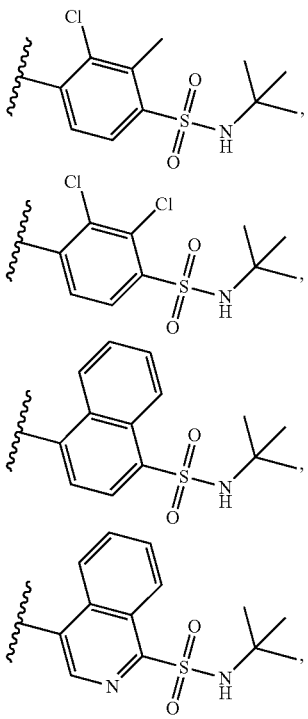

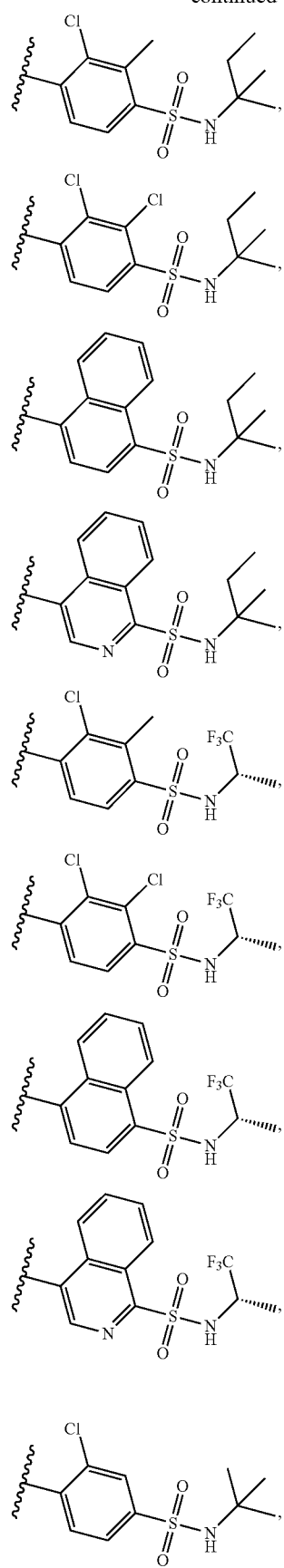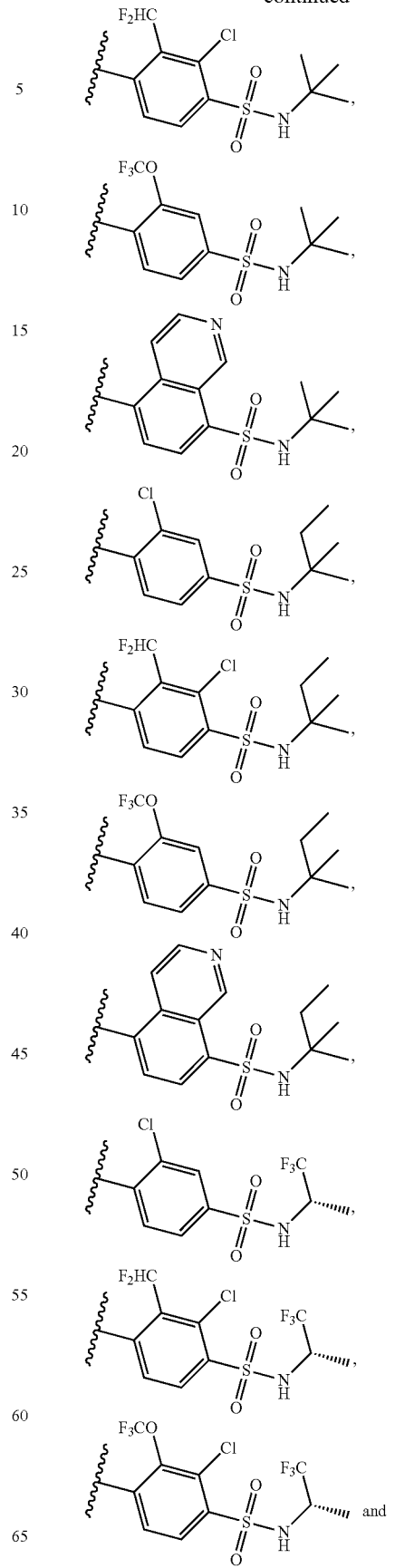

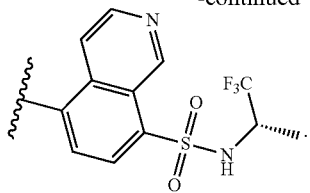

In another preferred embodiment in combination with any of the above or below embodiments of the third alternative $R^3$ is selected from

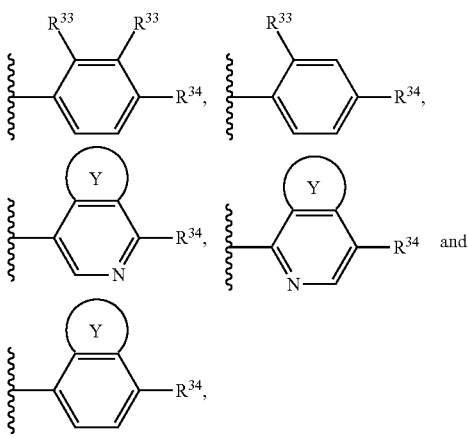

wherein $R^{33}$ is independently selected from H, halogen, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, and O-fluoro-$C_{1-6}$-alkyl, more preferably $R^{33}$ is independently selected from fluoro, chloro, $CF_3$, $CHF_2$, $OCF_3$, $OCHF_2$, methyl, $^t$butyl and $CMe_2OH$;

$R^{34}$ is selected from $C_{1-6}$-alkyl, halo-$C_{1-6}$-alkyl and $C_{0-6}$-alkylene-$C_{3-10}$-heterocycloalkyl,
  wherein alkyl, alkylene and heterocycloalkyl are unsubstituted or substituted by 1 to 3 substituents independently selected from the group consisting of halogen, $C_{1-6}$-alkyl, halo-$C_{1-6}$-alkyl, OH, oxo, $N(R^{31})_2$, O—$C_{1-6}$-alkyl, $C_{3-10}$-cycloalkyl, $C_{3-10}$-heterocycloalkyl; and Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or $CF_3$.

In more preferred embodiment in combination with any of the above or below embodiments of the third alternative $R^3$ is selected from

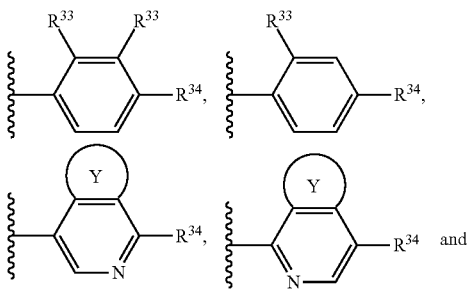

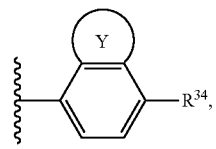

wherein $R^{33}$ is independently selected from H, halogen, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, and O-fluoro-$C_{1-6}$-alkyl, more preferably $R^{33}$ is independently selected from fluoro, chloro, $CF_3$, $CHF_2$, $OCF_3$, $OCHF_2$, methyl, $^t$butyl and $CMe_2OH$;

$R^{34}$ is selected from

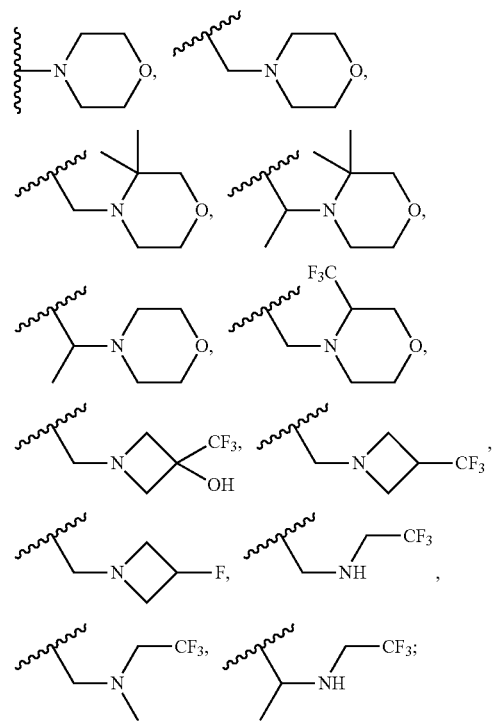

more preferably $R^{34}$ is

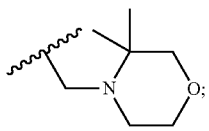 [SMILES: *CN1CCOCC1(C)C]

Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or $CF_3$.

In an alternative preferred embodiment in combination with any of the above or below embodiments of the third alternative $R^3$ is selected from

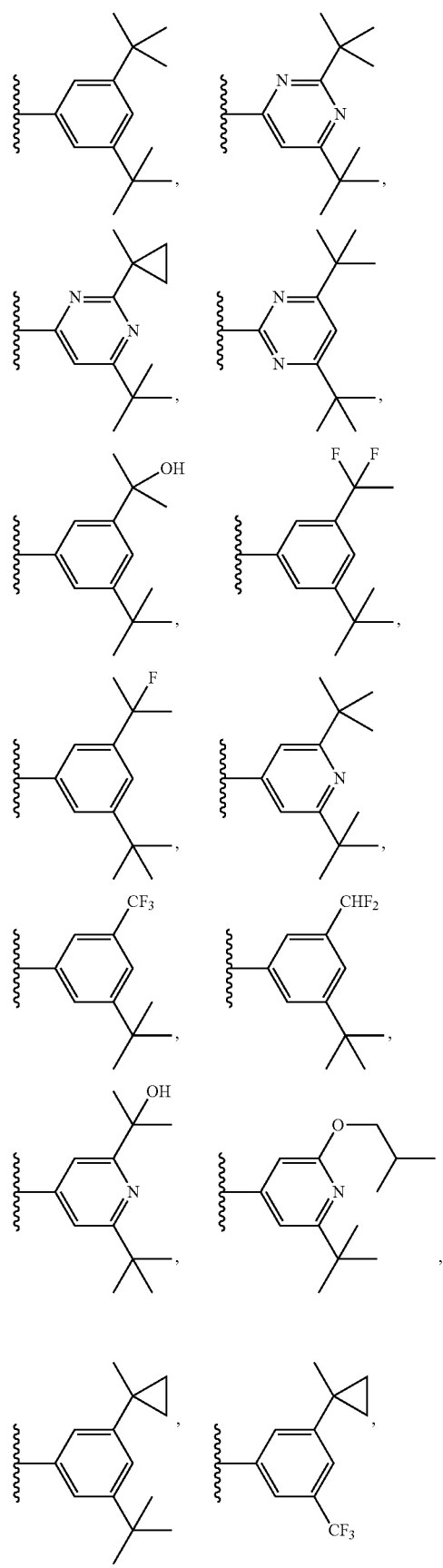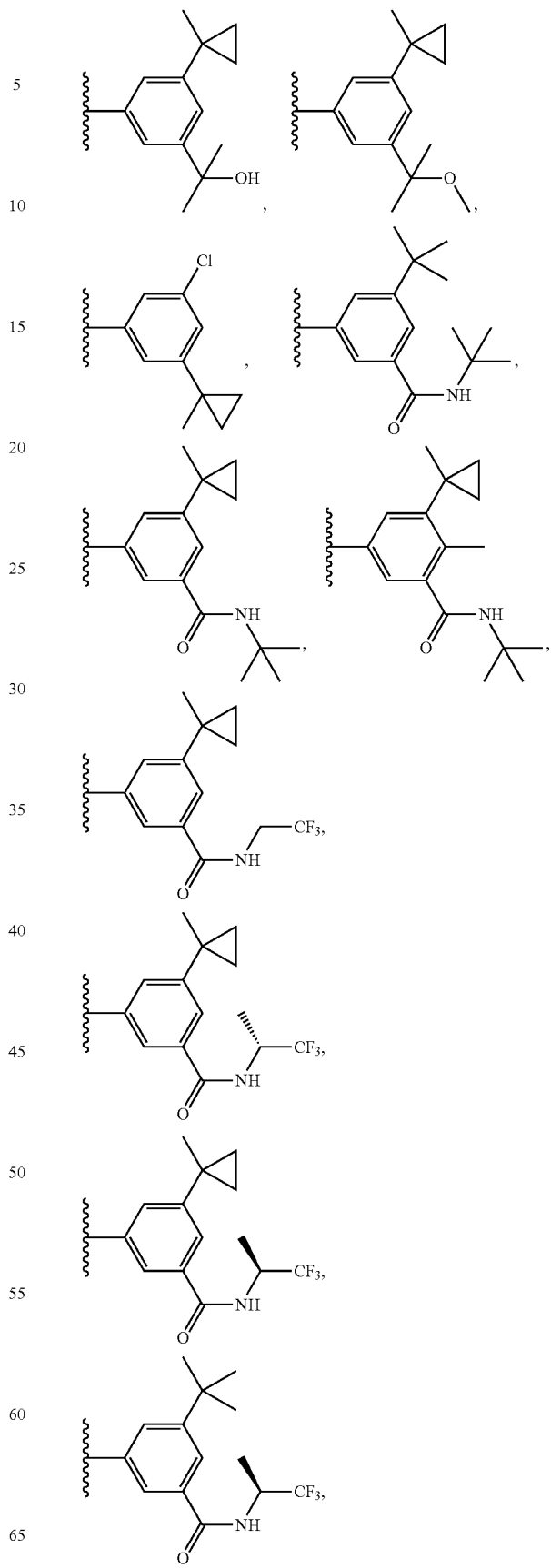

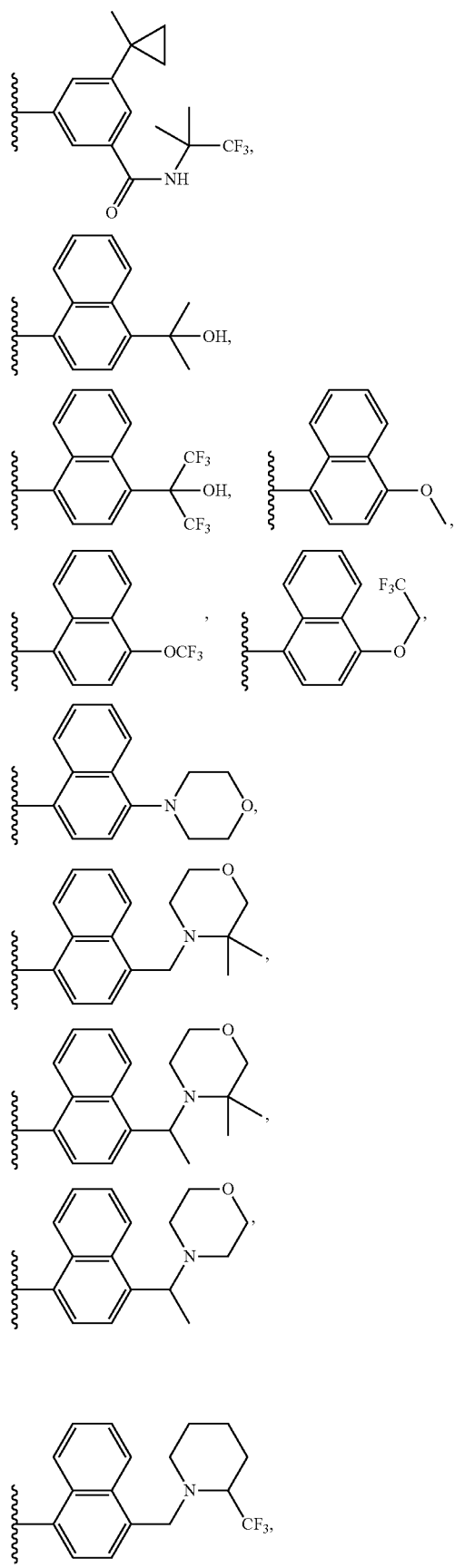
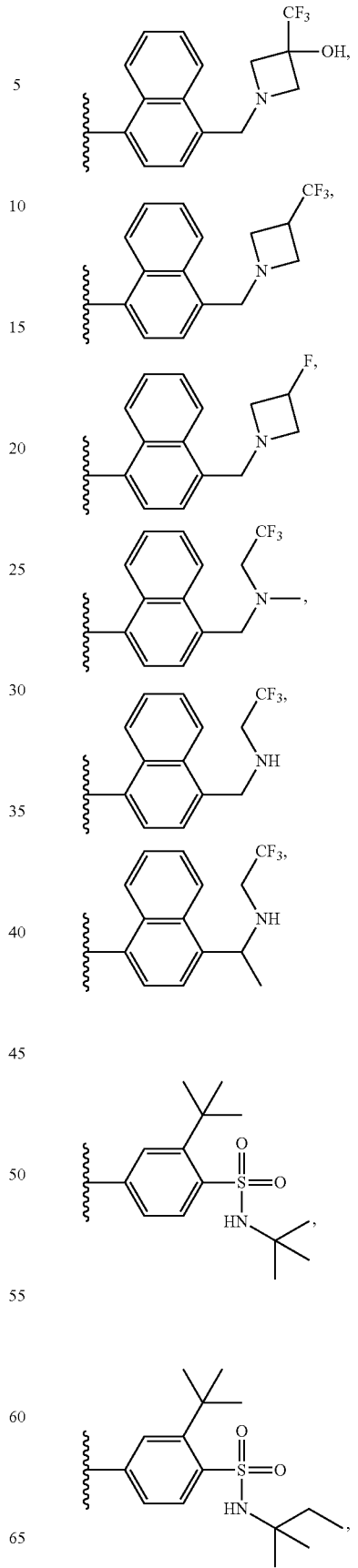

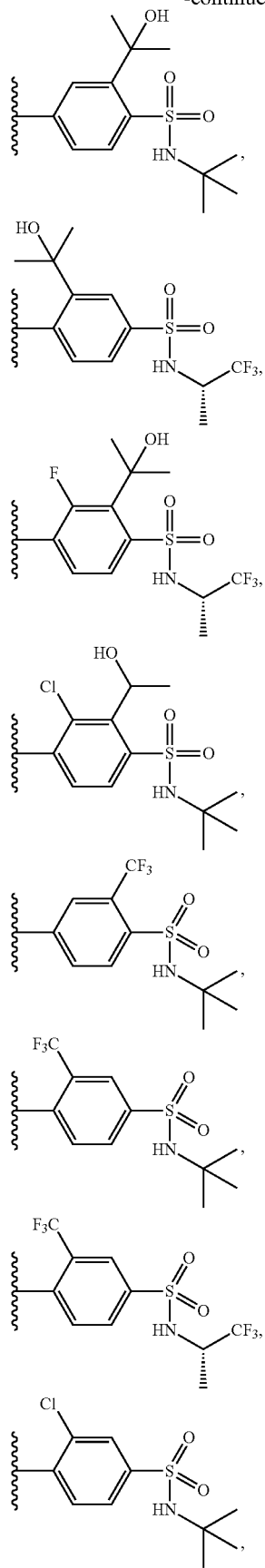
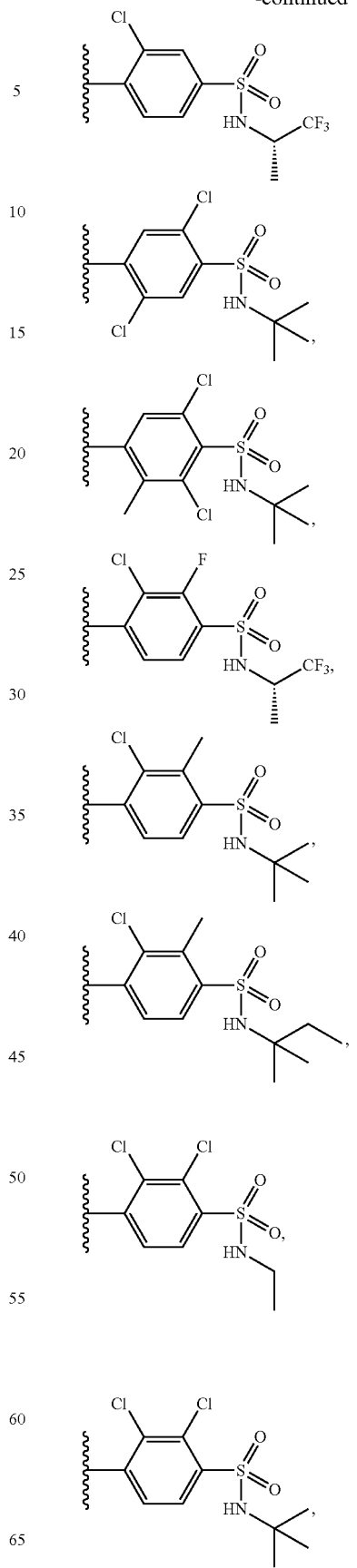

131
-continued
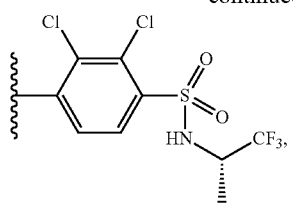
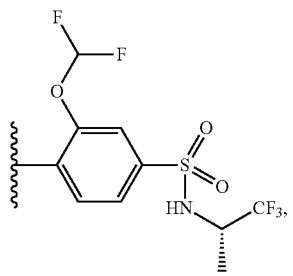
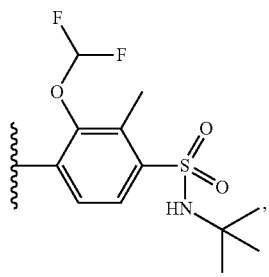
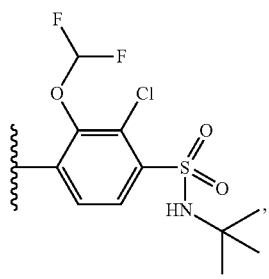
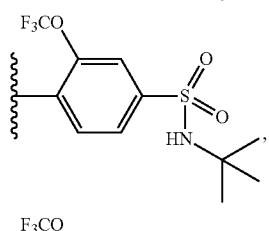
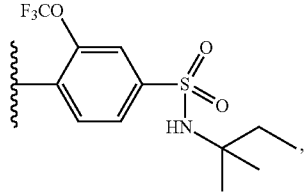
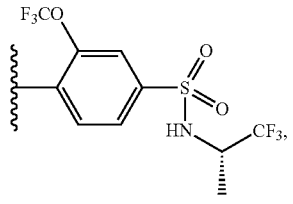
132
-continued
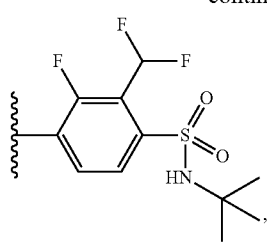
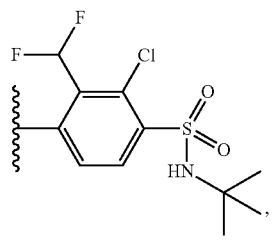
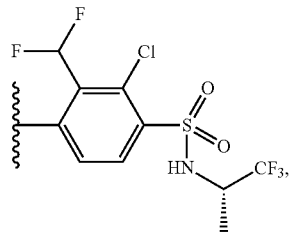
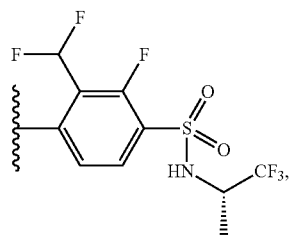
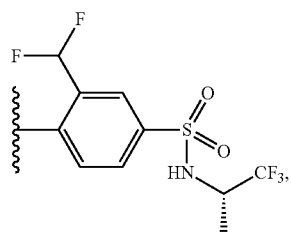
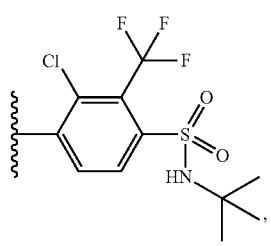
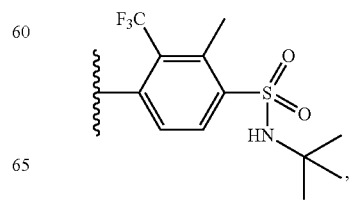

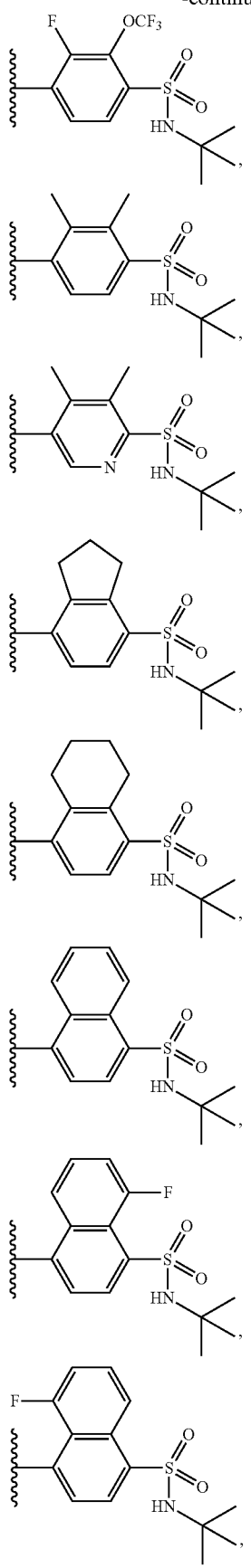
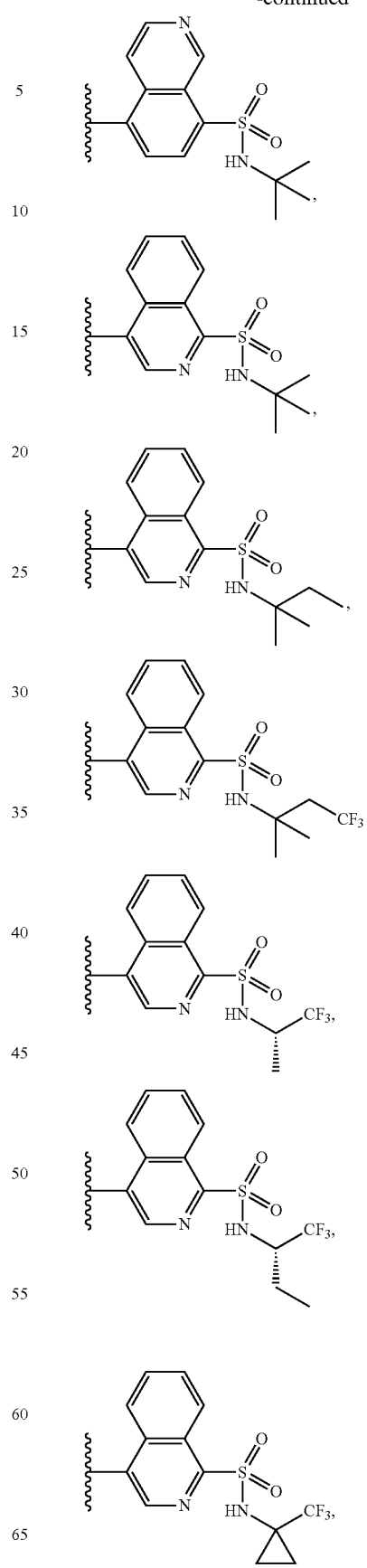

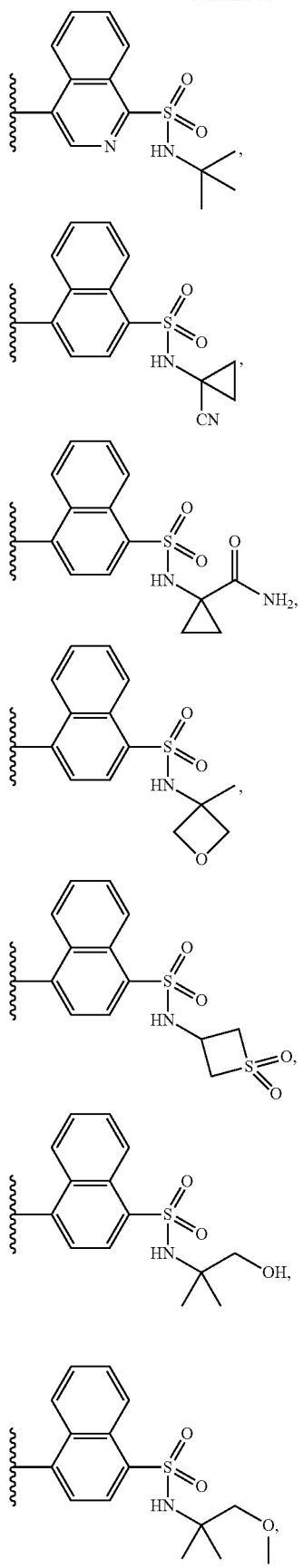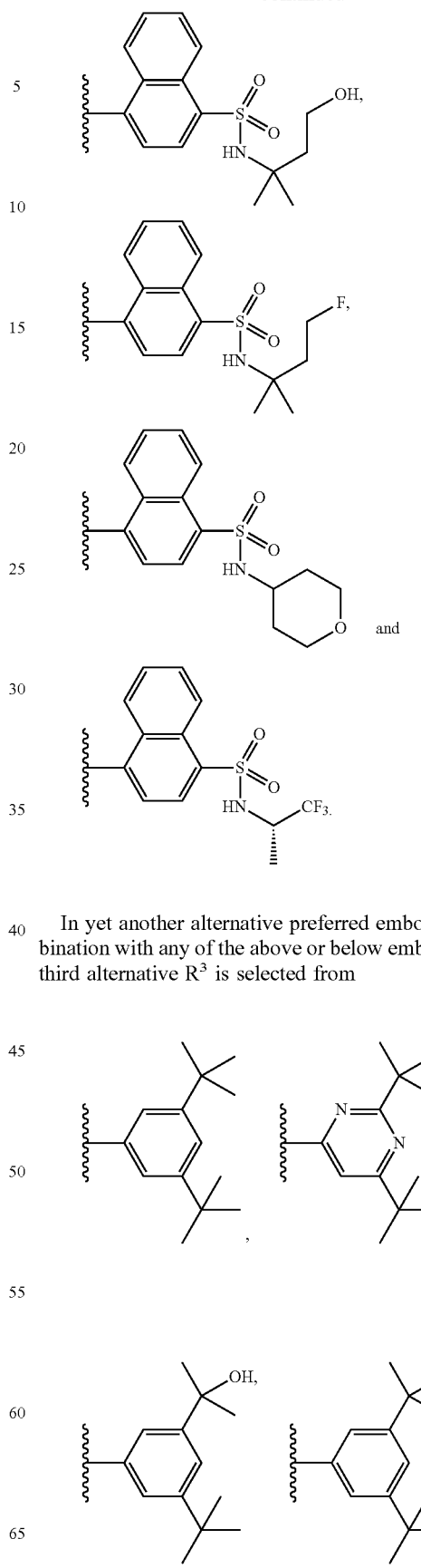
In yet another alternative preferred embodiment in combination with any of the above or below embodiments of the third alternative R³ is selected from

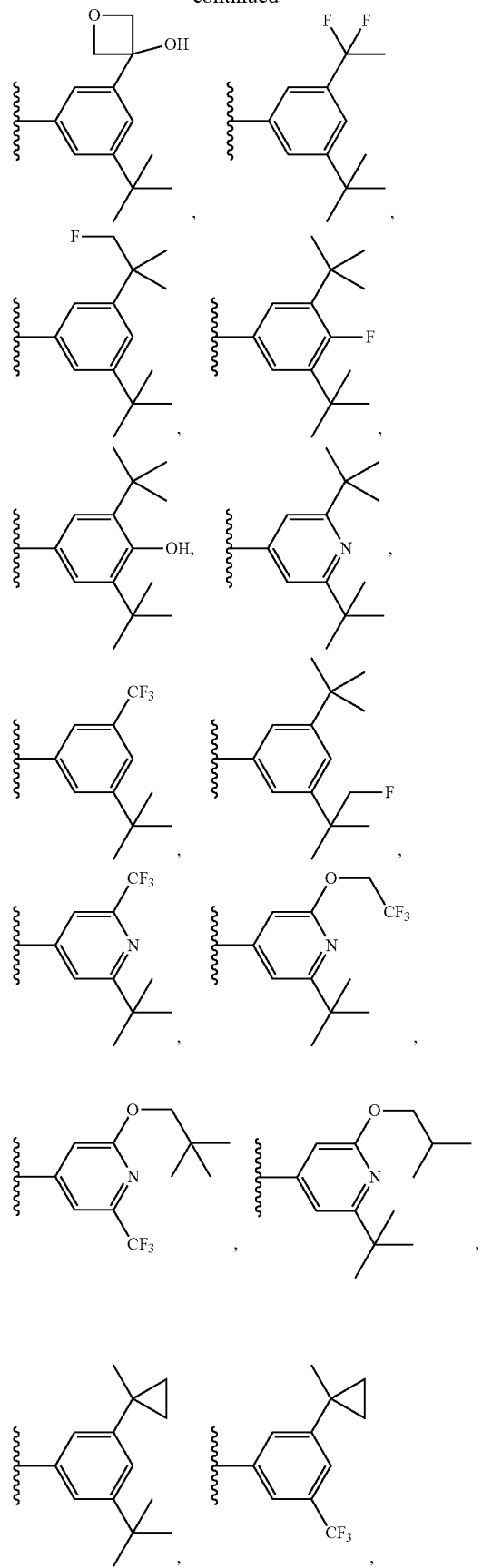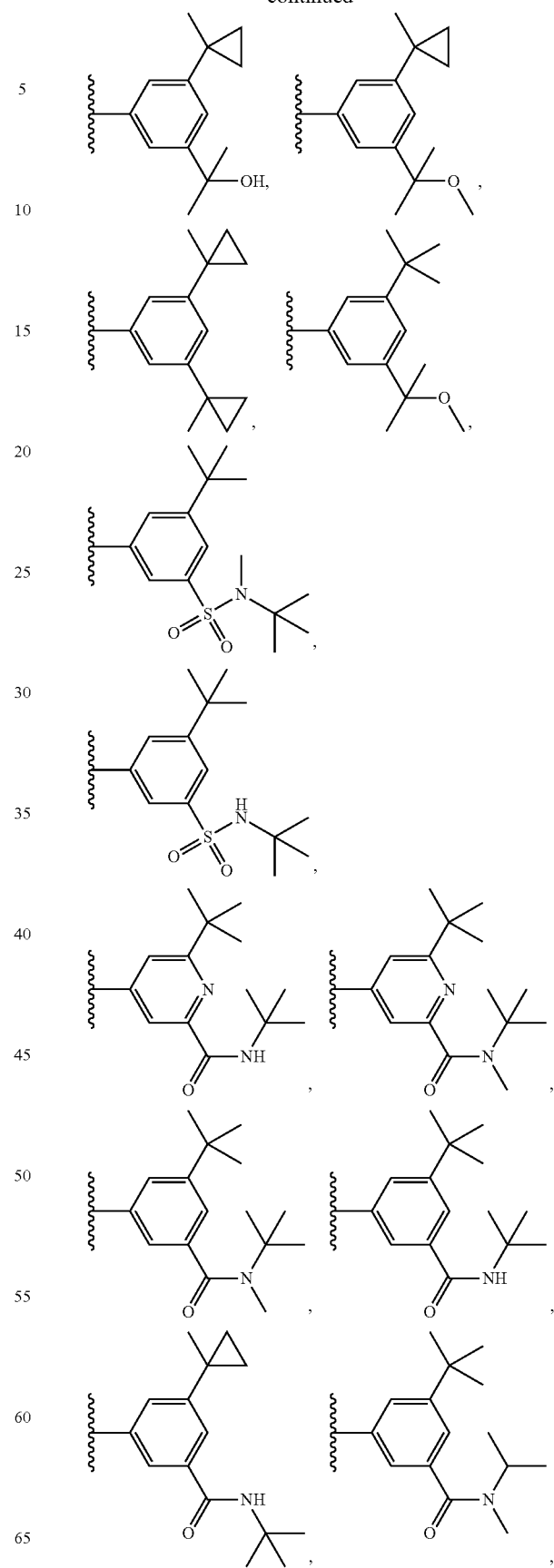

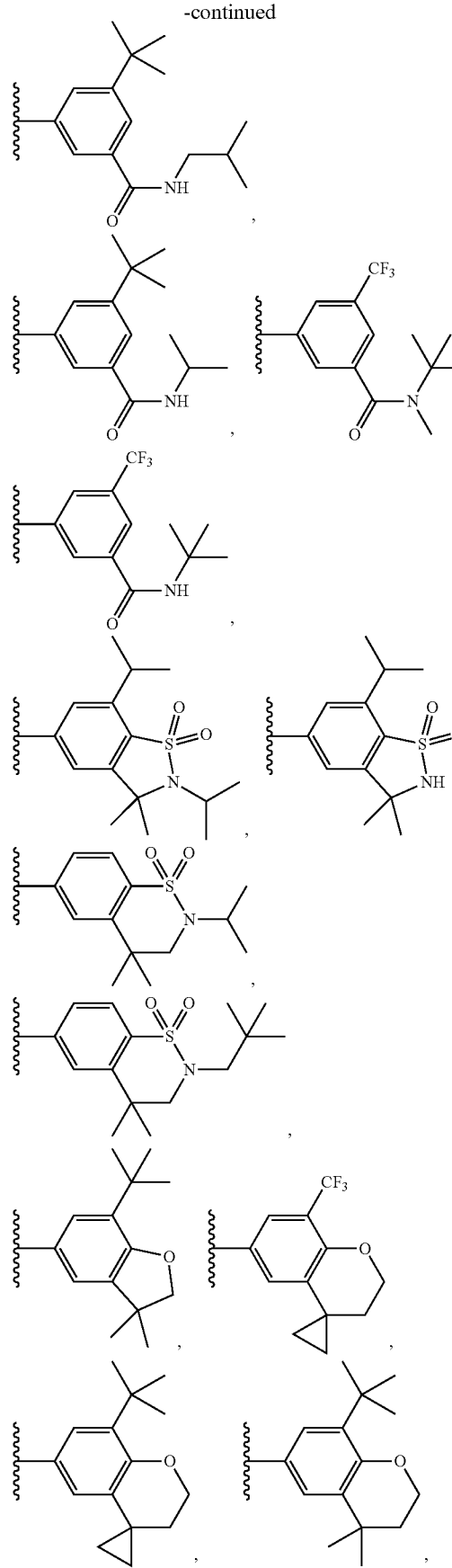
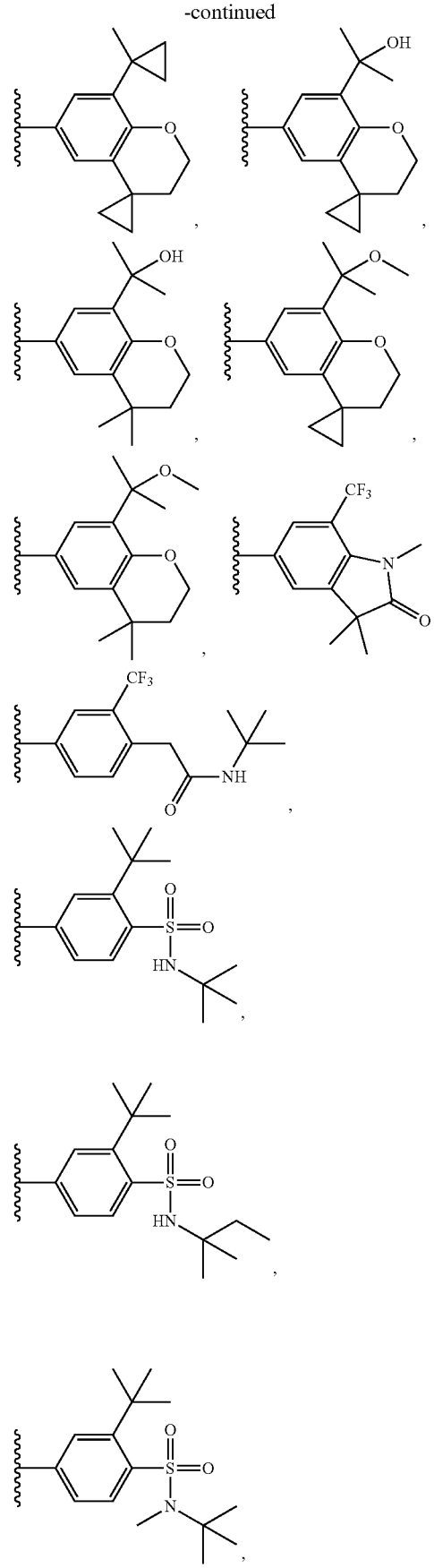

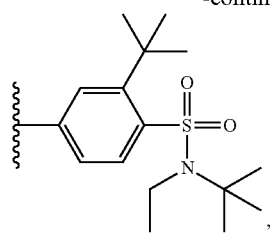

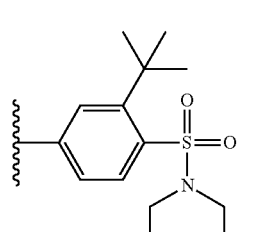
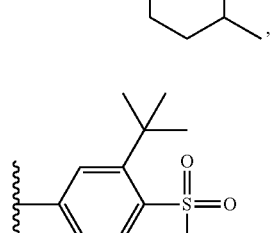
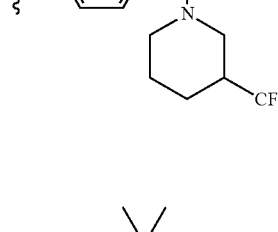
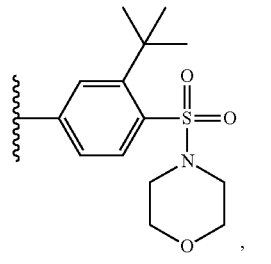
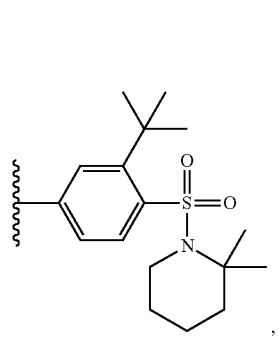
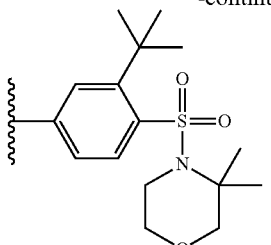
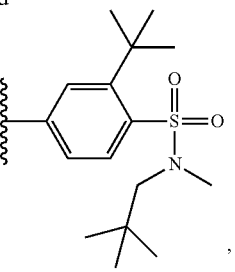
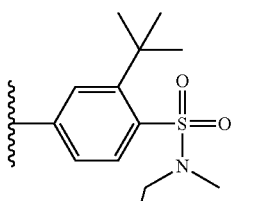
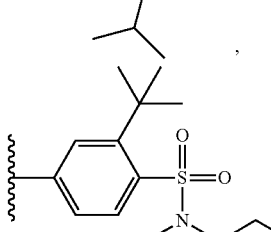
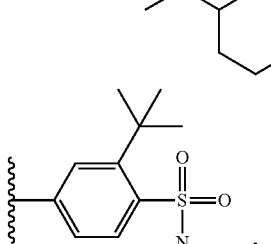

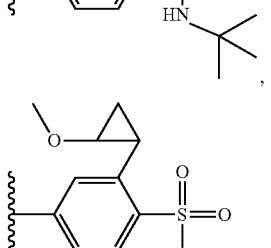
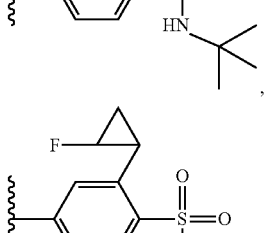
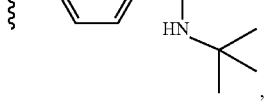

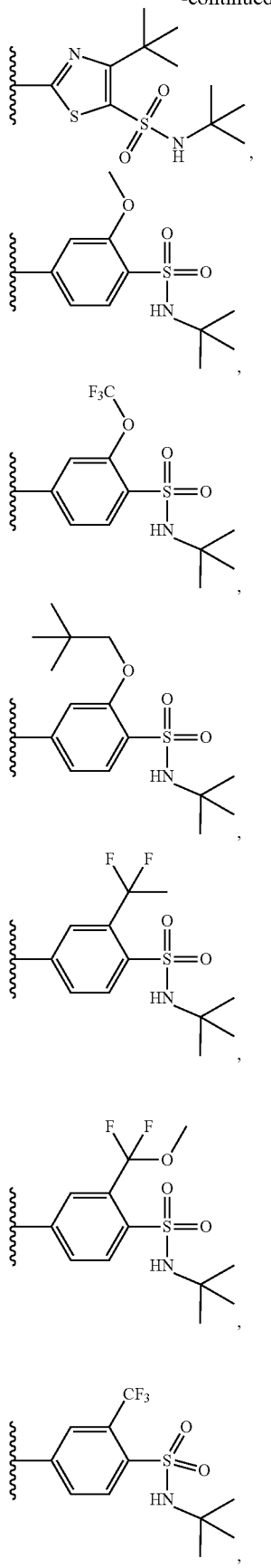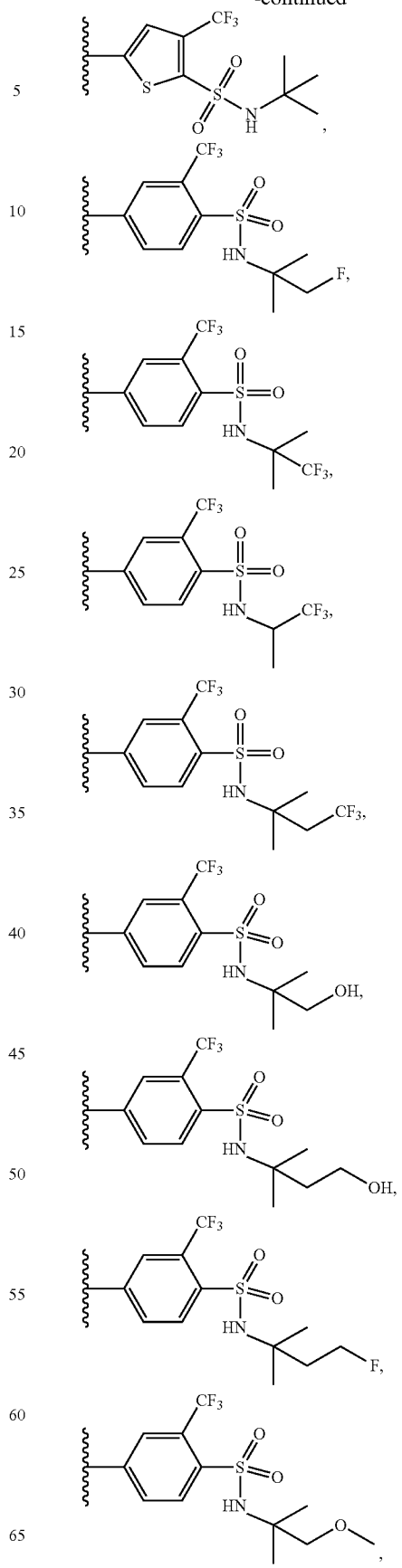

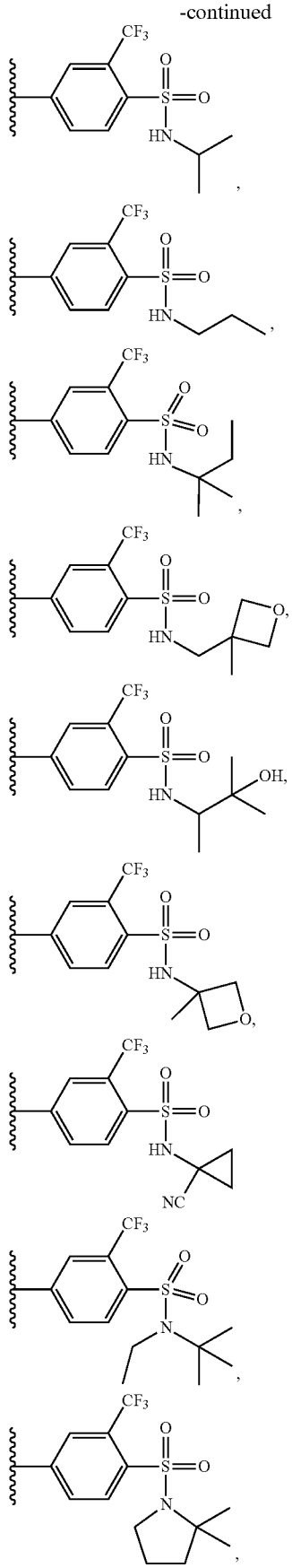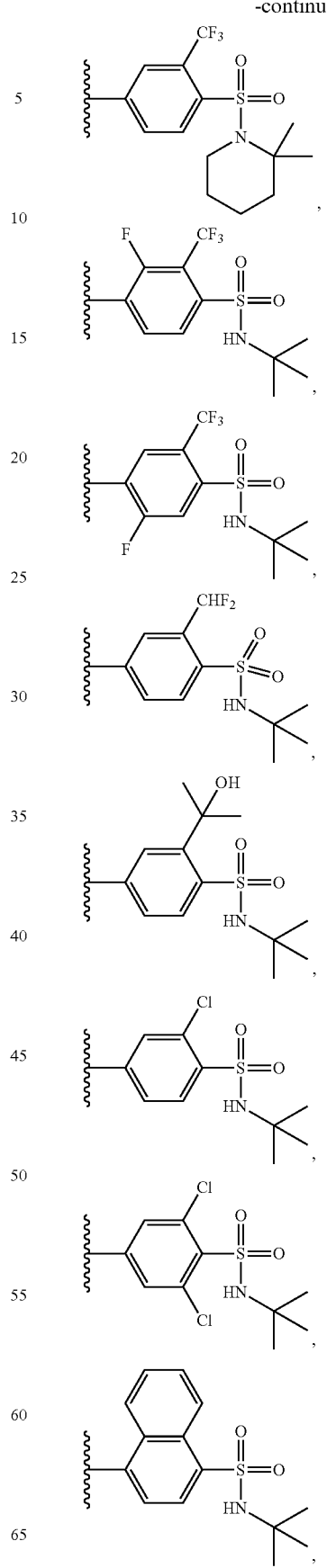

147
-continued
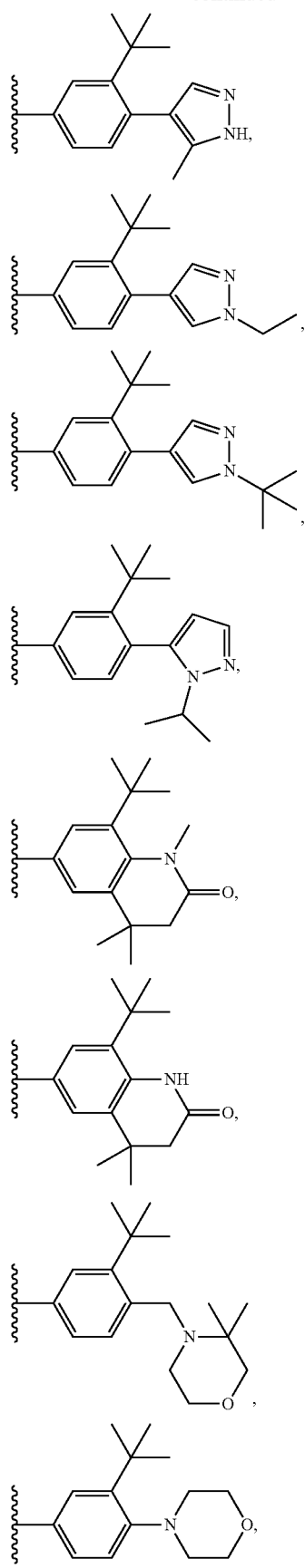
148
-continued
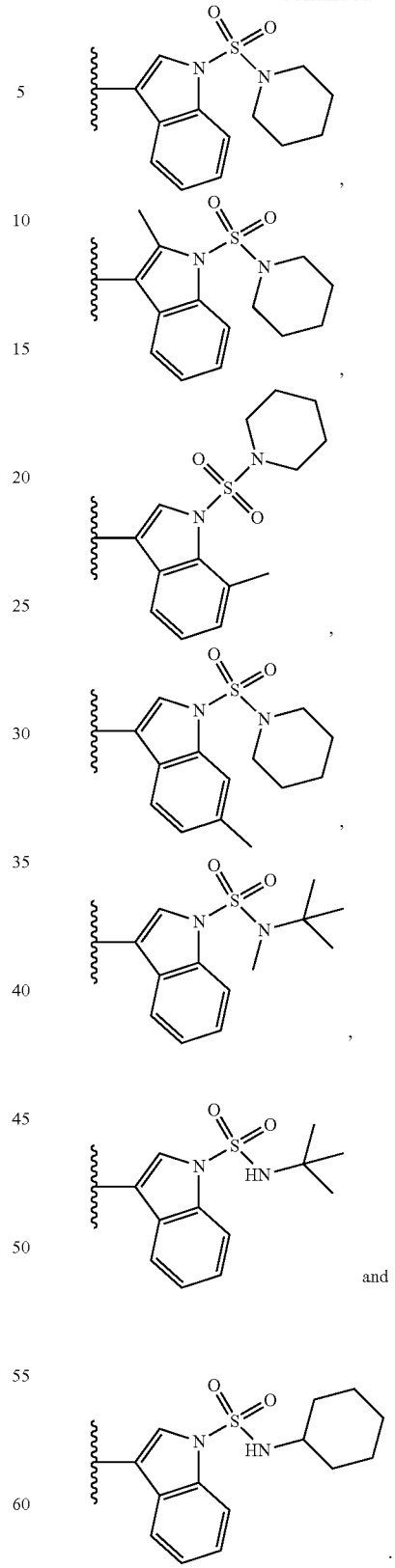
In a preferred embodiment in combination with any of the above or below embodiments of the third alternative R³ is selected from

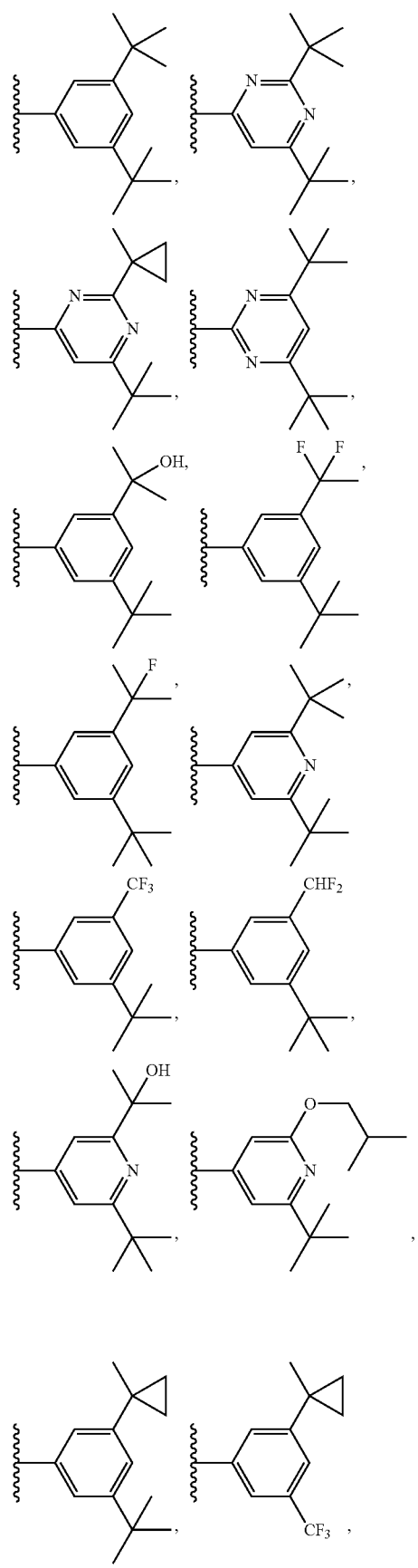
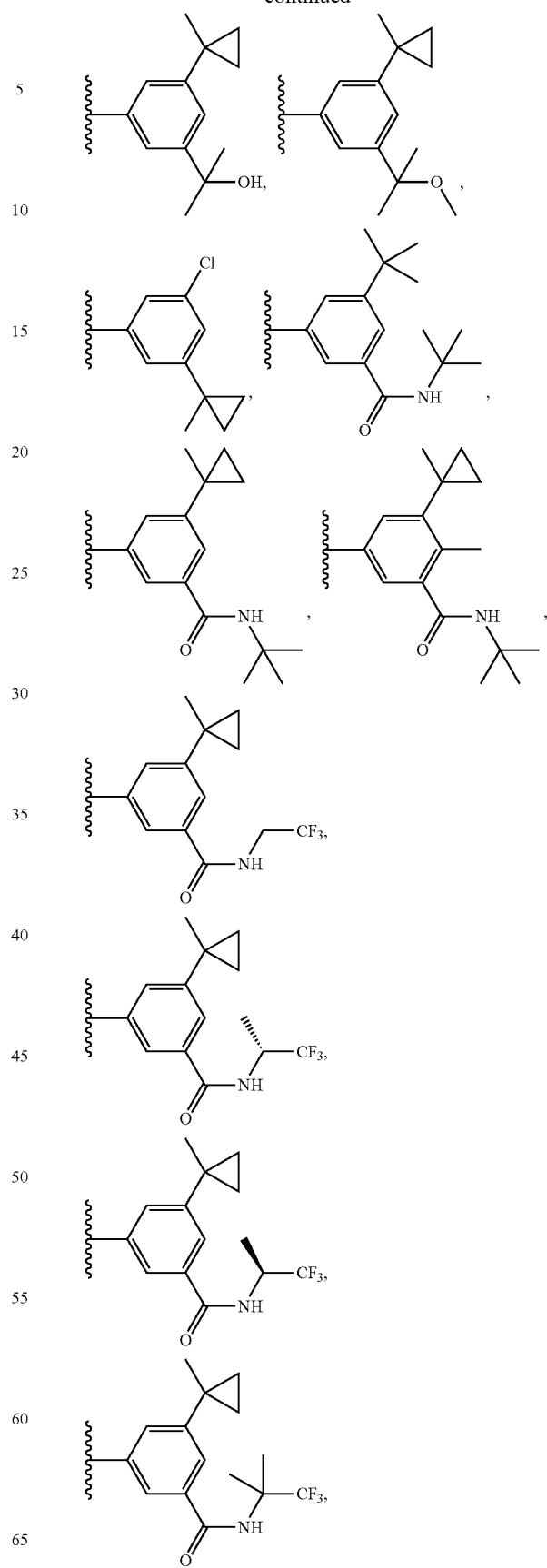

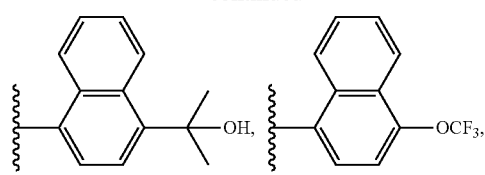
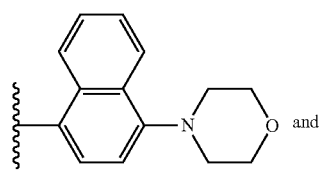
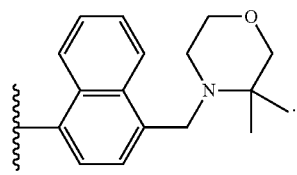
In another preferred embodiment in combination with any of the above or below embodiments of the third alternative the compound is represented by Formula (1).
In yet another preferred embodiment in combination with any of the above or below embodiments of the third alternative, the compound of Formula (1) is selected from the group consisting of
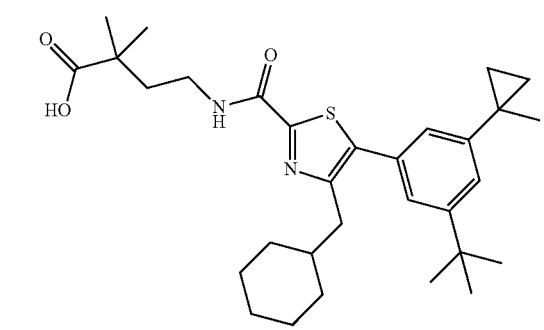
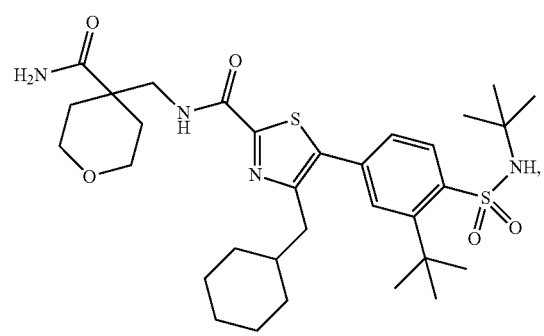
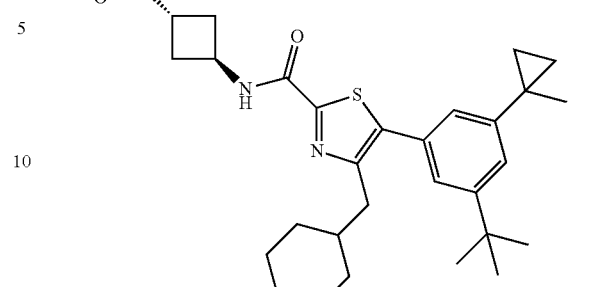
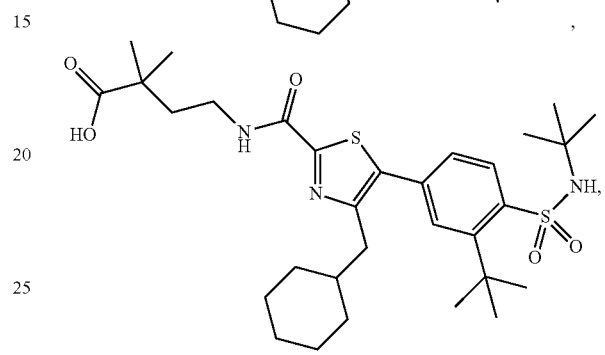
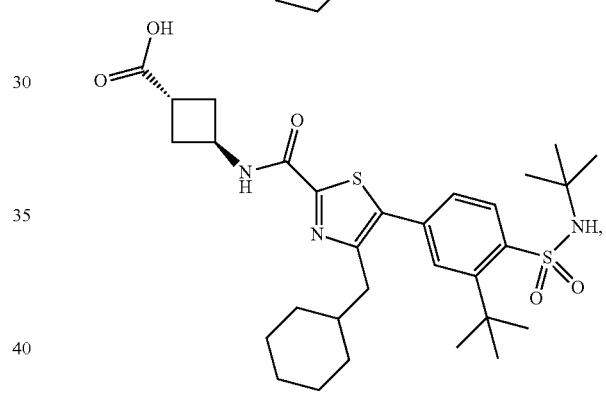

153
-continued
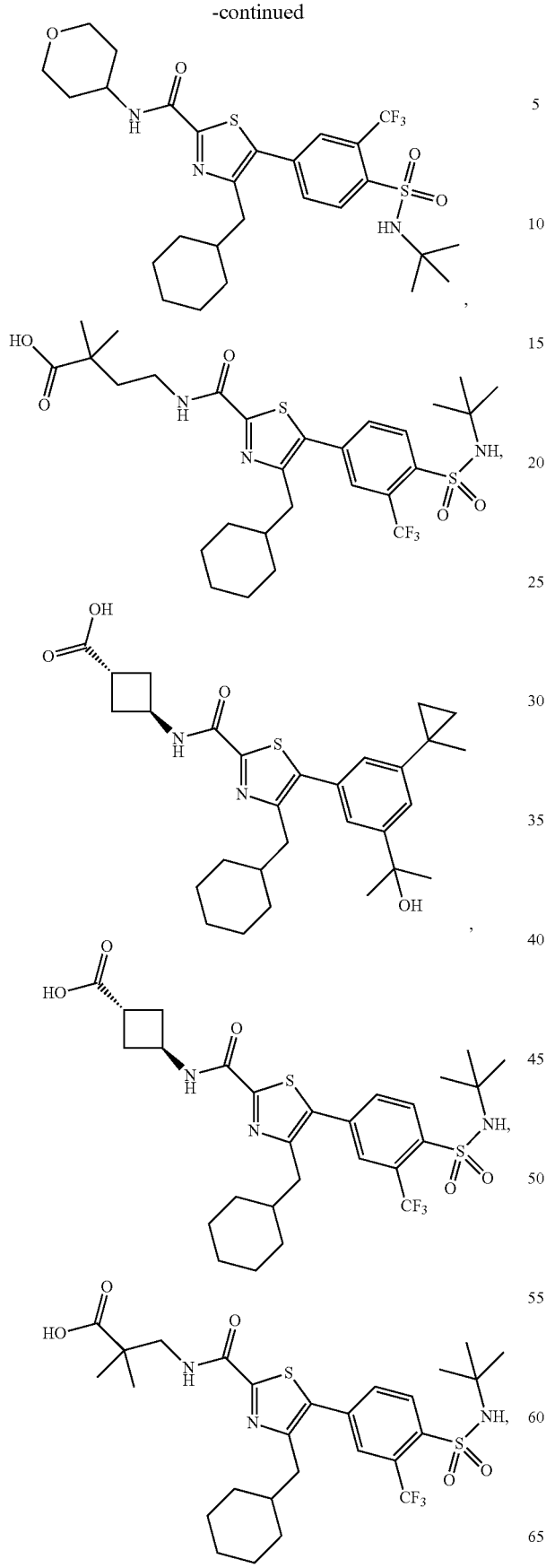
154
-continued
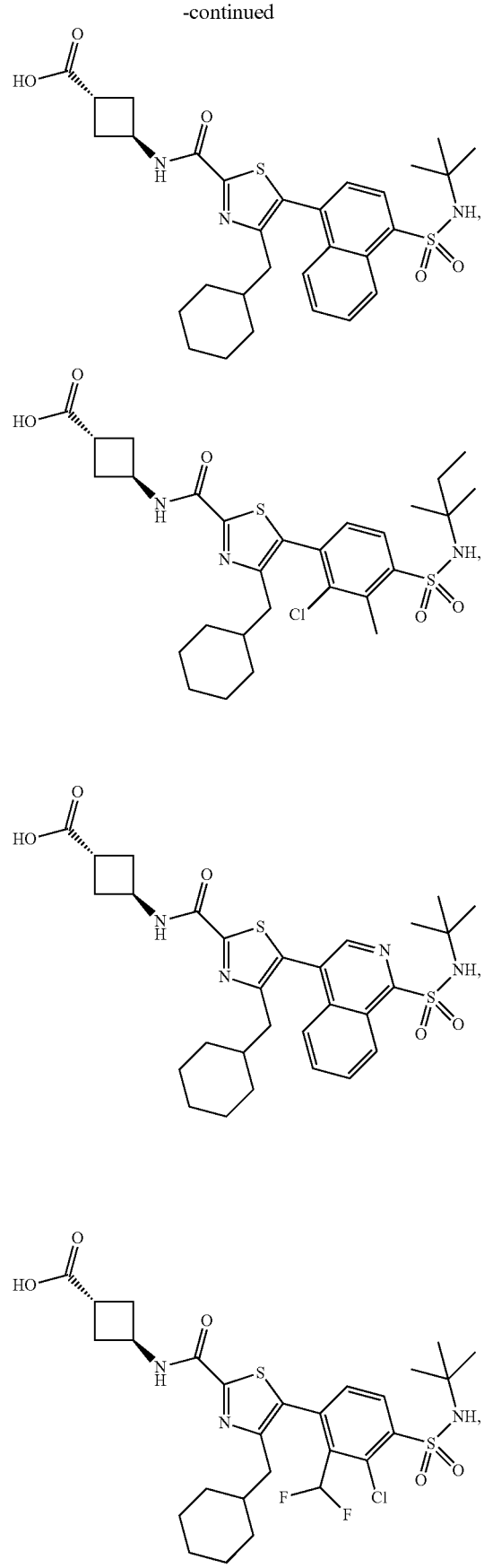

155
-continued
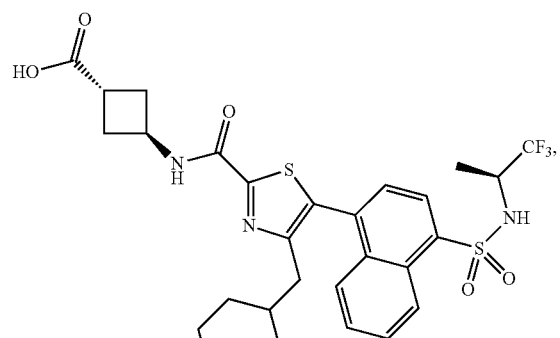
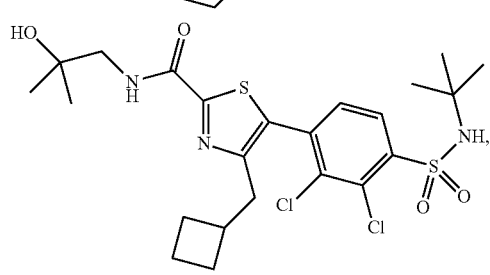
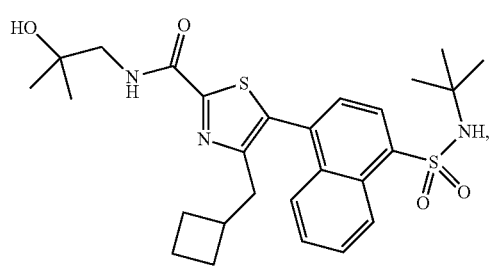
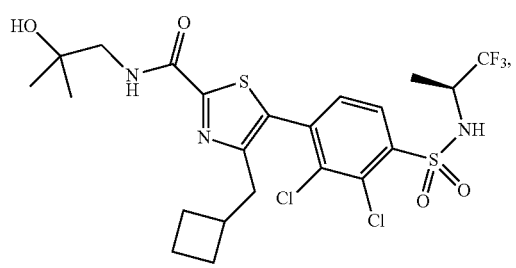
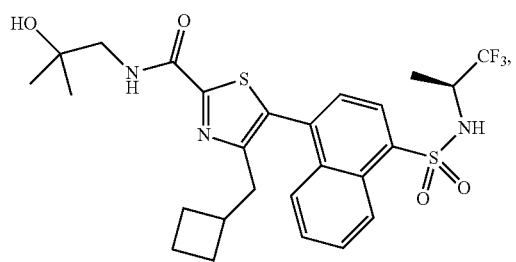
156
-continued
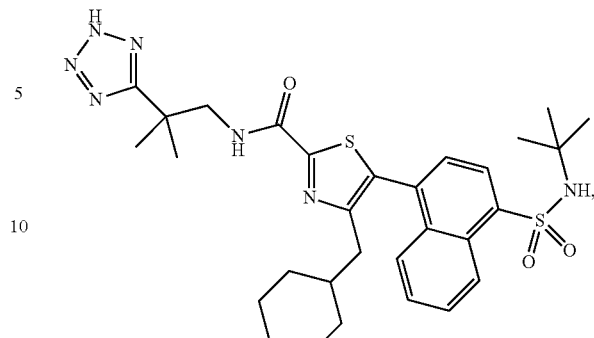
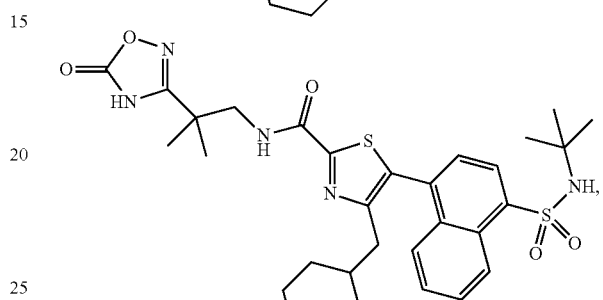
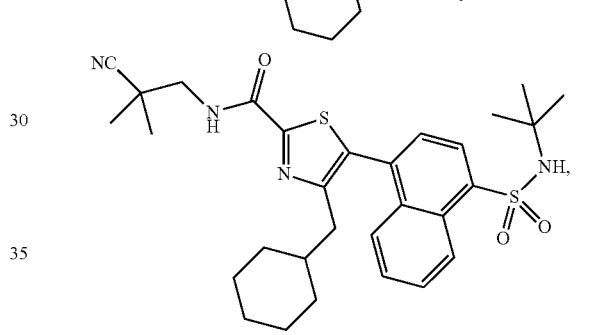
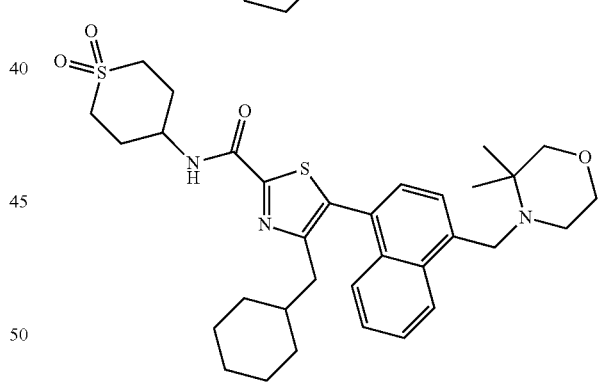
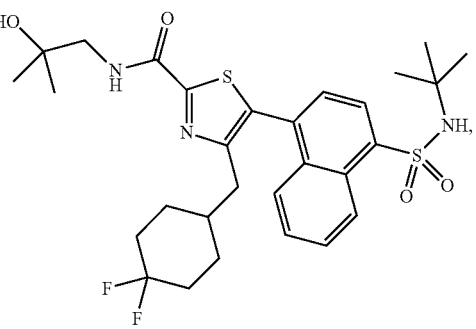

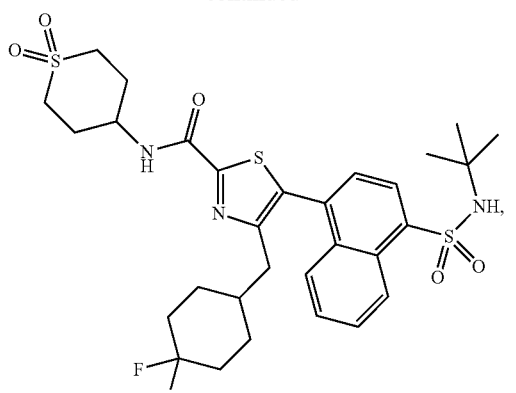
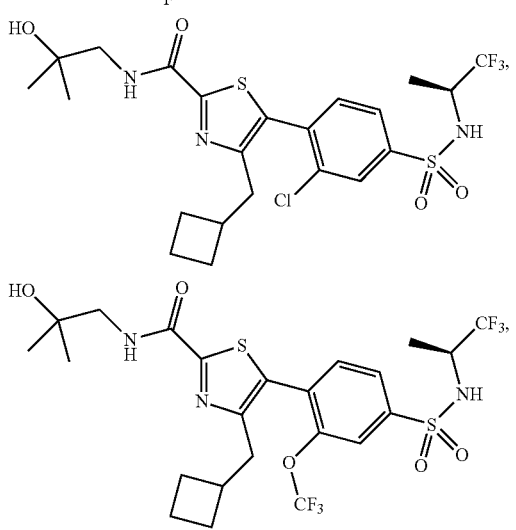
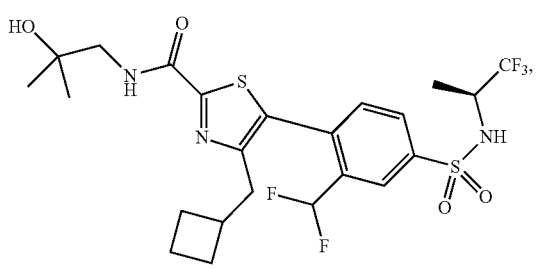
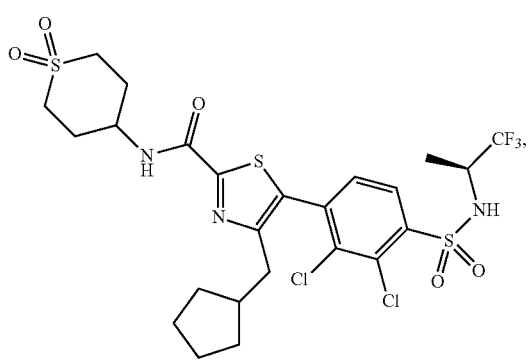
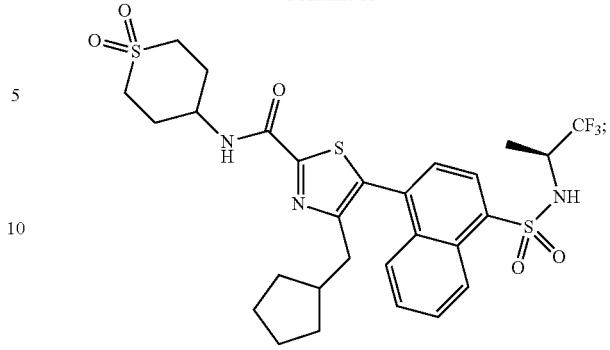

and an enantiomer, diastereomer, tautomer, N-oxide, solvate and pharmaceutically acceptable salt thereof.

The invention also provides the compound of the third alternative of the invention for use as a medicament.

Also provided is the compound of the third alternative of the invention for use in the treatment or prophylaxis of a disease or disorder associated with the inhibition or activation of the RORγ receptor.

Also provided is the compound of the third alternative of the invention in treating RORγ mediated inflammatory and autoimmune diseases. Preferably, the disease is selected from the group consisting of rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis.

Also provided is a pharmaceutical composition comprising the compound of the third alternative of the invention and a pharmaceutically acceptable carrier.

In a fourth alternative the present invention provides a compound according to Formula (2) or Formula (2')

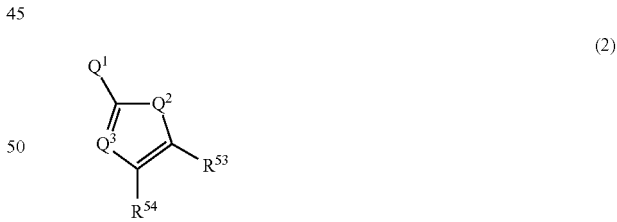

(2)

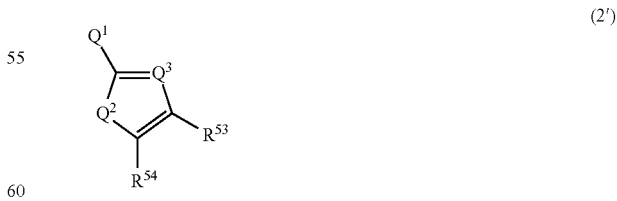

(2')

an enantiomer, diastereomer, tautomer, solvate, formulation and pharmaceutically acceptable salt thereof, wherein $Q^1$ is selected from CO—$NR^{51}R^{52}$, CO—$R^{52}$, $CO_2R^{51}$, $SO_2$—$NR^{51}R^{52}$, $SO_2$—$R^{52}$, $NR^{52}CO$—$R^{51}$ and $NR^{52}SO_2$—$R^{51}$;

$Q^2$ is selected from —O—, —S—, —CR$^{55}$=CR$^{56}$—, —N=CR$^{56}$—, —CR$^{55}$=N— and —N=N—;

$Q^3$ is selected from N and CR$^{55}$;

$R^{51}$ and $R^{52}$ are independently selected from H, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene-heteroaryl, $C_{0-10}$-alkylene-aryl, wherein alkyl, alkenyl, alkynyl, alkylene, cycloalkyl, heterocycloalkyl, aryl and heteroaryl is unsubstituted or substituted with 1 to 7 substituents independently selected from oxo, CN, OR$^{61}$, O—$C_{2-6}$-alkylene-OR$^{61}$, $C_{1-6}$-alkyl, halo-$C_{1-6}$-alkyl, halogen, CO$_2$R$^{61}$, CONR$^{61}$R$^{62}$, CONR$^{61}$SO$_2$R$^{62}$, COR$^{61}$, SO$_x$R$^{61}$, SO$_3$H, SO$_2$NR$^{61}$R$^{62}$, NR$^{61}$COR$^{61}$, NR$^{61}$SO$_2$R$^{61}$, NR$^{61}$—CO—NR$^{61}$R$^{62}$, NR$^{61}$—SO$_2$—NR$^{61}$R$^{62}$, $C_{3-6}$-cycloalkyl, O—$C_{3-6}$-cycloalkyl, $C_{3-6}$-heterocycloalkyl, O—$C_{3-6}$-heterocycloalkyl and NR$^{61}$R$^{62}$;

or $R^{51}$ and $R^{52}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, OR$^{61}$, SO$_x$R$^{61}$, SO$_3$H, NR$^{61}$SO$_2$R$^{61}$, SO$_2$NR$^{61}$R$^{62}$, CO$_2$R$^{61}$, CONR$^{61}$R$^{62}$, CONR$^{61}$SO$_2$R$^{62}$, COR$^{61}$, NR$^{61}$—CO—R$^{61}$, NR$^{61}$—CO—NR$^{61}$R$^{62}$, NR$^{61}$—SO$_2$—NR$^{61}$R$^{62}$, NR$^{61}$R$^{62}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl;

$R^{53}$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl are unsubstituted or substituted with 1 to 5 substituents independently selected from halogen, CN, $C_{1-6}$-alkyl, $C_{1-6}$-alkenyl, $C_{1-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-COOR$^{81}$, $C_{0-6}$-alkylene-C(O)R$^{81}$, $C_{0-6}$-alkylene-C(O)N(R$^{81}$)$_2$, $C_{0-6}$-alkylene-SO$_2$—N(R$^{81}$)$_2$, $C_{0-6}$-alkylene-SO$_2$—R$^{81}$, $C_{0-6}$-alkylene-(6-10-membered mono- or bicyclic aryl), $C_{0-6}$-alkylene-(6-10-membered mono- or bicyclic heteroaryl), wherein alkyl, alkenyl, alkynyl, alkylene, cycloalkyl, heterocycloalkyl and heteroaryl are unsubstituted or substituted by 1 to 3 substituents independently selected from the group consisting of $C_{1-6}$-alkyl, halo-$C_{1-6}$-alkyl, halogen, OH, oxo, =N—OR$^{82}$, N(R$^{81}$)$_2$, O—$C_{1-6}$-alkyl, O-halo-$C_{1-6}$-alkyl, COOH, CON(R$^{81}$)$_2$, CN, NR$^{81}$—COR$^{81}$, $C_{3-10}$-cycloalkyl, $C_{3-10}$-heterocycloalkyl, 6-10-membered mono- or bicyclic aryl, 6-10-membered mono- or bicyclic heteroaryl, or wherein two adjacent substituents may complete a 3- to 8-membered saturated or partially unsaturated ring containing carbon atoms and optionally containing 1 to 3 members selected from O, S, SO, SO$_2$ or NR$^{81}$, wherein the ring is unsubstituted or substituted with one to four substituents independently selected from halogen, oxo, =N—OR$^{82}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl;

$R^{54}$ is selected from $C_{0-6}$-alkylene-R$^{57}$, $C_3$-cycloalkyl-R$^{57}$, O—$C_{0-5}$-alkylene-R$^{57}$, NR$^{91}$—$C_{0-5}$-alkylene-R$^{57}$ and SO$_x$—$C_{0-5}$-alkylene-R$^{57}$, wherein alkylene is optionally substituted with 1 to 5 substituents independently selected from the group consisting of halogen, OH, oxo, =N—OR$^{82}$, N(R$^{81}$)$_2$, O—$C_{1-6}$-alkyl, COOH, CON(R$^{81}$)$_2$, CN, NR$^{81}$—COR$^{81}$, $C_{3-6}$-cycloalkyl and $C_{3-6}$-heterocycloalkyl;

$R^{55}$ and $R^{56}$ are independently selected from H, halogen, CN, $C_{1-6}$alkyl and O—$C_{1-6}$-alkyl, wherein alkyl is optionally substituted with 1 to 5 substituents independently selected from the group consisting of halogen, OH, oxo, O—$C_{1-3}$-alkyl; O-halo-$C_{1-3}$-alkyl and $C_{3-6}$-cycloalkyl;

$R^{57}$ is selected from $C_{1-10}$-alkyl, $C_{3-10}$-cycloalkyl, $C_{3-10}$-heterocycloalkyl, 6-10-membered mono- or bicyclic aryl and 6-10-membered mono- or bicyclic heteroaryl, wherein alkyl, cycloalkyl, heterocycloalkyl, aryl and heteroaryl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^{61}$ and $R^{81}$ independently selected from H, $C_{1-6}$-alkyl, $C_{3-10}$-cycloalkyl, $C_{3-10}$-heterocycloalkyl, phenyl, 5-6-membered heteroaryl containing 1 to 4 heteroatoms independently selected from N, O and S wherein alkyl, cycloalkyl and heterocycloalkyl is unsubstituted or substituted with 1 to 3 substituents selected from the group consisting of $C_{1-6}$-alkyl, halo-$C_{1-6}$-alkyl, OH, O—$C_{1-6}$-alkyl, O-halo-$C_{1-6}$-alkyl, phenyl, heteroaryl, halogen, NH$_2$, NH($C_{1-6}$-alkyl), N($C_{1-6}$-alkyl)$_2$, $C_{3-10}$-heterocycloalkyl and $C_{3-10}$-cycloalkyl, SO$_2$—$C_{1-3}$-alkyl, oxo, CN, wherein cycloalkyl and heterocycloalkyl is unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, heteroaryl, halogen, NH$_2$, NH($C_{1-6}$-alkyl), N($C_{1-6}$-alkyl)$_2$ and $C_{3-10}$-cycloalkyl, wherein phenyl and heteroaryl are unsubstituted or substituted with 1 to 3 substituents independently selected from the group consisting of OH, O—$C_{1-6}$-alkyl, O-halo-$C_{1-6}$-alkyl, halogen, $C_{1-6}$-alkyl, halo-$C_{1-6}$-alkyl, NH$_2$, NH($C_{1-6}$-alkyl), N($C_{1-6}$-alkyl)$_2$ and $C_{3-10}$-cycloalkyl;

$R^{62}$ and $R^{82}$ are independently selected from H, $C_{1-6}$-alkyl, halo-$C_{1-6}$-alkyl and $C_{3-10}$-cycloalkyl;

$R^{91}$ is selected from H, $C_{1-6}$-alkyl, $C_{3-6}$-cycloalkyl and $C_{3-6}$-heterocycloalkyl, wherein alkyl, cycloalkyl and heterocycloalkyl is unsubstituted or substituted with 1 to 3 substituents selected from the group consisting of OH, oxo, CN, halogen, O—$C_{1-6}$-alkyl, O-halo-$C_{1-6}$-alkyl, $C_{3-6}$-heterocycloalkyl and $C_{3-6}$-cycloalkyl;

x is independently selected from 0, 1 and 2; for use in the treatment or prophylaxis of a disease or disorder associated with the inhibition or activation of the RORγ receptor; with the proviso that compounds of Formula (2') with $Q^1$ is NHCO—R$^{51}$, $Q^2$ is sulfur, $Q^3$ is nitrogen, $R^{53}$ and $R^{57}$ are optionally substituted aryl and $R^{54}$ is COR$^{57}$ are excluded.

In a preferred embodiment in combination with any of the above or below embodiments of the fourth alternative $Q^1$ is selected from CO—NR$^{51}$R$^{52}$ and NR$^{52}$CO—R$^{51}$; $Q^2$ is selected from —O— and —S—; and $Q^3$ is N.

In a further preferred embodiment in combination with any of the above or below embodiments of the fourth alternative $R^{51}$ is selected from H, $C_{1-10}$-alkyl, $C_{0-10}$-alkylene-$C_{3-10}$-cycloalkyl, and $C_{0-10}$-alkylene-$C_{3-10}$-heterocycloalkyl, wherein alkyl, alkylene, cycloalkyl and heterocycloalkyl is unsubstituted or substituted with 1 to 7 substituents independently selected from oxo, $OR^{61}$, $C_{1-6}$-alkyl, halo-$C_{1-6}$-alkyl, halogen, $CO_2R^{61}$, $CONR^{61}R^{62}$, $CONR^{61}SO_2R^{62}$, $COR^{61}$, $NR^{61}COR^{61}$, $NR^6SO_2R^{61}$, $NR^{61}$—CO—$NR^{61}R^{62}$, $NR^{61}$—$SO_2$—$NR^{61}R^{62}$, $C_{3-6}$-cycloalkyl, O—$C_{3-6}$-cycloalkyl, $C_{3-6}$-heterocycloalkyl and O—$C_{3-6}$-heterocycloalkyl; $R^{52}$ is selected from the group consisting of H, $C_{1-6}$ alkyl and halo-$C_{1-6}$ alkyl; or $R^{51}$ and $R^{52}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{61}$, $SO_xR^{61}$, $SO_3H$, $NR^{61}SO_2R^{61}$, $SO_2NR^{61}R^{62}$, $CO_2R^{61}$, $CONR^{61}R^{62}$, $CONR^{61}SO_2R^{62}$, $COR^{61}$, $NR^{61}$—CO—$R^{61}$, $NR^{61}$—CO—$NR^{61}R^{62}$, $NR^{61}$—$SO_2$—$NR^{61}R^{62}$, $NR^{61}R^{62}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl.

In another preferred embodiment in combination with any of the above or below embodiments of the fourth alternative $R^{53}$ is selected from

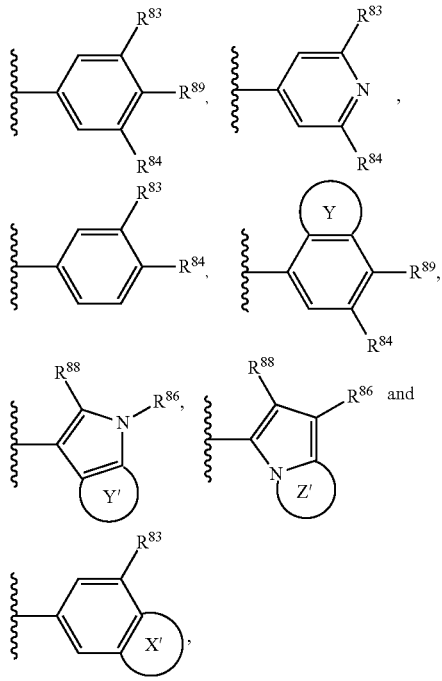

wherein
$R^{83}$ is selected from halogen, $C_{1-6}$-alkyl, fluoro-$C_{1-6}$-alkyl, $C_{1-4}$-alkylene-OH, $C_{1-4}$-alkylene-CN, $C_{1-4}$-alkylene-O—$C_{1-3}$-alkyl, $C_{1-4}$-alkylene-O-fluoro-$C_{1-3}$-alkyl, O—$C_{1-6}$-alkyl, O-fluoro-$C_{1-6}$-alkyl, $C_{3-10}$-cycloalkyl, $C(O)N(R^{87})_2$,
wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;
$R^{84}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{87})_2$, $S(O_2)N(R^{87})_2$,
wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;
$R^{86}$ is selected from $C_{1-6}$-alkyl, fluoro-$C_{1-6}$-alkyl, $C(O)N(R^{87})_2$, $S(O_2)N(R^{87})_2$,
$R^{87}$ is independently selected from H, $C_{1-6}$-alkyl, fluoro-$C_{1-6}$-alkyl, $C_{0-3}$-alkylene-$C_{1-6}$-cycloalkyl, $C_{1-6}$-alkylene-OH, $C_{1-6}$-alkylene-O—$C_{1-3}$-alkyl, $C_{1-6}$-alkylene-CN, wherein alkylene and cycloalkyl is unsubstituted or substituted with 1 to 3 substituents independently selected from F, $C_{1-3}$-alkyl and fluoro-$C_{1-3}$-alkyl,
and wherein two $R^{87}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, oxo, $C_{1-4}$-alkyl and halo-$C_{1-4}$-alkyl;
$R^{88}$ is selected from H, $C_{1-3}$-alkyl and fluoro-$C_{1-3}$-alkyl;
$R^{89}$ is selected from H, F or OH;
X' is an annelated saturated heterocycle selected from the group consisting of

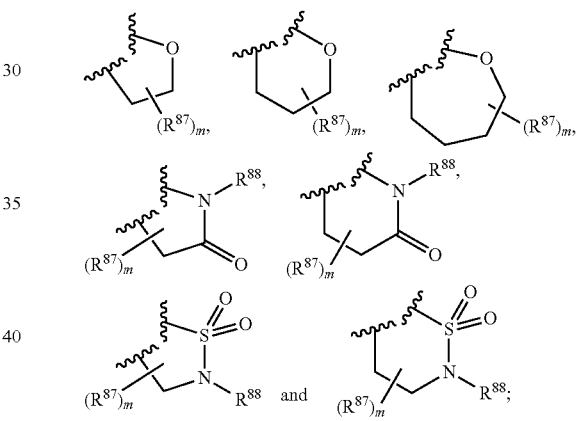

Y' is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, $C_{1-3}$-alkyl and fluoro-$C_{1-3}$-alkyl;
Z' is an annelated 6-membered cycle forming a heteroaryl containing 1 to 2 nitrogen atoms, wherein the heteroaryl is unsubstituted or substituted with 1 to 3 substituents selected from fluoro, $C_{1-3}$-alkyl and fluoro-$C_{1-3}$-alkyl; and m is selected from 1 to 4.

In yet another preferred embodiment in combination with any of the above or below embodiments of the fourth alternative $R^{54}$ is selected from $C_{1-6}$-alkylene-$R^{57}$, O—$R^{57}$, and $SO_2$—$R^{57}$,
wherein alkylene is optionally substituted with 1 to 5 substituents independently selected from the group consisting of halogen, OH, oxo, O—$C_{1-6}$-alkyl, CN and $C_{3-6}$-cycloalkyl;
$R^{57}$ is selected from $C_{1-10}$-alkyl, $C_{3-10}$-cycloalkyl, $C_{3-10}$-heterocycloalkyl, 6-10-membered mono- or bicyclic aryl and 6-10-membered mono- or bicyclic heteroaryl, wherein alkyl, cycloalkyl, heterocycloalkyl, aryl and heteroaryl are unsubstituted or substituted with 1 to 3 substituents independently selected from the group consisting of halogen, OH, oxo, O—$C_{1-3}$-alkyl, O-halo-$C_{1-3}$-alkyl, $C_{1-3}$-alkyl, halo-$C_{1-3}$-alkyl, cycloalkyl and heterocycloalkyl.

In a preferred embodiment in combination with any of the above or below embodiments of the fourth alternative, the disease or disorder associated with the inhibition or activation of the RORγ receptor is selected from the group consisting of rheumatoid arthritis, ankylosing spondylitis, lupus erythematosus, psoriasis, atopic eczema, inflammatory bowel diseases, Crohn's disease, ulcerative colitis, asthma, multiple sclerosis, type 1 diabetes, amyotrophic lateral sclerosis, Th17 mediated tissue inflammation, or of autoimmune etiology or a skin disease with associated symptoms such as pain, itching or excoriations.

Also provided is a pharmaceutical composition comprising a compound of the present invention and a pharmaceutically acceptable carrier or excipient.

In the context of the present invention "$C_{1-10}$-alkyl" means a saturated alkyl chain having 1 to 10 carbon atoms which may be straight chained or branched. Examples thereof include methyl, ethyl, propyl, isopropyl, n-butyl, isobutyl, tert-butyl, n-pentyl, isopentyl, neopentyl, hexyl, heptyl, octyl, nonyl and decyl.

The term "halo-$C_{1-10}$-alkyl" means that one or more hydrogen atoms in the alkyl chain are replaced by a halogen. A preferred example thereof is $CF_3$.

"$C_{2-10}$-alkenyl" means an alkyl chain having 1 to 10 carbon atoms which may be straight chained or branched, containing at least one carbon to carbon double bond. Examples thereof include ethenyl, propenyl, decenyl, 2-methylenehexyl and (2E,4E)-hexa-2,4-dienyl.

"$C_{2-10}$-alkynyl" means an alkyl chain having 1 to 10 carbon atoms which may be straight chained or branched, containing at least one carbon to carbon triple bond. Examples thereof include ethynyl, propynyl and decynyl.

A "$C_{3-10}$-alkylene" means that the respective group is divalent and connects the attached residue with the remaining part of the molecule. Moreover, in the context of the present invention, "$C_0$-alkylene" is meant to be represent a bond. The same applies to the divalent $C_3$-cycloalkylene.

A $C_{3-10}$-cycloalkyl group or $C_{3-10}$-carbocycle means a saturated or partially unsaturated mono-, bi- or multicyclic ring system comprising 3 to 10 carbon atoms. Examples include cyclopropyl, cyclobutyl, cyclopentyl, cyclohexyl, cyclohexenyl, bicyclo[2.2.2]octyl, bicyclo[2.2.1]heptyl, adamantyl and pentacyclo[4.2.0.0$^{2,5}$.0$^{3,8}$.0$^{4,7}$]octyl.

A $C_{3-10}$-heterocycloalkyl group means a saturated or partially unsaturated 3 to 10 membered carbon mono-, bi- or multicyclic ring wherein 1, 2 or 3 carbon atoms are replaced by 1, 2 or 3 heteroatoms, respectively, wherein the heteroatoms are independently selected from N, O, S, SO and $SO_2$. Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 3,6-dihydro-2H-thiopyranyl. The $C_{3-10}$-heterocycloalkyl group can be connected via a carbon or nitrogen atom.

A 5-14-membered mono-, bi- or tricyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bi- or tricyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl, pyrazolo[1,5-a]pyrimidinyl and dibenzo[b,d]furanyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

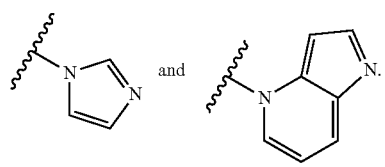 [SMILES: *n1ccnc1 ; *n1cccc2nccc1-2]

A 6-10-membered mono- or bicyclic aromatic ring system (within the application also referred to as aryl) means an aromatic carbon cycle such as phenyl or naphthalenyl.

The term "N-oxide" denotes compounds, where the nitrogen in the heteroaromatic system (preferably pyridinyl) is oxidized. Such compounds can be obtained in a known manner by reacting a compound of the present invention (such as in a pyridinyl group) with $H_2O_2$ or a peracid in an inert solvent.

Halogen is selected from fluorine, chlorine, bromine and iodine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

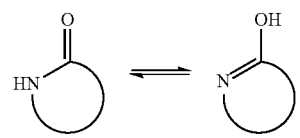

A $C_{3-10}$-cycloalkyl or $C_{3-10}$-heterocycloalkyl group can be connected straight or spirocyclic, e.g. when cyclohexane is substituted with the heterocycloalkyl group oxetane, the following structures are possible:

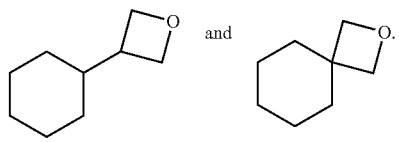 [SMILES: C1CCC(C2COC2)CC1 ; "and" ; C1CCC2(CC1)COC2]

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds used in the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound.

The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring such as cherry or orange flavour.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous), ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing RORγ-mediated conditions for which compounds of Formula (1), (1'), (2), (2'), (100), (100'), (200) and (200') are indicated, generally satisfactory results are obtained when the compounds are administered at a daily dosage of from about 0.1 milligram to about 100 milligram per kilogram of mammal body weight, preferably given as a single daily dose or in divided doses two to six times a day, or in sustained release form. For most large mammals, the total daily dosage is from about 1.0 milligram to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The present invention describes modulators, in the following also referred to as ligands, which bind to the RORγ receptor. Surprisingly, it has been found that compounds of Formula (1), (1'), (2), (2'), (100), (100'), (200) and (200') act as modulators of the RORγ receptor.

The term "modulator of the RORγ receptor" includes the inhibition or activation of the RORγ receptor, wherein the inhibition is preferred.

The RORγ receptor is considered to be involved in thymocyte development, thus the modulators described herein may be useful in the treatment of inflammatory skin diseases such as atopic eczema and psoriasis. It is further suggested that down-modulation of RORγ transcriptional activity with a ligand could result in a shift of the immune response towards a Th2 type response which could be beneficial in the treatment of certain allergic inflammatory conditions such as rheumatoid arthritis, systemic lupus erythomatosis, inflammatory bowel disease (Crohn's Disease) and multiple sclerosis (Tesmer et. al., *Immunol. Rev.* 2008, 223:97).

The compounds of Formula (1), (1'), (2), (2'), (100), (100'), (200) and (200') show antagonistic activity, with respect to the dose dependent modulation of the constitutive interaction of the RORγ ligand binding domain with peptides derived from the co-activators such as SRC-1, TRAP 220 or TIF-2.

It has been surprisingly found that the interaction between RORγ ligand binding domain and the peptides can be determined by a homogenous FRET based ligand-sensing assays. Even more surprising was the identification of compounds of Formula (1), (1'), (2), (2'), (100), (100'), (200) and (200') as ligands for RORγ.

The identification of high affinity ligands for RORγ with agonistic and antagonistic properties is the basis to enable experts knowledgeable in the field to establish assays for the identification of novel agonistic and antagonistic RORγ ligands from libraries of small molecules. The identification of ligands which bind to and modulate the activity of RORγ1 and RORγ2 is the first mandatory step to develop new small molecule based medicines with a potential to be developed for the treatment of diseases which are directly or indirectly controlled by the activity of RORγ1 or RORγ2. Such diseases include but are not restricted to inflammatory diseases, asthma, rheumatoid arthritis, autoimmune diseases or diseases with an autoimmune component such as systemic lupus erythomatosis, inflammatory bowel disease (Crohn's disease), ulcerative colitis, inflammatory skin diseases such as atopic eczema or psoriasis, multiple sclerosis or similar diseases.

Another aspect of the invention provides for combination therapy. Thiazoles and related compounds (e.g. a compound of Formula (1), (1'), (2), (2'), (100), (100'), (200) and (200')) or their pharmaceutically acceptable salts may be used in combination with additional therapeutic agents to treat medical disorders, such as medical disorders associated with inappropriate IL-17 pathway activity. Exemplary additional therapeutic agents include, for example, (1) a TNF-α inhibitor; (2) a non-selective COX-1/COX-2 inhibitor; (3) a selective COX-2 inhibitor, such as celecoxib and rofecoxib; (4) other agents for treating inflammatory disease and autoimmune disease including, for example, methotrexate, leflunomide, sulfasalazine, azathioprine, penicillamine, bucillamine, actarit, mizoribine, lobenzarit, hydroxychloroquine, d-penicillamine, aurothiomalate, auranofin, parenteral gold, oral gold, cyclophosphamide, Lymphostat-B, a BAFF/APRIL inhibitor, CTLA-4-Ig, or a mimetic of CTLA-4-Ig; (5) a leukotriene biosynthesis inhibitor, such as a 5-lipoxygenase (5-LO) inhibitor, or a 5-lipoxygenase activating protein (FLAP) antagonist; (6) a LTD4 receptor antagonist; (7) a phosphodiesterase type IV (PDE-IV) inhibitor, such as cilomilast (Ariflo) or roflumilast; (8) an antihistamine Hi receptor antagonist; (9) an α1- and α2-adrenoceptor agonist; (10) an anticholinergic agent; (11) a (3-adrenoceptor agonist; (12) an insulin-like growth factor type I (IGF-1) mimetic; (13) a glucocorticoid; (14) a kinase inhibitor such as an inhibitor of a Janus Kinase (e.g., JAK1 and/or JAK2 and/or JAK3 and/or TYK2), p38 MAPK, Syk or IKK2; (15) a B-cell target biologic such as rituximab; (16) a selective co-stimulation modulator such as abatacept; (17) an interleukin inhibitor or interleukin receptor inhibitor, such as the IL-1 inhibitor anakinra, IL-6 inhibitor tocilizumab and IL12/IL-23 inhibitor ustekimumab; (18) an anti-IL17 antibody, anti-IL21 antibody, or anti-IL22 antibody (19) a S1P1 agonist, such as fingolimod; (20) an interferon, such as interferon beta 1; (21) an integrin inhibitor such as natalizumab; (22) a mTOR inhibitor such as rapamycin, cyclosporin and tacrolimus; (23) a non-steroidal antiinflammatory agent (NSAID), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone); (24) a NRF2 pathway activator, such as the fumaric acid derivative, BG-12; and (25) a chemokine or chemokine receptor inhibitor, such as a CCR9 antagonist.

The amount thiazole or related compound (e.g. a compound of Formula (1), (1'), (2), (2'), (100), 100'), (200) and (200')) and additional therapeutic agent and the relative timing of administration may be selected in order to achieve a desired combined therapeutic effect. For example, when administering a combination therapy to a patient in need of such administration, the therapeutic agents in the combination or a pharmaceutical composition or compositions comprising the therapeutic agents, may be administered in any order such as, for example, sequentially, concurrently, together, simultaneously and the like. Further, for example, a thiazole or related compound may be administered during a time when the additional therapeutic agent(s) exerts its prophylactic or therapeutic effect, or vice versa.

The compounds of the present invention can be prepared by a combination of methods known in the art including the procedures described in Schemes I to V below.

Scheme I depicts the α-bromination of ketone A-I ($R^4$=$CR^8R^8$)$R^{40}$) or ester A-I ($R^4$=$OR^{40}$) to afford compound A-II. Subsequent cyclisation as previously described in US2005/065189 or WO2007/079186 using ethyl 2-amino- 2-thioxoacetate furnished thiazole A-III, which can be brominated (e.g. with 1,3-dibromo-5,5-dimethylhydantoin) to afford bromide A-IV. Saponification using an aqueous base (e.g. 1N NaOH) and coupling of amine $HNR^1R^2$ affords intermediate A-V, which subsequently gives rise to target compound A-VI by Pd-catalysed reaction (e.g. Suzuki coupling) using a suitable boronic acid or boronic ester. The thiazolo isomer can be prepared in a similar manner.

Scheme I

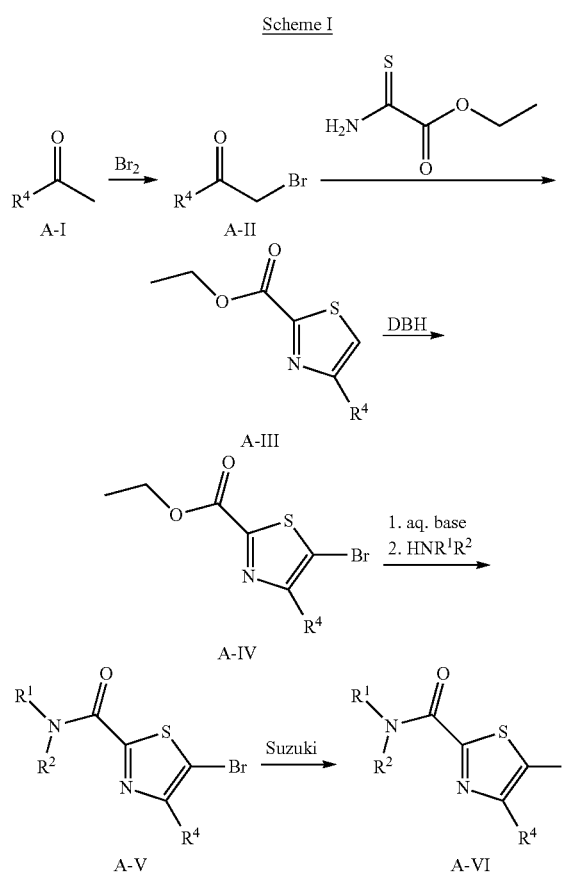

The sulfonamide derivatives can be prepared as shown in Scheme II. Again, α-bromination of a ketone gives intermediate B-II, which can be cyclisized to thiazole B-III by use of formamide and phosphorus sulfide. Incorporation of the sulfonamide moiety can be accomplished via bromination (→B-IV), Br—SH-exchange (→B-V) and oxidation of the thiol group with NCS to a sulfonyl chloride moiety and finally reaction with amine $HNR^1R^2$ to give target compound B-VI. An alternative route using a Grignard reagent is described in *Bioorg. Med. Chem.* 2009, 17:1307. The corresponding thiazolo isomer can be prepared in a similar manner.

Scheme II

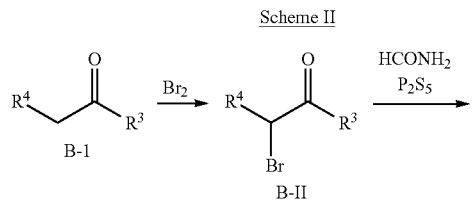

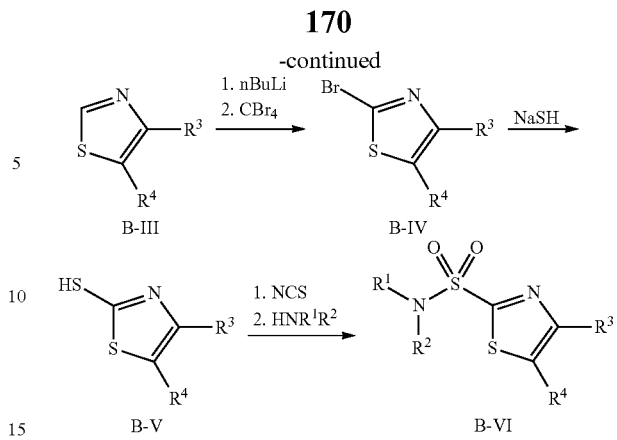

In Scheme III is depicted a synthetic route for oxazoles of the present invention where $R^{104}$ is in the 4-position and $R^{103}$ in the 5-position of the oxazole ring. The synthesis starts with an alkylation of (p-tolylsulfonyl)methyl isocyanide (TosMIC) to obtain intermediate C-I. A subsequent cylocondensation with aldehyde $R^{103}CHO$ furnishes oxazole intermediates C-II. The introduction of a carboxylic ester group at the 2-position of the oxazole ring can be achieved by first bromination (e.g. reaction with NBS) and then Pd-catalysed carbonylation, preferably with a lower alcohol as solvent. The ester can be further transformed into carboxamides by standard methods known in the art.

Scheme III

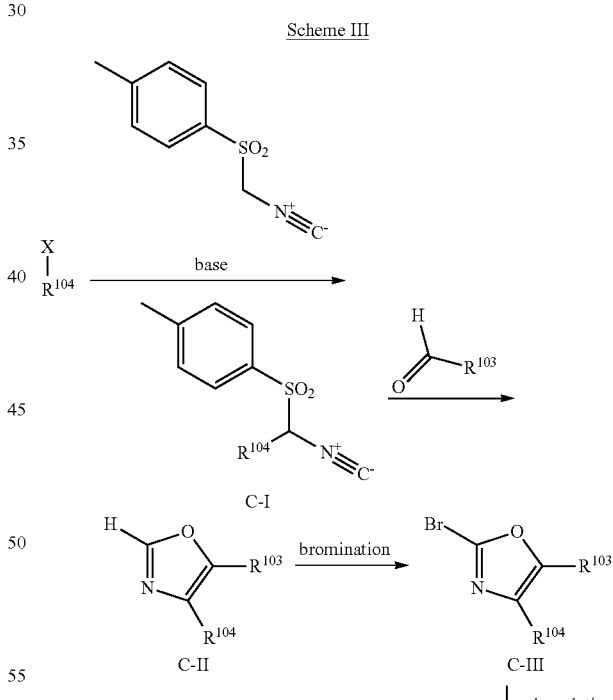

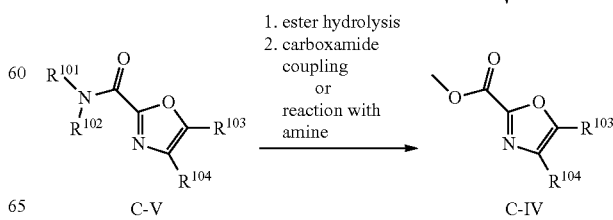

In Scheme IV is depicted the synthesis for oxazoles of the present invention where $R^{103}$ is in the 4-position and $R^{104}$ in the 5-position. The aromatic aldehyde $R^{103}$CHO is reacted with formamide in the presence of TMSCl and then with tosylsulfinic acid to form intermediate D-I which is dehydrated to form the substituted TosMIC intermediate D-II. After a cyclocondensation with $R^{104}$CHO, the 2-position of the oxazole ring can be substituted as depicted in Scheme III. Alternatively the oxazole ring can be metallated and then reacted with ethyl chloroformate to introduce the ester functionality which can be transformed into carboxamides by standard methods known in the art.

An alternative route for the synthesis of oxazoles with $R^{103}$ in the 4-position and $R^{104}$ in the 5-position is depicted in Scheme V. An aldehyde $R^{104}$CHO can be converted to the aminohydroxy intermediate E-I by a sequence of e.g. cyanohydrine formation followed by nitrile reduction. N-Acylation of E-I with ethyl 2-chloro-2-oxoacetate leads to E-II which can be oxidized to the cyclization precursor E-III. Treatment of E-II with a dehydrating reagent like e.g. POCl$_3$ leads to the formation of the heterocyclic intermediate E-IV. Pd catalysed coupling with $R^{103}$—Br yields intermediate D-IV. For the thiophene and furan derivatives the core decoration can be accomplished in a similar fashion.

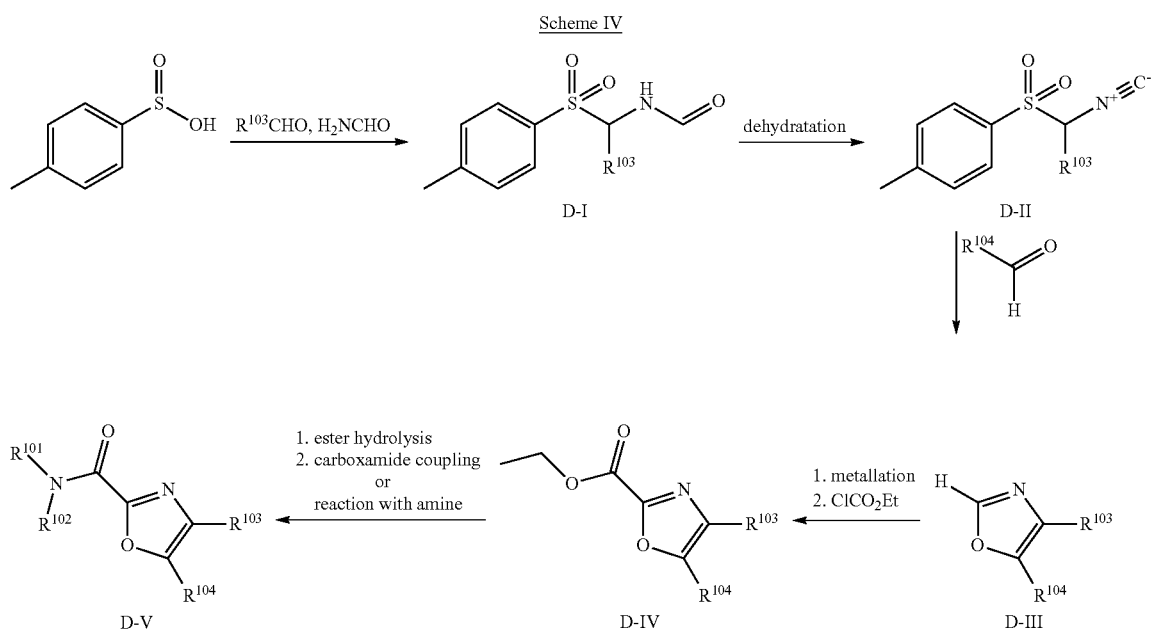

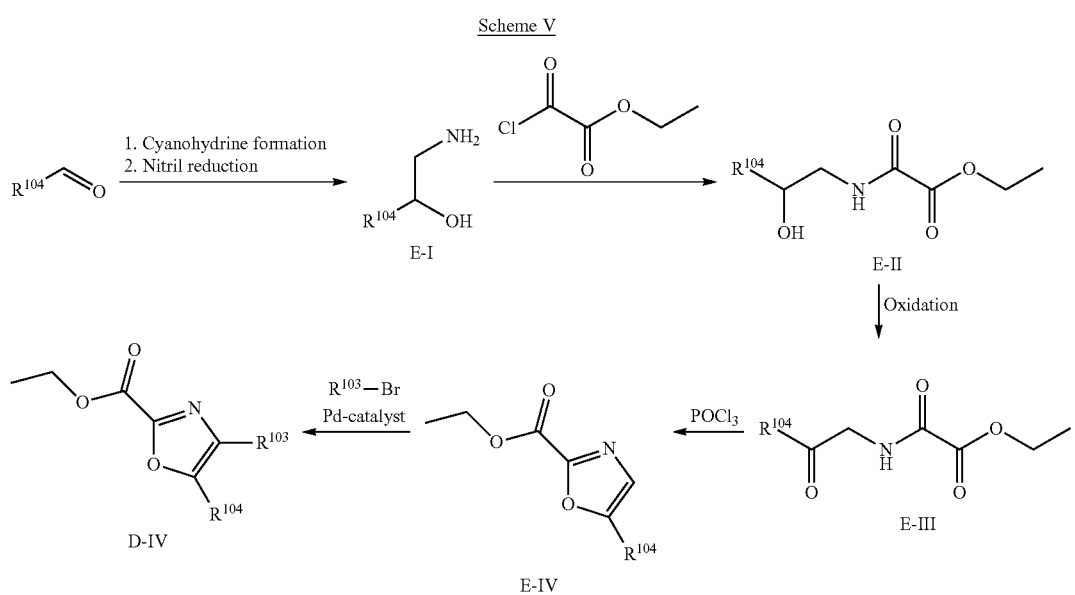

ABBREVIATIONS

Ac acetyl
ACN acetonitrile
AIBN azobisisobutyronitrile
aq. aqueous
$B_2Pin_2$ 4,4,4',4',5,5,5',5'-octamethyl-2,2'-bi-1,3,2-dioxaborolane
m-CPBA meta-chloroperbenzoic acid
CC chromatography on silica gel
Cy cyclohexyl
DAST diethylaminosulfur trifluoride
dba dibenzylideneacetone
DBH 1,3-Dibromo-5,5-dimethylhydantoin
DCM dichloromethane
DIPEA diisopropylethylamine
DMA dimethyl acetamide
DMF N,N-dimethylformamide
dppf 1,1'-bis(diphenylphosphino)ferrocene
DPPP 1,3-bis(diphenylphosphino)propane
DTBPy 2,6-di-tert-butylpyridine
EA ethyl acetate
HATU O-(7-azabenzotriazole-1-yl)-N,N,N',N'-tetramethyluronium hexafluorophosphate
MTBE tert-butylmethylether
NBS N-bromosuccinimide
NCS N-chlorosuccinimide
PCC pyridinium chlorochromate
Pin pinacolato ($OCMe_2CMe_2O$)
PivOH pivalic acid
PE petroleum ether
prep. preparative
sat. saturated
TEMPO (2,2,6,6-tetramethylpiperidin-1-yl)oxyl
TFA trifluoroacetic acid
THF tetrahydrofuran
TLC thin layer chromatography

EXPERIMENTAL SECTION

Preparative Example P1

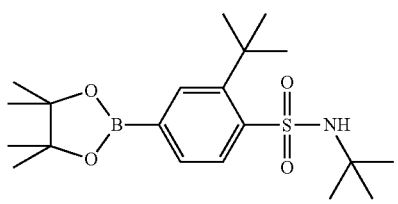

P1

Step 1: 4-Bromo-2-tert-butylaniline (P1a)

To a solution of NBS (218 mg, 1 mmol) in DMF was added a solution of 2-tert-butylaniline (149 mg, 1 mmol) in DMF at rt. The reaction mixture was stirred for 4 h at rt, then water (30 mL) was added and the mixture was extracted with EA (150 mL). The organic layer was washed with brine and dried over $Na_2SO_4$, concentrated and purified by CC (hexane/EA=3/1) to give compound P1a (180 mg, 79%).

Step 2: 4-Bromo-2-tert-butylbenzene-1-sulfonyl chloride (P1b)

4-Bromo-2-tert-butylaniline P1a (20 mmol) was added to a mixture of conc. HCl (11.2 mL) and AcOH (2.24 mL) at −10° C. To this mixture, a solution of $NaNO_2$ (1.52 g, 22 mmol) in minimum amount of water was added dropwise at −10° C. After stirring for 45 min at −10° C. the diazonium salt solution was obtained. $SO_2$ gas was bubbled into AcOH (22.4 mL) in a three-neck flask until saturation (30 min). Then CuCl (0.49 g, 0.49 mmol) was added and stirring was continued until the mixture turned green. The flask was placed in an ice bath and the diazonium salt solution was added dropwise at 5° C. After the addition was complete, the mixture was stirred overnight at rt and poured into ice water. The solid was collected by filtration to give the compound P1b (45%).

Step 3: 4-Bromo-N,2-di-tert-butylbenzenesulfonamide (P1c)

Compound P1b (1.0 mmol) and $NEt_3$ (2.0 mmol) were added into a solution of 2-methylpropan-2-amine (88 mg, 1.2 mmol) in toluene (20 mL). The mixture was stirred for 4 h at reflux, evaporated, poured into water and extracted with EA. The combined organic layers were washed with brine, dried over $Na_2SO_4$, filtered and evaporated to give compound P1c as a solid (330 mg, 85%)

Step 4: N,2-Di-tert-butyl-4-(4,4,5,5-tetramethyl-1,3,2-dioxaborolan-2-yl)benzenesulfonamide (P1)

A flask charged with $Pd(dppf)Cl_2$ (30 μmol), KOAc (294 mg, 3.0 mmol) and compound P1c (279 mg, 1.0 mmol) was flushed with $N_2$, then 1,4-dioxane (6 mL) and $B_2Pin_2$ (1.2 mmol) were added. After being stirred at 80° C. for an appropriate period, the product was extracted with benzene, washed with water and dried over $MgSO_4$. Kugelrohr distillation in vacuo gave compound P1 (200 mg, 50%).

Preparative Example P1/1 to P1/2

Using similar procedures at that described in Preparative Example P1, the following compound was prepared:

| # | Structure |
|---|---|
| P1/1 | 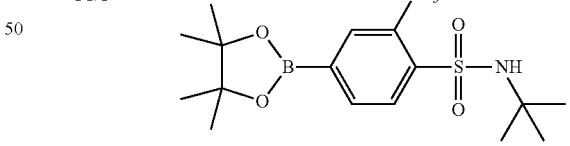 |
| P1/2 | 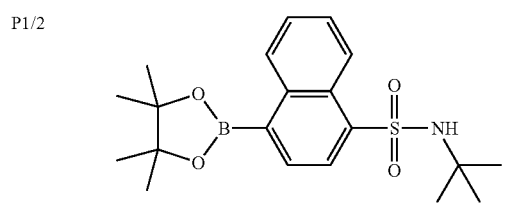 |

Preparative Example P2

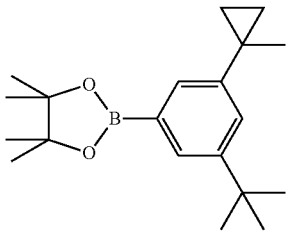

Step 1: 1-Bromo-3-(tert-butyl)-5-(prop-1-en-2-yl)benzene (P2a)

To a solution of 1,3-dibromo-5-(tert-butyl)benzene (2.92 g, 10 mmol) in dioxane (20 mL) was added Pd(PPh$_3$)$_4$ (3.0 g, 2.6 mmol), prop-1-en-2-ylboronic acid (1.0 g, 12 mmol), K$_2$CO$_3$ (2.8 g, 20 mmol) and H$_2$O (1 mL) under N$_2$. The resulting mixture was stirred at 90° C. overnight, concentrated and purified by CC (hexane) to give compound P2a (2.5 g, 100%; 80% by GC/MS) as a liquid.

Step 2: 1-Bromo-3-(tert-butyl)-5-(1-methylcyclopropyl)benzene (P2b)

To a solution of Et$_2$Zn (20 mL of 1M solution in hexanes, 20 mmol) in dry DCM (20 mL) at 0° C. was added freshly distilled TFA (1.8 mL, 20 mmol) in DCM (20 mL) over a period of approx. 30 min. The gray mixture was stirred at 0° C. for 20 min at which time CH$_2$I$_2$ (2.0 mL, 20 mmol) dissolved in DCM (20 mL) was added to the reaction flask by cannulation. The resulting slurry was stirred for 20 min before the addition of compound P2a (2.5 g, 10 mmol) dissolved in DCM (15 mL). The slurry was allowed to warm to rt over 30 min, quenched with sat. NH$_4$Cl (50 mL) and extracted with hexanes. The combined organic layers were dried over MgSO$_4$. Evaporation and purification by CC (hexane) afforded compound P2b (1.6 g, 60%) as a colorless oil.

Step 3: 2-(3-(tert-Butyl)-5-(1-methylcyclopropyl)phenyl)-4,4,5,5-tetramethyl-1,3,2-dioxaborolane (P2)

To a suspension of compound P2b (1.6 g, 70 mmol), B$_2$Pin$_2$ (3.0 g, 15 mmol), KOAc (2.32 g, 24 mmol) in dioxane (40 mL) was added Pd(dppf)Cl$_2$ (0.16 g) under N$_2$. The mixture was heated to 100° C. for 16 h, evaporated and purified by CC (PE/EA=4/1) to afford compound P2 (1.5 g, 68%) as a white solid.

Preparative Example P3

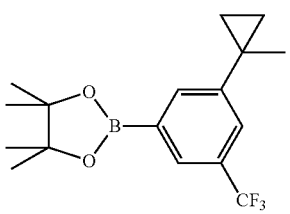

Step 1: 1-Bromo-3-(prop-1-en-2-yl)-5-(trifluoromethyl)benzene (P3a)

To a solution of 1,3-dibromo-5-(trifluoromethyl)benzene (3.03 g, 10 mmol) in dioxane (20 mL) was added Pd(PPh$_3$)$_4$ (300 mg, 0.26 mmol), prop-1-en-2-ylboronic acid (1.0 g, 12 mmol), K$_2$CO$_3$ (2.8 g, 20 mmol) and water (1 mL) under N$_2$. The mixture was stirred at 90° C. overnight, concentrated and purified by CC (hexane) to afford compound P3a (1.9 g, 71%) as an oil.

Step 2: 1-Bromo-3-(1-methylcyclopropyl)-5-(trifluoromethyl)benzene (P3b)

To a solution of Et$_2$Zn (4 mL of 1.0 M solution in hexanes, 4 mmol) in dry DCM (4 mL) at 0° C. was added freshly distilled TFA (0.36 mL, 4 mmol) in DCM (4 mL) very slowly (ca. 30 min). The grey mixture was stirred at 0° C. for 20 min while adding CH$_2$I$_2$ (0.4 mL, 4 mmol) in DCM (4 mL), stirred for additional 20 min before compound P3a (0.53 g, 2 mmol) dissolved in DCM (3 mL) was added. The slurry was allowed to warm to rt over 30 min, quenched with sat. NH$_4$Cl (5 mL) and extracted with hexanes. The combined organic layers were dried (MgSO$_4$), evaporated and purified by CC (hexane) to afford P3b (300 mg, 46%) as a colorless oil.

Step 3: 4,4,5,5-Tetramethyl-2-(3-(1-methylcyclopropyl)-5-(trifluoromethyl)phenyl)-1,3,2-dioxaborolane (P3)

To a suspension of compound P3b (300 mg, 1.0 mmol), B$_2$Pin$_2$ (380 mg, 1.5 mmol), KOAc (290 mg, 3 mmol) in dioxane (5 mL) was added Pd(dppf)Cl$_2$ (20 mg) under N$_2$. The mixture was heated to 100° C. for 16 h, evaporated and purified by CC (PE/EA=4/1) to give compound P3 (200 mg, 68%) as a white solid.

Preparative Example P4

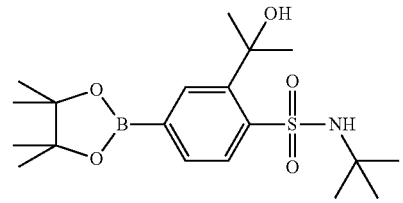

Step 1: 2-Amino-5-bromobenzonitrile (P4a)

To a solution of 2-aminobenzonitrile (14.9 g, 100 mmol) was added a solution of NBS (17.8 g, 100 mmol) in DMF at rt. The mixture was stirred overnight at rt, then water (30 mL) was added and the mixture was extracted with Et$_2$O (3×250 mL). The organic layer was washed with brine, dried over Na$_2$SO$_4$, concentrated and purified by CC to give compound P4a (19 g, 83%).

Step 2: 4-Bromo-2-cyanobenzene-1-sulfonyl chloride (P4b)

Compound P4a (10 g, 51 mmol) was added to a mixture of conc. HCl (28 mL) and AcOH (5.6 mL) at −10° C. Then a solution of NaNO₂ (3.8 g, 55 mmol) in a minimum amount of water was added dropwise at −10° C. After stirring for 45 min at −10° C. a diazonium salt solution was obtained. SO₂ gas was bubbled into AcOH (56 mL) until saturation (60 min). Then CuCl₂ (3 g) was added and stirring was continued until the mixture turned green. The flask was placed in an ice bath and the diazonium salt solution was added dropwise at 5° C. After addition was complete, the mixture was stirred overnight at rt and poured into ice water. The solid was collected by filtration to give the crude compound P4b (9 g, 71%)

Step 3:
4-Bromo-N-(tert-butyl)-2-cyanobenzenesulfonamide (P4c)

To a solution of compound P4b (5.0 g, 18 mmol) in pyridine (20 mL) was added 2-methylpropan-2-amine (3.3 g, 45 mmol) and the reaction was purged with N₂, heated at 50° C. for 1 h, cooled and concentrated. The residue was purified by CC (DCM/MeOH=100/1) to give compound P4c (3.0 g, 53%) as a yellow solid.

Step 4:
2-Acetyl-4-bromo-N-(tert-butyl)benzenesulfonamide (P4d)

A suspension of compound P4c (2 g, 6.3 mmol) in THF (20 mL) was added slowly to MeMgBr (6.3 mL, 3M in Et₂O, 19 mmol) and the mixture was heated to reflux for 3 h, placed in an ice bath and 6N HCl (58 mL) was added slowly. The mixture was then heated to reflux, cooled, made alkaline by addition of solid Na₂CO₃ and extracted with EA. The combined organic phases were dried over Na₂SO₄, evaporated and purified by CC (n-heptan/EA=100/0 to 60/40) to give compound P4d (0.6 g, 34%).

Step 5: 4-Bromo-N-(tert-butyl)-2-(2-hydroxypropan-2-yl)benzenesulfonamide (P4e)

Compound P4d (200 mg, 0.60 mmol) was dissolved in THF (15 mL) at 0° C. A 3M solution of MeMgBr in Et₂O (1 mL, 3.0 mmol) was added slowly and the reaction mixture was stirred at rt for 3 h, then another portion of a MeMgBr in Et₂O (1 mL, 3.0 mmol) was added. The mixture was evaporated, diluted with water (20 mL) and extracted with Et₂O. The organic layer was dried over MgSO₄, filtered, evaporated and purified by HPLC (DCM/MeOH=100/0 to 70/30) to give compound P4e (100 mg, 39%; 47% purity).

Step 6: N-(tert-Butyl)-2-(2-hydroxypropan-2-yl)-4-(4,4,5,5-tetramethyl-1,3,2-dioxaborolan-2-yl)benzenesulfonamide (P4)

To a solution of compound P4e (200 mg, 0.57 mmol), Pin₂B2 (290 mg, 1.14 mmol) and KOAc (160 mg, 1.7 mmol) in dioxane (10 mL) at rt under N₂ was added Pd(dppf)Cl₂ (42 mg, 0.05 mmol). The resulting mixture was stirred at rt for 1 h, then heated to 110° C. for 2 h, diluted with water (50 mL) and extracted with EA. The combined organic layers were concentrated and purified by CC(PE/EA=5/1) to give compound P4 (100 mg, 43%) as a colorless solid.

Preparative Example P5 and Preparative Example P6

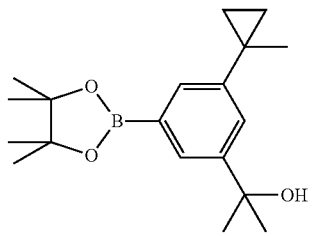

P5

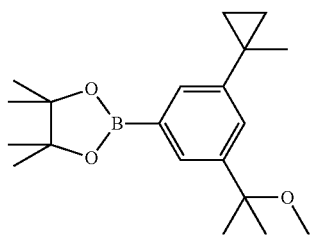

P6

Step 1:
3,5-Dibromo-N-methoxy-N-methylbenzamide (P5a)

The solution of 3,5-dibromobenzoic acid (26 g, 93 mmol) in SOCl₂ (100 mL) was heated at reflux for 2 h, concentrated, diluted with dry DCM (300 mL) and added slowly to a stirred solution of N,O-dimethylhydroxylamine hydrochloride (9.75 g, 100 mmol) and EtN₃ (28 g, 277 mmol) in dry DCM (300 mL) at 0° C. The solution was stirred for 1 h at rt, poured into water and the organic layer was separated. The organic layer was washed with water and brine, dried over Na₂SO₄, filtered and concentrated to give crude compound P5a (28 g, 93%) as an oil.

Step 2: 1-(3,5-Dibromophenyl)ethanone (P5b)

To a solution of compound P5a (1.0 g, 3.1 mmol) in dry THF (10 mL) was added MeMgCl (3M in Et₂O, 1 mL, 3.0 mmol) dropwise at 0° C. and the solution was stirred for 4 h at rt, then quenched with aq. NHCl₄ and extracted with tert-butylmethylether. The organic layer was washed with water and brine consecutively, dried over Na₂SO₄, filtered and concentrated to give crude compound P5b (0.70 g, 66%) as a yellow oil.

Step 3: 1,3-Dibromo-5-(prop-1-en-2-yl)benzene (P5c)

To a stirred solution of PPh₃CH₃Br (5.10 g, 14.4 mmol) in dry THF (50 mL) was added n-BuLi (2.5 M in n-hexane, 5.76 mL, 14.4 mmol) dropwise at −40° C. After stirring at this temperature for 0.5 h, a solution of compound P5b (2.0 g, 7.2 mmol) in dry THF (10 mL) was added dropwise. The resulting solution was allowed to warm to rt and stirred for 1 h, quenched with aq. NHCl₄ and extracted with Et₂O. The organic layer was concentrated and purified by CC (PE) to give compound P5c (1.6 g, 80%) as a light yellow oil.

Step 4:
1,3-Dibromo-5-(1-methylcyclopropyl)benzene (P5d)

To a solution of compound P5c (1.6 g, 5.8 mmol) and Pd(OAc)₂ (350 mg) in THF (20 mL) was added dropwise at 0° C. a solution of CH$_2$N$_2$ (487 mg, 11.6 mmol) in Et$_2$O (20 mL) and the mixture was stirred for 1 h at rt. The suspension was filtered and the filtrate was concentrated and purified by CC (PE) to give compound P5d (1.4 g, 82%) as a colorless oil.

Step 5: 2-(3-Bromo-5-(1-methylcyclopropyl)phenyl)propan-2-ol (P5e)

To a stirred solution of compound P5d (0.5 g, 1.7 mmol) in dry THF (5 mL) was added dropwise n-BuLi (0.74 mL, 1.87 mmol) at −78° C. After 1 h at this temperature, dry acetone (118 mg, 2.04 mmol) was added dropwise. The solution was allowed to warm to rt and stirred overnight, then quenched with aq. NHCl$_4$ and extracted with EA. The combined organic layers were concentrated and purified by CC (PE/EA=20/1) to give compound P5e (250 mg, 52%) as a colorless oil.

Step 6: 1-Bromo-3-(2-methoxypropan-2-yl)-5-(1-methylcyclopropyl)benzene (P5f)

To a solution of compound P5e (1.5 g, 5.6 mmol) in dry THF (10 mL) was added NaH (450 mg, 11.2 mmol) under N$_2$ and the suspension was stirred for 1 h at rt. Then MeI (2.3 g, 16.8 mmol) was added and the solution was stirred at 70° C. in a sealed tube overnight, poured into water and extracted with Et$_2$O. The organic layer was washed with brine, dried over Na$_2$SO$_4$, filtered, concentrated and purified by CC (PE) to give compound P5f (1.6 g, 100%) as a colorless oil.

Step 7: 2-(3-(1-Methylcyclopropyl)-5-(4,4,5,5-tetramethyl-1,3,2-dioxaborolan-2-yl)phenyl)propan-2-ol (P5)

Compound P5 was prepared from compound P5e similar as described in Preparative Example 4, Step 6.

Step 8: 2-(3-(2-Methoxypropan-2-yl)-5-(1-methylcyclopropyl)phenyl)-4,4,5,5-tetramethyl-1,3,2-dioxaborolane (P6)

Compound P6 was prepared from compound P5f similar as described in Preparative Example 4, Step 6.

Preparative Example P7

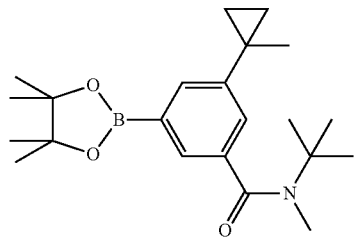

P7

Step 1: Methyl 3-bromo-5-(prop-1-en-2-yl)benzoate (P7a)

To a solution of methyl 3-bromo-5-iodobenzoate (3.40 g, 10 mmol) in dioxane (20 mL) was added Pd(PPh$_3$)$_4$ (300 mg, 0.26 mmol), prop-1-en-2-yl boronic acid (1.0 g, 12 mmol), K$_2$CO$_3$ (2.8 g, 20 mmol) and H$_2$O (1 mL) under N$_2$ atmosphere. The mixture was stirred overnight at 90° C. Then the mixture was concentrated and purified by CC (PE/EA=6/1) to afford compound P7a (1.9 g, 71%) as a solid.

Step 2: Methyl 3-bromo-5-(1-methylcyclopropyl)benzoate (P7b)

To a solution of Et$_2$Zn (4 mL of 1.0M solution in hexanes, 4.0 mmol) in dry DCM (4 mL) at 0° C. was added freshly distilled TFA (0.36 mL, 4.0 mmol) in DCM (4 mL) very slowly (ca. 30 min). The gray mixture was stirred at 0° C. for 20 min at which time diodomethene (0.4 mL, 4.0 mmol) dissolved in DCM (4 mL) was introduced by cannulation. The resulting slurry was stirred for 20 min before the addition of compound P7a (0.53 g, 2.0 mmol) dissolved in DCM (3 mL). The slurry allowed to warm to rt over 30 min. Progress of the reaction was monitored by TLC. When deemed complete, the reaction was quenched by the addition of sat. aq. NH$_4$Cl (5 mL) and the layers were separated. The aq. layer was extracted with hexane (2×) and dried over MgSO$_4$. Evaporation and purification by CC (PE/EA=7/1) afforded compound P7b (300 mg, 46%) as a clear colorless oil.

Step 3: 3-Bromo-5-(1-methylcyclopropyl)benzoic acid (P7c)

Compound P7b (270 mg, 1.0 mmol) and LiOH (50 mg, 2.0 mmol) were mixed in THF (3 mL) and H$_2$O (3 mL). The mixture was stirred for 10 h, then the pH was adjusted to pH 3 with aq. HCl and extracted with EA (3×10 mL). The organic layer was dried and concentrated to afford the crude product P7c (250 mg, 100%).

Step 4: 3-Bromo-N-(tert-butyl)-N-methyl-5-(1-methylcyclopropyl)benzamide (P7d)

To a solution of compound P7c (250 mg, 1.0 mmol) in DMF (5 mL) was added HATU (380 mg, 1.0 mmol) and Et$_3$N (202 mg, 2.0 mmol) and the mixture was stirred overnight. After removal of the solvents the crude product was purified with prep. HPLC to afford compound P7d (300 mg, 95%).

Step 5: N-(tert-Butyl)-N-methyl-3-(1-methylcyclopropyl)-5-(4,4,5,5-tetramethyl-1,3,2-dioxaborolan-2-yl)benzamide (P7)

To a suspension of compound P7d (323 mg, 1.0 mmol), B$_2$Pin$_2$ (380 mg, 1.5 mmol), KOAc (290 mg, 3.0 mmol) in dioxane (5 mL) was added Pd(dppf)Cl$_2$ (20 mg) under N$_2$ atmosphere. The mixture was heated to 100° C. for 16 h. The mixture was purified by CC (PE/EA=4/1) to afford compound P7 (200 mg, 68%) as a white solid.

Preparative Example P7/1 to P7/2

Using similar procedures at that described in Preparative Example P7, the following compounds were prepared:

| # | Structure |
|---|---|
| P7/1 | 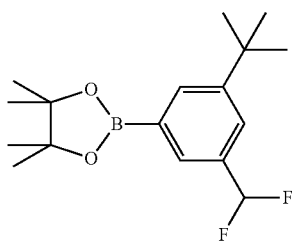 |
| P7/2 | 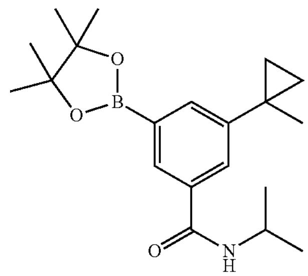 [SMILES: CC(C)NC(=O)c1cc(B2OC(C)(C)C(C)(C)O2)cc(C2(C)CC2)c1] |

Preparative Example P8

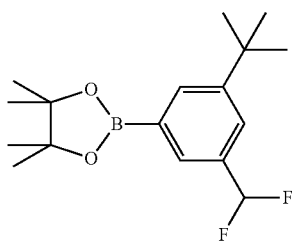

Step 1: 3-Bromo-5-(tert-butyl)benzaldehyde (P8a)

To a solution of 1,3-dibromo-5-(tert-butyl)benzene (55 g, 190 mmol) in dry THF (500 mL) was added n-BuLi (2.5M in hexane, 88 mL, 220 mmol) at −78° C. under N₂ and the solution was stirred for 1 h at this temperature. Then DMF (20.8 g, 285 mmol) was added slowly and the solution was stirred for 3 h at −78° C., warmed to rt, quenched with sat. NH₄Cl, extracted with EA. The organic layer was washed with water and brine, dried over Na₂SO₄, filtered, concentrated and purified by CC (PE) to give compound P8a (40 g, 82%) as a colorless oil.

Step 2: 1-Bromo-3-(tert-butyl)-5-(difluoromethyl)benzene (P8b)

A solution of compound P8a (256 mg, 1.0 mmol) and DAST (158 mg, 2.0 mmol) in DCM (5 mL) was reacted under microwave condition (70° C.) for 15 min, washed with sat. NaHCO₃, water and brine consecutively, dried over Na₂SO₄, filtered and concentrated to give a residue. This reaction was repeated ten times and the combined residues were purified by CC (PE) to give compound P8b (2.2 g, 82%) as a colorless oil.

Step 3: 2-(3-(tert-Butyl)-5-(difluoromethyl)phenyl)-4,4,5,5-tetramethyl-1,3,2-dioxaborolane (P8)

Compound P8 was prepared from compound P8b similar as described in Preparative Example 4, Step 6.

Preparative Example P9

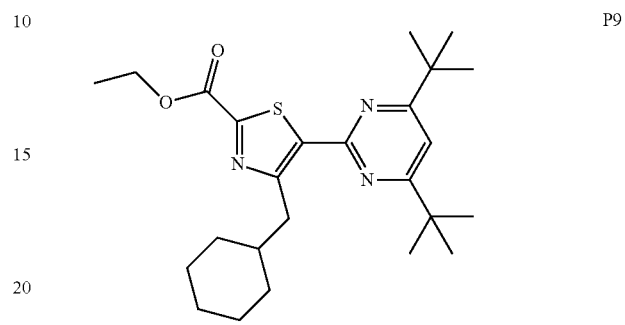

Step 1: 4,6-Di-tert-butyl-2-chloropyrimidine (P9a)

A mixture of 2,4,6-trichloropyrimidine (46 mg, 250 μmol) and CuI (3 mg, 12 μmol) in dry THF (10 mL) was cooled to −20° C. and purged with N₂ for 10 min. Then a tert-BuMgCl solution (2M in THF, 64 mg, 0.55 mmol) was added dropwise at a rate such that the reaction solution did not exceed 0° C. After the addition, the solution was stirred at rt for 24 h, diluted with tert-BuOMe and washed with a sat. NH₄Cl solution and then brine, dried (Na₂SO₄), concentrated and purified by CC (PE/EA=100/1) to give compound P9a (45 mg, 80%) as yellow solid.

Step 2: Ethyl 4-(cyclohexylmethyl)-5-(4,6-di-tert-butylpyrimidin-2-yl)thiazole-2-carboxylate (P9)

The solution of P9a (45 mg, 0.2 mmol), methyl 4-(cyclohexylmethyl)thiazole-2-carboxylate (50 mg, 0.2 mmol), K₂CO₃ (46 mg, 0.33 mmol), Pd(OAc)₂ (2 mg, 4 μmol), PCy₃.HBF₄ (4 mg, 8 μmol) and PivOH (6 mg, 0.06 mmol) in a solution of DMA (2 mL) was heated under Ar at 100° C. overnight, cooled to rt, partitioned between EA and water and separated. The organic phase was washed with water and brine, dried over Na₂SO₄, filtered, concentrated and purified by CC (PE/EA=10/1 to 5/1) to give compound P9 (57 mg, 65%) as a white solid.

Preparative Example P9/1 to P9/2

Using similar procedures at that described in Preparative Example P9, the following compounds were prepared:

| # | Structure |
|---|---|
| P9/1 | 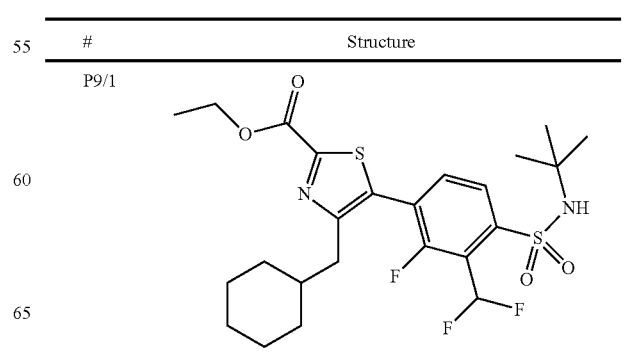 |

-continued

| # | Structure |
|---|---|
| P9/2 | 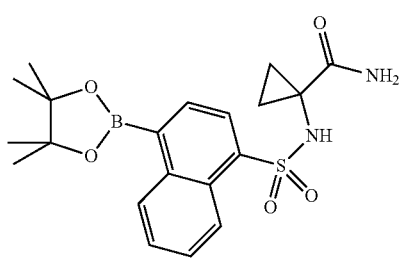 |

Preparative Example P10

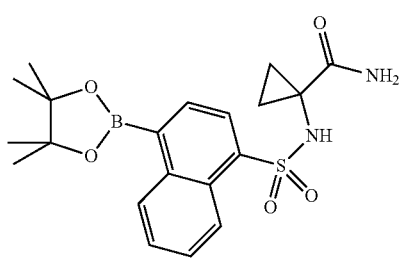

P10

Step 1: 1-(4-Bromonaphthalene-1-sulfonamido)cyclopropanecarboxamide (P10a)

The solution of 4-bromo-N-(1-cyanocyclopropyl)naphthalene-1-sulfonamide (200 mg, 0.57 mmol), 2N NaOH (0.6 mL, 1.20 mmol) and 30% aq. $H_2O_2$ (0.5 mL) in MeOH (3 mL) was heated at 60° C. for 3 h, cooled and extracted with $Et_2O$ twice. The combined organic layers were washed with water and brine, dried over $Na_2SO_4$, filtered and concentrated to give compound P10a (188 mg, 89%) as a white solid.

Step 2: 1-(4-(4,4,5,5-Tetramethyl-1,3,2-dioxaborolan-2-yl)naphthalene-1-sulfonamido)cyclopropanecarboxamide (P10)

The solution of compound P10a (188 mg, 0.51 mmol), $(Bpin)_2$ (153 mg, 0.60 mmol), KOAc (196 mg, 2.0 mmol) and $Pd(dppf)Cl_2$ (20 mg) in dioxane (5 mL) was heated for 16 h at 95° C. under $N_2$, cooled, filtered, diluted with water and extracted with EA twice. The combined organic layers were washed with water and brine, dried over $Na_2SO_4$, filtered, concentrated and purified by (PE/EA=10/1) to give compound P10 (60 mg, 28%) as a white solid.

Preparative Example P11

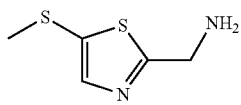

P11

Step 1: 5-Bromo-N-(tert-butyl)thiazole-2-carboxamide (P11a)

A solution of 5-bromothiazole-2-carboxylic acid (2.70 g, 13.0 mmol), HATU (5.71 g, 15.0 mmol) and tert-butylamine (4.1 mL, 39.0 mmol) in dry THF (30 mL) was stirred overnight under Ar. The resulting solution was partitioned between EA and sat. $Na_2CO_3$. The organic layer was washed with 1N HCl and brine, dried over $Na_2SO_4$, filtered, concentrated and purified by CC (PE/EA=4/1) to give compound P11a (3.42 g, 100%) as a yellow solid.

Step 2: N-(tert-Butyl)-5-(methylthio)thiazole-2-carboxamide (P11b)

To a solution of compound P11a (3.42 g, 13.0 mmol) in dry THF (40 mL) was added n-BuLi (2.5M in hexane, 10.4 mL, 26.0 mmol) at −78° C. under Ar and the solution was stirred for 2 h at −78° C. Then $Me_2S$ (2.4 g, 26.0 mmol) was added at −78° C. and the solution was stirred at rt for 2 h, quenched by water and extracted with EA twice. The combined organic layers were dried over $Na_2SO_4$, filtered, concentrated and purified by CC (PE/EA=5/1) to give compound P11b (2.50 g, 90%) as a brown solid.

Step 3: 5-(Methylthio)thiazole-2-carboxamide (P1c)

To a solution of compound P11b (2.50 g, 10.9 mmol) in dry DCM (15 mL) was added TFA (15 mL) at 0° C. and the solution was stirred at rt overnight, concentrated and diluted with DCM. The solution was washed with 1N NaOH twice and brine, dried over $Na_2SO_4$, filtered and concentrated to give compound P11c (1.77 g, 93%) as a yellow solid.

Step 4: (5-(Methylthio)thiazol-2-yl)methanamine (P11)

A solution of compound P11c (1.77 g, 10.2 mmol) in dry THF (20 mL) was added a solution of $LiAlH_4$ in THF (1M, 20.0 mL, 20.0 mmol) under stirring and the suspension was further stirred at 8° C. for 3 h, cooled to 0° C. and quenched slowly by addition of $H_2O$, 15% aq. NaOH and $H_2O$. The suspension was stirred until all $LiAlH_4$ was neutralized and a white precipitate was formed, filtered and the precipitate was washed with $Et_2O$. The combined organic layers were dried over $Na_2SO_4$, filtered, concentrated and purified by prep-HPLC to give compound P11 (410 mg, 25%) as a brown oil.

Preparative Example P12

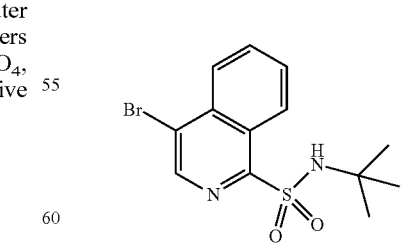

P12

Step 1: 4-Bromoisoquinolin-1-ol (P12a)

To a solution of isoquinolin-1-ol (5.0 g, 34.5 mmol) in DCM (100 mL) was added a solution of $Br_2$ (6.0 g, 37.7 mmol) in DCM (20 mL) and the mixture was stirred for 4 h. The formed solid was collected by filtration, washed with DCM and re-crystallized from Et$_2$O to give compound P12a (5.0 g, 62%) as a yellow solid.

Step 2: 4-Bromoisoquinoline-1-thiol (P12b)

A mixture of compound P12a (1.0 g, 4.40 mmol), pyridine (0.3 mL) and Lawesson's reagent (3.5 g, 8.00 mmol) in toluene (20 mL) was stirred under reflux for 2 h, cooled to 40° C. and the precipitated crystals were collected by filtration and dried in vacuum to give compound P12b (600 mg, 56%) as pale yellow crystal.

Step 3: 4-Bromoisoquinoline-1-sulfonyl chloride (P12c)

To a solution of compound P12b (3.0 g, 12.4 mmol) in a mixture of MeCN (30 mL), AcOH (10 mL) and water (5 mL) was added NCS (4.7 g, 36.0 mmol) and the solution was allowed to warm to 50° C. and stirred for overnight before being partitioned between brine and EA. The organic layer was dried over Na$_2$SO$_4$, filtered, concentrated and purified by CC (PE/EA=10/1) to give compound P12c (1.1 g, 29%) as a yellow powder.

Step 4: 4-Bromo-N-(tert-butyl)isoquinoline-1-sulfonamide (P12)

To a solution of t-BuNH$_2$ (731 mg, 10.0 mmol) in dry DCM (10 mL) was added a solution of compound P12c (1.1 g, 3.59 mmol) in dry DCM (15 mL) at 0° C. and the solution was stirred at rt for 3 h and quenched by water. The organic layer was washed with water and brine, dried over Na$_2$SO$_4$, filtered, concentrated and purified by CC (PE/EA=6/1) to give compound P12 (800 mg, 65%) as a yellow solid.

Preparative Example P13

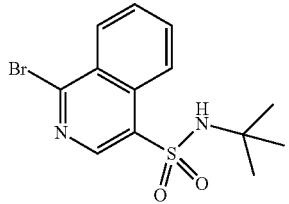

P13

Step 1: 4-Nitroisoquinolin-1-ol (P13a)

To a hot solution of isoquinolin-1-ol (10.0 g, 69.0 mmol) in a mixture of AcOH (40 mL) and water (10 mL) was added nitric acid (13 mL, 207 mmol) over 1 h at 65° C. (maintained the reaction temperature between 68-70° C.) and the solution was stirred at 65° C. for 3 h, cooled to rt and diluted with water. The formed solid was collected by filtration and dried in vacuum to give compound P13a (8.0 g, 61%) as a yellow solid.

Step 2: 4-Aminoisoquinolin-1-ol (P13b)

To a solution of compound P13a (8.0 g, 42.1 mmol) and NH$_4$Cl (5.35 g, 100 mmol) in EtOH (100 mL) was added Fe dust (4.48 g, 80.0 mmol) at rt and the suspension was stirred at 70° C. for 3 h and filtered through a celite pad. The filtrate was concentrated, diluted with EA, washed with water and brine, dried over Na$_2$SO$_4$ and concentrated to give compound P13b (6.1 g, 90%) as a brown solid.

Step 3: 1-Bromoisoquinolin-4-amine (P13c)

A solution of compound P13b (6.1 g, 38.1 mmol) and PBr$_3$ (28.7 g, 100 mmol) was stirred at 135° C. for overnight, cooled to rt, diluted with water, adjusted to pH=8 with Na$_2$CO$_3$ (solid) and extracted with EA (3×). The combined organic layers were washed with sat. NaHCO$_3$ and brine, dried over Na$_2$SO$_4$, filtered, concentrated and purified by CC (PE/EA=1/1) to give compound P13c (4.4 g, 52%) as a pale yellow solid.

Step 4: 1-Bromo-N-(tert-butyl)isoquinoline-4-sulfonamide (P13)

To a solution of compound P13c (3.0 g, 13.5 mmol), HOAc (50 mL) and a solution of HBr in AcOH (48%, 10 mL) in MeCN (50 mL) was added a solution of NaNO$_2$ (1.12 g, 16.2 mmol) in water (20 mL) at 0° C. After stirring 20 min, SO$_2$ gas was bubbled in over 20 min, keeping the reaction temperature <0° C. A solution of CuCl$_2$.2H$_2$O (1.67 g, 8.1 mmol) in water (10 mL) was added and the solution was stirred for 3 h at rt, concentrated and dissolved in DCM (15 mL). To this solution was added tert-BuNH$_2$ (1.9 g, 26 mmol) and the solution was stirred at rt for overnight. The resulting suspension was filtered and the filtrate was diluted with water. The organic layer was washed with brine, dried over Na$_2$SO$_4$, filtered, concentrated and purified by CC (PE/EA=8/1) to give crude compound P13 (300 mg, 6.5%) with 10% of chloride determined by LCMS as a white solid.

Preparative Example P14

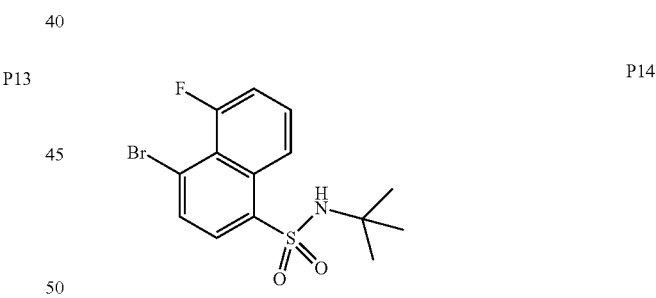

P14

Step 1: 5-Nitronaphthalen-1-amine (P14a)

A solution of sodium sulfide (31.7 g, 330 mmol) and sodium bicarbonate in water (70 mL) was heated to 70° C. and the a suspension of 1,5-dinitronaphthalene (20 g, 91.6 mmol) in methanol (300 mL) was added dropwise at reflux. The resultant mixture was stirred for 5 min, cooled to 0° C., quenched with ice and stirred for further 10 min followed by acidification with conc. HCl. The resulting mixture was stirred for 30 min, then washed with EA twice. The aq. layer was basified with aq. ammonia and extracted with EA twice. The combined organic layers were washed with water twice and brine twice consecutively, dried over Na$_2$SO$_4$, filtrated and concentrated to give compound P14a (12.0 g, 71%) as a brown solid.

Step 2: 1-Fluoro-5-nitronaphthalene (P14b)

To a suspension of compound P14a (12 g, 63.8 mmol) in a mixture of water/conc. HCl (1/1, 100 mL) was added NaNO$_2$ (6.60 g, 95.7 mmol) portionwise at −5° C. and the mixture was stirred for 15 min at −5° C. Then a 60% w/w hexafluorophosphoric acid solution (60 mL) was added. The brown precipitate was filtered and washed with cold water and Et$_2$O and then dried in vacuum. The resulting solid was suspended in toluene and heated to 110° C. for 2 h, cooled to rt, concentrated and purified by CC (PE) to give compound P14b (4.50 g, 37%) as a yellow solid.

Step 3: 5-Fluoronaphthalen-1-amine (P14c)

A solution of compound P14b (19.1 g, 100 mmol) in EtOH (500 mL, containing 50 mL 12N HCl) was heated to reflux and Fe powder (16.8 g, 300 mmol) was added in small portions and heating was continued for 2 h. The resulting mixture was cooled to rt and neutralized with 1N NaOH. The aq. layer was extracted with DCM (3×). The combined organic layers were washed with water and brine, dried over MgSO$_4$, filtered, concentrated and purified by CC (PE/EA=3/1) to give compound P14c (11.6 g, 72%) as a yellow solid.

Step 4: 4-Bromo-5-fluoronaphthalen-1-amine (P14d)

To a solution of compound P14c (7.0 g, 43.4 mmol) in THF (100 mL) at −78° C. was added NBS (7.73 g, 43.4 mmol) and the solution was stirred for 1 h at −78° C., diluted with water and extracted with EA twice. The combined organic layers was dried over Na$_2$SO$_4$, filtered, concentrated and purified by CC (PE/EA=4/1) to give compound P14d (6.5 g, 62%) as an off-white solid.

Step 5: 4-Bromo-5-fluoronaphthalene-1-sulfonyl chloride (P14e)

To a solution of compound P14d (7.1 g, 29.6 mmol), HOAc (50 mL) and a solution of HBr in AcOH (48%, 100 mL) in MeCN (230 mL) was added a solution of NaNO$_2$ (2.45 g, 35.5 mmol) in water (50 mL) at 0° C. After stirring 20 min, SO$_2$ gas was bubbled in over 1 h, keeping the reaction temperature <0° C. A solution of CuCl$_2$.2H$_2$O (3.02 g, 17.8 mmol) in water (10 mL) was added and the solution was stirred for 3 h at rt, concentrated and purified by CC (PE/EA=30/1) to give compound P14e (5.4 g, 56%) as a pale yellow oil.

Step 6: 4-Bromo-N-(tert-butyl)-5-fluoronaphthalene-1-sulfonamide (P14)

To a solution of compound P14e (3.0 g, 9.27 mmol) in pyridine (15 mL) was added tert-BuNH$_2$ (2.0 g, 27.3 mmol) and the solution was stirred at rt for overnight, concentrated and purified by CC (PE/EA=30/1) to give compound P14 (1.71 g, 51%) as a white solid.

Preparative Example P15

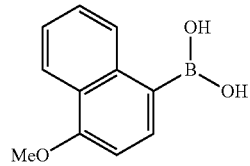

(4-Methoxynaphthalen-1-yl)boronic acid (P15)

A mixture of 1-bromo-4-methoxynaphthalene (2.0 g, 8.44 mmol) in Et$_2$O (10 mL) was cooled down to −70° C. under N$_2$ and then n-BuLi in hexane (3.37 mL, 8.44 mmol) was added dropwise. The solution was stirred under N$_2$ for 2 h, then warmed to rt and triisopropyl borate (1.74 g, 9.28 mmol) was added. The mixture was stirred for 16 h under N$_2$. Then 2M HCl (10 mL) and Et$_2$O (10 mL) was added to the mixture which was washed by brine till it turned neutral. The organic layer was dried over Na$_2$SO$_4$, filtered, concentrated and the residue was washed with EA to give compound P15 (500 mg, 29%) as a colorless solid.

Preparative Example P16

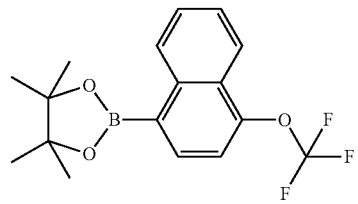

Step 1: 4-Bromonaphthalen-1-ol (P16a)

A solution of naphthalen-1-ol (35.0 g, 243 mmol) in ACN (300 mL) was cooled to 0° C. Then NBS (42.7 g, 243 mmol) in ACN (500 mL) was added dropwise and the mixture was stirred for 1 h, concentrated and dissolved in DCM. The solution was washed with brine, dried over Na$_2$SO$_4$, filtered, concentrated and washed with PE to give compound P16a (30.0 g, 55%) as an off-white solid.

Step 2: 1-Bromo-4-(bromodifluoromethoxy)naphthalene (P16b)

NaH (60%, 1.26 g, 31.5 mmol) was added to a solution of compound P16a (2.0 g, 10.5 mmol) in DMF (20 mL) in a 75 mL seal tube slowly under ice-bath cooling. After stirring for 10 min, t-BuOK (1.3 g, 11.6 mmol) and CF$_2$Br$_2$ (8.8 g, 42.0 mmol) were added slowly to the mixture. The sealed tube was quickly closed and heated to 70° C. overnight. The resulting mixture was poured into water and extracted with EA twice. The combined organic layers were washed with water (3×) and brine consecutively, dried over Na$_2$SO$_4$, filtered, concentrated and purified by CC (PE) to give compound P16b (1.6 g, 43%) as a colorless oil.

Step 3: 1-Bromo-4-(trifluoromethoxy)naphthalene (P16c)

A solution of compound P16b (3.5 g, 10.0 mmol) in DCM (70 mL) was cooled to −78° C. under N₂, then AgBF₄ (4.3 g, 22.0 mmol) was added and the solution was warmed to rt slowly and stirred overnight. NaHCO₃ solution was added to the mixture until pH>8. Then the resulting suspension was filtered and the filtrate was extracted with DCM twice. The combined organic layers were washed with brine, dried over Na₂SO₄, filtered and concentrated to give compound P16c (3.0 g, quant.) as a brown oil.

Step 4: 4,4,5,5-Tetramethyl-2-(4-(trifluoromethoxy)naphthalen-1-yl)-1,3,2-dioxaborolane (P16)

A mixture of compound P16c (1.0 g, 3.45 mmol), Pin₂B2 (1.75 g, 6.9 mmol), AcOK (1.0 g, 10.4 mmol) and Pd(dppf)Cl₂.CH₂Cl₂ (282 mg, 0.35 mmol) in 1,4-dioxane (20 mL) was bubbled with N₂ for 10 min and the mixture was stirred at 80° C. for 16 h under N₂, cooled to rt and diluted with EA and filtered. The filtrate was concentrated and purified by CC (PE) to give compound P16 (0.90 g, 77%) as an off-white solid.

Preparative Example P17

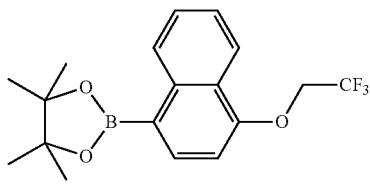

P17

Step 1: 1-Bromo-4-(2,2,2-trifluoroethoxy)naphthalene (P17a)

A mixture of 4-bromonaphthalen-1-ol (5.00 g, 22.4 mmol), 1,1,1-Trifluoro-2-iodoethane (5.65 g, 26.9 mmol) and Cs₂CO₃ (15 g, 46.1 mmol) in DMF (150 mL) was stirred at 100° C. for 16 h, cooled to rt, diluted with EA and then filtered. The filtrate was concentrated and purified by CC (PE) to give compound P17a (2.8 g, 41%) as a colorless solid.

Step 2: 4,4,5,5-Tetramethyl-2-(4-(2,2,2-trifluoroethoxy)naphthalen-1-yl)-1,3,2-dioxaborolane (P17)

A mixture of compound P17a (500 mg, 1.64 mmol), B₂Pin₂ (835 mg, 3.29 mmol) and KOAc (483 mg, 4.93 mmol) in dioxane (30 mL) was bubbled with N₂ for 10 min, then Pd(dppf)Cl₂.CH₂Cl₂ (134 mg, 0.164 mmol) was added and the mixture was stirred at 80° C. for 16 h under N₂, diluted with EA, filtered, concentrated and purified by CC (EA/PE=1/20) to give compound P17 (180 mg, 31%) as a colorless solid.

Preparative Example P18

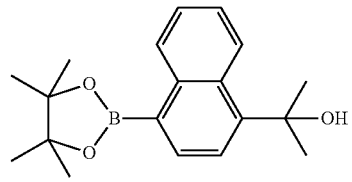

P18

Step 1: 2-(4-Bromonaphthalen-1-yl)propan-2-ol (P18a)

To a solution of 1,4-dibromonaphthalene (2.0 g, 7.0 mmol) in dry Et₂O (50 mL) was added n-BuLi (2.5M in hexanes, 3.1 mL, 7.7 mmol) at 0° C. and the solution was stirred for 20 min. Then acetone (488 mg, 8.4 mmol) was added and the solution was warmed to rt and stirred at this temperature for 1 h, quenched with water and extracted with Et₂O (3×). The combined organic layers were washed with brine, dried over Na₂SO₄, filtered, concentrated and purified by CC (PE/EA=10/1) to give compound P18a (1.2 g, 65%) as an off-white solid.

Step 2: 2-(4-(4,4,5,5-Tetramethyl-1,3,2-dioxaborolan-2-yl)naphthalen-1-yl)propan-2-ol (P18)

A solution of compound P18a (600 mg, 2.3 mmol), B₂Pin₂ (690 mg, 2.7 mmol), KOAc (450 mg, 4.6 mmol) and Pd(dppf)Cl₂ (150 mg, 0.2 mmol) in dioxane (10 mL) was heated overnight at 85° C. under N₂, cooled to rt, filtered and the filtrate diluted with water. The aqueous layer was extracted with EA twice. The combined organic layers were washed with water and brine, dried over Na₂SO₄, filtered, concentrated and purified by CC (PE/EA=20/1) to give compound P18 (600 mg, 83%) as a colorless solid.

Preparative Example P19

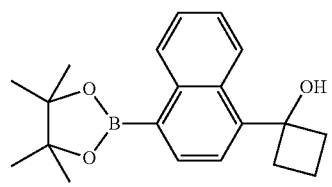

P19

Step 1: 3-(4-Bromonaphthalen-1-yl)oxetan-3-ol (P19a)

To a solution of 1,4-dibromonaphthalene (2.0 g, 7.0 mmol) in dry Et₂O (50 mL) was added n-BuLi (2.5M in hexanes, 3.1 mL, 7.7 mmol) at 0° C. and the solution was stirred for 20 min. Then oxetan-3-one (604 mg, 8.4 mmol) was added and the solution was warmed to rt and stirred at this temperature for 1 h, quenched with water and extracted with Et₂O (3×). The combined organic layers were washed with brine, dried over Na₂SO₄, filtered, concentrated and purified by CC (PE/EA=5/1) to give compound P19a (1.20 g, 61%) as an off-white solid.

Step 2: 3-(4-(4,4,5,5-Tetramethyl-1,3,2-dioxaborolan-2-yl)naphthalen-1-yl)oxetan-3-ol (P19)

The solution of compound P19a (500 mg, 1.8 mmol), $B_2Pin_2$ (559 mg, 2.2 mmol), KOAc (353 mg, 3.6 mmol) and $Pd(dppf)Cl_2$ (145 mg, 0.2 mmol) in dioxane (10 mL) was heated overnight at 85° C. under $N_2$, cooled to rt, filtered and the filtrate was diluted with water. The aqueous layer was' extracted with EA twice. The combined organic layers were washed with water and brine, dried over $Na_2SO_4$, filtered, concentrated and purified by CC (PE/EA=20/1) to give compound P19 (110 mg, 15%) as a colorless solid.

Preparative Example P20

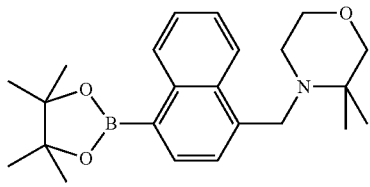

Step 1: 4-Bromo-1-naphthaldehyde (P20a)

To a solution of 1,4-dibromonaphthalene (2.0 g, 7.0 mmol) in dry $Et_2O$ (50 mL) was added n-BuLi (2.5M in hexanes, 3.1 mL, 7.7 mmol) at 0° C. and the solution was stirred for 20 min. Then DMF (1.62 mL, 21 mmol) was added and the solution was warmed to rt and stirred at this temperature for 1 h, quenched with water and extracted with $Et_2O$ (3×). The combined organic layers were washed with brine, dried over $Na_2SO_4$, filtered, concentrated and purified by CC (PE/EA=50/1) to give compound P20a (1.02 g, 62%) as an off-white solid.

Step 2: (4-Bromonaphthalen-1-yl)methyl methanesulfonate (P20b)

To a solution of compound P20a (1.02 g, 4.3 mmol) in MeOH (10 mL) was added $NaBH_4$ (378 mg, 10 mmol) slowly and the suspension was stirred at rt for 1 h, was quenched with sat. $NH_4Cl$, concentrated and diluted with EA and water. The organic layer was washed with brine, dried over $Na_2SO_4$, filtered and concentrated to give a residue. To this residue was added DCM (10 mL), $NEt_3$ (1.01 g, 10 mmol) and MsCl (1.15 g, 10 mmol) and the mixture was stirred for 1 h, quenched with water and the organic layer was dried over $Na_2SO_4$, filtered and concentrated to give crude compound P20b (700 mg, 52%) as a colorless oil.

Step 3: 4-((4-Bromonaphthalen-1-yl)methyl)-3,3-dimethylmorpholine (P20c)

A suspension of compound P20b (700 mg, 2.2 mmol), 3,3-dimethyl-morpholine (512 mg, 4.4 mmol) and $K_2CO_3$ (828 mg, 6.0 mmol) in ACN (10 mL) was refluxed overnight, cooled to rt, filtered, concentrated and purified by CC (PE/EA=5/1) to give compound P20c (460 mg, 54% over two steps) as a colorless solid.

Step 4: 3,3-Dimethyl-4-((4-(4,4,5,5-tetramethyl-1,3,2-dioxaborolan-2-yl)naphthalen-1-yl)methyl)morpholine (P20)

A solution of compound P20c (460 mg, 1.38 mmol), $B_2Pin_2$ (953 mg, 3.75 mmol), KOAc (368 mg, 3.75 mmol) and $Pd(dppf)Cl_2$ (51 mg, 0.06 mmol) in dioxane (10 mL) was heated overnight at 90° C. under $N_2$, cooled to rt, filtered and the filtrate was diluted with water. The aqueous layer was extracted with EA twice. The combined organic layers were washed with water and brine, dried over $Na_2SO_4$, filtered, concentrated and purified by CC (PE/EA=5/1) to give compound P20 (110 mg, 21%) as a colorless solid.

Preparative Example P21

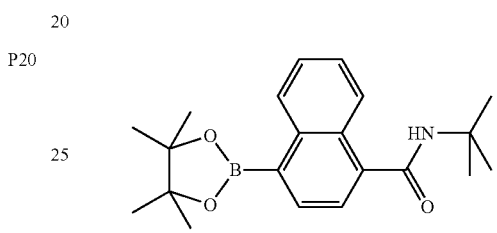

Step 1: 4-Bromo-N-(tert-butyl)-1-naphthamide (P21a)

A mixture of 4-bromo-1-naphthoic acid (4.0 g, 16 mmol) in thionyl chloride (20 mL) was heated under reflux for 2 h, cooled to rt and concentrated to give the acid chloride. The crude intermediate was dissolved in dry DCM (40 mL) and treated with t-BuNH$_2$ (2.92 g, 40 mmol), and the mixture was stirred at rt for 20 h and quenched with 1M HCl. The organic layer was washed with 1M HCl and brine, dried over $Na_2SO_4$, concentrated and purified by CC (PE/EA=8/1) to give compound P21a (3.8 g, 78%) as a colorless solid.

Step 2: N-(tert-Butyl)-4-(4,4,5,5-tetramethyl-1,3,2-dioxaborolan-2-yl)-1-naphthamide (P21)

The solution of compound P21a (1.5 g, 5.0 mmol), $B_2Pin_2$ (1.5 g, 6.0 mmol), KOAc (980 mg, 10.0 mmol) and $Pd(dppf)Cl_2$ (366 mg, 0.5 mmol) in dioxane (15 mL) was heated overnight at 90° C. under $N_2$, cooled to rt, filtered and the filtrate was diluted with water. The aqueous layer was extracted with EA twice. The combined organic layers were washed with water and brine, dried over $Na_2SO_4$, filtered, concentrated and purified by CC (PE/EA=10/1) to give compound P21 (1.7 g, 96%) as a colorless solid.

Preparative Example P22

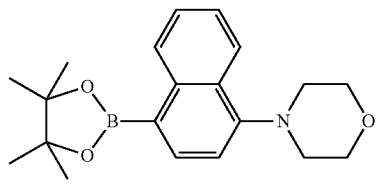

Step 1: 4-(4-Bromonaphthalen-1-yl)morpholine (P22a)

To a solution of 4-bromonaphthalen-1-amine (2.0 g, 9.0 mmol) in DMF (20 mL) was added 1-bromo-2-(2-bromoethoxy)ethane (1.43 mL, 9.0 mmol) and potassium carbonate (2.76 g, 20 mmol). The mixture was heated at 100° C. for 48 h, cooled to rt, diluted with water and extracted with EA (3×). The combined organic layers were washed with water and brine, dried over $Na_2SO_4$, filtered, concentrated and purified by CC (PE/EA=4/1) to give compound P22a (900 mg, 34%) as a yellow solid.

Step 2: 4-(4-(4,4,5,5-Tetramethyl-1,3,2-dioxaborolan-2-yl)naphthalen-1-yl)morpholine (P22)

A solution of compound P22a (900 mg, 3.1 mmol), $B_2Pin_2$ (945 mg, 3.7 mmol), KOAc (608 mg, 6.2 mmol) and $Pd(dppf)Cl_2$ (220 mg, 0.3 mmol) in dioxane (10 mL) was heated overnight at 90° C. under $N_2$, cooled to rt, filtered and the filtrate was diluted with water. The aqueous layer was extracted with EA twice. The combined organic layers were washed with water and brine, dried over $Na_2SO_4$, filtered, concentrated and purified by CC (PE/EA=4/1) to give compound P22 (770 mg, 73%) as a colorless solid.

Preparative Example P23

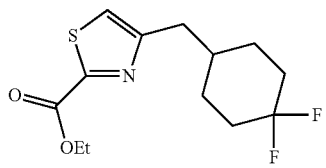

P23

Step 1: 1-Bromo-3-(4,4-difluorocyclohexyl)propan-2-one (P23a)

2-(4,4-Difluorocyclohexyl)acetic acid (4.0 g, 22.5 mmol) in $SOCl_2$ (50 mL) was refluxed for 2 h and concentrated. The brown oil was dissolved in ACN (50 mL) and cooled to 0° C. $TMSCHN_2$ (1N, 34 mmol) was added dropwise and the mixture was stirred at rt for 2 h. It was cooled to 0° C. again, and HBr in HOAc (3 mL) was added dropwise. The mixture was stirred at rt overnight. $H_2O$ (100 mL) and EA (100 mL) was added. The aq. phase was extracted with EA (80 mL×2), the combined organic phases were washed with brine and concentrated. The residue was purified by CC (PE/EA=25/1) to afford compound P23a (2.51 g, 44%) as a colorless oil.

Step 2: Ethyl 4-((4,4-difluorocyclohexyl)methyl)thiazole-2-carboxylate (P23)

A mixture of compound P23a (2.51 g, 9.9 mmol) and ethyl 2-amino-2-thioxoacetate (1.45 g, 10.9 mmol) in ethanol (50 mL) was stirred at 90° C. overnight. After concentration to dryness the residue was purified by CC (PE/EA=15:1) to give P23 (1.6 g, 65%) as a brown solid.

Preparative Example P24

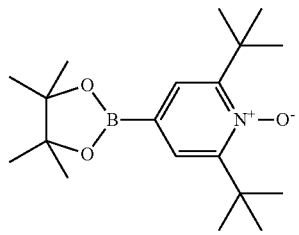

P24

Step 1: 2,6-Di-tert-butylpyridine 1-oxide (P24a)

To a solution of 2,6-di-tert-butylpyridine (6.00 g, 31.4 mmol) in EA (100 mL) was added m-CPBA (16.5 g, 95.6 mmol) and the solution was refluxed for overnight, washed with sat. $NaHCO_3$ and sat. $NaS_2O_3$ consecutively, dried over $Na_2SO_4$, filtered, concentrated and purified by CC (PE/EA=30/1) to give compound P24a (186 mg, 3%) as a white solid.

Step 2: 2,6-Di-tert-butyl-4-(4,4,5,5-tetramethyl-1,3,2-dioxaborolan-2-yl)pyridine 1-oxide (P24)

A solution of compound P24a (118 mg, 570 μmol), $[Ir(COD)(OMe)]_2$ (13 mg, 20 μmol), DTBPy (11 mg, 40 μmol) and $(BPin)_2$ (174 mg, 680 μmol) in dry THF (5 mL) was refluxed for 16 h, concentrated and purified by CC (PE/EA=30/1) to give compound P24 (98 mg, 52%) as a white solid.

Preparative Example P25

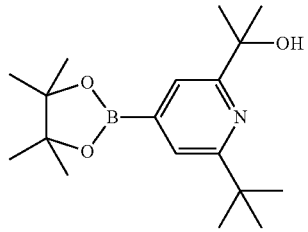

P25

Step 1: 2-(6-(tert-Butyl)pyridin-2-yl)propan-2-ol (P25a)

A solution of 1-(6-(tert-butyl)pyridin-2-yl)ethanone (3.20 g, 18.1 mmol) in THF (20 mL) was cooled to −78° C. and $CH_3MgBr$ in THF (1M, 3.6 mL, 3.6 mol) was added dropwise. The mixture was stirred at −78° C. and allowed to warm to rt for 3 h, quenched with aq. saturated $NH_4Cl$, extracted with EA (3×) and then the combined organic layers were dried over $Na_2SO_4$. The solvent was filtered, concentrated and purified by CC (PE/EA=5/1) to give compound P25a (3.1 g, 89%) as an oil.

Step 2: 2-(6-(tert-Butyl)-4-(4,4,5,5-tetramethyl-1,3,2-dioxaborolan-2-yl)pyridin-2-yl)propan-2-ol (P25)

A solution of compound P25a (1.00 g, 5.18 mmol), $[Ir(COD)(OMe)]_2$ (100 mg, 0.16 mmol), DTBPy (83 mg, 0.31 mmol) and (BPin)$_2$ (1.58 g, 6.2 mmol) in THF (10 mL) was stirred at 80° C. overnight, concentrated and purified by CC (PE/EA=10/1 to 1/1)) to give compound P25 (0.9 g, 54%) as a slight yellow solid.

Preparative Example P26

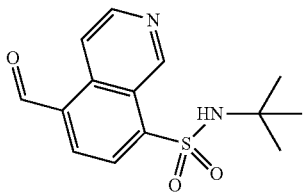

Step 1: 5-Bromoisoquinoline-8-sulfonic acid (P26a)

A solution of 5-bromoisoquinoline (50 g, 250 mmol) in fuming sulphuric acid (500 mL) was heated to 200° C. and stirred for 4 h. After cooling to rt the mixture was poured into 2500 mL ice water. A white solid was obtained by filtration, washed with water and acetone and dried in vacuum to give compound P26a (59 g, 90%) as a white solid.

Step 2: 5-Bromo-N-(tert-butyl)isoquinoline-8-sulfonamide (P26b)

A solution of P26a (28 g, 100 mmol) and DMF (4 mL) in SOCl$_2$ (300 mL) was heated to reflux for 5 h. The excess of SOCl$_2$ was removed under reduced pressure. A solution of tert-butylamine (37 g, 500 mmol) in DCM (100 mL) was added dropwise to a solution of the crude residue in 150 mL DCM at 0° C. The reaction mixture was stirred for 2 h at rt, quenched with water and extracted with DCM. The organic layer was concentrated to dryness to give a yellow solid, which was washed with Et$_2$O and dried in vacuum to give compound P26b (22 g, 63%) as a yellow solid.

Step 3: N-(tert-Butyl)-5-formylisoquinoline-8-sulfonamide (P26)

A solution of n-butyllithium (46 mL, 114 mmol) in hexane was added dropwise to a solution of P26b (15 g, 52 mmol) in THF/Et$_2$O (200 mL/200 mL) at −78° C. Then the reaction was stirred for 30 min at this temperature. A solution of DMF (4 mL) in THF was added slowly to the reaction mixture at −78° C. and stirring was continued for 3 h. The reaction was quenched with a solution of NH$_4$Cl and extracted with EA. The organic layer was washed with brine, dried with Na$_2$SO$_4$, concentrated and purified by CC (PE/E=6/1) to give compound P26 (5.5 g, 36%) as a yellow solid.

Additional Preparative Examples

The synthesis of additional Preparative Examples (e.g. boronic esters) is described in WO2012/139775 and in PCT/EP2012/004977.

Example 1

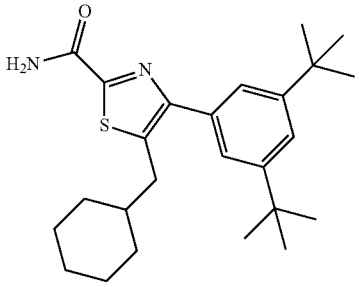

Step 1: 3-Cyclohexyl-1-(3,5-di-tert-butylphenyl) propan-1-one (1a)

A solution of 1,3-di-tert-butylbenzene (4.36 g, 22.9 mmol) in dry CH$_2$Cl$_2$ (20 mL) was sequentially treated at 0° C. with 3-cyclohexylpropanoyl chloride (4.00 g, 22.9 mmol) and AlCl$_3$ (3.35 g, 25.2 mmol) and the solution was stirred at 0° C. for 2 h. The resulting solution was poured into 0.1N HCl and the organic layer was separated. The aq. phase was extracted with EA. The combined organic layers were washed with sat. NaHCO$_3$ and brine consecutively, dried over Na$_2$SO$_4$, filtered, concentrated and purified by CC (DCM/PE=1/6) to give compound 1a (2.3 g, 30%) as a light yellow oil.

Step 2: 2-Bromo-3-cyclohexyl-1-(3,5-di-tert-butyl-phenyl)propan-1-one (1b)

To a solution of compound 1a (2.0 g, 6.02 mmol) in AcOH (20 mL) was added Br$_2$ (0.96 g, 6.02 mmol) at 0° C. and the solution was stirred at rt for 1 h. The resulting solution was poured into sat. Na$_2$SO$_3$ and extracted with EA twice. The combined organic layers were washed with water and brine consecutively, dried over Na$_2$SO$_4$, filtered, concentrated and purified by CC (DCM/PE=1/8) to give compound 1b (2.2 g, 89%) as a colorless oil.

Step 3: Ethyl 5-(cyclohexylmethyl)-4-(3,5-di-tert-butylphenyl)thiazole-2-carboxylate (1c)

The solution of compound 1b (0.47 g, 1.2 mmol) and ethyl thiooxamate (0.24 g, 1.8 mmol) in n-BuOH (10 mL) was heated at reflux for 16 h. After concentration under reduced pressure, the residue was dissolved in a mixture of water and EA and the organic layer was separated. The aq. layer was extracted with EA twice. The combined organic layers were washed with water and brine consecutively, dried over Na$_2$SO$_4$, filtered, concentrated and purified by CC (DCM/PE=1/5) to give compound 1c (0.2 g, 38%) as a yellow oil.

Step 4: 5-(Cyclohexylmethyl)-4-(3,5-di-tert-butyl-phenyl)thiazole-2-carboxamide (1)

To a solution of compound 1c (0.15 g, 0.34 mmol) in methanol (5 mL) was bubbled NH$_3$ and the solution was heated at reflux for 16 h. After concentration under reduced pressure, the residue was purified by CC (EA/PE=1/6) to give compound 1 (100 mg, 71%) as a white solid. $^1$H-NMR (CDCl$_3$, 300 MHz) δ: 0.92-0.97 (2H, m), 1.14-1.28 (4H, m), 1.37 (18H, s), 1.57-1.80 (5H, m), 2.80 (2H, d, J=7.2 Hz), 5.53 (1H, br s), 7.17 (1H, br s), 7.37 (2H, d, J=2.1 Hz), 7.46 (1H, t, J=1.8 Hz). MS 413.4 (M+1).

Example 2

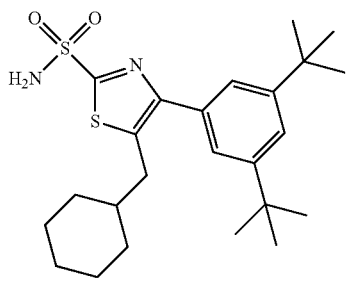

2

Step 1: 5-(Cyclohexylmethyl)-4-(3,5-di-tert-butyl-phenyl)thiazole (2a)

To a solution of compound 1b (1.70 g, 4.14 mmol) in 1,4-dioxane (15 mL) was added formamide (0.37 g, 8.3 mmol) and phosphorus pentasulfide (0.37 g, 1.67 mmol) and the solution was heated at reflux for 16 h. 2N HCl was added and the solution was refluxed for another 1 h. After concentration under reduced pressure, the residue was dissolved in dilute 2N NaOH and the solution was extracted with EA twice. The combined organic layers were washed with water and sat. Na$_2$CO$_3$, dried over Na$_2$SO$_4$, filtered, concentrated and purified by CC (DCM/PE=1/3) to give compound 2a (0.9 g, 59%) as a colorless sticky oil.

Step 2: 2-Bromo-5-(cyclohexylmethyl)-4-(3,5-di-tert-butylphenyl)thiazole (2b)

To a solution of compound 2a (0.30 g, 0.90 mmol) in dry THF (5 mL) was added a solution of n-BuLi (2.5M in n-hexane, 0.4 mL, 1.0 mmol) at −78° C. and the solution was stirred for 30 min. CBr$_4$ (0.33 g, 1.0 mmol) in dry THF (1 mL) was added at −78° C. and the solution was stirred at rt for 1 h. The resulting solution was quenched with sat. NH$_4$Cl and extracted with EA twice. The combined organic layers were washed with water and brine consecutively, dried over Na$_2$SO$_4$, filtered, concentrated and purified by CC (DCM/PE=1/4) to give compound 2b (0.36 g, 86%) as a white solid.

Step 3: 5-(Cyclohexylmethyl)-4-(3,5-di-tert-butyl-phenyl)thiazole-2-thiol (2c)

To a solution of compound 2b (0.35 g, 0.78 mmol) in EtOH (5 mL) was added NaSH (87 mg, 1.6 mmol) and the solution was heated at reflux for 24 h. After concentration under reduced pressure, the residue was dissolved in a mixture of water and EA and the organic layer was separated. The aq. layer was extracted with EA twice. The combined organic layers were washed with water and brine consecutively, dried over Na$_2$SO$_4$, filtered, concentrated and purified by CC (EA/PE=1/4) to give compound 2c (80 mg, 26%) as a white solid.

Step 4: 5-(Cyclohexylmethyl)-4-(3,5-di-tert-butyl-phenyl)thiazole-2-sulfonamide (2)

To a solution of compound 2c (45 mg, 0.11 mmol) in CH$_2$Cl$_2$ (5 mL) was added NCS (58 mg, 0.44 mmol) and the solution was stirred at rt for 2 h. Water was added and the solution was extracted with CH$_2$Cl$_2$ twice. The combined organic layers were washed with sat. NaHCO$_3$ and brine consecutively, dried over Na$_2$SO$_4$, filtered and concentrated. The residue was dissolved in a mixture of acetone (3 mL) and NH$_4$OH (5 mL) and the solution was stirred for 30 min. The organic layer was removed under reduced pressure and the aq. layer was extracted with EA twice. The combined organic layers were washed with water and brine consecutively, dried over Na$_2$SO$_4$, filtered, concentrated and purified by CC (EA/PE=1/4) to give compound 2 (27 mg, 55%) as a white solid. $^1$H-NMR (CDCl$_3$, 300 MHz) δ: 0.85-0.96 (2H, m), 1.16-1.25 (4H, m), 1.35 (18H, s), 1.60-1.76 (5H, m), 2.80 (2H, d, J=6.9 Hz), 5.29 (2H, br s), 7.34 (2H, d, J=1.8 Hz), 7.46 (1H, t, J=2.1 Hz). MS 449.4 (M+1).

Example 3

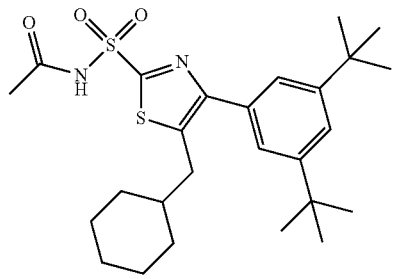

3

N-((5-(Cyclohexylmethyl)-4-(3,5-di-tert-butylphe-nyl)thiazol-2-yl)sulfonyl)acetamide (3)

To a solution of compound 2 (20 mg, 45 μmol) in CH$_2$Cl$_2$ (2 mL) was added NEt$_3$ (50 μL) and Ac$_2$O (50 μL) and the solution was stirred at rt for 1 h. Water was added to quench the reaction and the organic layer was separated. The aq. phase was extracted with DCM twice. The combined organic layers were washed with water and brine consecutively, dried over Na$_2$SO$_4$, filtered, concentrated and purified by CC (EA/PE=1/3) to give compound 3 (18 mg, 81%) as a white solid. $^1$H-NMR (CDCl$_3$, 300 MHz) δ: 0.94-0.97 (2H, m), 1.17-1.28 (4H, m), 1.36 (18H, s), 1.67-1.79 (5H, m), 1.86 (3H, s), 2.76 (2H, d, J=6.9 Hz), 7.30 (2H, d, J=1.8 Hz), 7.50 (1H, t, J=1.8 Hz). MS 491.4 (M+1).

Example 4

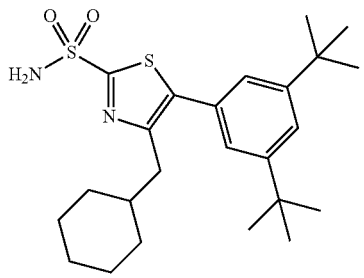

Step 1: 1-Allyl-3,5-di-tert-butylbenzene (4a)

To a solution of (3,5-di-tert-butylphenyl)boronic acid (12.0 g, 52.0 mmol) in dry toluene (300 mL) was added $K_2CO_3$ (27.6 g, 200 mmol), $Pd_2(dba)_3$ (2.0 g) and 3-bromoprop-1-ene (6.2 g, 52 mmol) by injection under nitrogen atmosphere and the suspension was stirred at reflux overnight, then cooled to rt and filtered. The filtrate was concentrated and purified by CC (PE) to give product 4a (7.3 g, 62%) as a light yellow oil.

Step 2: 2-(3,5-Di-tert-butylbenzyl)oxirane (4b)

To a solution of compound 4a (7.3 g, 32 mmol) in $CH_2Cl_2$ (70 mL) was added m-CPBA (6.6 g, 38 mmol) at rt and the solution was stirred for 2 h, quenched with aq. $Na_2S_2O_3$ and the organic layer was separated, washed with water and brine consecutively, dried over $Na_2SO_4$, filtered, concentrated and CC (PE) to give compound 4b (6.0 g, 76%) as a colorless oil.

Step 3: 1-Cyclohexyl-3-(3,5-di-tert-butylphenyl)propan-2-ol (4c)

To a solution of CuBr (150 mg) and cyclohexylmagnesium chloride (2M in $Et_2O$, 15 mL, 30 mmol) was added a solution of compound 4b (6.0 g, 24.4 mmol) in dry THF (10 mL) slowly at −30° C. and the solution was stirred at rt for 30 min, then quenched with sat. $NH_4Cl$ and extracted with MTBE (3×). The combined organic layers were concentrated to give crude compound 4c (6.5 g, 82%) as a yellow oil.

Step 4: 1-Cyclohexyl-3-(3,5-di-tert-butylphenyl)propan-2-one (4d)

A solution of $H_5IO_6$ (5.5 g 24 mmol) in ACN (100 mL) was stirred vigorously at rt for 15 min. After cooling to 0° C., compound 4c (6.5 g, 20 mmol) was added, followed by the addition of PCC (10.3 g, 48 mmol) in CAN (20 mL) and the solution was stirred for 2 h at 0° C., diluted with MTBE and passed on a pad of silica gel. The collected solution was concentrated to give the crude compound 4d (6.0 g, 91%) as a brown oil.

Step 5: 1-Bromo-3-cyclohexyl-1-(3,5-di-tert-butylphenyl)propan-2-one (4e)

To a solution of compound 4d (6.0 g, 18.3 mmol) in $CCl_4$ (100 mL) was added a solution of $Br_2$ (1M in $CH_2Cl_2$, 2.93 g, 18.3 mmol) at −15° C. and the solution was stirred at 0° C. for 1 h, then poured into sat. $Na_2SO_3$ and extracted with EA twice. The combined organic layers were washed with water and brine consecutively, dried over $Na_2SO_4$, filtered, concentrated and purified by CC (PE) to give compound 4e (6.5 g, 87%) as a colorless oil.

Step 6: 4-(Cyclohexylmethyl)-5-(3,5-di-tert-butylphenyl)thiazol-2-amine (4f)

To a solution of compound 4e (6.5 g, 16 mmol) in EtOH (150 mL) was added thiourea (4.9 g, 64 mmol) and the solution was heated at 80° C. for 4 h, cooled to rt and a solution of sat. $NaHCO_3$ was added. The formed solid was collected by filtration and dried in vacuo to give compound 4f (6.0 g, 98%) as a light yellow solid.

Step 7: 2-Bromo-4-(cyclohexylmethyl)-5-(3,5-di-tert-butylphenyl)thiazole (4g)

The solution of $CuBr_2$ (4.05 g, 18 mmol) and tert-butyl nitrite (2.1 g, 19 mmol) in ACN (75 mL) was heated at reflux until gas evolution stopped. Compound 4f (5.7 g, 15 mmol) was added and the solution was heated at reflux until gas evolution stopped again, then diluted with EA and washed repeatedly with sat. $Na_2CO_3$. The organic layer was dried over $MgSO_4$, filtered, concentrated and purified by CC (DCM/PE=2/1) to give compound 4g (4.4 g, 67%) as a light yellow solid.

Step 8: 4-(Cyclohexylmethyl)-5-(3,5-di-tert-butylphenyl)thiazole-2-thiol (4 h)

To a solution of compound 4g (4.2 g, 9.4 mmol) in EtOH (150 mL) was added NaSH (2.1 g, 38 mmol) and thiourea (2.9 g, 38 mmol) and the solution was heated at reflux for 24 h. After concentration, the residue was diluted with water and extracted with EA twice. The combined organic layers were washed with water and brine consecutively, dried over $Na_2SO_4$, filtered, concentrated and purified by CC (EA/PE=1/9) to give compound 4h (1.8 g, 48%) as a white solid.

Step 9: 4-(Cyclohexylmethyl)-5-(3,5-di-tert-butylphenyl)thiazole-2-sulfonamide (4)

To a solution of compound 4h (150 mg, 0.38 mmol) in $CH_2Cl_2$ (15 mL) was added NCS (200 mg, 1.5 mmol) and the solution was stirred at rt for 1. Water was added to quench the reaction and the solution was extracted with $CH_2Cl_2$. The organic layer washed with sat. $NaHCO_3$ and brine consecutively, dried over $Na_2SO_4$, filtered and concentrated. The residue was taken up in acetone (10 mL) and $NH_4OH$ (10 mL) and the solution was stirred for 15 min, concentrated and extracted with EA twice. The combined organic layers were washed with water and brine consecutively, dried over $Na_2SO_4$, filtered, concentrated and purified by CC (EA/PE=1/4) to give compound 4 (70 mg, 41%) as a white solid. $^1$H-NMR ($CDCl_3$, 300 MHz) δ: 0.87-0.96 (2H, m), 1.12-1.25 (3H, m), 1.35 (18H, s), 1.63-1.74 (5H, m), 1.78-1.85 (1H, m), 2.67 (2H, d, J=7.2 Hz), 5.39 (2H, s), 7.23 (2H, d, J=2.0 Hz), 7.49 (1H, t, J=2.0 Hz). MS 449.1 (M+1).

Example 5

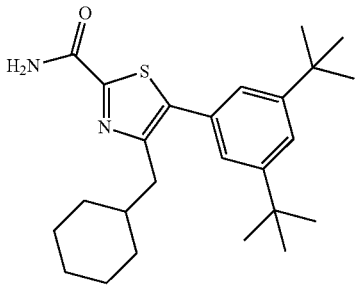

Step 1: 2-(3,5-Di-tert-butylphenyl)acetonitrile (5a)

A solution of 1,3-di-tert-butyl-5-methylbenzene (25 g, 12.3 mmol), NBS (24 g, 13.5 mmol), AIBN (50 mg, 0.31 mmol) in CCl$_4$ (250 mL) was heated at reflux for 12 h. The resulting solution was cooled to rt and placed in the refrigerator overnight. The formed solid was filtered and the filtrate was concentrated under reduced pressure. The residue was dissolved in DMF (200 mL) and NaCN (9.0 g, 18.4 mmol) was added. The solution was stirred at 50° C. for 16 h, poured into water and extracted with EA twice. The combined organic layers were washed with water and brine consecutively, dried over Na$_2$SO$_4$, filtered, concentrated and purified by CC (PE) to give compound 5a (16.9 g, 60%) as a colorless oil.

Step 2: 2-(3,5-Di-tert-butylphenyl)acetic acid (5b)

To a solution of compound 5a (16.9 g, 73.8 mmol) in a mixture of THF (130 mL) and EtOH (80 mL) was added aq. KOH solution (40 wt %, 80 mL) and the solution was vigorously stirred at 100° C. for 6 d, cooled to rt and acidified with 2N aq. HCl to pH=3. The suspension was extracted with EA three times. The combined organic layers were washed with brine, dried over Na$_2$SO$_4$, filtered, concentrated and purified by CC (EA/PE=1/6) to give compound 5b (6.4 g, 35%) as a white solid.

Step 3: 2-(3,5-Di-tert-butylphenyl)-N-methoxy-N-methylacetamide (5c)

A solution of compound 5b (6.4 g, 25.7 mmol) in SOCl$_2$ (5 mL) was heated at reflux for 1 h, concentrated under reduced pressure and diluted in dry CH$_2$Cl$_2$ (40 mL). This solution was slowly added to a solution of N,O-dimethyhydroxylamine hydrochloride (2.52 g, 25.7 mmol) and DIEA (9.9 g, 77 mmol) in dry CH$_2$Cl$_2$ (30 mL) at 0° C. and the solution was stirred at rt overnight, quenched with water and extracted with EA twice. The combined organic layers were washed with 1N aq. HCl, sat. Na$_2$CO$_3$ and brine consecutively, dried over Na$_2$SO$_4$, filtered, concentrated and purified by CC (EA/PE=1/6) to give compound 5c (5.1 g, 68%) as a white solid.

Step 4: 1-Cyclohexyl-3-(3,5-di-tert-butylphenyl)propan-2-one (5d)

To a solution of compound 5c (2.5 g, 8.6 mmol) in dry THF (20 mL) was added a solution of cyclohexanyl magnesium bromide (0.57 M in Et$_2$O, 15 mL, 8.6 mmol) at 0° C. and the solution was stirred at rt for 3 h, quenched with sat. NH$_4$Cl and extracted with EA twice. The combined organic layers were washed with water and brine consecutively, dried over Na$_2$SO$_4$, filtered, concentrated and purified by CC (DCM/PE=1/6) to give compound 5d (187 mg, 7%) as a colorless sticky oil.

Step 5: 1-Bromo-3-cyclohexyl-1-(3,5-di-tert-butylphenyl)propan-2-one (5e)

To a solution of compound 5d (687 mg, 2.10 mmol) in AcOH (5 mL) was added a solution of Br$_2$ (335 mg, 2.1 mmol) in AcOH (1 mL) slowly at 0° C. and the solution was stirred at rt for 30 min, poured into sat. Na$_2$SO$_3$ and extracted with EA. The combined organic layers were washed with water and brine consecutively, dried over Na$_2$SO$_4$, filtered, concentrated and purified by CC (DCM/PE=1/8) to give compound 5e (0.50 g, 59%) as a yellow oil.

Step 6: Ethyl 4-(cyclohexylmethyl)-5-(3,5-di-tert-butylphenyl)thiazole-2-carboxylate (5f)

The solution of compound 5e (84 mg, 0.2 mmol) and ethyl thiooxamate (55 mg, 0.41 mmol) in n-BuOH (5 mL) was heated at reflux for 2 h and then concentrated under reduced pressure. The residue was dissolved in a mixture of water and EA and the organic layer was separated, washed with water and brine consecutively, dried over Na$_2$SO$_4$, filtered, concentrated and purified by CC (DCM/PE=1/5) to give compound 5f (60 mg, 67%) as a light yellow sticky oil.

Step 7: 4-(Cyclohexylmethyl)-5-(3,5-di-tert-butylphenyl)thiazole-2-carboxamide (5)

To a solution of compound 5f (60 mg, 0.14 mmol) in MeOH (10 mL) was bubbled NH$_3$ and the solution was heated at 90° C. for 16 h and concentrated under reduced pressure. The residue was purified by CC (EA/PE=1/6) to give 5 (30 mg, 52%) as a white solid. $^1$H-NMR (400 MHz, CDCl$_3$) δ: 0.87-1.00 (2H, m), 1.15-1.25 (4H, m), 1.35 (18H, s), 1.61-1.72 (5H, m), 1.79-1.84 (1H, m), 2.66 (2H, d, J=6.8 Hz), 5.61 (1H, br s), 7.16 (1H, br s), 7.25 (2H, d, J=2.0 Hz), 7.46 (1H, t, J=2.0 Hz). MS 413.2 (M+1).

Example 6

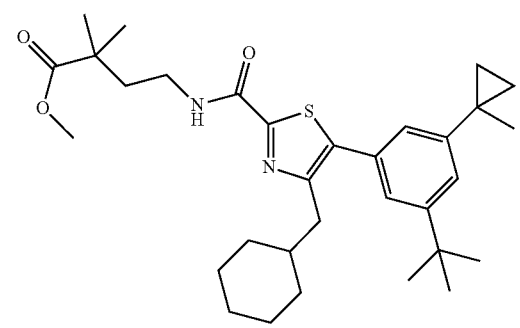

Step 1: 1-Bromo-3-cyclohexylpropan-2-one (6a)

To an ice-cooled solution of 1-cyclohexylpropan-2-one (19.6 g, 140 mmol) in MeOH (150 mL) was added Br$_2$ (22.4 g, 140 mmol) in a single portion and the reaction temperature was kept below 15° C. until the red color of the solution turned colorless. H$_2$O was added and the solution was extracted with Et$_2$O (3×). The combined organic layers were combined, washed with 10% aq. K$_2$CO$_3$ (3×), dried over Na$_2$SO$_4$, filtered and concentrated to give crude compound 6a (22 g) as a yellowish liquid.

Step 2: Ethyl 4-(cyclohexylmethyl)thiazole-2-carboxylate (6b)

A solution of compound 6a (20 g, 92 mmol) and ethylthioxamate (14.6 g, 110 mmol) in EtOH (300 mL) was heated at 80° C. for 6 h, then cooled to 0° C., diluted with water and EA and then neutralized to pH=7 using NH$_4$OH. The aq. layer was extracted with EA (3×). The combined organic layers were dried over Na$_2$SO$_4$, filtered, concentrated and purified by CC (PE/EA=20/1) to give compound 6b (14.5 g, 63% over two steps) as a yellow oil.

Step 3: Ethyl 5-bromo-4-(cyclohexylmethyl)thiazole-2-carboxylate (6c)

To a solution of compound 6b (14.5 g, 57.3 mmol) in CH$_2$Cl$_2$ (300 mL) was added TFA (3.26 g, 28.6 mmol) and DBH (8.17 g, 28.6 mmol) and the solution was stirred for 15 h at rt. A saturated solution of sodium hydrosulfite was then added. The organic phase was neutralized (pH=7) with 2M Na$_2$CO$_3$ solution and then washed with water, dried over MgSO$_4$, filtered, concentrated and purified by CC (PE/EA=10/1 to 5/1) to give compound 6c (12.1 g, 64%) as a white solid.

Step 4: Ethyl 5-(3-(tert-butyl)-5-(1-methylcyclopropyl)phenyl)-4-(cyclohexylmethyl)thiazole-2-carboxylate (6d)

A solution of compound 6c (2.0 g, 6.0 mmol), 2-(3-(tert-butyl)-5-(1-methylcyclopropyl)phenyl)-4,4,5,5-tetramethyl-1,3,2-dioxaborolane (2.3 g, 7.2 mmol), Na$_2$CO$_3$ (2.5 g, 24 mmol) and Pd(dppf)Cl$_2$ (438 mg, 0.6 mmol) in toluene (30 mL), EtOH (15 mL) and water (15 mL) was heated at 70° C. for 15 h before cooled to rt. The resulting solution was partitioned between EA and water and the layers were separated. The organic phase was washed with water and brine, dried over Na$_2$SO$_4$, filtered, concentrated and purified by CC (PE/EA=10/1 to 5/1) to give compound 6d (1.5 g, 57%) as a white solid.

Step 5: 5-(3-(tert-Butyl)-5-(1-methylcyclopropyl)phenyl)-4-(cyclohexylmethyl)thiazole-2-carboxylic acid (6e)

To a solution of compound 6d (1.5 g, 3.4 mmol) in a solution of MeOH (50 mL) and H$_2$O (10 mL) was added KOH (765 mg, 13.6 mmol) and then the solution was stirred for 4 h at 90° C., then concentrated and diluted with H$_2$O. 1 N HCl solution was added to adjust pH to 5, which was then extracted with DCM. The organic layer was washed with brine, dried over Na$_2$SO$_4$, filtered and concentrated to give compound 6e (1.2 g, 86%) as a white solid.

Step 6: Methyl 4-(5-(3-(tert-butyl)-5-(1-methylcyclopropyl)phenyl)-4-(cyclohexylmethyl)thiazole-2-carboxamido)-2,2-dimethylbutanoate (6)

To a solution of compound 6e (300 mg, 0.73 mmol) in DMF (3 mL) was added HATU (416 mg, 1.09 mmol), DIEA (283 mg, 2.2 mmol) and methyl 4-amino-2,2-dimethylbutanoate hydrochloride (125 mg, 0.87 mmol) and the solution was stirred for 20 min, then H$_2$O and EA was added. The organic layer was washed with brine, dried over Na$_2$SO$_4$, filtered, concentrated and purified by CC (PE/EA=5/1) to give compound 8 (300 mg, 76%) as white powder. $^1$H-NMR (300 MHz, CDCl$_3$) δ: 7.29 (s, 1H), 7.22 (s, 1H), 7.10 (s, 1H), 3.68 (s, 3H), 3.48 (dd, J=4.5 Hz, J=11.4 Hz, 2H), 2.60-2.63 (m, 2H), 1.92-1.96 (m, 2H), 1.80-1.84 (m, 1H), 1.62-1.70 (m, 7H), 1.43 (s, 3H), 1.34 (s, 9H), 1.27 (s, 6H), 1.14-1.25 (m, 3H), 0.87-0.96 (m, 3H), 0.75-0.78 (m, 2H). MS 539.4 (M+1)$^+$.

Example 6/1 to 6/64

The following Examples were prepared similar as in Example 6. Due to some extent of decarboxylation upon storage it is preferred not to neutralize the reaction mixture in Step 6e above but to use the potassium salt for the amide coupling.

| # | Structure | Analytical data |
|---|---|---|
| 6/1 | 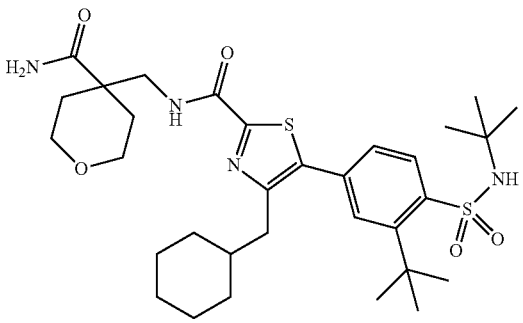 [SMILES: CC(C)(C)NS(=O)(=O)c1ccc(-c2sc(C(=O)NCC3(C(N)=O)CCOCC3)nc2CC2CCCCC2)cc1C(C)(C)C] | $^1$H-NMR (400 MHz, CDCl$_3$) δ: 8.22 (d, J = 7.6 Hz, 1H), 7.64-7.67 (m, 2H), 7.32-7.35 (m, 1H), 5.93 (br s, 1H), 5.65 (br s, 1H), 4.66 (s, 1H), 3.86 (br s, 2H), 3.72-3.76 (m, 4H), 2.65 (d, J = 5.2 Hz, 2H), 1.89-2.00 (m, 2H), 1.69-1.78 (m, 3H), 1.62 (s, 15H), 1.34 (s, 9H), 1.07-1.28 (m, 3H), 0.85-0.91 (m, 2H). MS 633.3 (M + 1)$^+$ |

| # | Structure | Analytical data |
|---|---|---|
| 6/2 | 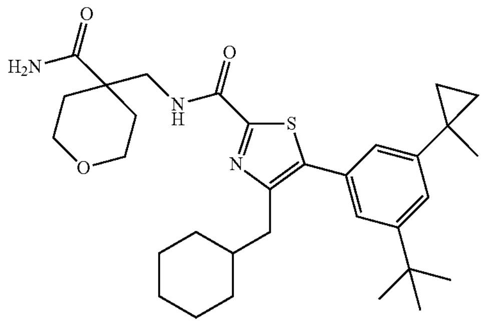 [SMILES: CC(C)(C)c1cc(-c2sc(C(=O)NCC3(C(N)=O)CCOCC3)nc2CC2CCCCC2)cc(C2(C)CC2)c1] | $^1$H-NMR (400 MHz, CDCl$_3$) δ: 7.58-7.61 (m, 1H), 7.30 (s, 1H), 7.22 (s, 1H), 7.09 (s, 1H), 5.91 (br s, 1H), 5.53 (br s, 1H), 3.86-3.92 (m, 2H), 3.68-3.74 (m, 4H), 2.63 (d, J = 6.8 Hz, 2H), 1.99-2.03 (m, 2H), 1.58-1.83 (m, 9H), 1.43 (s, 3H), 1.34 (s, 9H), 1.10-1.27 (m, 3H), 0.87-0.93 (m, 3H), 0.75-0.77 (m, 2H). MS 552.3 (M + 1)$^+$ |
| 6/3 | 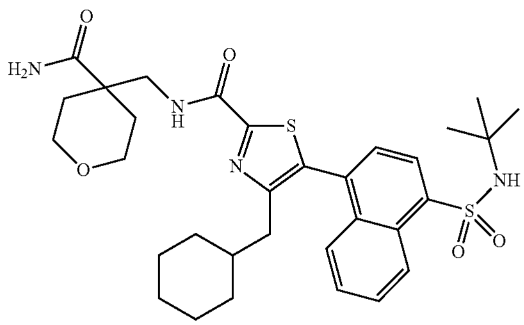 [SMILES: CC(C)(C)NS(=O)(=O)c1ccc(-c2sc(C(=O)NCC3(C(N)=O)CCOCC3)nc2CC2CCCCC2)c2ccccc12] | $^1$H-NMR (CDCl$_3$, 300 MHz) δ: 0.52-0.70 (m, 2H), 0.90-1.40 (m, 12H), 1.45-1.71 (m, 8H), 1.74-1.83 (m, 2H), 2.00-2.08 (m, 2H), 2.29-2.34 (m, 2H), 3.69-3.81 (m, 4H), 3.87-3.94 (m, 2H), 4.72 (s, 1H), 4.69 (s, 1H), 5.54 (br s, 1H), 5.93 (br s, 1H), 7.49-7.60 (m, 2H), 7.68-7.73 (s, 3H), 8.34 (d, J = 7.5 Hz, 1H), 8.68 (d, J = 8.7 Hz, 1H). MS 627.3 (M + 1)$^+$ |
| 6/4 | 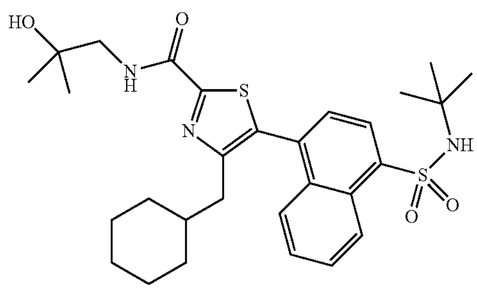 [SMILES: CC(C)(O)CNC(=O)c1nc(CC2CCCCC2)c(-c2ccc(S(=O)(=O)NC(C)(C)C)c3ccccc23)s1] | $^1$H-NMR (CDCl$_3$, 400 MHz) δ: 0.60-0.69 (m, 2H), 0.88-1.02 (m, 1H), 1.06-1.15 (m, 2H), 1.22 (s, 9H), 1.36 (s, 6H), 1.43-1.72 (m, 6H), 2.20 (br s, 1H), 2.35 (br s, 1H), 3.53 (d, J = 6.8 Hz, 2H), 4.70 (s, 1H), 7.52 (d, J = 7.6 Hz, 1H), 7.56-7.60 (m, 1H), 7.69-7.75 (m, 3H), 8.35 (d, J = 7.6 Hz, 1H), 8.69 (d, J = 8.8 Hz, 1H). MS 558.2 (M + 1)$^+$ |
| 6/5 | 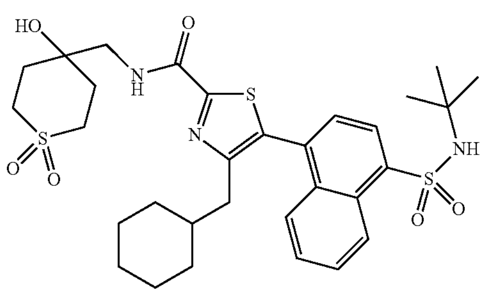 [SMILES: CC(C)(C)NS(=O)(=O)c1ccc(-c2sc(C(=O)NCC3(O)CCS(=O)(=O)CC3)nc2CC2CCCCC2)c2ccccc12] | $^1$H-NMR (CDCl$_3$, 300 MHz) δ: 0.63-0.71 (m, 2H), 0.88-1.12 (m, 3H), 1.22 (s, 9H), 1.47-1.70 (m, 6H), 2.18-2.21 (m, 4H), 2.35-2.36 (m, 2H), 2.89-2.95 (m, 2H), 3.44-3.55 (m, 2H), 3.59 (d, J = 6.0 Hz, 2H), 4.69 (s, 1H), 7.50 (d, J = 7.5 Hz, 1H), 7.55-7.60 (m, 1H), 7.68-7.77 (m, 3H), 8.36 (d, J = 7.5 Hz, 1H), 8.70 (d, J = 8.4 Hz, 1H). MS 648.2 (M + 1)$^+$ |
| 6/6 | 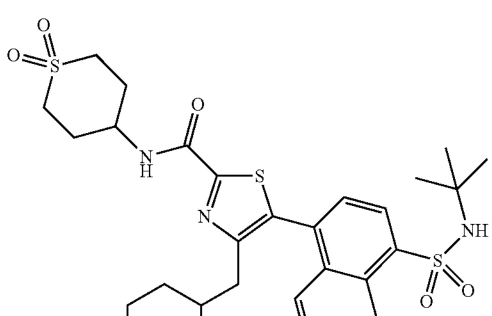 | $^1$H-NMR (CDCl$_3$, 400 MHz) δ: 0.60-0.69 (m, 2H), 0.96-1.20 (m, 3H), 1.22 (s, 9H), 1.36 (s, 6H), 1.48-1.70 (m, 6H), 2.32-2.42 (m, 4H), 2.46-2.51 (m, 2H), 3.15-.20 (m, 4H), 4.26-4.30 (m, 1H), 4.63 (s, 1H), 7.27-7.31 (m, 1H), 7.51 (d, J = 7.6 Hz, 1H), 7.55-7.59 (m, 1H), 7.71 (d, J = 8.0 Hz, 1H), 8.35 (d, J = 7.6 Hz, 1H), 8.69 (d, J = 8.4 Hz, 1H). MS 615.8 (M − 1)$^−$ |

| # | Structure | Analytical data |
|---|---|---|
| 6/7 | 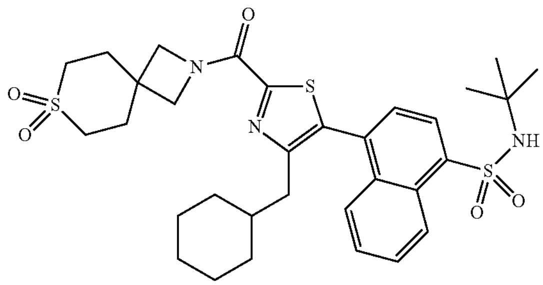 | ¹H-NMR (CDCl₃, 400 MHz) δ: 0.70-0.72 (m, 2H), 0.98-1.26 (m, 2H), 1.22 (s, 9H), 1.50-1.56 (m, 6H), 1.89 (t, J = 5.4 Hz, 2H), 2.33-2.37 (m, 2H), 3.68-3.73 (m, 4H), 4.01 (s, 2H), 4.49 (s, 2H), 4.62 (s, 1H), 7.50 (d, J = 7.8 Hz, 1H), 7.55-7.59 (m, 1H), 7.71-7.74 (m, 2H), 8.35 (d, J = 7.8 Hz, 1H), 8.68 (d, J = 8.1 Hz, 1H). MS 596.3 (M + 1)⁺ |
| 6/8 | 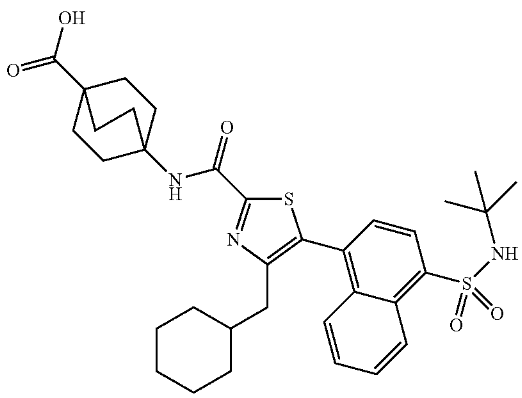 [SMILES: CC(C)(C)NS(=O)(=O)c1ccc(-c2sc(C(=O)NC34CCC(C(=O)O)(CC3)CC4)nc2CC2CCCCC2)c2ccccc12] | ¹H-NMR (CDCl₃, 400 MHz) δ: 0.61-0.65 (m, 2H), 1.03-1.12 (m, 3H), 1.21 (s, 9H), 1.45-1.66 (m, 6H), 1.89-1.91 (m, 6H), 1.97-2.17 (m, 6H), 2.31 (br s, 2H), 4.65 (s, 1H), 7.07 (s, 1H), 7.49 (d, J = 7.8 Hz, 1H), 7.55-7.58 (m, 1H), 7.70-7.73 (m, 2H), 8.34 (d, J = 7.8 Hz, 1H), 8.67 (d, J = 8.4 Hz, 1H). MS 638.3 (M + 1)⁺ |
| 6/9 | 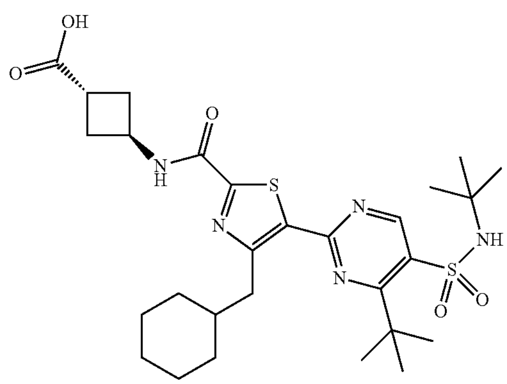 | ¹H-NMR (400 MHz, CDCl₃) δ: 7.58 (d, 1H, J = 7.6 Hz), 7.14 (s, 1H), 4.86-4.79 (m, 1H), 3.37 (d, 2H, J = 7.6 Hz), 3.22-3.17 (m, 1H), 2.85-2.79 (m, 2H), 2.55-2.47 (m, 2H), 1.92-1.68 (m, 6H), 1.37 (s, 18H), 1.30-1.06 (m, 5H). MS 513.3 (M + 1)⁺ |
| 6/10 | 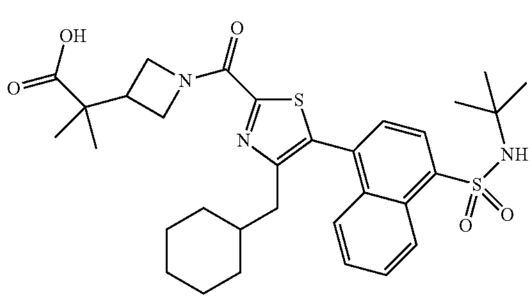 [SMILES: CC(C)(C)NS(=O)(=O)c1ccc(-c2sc(C(=O)N3CC(C(C)(C)C(=O)O)C3)nc2CC2CCCCC2)c2ccccc12] | ¹H-NMR (CDCl₃, 300 MHz) δ: 0.64-0.72 (m, 2H), 0.95-1.20 (m, 3H), 1.22 (s, 9H), 1.26 (s, 3H), 1.37 (s, 3H), 1.51-1.53 (m, 3H), 1.57-1.75 (m, 4H), 2.34 (br s, 2H), 2.62-2.71 (m, 1H), 3.58-3.65 (m, 2H), 4.10-4.16 (m, 1H), 4.44-4.50 (m, 1H), 4.62 (s, 1H), 7.40-7.45 (m, 2H), 7.51 (d, J = 7.5 Hz, 1H), 7.56-7.61 (m, 1H), 7.70-7.71 (m, 2H), 8.35 (d, J = 7.8 Hz, 1H), 8.69 (d, J = 11.4 Hz, 1H). MS 612.3 (M + 1)⁺ |

-continued

| # | Structure | Analytical data |
|---|---|---|
| 6/11 | 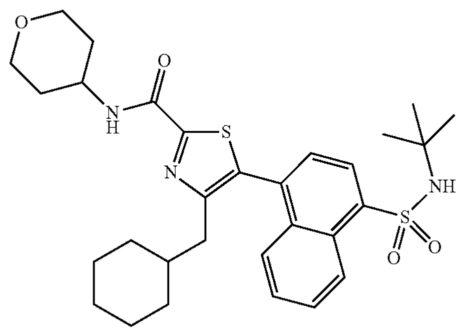 [SMILES: CC(C)(C)NS(=O)(=O)c1ccc(-c2sc(C(=O)NC3CCOCC3)nc2CC2CCCCC2)c2ccccc12] | $^1$H-NMR (400 MHz, CDCl$_3$) δ: 0.60-0.69 (m, 2H), 0.96-1.02 (m, 1H), 1.06-1.51 (m, 2H), 1.22 (s, 9H) 1.49-1.59 (m, 5H), 1.63-1.77 (m, 3H), 2.06 (dd, J = 12.8 Hz, 2.4 Hz, 2H), 2.35 (br s, 2H), 3.57 (td, J = 11.2 Hz, 1.6 Hz, 2H), 4.03-4.06 (m, 2H), 4.18-4.26 (m, 1H), 4.68-4.69 (m, 1H), 7.21 (d, J = 8.0 Hz, 1H), 7.51 (d, J = 7.6 Hz, 1H), 7.55-7.59 (m, 1H), 7.69-7.74 (m, 2H), 8.35 (d, J = 7.6 Hz, 1H), 8.69 (d, J = 8.4 Hz, 1H). MS 570.2 [M + 1]$^+$ |
| 6/12 | 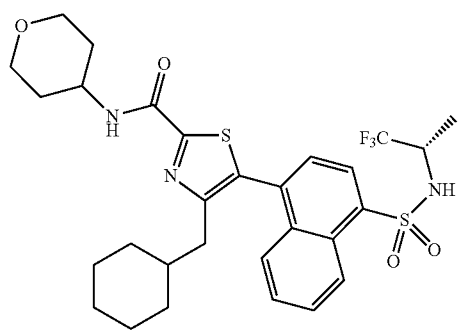 [SMILES: C[C@H](NS(=O)(=O)c1ccc(-c2sc(C(=O)NC3CCOCC3)nc2CC2CCCCC2)c2ccccc12)C(F)(F)F] | $^1$H-NMR (300 MHz, CDCl$_3$) δ: 0.48-1.04 (m, 2H), 0.95-1.12 (m, 3H), 1.24-1.33 (m, 4H), 1.47-1.55 (m, 2H), 1.64-1.78 (m, 4H), 2.02-2.10 (br s, 2H), 3.49-3.60 (m, 2H), 3.99-4.07 (m, 3H), 4.19-4.24 (m, 1H), 7.20-7.23 (m, 1H), 7.51-7.61 (m, 2H), 7.71-7.76 (m, 2H), 8.33 (d, J = 7.5 Hz, 1H), 8.65 (d, J = 8.4 Hz, 1H). MS 610.2 [M + 1]$^+$ |
| 6/13 | 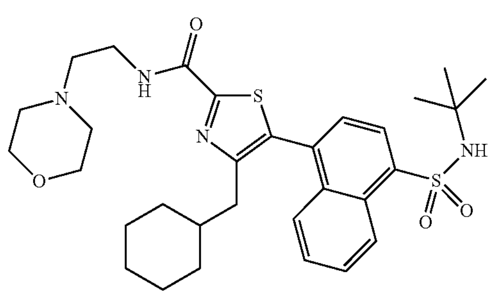 [SMILES: CC(C)(C)NS(=O)(=O)c1ccc(-c2sc(C(=O)NCCN3CCOCC3)nc2CC2CCCCC2)c2ccccc12] | $^1$H-NMR (CDCl$_3$, 300 MHz) δ: 0.70-0.74 (m, 2H), 0.98-1.18 (m, 2H), 1.22 (s, 9H), 1.55-1.65 (m, 6H), 2.35 (d, J = 5.4 Hz, 2H), 2.55-2.58 (m, 4H), 2.67 (t, J = 6.0 Hz, 2H), 3.61 (q, J = 6.0 Hz, 2H), 3.77 (t, J = 4.8 Hz, 4H), 4.66 (s, 1H), 7.51 (d, J = 7.5 Hz, 1H), 7.56-7.59 (m, 1H), 7.68-7.75 (m, 3H), 8.35 (d, J = 7.2 Hz, 1H), 8.69 (d, J = 8.7 Hz, 1H). MS 599.3 (M + 1)$^+$ |
| 6/14 | 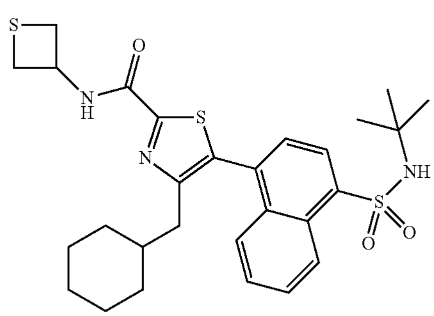 [SMILES: CC(C)(C)NS(=O)(=O)c1ccc(-c2sc(C(=O)NC3CSC3)nc2CC2CCCCC2)c2ccccc12] | $^1$H-NMR (CDCl$_3$, 300 MHz) δ: 0.63-0.66 (m, 2H), 0.88-1.18 (m, 2H), 1.22 (s, 9H), 1.48-1.53 (m, 7H), 2.34-2.35 (m, 2H), 3.44-3.50 (m, 2H), 3.56-3.62 (m, 2H), 4.64 (s, 1H), 5.45-5.47 (m, 1H), 7.50 (d, J = 7.5 Hz, 1H), 7.56-7.59 (m, 1H), 7.69-7.73 (m, 3H), 8.35 (d, J = 7.5 Hz, 1H), 8.68 (d, J = 8.7 Hz, 1H). MS 558.2 (M + 1)$^+$ |
| 6/15 | 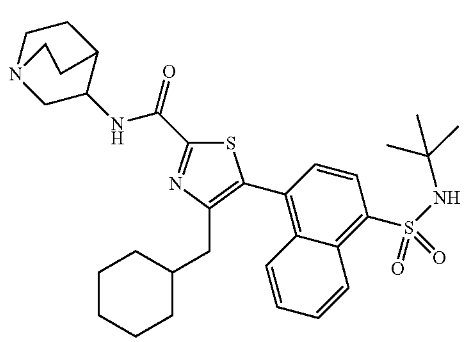 [SMILES: CC(C)(C)NS(=O)(=O)c1ccc(-c2sc(C(=O)NC3CN4CCC3CC4)nc2CC2CCCCC2)c2ccccc12] | $^1$H-NMR (CDCl$_3$, 300 MHz) δ: 0.63-0.67 (m, 2H), 0.96-1.13 (m, 2H), 1.22 (s, 9H), 1.49-1.59 (m, 6H), 1.68-1.77 (m, 4H), 2.10-2.13 (m, 1H), 2.36 (br s, 2H), 2.71-3.02 (m, 6H), 3.46-3.51 (m, 1H), 4.16-4.19 (m, 1H), 4.67 (s, 1H), 7.44 (d, J = 7.5 Hz, 1H), 7.51 (d, J = 7.5 Hz, 1H), 7.54-7.59 (m, 1H), 7.68-7.75 (m, 2H), 8.35 (d, J = 7.5 Hz, 1H), 8.69 (d, J = 8.7 Hz, 1H). MS 595.3 (M + 1)$^+$ |

| # | Structure | Analytical data |
|---|---|---|
| 6/16 | 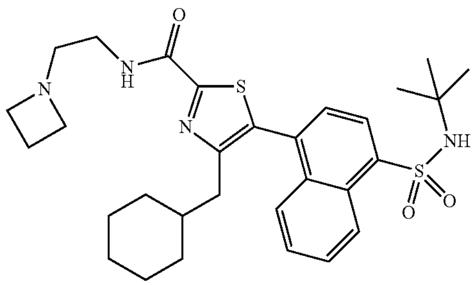 [SMILES: CC(C)(C)NS(=O)(=O)c1ccc(-c2sc(C(=O)NCCN3CCC3)nc2CC2CCCCC2)c2ccccc12] | $^1$H-NMR (CDCl$_3$, 300 MHz) δ: 0.59-0.65 (m, 2H), 0.98-1.16 (m, 3H), 1.21 (s, 9H), 1.45-1.69 (m, 3H), 2.32-2.44 (m, 3H), 2.74-2.81 (m, 1H), 3.45-3.48 (m, 3H), 3.78-3.97 (m, 6H), 4.52 (br s, 2H), 4.79 (s, 1H), 7.50 (d, J = 7.2 Hz, 1H), 7.56-7.59 (m, 1H), 7.68-7.73 (m, 2H), 8.21-8.23 (m, 1H), 8.34 (d, J = 7.8 Hz, 1H), 8.68 (d, J = 8.1 Hz, 1H). MS 569.3 (M + 1)$^+$ |
| 6/17 | 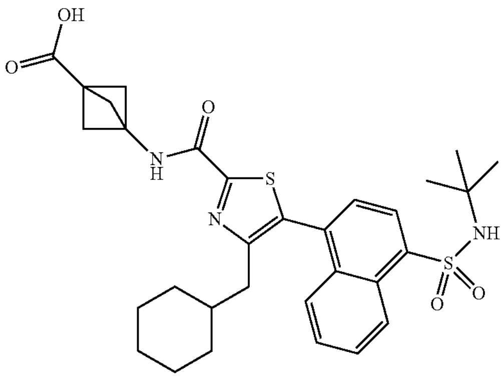 [SMILES: CC(C)(C)NS(=O)(=O)c1ccc(-c2sc(C(=O)NC34CC(C(=O)O)(C3)C4)nc2CC2CCCCC2)c2ccccc12] | $^1$H-NMR (CDCl$_3$, 300 MHz) δ: 0.62-0.66 (m, 2H), 0.95-1.12 (m, 3H), 1.22 (s, 9H), 1.47-1.56 (m, 4H), 2.33 (br s, 2H), 2.58 (s, 6H), 4.74 (s, 1H), 7.51 (d, J = 7.5 Hz, 1H), 7.57-7.59 (m, 1H), 7.71 (t, J = 7.8 Hz, 1H), 8.35 (d, J = 7.5 Hz, 1H), 8.69 (d, J = 8.4 Hz, 1H). MS 596.2 (M + 1)$^+$ |
| 6/18 | 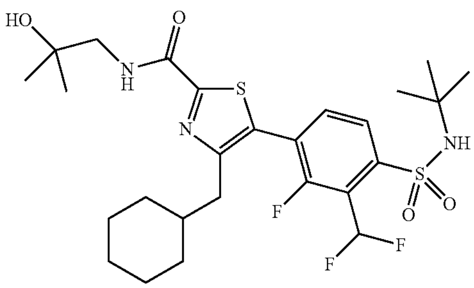 [SMILES: CC(C)(O)CNC(=O)c1nc(CC2CCCCC2)c(-c2ccc(S(=O)(=O)NC(C)(C)C)c(C(F)F)c2F)s1] | $^1$H-NMR (400 MHz, CDCl$_3$) δ: 7.98 (d, 1H, J = 8.0 Hz), 7.71-7.55 (m, 3H), 4.60 (s, 1H), 3.51 (d, 2H, J = 6.4 Hz), 2.53 (d, 2H, J = 7.2 Hz), 1.77-1.56 (m, 6H), 1.34 (s, 6H), 1.29 (s, 9H), 1.26-1.06 (m, 3H), 0.83-0.78 (m, 2H). MS 576.3 (M + 1)$^+$ |
| 6/19 | 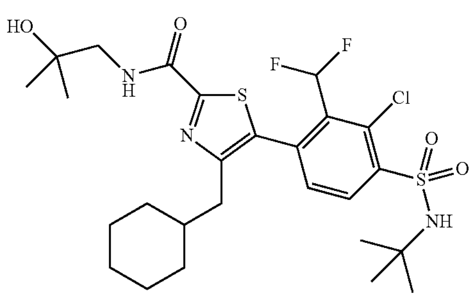 [SMILES: CC(C)(O)CNC(=O)c1nc(CC2CCCCC2)c(-c2ccc(S(=O)(=O)NC(C)(C)C)c(Cl)c2C(F)F)s1] | $^1$H-NMR (400 MHz, CDCl$_3$) δ: 8.31 (d, 1H, J = 8.0 Hz), 7.68 (t, 1H, J = 6.0 Hz), 7.36 (d, 1H, J = 8.0 Hz), 6.88 (t, 1H, J = 53 Hz), 5.05 (s, 1H), 3.51 (br s, 2H), 2.48-2.24 (m, 2H), 1.76-1.44 (m, 6H), 1.35 (s, 6H), 1.28-1.20 (m, 13H), 0.82-0.74 (m, 2H). MS 592.2 (M + 1)$^+$ |
| 6/20 | 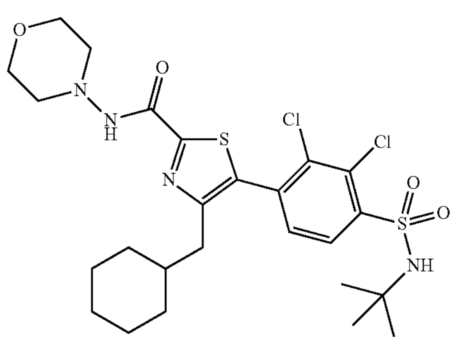 [SMILES: CC(C)(C)NS(=O)(=O)c1ccc(-c2sc(C(=O)NN3CCOCC3)nc2CC2CCCCC2)c(Cl)c1Cl] | $^1$H-NMR (300 MHz, CDCl$_3$) δ: 0.74-0.82 (m, 2H), 1.12-1.20 (m, 3H), 1.28 (s, 9H), 1.51-1.74 (m, 5H), 2.41 (d, J = 7.2 Hz, 2H), 3.02-3.05 (m, 4H), 3.87-3.90 (m, 4H), 5.06 (s, 1H), 7.37 (d, J = 8.1 Hz, 1H), 8.03 (s, 1H), 8.12 (d, J = 8.1 Hz, 1H). MS 589.2 [M + 1]$^+$ |

| # | Structure | Analytical data |
|---|---|---|
| 6/21 | 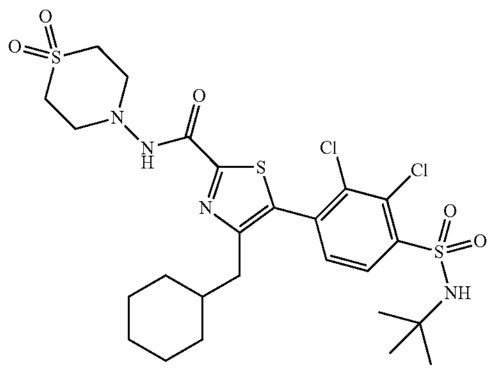 [SMILES: CC(C)(C)NS(=O)(=O)c1ccc(-c2sc(C(=O)NN3CCS(=O)(=O)CC3)nc2CC2CCCCC2)c(Cl)c1Cl] | $^1$H-NMR (300 MHz, CDCl$_3$) δ: 0.74-0.78 (m, 2H), 1.11-1.19 (m, 3H), 1.28 (s, 9H), 1.52-1.70 (m, 6H), 2.40 (d, J = 6.9 Hz, 2H), 3.27-3.30 (m, 4H), 3.61-3.65 (m, 4H), 5.09 (s, 1H), 7.36 (d, J = 8.4 Hz, 1H), 8.13 (d, J = 8.4 Hz, 1H), 8.42 (s, 1H). MS 637.1 [M + 1]$^+$ |
| 6/22 | 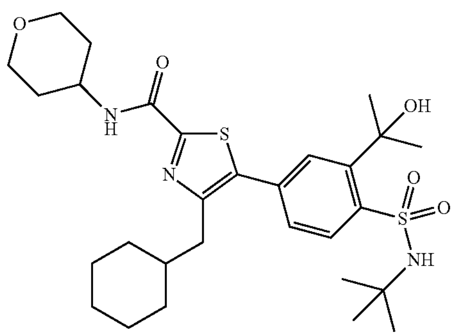 [SMILES: CC(C)(C)NS(=O)(=O)c1ccc(-c2sc(C(=O)NC3CCOCC3)nc2CC2CCCCC2)cc1C(C)(C)O] | $^1$H-NMR (CDCl$_3$, 300 MHz) δ: 0.80-0.89 (m, 2H), 1.05-1.19 (m, 3H), 1.27 (s, 9H), 1.61-1.66 (m, 6H), 1.69 (s, 7H), 1.73-1.78 (m, 1H), 2.02 (dd, J = 12.3 Hz, 3.2 Hz, 2H), 2.63 (d, J = 7.2 Hz, 2H), 3.54 (td, J = 11.6 Hz, 1.8 Hz, 2H), 4.00-4.04 (m, 2H), 4.14-4.20 (m, 1H), 7.15 (d, J = 8.4 Hz, 1H), 7.35-7.39 (m, 2H), 8.21-8.24 (m, 1H), MS 578.3 (M + 1)$^+$ |
| 6/23 | 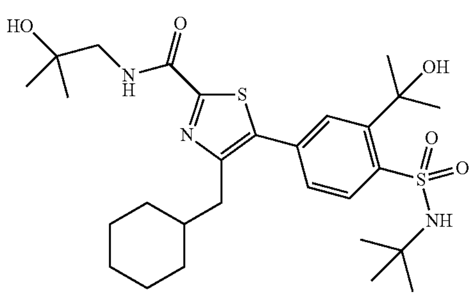 [SMILES: CC(C)(O)CNC(=O)c1nc(CC2CCCCC2)c(-c2ccc(S(=O)(=O)NC(C)(C)C)c(C(C)(C)O)c2)s1] | $^1$H-NMR (CDCl$_3$, 300 MHz) δ: 0.83-0.89 (m, 2H), 1.12-1.27 (m, 3H), 1.28 (s, 11H), 1.33 (s, 6H), 1.61-1.67 (m, 5H), 1.70 (s, 6H), 2.64 (d, J = 7.2 Hz, 2H), 3.50 (d, J = 6.6 Hz, 2H), 7.37-7.40 (m, 2H), 7.64-7.66 (m, 1H), 8.24 (d, J = 9.0 Hz, 1H). MS 566.3 (M + 1)$^+$ |
| 6/24 | 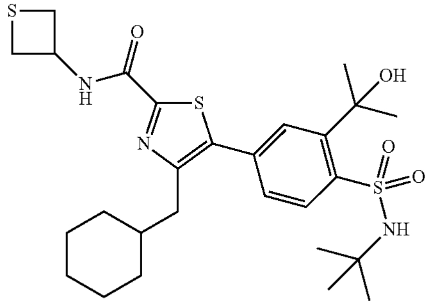 [SMILES: CC(C)(C)NS(=O)(=O)c1ccc(-c2sc(C(=O)NC3CSC3)nc2CC2CCCCC2)cc1C(C)(C)O] | $^1$H-NMR (CDCl$_3$, 300 MHz) δ: 0.83-0.89 (m, 2H), 1.12-1.27 (m, 3H), 1.27 (s, 11H), 1.54-1.67 (m, 4H), 1.70 (s, 6H), 1.73-1.83 (m, 1H), 2.64 (d, J = 7.2 Hz, 2H), 3.42-3.58 (m, 4H), 4.38-4.39 (m, 1H), 5.39-5.47 (m, 1H), 6.23-6.24 (m, 1H), 7.27-7.39 (m, 2H), 7.60-7.64 (m, 1H), 8.22-8.25 (m, 1H). MS 566.2 (M + 1)$^+$ |

| # | Structure | Analytical data |
|---|---|---|
| 6/25 | 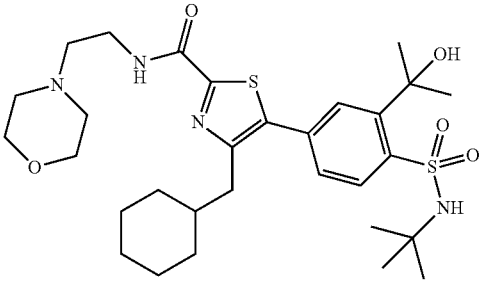 [SMILES: CC(C)(C)NS(=O)(=O)c1ccc(-c2sc(C(=O)NCCN3CCOCC3)nc2CC2CCCCC2)cc1C(C)(C)O] | ¹H-NMR (CDCl₃, 300 MHz) δ: 0.83-0.89 (m, 2H), 1.12-1.27 (m, 3H), 1.28 (s, 11H), 1.58-1.66 (m, 3H), 1.70 (s, 7H), 1.73-1.79 (m, 1H), 2.52-2.55 (m, 4H), 2.62-2.66 (m, 4H), 3.55-3.60 (m, 2H), 3.73-3.76 (m, 4H), 4.40 (s, 1H), 6.24 (s, 1H), 7.37-7.40 (m, 2H), 7.68-7.70 (m, 1H), 8.24 (d, J = 8.7 Hz, 1H). MS 607.3 (M + 1)⁺ |
| 6/26 | 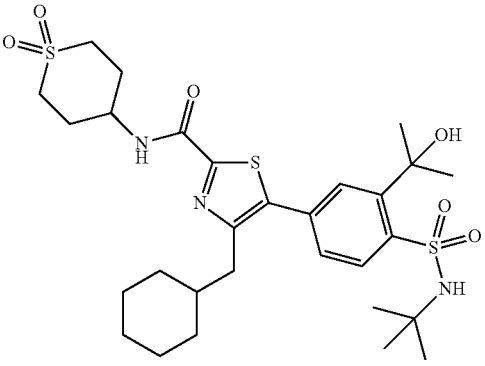 [SMILES: CC(C)(C)NS(=O)(=O)c1ccc(-c2sc(C(=O)NC3CCS(=O)(=O)CC3)nc2CC2CCCCC2)cc1C(C)(C)O] | ¹H-NMR (CDCl₃, 300 MHz) δ: 0.83-0.89 (m, 2H), 1.12-1.27 (m, 3H), 1.28 (s, 10H), 1.59-1.68 (m, 5H), 1.70 (s, 6H), 1.73-1.81 (m, 1H), 2.31-2.48 (m, 5H), 2.63-2.65 (m, 2H), 3.14-3.18 (m, 4H), 4.24-4.26 (m, 1H), 7.22 (d, J = 8.4 Hz, 1H), 7.36-7.39 (m, 2H), 8.23-8.26 (m, 1H). MS 626.3 (M + 1)⁺ |
| 6/27 | 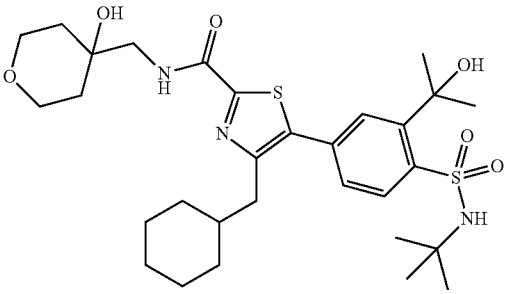 [SMILES: CC(C)(C)NS(=O)(=O)c1ccc(-c2sc(C(=O)NCC3(O)CCOCC3)nc2CC2CCCCC2)cc1C(C)(C)O] | ¹H-NMR (CDCl₃, 300 MHz) δ: 0.82-0.90 (m, 2H), 1.06-1.23 (m, 3H), 1.27 (s, 12H), 1.60-1.64 (m, 3H), 1.70-1.80 (m, 11H), 2.63 (d, J = 6.9 Hz, 2H), 3.53 (d, J = 6.3 Hz, 2H), 3.78-3.81 (m, 5H), 7.36-7.38 (m, 2H), 7.61-7.65 (m, 1H), 8.22-8.25 (m, 1H). MS 608.3 (M + 1)⁺ |
| 6/28 | 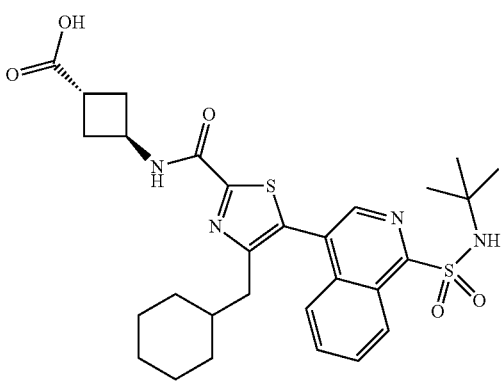 [SMILES: CC(C)(C)NS(=O)(=O)c1ncc(-c2sc(C(=O)N[C@H]3C[C@H](C(=O)O)C3)nc2CC2CCCCC2)c2ccccc12] | ¹H-NMR (300 MHz, CDCl₃) δ: 0.63-0.74 (m, 2H), 0.97-1.26 (m, 3H), 1.38 (s, 9H), 1.51-1.59 (m, 5H), 1.70-1.87 (m, 1H), 2.40 (d, J = 7.2 Hz, 2H), 2.50-2.60 (m, 2H), 2.82-2.90 (m, 2H), 3.20-3.26 (m, 1H), 4.81-4.89 (m, 1H), 5.30 (s, 1H), 7.54 (d, J = 7.8 Hz, 1H), 7.70-7.82 (m, 3H), 8.46 (s, 1H), 9.08-9.11 (m, 1H). MS 585.2 [M + 1]⁺ |

| # | Structure | Analytical data |
|---|---|---|
| 6/29 | 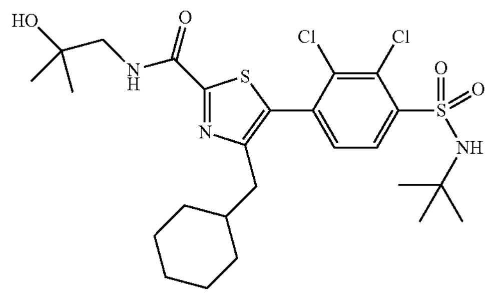 [SMILES: CC(C)(O)CNC(=O)c1nc(CC2CCCCC2)c(-c2ccc(S(=O)(=O)NC(C)(C)C)c(Cl)c2Cl)s1] | ¹H-NMR (300 MHz, CDl₃) δ: 0.73-0.77 (m, 2H), 1.11-1.19 (m, 3H), 1.28 (s, 9H), 1.33 (s, 6H), 1.53-1.61 (m, 2H), 1.71-1.76 (m, 3H), 2.40 (d, J = 6.9 Hz, 2H), 3.50 (d, J = 6.3 Hz, 2H), 5.09 (s, 1H), 5.07 (s, 1H), 7.38 (d, J = 8.1 Hz, 1H), 7.63-7.66 (m, 1H), 8.13 (d, J = 8.1 Hz, 1H). MS 576.2 [M + 1]⁺ |
| 6/30 | 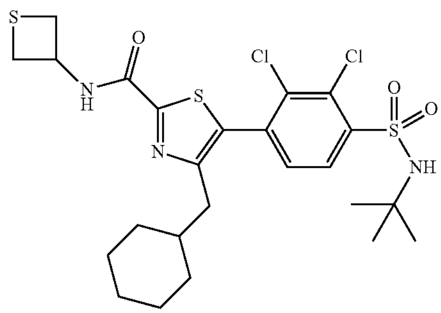 [SMILES: CC(C)(C)NS(=O)(=O)c1ccc(-c2sc(C(=O)NC3CSC3)nc2CC2CCCCC2)c(Cl)c1Cl] | ¹H-NMR (300 MHz, CDCl₃) δ: 0.74-0.82 (m, 2H), 1.04-1.23 (m, 5H), 1.25 (s, 9H), 1.53-1.73 (m, 4H), 2.40 (d, J = 6.9 Hz, 2H), 3.42-3.47 (m, 2H), 3.56 (t, J = 9.6 Hz, 2H), 5.07 (s, 1H), 5.42 (q, J = 8.7 Hz, 1H), 7.37 (d, J = 8.1 Hz, 1H), 7.66 (d, J = 8.4 Hz, 1H), 8.12 (d, J = 8.1 Hz, 1H). MS 576.1 (M + 1)⁺ |
| 6/31 | 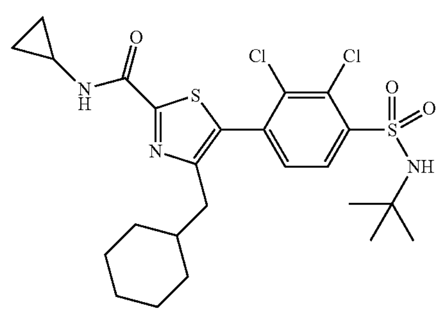 [SMILES: CC(C)(C)NS(=O)(=O)c1ccc(-c2sc(C(=O)NC3CC3)nc2CC2CCCCC2)c(Cl)c1Cl] | ¹H-NMR (300 MHz, CDCl₃) δ: 0.68-0.80 (m, 4H), 0.87-0.94 (m, 2H), 1.03-1.18 (m, 3H), 1.27 (s, 9H), 1.51-1.74 (m, 5H), 2.38 (d, J = 7.2 Hz, 2H), 2.87-2.94 (m, 1H), 5.07 (s, 1H), 7.30 (d, J = 3.0 Hz, 1H), 7.37 (d, J = 8.4 Hz, 1H), 8.12 (d, J = 8.4 Hz, 1H). MS 544.2 (M + 1)⁺ |
| 6/32 | 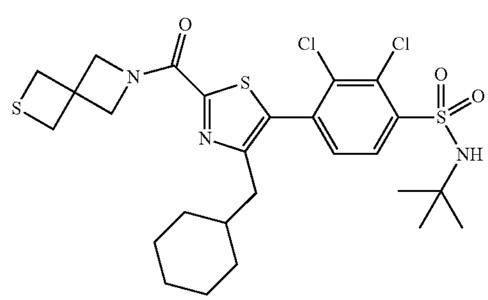 [SMILES: CC(C)(C)NS(=O)(=O)c1ccc(-c2sc(C(=O)N3CC4(CSC4)C3)nc2CC2CCCCC2)c(Cl)c1Cl] | ¹H-NMR (300 MHz, CDCl₃) δ: 0.77-0.81 (m, 2H), 1.13-1.23 (m, 3H), 1.28 (s, 9H), 1.57-1.63 (m, 7H), 2.40 (d, J = 6.9 Hz, 2H), 3.44-3.49 (m, 4H), 4.26 (s, 2H), 4.77 (s, 2H), 5.06 (s, 1H), 5.42 (q, J = 8.7 Hz, 1H), 7.36 (d, J = 8.1 Hz, 1H), 8.11 (d, J = 8.1 Hz, 1H). MS 602.1 (M + 1)⁺ |
| 6/33 | 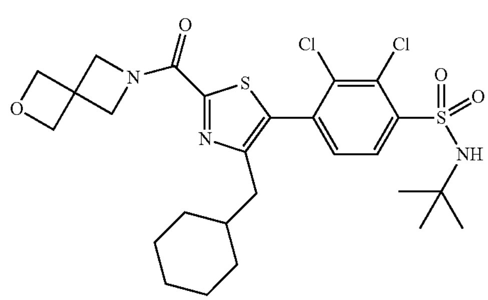 [SMILES: CC(C)(C)NS(=O)(=O)c1ccc(-c2sc(C(=O)N3CC4(COC4)C3)nc2CC2CCCCC2)c(Cl)c1Cl] | ¹H-NMR (300 MHz, CDCl₃) δ: 0.77-0.81 (m, 2H), 1.20-1.26 (m, 3H), 1.28 (s, 9H), 1.54-1.63 (m, 7H), 2.40 (d, J = 7.2 Hz, 2H), 4.39 (s, 2H), 4.87-4.89 (m, 6H), 5.06 (s, 1H), 7.36 (d, J = 8.1 Hz, 1H), 8.11 (d, J = 8.1 Hz, 1H). MS 586.1 (M + 1)⁺ |

| # | Structure | Analytical data |
|---|---|---|
| 6/34 | 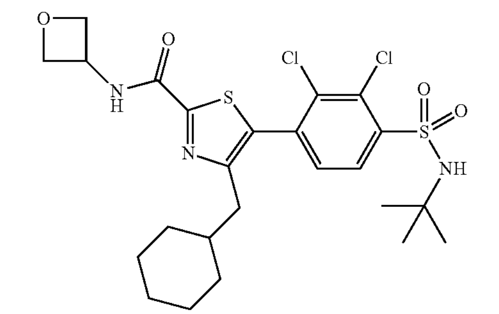 [SMILES: CC(C)(C)NS(=O)(=O)c1ccc(-c2sc(C(=O)NC3COC3)nc2CC2CCCCC2)c(Cl)c1Cl] | $^1$H-NMR (300 MHz, CDCl$_3$) δ: 0.75-0.83 (m, 2H), 1.06-1.21 (m, 3H), 1.28 (s, 9H), 1.54-1.78 (m, 5H), 2.42 (d, J = 7.2 Hz, 2H), 4.72 (t, J = 6.6 Hz, 2H), 5.00-5.07 (m, 3H), 5.22-5.30 (m, 1H), 7.38 (d, J = 8.4 Hz, 1H), 7.75 (d, J = 7.8 Hz, 1H), 8.13 (d, J = 8.1 Hz, 1H). MS 560.1 (M + 1)$^+$ |
| 6/35 | 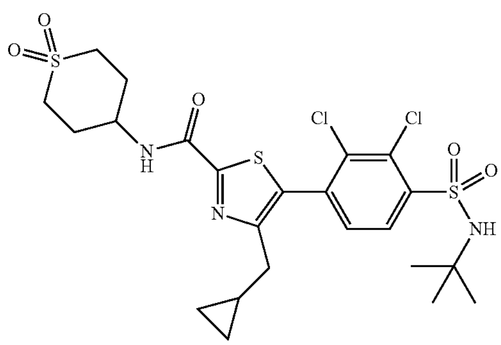 [SMILES: CC(C)(C)NS(=O)(=O)c1ccc(-c2sc(C(=O)NC3CCS(=O)(=O)CC3)nc2CC2CC2)c(Cl)c1Cl] | $^1$H-NMR (300 MHz, CDCl$_3$) δ: −0.02-0.04 (m, 2H), 0.40-0.46 (m, 2H), 0.93-1.02 (m, 1H), 1.28 (s, 9H), 2.27-2.48 (m, 6H), 3.15-3.18 (m, 4H), 4.21-4.27 (m, 1H), 5.07 (s, 1H), 7.26-7.27 (m, 1H), 7.40 (d, J = 8.1 Hz, 1H), 8.13 (d, J = 8.1 Hz, 1H). MS 594.1 [M + 1]$^+$ |
| 6/36 | 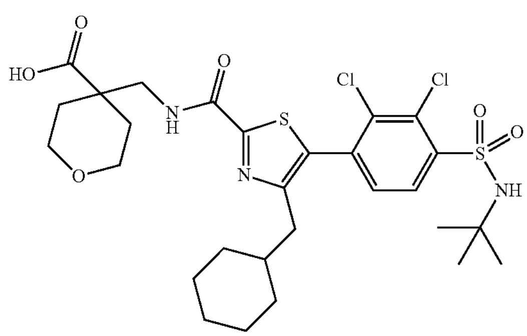 [SMILES: CC(C)(C)NS(=O)(=O)c1ccc(-c2sc(C(=O)NCC3(C(=O)O)CCOCC3)nc2CC2CCCCC2)c(Cl)c1Cl] | $^1$H-NMR (300 MHz, CDCl$_3$) δ: 0.72-0.80 (m, 2H), 1.06-1.16 (m, 3H), 1.28 (s, 9H), 1.51-1.75 (m, 9H), 2.15-2.21 (m, 2H), 2.41 (d, J = 7.2 Hz, 2H), 3.60-3.67 (m, 2H), 3.76 (d, J = 6.9 Hz, 2H), 3.88-3.95 (m, 2H), 5.10 (s, 1H), 7.37 (d, J = 8.1 Hz, 1H), 7.78 (t, J = 6.9 Hz, 1H), 8.13 (d, J = 8.1 Hz, 1H). MS 646.2 [M + 1]$^+$ |
| 6/37 | 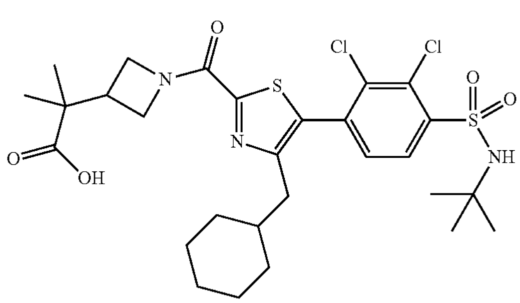 [SMILES: CC(C)(C)NS(=O)(=O)c1ccc(-c2sc(C(=O)N3CC(C(C)(C)C(=O)O)C3)nc2CC2CCCCC2)c(Cl)c1Cl] | $^1$H-NMR (300 MHz, CDCl$_3$) δ: 0.72-0.88 (m, 2H), 1.06-1.16 (m, 3H), 1.28 (s, 9H), 1.51-1.75 (m, 6H), 2.36-2.47 (m, 2H), 3.06-3.11 (m, 1H), 4.05-4.11 (m, 1H), 4.23-4.30 (m, 1H), 4.53-4.59 (m, 1H), 4.74-4.80 (m, 1H), 5.09 (s, 1H), 7.37 (t, J = 8.1 Hz, 1H), 8.11 (d, J = 8.1 Hz, 1H). MS 630.2 [M + 1]$^+$ |

| # | Structure | Analytical data |
|---|---|---|
| 6/38 | 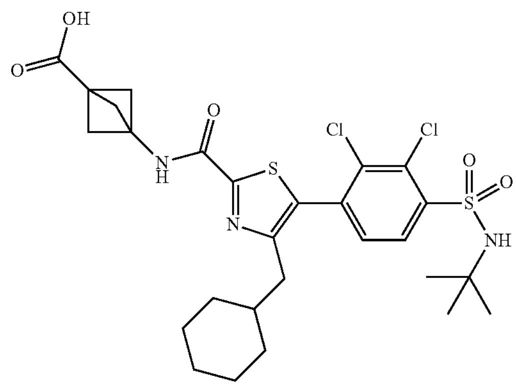 [SMILES: CC(C)(C)NS(=O)(=O)c1ccc(-c2sc(C(=O)NC34CC(C(=O)O)(C3)C4)nc2CC2CCCCC2)c(Cl)c1Cl] | $^1$H-NMR (300 MHz, CDCl$_3$) δ: 0.73-0.1 (m, 2H), 1.09-1.20 (m, 3H), 1.28 (s, 9H), 1.52-1.72 (m, 4H), 2.40 (d, J = 7.5 Hz, 2H), 2.56 (s, 6H), 5.10 (s, 1H), 7.38 (d, J = 8.1 Hz, 1H), 7.67 (s, 1H), 8.13 (d, J = 8.4 Hz, 1H). MS 614.2 [M + 1]$^+$ |
| 6/39 | 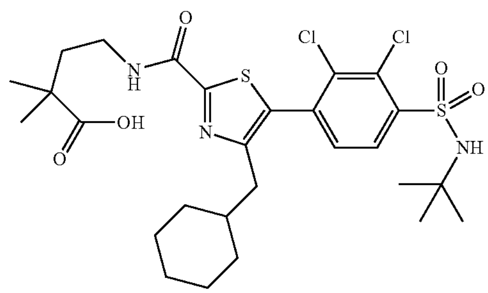 [SMILES: CC(C)(C)NS(=O)(=O)c1ccc(-c2sc(C(=O)NCCC(C)(C)C(=O)O)nc2CC2CCCCC2)c(Cl)c1Cl] | $^1$H-NMR (300 MHz, CDCl$_3$) δ: 0.73-0.81 (m, 2H), 1.06-1.24 (m, 3H), 1.27 (s, 9H), 1.31 (s, 6H), 1.52-1.74 (m, 6H), 1.94-1.99 (m, 2H), 2.40 (d, J = 7.2 Hz, 2H), 3.49-3.57 (m, 2H), 5.12 (s, 1H), 7.38 (d, J = 8.1 Hz, 1H), 7.46 (t, J = 8.4 Hz, 1H), 8.12 (d, J = 8.1 Hz, 1H). MS 618.2 [M + 1]$^+$ |
| 6/40 | 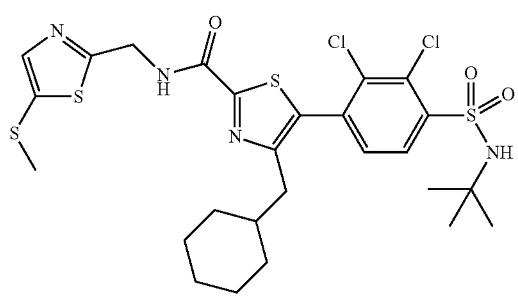 [SMILES: CSc1cnc(CNC(=O)c2nc(CC3CCCCC3)c(-c3ccc(S(=O)(=O)NC(C)(C)C)c(Cl)c3Cl)s2)s1] | $^1$H-NMR (300 MHz, CDCl$_3$) δ: 0.73-0.77 (m, 2H), 1.10-1.18 (m, 3H), 1.28 (s, 9H), 1.52-1.61 (m, 6H), 2.40 (d, J = 6.9 Hz, 2H), 2.47 (s, 3H), 4.91 (d, J = 6.0 Hz, 2H), 5.12 (s, 1H), 7.37 (d, J = 8.1 Hz, 1H), 7.62 (s, 1H), 7.96 (t, 1H), 8.12 (d, J = 8.4 Hz, 1H). MS 647.1 [M + 1]$^+$ |
| 6/41 | 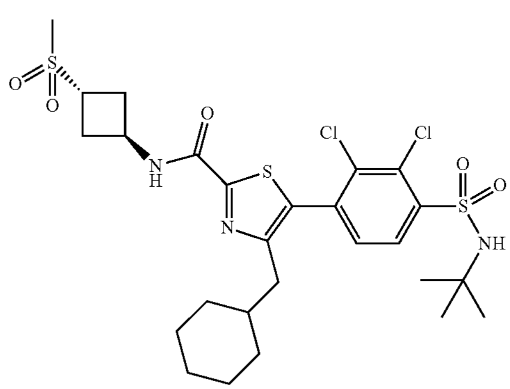 [SMILES: CC(C)(C)NS(=O)(=O)c1ccc(-c2sc(C(=O)N[C@H]3C[C@H](S(C)(=O)=O)C3)nc2CC2CCCCC2)c(Cl)c1Cl] | $^1$H-NMR (300 MHz, CDCl$_3$) δ: 0.74-0.82 (m, 2H), 1.05-1.25 (m, 3H), 1.28 (s, 9H), 1.55-1.80 (m, 5H), 2.41 (d, J = 7.5 Hz, 2H), 2.59-2.70 (m, 2H), 2.81-2.91 (m, 5H), 3.54-3.64 (m, 1H), 4.67-4.76 (m, 1H), 5.07 (s, 1H), 7.38 (d, J = 7.8 Hz, 1H), 7.58 (d, J = 8.7 Hz, 1H), 8.12 (d, J = 8.4 Hz, 1H). MS 636.5 (M + 1)$^+$ |

| # | Structure | Analytical data |
|---|---|---|
| 6/42 | 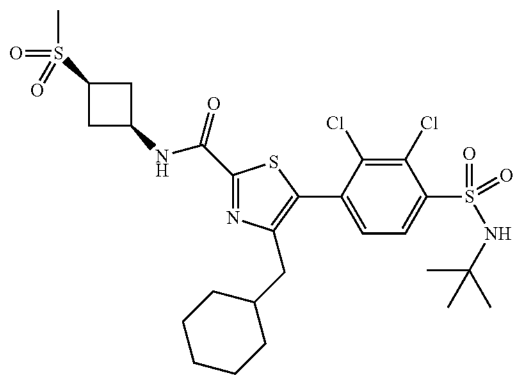 [SMILES: CC(C)(C)NS(=O)(=O)c1ccc(-c2sc(C(=O)N[C@H]3C[C@@H](S(C)(=O)=O)C3)nc2CC2CCCCC2)c(Cl)c1Cl] | ¹H-NMR (300 MHz, CDCl₃) δ: 0.75-0.82 (m, 2H), 1.09-1.19 (m, 3H), 1.28 (s, 9H), 1.53-1.72 (m, 5H), 2.40 (d, J = 7.2 Hz, 2H), 2.76-2.84 (m, 2H), 2.89 (s, 3H), 2.96-3.06 (m, 2H), 3.81-3.87 (m, 1H), 4.69-4.74 (m, 1H), 5.07 (s, 1H), 7.38 (d, J = 8.1 Hz, 1H), 7.48 (d, J = 6.9 Hz, 1H), 8.13 (d, J = 8.1 Hz, 1H). MS 636.5 (M + 1)⁺ |
| 6/43 | 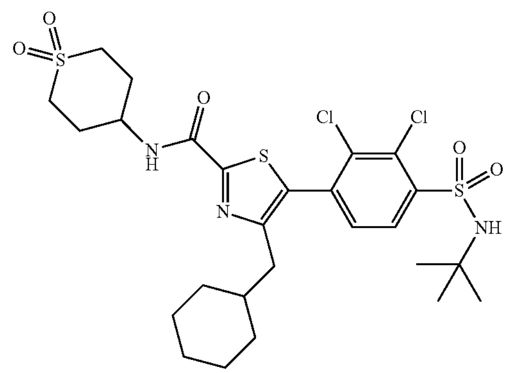 [SMILES: CC(C)(C)NS(=O)(=O)c1ccc(-c2sc(C(=O)NC3CCS(=O)(=O)CC3)nc2CC2CCCCC2)c(Cl)c1Cl] | ¹H-NMR (300 MHz, DMSO-d₆) δ: 0.66-0.74 (m, 2H), 1.00-1.10 (m, 3H), 1.13 (s, 9H), 1.21 (s, 2H), 1.46-1.49 (m, 5H), 1.62-1.66 (m, 1H), 2.02-2.07 (m, 2H), 2.16-2.28 (m, 2H), 2.42 (d, J = 6.9 Hz, 2H), 3.05-3.09 (m, 2H), 4.17-4.21 (m, 1H), 7.66 (d, J = 8.4 Hz, 1H), 8.02 (s, 1H), 8.08 (d, J = 8.4 Hz, 1H), 9.00 (d, J = 8.1 Hz, 1H). MS 636.1 (M + 1)⁺ |
| 6/44 | 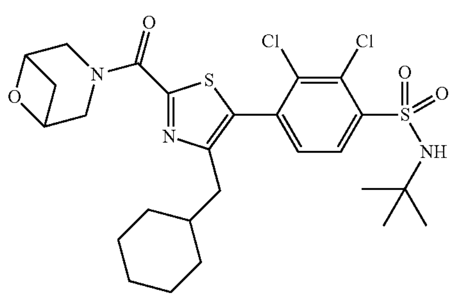 [SMILES: CC(C)(C)NS(=O)(=O)c1ccc(-c2sc(C(=O)N3CC4CC(C3)O4)nc2CC2CCCCC2)c(Cl)c1Cl] | ¹H-NMR (300 MHz, CDCl₃) δ: 0.77-0.82 (m, 2H), 1.07-1.18 (m, 3H), 1.28 (s, 9H), 1.50-1.59 (m, 1H), 1.73-1.76 (m, 4H), 1.87 (br s, 1H), 1.97 (d, J = 9.3 Hz, 2H), 2.42 (d, J = 6.6 Hz, 2H), 3.30-3.33 (m, 1H), 3.87-3.92 (m, 1H), 4.04-4.09 (m, 1H), 4.35-4.40 (m, 1H), 4.74-4.78 (m, 3H), 5.08 (s, 1H), 7.39 (d, J = 10.5 Hz, 1H), 8.12 (d, J = 7.8 Hz, 1H). MS 586.2 (M + 1)⁺ |
| 6/45 | 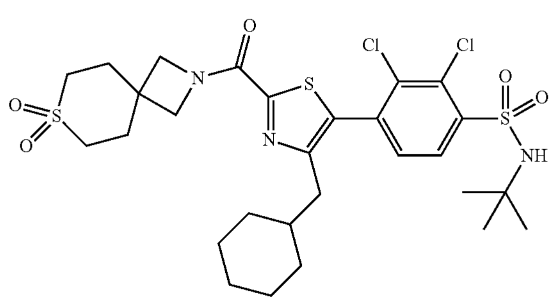 [SMILES: CC(C)(C)NS(=O)(=O)c1ccc(-c2sc(C(=O)N3CC4(CCS(=O)(=O)CC4)C3)nc2CC2CCCCC2)c(Cl)c1Cl] | ¹H-NMR (300 MHz, CDCl₃) δ: 0.77-0.85 (m, 2H), 1.10-1.20 (m, 3H), 1.28 (s, 9H), 1.54-1.65 (m, 5H), 2.40-2.46 (m, 6H), 3.05-3.08 (m, 4H), 4.03 (s, 2H), 4.51 (s, 2H), 5.08 (s, 1H), 7.37 (d, J = 8.1 Hz, 1H), 8.12 (d, J = 8.1 Hz, 1H). MS 662.4 (M + 1)⁺ |

| # | Structure | Analytical data |
|---|---|---|
| 6/46 | 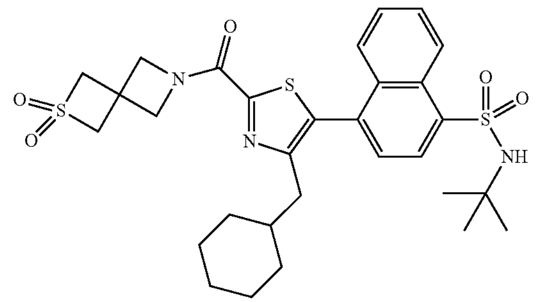 [SMILES: CC(C)(C)NS(=O)(=O)c1ccc(-c2sc(C(=O)N3CC4(C3)CS(=O)(=O)C4)nc2CC2CCCCC2)c2ccccc12] | ¹H-NMR (300 MHz, CDCl₃) δ: 0.65-0.69 (m, 2H), 1.05-1.12 (m, 3H), 1.22 (s, 9H), 1.47-1.52 (m, 5H), 1.60-1.75 (m, 1H), 2.28-2.36 (m, 2H), 4.44 (s, 4H), 4.50 (s, 2H), 4.63 (s, 1H), 5.03 (s, 2H), 7.50-7.59 (m, 2H), 7.68-7.71 (m, 2H), 8.35 (d, J = 7.2 Hz, 1H), 8.68 (d, J = 8.4 Hz, 1H). MS 616.2 [M + 1]⁺ |
| 6/47 | 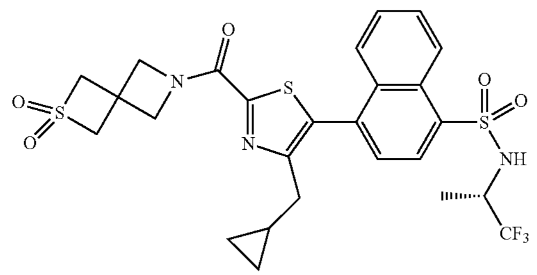 [SMILES: C[C@H](NS(=O)(=O)c1ccc(-c2sc(C(=O)N3CC4(C3)CS(=O)(=O)C4)nc2CC2CC2)c2ccccc12)C(F)(F)F] | ¹H-NMR (300 MHz, CDCl₃) δ: −0.17 to −0.12 (m, 2H), 0.29-0.35 (m, 2H), 0.90-0.95 (m, 1H), 1.31 (d, J = 7.2 Hz, 3H), 2.35-2.51 (m, 6H), 3.17-3.20 (m, 4H), 3.97-4.05 (m, 1H), 4.27-4.32 (m, 1H), 5.03 (d, J = 9.9 Hz, 1H), 7.33 (d, J = 8.1 Hz, 1H), 7.55 (d, J = 7.5 Hz, 1H), 7.57-7.63 (m, 1H), 7.72-7.77 (m, 2H), 8.32 (d, J = 7.8 Hz, 1H), 8.65 (d, J = 8.4 Hz, 1H). MS 616.2 [M + 1]⁺ |
| 6/48 | 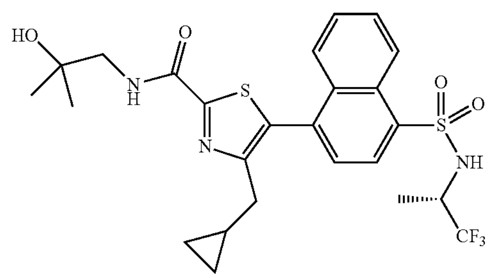 [SMILES: C[C@H](NS(=O)(=O)c1ccc(-c2sc(C(=O)NCC(C)(C)O)nc2CC2CC2)c2ccccc12)C(F)(F)F] | ¹H-NMR (300 MHz, CDCl₃) δ: −0.17 to −0.12 (m, 2H), 0.28-0.34 (m, 2H), 0.90-0.96 (m, 1H), 1.30 (d, J = 6.9 Hz, 3H), 1.35 (s, 6H), 2.18 (s, 1H), 2.38 (d, J = 6.9 Hz, 2H), 3.53 (d, J = 6.3 Hz, 2H), 3.97-4.05 (m, 1H), 5.12 (d, J = 9.6 Hz, 1H), 7.55 (d, J = 7.8 Hz, 1H), 7.60-7.62 (m, 1H), 7.70-7.79 (m, 3H), 8.32 (d, J = 7.5 Hz, 1H), 8.65 (d, J = 8.7 Hz, 1H). MS 556.2 [M + 1]⁺ |
| 6/49 | 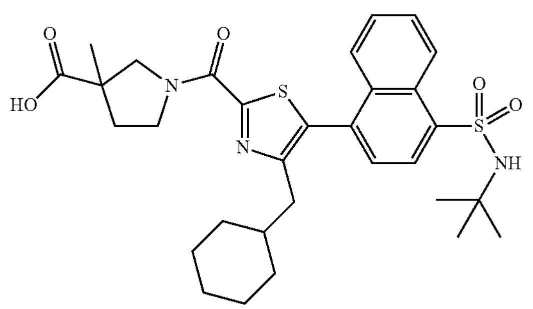 [SMILES: CC(C)(C)NS(=O)(=O)c1ccc(-c2sc(C(=O)N3CCC(C)(C(=O)O)C3)nc2CC2CCCCC2)c2ccccc12] | ¹H-NMR (400 MHz, CD₃OD) δ: 0.57-0.65 (m, 2H), 1.04 (m, 12H), 1.36-1.45 (m, 8H), 1.58-1.60 (m, 1H), 1.85-1.97 (m, 1H), 2.26-2.43 (m, 2H), 3.37-4.67 (m, 4H), 7.53-7.56 (m, 2H), 7.63-7.67 (m, 2H), 8.23 (d, J = 7.2 Hz, 1H), 8.73 (d, J = 9.2 Hz, 1H). MS 598.3 [M + 1]⁺ |
| 6/50 | 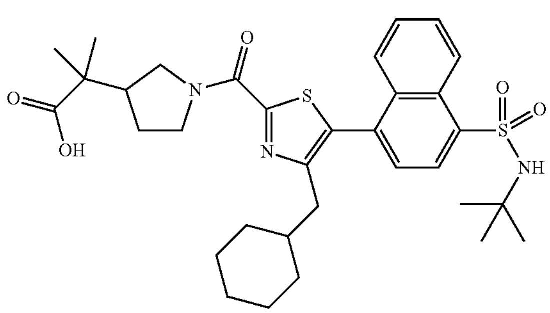 [SMILES: CC(C)(C)NS(=O)(=O)c1ccc(-c2sc(C(=O)N3CCC(C(C)(C)C(=O)O)C3)nc2CC2CCCCC2)c2ccccc12] | ¹H-NMR (400 MHz, CD₃OD) δ: 0.65-0.81 (m, 2H), 0.96-1.12 (m, 3H), 1.14 (s, 9H), 1.28 (s, 6H), 1.52-1.56 (m, 5H), 1.65-1.72 (m, 1H), 1.82-1.98 (m, 1H), 2.04-2.16 (m, 1H), 2.39 (br s, 2H), 2.57-2.68 (m, 1H), 3.47-3.61 (m, 1H), 3.84-4.03 (m, 2H), 4.46-4.59 (m, 1H), 7.61-7.65 (m, 2H), 7.73-7.76 (m, 2H), 8.33 (d, J = 7.6 Hz, 1H), 8.83 (d, J = 8.4 Hz, 1H). MS 626.3 [M + 1]⁺ |

-continued

| # | Structure | Analytical data |
|---|---|---|
| 6/51 | 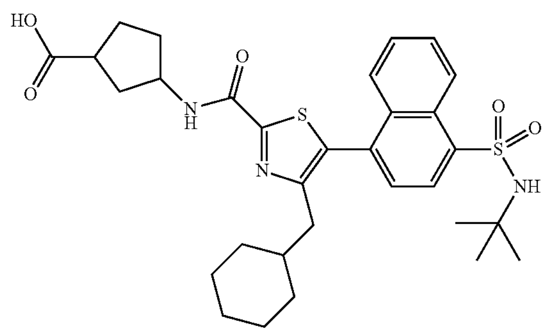 [SMILES: CC(C)(C)NS(=O)(=O)c1ccc(-c2sc(C(=O)NC3CCC(C(=O)O)C3)nc2CC2CCCCC2)c2ccccc12] | ¹H-NMR (400 MHz, CD₃OD) δ: 0.53-0.58 (m, 2H), 1.06-1.13 (m, 12H), 1.48-1.85 (m, 7H), 1.96-2.08 (m, 4H), 2.33-2.41 (m, 3H), 2.92-2.96 (m, 1H), 4.43-4.47 (m, 1H), 7.62-7.75 (m, 4H), 8.32 (d, J = 6.0 Hz, 1H), 8.83 (d, J = 8.4 Hz, 1H). MS 598.3 (M + 1)⁺ |
| 6/52 | 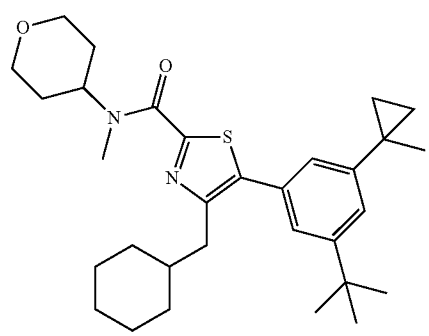 [SMILES: CN(C(=O)c1nc(CC2CCCCC2)c(-c2cc(C(C)(C)C)cc(C3(C)CC3)c2)s1)C1CCOCC1] | ¹H-NMR (400 MHz, CD₃OD) δ: 0.67-0.76 (m, 4H), 0.78-0.82 (m, 2H), 1.09-1.11 (m, 3H), 1.25 (s, 9H), 1.33 (s, 3H), 1.50-1.56 (m, 6H), 1.68-1.70 (m, 2H), 1.92-1.95 (m, 2H), 2.57 (d, J = 7.2 Hz, 2H), 2.94 (s, 2H), 3.48-3.80 (m, 3H), 3.94-3.98 (m, 2H), 4.52-4.62 (br s, 0.3 H), 5.26-5.28 (br s, 0.7 H), 7.04 (s, 1H), 7.16 (s, 1H), 7.28 (s, 1H). MS 509.4 (M + 1) |
| 6/53 | 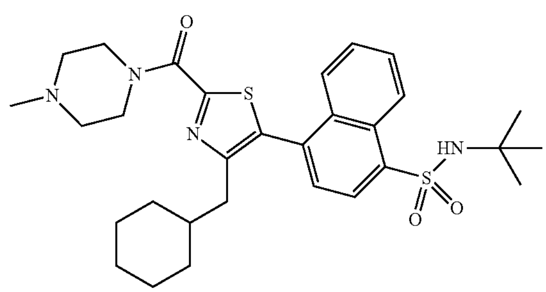 [SMILES: CN1CCN(C(=O)c2nc(CC3CCCCC3)c(-c3ccc(S(=O)(=O)NC(C)(C)C)c4ccccc34)s2)CC1] | ¹H-NMR (400 MHz, d₆-DMSO): 8.80 (d, 1H, J = 8.4 Hz), 8.25 (d, 1H, J = 7.6 Hz), 7.93 (s, 1H), 7.79-7.60 (m, 4H), 4.35 (s, 2H), 3.70 (s, 2H), 2.44 (s, 4H), 2.33 (s, 2H), 2.23 (s, 3H), 1.57 (s, 1H), 1.45-1.43 (m, 5H), 1.10-1.91 (m, 12H), 0.67-0.62 (m, 2H). MS 569.2 (M + 1)⁺ |
| 6/54 | 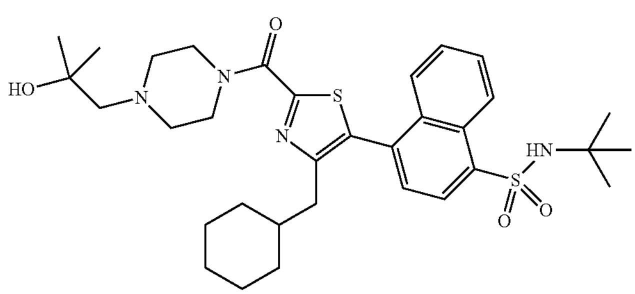 | ¹H-NMR (400 MHz, d₆-DMSO) δ: 9.42 (s, 1H), 8.81 (d, 1H, J = 8.8 Hz), 8.27 (d, 1H, J = 7.6 Hz), 7.95 (s, 1H), 7.80-7.69 (m, 4H), 5.36 (s, 2H), 4.43-4.41 (m, 1H), 4.09-4.07 (m, 2H), 3.70-3.60 (m, 2H), 3.39-3.33 (m, 2H), 1.59-1.55 (m, 1H), 1.45-1.43 (m, 5H), 1.28 (s, 6H), 1.08-0.91 (m, 12H), 0.67-0.58 (m, 2H). MS 637.3 (M + 1)⁺ |
| 6/55 | 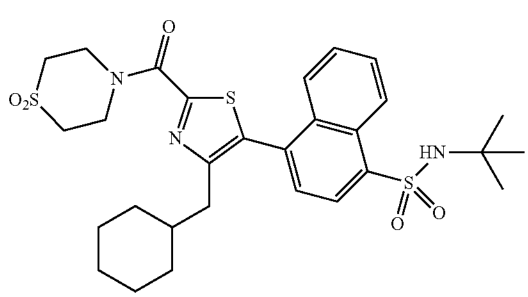 [SMILES: CC(C)(C)NS(=O)(=O)c1ccc(-c2sc(C(=O)N3CCS(=O)(=O)CC3)nc2CC2CCCCC2)c2ccccc12] | ¹H-NMR (400 MHz, CDCl₃) δ: 0.64-0.74 (m, 2H), 0.98-1.14 (m, 3H), 1.22 (s, 9H), 1.48-1.55 (m, 5H), 1.81 (m, 1H), 2.36 (m, 2H), 3.22 (m, 2H), 3.31 (m, 2H), 4.33 (m, 2H), 4.81 (m, 1H), 5.00 (m, 2H), 7.50-7.60 (m, 2H), 7.70-7.83 (m, 2H), 8.36 (d, J = 7.6 Hz, 1H), 8.71 (d, J = 8.8 Hz, 1H). MS 604.3 (M + 1)⁺ |

| # | Structure | Analytical data |
|---|---|---|
| 6/56 | 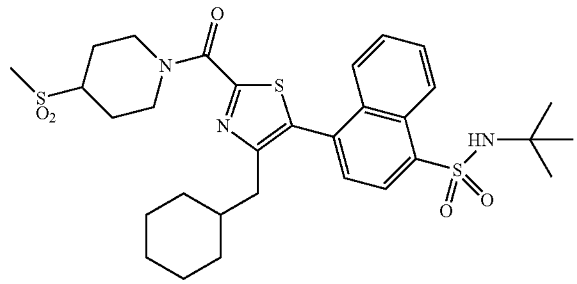 [SMILES: CC(C)(C)NS(=O)(=O)c1ccc(-c2sc(C(=O)N3CCC(S(C)(=O)=O)CC3)nc2CC2CCCCC2)c2ccccc12] | ¹H-NMR (400 MHz, CD₃OD) δ: 0.52-0.60 (m, 2H), 0.85-1.03 (m, 12H), 1.37-1.39 (m, 5H), 1.50-1.55 (m, 1H), 1.71-1.83 (m, 2H), 2.16-2.20 (m, 4H), 2.87-2.94 (m, 4H), 3.34-3.42 (m, 2H), 4.68 (d, J = 12.4 Hz, 1H), 5.61 (d, J = 11.6 Hz, 1H), 7.44-7.52 (m, 2H), 7.60-7.66 (m, 2H), 8.20-8.22 (m, 1H), 8.71-8.78 (m, 1H). MS 632.3 (M + 1)⁺ |
| 6/57 | 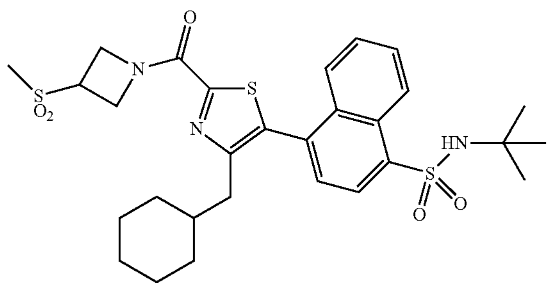 [SMILES: CC(C)(C)NS(=O)(=O)c1ccc(-c2sc(C(=O)N3CC(S(C)(=O)=O)C3)nc2CC2CCCCC2)c2ccccc12] | ¹H-NMR (400 MHz, CD₃OD) δ: 0.70-0.75 (m, 2H), 1.00-1.16 (m, 12H), 1.52-1.65 (m, 5H), 1.67-1.71 (m, 1H), 2.40 (s, 2H), 3.08 (s, 3H), 4.41-4.60 (m, 3H), 5.03-5.15 (m, 2H), 7.58-7.65 (m, 2H), 7.72-7.88 (m, 2H), 8.35 (d, J = 7.6 Hz, 1H), 8.85 (d, J = 8.8 Hz, 1H). MS 604.3 (M + 1)⁺ |
| 6/58 | 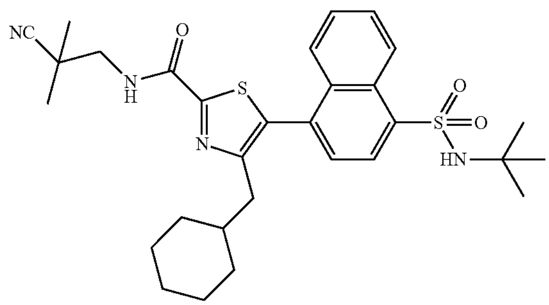 [SMILES: CC(C)(C#N)CNC(=O)c1nc(CC2CCCCC2)c(-c2ccc(S(=O)(=O)NC(C)(C)C)c3ccccc23)s1] | ¹H-NMR (400 MHz, CDCl₃) δ: 8.69 (d, J = 8.4 Hz, 1H), 8.36 (d, J = 7.6 Hz, 1H), 7.75-7.69 (m, 3H), 7.61-7.57 (m, 1H), 7.52 (d, J = 7.2 Hz, 1H), 4.66 (s, 1H), 3.67 (m, 2H), 2.39 (m, 2H), 1.95 (m, 2H), 1.72-1.69 (m, 1H), 1.56-1.48 (m, 11H), 1.24-0.96 (m, 12H), 0.69-0.60 (m, 2 H). MS 567.2 (M + 1)⁺ |
| 6/59 | 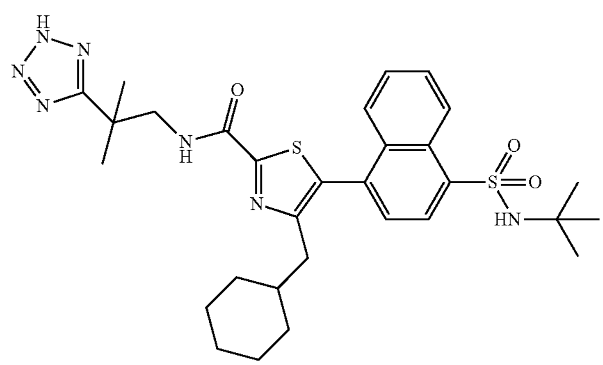 [SMILES: CC(C)(C)NS(=O)(=O)c1ccc(-c2sc(C(=O)NCC(C)(C)c3nn[nH]n3)nc2CC2CCCCC2)c2ccccc12] | ¹H-NMR (400 MHz, DMSO-d₆) δ: 8.8.6 (m, 1H), 8.80 (d, J = 8.8 Hz, 1H), 8.25 (d, J = 6.8 Hz, 1H), 7.94 (m, 1H), 7.78-7.67 (m, 4H), 3.59 (m, 2H), 2.41-2.33 (m, 2H), 1.60-1.31 (m, 12H), 1.07-1.95 (m, 12H), 0.58-0.55 (m, 2H). MS 610.2 (M + 1)⁺ |
| 6/60 | 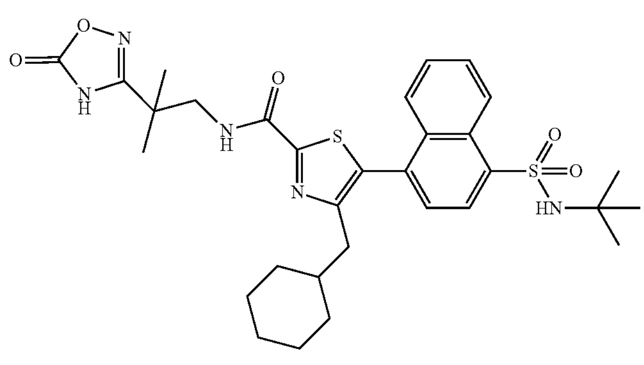 [SMILES: CC(C)(C)NS(=O)(=O)c1ccc(-c2sc(C(=O)NCC(C)(C)c3noc(=O)[nH]3)nc2CC2CCCCC2)c2ccccc12] | ¹H-NMR (400 MHz, DMSO-d₆) δ: 8.94 (m, 1H), 8.80 (d, J = 8.8 Hz, 1H), 8.25 (d, J = 7.6 Hz, 1H), 7.94 (s, 1H), 3.49 (m, 2H), 2.36-2.31 (m, 2H), 1.60 (m, 1H), 1.50-1.40 (m, 5H), 1.25 (s, 6H), 1.07-0.88 (m, 12 H), 0.60-0.51 (m, 2H). MS 626.2 (M + 1)⁺ |

| # | Structure | Analytical data |
|---|---|---|
| 6/61 | 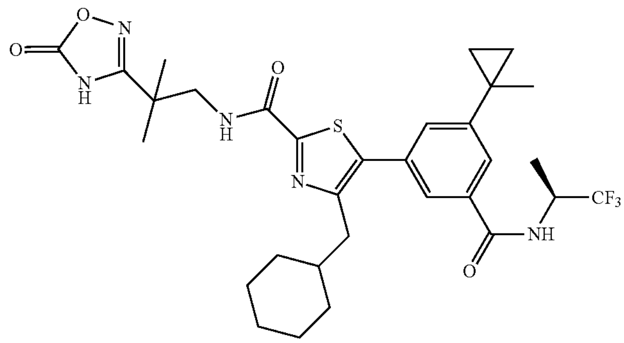 | $^1$H-NMR (400 MHz, DMSO-d$_6$) δ: 12.25 (br s, 1H), 8.93 (d, J = 8.4 Hz, 1H), 7.77 (m, 2H), 7.49 (m, 1H), 4.88 (m, 1H), 3.47 (m, 2H), 2.64 (m, 2H), 1.80 (m, 1H), 1.61-1.58 (m, 5H), 1.44 (s, 3H), 1.38 (d, J = 6.8 Hz, 3H), 1.23 (s, 6H), 1.16-1.09 (m, 3H), 0.97-0.84 (m, 6H). MS 643.2 (M + 1)$^+$ |
| 6/62 | 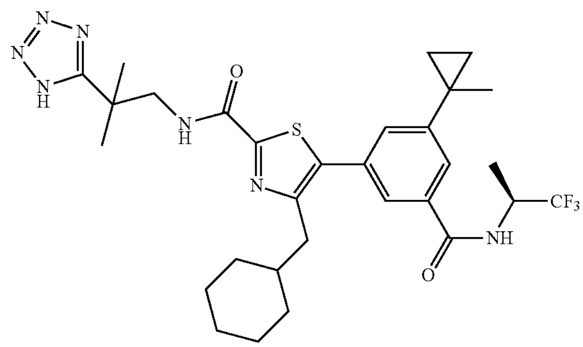 [SMILES: C[C@H](NC(=O)c1cc(-c2sc(C(=O)NCC(C)(C)c3nnn[nH]3)nc2CC2CCCCC2)cc(C2(C)CC2)c1)C(F)(F)F] | $^1$H-NMR (400 MHz, CDCl$_3$) δ: 7.88 (m, 1H), 7.70 (m, 1H), 7.55 (m, 1H), 7.42 (m, 1H), 6.16 (d, J = 8.8 Hz, 1H), 4.96 (m, 1H), 3.86 (d, J = 7.2 Hz, 2H), 2.58 (d, J = 6.8 Hz, 2H), 1.78-1.59 (m, 12H), 1.46-1.45 (m, 6H), 1.20-1.11 (m, 3H), 0.94-0.83 (m, 6H). MS 618.2 (M + 1)$^+$ |
| 6/63 | 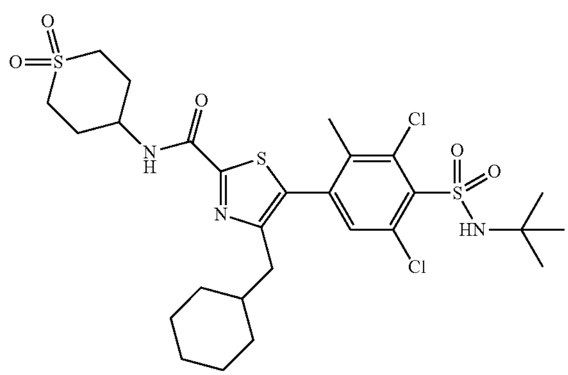 [SMILES: Cc1c(-c2sc(C(=O)NC3CCS(=O)(=O)CC3)nc2CC2CCCCC2)cc(Cl)c(S(=O)(=O)NC(C)(C)C)c1Cl] | $^1$H-NMR (DMSO-d$_6$, 300 MHz) δ: 0.70-0.77 (m, 2H), 1.04-1.08 (m, 3H), 1.17 (s, 9H), 1.46-1.56 (m, 5H), 1.66-1.72 (m, 1H), 2.04-2.11 (m, 2H), 2.21 (s, 3H), 2.22-2.27 (m, 2H), 2.37 (d, J = 6.9 Hz, 2H), 3.06-3.10 (m, 2H), 3.39-3.40 (m, 2H), 4.19-4.22 (m, 1H), 7.61 (s, 1H), 8.02 (s, 1H), 8.99 (d, J = 11.6 Hz, 1H). MS 650.2 (M + 1)$^+$ |
| 6/64 | 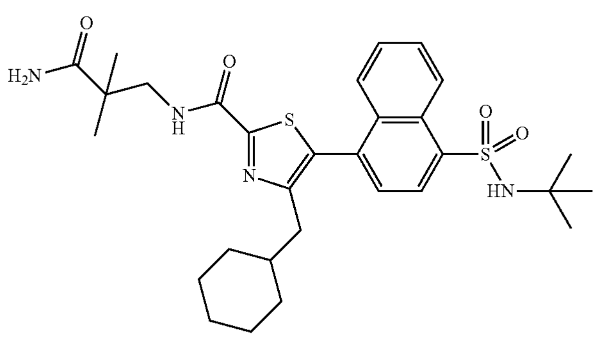 [SMILES: CC(C)(C)NS(=O)(=O)c1ccc(-c2sc(C(=O)NCC(C)(C)C(N)=O)nc2CC2CCCCC2)c2ccccc12] | $^1$H-NMR (400 MHz, DMSO-d$_6$) δ: 8.80 (d, J = 8.8 Hz, 1H), 8.31 (m, 1H), 8.26 (d, J = 8.4 Hz, 1H), 7.94 (s, 1H), 7.79-7.65 (m, 4H), 7.35 (s, 1H), 7.09 (s, 1H), 3.41 (d, J = 6.4 Hz, 2H), 2.42-2.33 (m, 2H), 1.60-1.42 (m, 6H), 1.16 (s, 6H), 1.07-0.88 (m, 12H), 0.62-0.54 (m, 2H). MS 585.2 (M + 1)$^+$. |

Example 7

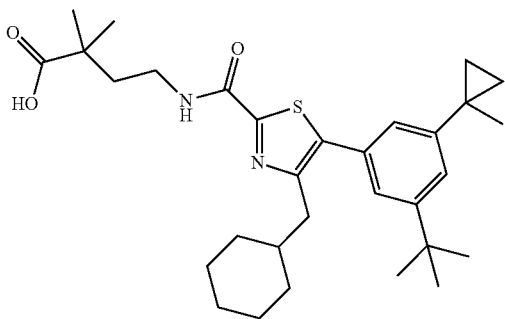

4-(5-(3-(tert-Butyl)-5-(1-methylcyclopropyl)phenyl)-4-(cyclohexylmehthyl)thiazole-2-carboxamido)-2,2-dimethylbutanoic acid (7)

To a solution of compound 6 (300 mg, 0.55 mmol) in a solution of MeOH (10 mL) and H$_2$O (2 mL) was added KOH (125 mg, 2.23 mmol) and the solution was stirred for 4 h at 50° C., concentrated under reduced pressure, diluted with H$_2$O and adjusted to pH=5 with 1N HCl. The solution was extracted with DCM and the organic layer was washed with brine, dried over Na$_2$SO$_4$, filtered, concentrated and purified by prep-HPLC to give compound 7 (40 mg, 14%) as a white solid. $^1$H-NMR (300 MHz, CDCl$_3$) δ: 7.44 (t, 1H), 7.29 (s, 1H), 7.21 (s, 1H), 7.09 (s, 1H), 3.50-3.56 (m, 2H), 2.63 (d, J=5.7 Hz, 2H), 1.95-1.99 (m, 2H), 1.77-1.81 (m, 1H), 1.62-1.68 (m, 5H), 1.43 (s, 3H), 1.33 (s, 9H), 1.31 (s, 6H), 1.13-1.29 (m, 3H), 0.87-0.93 (m, 3H), 0.75-0.78 (m, 2H). MS 525.3 (M+1)$^+$.

Example 7/1 to 7/27

The following Examples were prepared similar as in Example 7:

| # | Structure | Analytical data |
|---|---|---|
| 7/1 | 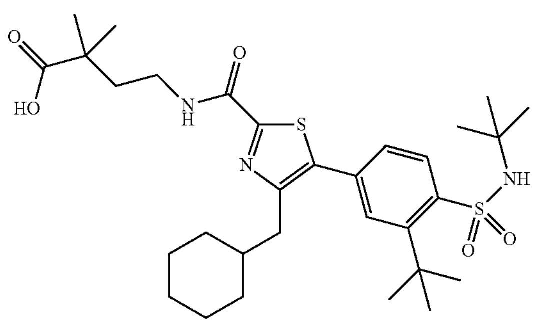 [SMILES: CC(C)(C)NS(=O)(=O)c1ccc(-c2sc(C(=O)NCCC(C)(C)C(=O)O)nc2CC2CCCCC2)cc1C(C)(C)C] | $^1$H-NMR (300 MHz, CDCl$_3$) δ: 8.19 (d, J = 8.4 Hz, 1H), 7.67 (d, J = 1.5 Hz, 1H), 7.52-7.48 (t, J = 5.7 Hz, 1H), 7.30 (dd, J = 9.6, 1.5 Hz, 1H), 4.69 (s, 1H), 3.50-3.57 (m, 2H), 2.63 (2H, d, J = 6.9 Hz), 1.95-2.00 (m, 2H), 1.74-1.78 (m, 1H), 1.66-1.61 (m, 5H), 1.62 (s, 9H), 1.33 (s, 9H), 1.08-1.25 (m, 3H), 0.83-0.94 (m, 2H). MS 606.3 (M + 1)$^+$ |
| 7/2 | 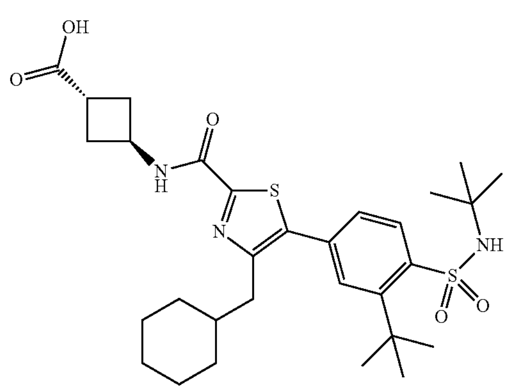 [SMILES: CC(C)(C)NS(=O)(=O)c1ccc(-c2sc(C(=O)N[C@H]3C[C@H](C(=O)O)C3)nc2CC2CCCCC2)cc1C(C)(C)C] | $^1$H-NMR (300 MHz, CDCl$_3$) δ: 8.23 (d, J = 8.4 Hz, 1H), 7.68 (d, J = 1.5 Hz, 1H), 7.49 (d, J = 8.1 Hz, 1H), 7.36 (dd, J = 8.1, 1.5 Hz, 1H), 4.79-4.88 (m, 1H), 4.64 (s, 1H), 3.16-3.25 (m, 1H), 2.78-2.88 (m, 2H), 2.67 (d, J = 7.2 Hz, 2H), 2.48-2.57 (m, 2H), 1.77-1.84 (m, 1H), 1.62-1.67 (m, 5H), 1.64 (s, 9H), 1.34 (s, 9H), 1.07-1.28 (m, 3H), 0.85-0.92 (m, 2H). MS 590.3 (M + 1)$^+$ |

| # | Structure | Analytical data |
|---|---|---|
| 7/3 | 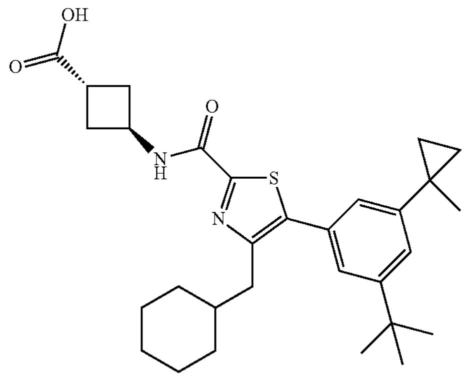 [SMILES: CC(C)(C)c1cc(-c2sc(C(=O)N[C@H]3C[C@H](C(=O)O)C3)nc2CC2CCCCC2)cc(C2(C)CC2)c1] | $^1$H-NMR (300 MHz, CDCl$_3$) δ: 7.55 (d, J = 6.9 Hz, 1H), 7.31 (s, 1H), 7.23 (s, 1H), 7.11 (s, 1H), 4.80-4.86 (m, 1H), 3.18-3.21 (br s, 1H), 2.80-2.83 (m, 2H), 2.65 (d, J = 6.9 Hz, 1H), 2.51-2.53 (m, 2H), 1.79-1.84 (m, 1H), 1.67-1.70 (m, 5H), 1.44 (s, 3H), 1.35 (s, 9H), 1.07-1.29 (m, 3H), 0.87-0.93 (m, 4H), 0.75-0.77 (m, 2H), MS 509.3 (M + 1)$^+$ |
| 7/4 | 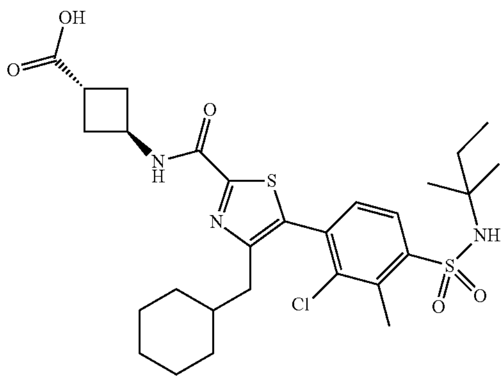 [SMILES: CCC(C)(C)NS(=O)(=O)c1ccc(-c2sc(C(=O)N[C@H]3C[C@H](C(=O)O)C3)nc2CC2CCCCC2)c(Cl)c1C] | $^1$H-NMR (300 MHz, CDCl$_3$) δ: 0.74-0.81 (m, 2H), 0.85-0.90 (m, 3H), 1.12-1.21 (m, 3H), 1.29 (s, 6H), 1.54-1.63 (m, 8H), 2.47-2.57 (m, 2H), 2.78 (s, 3H), 2.80-2.87 (m, 2H), 3.16-3.24 (m, 1H), 4.50 (s, 1H), 4.80-4.83 (m, 1H), 7.28 (d, J = 8.4 Hz, 1H), 7.50 (d, J = 8.4 Hz, 1H), 8.05 (d, J = 8.4 Hz, 1H). MS 596.2 [M + 1]$^+$ |
| 7/5 | 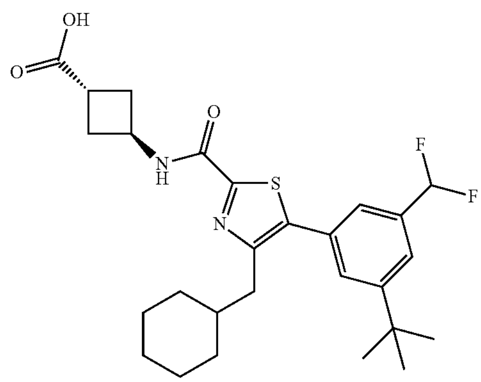 [SMILES: CC(C)(C)c1cc(-c2sc(C(=O)N[C@H]3C[C@H](C(=O)O)C3)nc2CC2CCCCC2)cc(C(F)F)c1] | $^1$H-NMR (DMSO-d$_6$, 300 MHz) δ: 0.81-0.89 (m, 2H), 1.09-1.17 (m, 3H), 1.34 (s, 9H), 1.52-1.60 (m, 5H), 1.79-1.85 (m, 1H), 2.39-2.47 (m, 3H), 2.53-2.57 (m, 1H), 2.66 (d, J = 7.2 Hz, 2H), 3.20-3.33 (m, 2H), 4.54-4.63 (m, 1H), 7.09 (t, J = 25.8 Hz, 1H), 7.47 (s, 1H), 7.65 (d, J = 1.2 Hz, 1H), 9.07 (d, J = 8.1 Hz, 1H). MS 505.3 (M + 1)$^+$ |
| 7/6 | 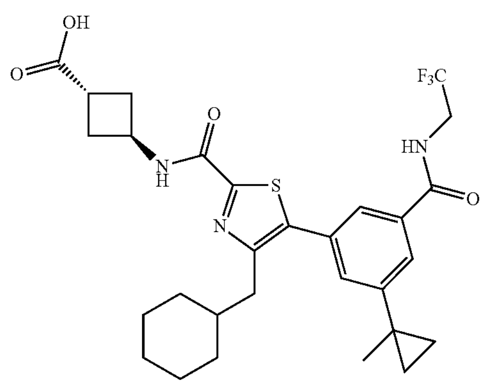 [SMILES: CC1(c2cc(C(=O)NCC(F)(F)F)cc(-c3sc(C(=O)N[C@H]4C[C@H](C(=O)O)C4)nc3CC3CCCCC3)c2)CC1] | $^1$H-NMR (400 MHz, CD$_3$OD) δ: 0.77-0.78 (m, 2H), 0.80-0.82 (m, 2H), 0.86-0.87 (m, 2H), 1.11-1.23 (m, 3H), 1.38 (s, 3H), 1.54-1.56 (m, 5H), 1.75-1.77 (m, 1H), 2.39-2.47 (m, 2H), 2.51-2.60 (m, 4H), 2.98-2.99 (m, 1H), 4.00 (q, J = 9.2 Hz, 2H), 4.61-4.65 (m, 1H), 7.43 (d, J = 0.8 Hz, 1H), 7.64 (d, J = 1.6 Hz, 1H), 7.72 (d, J = 1.6 Hz, 1H). MS 578.3 [M + 1]$^+$ |

| # | Structure | Analytical data |
|---|---|---|
| 7/7 | 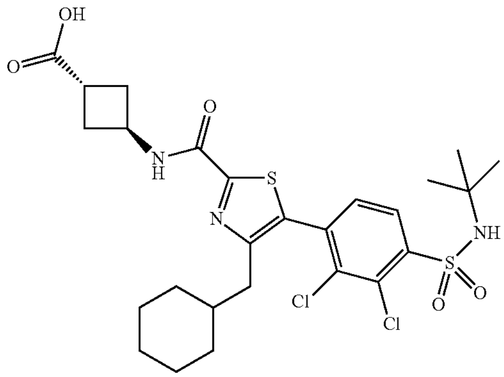 [SMILES: CC(C)(C)NS(=O)(=O)c1ccc(-c2sc(C(=O)N[C@H]3C[C@H](C(=O)O)C3)nc2CC2CCCCC2)c(Cl)c1Cl] | ¹H-NMR (300 MHz, CD₃OD) δ: 0.78-0.84 (m, 2H), 1.06-1.15 (m, 2H), 1.22 (s, 9H), 1.54-1.57 (m, 6H), 1.72-1.77 (m, 1H), 2.48-2.67 (m, 6H), 3.05-3.10 (m, 1H), 4.70-4.83 (m, 1H), 7.56 (d, J = 8.4 Hz, 1H), 8.16 (d, J = 8.4 Hz, 1H). MS 602.1 [M + 1]⁺ |
| 7/8 | 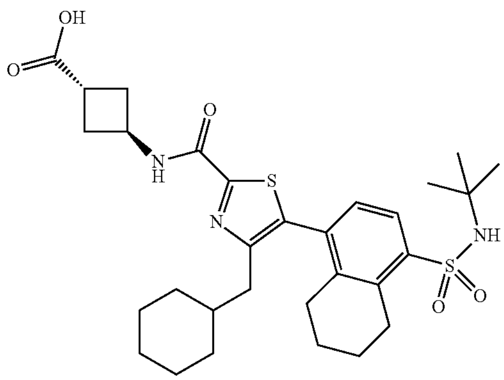 [SMILES: CC(C)(C)NS(=O)(=O)c1ccc(-c2sc(C(=O)N[C@H]3C[C@H](C(=O)O)C3)nc2CC2CCCCC2)c2c1CCCC2] | ¹H-NMR (300 MHz, CD₃OD) δ: 0.73-0.84 (m, 2H), 1.13-1.26 (m, 10H), 1.49-1.61 (m, 6H), 1.67-1.84 (m, 5H), 2.37-2.64 (m, 9H), 3.09 (br s, 1H), 3.26-3.30 (m, 2H), 4.71-4.76 (m, 1H), 7.22 (d, J = 7.8 Hz, 1H), 7.92-7.95 (d, J = 7.8 Hz, 1H). MS 588.2 [M + 1]⁺ |
| 7/9 | 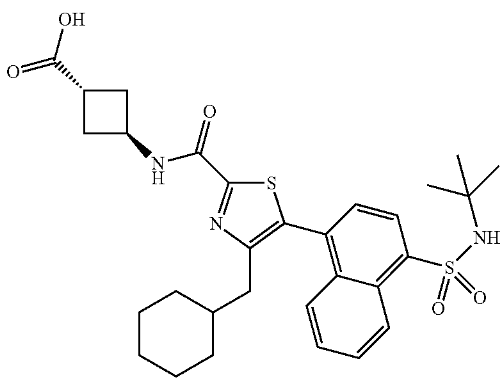 [SMILES: CC(C)(C)NS(=O)(=O)c1ccc(-c2sc(C(=O)N[C@H]3C[C@H](C(=O)O)C3)nc2CC2CCCCC2)c2ccccc12] | ¹H-NMR (400 MHz, CDCl₃) δ: 0.60-0.69 (m, 2H), 0.96-1.02 (m, 1H), 1.06-1.15 (m, 2H), 1.22 (s, 9H), 1.49-1.59 (m, 5H), 1.63-1.77 (m, 3H), 2.06 (dd, J = 9.6 Hz, 2.8 Hz, 2H), 2.35 (br s, 2H), 3.57 (td, J = 11.2 Hz, 1.6 Hz, 1H), 4.03-4.06 (m, 2H), 4.18-4.26 (m, 1H), 4.65-4.72 (m, 1H), 7.21 (d, J = 8.0 Hz, 1H), 7.51 (d, J = 7.6 Hz, 1H), 7.55-7.59 (m, 1H), 7.69-7.74 (m, 2H), 8.35 (d, J = 7.6 Hz, 1H), 8.69 (d, J = 8.4 Hz, 1H). MS 584.2 [M + 1]⁺ |
| 7/10 | 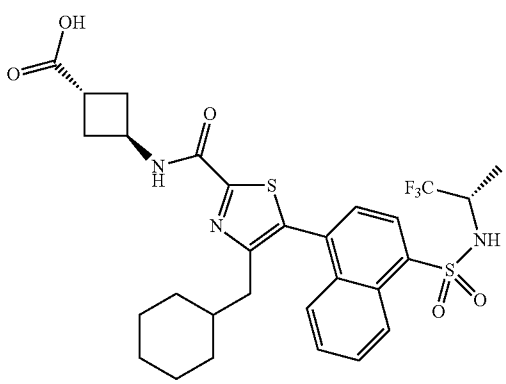 [SMILES: C[C@H](NS(=O)(=O)c1ccc(-c2sc(C(=O)N[C@H]3C[C@H](C(=O)O)C3)nc2CC2CCCCC2)c2ccccc12)C(F)(F)F] | ¹H-NMR (300 MHz, CDCl₃) δ: 0.52-1.04 (m, 2H), 0.75-1.17 (m, 3H), 1.25-1.31 (m, 4H), 1.47-1.70 (m, 6H), 2.32-2.34 (m, 2H), 2.50-2.60 (m, 2H), 2.81-2.89 (m, 2H), 3.18-3.26 (m, 1H), 3.97-4.05 (m, 1H), 4.81-4.89 (m, 1H), 4.98 (d, J = 9.6 Hz, 1H), 7.51-7.62 (m, 3H), 7.72-7.76 (m, 2H), 8.33 (d, J = 7.5 Hz, 1H), 8.65 (d, J = 8.1 Hz, 1H). MS 624.2 [M + 1]⁺ |

-continued

| # | Structure | Analytical data |
|---|---|---|
| 7/11 | 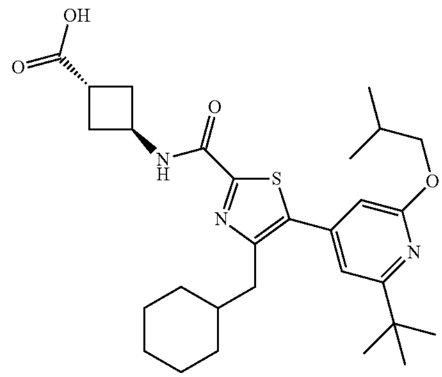 [SMILES: CC(C)COc1cc(-c2sc(C(=O)N[C@H]3C[C@H](C(=O)O)C3)nc2CC2CCCCC2)cc(C(C)(C)C)n1] | $^1$H-NMR (400 MHz, DMSO-d$_6$) δ: 0.82-0.91 (m, 2H), 0.97 (d, J = 6.8 Hz, 6H), 1.06-1.23 (m, 3H), 1.32 (s, 9H), 1.52-1.59 (m, 5H), 1.78-1.86 (m, 1H), 2.05-2.08 (m, 1H), 2.39-2.44 (m, 2H), 2.52-2.55 (m, 2H), 2.70 (d, J = 6.8 Hz, 2H), 2.92-2.96 (m, 1H), 4.11 (d, J = 6.8 Hz, 2H), 4.55-4.61 (m, 1H), 6.68 (s, 1H), 7.01 (s, 1H), 9.11 (d, J = 8.4 Hz, 1H), 12.24 (s, 1H). MS 528.3 (M + 1)$^+$ |
| 7/12 | 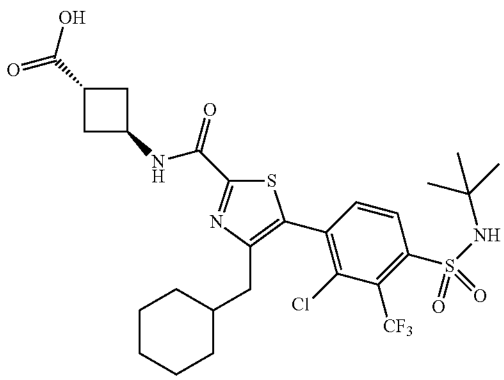 | $^1$H-NMR (400 MHz, CDCl$_3$) δ: 8.36 (d, 1H, J = 8.4 Hz), 7.60 (d, 1H, J = 8.4 Hz), 7.46 (d, 1H, J = 7.6 Hz), 4.86-4.80 (m, 2H), 3.19 (t, 1H, J = 4.8 Hz), 2.85-2.80 (m, 2H), 2.56-2.48 (m, 2H), 2.38 (d, 2H, J = 6.8 Hz), 1.75-1.54 (m, 6H), 1.31 (s, 9H), 1.27-1.05 (m, 3H), 0.81-0.72 (m, 2H). MS 636.2 (M + 1)$^+$ |
| 7/13 | 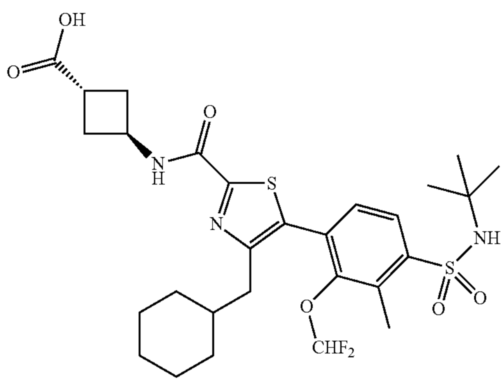 [SMILES: Cc1c(S(=O)(=O)NC(C)(C)C)ccc(-c2sc(C(=O)N[C@H]3C[C@H](C(=O)O)C3)nc2CC2CCCCC2)c1OC(F)F] | $^1$H-NMR (400 MHz, CDCl$_3$) δ: 8.06 (d, 1H, J = 7.0 Hz), 7.48-7.45 (m, 1H), 7.32 (d, 1H, J = 8.4 Hz), 6.06 (t, 1H, J = 74 Hz), 4.84-4.78 (m, 1H), 4.52 (s, 1H), 3.24-3.19 (m, 1H), 2.86-2.79 (m, 2H), 2.67-2.49 (m, 7H), 1.79-1.53 (m, 6H), 1.27-1.05 (m, 12H), 0.83-0.73 (m, 2H). MS 614.2 (M + 1)$^+$ |
| 7/14 | 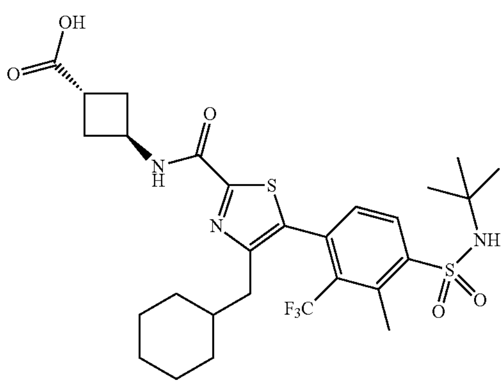 [SMILES: Cc1c(S(=O)(=O)NC(C)(C)C)ccc(-c2sc(C(=O)N[C@H]3C[C@H](C(=O)O)C3)nc2CC2CCCCC2)c1C(F)(F)F] | $^1$H-NMR (400 MHz, CDCl$_3$) δ: 8.29 (d, 1H, J = 8.4 Hz), 7.49 (d, 1H, J = 8.0 Hz), 7.25 (d, 1H, J = 8.0 Hz), 4.85-4.78 (m, 1H), 4.66 (s, 1H), 3.23-3.18 (m, 1H), 2.86-2.79 (m, 5H), 2.56-2.47 (m, 3H), 2.21-2.15 (m, 1H), 1.74-1.59 (m, 5H), 1.46-1.43 (m, 1H), 1.29-1.12 (m, 12H), 0.88-0.60 (m, 2H). MS 616.2 (M + 1)$^+$ |

| # | Structure | Analytical data |
|---|---|---|
| 7/15 | 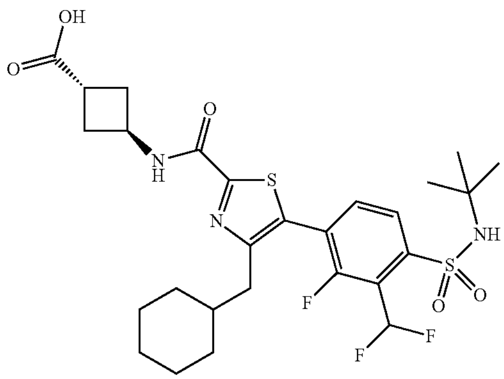 [SMILES: CC(C)(C)NS(=O)(=O)c1ccc(-c2sc(C(=O)N[C@H]3C[C@H](C(=O)O)C3)nc2CC2CCCCC2)c(F)c1C(F)F] | ¹H-NMR (400 MHz, CDCl₃) δ: 7.97 (d, 1H, J = 8.4 Hz), 7.71-7.50 (m, 3H), 4.85-4.79 (m, 1H), 4.69 (s, 1H), 3.23-3.19 (m, 1H), 2.86-2.80 (m, 2H), 2.56-2.47 (m, 4H), 1.77-1.55 (m, 6H), 1.26 (s, 9H), 1.24-0.74 (m, 5H). MS 602.2 (M + 1)⁺ |
| 7/16 | 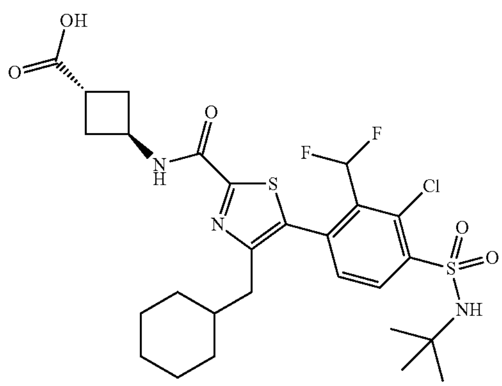 [SMILES: CC(C)(C)NS(=O)(=O)c1ccc(-c2sc(C(=O)N[C@H]3C[C@H](C(=O)O)C3)nc2CC2CCCCC2)c(C(F)F)c1Cl] | ¹H-NMR (400 MHz, CDCl₃) δ: 8.31 (d, 1H, J = 8.0 Hz), 7.48 (d, 1H, J = 8.0 Hz), 7.35 (d, 1H, J = 8.4 Hz), 6.87 (t, 1H, J = 53 Hz), 5.08 (s, 1H), 4.85-4.79 (m, 1H), 3.23-3.17 (m, 1H), 2.84-2.79 (m, 2H), 2.54-2.21 (m, 4H), 1.74-1.49 (m, 6H), 1.26-0.65 (m, 14H). MS 618.2 (M + 1)⁺ |
| 7/17 | 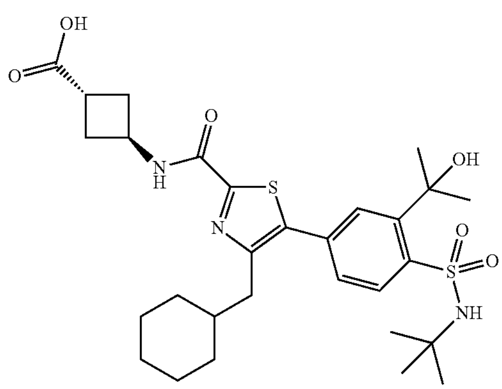 [SMILES: CC(C)(C)NS(=O)(=O)c1ccc(-c2sc(C(=O)N[C@H]3C[C@H](C(=O)O)C3)nc2CC2CCCCC2)cc1C(C)(C)O] | ¹H-NMR (CDCl₃, 300 MHz) δ: 0.84-0.88 (m, 2H), 1.13-1.26 (m, 3H), 1.28 (s, 12H), 1.60-1.64 (m, 5H), 1.70 (s, 6H), 1.74-1.77 (m, 1H), 2.48-2.53 (m, 2H), 2.64 (d, J = 7.2 Hz, 2H), 2.78-2.87 (m, 2H), 3.18-3.20 (m, 1H), 4.80-4.83 (m, 1H), 7.37-7.39 (m, 2H), 7.47 (d, J = 7.8 Hz, 1H), 8.24 (d, J = 8.7 Hz, 1H). MS 592.3 (M + 1)⁺ |
| 7/18 | 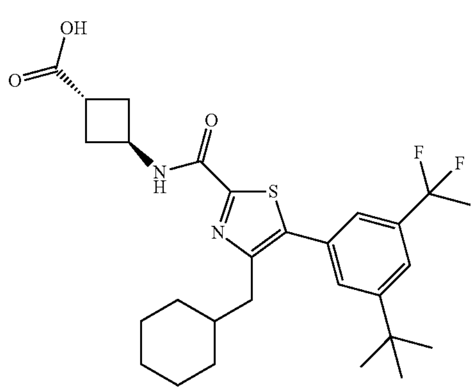 [SMILES: CC(C)(C)c1cc(-c2sc(C(=O)N[C@H]3C[C@H](C(=O)O)C3)nc2CC2CCCCC2)cc(C(C)(F)F)c1] | ¹H-NMR (DMSO-d₆, 300 MHz) δ: 0.88-0.95 (m, 2H), 1.18-1.35 (m, 3H), 1.39 (s, 9H), 1.55-1.67 (m, 5H), 1.95 (t, J = 18.3 Hz, 3H), 2.37-2.47 (m, 2H), 2.60-2.69 (m, 4H), 3.00-3.02 (m, 1H), 4.66-4.71 (m, 1H), 7.40 (s, 1H), 7.56 (s, 1H), 7.61 (s, 1H). MS 519.3 [M + 1]⁺ |

| # | Structure | Analytical data |
|---|---|---|
| 7/19 | 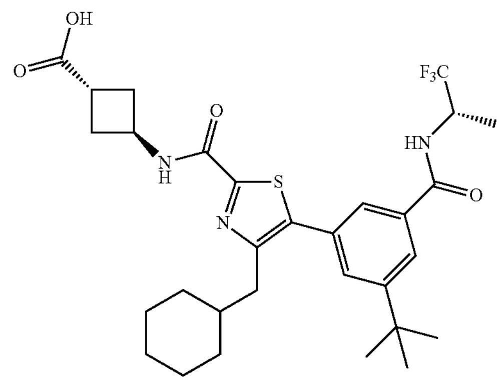 [SMILES: C[C@H](NC(=O)c1cc(-c2sc(C(=O)N[C@H]3C[C@H](C(=O)O)C3)nc2CC2CCCCC2)cc(C(C)(C)C)c1)C(F)(F)F] | ¹H-NMR (300 MHz, CDCl₃) δ: 0.87-0.94 (m, 2H), 1.15-1.26 (m, 3H), 1.33 (s, 9H), 1.45 (d, J = 6.9 Hz, 3H), 1.64-1.67 (m, 4H), 1.70-1.88 (m, 1H), 2.47-2.54 (m, 2H), 2.60 (d, J = 6.9 Hz, 2H), 2.76-2.83 (m, 2H), 3.15-3.22 (m, 1H), 4.78-4.81 (m, 1H), 4.95-4.98 (m, 1H), 6.51 (d, J = 9.6 Hz, 1H), 7.53-7.58 (m, 3H), 7.89 (s, 1H). MS 594.3 [M + 1]⁺ |
| 7/20 | 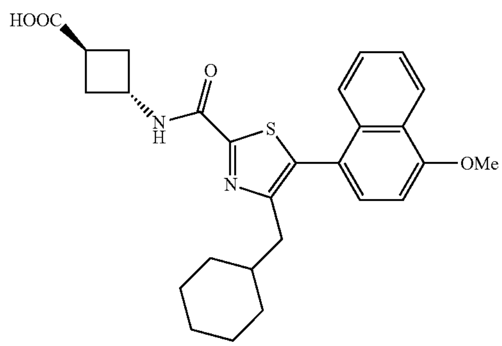 [SMILES: COc1ccc(-c2sc(C(=O)N[C@H]3C[C@H](C(=O)O)C3)nc2CC2CCCCC2)c2ccccc12] | ¹H-NMR (400 MHz, DMSO-d₆) δ: 0.62-0.65 (m, 2H), 0.96 (m, 1H), 1.03-1.11 (m, 2H), 1.47-1.50 (m, 5H), 1.74-1.76 (m, 1H), 2.32-2.41 (m, 4H), 2.55-2.58 (m, 2H), 2.96 (m, 1H), 4.04 (s, 3H), 4.60-4.62 (m, 1H), 7.09 (d, J = 7.6 Hz, 1H), 7.47-7.57 (m, 4H), 8.24-8.27 (m, 1H), 9.14 (d, J = 8.4 Hz, 1H), 12.27 (s, 1H). MS 479 [M + 1]⁺ |
| 7/21 | 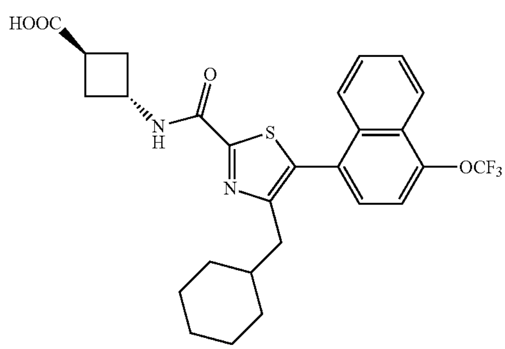 [SMILES: O=C(N[C@H]1C[C@H](C(=O)O)C1)c1nc(CC2CCCCC2)c(-c2ccc(OC(F)(F)F)c3ccccc23)s1] | ¹H-NMR (400 MHz, CD₃OD) δ: 0.63-0.73 (m, 2H), 0.99-1.17 (m, 3H), 1.53-1.55 (m, 5H), 1.75-1.79 (m, 1H), 2.41 (m, 2H), 2.51-2.59 (m, 2H), 2.63-2.69 (m, 2H), 3.08-3.12 (m, 1H), 4.75 (m, 1H), 7.56 (m, 2H), 7.61-7.72 (m, 3H), 8.21 (d, J = 8.4 Hz, 1H). MS 533 [M + 1]⁺ |
| 7/22 | 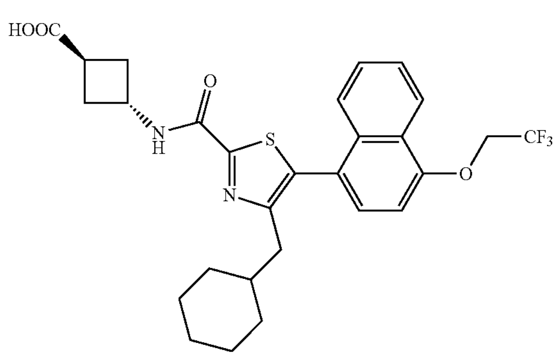 [SMILES: O=C(N[C@H]1C[C@H](C(=O)O)C1)c1nc(CC2CCCCC2)c(-c2ccc(OCC(F)(F)F)c3ccccc23)s1] | ¹H-NMR (400 MHz, CD₃OD) δ: 0.69-0.75 (m, 2H), 1.06-1.17 (m, 3H), 1.56-1.62 (m, 5H), 1.79 (m, 1H), 2.44 (m, 2H), 2.56-2.61 (m, 2H), 2.65-2.71 (m, 2H), 3.14-3.15 (m, 1H), 4.76-4.90 (m, 3H), 7.14 (d, J = 8.4 Hz, 1H), 7.47-7.48 (d, J = 7.6 Hz, 1H), 7.59-7.63 (m, 3H), 8.34 (d, J = 7.6 Hz, 1H). MS 547.2 [M + 1]⁺ |

| # | Structure | Analytical data |
|---|---|---|
| 7/23 | 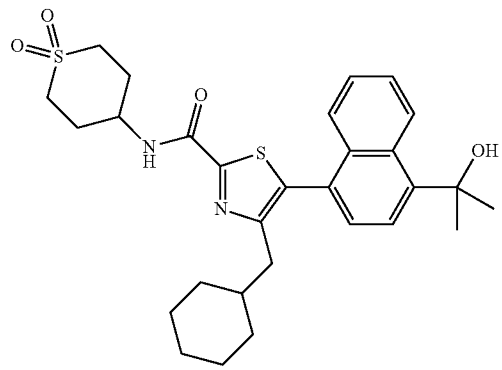 [SMILES: CC(C)(O)c1ccc(-c2sc(C(=O)NC3CCS(=O)(=O)CC3)nc2CC2CCCCC2)c2ccccc12] | ¹H-NMR (300 MHz, CDCl₃) δ: 0.62-0.77 (m, 2H), 0.96-1.26 (m, 3H), 1.51 (s, 3H), 1.54-1.57 (m, 2H), 1.69-1.81 (m, 1H), 1.92 (s, 6H), 2.03 (s, 1H), 2.32-2.51 (m, 6H), 3.15-3.21 (m, 4H), 4.23-4.33 (m, 1H), 7.27-7.65 (m, 6H), 8.95 (d, J = 8.4 Hz, 1H). MS 541.3 [M + 1]⁺ |
| 7/24 | 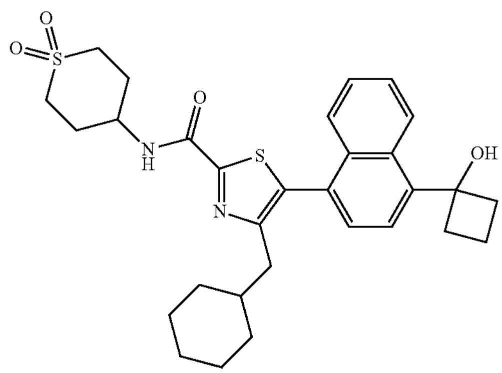 [SMILES: O=C(NC1CCS(=O)(=O)CC1)c1nc(CC2CCCCC2)c(-c2ccc(C3(O)CCC3)c3ccccc23)s1] | ¹H-NMR (300 MHz, CDCl₃) δ: 0.64-0.76 (m, 2H), 0.98-1.18 (m, 3H), 1.52-1.54 (m, 3H), 1.58-1.61 (m, 2H), 1.71-1.79 (m, 1H), 2.33-2.52 (m, 6H), 2.77 (s, 1H), 3.17-3.20 (m, 4H), 4.24-4.33 (m, 1H), 5.20 (d, J = 6.9 Hz, 1H), 5.38 (d, J = 6.9 Hz, 1H), 7.31 (d, J = 7.8 Hz, 1H), 7.44-7.62 (m, 4H), 7.67 (d, J = 8.4 Hz, 1H), 7.82 (d, J = 8.4 Hz, 1H). MS 555.2 [M + 1]⁺ |
| 7/25 | 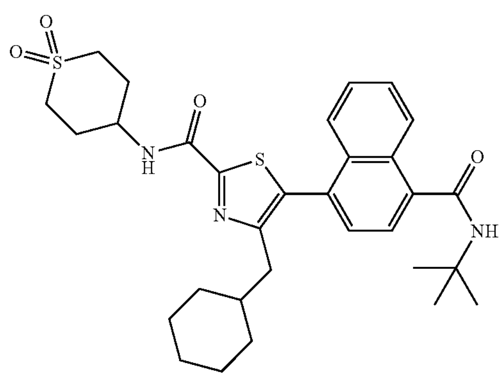 [SMILES: CC(C)(C)NC(=O)c1ccc(-c2sc(C(=O)NC3CCS(=O)(=O)CC3)nc2CC2CCCCC2)c2ccccc12] | ¹H-NMR (300 MHz, CDCl₃) δ: 0.65-0.70 (m, 2H), 1.11-1.17 (m, 3H), 1.50-1.61 (m, 14H), 1.71-1.79 (m, 1H), 2.33-2.48 (m, 6H), 3.16-3.30 (m, 4H), 4.26-4.30 (m, 1H), 5.85 (s, 1H), 7.26-7.31 (m, 1H), 7.41 (d, J = 7.2 Hz, 1H), 7.49-7.562 (m, 1H), 7.58-7.63 (m, 3H), 8.30-8.34 (m, 1H). MS 582.2 [M + 1]⁺ |
| 7/26 | 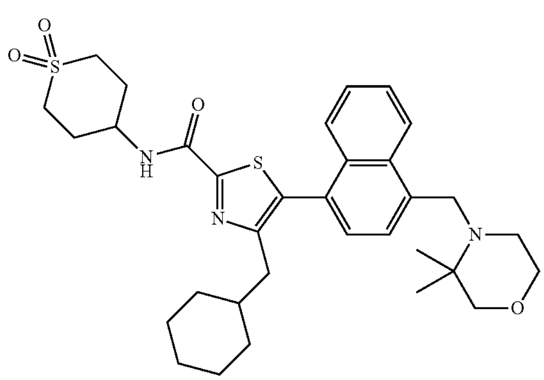 [SMILES: CC1(C)COCCN1Cc1ccc(-c2sc(C(=O)NC3CCS(=O)(=O)CC3)nc2CC2CCCCC2)c2ccccc12] | ¹H-NMR (300 MHz, CDCl₃) δ: 0.65-0.74 (m, 2H), 1.00-1.16 (m, 3H), 1.28 (s, 6H), 1.52-1.58 (m, 5H), 1.71-1.79 (m, 1H), 2.33-2.51 (m, 8H), 3.16-3.19 (m, 4H), 3.47 (s, 2H), 3.66-3.69 (m, 2H), 4.06 (s, 2H), 4.27-4.29 (m, 1H), 7.29-7.68 (m, 6H), 8.36 (d, J = 8.4 Hz, 1H). MS 610.3 [M + 1]⁺ |

-continued

| # | Structure | Analytical data |
|---|---|---|
| 7/27 | 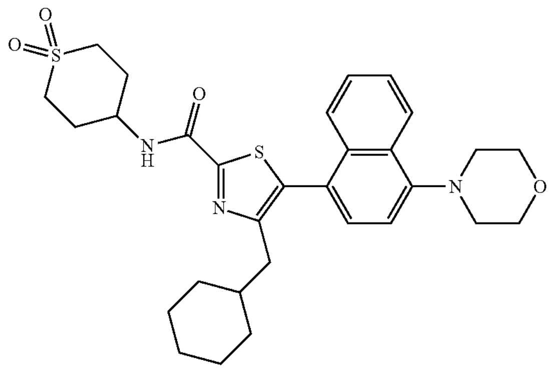 [SMILES: O=C(NC1CCS(=O)(=O)CC1)c1nc(CC2CCCCC2)c(-c2ccc(N3CCOCC3)c3ccccc23)s1] | ¹H-NMR (300 MHz, CDCl₃) δ: 0.65-0.74 (m, 2H), 1.00-1.16 (m, 3H), 1.50-1.51 (m, 3H), 1.54-1.59 (m, 2H), 1.71-1.79 (m, 1H), 2.37-2.51 (m, 6H), 3.16-3.20 (m, 8H), 4.00-4.03 (m, 4H), 4.27-4.29 (m, 1H), 7.12 (d, J = 7.8 Hz, 1H), 7.26-7.29 (m, 1H), 7.37 (d, J = 7.8 Hz, 1H), 7.45-7.57 (m, 3H), 8.28 (d, J = 8.4 Hz, 1H). MS 568.2 [M + 1]⁺ |

Example 8

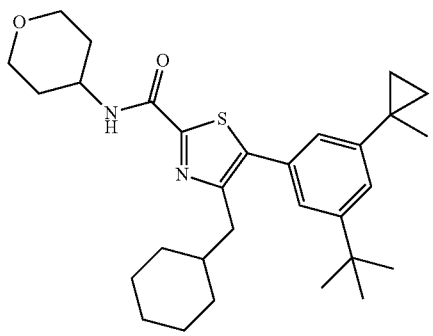

Step 1: 5-Bromo-4-(cyclohexylmethyl)-N-(tetrahydro-2H-pyran-4-yl)thiazole-2-carboxamide (8a)

To a solution of 6c (0.20 g, 0.60 mmol) in toluene (0.6 mL) was added tetrahydro-2H-pyran-4-amine (182 mg, 1.8 mmol) and the resulting solution was heated at 130° C. for 15 h. The reaction mixture was then cooled to rt and purified by CC (PE/EA=10/1 to 5/1) to afford compound 8a (0.21 g, 91%) as a white solid.

Step 2: 5-(3-(tert-Butyl)-5-(1-methylcyclopropyl)phenyl)-4-(cyclohexylmethyl)-N-(tetrahydro-2H-pyran-4-yl)thiazole-2-carboxamide (8)

Compound 8a (210 mg, 540 μmol), 2-(3-(tert-butyl)-5-(1-methylcyclopropyl)phenyl)-4,4,5,5-tetramethyl-1,3,2-dioxaborolane (180 mg, 560 μmol), Na₂CO₃ (180 mg, 1.69 mmol), Pd(dppf)Cl₂.CH₂Cl₂ (44 mg, 54 μmol) in toluene (3 mL), EtOH (1.5 mL) and water (1.5 mL) were heated at 70° C. for 15 h before cooled to rt. The mixture was partitioned between EA (10 mL) and water (10 mL) and the layers were separated. The organic phase was washed with water and brine, dried over Na₂SO₄, concentrated and purified by CC (PE/EA=10/1 to 5/1) to give compound 8 (189 mg, 75%). ¹H-NMR (400 MHz, CDCl₃) δ: 7.30 (s, 1H), 7.22 (s, 1H), 7.13 (d, J=8.1 Hz, 1H), 7.10 (s, 1H), 4.15-4.21 (m, 1H), 4.02 (d, J=8.8 Hz, 2H), 3.52-3.57 (m, 2H), 2.64 (d, J=7.1 Hz, 2H), 2.01-2.04 (m, 2H), 1.79-1.83 (m, 1H), 1.63-1.72 (m, 7H), 1.43 (s, 3H), 1.34 (s, 9H), 1.01-1.25 (m, 3H), 0.87-0.95 (m, 4H), 0.76-0.79 (m, 2H). MS 495.3 (M+1)⁺.

Example 8/1 to 8/12

The following Example was prepared similar as in Example 8:

| # | Structure | Analytical data |
|---|---|---|
| 8/1 | 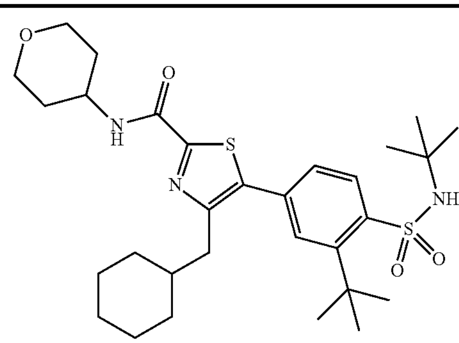 | ¹H-NMR (400 MHz, CDCl₃) δ: 8.22 (d, J = 8.3 Hz, 1H), 7.67 (d, J = 1.7 Hz, 1H), 7.35 (dd, J = 8.3 Hz, J = 1.7 Hz, 1H), 7.12 (d, J = 7.1 Hz, 1H), 4.46 (s, 1H), 4.17-4.20 (m, 1H), 4.02-4.04 (m, 2H), 3.53-3.57 (m, 2H), 2.66 (d, J = 7.2 Hz, 2H), 2.01-2.04 (m, 2H), 1.76-1.81 (m, 1H), 1.62-1.72 (m, 7H), 1.62 (s, 9H), 1.33 (s, 9H), 1.07-1.25 (m, 3H), 0.85-0.92 (m, 2H). MS 606.3 [M + 1]⁺ |

| # | Structure | Analytical data |
|---|---|---|
| 8/2 | 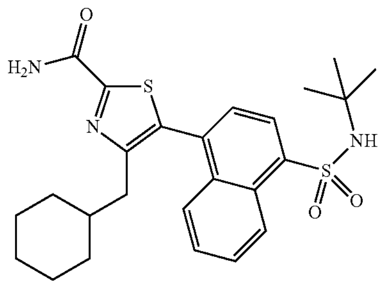 [SMILES: CC(C)(C)NS(=O)(=O)c1ccc(-c2sc(C(N)=O)nc2CC2CCCCC2)c2ccccc12] | ¹H-NMR (300 MHz, CDCl₃) δ: 0.59-0.71 (m, 2H), 0.94-1.19 (m, 3H), 1.22 (s, 11H), 1.48-1.58 (m, 4H), 1.65-1.74 (m, 2H), 2.34-2.35 (m, 2H), 4.71 (s, 1H), 5.67 (br s, 1H), 7.25 (br s, 1H), 7.51-7.60 (m, 2H), 7.69-7.74 (m, 2H), 8.35 (d, J = 7.5 Hz, 1H), 8.70 (d, J = 8.7 Hz, 1H). MS 486.2 (M + 1)⁺ |
| 8/3 | 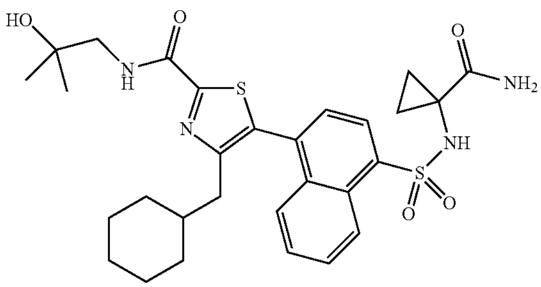 [SMILES: CC(C)(O)CNC(=O)c1nc(CC2CCCCC2)c(-c2ccc(S(=O)(=O)NC3(C(N)=O)CC3)c3ccccc23)s1] | ¹H-NMR (300 MHz, CDCl₃) δ: 0.63-0.80 (m, 4H), 0.88-1.30 (m, 5H), 1.35 (s, 6H), 1.37-1.56 (m, 6H), 2.32-2.36 (m, 2H), 3.53 (d, J = 6.6 Hz, 2H), 5.60-5.63 (m, 1H), 5.87 (s, 1H), 6.89-6.91 (m, 1H), 7.55-7.63 (m, 2H), 7.69-7.80 (m, 3H), 8.34 (d, J = 7.8 Hz, 1H), 8.58 (d, J = 8.4 Hz, 1H). MS 585.2 [M + 1]⁺. |
| 8/4 | 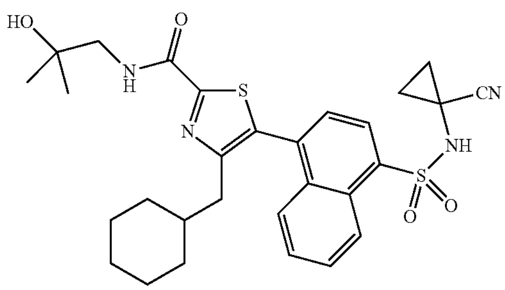 [SMILES: CC(C)(O)CNC(=O)c1nc(CC2CCCCC2)c(-c2ccc(S(=O)(=O)NC3(C#N)CC3)c3ccccc23)s1] | ¹H-NMR (300 MHz, CDCl₃) δ: 0.63-0.68 (m, 2H), 0.86-0.90 (m, 2H), 1.09-1.13 (m, 3H), 1.13-1.14 (m, 2H), 1.27 (s, 6H), 1.29-1.52 (m, 5H), 1.60-1.70 (m, 1H), 2.16 (s, 1H), 2.34-2.36 (m, 2H), 3.51-3.54 (m, 2H), 5.58-5.63 (m, 1H), 7.60 (d, J = 7.2 Hz, 2H), 7.64-7.80 (m, 3H), 8.46 (d, J = 7.5 Hz, 1H), 8.67 (d, J = 8.7 Hz, 1H). MS 567.2 [M + 1]⁺ |
| 8/5 | 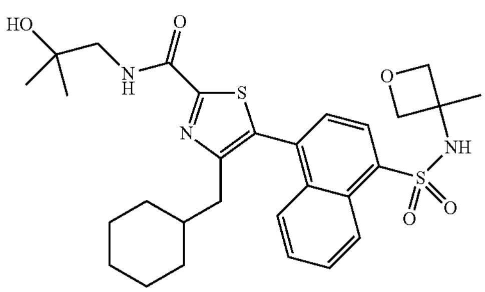 [SMILES: CC(C)(O)CNC(=O)c1nc(CC2CCCCC2)c(-c2ccc(S(=O)(=O)NC3(C)COC3)c3ccccc23)s1] | ¹H-NMR (300 MHz, CDCl₃) δ: 0.64-0.72 (m, 2H), 0.98-1.15 (m, 3H), 1.36 (s, 6H), 1.49-1.61 (m, 8H), 1.68-1.75 (m, 1H), 2.13 (s, 1H), 2.35-2.37 (m, 2H), 3.53 (d, J = 6.6 Hz, 2H), 4.34 (d, J = 6.6 Hz, 2H), 4.72 (d, J = 6.6 Hz, 2H), 5.20 (s, 1H), 7.54 (d, J = 7.5 Hz, 1H), 7.58-7.78 (m, 4H), 8.33 (d, J = 7.5 Hz, 1H), 8.68 (d, J = 8.7 Hz, 1H). MS 572.2 [M + 1]⁺ |
| 8/6 | 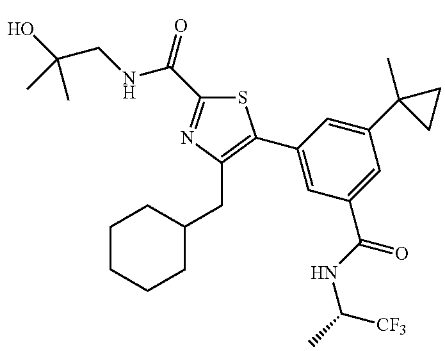 [SMILES: C[C@H](NC(=O)c1cc(-c2sc(C(=O)NCC(C)(C)O)nc2CC2CCCCC2)cc(C2(C)CC2)c1)C(F)(F)F] | ¹H-NMR (300 MHz, CDCl₃) δ: 0.75-0.88 (m, 2H), 0.89-1.01 (m, 2H), 1.05-1.30 (m, 5H), 1.32 (s, 6H), 1.42-1.46 (m, 6H), 1.59-1.83 (m, 6H), 2.19 (s, 1H), 2.60 (d, J = 10.5 Hz, 2H), 2.60 (d, J = 6.3 Hz, 2H), 4.91-4.99 (m, 1H), 4.94-4.99 (m, 1H), 6.11 (d, J = 9.9 Hz, 1H), 7.25-7.26 (m, 1H), 7.44-7.45 (m, 1H), 7.60-7.64 (m, 1H), 7.68-7.69 (m, 1H). MS 566.3 [M + 1]⁺ |

-continued

| # | Structure | Analytical data |
|---|---|---|
| 8/7 | 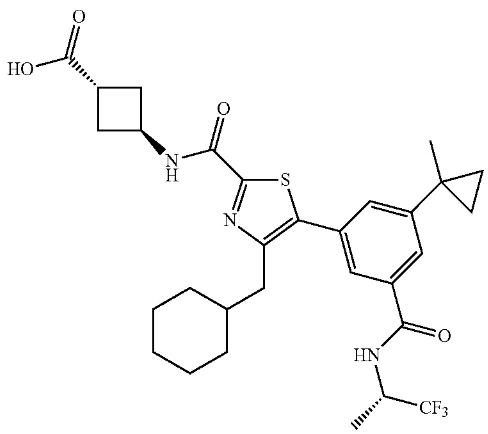 [SMILES: C[C@H](NC(=O)c1cc(-c2sc(C(=O)N[C@H]3C[C@H](C(=O)O)C3)nc2CC2CCCCC2)cc(C2(C)CC2)c1)C(F)(F)F] | $^1$H-NMR (300 MHz, CDCl$_3$) δ: 0.75-0.88 (m, 2H), 0.89-1.01 (m, 2H), 1.05-1.30 (m, 5H), 1.46 (s, 6H), 1.59-1.83 (m, 6H), 2.45-2.56 (m, 2H), 2.60 (d, J = 6.9 Hz, 2H), 2.77-2.85 (m, 2H), 3.15-3.22 (m, 1H), 4.77-4.82 (m, 1H), 4.94-4.99 (m, 1H), 6.25 (d, J = 9.6 Hz, 1H), 7.43 (s, 1H), 7.48 (d, J = 7.8 Hz, 2H), 7.55 (s, 1H), 7.69 (s, 1H). MS 592.3 [M + 1]$^+$ |
| 8/8 | 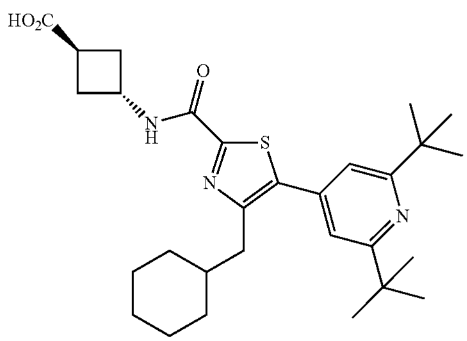 [SMILES: CC(C)(C)c1cc(-c2sc(C(=O)N[C@H]3C[C@H](C(=O)O)C3)nc2CC2CCCCC2)cc(C(C)(C)C)n1] | $^1$H-NMR (400 MHz, DMSO-d$_6$) δ: 0.89-0.94 (m, 2H), 1.12-1.23 (m, 3H), 1.34 (s, 18H), 1.58-1.67 (m, 5H), 1.75-1.86 (m, 1H), 2.39-2.44 (m, 2H), 2.48-2.52 (m, 2H), 2.70 (d, J = 7.2 Hz, 2H), 2.92-2.97 (m, 1H), 4.56-4.60 (m, 1H), 7.26 (s, 2H), 9.11 (d, J = 8.0 Hz, 1H), 12.25 (s, 1H). MS 512.4 (M + 1)$^+$ |
| 8/9 | 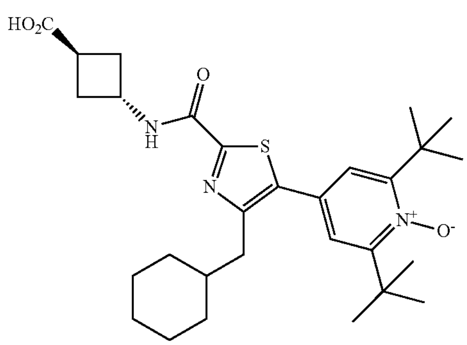 [SMILES: CC(C)(C)c1cc(-c2sc(C(=O)N[C@H]3C[C@H](C(=O)O)C3)nc2CC2CCCCC2)cc(C(C)(C)C)[n+]1[O-]] | $^1$H-NMR (400 MHz, DMSO-d$_6$) δ: 0.94-0.97 (m, 2H), 1.14-1.19 (m, 3H), 1.47 (s, 18H), 1.50-1.55 (m, 5H), 1.61-1.65 (m, 1H), 2.39-2.43 (m, 2H), 2.47-2.50 (m, 2H), 2.70 (d, J = 7.2 Hz, 2H), 2.92-2.96 (m, 1H), 4.57-4.59 (m, 1H), 7.37 (s, 2H), 9.11 (d, J = 8.0 Hz, 1H), 12.21 (br s, 1H). MS 528.3 (M + 1)$^+$ |
| 8/10 | 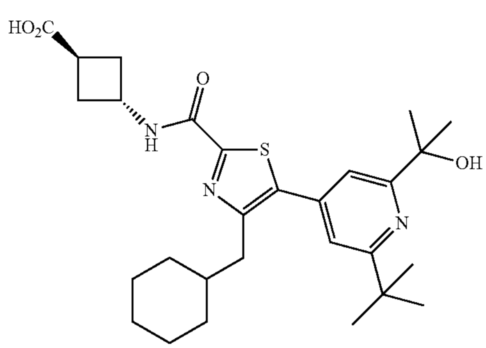 [SMILES: CC(C)(C)c1cc(-c2sc(C(=O)N[C@H]3C[C@H](C(=O)O)C3)nc2CC2CCCCC2)cc(C(C)(C)O)n1] | $^1$H-NMR (400 MHz, CD$_3$OD) δ: 0.95-1.01 (m, 2H), 1.20-1.30 (m, 3H), 1.46 (s, 9H), 1.62 (s, 6H), 1.68-1.70 (m, 5H), 1.91-1.92 (m, 1H), 2.52-2.69 (m, 4H), 2.80 (d, J = 7.2 Hz, 2H), 3.09-3.12 (m, 1H), 4.76 (t, J = 8.0 Hz, 1H), 7.48 (s, 1H), 7.65 (s, 1H). MS 514.3 (M + 1)$^+$ |

| # | Structure | Analytical data |
|---|---|---|
| 8/11 | 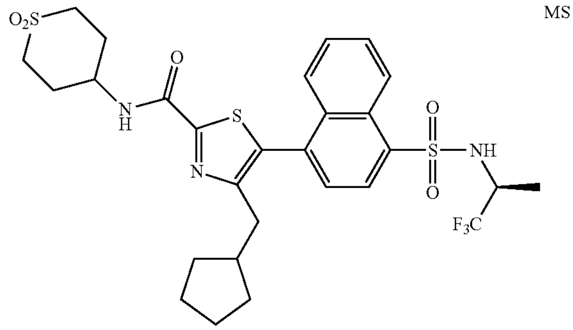 | MS 644.1.3 (M + 1)+ |
| 8/12 | 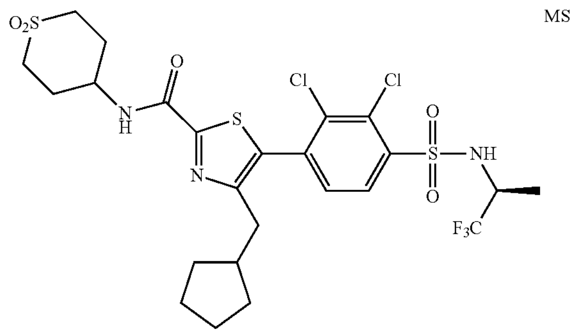 | MS 662.0 (M + 1)+ |

Example 9

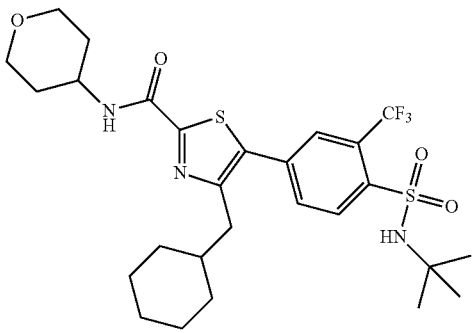

Step 1:
5-Bromo-4-(cyclohexylmethyl)thiazole-2-carboxylic acid (9a)

To a solution of compound 6c (72 mg, 0.23 mmol) in EtOH (2 mmol) was added 4N NaOH (1 mL). The mixture was stirred at rt overnight, evaporated and the residue was adjusted pH<2 with 4N HCl, extracted with EA (3×) and the combined organic layer was washed with brine and dried over Na$_2$SO$_4$. After filtration, the filtrate was evaporated to give compound 9a (60 mg, 87%) as a white solid.

Step 2:
5-Bromo-4-(cyclohexylmethyl)thiazole-2-carbonyl chloride (9b)

Oxalyl dichloride (48 mg, 0.38 mmol) was added to a mixture of compound 9a (57 mg, 0.19 mmol) in DCM (5 mL) of at 0° C. After stirred for 80 min at rt the mixture was evaporated to give compound 9b (55 mg, 91%) as a yellow oil.

Step 3: 5-Bromo-4-(cyclohexylmethyl)-N-(tetrahydro-2H-pyran-4-yl)thiazole-2-carboxamide (9c)

To a solution of compound 9b (50 mg, 0.16 mmol) in DCM (2.5 mL) was added TEA (33 mg, 0.32 mmol) and tetrahydro-2H-pyran-4-amine (20 mg, 0.19 mmol). The mixture was stirred overnight, quenched with water and extracted with EA. The organic layer was separated and washed with brine, dried over Na$_2$SO$_4$, filtered and evaporated to give compound 9c (51 mg, 85%) as a yellow solid.

Step 4: 5-(4-(N-(tert-Butyl)sulfamoyl)-3-(trifluoromethyl)phenyl)-4-(cyclohexylmethyl)-N-(tetrahydro-2H-pyran-4-yl)thiazole-2-carboxamide (9)

A suspension of compound 9c (46 mg, 0.12 mmol), Na$_2$CO$_3$ (32 mg, 0.32 mmol), N-(tert-butyl)-4-(4,4,5,5-tetramethyl-1,3,2-dioxaborolan-2-yl)-2-(trifluoromethyl)benzenesulfonamide (59 mg, 0.14 mmol), Pd(dppf)Cl$_2$ (30 mg) in DMF/H$_2$O (10:1, 10 mL) was heated overnight under N$_2$ at 90° C., cooled, concentrated and extracted with EA. The organic layer was washed with brine, dried over MgSO$_4$, filtered, evaporated and purified by prep-HPLC to give compound 9 (41 mg, 59%) as a white solid. $^1$H-NMR (400 MHz, DMSO-d$_6$) δ: 8.78 (d, 1H, J=8.4 Hz), 8.30 (d, 1H, J=8.4 Hz), 8.20 (dd, 1H, J=8.4, J=1.6 Hz), 7.95-7.98 (m, 2H), 3.99-4.04 (m, 1H), 3.87-3.90 (m, 2H), 3.34-3.41 (m, 2H), 2.68 (d, 2H, J=6.8 Hz), 1.71-1.80 (m, 5H), 1.52-1.55 (m, 5H), 1.19 (s, 9H), 1.03-1.16 (m, 3H), 0.76-0.84 (m, 2H). MS 488.2 (M+1)+.

Example 9/1 to 9/11

The following Examples were prepared similar as in Example 9:

| # | Structure | Analytical data |
|---|---|---|
| 9/1 | 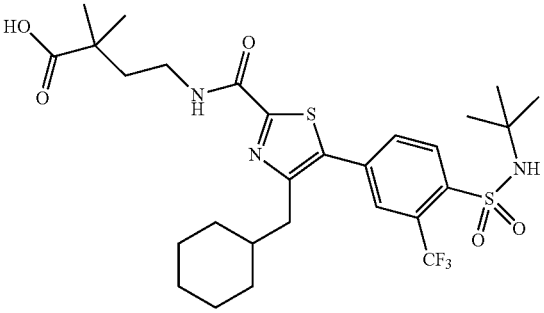 [SMILES: CC(C)(C)NS(=O)(=O)c1ccc(-c2sc(C(=O)NCCC(C)(C)C(=O)O)nc2CC2CCCCC2)cc1C(F)(F)F] | $^1$H-NMR (400 MHz, CDCl$_3$) δ: 8.36 (d, 1H, J = 8.4 Hz), 7.87 (d, 1H, J = 1.2 Hz), 7.71 (dd, 1H, J = 8.4, J = 1.8 Hz), 7.39 (t, 1H, J = 6.0 Hz), 4.75 (s, 1H), 3.51-3.57 (m, 2H), 2.63 (d, 2H, J = 6.8 Hz), 1.95-2.01 (m, 2H), 1.77-1.81 (m, 1H), 1.62-1.68 (m, 5H), 1.32 (s, 5H), 1.29 (s, 9H), 1.10-1.26 (m, 3H), 0.83-0.92 (m, 2H). MS 618.2 (M + 1)$^+$ |
| 9/2 | 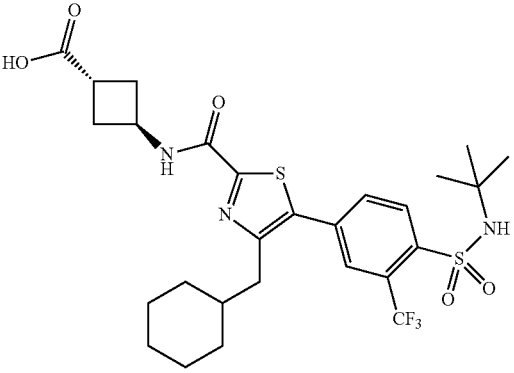 [SMILES: CC(C)(C)NS(=O)(=O)c1ccc(-c2sc(C(=O)N[C@H]3C[C@H](C(=O)O)C3)nc2CC2CCCCC2)cc1C(F)(F)F] | $^1$H-NMR (400 MHz, CDCl$_3$) δ: 8.37 (d, 1H, J = 8.4 Hz), 7.88 (s, 1H), 7.72 (dd, 1H, J = 8.0, J = 1.6 Hz), 7.45 (d, 1H, J = 7.6 Hz), 4.78-4.84 (m, 1H), 4.73 (s, 1H), 3.21-3.24 (m, 1H), 2.79-2.83 (m, 2H), 2.65 (d, 2H), 2.51-2.56 (m, 2H), 1.62-1.68 (m, 6 H), 1.29 (s, 9H), 1.11-1.26 (m, 3H), 0.84-0.93 (m, 2H). MS 602.2 (M + 1)$^+$ |
| 9/3 | 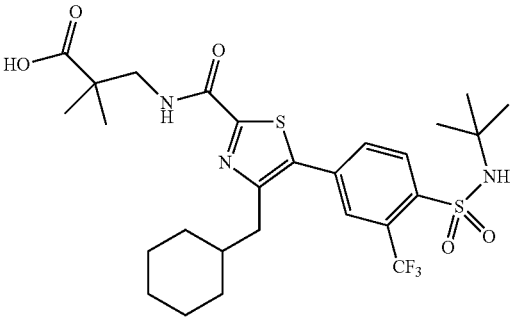 [SMILES: CC(C)(C)NS(=O)(=O)c1ccc(-c2sc(C(=O)NCC(C)(C)C(=O)O)nc2CC2CCCCC2)cc1C(F)(F)F] | $^1$H-NMR (400 MHz, CDCl$_3$) δ: 8.35 (d, 1H, J = 8.4 Hz), 7.87 (s, 1H), 7.68-7.76 (m, 2H), 4.72 (s, 1H), 3.63 (d, 2H, J = 6.4 Hz), 2.64 (d, 2H, J = 7.2 Hz), 1.44-1.64 (m, 6H), 1.34 (m, 6H), 1.29 (s, 9H), 1.09-1.25 (m, 3H), 0.83-0.92 (m, 2H). MS 604.2 (M + 1)$^+$ |
| 9/4 | 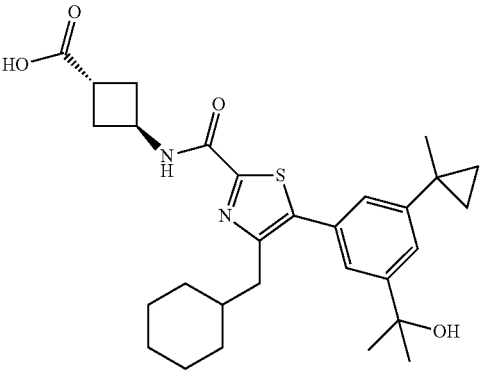 [SMILES: CC(C)(O)c1cc(-c2sc(C(=O)N[C@H]3C[C@H](C(=O)O)C3)nc2CC2CCCCC2)cc(C2(C)CC2)c1] | $^1$H-NMR (400 MHz, CD$_3$OD) δ: 0.77-0.80 (m, 2H), 0.88-0.95 (m, 4H), 1.12-1.23 (m, 3H), 1.43 (s, 3H), 1.54 (s, 6H), 1.64-1.67 (m, 5H), 1.79-1.89 (m, 1H), 2.48-2.56 (m, 2H), 2.61-2.70 (m, 4H), 3.05-3.13 (m, 1H), 4.68-4.76 (m, 1H), 7.18 (t, J = 2.0 Hz, 1H), 7.36 (t, J = 2.0 Hz, 1H), 7.36 (t, J = 2.0 Hz, 1H). MS 511.3 (M + 1)$^+$ |

-continued
| # | Structure | Analytical data |
|---|---|---|
| 9/5 | 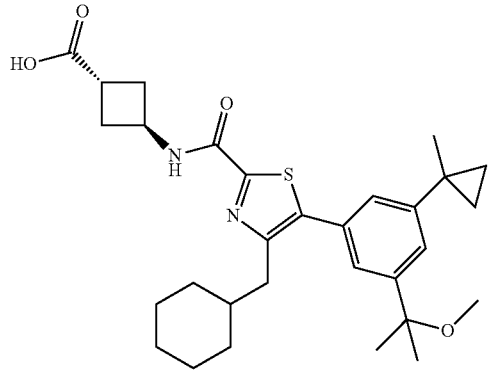 [SMILES: COC(C)(C)c1cc(-c2sc(C(=O)N[C@H]3C[C@H](C(=O)O)C3)nc2CC2CCCCC2)cc(C2(C)CC2)c1] | ¹H-NMR (400 MHz, CDCl₃) δ: 0.78-0.80 (m, 2H), 0.86-0.94 (m, 4H), 1.10-1.23 (m, 3H), 1.44 (s, 3H), 1.54 (s, 6H), 1.64-1.68 (m, 5H), 1.74-1.85 (m, 1H), 2.50-2.52 (m, 2H), 2.65 (d, J = 7.2 Hz, 2H), 2.80-2.84 (m, 2H), 3.11 (s, 3H), 3.15-3.23 (m, 1H), 4.77-4.87 (m, 1H), 7.16 (t, J = 1.6 Hz, 1H), 7.25 (t, J = 1.6 Hz, 1H), 7.30 (d, J = 1.6 Hz, 1H), 7.50 (d, J = 8.0 Hz, 1H). MS 525.3 (M + 1)⁺. |
| 9/6 | 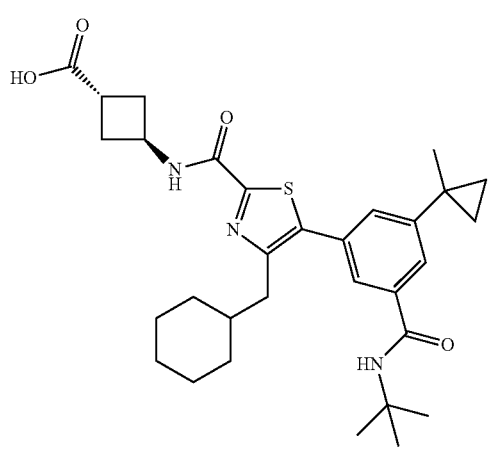 [SMILES: CC(C)(C)NC(=O)c1cc(-c2sc(C(=O)N[C@H]3C[C@H](C(=O)O)C3)nc2CC2CCCCC2)cc(C2(C)CC2)c1] | ¹H-NMR (400 MHz, CDCl₃) δ: 7.66 (t, J = 1.6 Hz, 1H), 7.45-7.38 (m, 2H), 7.38 (d, J = 1.6 Hz, 1H), 5.89 (s, 1H), 4.83-4.77 (m, 1H), 3.24-3.18 (m, 1H), 2.85-2.80 (m, 2H), 2.58 (d, 2H, J = 6.4 Hz), 2.55-2.47 (m, 2H), 1.82-1.52 (m, 6H), 1.49 (m, 9H), 1.44 (s, 3H), 1.27-1.12 (m, 3H), 0.93-0.88 (m, 6H). MS 552.3 (M + 1)⁺ |
| 9/7 | 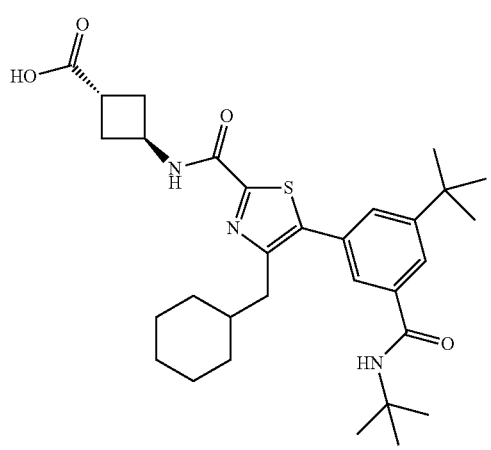 [SMILES: CC(C)(C)NC(=O)c1cc(-c2sc(C(=O)N[C@H]3C[C@H](C(=O)O)C3)nc2CC2CCCCC2)cc(C(C)(C)C)c1] | ¹H-NMR (400 MHz, CDCl₃) δ: 7.85 (t, J = 1.6 Hz, 1H), 7.52 (t, J = 1.6 Hz, 1H), 7.46-7.44 (m, 2H), 5.90 (s, 1H), 4.84-4.78 (m, 1H), 3.21-3.18 (m, 1H), 2.86-2.80 (m, 2H), 2.62 (d, 2H, J = 6.4 Hz), 2.55-2.48 (m, 2H), 1.83-1.66 (m, 6H), 1.49 (s, 9H), 1.37 (s, 9H), 1.34-1.09 (m, 3H), 0.94-0.86 (m, 2H). MS 554.3 (M + 1)⁺ |

-continued

| # | Structure | Analytical data |
|---|---|---|
| 9/8 | 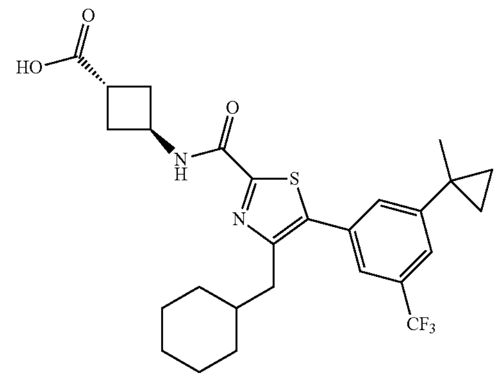 [SMILES: CC1(c2cc(-c3sc(C(=O)N[C@H]4C[C@H](C(=O)O)C4)nc3CC3CCCCC3)cc(C(F)(F)F)c2)CC1] | $^1$H-NMR (400 MHz, CDCl$_3$) δ: 7.50 (s, 1H), 7.43-7.44 (m, 3H), 4.78-4.84 (m, 1H), 3.19-3.23 (m, 1H), 2.82-2.85 (m, 2H), 2.60 (d, 2H), 2.50-2.56 (m, 2H), 1.79-1.84 (m, 1H), 1.63-1.68 (m, 5H), 1.46 (s, 3H), 1.11-1.28 (m, 3H), 0.85-0.94 (m, 6H). MS 521.2 (M + 1)$^+$. |
| 9/9 | 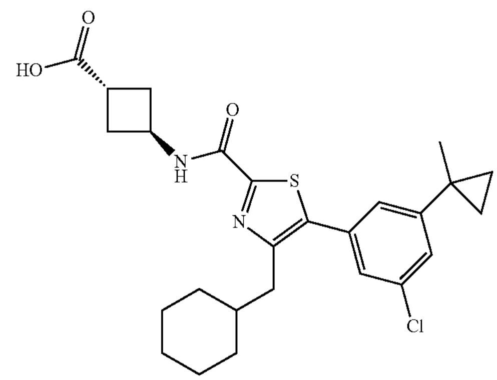 [SMILES: CC1(c2cc(Cl)cc(-c3sc(C(=O)N[C@H]4C[C@H](C(=O)O)C4)nc3CC3CCCCC3)c2)CC1] | $^1$H-NMR (400 MHz, CDCl$_3$) δ: 7.42 (m, 1H), 7.24 (s, 1H), 7.18 (s, 1H), 7.13 (s, 1H), 4.81-4.75 (m, 1H), 3.21-3.18 (m, 1H), 2.84-2.80 (m, 2H), 2.62 (d, J = 5.6 Hz, 2H), 2.55-2.47 (m, 2H), 1.81-1.78 (m, 1H), 1.66-1.55 (m, 5H), 1.42 (s, 3H), 1.31-1.17 (m, 3H), 0.90-0.78 (m, 6H). MS 487.2 (M + 1)$^+$ |
| 9/10 | 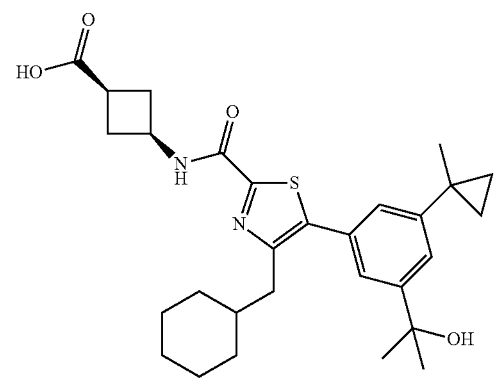 [SMILES: CC(C)(O)c1cc(-c2sc(C(=O)N[C@H]3C[C@@H](C(=O)O)C3)nc2CC2CCCCC2)cc(C2(C)CC2)c1] | $^1$H-NMR (CDCl$_3$, 400 MHz) δ: 0.77-0.80 (m, 2H), 0.83-0.93 (m, 4H), 1.12-1.25 (m, 4H), 1.43 (s, 3H), 1.60 (s, 6H), 1.64-1.66 (m, 5H), 1.69-1.83 (m, 1H), 2.46-2.53 (m, 2H), 2.64 (d, J = 7.2 Hz, 2H), 2.74-2.82 (m, 2H), 2.95-3.02 (m, 1H), 4.62-4.69 (m, 1H), 7.16 (t, J = 1.6 Hz, 1H), 7.30 (t, J = 1.6 Hz, 1H), 7.43 (t, J = 1.6 Hz, 1H), 8.00 (d, J = 8.0 Hz, 1H). MS 511.3 (M + 1)$^+$ |
| 9/11 | 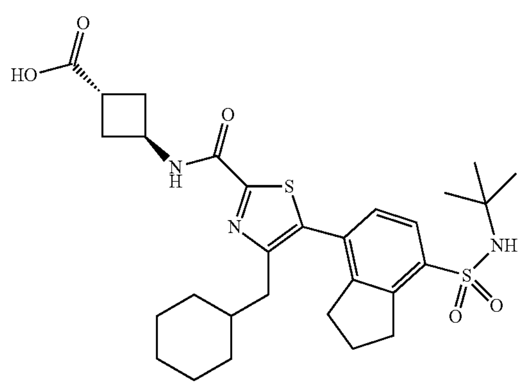 [SMILES: CC(C)(C)NS(=O)(=O)c1ccc(-c2sc(C(=O)N[C@H]3C[C@H](C(=O)O)C3)nc2CC2CCCCC2)c2c1CCC2] | $^1$H-NMR (400 MHz, CD$_3$OD) δ: 0.76-0.84 (m, 2H), 1.06-1.20 (m, 4H), 1.23 (s, 9H), 1.55-1.62 (m, 5H), 1.76-1.80 (m, 1H), 2.12-2.20 (m, 2H), 2.51-2.58 (m, 4H), 2.64-2.69 (m, 2H), 2.83-2.87 (m, 2H), 3.08-3.13 (m, 1H), 3.48-3.54 (m, 1H), 4.73-4.78 (m, 1H), 7.33 (d, J = 8.0 Hz, 1H), 7.83 (d, J = 8.4 Hz, 1H). MS 574.3 [M + 1]$^+$ |

Example 10

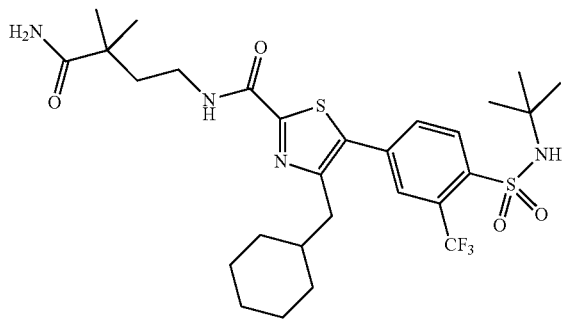

N-(4-Amino-3,3-dimethyl-4-oxobutyl)-5-(4-(N-(tert-butyl)sulfamoyl)-3-(trifluoromethyl)phenyl)-4-(cyclohexylmethyl)thiazole-2-carboxamide (10)

To a solution of compound 9/1 (90 mg, 0.15 mmol) in dry DMF (2 mL) was added HATU (86 mg, 0.23 mmol) and DIPEA (48 mg, 0.38 mmol). The mixture was stirred for 60 min and then NH$_4$Cl (10 mg, 0.18 mmol) was added. The reaction mixture was stirred overnight, quenched with water and extracted with EA. The organic layer was washed with brine, dried over Na$_2$SO$_4$, filtered, evaporated and purified by prep-HPLC to give compound 10 (17 mg, 19%) as a white solid. $^1$H-NMR (400 MHz, CDCl$_3$) δ: 8.36 (d, 1H, J=8.0 Hz), 7.88 (s, 1H), 7.71 (dd, 2H, J=8.0, J=1.6 Hz), 7.46 (t, 1H, J=5.6 Hz), 6.10 (br s, 1H), 5.28 (br s, 1H), 4.72 (s, 1H), 3.49-3.55 (m, 2H), 2.63 (d, 2H, J=6.8 Hz), 1.93-2.00 (m, 2H), 1.79-1.82 (m, 1H), 1.62-1.65 (m, 5H), 1.29 (m, 15H), 1.10-1.25 (m, 3H), 0.88-0.93 (m, 2H). MS 617.3 (M+1)$^+$.

Example 10/1 to 10/4

The following Examples were prepared from the corresponding acids via amide coupling similar as described in Example 10:

| # | Structure | Analytical data |
|---|---|---|
| 10/1 | 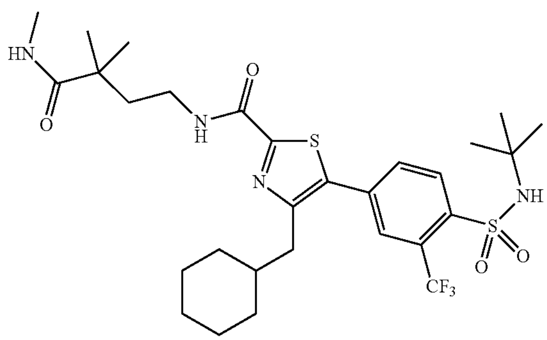 [SMILES: CNC(=O)C(C)(C)CCNC(=O)c1nc(CC2CCCCC2)c(-c2ccc(S(=O)(=O)NC(C)(C)C)c(C(F)(F)F)c2)s1] | $^1$H-NMR (400 MHz, CDCl$_3$) δ: 8.36 (d, 1H, J = 8.0 Hz), 7.87 (s, 1H), 7.71 (dd, 1H, J = 8.4, J = 1.6 Hz), 7.46 (t, J = 6.0 Hz, 1H), 6.02 (br s, 1H), 4.71 (s, 1H), 3.46-3.51 (m, 1H), 2.78 (d, 3H, J = 4.8 Hz), 2.63 (d, 2H, J = 7.2 Hz), 1.92-1.96 (m, 2H), 1.81-1.84 (m, 1H), 1.50-1.67 (m, 5H), 1.28-1.10 (m, 18H), 0.86-0.93 (m, 2H). MS 631.3 (M + 1)$^+$ |
| 10/2 | 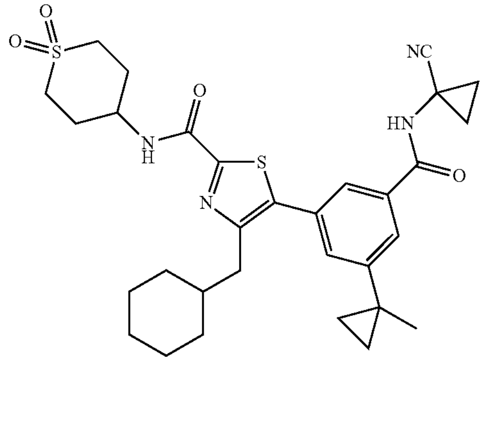 [SMILES: CC1(c2cc(C(=O)NC3(C#N)CC3)cc(-c3sc(C(=O)NC4CCS(=O)(=O)CC4)nc3CC3CCCCC3)c2)CC1] | $^1$H-NMR (300 MHz, CDCl$_3$) δ: 0.83-0.92 (m, 6H), 1.09-1.27 (m, 3H), 1.36-1.41 (m, 2H), 1.44 (s, 3H), 1.62-1.79 (m, 8H), 2.32-2.47 (m, 4H), 2.61 (d, J = 6.9 Hz, 2H), 3.14-3.18 (m, 4H), 4.20-4.26 (m, 1H), 6.86 (s, 1H), 7.22-7.23 (m, 1H), 7.44 (s, 1H), 7.55 (s, 1H), 7.68 (s, 1H). MS Found: 595.7 (M + 1)$^+$ |

| # | Structure | Analytical data |
|---|---|---|
| 10/3 | 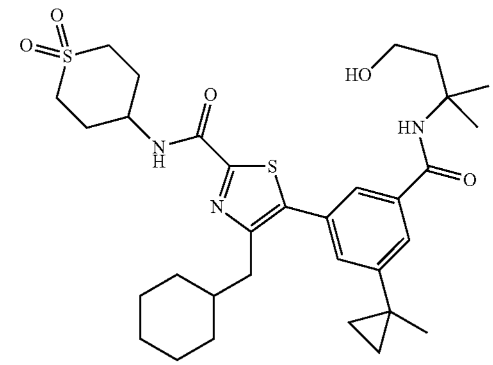 [SMILES: CC(C)(CCO)NC(=O)c1cc(-c2sc(C(=O)NC3CCS(=O)(=O)CC3)nc2CC2CCCCC2)cc(C2(C)CC2)c1] | $^1$H-NMR (300 MHz, CDCl$_3$) δ: 0.83-0.92 (m, 6H), 1.12-1.27 (m, 3H), 1.43 (s, 3H), 1.56 (s, 6H), 1.61-1.80 (m, 6H), 1.89-1.93 (m, 3H), 2.30-2.48 (m, 4H), 2.62 (d, J = 6.9 Hz, 2H), 3.14-3.19 (m, 4H), 3.94-3.98 (m, 2H), 4.23-4.27 (m, 1H), 7.23 (d, J = 8.4 Hz, 1H), 7.49 (s, 1H), 7.53 (t, J = 1.8 Hz, 1H), 7.70 (t, J = 1.8 Hz, 1H). MS 616.3 (M + 1)$^+$ |
| 10/4 | 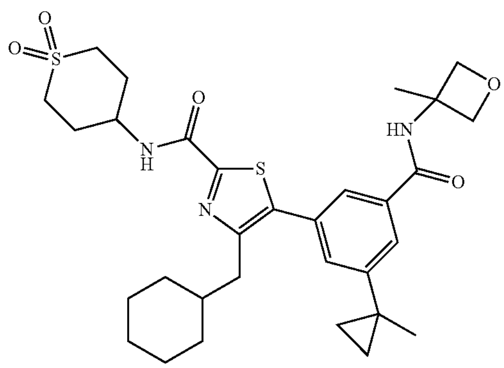 [SMILES: CC1(NC(=O)c2cc(-c3sc(C(=O)NC4CCS(=O)(=O)CC4)nc3CC3CCCCC3)cc(C3(C)CC3)c2)COC1] | $^1$H-NMR (300 MHz, CDCl$_3$) δ: 0.84-0.91 (m, 6H), 1.09-1.32 (m, 4H), 1.45 (s, 3H), 1.77 (s, 5H), 2.29-2.49 (m, 4H), 2.62 (d, J = 6.9 Hz, 2H), 3.14-3.15 (m, 4H), 4.23-4.25 (m, 1H), 4.59 (d, J = 6.3 Hz, 2H), 4.86 (d, J = 6.3 Hz, 2H), 6.47 (s, 1H), 7.22 (s, 1H), 7.41 (s, 1H), 7.54 (s, 1H), 7.68 (s, 1H). MS 600.3 (M + 1)$^+$ |

Example 11

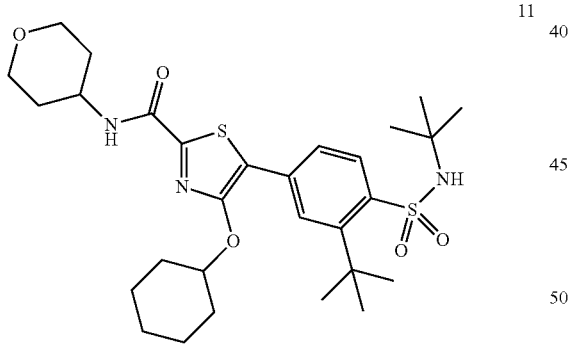

Step 1: Cyclohexyl 2-bromoacetate (11a)

If one were to treat cyclohexyl acetate with Br$_2$ in MeOH, compound 11a can be obtained.

Step 2: Ethyl 4-(cyclohexyloxy)thiazole-2-carboxylate (11b)

If one were to treat compound 11a with ethyl 2-amino-2-thioxoacetate in ethanol similar as described in Example 6, Step 2, compound 11b can be obtained.

Step 3: 5-(3-(tert-Butyl)-4-(N-(tert-butyl)sulfamoyl)phenyl)-4-(cyclohexyloxy)-N-(tetrahydro-2H-pyran-4-yl)thiazole-2-carboxamide (11)

If one were to treat compound 11b similar as described in Example 6, Step 3 to 6, compound 11 can be obtained.

Example 12

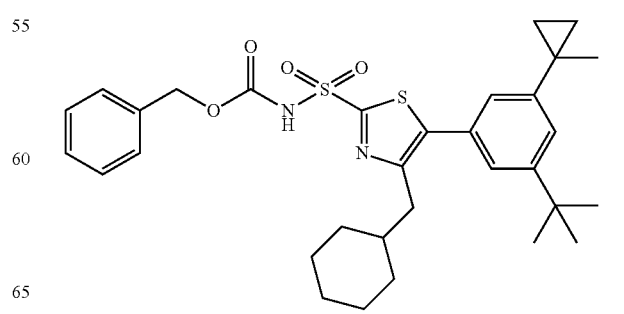

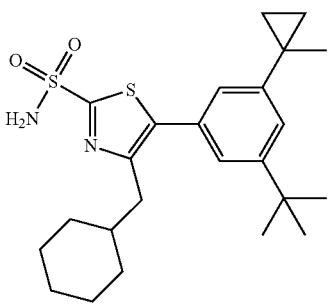

Step 1: 4-(Cyclohexylmethyl)thiazol-2-amine (12a)

A solution of 1-bromo-3-cyclohexylpropan-2-one (2.8 g, 12.8 mmol) and thiourea (1.07 g, 14.1 mmol) in EtOH (20 mL) was refluxed for 4 h, concentrated and portioned between DCM and sat. NaHCO$_3$. The organic layer was washed with brine, dried over Na$_2$SO$_4$, filtered, concentrated and purified by CC (PE/EA=3/1) to give compound 12a (1.1 g, 44%) as a yellow solid.

Step 2: 5-Bromo-4-(cyclohexylmethyl)thiazol-2-amine (12b)

To a solution of compound 12a (1.0 g, 5.1 mmol) in MeCN (10 mL) was added NBS (1.1 g, 6.1 mmol) and the solution was stirred overnight at rt, diluted with sat. NaHCO$_3$ and extracted with EA. The organic layer was washed water and brine consecutively, dried over Na$_2$SO$_4$, filtered and concentrated to give crude compound 12b (1.14 g, 81%) as a pale yellow solid.

Step 3: 2,5-Dibromo-4-(cyclohexylmethyl)thiazole (12c)

To a solution of compound 12b (1.14 g, 4.1 mmol) in MeCN (15 mL) was added CuBr$_2$ (1.37 g, 6.1 mmol) and isoamyl nitrite (900 mg, 7.65 mmol) at 0° C. and the solution was stirred at this temperature for 1 h, concentrated and diluted with water. The aq. phase was extracted with EA and the organic layer was washed with water and brine consecutively, dried over Na$_2$SO$_4$, filtered, concentrated and purified by CC (PE/EA=5/1) to give compound 12c (800 mg, 57%) as a brown-red oil.

Step 4: 5-Bromo-4-(cyclohexylmethyl)thiazole-2-sulfonamide (12d)

The solution of compound 12c (3.1 g, 9.14 mmol), BnSH (1.7 g, 13.7 mmol) and K$_2$CO$_3$ (2.52 g, 18.3 mmol) in DMF (30 mL) was stirred at 60° C. for 2 h, cooled to rt, diluted with water and extracted with EA (3×). The combined organic layers were washed with water (3×) and brine twice consecutively, dried over Na$_2$SO$_4$, filtered and concentrated to give a residue. To this residue was added CCl$_4$ (15 mL) and water (1.5 mL) and the solution was stirred for 1 min. Cl$_2$ was bubbled through the system for 30 min. The organic layer was separated, washed with water, dried over Na$_2$SO$_4$, filtered and concentrated to give a residue. This residue was dissolved in THF (10 mL) and then 20% aq. NH$_4$OH (5 mL) was added. The solution was stirred at rt overnight, concentrated and extracted with EA. The organic layer was separated, washed with water, dried over Na$_2$SO$_4$, filtered, concentrated and purified by CC (PE/EA=2/1) to give compound 12d (1.3 g, 42%) as a brown solid.

Step 5: Benzyl (5-bromo-4-(cyclohexylmethyl)thiazol-2-yl)sulfonylcarbamate (12e)

To a solution of compound 12d (550 mg, 2.0 mmol) and NEt$_3$ (404 mg, 7.0 mmol) and DIPEA (3.09 g, 4.0 mmol) in THF (10 mL) was added Cbz-Cl (525 mg, 3.0 mmol) at 0° C. under nitrogen and the solution was stirred at rt for 3 h, poured into water and extracted with EA twice. The combined organic layers were washed with water and brine consecutively, dried over Na$_2$SO$_4$, filtered, concentrated and purified by CC (PE/EA=3/1) to give compound 12e (230 mg, 28%) as a yellow solid.

Step 6: Benzyl (5-(3-(tert-butyl)-5-(1-methylcyclopropyl)phenyl)-4-(cyclohexylmethyl)thiazol-2-yl)sulfonylcarbamate (12)

A solution of compound 12e (400 mg, 0.98 mmol), compound P2 (458 mg, 1.46 mmol), K$_2$CO$_3$ (552 mg, 4.0 mmol) and Pd(PPh$_3$)Cl$_2$ (40 mg) in a mixture of EtOH (3 mL), toluene (6 mL) and water (3 mL) was stirred at 90° C. overnight under nitrogen, concentrated, poured into water and extracted with EA. The organic layer was washed with water and brine consecutively, dried over Na$_2$SO$_4$, filtered, concentrated and purified by CC (PE/EA=1/1) to give compound 12 (200 mg, 35%) as a white solid. $^1$H-NMR (CDCl$_3$, 400 MHz) δ: 0.78-0.80 (m, 2H), 0.84-0.90 (m, 4H), 1.11-1.15 (m, 3H), 1.24-1.27 (m, 1H), 1.31 (s, 9H), 1.47 (s, 3H), 1.58-1.61 (m, 5H), 1.66-1.73 (m, 1H), 2.59 (d, J=6.8 Hz, 2H), 5.00 (s, 2H), 7.06 (s, 1H), 7.23 (s, 1H), 7.28-7.33 (m, 6H). MS 581.3 (M+1)$^+$.

Step 6: 5-(3-(tert-Butyl)-5-(1-methylcyclopropyl)phenyl)-4-(cyclohexylmethyl)thiazole-2-sulfonamide (13)

The solution of compound 12 (130 mg, 0.22 mmol) and 10% Pd/C (50% wet, 15 mg) in MeOH (5 mL) was stirred overnight at rt under H$_2$ atmosphere, concentrated and purified by prep-HPLC to give compound 13 (25 mg, 25%) as a white solid. $^1$H-NMR (300 MHz, CDCl$_3$) δ: 7.33 (t, 1H, J=1.7 Hz), 7.21 (t, 1H, J=1.7 Hz), 7.09 (t, 1H, J=1.7 Hz), 5.56 (s, 2H), 2.66 (d, 2H, J=6.9 Hz), 1.76-1.81 (m, 1H), 1.63-1.68 (m, 5H), 1.43 (s, 3H), 1.34 (s, 9H), 1.13-1.22 (m, 3H), 0.76-0.96 (m, 6H). MS 447.1 (M+1)$^+$.

Example 13/1 to 13/3

The following Examples were prepared similar as in Example 12:

| # | Structure | Analytical data |
|---|---|---|
| 13/1 | 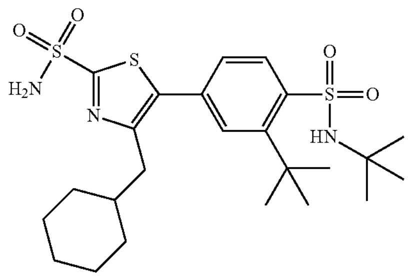 [SMILES: CC(C)(C)NS(=O)(=O)c1ccc(-c2sc(S(N)(=O)=O)nc2CC2CCCCC2)cc1C(C)(C)C] | $^1$H-NMR (300 MHz, CDCl$_3$) δ: 8.24 (d, 1H, J = 8.1 Hz), 7.67 (d, 1H, J = 0.9 Hz), 7.32 (d, 1H, J = 7.5 Hz), 5.40 (s, 2H), 4.64 (s, 1H), 2.68 (d, 2H, J = 6.9 Hz), 1.79-1.82 (m, 1H), 1.59-1.64 (m, 14H), 1.34 (s, 9H), 1.13-1.26 (m, 3H), 0.81-0.92 (m, 2 H). MS 528.2 (M + 1)$^+$ |
| 13/2 | 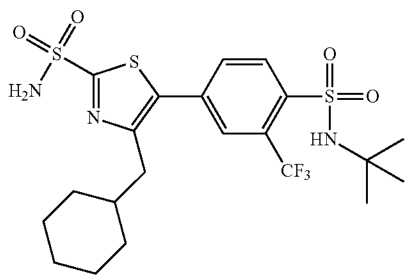 [SMILES: CC(C)(C)NS(=O)(=O)c1ccc(-c2sc(S(N)(=O)=O)nc2CC2CCCCC2)cc1C(F)(F)F] | $^1$H-NMR (CDCl$_3$, 400 MHz) δ: 0.86-0.92 (m, 2H), 1.09-1.15 (m, 3H), 1.18-1.29 (m, 10H), 1.64-1.67 (m, 5H), 1.75-1.85 (m, 1H), 2.66 (d, J = 6.8 Hz, 2H), 4.75 (s, 1H), 5.35 (s, 2H), 7.72 (d, J = 8.4 Hz, 1H), 7.87 (s, 1H), 8.39 (d, J = 8.4 Hz, 1H). MS 540.2 (M + 1)$^+$ |
| 13/3 | 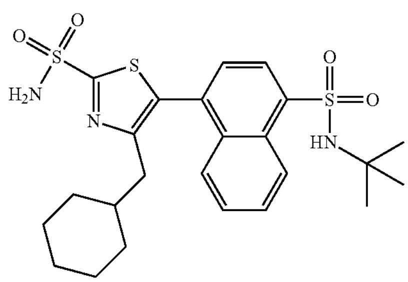 [SMILES: CC(C)(C)NS(=O)(=O)c1ccc(-c2sc(S(N)(=O)=O)nc2CC2CCCCC2)c2ccccc12] | $^1$H-NMR (300 MHz, CDCl$_3$) δ: 0.62-0.66 (m, 2H), 0.90-1.03 (m, 3H), 1.23 (s, 9H), 1.44-1.55 (m, 6H), 2.38 (br s, 2H), 4.68 (s, 1H), 5.30 (br s, 1H), 7.52 (d, J = 7.5 Hz, 1H), 7.61-7.63 (m, 1H), 7.70-7.76 (m, 2H), 8.36 (d, J = 7.5 Hz, 1H), 8.70 (d, J = 8.7 Hz, 1H). MS 522.2 [M + 1]$^+$ |

Example 14

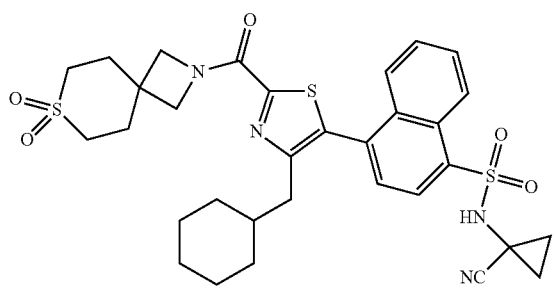

Step 1: Benzyl(naphthalen-1-yl)sulfane (14a)

To a suspension of naphthalene-1-thiol (40 g, 0.25 mol) and K$_2$CO$_3$ (138 g, 1.00 mol) in DMF (150 mL) was added BnBr (85.5 g, 0.50 mol) and the suspension was stirred at 45° C. overnight, cooled to rt, filtered and the filtrate was washed with EA. The combined organic phase was concentrated and purified by CC (PE) to give compound 14a (59 g, 94%) as a yellow solid.

Step 2: Benzyl(4-bromonaphthalen-1-yl)sulfane (14b)

To a solution of compound 14a (59 g, 236 mmol) in CCl$_4$ (500 mL) was added NBS (160 g, 1.00 mol) at −78° C. and the solution was stirred at this temperature for 1 h, quenched with water and stirred at rt for 1 h. The organic layer was washed with water and brine, dried over Na$_2$SO$_4$, filtered, concentrated and purified by CC (PE) to give crude compound 14b (18 g, 23%) as a pale red solid.

Step 3: Ethyl 5-(4-(benzylthio)naphthalen-1-yl)-4-(cyclohexylmethyl)thiazole-2-carboxylate (14c)

The solution of compound 14b (2.34 g, 7.10 mmol), ethyl 4-(cyclohexylmethyl)thiazole-2-carboxylate (1.80 g, 7.10 mmol), KOAc (1.39 g, 14.2 mmol), PPh$_3$ (2.05 g, 7.80 mmol) and Pd(OAc)$_2$ (160 mg, 0.71 mmol) in a solution of DMF (30 mL) was heated at 110° C. overnight, cooled to rt, diluted with EA and water. The organic phase was washed with water and brine, dried over Na$_2$SO$_4$, filtered, concentrated and purified by CC (PE/EA=10/1) to give compound 14c (1.40 g, 39%) as a white solid.

Step 4: Ethyl 5-(4-(chlorosulfonyl)naphthalen-1-yl)-4-(cyclohexylmethyl)thiazole-2-carboxylate (14d)

To an ice cold solution of compound 14c (1.40 g, 2.79 mmol) in AcOH (15 mL) was added a solution of $Cl_2$ in AcOH (~1M, 10 mL, 10 mmol) and the solution was allowed to warm to rt and stirred for overnight, quenched with water and extracted with $Et_2O$ twice. The combined organic layers were washed with water and brine, dried over $Na_2SO_4$, filtered, concentrated and purified by CC (PE/EA=10/1) to give compound 14d (550 mg, 41%) as a light yellow oil.

Step 5: Ethyl 5-(4-(N-(1-cyanocyclopropyl)sulfamoyl)naphthalen-1-yl)-4-(cyclohexylmethyl)thiazole-2-carboxylate (14e)

The solution of compound 14d (150 mg, 0.314 mmol) and DIEA (129 mg, 1.00 mmol) in dry DCM (2 mL) was added 1-aminocyclopropanecarbonitrile (33 mg, 0.40 mmol) at 0° C. and the solution was stirred at this temperature overnight, washed with water and brine, dried over $Na_2SO_4$, filtered, concentrated and purified by CC (PE/EA=6/1) to give compound 14e (101 mg, 61%) as a white solid.

Step 6: N-(1-Cyanocyclopropyl)-4-(4-(cyclohexylmethyl)-2-(7,7-dioxido-7-thia-2-azaspiro[3.5]nonane-2-carbonyl)thiazol-5-yl)naphthalene-1-sulfonamide (14)

Compound 14e was saponified and then coupled with the appropriate amine 7-thia-2-azaspiro[3.5]nonane 7,7-dioxide to give compound 14 (27%) as a white solid. $^1$H-NMR ($CDCl_3$, 300 MHz) δ: 0.68-0.74 (m, 2H), 0.98-1.21 (m, 3H), 1.25 (s, 2H), 1.38 (s, 2H), 1.48-1.56 (m, 6H), 2.34-2.36 (m, 2H), 2.46 (s, 4H), 3.08 (br s, 4H), 4.06 (s, 2H), 4.55 (s, 2H), 5.65 (s, 1H), 7.60 (t, J=7.8 Hz, 2H), 7.76 (t, J=8.4 Hz, 2H), 8.45 (d, J=7.8 Hz, 1H), 8.68 (d, J=8.4 Hz, 1H). MS 653.2 $(M+1)^+$.

Example 14/1 to 14/7

The following Examples were prepared similar as in Example 14:

| # | Structure | Analytical data |
|---|---|---|
| 14/1 | 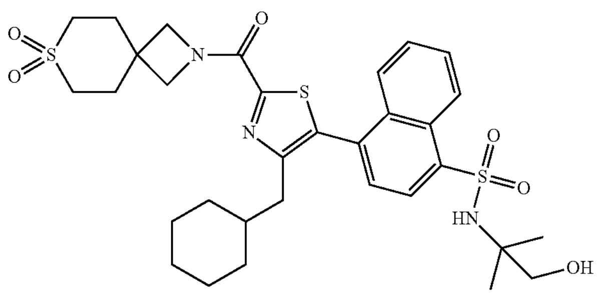 [SMILES: CC(C)(CO)NS(=O)(=O)c1ccc(-c2sc(C(=O)N3CC4(CCS(=O)(=O)CC4)C3)nc2CC2CCCCC2)c2ccccc12] | $^1$H-NMR ($CDCl_3$, 300 MHz) δ: 0.59-0.74 (m, 2H), 0.97-1.07 (m, 3H), 1.20 (s, 6H), 1.38 (s, 2H), 1.53-1.68 (m, 6H), 2.32-2.36 (m, 2H), 2.46-2.47 (m, 4H), 3.07-3.09 (m, 4H), 3.47 (s, 2H), 4.06 (s, 2H), 4.55 (s, 2H), 5.05 (s, 1H), 7.51 (d, J = 7.5 Hz, 1H), 7.55-7.61 (m, 1H), 7.70-7.74 (m, 2H), 8.35 (d, J = 7.5 Hz, 1H), 8.71 (d, J = 5.7 Hz, 1H). MS 660.2 $(M + 1)^+$ |
| 14/2 | 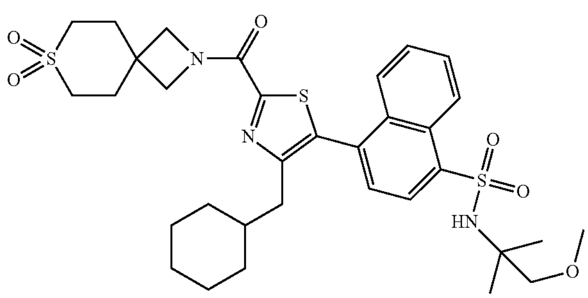 [SMILES: COCC(C)(C)NS(=O)(=O)c1ccc(-c2sc(C(=O)N3CC4(CCS(=O)(=O)CC4)C3)nc2CC2CCCCC2)c2ccccc12] | $^1$H-NMR ($CDCl_3$, 300 MHz) δ: 0.68-0.71 (m, 2H), 1.03-1.10 (m, 3H), 1.18 (s, 6H), 1.26 (s, 2H), 1.51-1.52 (m, 3H), 1.55-1.58 (m, 1H), 2.33-2.36 (m, 2H), 2.44-2.48 (m, 4H), 3.05 (s, 2H), 3.06-3.10 (m, 4H), 3.15 (s, 3H), 4.05 (s, 2H), 4.55 (s, 2H), 5.23 (s, 1H), 7.49 (d, J = 5.7 Hz, 1H), 7.51-7.56 (m, 1H), 7.68-7.72 (m, 2H), 8.34 (d, J = 7.8 Hz, 1H), 8.69 (d, J = 5.7 Hz, 1H). MS 674.2 $(M + 1)^+$ |
| 14/3 | 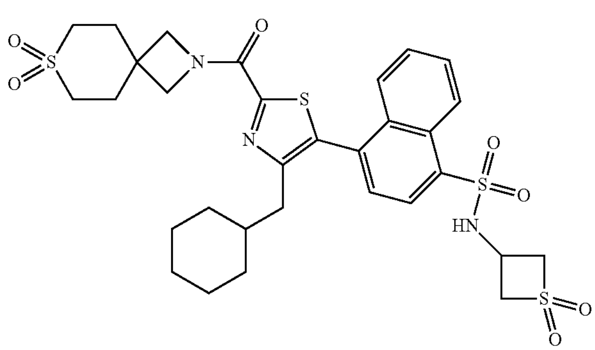 [SMILES: O=C(c1nc(CC2CCCCC2)c(-c2ccc(S(=O)(=O)NC3CS(=O)(=O)C3)c3ccccc23)s1)N1CC2(CCS(=O)(=O)CC2)C1] | $^1$H-NMR ($CDCl_3$, 300 MHz) δ: 0.68-0.71 (m, 2H), 1.03-1.10 (m, 3H), 1.13 (s, 2H), 1.51-1.52 (m, 3H), 1.58-1.71 (m, 1H), 2.33-2.36 (m, 2H), 2.45-2.49 (m, 4H), 3.07-3.11 (m, 2H), 3.84-3.89 (m, 2H), 4.07 (s, 2H), 4.22-4.36 (m, 3H), 4.55 (s, 2H), 5.68-5.72 (m, 1H), 7.53 (d, J = 7.5 Hz, 1H), 7.59-7.64 (m, 1H), 7.73-7.77 (m, 2H), 8.31 (d, J = 7.5 Hz, 1H), 8.67 (d, J = 8.4 Hz, 1H). MS 692.2 $(M + 1)^+$ |

| # | Structure | Analytical data |
|---|---|---|
| 14/4 | 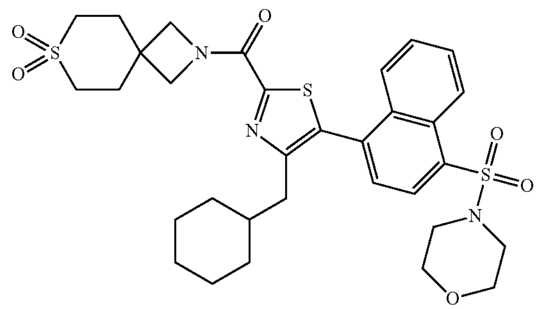 [SMILES: O=C(c1nc(CC2CCCCC2)c(-c2ccc(S(=O)(=O)N3CCOCC3)c3ccccc23)s1)N1CC2(CCS(=O)(=O)CC2)C1] | $^1$H-NMR (CDCl$_3$, 300 MHz) δ: 0.67-0.72 (m, 2H), 1.05-1.08 (m, 3H), 1.16-1.25 (m, 2H), 1.57-1.69 (m, 4H), 2.35-2.37 (m, 2H), 2.45-2.49 (m, 4H), 3.07-3.10 (m, 4H), 3.23-3.26 (m, 4H), 3.72-3.75 (m, 4H), 4.06 (s, 2H), 4.55 (s, 2H), 7.42 (d, J = 7.5 Hz, 1H), 7.56-7.62 (m, 1H), 7.68-7.72 (m, 2H), 8.24 (d, J = 7.5 Hz, 1H), 8.85 (d, J = 7.8 Hz, 1H). MS 658.2 (M + 1)$^+$ |
| 14/5 | 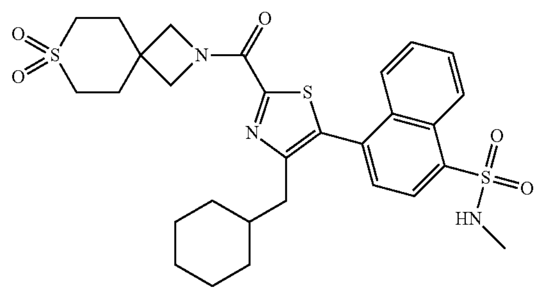 [SMILES: CNS(=O)(=O)c1ccc(-c2sc(C(=O)N3CC4(CCS(=O)(=O)CC4)C3)nc2CC2CCCCC2)c2ccccc12] | $^1$H-NMR (CDCl$_3$, 300 MHz) δ: 0.67-0.72 (m, 2H), 1.05-1.08 (m, 3H), 1.16-1.25 (m, 2H), 1.51-1.60 (m, 4H), 2.35-2.37 (m, 2H), 2.46-2.47 (m, 4H), 2.68-2.70 (m, 3H), 3.06-3.09 (m, 4H), 4.06 (s, 2H), 4.55 (s, 2H), 4.65-4.68 (m, 1H), 7.50-7.58 (m, 2H), 7.69-7.73 (m, 2H), 8.29 (d, J = 7.2 Hz, 1H), 8.75 (d, J = 8.7 Hz, 1H). MS 602.2 (M + 1)$^+$ |
| 14/6 | 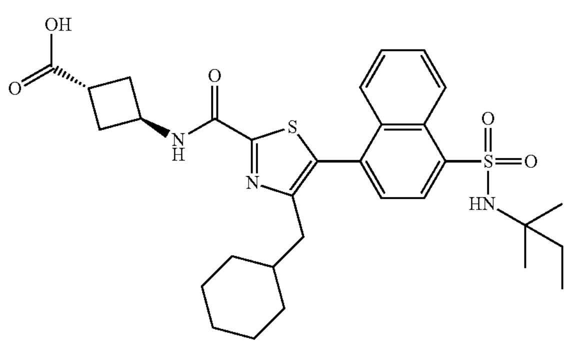 [SMILES: CCC(C)(C)NS(=O)(=O)c1ccc(-c2sc(C(=O)N[C@H]3C[C@H](C(=O)O)C3)nc2CC2CCCCC2)c2ccccc12] | $^1$H-NMR (CDCl$_3$, 300 MHz) δ: 0.57-0.69 (m, 2H), 0.76 (t, J = 7.2 Hz, 3H), 0.95-1.09 (m, 3H), 1.15 (s, 6H), 1.47-1.73 (m, 8H), 2.29-2.38 (m, 2H), 2.50-2.61 (m, 2H), 2.82-2.90 (m, 2H), 3.18-3.28 (m, 1H), 4.67 (s, 1H), 4.82-4.90 (m, 1H), 7.51 (d, J = 7.5 Hz, 1H), 7.55-7.60 (m, 2H), 7.69-7.74 (m, 2H), 8.35 (d, J = 7.8 Hz, 1H), 8.69 (d, J = 9.0 Hz, 1H). MS 598.3 (M + 1)$^+$ |
| 14/7 | 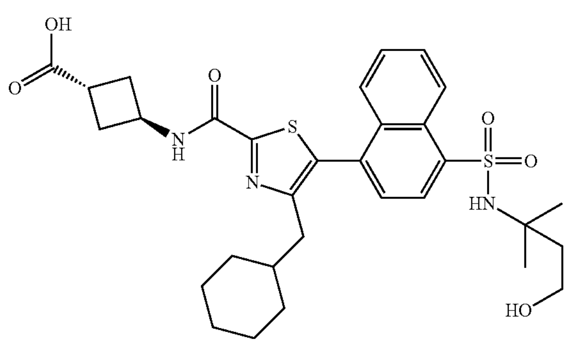 [SMILES: CC(C)(CCO)NS(=O)(=O)c1ccc(-c2sc(C(=O)N[C@H]3C[C@H](C(=O)O)C3)nc2CC2CCCCC2)c2ccccc12] | $^1$H-NMR (CDCl$_3$, 300 MHz) δ: 0.59-0.70 (m, 2H), 1.00-1.13 (m, 3H), 1.25 (s, 6H), 1.48-1.57 (m, 5H), 1.71-1.75 (m, 3H), 2.35 (br s, 2H), 2.50-2.60 (m, 2H), 2.82-2.88 (m, 2H), 3.19-3.26 (m, 1H), 3.85 (t, J = 5.7 Hz, 1H), 7.68-7.73 (m, 2H), 8.35 (d, J = 7.5 Hz, 1H), 8.69 (d, J = 8.7 Hz, 1H). MS 614.3 (M + 1)$^+$ |

Example 15 and Example 16

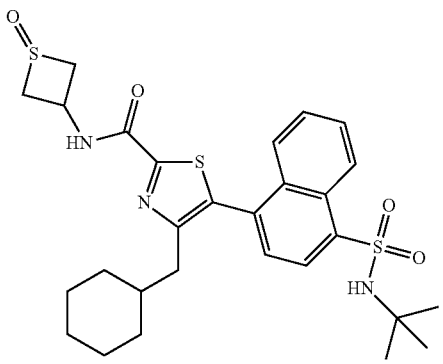

15

16

To a solution of compound 6/14 (250 mg, 0.45 mmol) in DCM (10 mL) was added m-CPBA (102 mg, 0.50 mmol) and the solution was stirred at rt for 30 min, quenched with aq. $Na_2SO_3$ and extracted with EA (3×). The combined organic layers were washed with water and brine, dried over $Na_2SO_4$, filtered, concentrated and purified by prep-HPLC to give compound 15 (35 mg, 14%) as a white solid and compound 16 (33 mg, 12%) as a white solid. For compound 15: $^1$H-NMR (CDCl$_3$, 300 MHz) δ: 0.64-0.68 (m, 2H), 0.92-1.18 (m, 2H), 1.25 (s, 9H), 1.48-1.53 (m, 7H), 2.36 (br s, 2H), 3.40 (td, J=3.0 Hz, 9.6 Hz, 2H), 4.23 (td, J=3.0 Hz, 7.8 Hz, 2H), 4.64 (s, 1H), 7.51 (d, J=7.8 Hz, 1H), 7.57-7.60 (m, 1H), 7.65-7.74 (m, 3H), 8.35 (d, J=7.5 Hz, 1H), 8.69 (d, J=8.4 Hz, 1H). MS 574.2 [M+1]$^+$. For compound 16: $^1$H-NMR (CDCl$_3$, 300 MHz) δ: 0.62-0.66 (m, 2H), 0.88-1.14 (m, 2H), 1.22 (s, 9H), 1.46-1.52 (m, 7H), 2.34 (br s, 2H), 4.22-4.28 (m, 2H), 4.61-4.70 (m, 4H), 4.91-4.93 (m, 1H), 7.51 (d, J=7.5 Hz, 1H), 7.58-7.60 (m, 1H), 7.68-7.74 (m, 2H), 7.83 (d, J=6.9 Hz, 1H), 8.36 (d, J=7.5 Hz, 1H), 8.69 (d, J=8.4 Hz, 1H). MS 590.2 [M+1]$^+$.

Example 15/1 to 15/9

The following Examples were prepared similar as in Example 15:

| # | Structure | Analytical data |
|---|---|---|
| 15/1 | 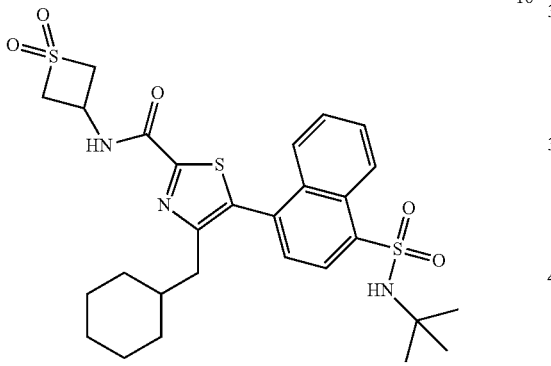<br>Isomer 1 | $^1$H-NMR (CDCl$_3$, 300 MHz) δ: 0.82-0.86 (m, 2H), 1.12-1.20 (m, 3H), 1.27 (s, 10H), 1.58-1.67 (m, 5H), 1.70 (s, 6H), 1.73-1.77 (m, 1H), 2.63 (m, 1H), 5.33-5.35 (m, 1H), 6.25-6.26 (m, 1H), 7.36-7.39 (m, 2H), 7.57 (d, J = 6.6 Hz, 1H), 8.25 (d, J = 9.0 Hz, 1H). MS 582.2 (M + 1)$^+$ |

| # | Structure | Analytical data |
|---|---|---|
| 15/2 | 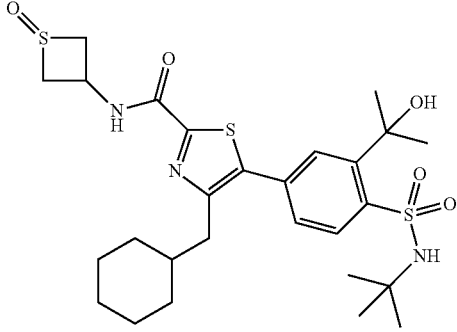 Isomer 2 | $^1$H-NMR (CDCl$_3$, 300 MHz) δ: 0.85-0.89 (m, 2H), 1.16-1.25 (m, 3H), 1.28 (s, 9H), 1.58-1.64 (m, 5H), 1.70 (s, 6H), 1.75-1.81 (m, 1H), 2.65 (d, J = 7.2 Hz, 2H), 3.33-3.42 (m, 2H), 4.18-4.25 (m, 2H), 4.38-4.40 (m, 1H), 4.61-4.64 (m, 1H), 6.25-6.26 (m, 1H), 7.36-7.39 (m, 2H), 7.59 (d, J = 8.1 Hz, 1H), 8.23-8.26 (m, 1H). MS 582.2 (M + 1)$^+$ |
| 15/3 | 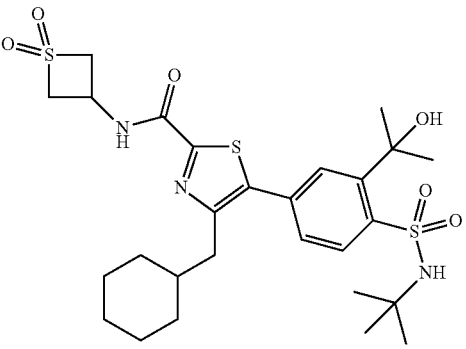 [SMILES: CC(C)(C)NS(=O)(=O)c1ccc(-c2sc(C(=O)NC3CS(=O)(=O)C3)nc2CC2CCCCC2)cc1C(C)(C)O] | $^1$H-NMR (CDCl$_3$, 300 MHz) δ: 0.84-0.87 (m, 2H), 1.14-1.25 (m, 3H), 1.27 (s, 12H), 1.59-1.64 (m, 5H), 1.70 (s, 6H), 1.74-1.80 (m, 1H), 2.65 (d, J = 7.2 Hz, 2H), 4.19-4.25 (m, 2H), 4.60-4.67 (m, 1H), 4.88-4.90 (m, 1H), 7.36-7.39 (m, 1H), 7.78 (d, J = 7.2 Hz, 1H), 8.25 (d, J = 9.0 Hz, 1H). MS 598.2 (M + 1)$^+$ |
| 15/4 | 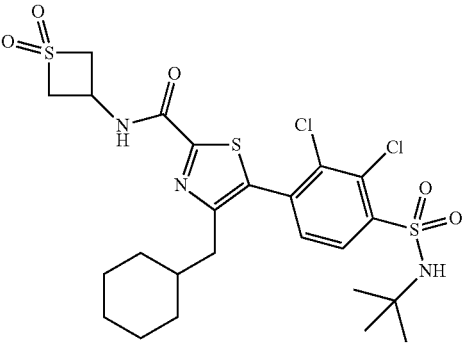 [SMILES: CC(C)(C)NS(=O)(=O)c1ccc(-c2sc(C(=O)NC3CS(=O)(=O)C3)nc2CC2CCCCC2)c(Cl)c1Cl] | $^1$H-NMR (300 MHz, CDCl$_3$) δ: 0.65-0.83 (m, 2H), 1.04-1.25 (m, 3H), 1.28 (s, 9H), 1.53-1.55 (m, 4H), 1.71-1.77 (m, 1H), 2.42 (d, J = 7.2 Hz, 2H), 4.19-4.25 (m, 2H), 4.59-4.69 (m, 2H), 4.87-4.91 (m, 1H), 5.07 (s, 1H), 7.38 (d, J = 8.1 Hz, 1H), 7.77 (d, J = 9.3 Hz, 1H), 8.14 (d, J = 8.1 Hz, 1H). MS 608.1 (M + 1)$^+$ |
| 15/5 | 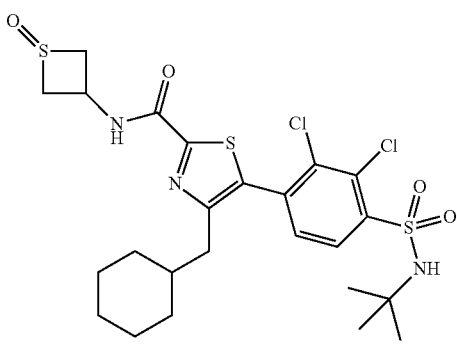 [SMILES: CC(C)(C)NS(=O)(=O)c1ccc(-c2sc(C(=O)NC3CS(=O)C3)nc2CC2CCCCC2)c(Cl)c1Cl] | $^1$H-NMR (300 MHz, CDCl$_3$) δ: 0.76-0.83 (m, 2H), 1.06-1.26 (m, 3H), 1.28 (s, 9H), 1.54-1.63 (m, 4H), 1.71-1.76 (m, 1H), 2.23-2.27 (m, 2H), 2.42 (d, J = 7.5 Hz, 2H), 3.40-3.48 (m, 2H), 4.19-4.25 (m, 2H), 4.63-4.66 (m, 1H), 5.11 (s, 1H), 7.37 (d, J = 8.4 Hz, 1H), 7.68 (d, J = 7.8 Hz, 1H), 8.13 (d, J = 8.4 Hz, 1H). MS 592.1 (M + 1)$^+$ |

| # | Structure | Analytical data |
|---|---|---|
| 15/6 | 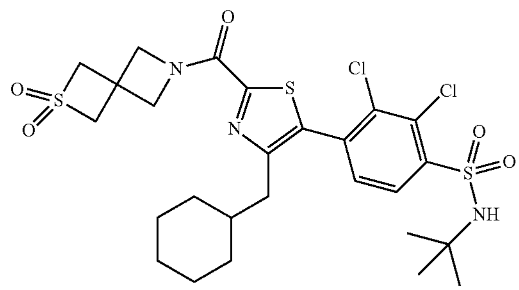 [SMILES: CC(C)(C)NS(=O)(=O)c1ccc(-c2sc(C(=O)N3CC4(C3)CS(=O)(=O)C4)nc2CC2CCCCC2)c(Cl)c1Cl] | ¹H-NMR (300 MHz, CDCl₃) δ: 0.77-0.83 (m, 2H), 1.10-1.20 (m, 3H), 1.28 (s, 9H), 1.53-1.77 (m, 5H), 2.40 (d, J = 6.9 Hz, 2H), 4.43 (s, 4H), 4.48 (s, 2H), 4.99 (s, 2H), 5.08 (s, 1H), 7.37 (d, J = 6.3 Hz, 1H), 8.12 (d, J = 6.0 Hz, 1H). MS 634.1 (M + 1)⁺ |
| 15/7 | 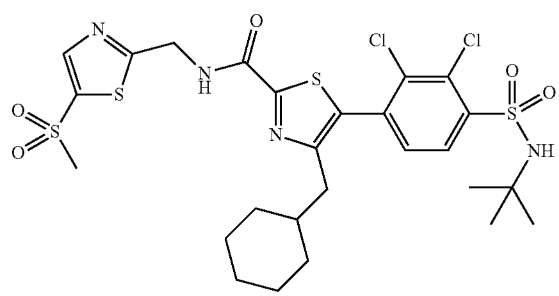 [SMILES: CC(C)(C)NS(=O)(=O)c1ccc(-c2sc(C(=O)NCc3ncc(S(C)(=O)=O)s3)nc2CC2CCCCC2)c(Cl)c1Cl] | ¹H-NMR (300 MHz, CDCl₃) δ: 0.75-0.79 (m, 2H), 1.15-1.19 (m, 3H), 1.28 (s, 9H), 1.52-1.63 (m, 6H), 2.42 (d, J = 6.9 Hz, 2H), 3.22 (s, 3H), 5.00 (d, J = 6.6 Hz, 2H), 5.07 (s, 1H), 7.39 (d, J = 8.4 Hz, 1H), 8.00-8.03 (m, 1H), 8.14 (d, J = 8.4 Hz, 1H), 8.25 (s, 1H). MS 679.1 [M + 1]⁺ |
| 15/8 | 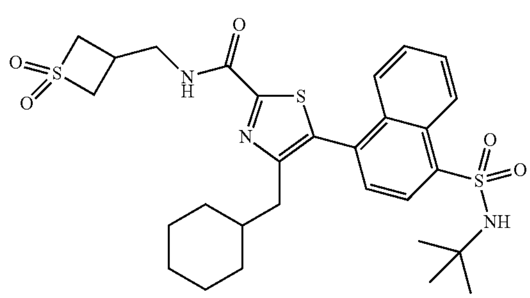 [SMILES: CC(C)(C)NS(=O)(=O)c1ccc(-c2sc(C(=O)NCC3CS(=O)(=O)C3)nc2CC2CCCCC2)c2ccccc12] | ¹H-NMR (300 MHz, CDCl₃) δ: 0.63-0.71 (m, 2H), 1.00-1.13 (m, 3H), 1.23 (s, 9H), 1.48-1.58 (m, 5H), 2.34 (br s, 1H), 3.02-3.07 (m, 1H), 3.80 (t, J = 6.6 Hz, 2H), 3.98-4.05 (m, 2H), 4.24-4.32 (m, 2H), 4.63 (s, 1H), 7.51 (d, J = 7.8 Hz, 1H), 7.58-7.63 (m, 2H), 7.70-7.73 (m, 2H), 8.36 (d, J = 7.5 Hz, 1H), 8.69 (d, J = 8.1 Hz, 1H). MS 604.2 [M + 1]⁺ |
| 15/9 | 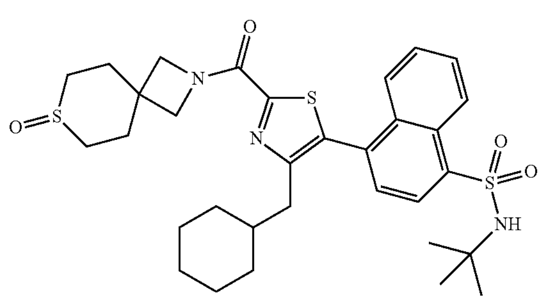 [SMILES: CC(C)(C)NS(=O)(=O)c1ccc(-c2sc(C(=O)N3CC4(CCS(=O)CC4)C3)nc2CC2CCCCC2)c2ccccc12] | ¹H-NMR (400 MHz, CDCl₃) δ: 8.68 (d, 1H, J = 8.8 Hz), 8.34 (d, 1H, J = 7.6 Hz), 7.73-7.69 (m, 2H), 7.58-7.49 (m, 2H), 4.63 (s, 1H), 4.51 (s, 2H), 4.02-4.01 (m, 2H), 3.06-3.03 (m, 2H), 2.83-2.73 (m, 2H), 2.65-2.59 (m, 2H), 2.38-2.35 (m, 2H), 2.08-2.04 (m, 2H), 1.65-1.57 (m, 6H), 1.22 (s, 9H), 1.19-1.03 (m, 3H), 0.74-0.65 (m, 2H). MS 628.2 (M + 1)⁺ |

Example 17

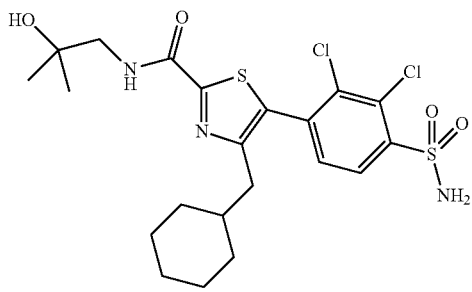

4-(Cyclohexylmethyl)-5-(2,3-dichloro-4-sulfamoyl-phenyl)-N-(2-hydroxy-2-methylpropyl)thiazole-2-carboxamide (17)

A solution of compound 6/29 (260 mg, 0.45 mmol) in TFA (2 mL) was stirred for 2 h at 55° C., concentrated, diluted with EA, washed with brine, dried over $Na_2SO_4$, filtered, concentrated and purified by prep-HPLC to give compound 17 (90 mg, 39%) as a white solid. $^1$H-NMR (300 MHz, $CDCl_3$) δ: 0.71-0.83 (m, 2H), 1.04-1.30 (m, 3H), 1.33 (s, 6H), 1.55-1.80 (m, 8H), 2.00 (s, 1H), 2.41 (d, J=6.9 Hz, 2H), 3.49 (d, J=6.9 Hz, 2H), 5.38 (s, 2H), 7.39 (d, J=8.4 Hz, 1H), 7.65 (t, J=6.3 Hz, 1H), 8.11 (d, J=8.1 Hz, 1H). MS 520.1 $(M+1)^+$.

Example 17/1 to 17/2

The following Examples were prepared similar as in Example 17:

| # | Structure | Analytical data |
|---|-----------|-----------------|
| 17/1 | 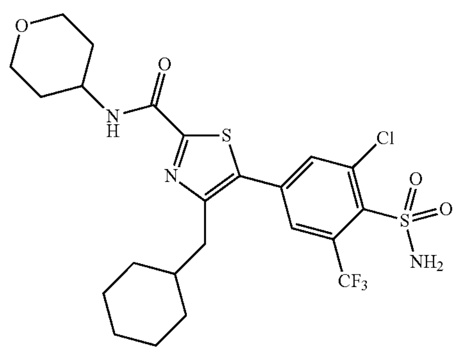 [SMILES: NS(=O)(=O)c1c(Cl)cc(-c2sc(C(=O)NC3CCOCC3)nc2CC2CCCCC2)cc1C(F)(F)F] | $^1$H-NMR (300 MHz, $CDCl_3$) δ: 0.86-0.97 (m, 2H), 1.13-1.30 (m, 3H), 1.57-1.82 (m, 7H), 1.84-1.87 (m, 1H), 2.00-2.06 (m, 2H), 2.64 (d, J = 7.2 Hz, 2H), 3.51-3.59 (m, 2H), 4.01-4.06 (m, 2H), 4.13-4.22 (m, 1H), 5.51-5.53 (m, 2H), 7.10-7.13 (m, 1H), 7.80 (s, 1H), 7.87 (s, 1H). MS 566.1 $(M + 1)^+$ |
| 17/2 | 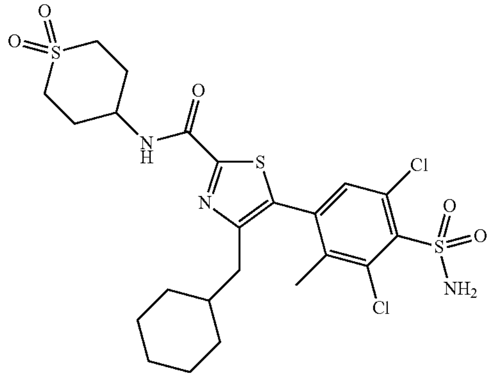 [SMILES: Cc1c(-c2sc(C(=O)NC3CCS(=O)(=O)CC3)nc2CC2CCCCC2)cc(Cl)c(S(N)(=O)=O)c1Cl] | $^1$H-NMR ($CDCl_3$, 300 MHz) δ: 0.74-0.86 (m, 2H), 1.13-1.25 (m, 3H), 1.53-1.74 (m, 6H), 2.26 (s, 3H), 2.35-2.47 (m, 6H), 3.15-3.17 (m, 4H), 4.24-4.28 (m, 1H), 5.58 (s, 2H), 7.22 (d, J = 11.2 Hz, 1H), 7.36 (s, 1H). MS 594.1 $(M + 1)^+$ |

Example 18

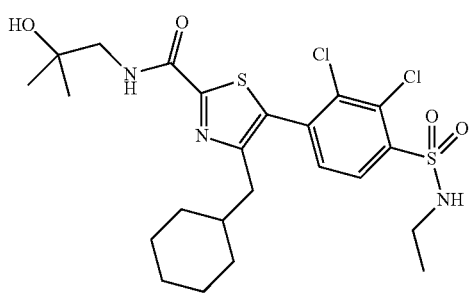

4-(Cyclohexylmethyl)-5-(2,3-dichloro-4-(N-ethyl-sulfamoyl)phenyl)-N-(2-hydroxy-2-methylpropyl)thiazole-2-carboxamide (18)

The solution of compound 17 (40 mg, 0.07 mmol) and aq. $CH_3CHO$ (0.5 mL) in MeOH (5 mL) was stirred for 10 min at rt. Then $NaBH_3CN$ (50 mg, 0.7 mmol) was added and the solution was stirred for 3 d at rt, diluted with DCM, washed with brine, dried over $Na_2SO_4$, filtered, concentrated and purified by prep-HPLC to give compound 18 (26 mg, 62%) as a white solid. $^1$H-NMR (300 MHz, $CD_3OD$) δ: 0.74-0.84 (m, 2H), 1.06-1.20 (m, 5H), 1.26 (s, 6H), 1.56-1.60 (m, 4H), 1.77 (br s, 1H), 2.49 (d, J=6.9 Hz, 2H), 3.00 (q, J=6.9 Hz, 2H), 3.31 (s, 1H), 3.42 (s, 2H), 7.57 (t, J=8.1 Hz, 1H), 8.11 (d, J=7.8 Hz, 1H). MS 548.2 $(M+1)^+$.

Example 19

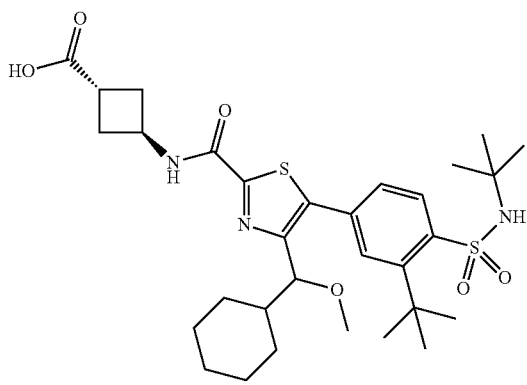

Step 1: 2-Cyclohexyl-2-methoxyacetic acid (19a)

To a solution of NaH (21.4 g, 357 mmol) in dry THF (360 mL) was added cyclohexanecarbaldehyde (20 g, 179 mmol) and $CHCl_3$ (42.6 g, 536 mmol) at 0° C. under $N_2$ and the solution was stirred at this temperature for 3 h. Then a solution of NaOH (50 g, 1.25 mol) in MeOH (214 mL) was added and the solution was stirred at 65° C. for 3 h, quenched with water and extracted with $Et_2O$. The aq. layer was adjusted pH to 1 with conc. HCl and extracted with $Et_2O$ twice. The combined organic layers were washed with water and brine, dried over $Na_2SO_4$, filtered and concentrated to give crude compound 19a (12.9 g, 42%) as a brown oil.

Step 2: 2-Cyclohexyl-N,2-dimethoxy-N-methylacetamide (19b)

A solution of crude compound 19a (12.9 g, 75.0 mmol) in dry DMF (300 mL) was cooled with an ice bath and HATU (28.5 g, 75.0 mmol) was added. After being stirred at rt for 30 min, DIEA (29.0 g, 225 mmol) and N,O-dimethylhydroxylamine hydrochloride (8.80 g, 90 mmol) were added and the mixture was stirred at rt for 2 h, quenched with water and extracted with EA twice. The combined organic layers were washed with water (3×) and brine, dried over $Na_2SO_4$, filtered, concentrated and purified by CCl (PE/EA=9/1) to give compound 19b (8.4 g, 52%) as a pale yellow liquid.

Step 3: 1-Cyclohexyl-1-methoxypropan-2-one (19c)

To a solution of compound 19b (8.40 g, 39.1 mmol) in dry THF (100 mL) was added MeMgBr (3M in $Et_2O$, 30 mL, 90 mol) under ice cooling and the solution was stirred at rt for 3 h, quenched carefully with saturated aq. $NH_4Cl$. The organic phase was separated and concentrated, diluted with EA, washed with water and brine, dried over $Na_2SO_4$, filtered, concentrated and purified by CC (PE/EA=40/1) to give compound 19c (6.1 g, 92%) as a pale yellow oil.

Step 4: 3-Bromo-1-cyclohexyl-1-methoxypropan-2-one (19d)

To an ice-cooled solution of compound 19c (6.1 g, 35.9 mmol) in MeOH (60 mL) was added $Br_2$ (5.74 g, 35.9 mmol) in a single portion and the reaction temperature was kept below 15° C. until the red color of the solution turned colorless. $H_2O$ was added and the solution was extracted with in $Et_2O$ (3×). The combined organic layers were washed with 10% aq. $K_2CO_3$ (3×), dried over $Na_2SO_4$, filtered and concentrated to give compound 19d (8.5 g, 95%) as a yellowish liquid.

Step 5: Ethyl 4-(cyclohexyl(methoxy)methyl)thiazole-2-carboxylate (19e)

A solution of compound 19d (8.5 g, 34.1 mmol) and ethylthioxamate (5.05 g, 38.0 mmol) in EtOH (100 mL) was heated at 80° C. for 6 h and then cooled to 0° C. The resulting solution was diluted with water and EA and then neutralized to pH=7 using $NH_4OH$. The aq. layer was extracted with EA (3×). The combined organic layers were dried over $Na_2SO_4$, filtered, concentrated and purified by CC (PE/EA=40/1) to give compound 19e (5.4 g, 56%) as a pale yellow oil.

Step 6: Ethyl 5-(3-(tert-butyl)-4-(N-(tert-butyl)sulfamoyl)phenyl)-4-(cyclohexyl(methoxy)methyl)thiazole-2-carboxylate (19f)

A solution of compound 19e (2.2 g, 7.78 mmol), 4-bromo-N,2-di-tert-butylbenzenesulfonamide (3.24 g, 9.32 mmol), $Pd(OAc)_2$ (200 mg) and $PPh_3$ (2.24 g, 8.54 mmol) in DMF (80 mL) was bubbled with $N_2$ for 5 min and then stirred at 170° C. for 3 h and then 130° C. overnight, cooled, diluted with water and extracted with EA. The organic layer was washed with brine, dried over Na₂SO₄, filtered, concentrated and purified by CC (PE/EA=15/1) and then prep-HPLC to give compound 19f (280 mg, 6.5%) as a pale yellow solid.

Step 7: Potassium 5-(3-(tert-butyl)-4-(N-(tert-butyl)sulfamoyl)phenyl)-4-(cyclohexyl(methoxy)methyl)thiazole-2-carboxylate (19g)

The solution of compound 19f (280 mg, 0.51 mmol) and KOH (84 mg, 1.50 mmol) in MeOH (5 mL) was stirred at rt for 1 h and concentrated to give crude compound 19g (350 mg) as a white solid.

Step 8: trans-Methyl 3-(5-(3-(tert-butyl)-4-(N-(tert-butyl)sulfamoyl)phenyl)-4-(cyclohexyl(methoxy)methyl)thiazole-2-carboxamido)cyclobutanecarboxylate (19 h)

The solution of compound 19g (250 mg, 0.364 mmol), trans methyl 3-aminocyclo butanecarboxylate hydrochloride (93 mg, 0.56 mmol), DIEA (867 mg, 6.72 mmol) and HATU (213 mg, 0.56 mmol) in DMF (5 mL) was stirred overnight at rt, diluted with water and extracted with EA (3×). The combined organic layers were washed with water (3×) and brine consecutively, dried over Na₂SO₄, filtered, concentrated and purified by CC (PE/EA=6/1) to give compound 19h (91 mg, 39%) as a yellow solid.

Step 9: trans-3-(5-(3-(tert-Butyl)-4-(N-(tert-butyl)sulfamoyl)phenyl)-4-(cyclohexyl(methoxy)methyl)thiazole-2-carboxamido)cyclobutanecarboxylic acid (19)

To a solution of compound 19h (91 mg, 0.14 mmol) in a mixture of THF/MeOH/water (2 mL/2 mL/1 mL) was added LiOH.H₂O (11 mg, 0.26 mmol) and the solution was stirred at rt for 2 h, diluted with water and extracted with EA. The aq. layer was adjusted with 1N HCl to pH=2 and then extracted with DCM. The combined organic phase was washed with brine, dried over Na₂SO₄, filtered, concentrated and purified by prep-HPLC to give compound 19 (45 mg, 52%) as a white solid. $^1$H-NMR (400 MHz, CDCl₃) δ: 0.75-1.02 (m, 2H), 1.10-1.31 (m, 4H), 1.34 (s, 9H), 1.60-1.68 (m, 11H), 1.73-1.78 (m, 1H), 1.92-2.00 (m, 1H), 2.18 (d, J=12.8 Hz, 1H), 2.47-2.55 (m, 2H), 2.77-2.83 (m, 2H), 3.15 (s, 3H), 3.17-3.22 (m, 1H), 3.94 (d, J=9.2 Hz, 1H), 4.60 (s, 1H), 4.78-4.84 (m, 1H), 7.35 (dd, J=8.0 Hz, 2.0 Hz, 1H), 7.59 (d, J=7.6 Hz, 1H), 7.68 (d, J=2.0 Hz, 1H), 8.25 (d, J=8.0 Hz, 1H). MS 620.2 [M+1].

Example 19/1 to 19/14

The following Examples were prepared similar as in Example 19:

| # | Structure | Analytical data |
|---|---|---|
| 19/1 | 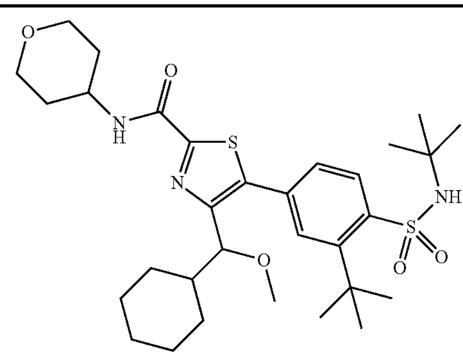 | $^1$H-NMR (400 MHz, CDCl₃) δ: 0.75-1.01 (m, 2H), 1.10-1.31 (m, 4H), 1.34 (s, 9H), 1.62 (s, 9H), 1.65-1.78 (m, 5H), 1.92-2.02 (m, 3H), 2.18 (d, J = 14.0 Hz, 1H), 3.14 (s, 3H), 3.53 (td, J = 11.6 Hz, 2.0 Hz, 2H), 3.93 (d, J = 9.2 Hz, 1H), 4.03 (d, J = 11.6 Hz, 2H), 4.08-4.20 (m, 1H), 7.24 (d, J = 8.4 Hz, 1H), 7.35 (dd, J = 8.4 Hz, 1.6 Hz, 1H), 7.69 (d, J = 1.6 Hz, 1H), 8.25 (d, J = 8.4 Hz, 1H). MS 606.3 [M + 1]⁺ |
| 19/2 | 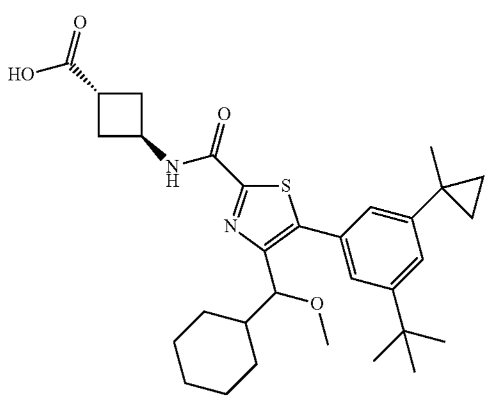 [SMILES: COC(c1nc(C(=O)N[C@H]2C[C@H](C(=O)O)C2)sc1-c1cc(C(C)(C)C)cc(C2(C)CC2)c1)C1CCCCC1] | $^1$H-NMR (300 MHz, CDCl₃) δ: 0.75-0.79 (m, 2H), 0.80-0.85 (m, 2H), 1.00-1.29 (m, 6H), 1.34 (s, 9H), 1.41 (s, 3H), 1.54-1.78 (m, 3H), 1.93-2.00 (m, 1H), 2.16-2.21 (m, 1H), 2.46-2.56 (m, 2H), 2.76-2.84 (m, 2H), 3.14 (s, 3H), 3.16-3.22 (m, 1H), 3.93 (d, J = 9.3 Hz, 1H), 4.77-4.84 (m, 1H), 7.05-7.06 (m, 1H), 7.18-7.19 (m, 1H), 7.32-7.33 (m, 1H), 7.57 (d, J = 8.1 Hz, 1H). MS 539.3 [M+ 1]⁺ |

| # | Structure | Analytical data |
|---|---|---|
| 19/3 | 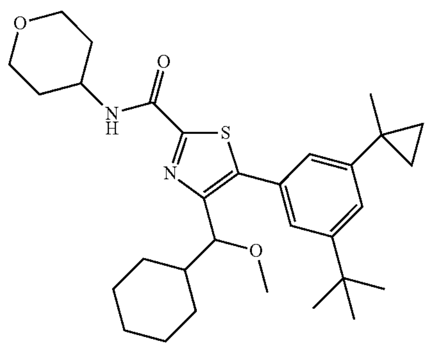 [SMILES: COC(c1nc(C(=O)NC2CCOCC2)sc1-c1cc(C(C)(C)C)cc(C2(C)CC2)c1)C1CCCCC1] | ¹H-NMR (300 MHz, CDCl₃) δ: 0.75-0.79 (m, 2H), 0.80-0.85 (m, 2H), 1.00-1.29 (m, 5H), 1.33 (s, 9H), 1.44 (s, 3H), 1.57 (s, 1H), 1.60-1.76 (m, 5H), 1.93-2.03 (m, 3H), 2.15-2.21 (m, 3H), 2.21 (d, J = 12.6 Hz, 1H), 3.12 (s, 3H), 3.48-3.57 (m, 2H), 3.91 (d, J = 9.0 Hz, 1H), 4.01-4.04 (m, 2H), 4.12-4.20 (m, 1H), 7.04-7.06 (m, 1H), 7.18-7.19 (m, 1H), 7.22-7.24 (m, 1H), 7.27-7.33 (m, 1H). MS 525.3 [M + 1]⁺ |
| 19/4 | 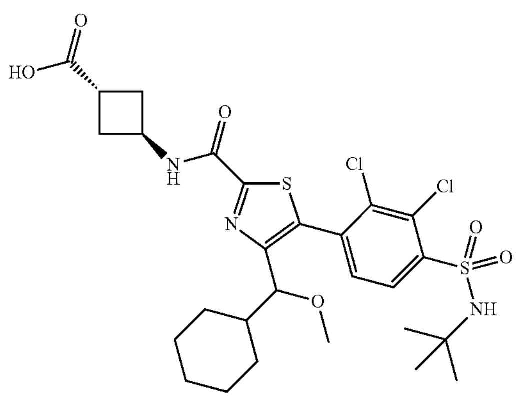 [SMILES: COC(c1nc(C(=O)N[C@H]2C[C@H](C(=O)O)C2)sc1-c1ccc(S(=O)(=O)NC(C)(C)C)c(Cl)c1Cl)C1CCCCC1] | ¹H-NMR (300 MHz, CDCl₃) δ: 0.75-0.78 (m, 2H), 0.91-0.96 (m, 3H), 1.29 (s, 9H), 1.62-1.91 (m, 5H), 2.13 (d, J = 9.9 Hz, 1H), 2.45-2.55 (m, 2H), 2.78-2.83 (m, 3H), 3.19 (s, 3H), 3.59 (d, J = 9.0 Hz, 1H), 4.79-4.82 (m, 1H), 5.08 (s, 1H), 7.39 (d, J = 8.1 Hz, 1H), 7.57 (d, J = 7.2 Hz, 1H), 8.15 (d, J = 8.1 Hz, 1H). MS 632.1 [M + 1]⁺ |
| 19/5 | 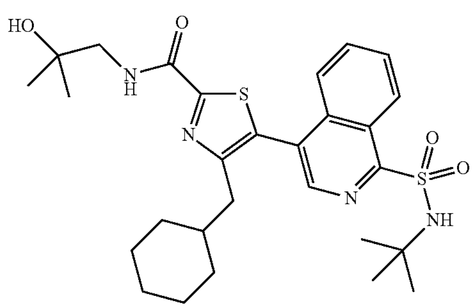 [SMILES: CC(C)(O)CNC(=O)c1nc(CC2CCCCC2)c(-c2cnc(S(=O)(=O)NC(C)(C)C)c3ccccc23)s1] | ¹H-NMR (300 MHz, CDCl₃) δ: 0.65-0.73 (m, 2H), 1.00-1.14 (m, 3H), 1.27 (s, 9H), 1.35 (s, 6H), 1.40 (s, 9H), 1.48-1.63 (m, 3H), 1.70-1.75 (m, 1H), 2.17 (s, 1H), 2.39 (d, J = 7.2 Hz, 2H), 3.53 (d, J = 6.6 Hz, 2H), 5.27 (s, 1H), 7.68-7.81 (m, 4H), 8.46 (s, 1H), 9.06-9.10 (m, 1H). MS 559.2 [M + 1]⁺ |
| 19/6 | 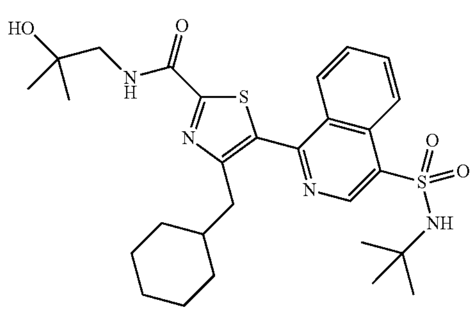 [SMILES: CC(C)(O)CNC(=O)c1nc(CC2CCCCC2)c(-c2ncc(S(=O)(=O)NC(C)(C)C)c3ccccc23)s1] | ¹H-NMR (300 MHz, CDCl₃) δ: 0.60-0.65 (m, 2H), 1.00-1.14 (m, 3H), 1.28 (s, 9H), 1.35 (s, 6H), 1.49-1.59 (m, 3H), 2.50 (d, J = 7.2 Hz, 2H), 3.53 (d, J = 6.3 Hz, 2H), 4.75 (s, 1H), 7.68-7.73 (m, 2H), 7.89-7.95 (m, 1H), 8.01 (d, J = 8.4 Hz, 1H), 8.66 (d, J = 8.4 Hz, 1H), 9.26 (s, 1H). MS 559.3 [M + 1]⁺ |

| # | Structure | Analytical data |
|---|---|---|
| 19/7 | 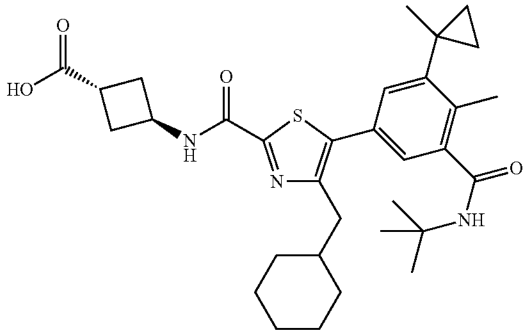 [SMILES: Cc1c(C(=O)NC(C)(C)C)cc(-c2sc(C(=O)N[C@H]3C[C@H](C(=O)O)C3)nc2CC2CCCCC2)cc1C1(C)CC1] | ¹H-NMR (400 MHz, CDCl₃): δ 7.47 (d, 1H, J = 8.0 Hz), 7.39 (d, 1H, J = 1.6 Hz), 7.17 (d, 1H, J = 1.6 Hz), 5.58 (s, 1H), 4.78-4.83 (m, 1H), 3.16-3.22 (m, 1H), 2.79-2.85 (m, 2H), 2.62 (d, 2H, J = 7.2 Hz), 2.47-2.53 (m, 5H), 1.66-1.82 (m, 6H), 1.48 (s, 9H), 1.32 (s, 3H), 1.11-1.27 (m, 3H), 0.86-0.90 (m, 2H), 0.78 (s, 4H). MS 566.3 (M + 1)⁺ |
| 19/8 | 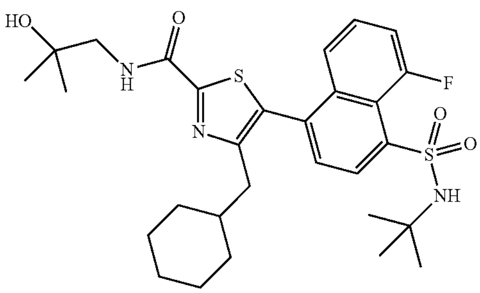 [SMILES: CC(C)(O)CNC(=O)c1nc(CC2CCCCC2)c(-c2ccc(S(=O)(=O)NC(C)(C)C)c3c(F)cccc23)s1] | ¹H-NMR (300 MHz, CDCl₃) δ: 0.46-0.53 (m, 2H), 0.85-0.96 (m, 3H), 1.24 (s, 9H), 1.27-1.33 (m, 9H), 1.47-1.74 (m, 6H), 2.26-2.36 (m, 3H), 3.52 (d, J = 6.3 Hz, 2H), 5.17 (d, J = 8.4 Hz, 1H), 7.39-7.59 (m, 4H), 7.71 (t, J = 6.3 Hz, 1H), 8.54 (d, J = 7.8 Hz, 1H). MS 576.2 [M + 1]⁺ |
| 19/9 | 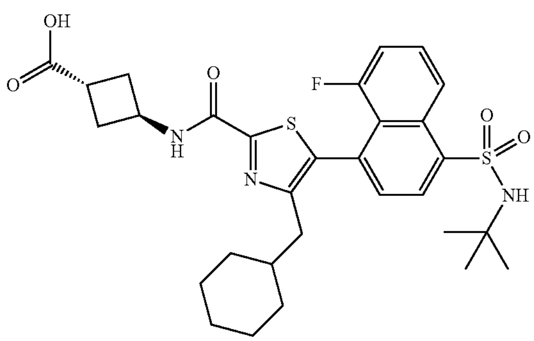 [SMILES: CC(C)(C)NS(=O)(=O)c1ccc(-c2sc(C(=O)N[C@H]3C[C@H](C(=O)O)C3)nc2CC2CCCCC2)c2c(F)cccc12] | ¹H-NMR (300 MHz, CDCl₃) δ: 0.62-0.71 (m, 2H), 0.90-1.19 (m, 3H), 1.22 (s, 9H), 1.34 (s, 6H), 1.53-1.54 (m, 4H), 1.61-1.70 (m, 1H), 2.16-2.27 (m, 2H), 2.41-2.47 (m, 1H), 3.51 (d, J = 6.6 Hz, 2H), 4.61 (s, 1H), 7.14-7.21 (m, 1H), 7.51-7.54 (m, 1H), 7.66-7.77 (m, 2H), 8.34-8.38 (m, 1H), 8.75-8.79 (m, 1H). MS 602.2 [M + 1]⁺ |
| 19/10 | 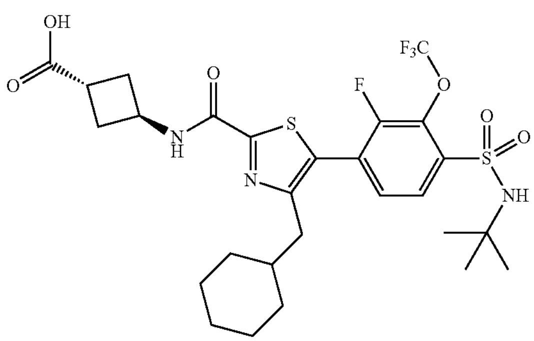 [SMILES: CC(C)(C)NS(=O)(=O)c1ccc(-c2sc(C(=O)N[C@H]3C[C@H](C(=O)O)C3)nc2CC2CCCCC2)c(F)c1OC(F)(F)F] | ¹H-NMR (400 MHz, CD₃OD) δ: 0.74-0.82 (m, 2H), 1.07-1.19 (m, 3H), 1.24 (s, 9H), 1.53-1.60 (m, 5H), 1.73-1.78 (m, 1H), 2.47-2.66 (m, 6H), 3.04-3.10 (m, 1H), 4.69-4.77 (m, 1H), 7.61 (dd, J = 8.0 Hz, 6.4 Hz, 1H), 7.93 (d, J = 8.0 Hz, 1H). MS 634.2 [M − 1]⁻ |

| # | Structure | Analytical data |
|---|---|---|
| 19/11 | 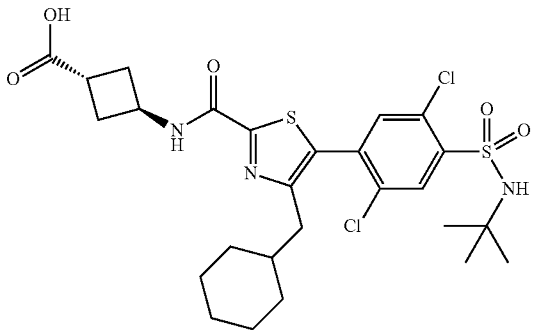 [SMILES: CC(C)(C)NS(=O)(=O)c1cc(Cl)c(-c2sc(C(=O)N[C@H]3C[C@H](C(=O)O)C3)nc2CC2CCCCC2)cc1Cl] | $^1$H-NMR (400 MHz, CD$_3$OD) δ: 0.78-0.87 (m, 2H), 1.10-1.26 (m, 3H), 1.32 (s, 9H), 1.59-1.62 (m, 5H), 1.77-1.81 (m, 1H), 2.51-2.59 (m, 4H), 2.2.63-2.69 (m, 2H), 3.08-3.13 (m, 1H), 4.73-4.77 (m, 1H), 7.75 (s, 1H), 8.24 (s, 1H). MS 600.2 [M − 1]$^-$ |
| 19/12 | 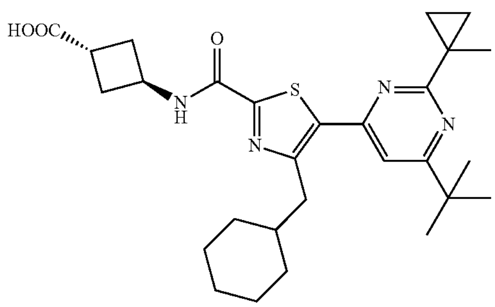 | $^1$H-NMR (400 MHz, CDCl$_3$) δ: 7.48 (d, 1H, J = 8.0 Hz), 7.24 (s, 1H), 4.82-4.80 (m, 1H), 3.19-3.18 (m, 1H), 3.07 (d, 2H, J = 7.2 Hz), 2.85-2.78 (m, 2H), 2.54-2.46 (m, 2H), 1.85-1.68 (m, 6H), 1.58 (s, 3H), 1.42-1.40 (m, 2H), 1.33 (s, 9H), 1.29-1.05 (m, 5H), 0.90-0.88 (m, 2H). MS 511.3 (M + 1)$^+$ |
| 19/13 | 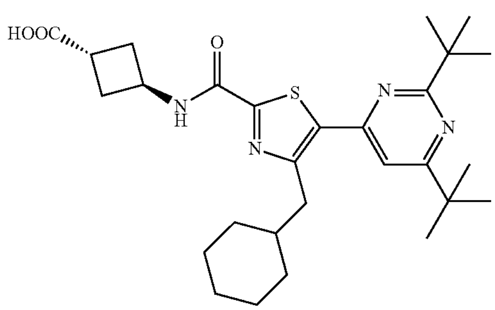 | $^1$H-NMR (400 MHz, CDCl$_3$) δ: 7.51 (d, 1H, J = 8.0 Hz), 7.29 (s, 1H), 4.85-4.79 (m, 1H), 3.22-3.17 (m, 1H), 3.11 (d, 2H, J = 7.2 Hz), 2.86-2.79 (m, 2H), 2.55-2.47 (m, 2H), 1.87-1.85 (m, 1H), 1.72-1.69 (m, 5H), 1.42 (s, 9H), 1.40 (s, 9H), 1.36-1.06 (m, 5H). MS 513.3 (M + 1)$^+$ |
| 19/14 | 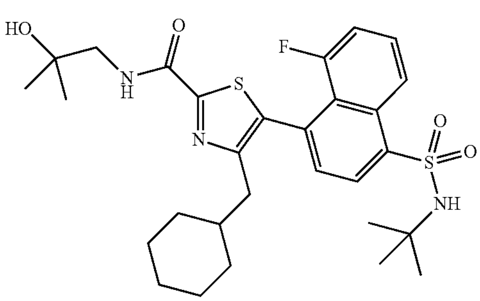 [SMILES: CC(C)(O)CNC(=O)c1nc(CC2CCCCC2)c(-c2ccc(S(=O)(=O)NC(C)(C)C)c3cccc(F)c23)s1] | $^1$H-NMR (300 MHz, CDCl$_3$) δ: 0.62-0.71 (m, 2H), 0.90-1.19 (m, 3H), 1.21 (s, 9H), 1.34 (s, 6H), 1.47-1.57 (m, 4H), 1.61-1.70 (m, 1H), 2.15-2.27 (m, 1H), 2.42-2.60 (m, 3H), 2.80-2.89 (m, 2H), 3.40-3.51 (m, 1H), 4.73 (s, 1H), 4.80-4.88 (m, 1H), 7.14-7.21 (m, 1H), 7.51-7.57 (m, 2H), 7.72-7.77 (m, 2H), 8.34-8.38 (m, 1H), 8.76-8.80 (m, 1H). MS 576.3 [M + 1]$^+$ |

Example 20 trans-3-(4-(Cyclohexylmethyl-5-(4-(N-(4-fluoro-2-methylbutan-2-yl)sulfamoyl)naphthalen-1-yl)thiazole-2-carboxamido)cyclobutanecarboxylic acid (20)

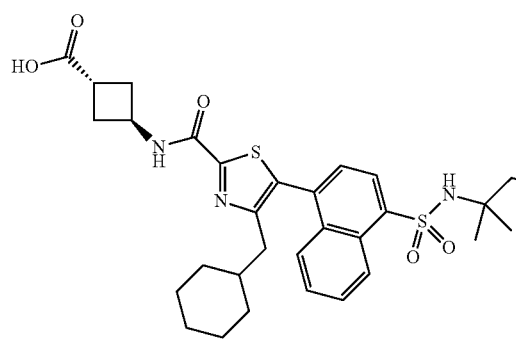

To a solution of compound 14/7 (200 mg, 0.33 mmol) in DCM (6 mL) was added DAST (161 mg, 1.00 mmol) at 0° C. and the solution was stirred at rt overnight, washed with water and extracted with CH$_2$Cl$_2$. The organic layer was dried with MgSO$_4$, filtered, concentrated and purified by CC (DCM/MeOH=10/1) to give compound 20 (170 mg, 84%) as a white solid. $^1$H-NMR (CDCl$_3$, 300 MHz) δ: 0.58-0.69 (m, 2H), 0.95-1.13 (m, 3H), 1.23-1.25 (m, 6H), 1.48-1.72 (m, 6H), 1.91-2.04 (m, 2H), 2.34 (br s, 2H), 2.50-2.60 (m, 2H), 2.82-2.89 (m, 2H), 3.19-3.25 (m, 1H), 4.45-6.64 (m, 2H), 4.82-4.90 (m, 1H), 5.07 (d, J=3.0 Hz, 1H), 7.50-7.60 (m, 3H), 7.70-7.74 (m, 2H), 8.33 (d, J=7.8 Hz, 1H), 8.66 (d, J=9.3 Hz, 1H). MS 616.3 (M+1).

Example 21

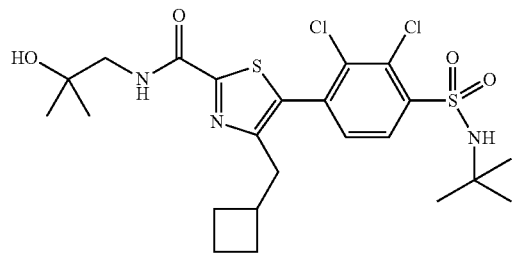

5-(4-(N-(tert-butyl)sulfamoyl)-2,3-dichlorophenyl)-4-(cyclobutylmethyl)-N-(2-hydroxy-2-methylpropyl)thiazole-2-carboxamide (21)

A solution of 4-(cyclobutylmethyl)-N-(2-hydroxy-2-methylpropyl)thiazole-2-carboxamide (27 mg, 0.1 mmol, prepared using similar procedures as described above), 4-bromo-N-(tert-butyl)-2,3-dichlorobenzenesulfonamide (36 mg, 0.1 mmol), K$_2$CO$_3$ (21 mg, 0.15 mmol), Pd(OAc)$_2$ (1 mg, 2 μmol), PCy$_3$.HBF$_4$ (2 mg, 4 μmol) and PivOH (4 mg, 0.03 mmol) in a solution of DMA (2 mL) was heated under argon at 100° C. overnight, cooled to rt, partitioned between EA and water, and the layers were separated. The organic phase was washed with water and brine, dried over Na$_2$SO$_4$, filtered, concentrated and purified by CC (PE/EA=10/1 to 5/1) to give compound 21 as a white solid (33 mg, 64%). $^1$H-NMR (400 MHz, CDCl$_3$) δ: 8.13 (d, 1H, J=8.4 Hz), 7.65 (s, 1H), 7.39 (d, 1H, J=8.0 Hz), 5.06 (s, 1H), 3.50 (d, 2H, J=6.4 Hz), 2.63 (s, 3H), 1.98-1.94 (m, 2H), 1.81-1.71 (m, 2H), 1.58-1.53 (m, 2H), 1.31 (s, 6H), 1.30 (s, 9H). MS 548.2 (M+1)$^+$.

Example 21/1 to 21/25

The following examples were prepared according to Example 21.

| # | Structure | Analytical data |
|---|---|---|
| 21/1 | 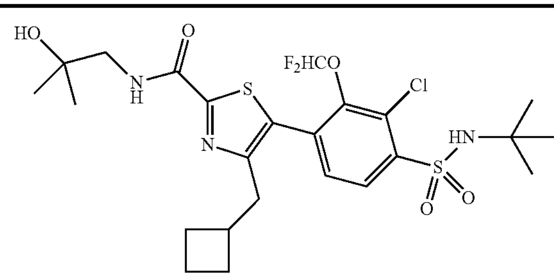 | $^1$H-NMR (400 MHz, CDCl$_3$) δ: 8.13 (d, 1H, J = 8.4 Hz), 7.62 (t, 1H, J = 6.4 Hz), 7.43 (d, 1H, J = 8.4 Hz), 6.50-6.13 (m, 1H), 5.02 (s, 1H), 3.49 (d, 2H, J = 6.0 Hz), 2.73-2.65 (m, 3H), 2.02-1.95 (m, 2H), 1.85-1.52 (m, 4H), 1.33 (s, 6H), 1.27 (s, 9H). MS 579.6 (M + 1)$^+$ |
| 21/2 | 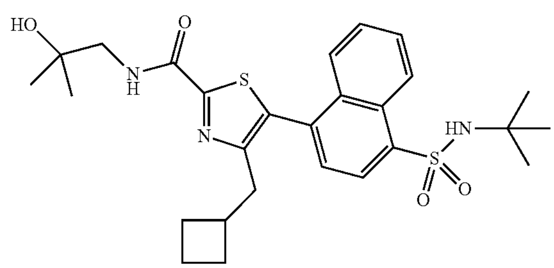 [SMILES: CC(C)(O)CNC(=O)c1nc(CC2CCC2)c(-c2ccc(S(=O)(=O)NC(C)(C)C)c3ccccc23)s1] | $^1$H-NMR (400 MHz, CDCl$_3$) δ: 8.69 (d, 1H, J = 8.8 Hz), 8.35 (d, 1H, J = 7.6 Hz), 7.72 (t, 3H, J = 8.0 Hz), 7.59 (t, 1H, J = 7.6 Hz), 7.52 (d, 1H, J = 7.6 Hz), 4.66 (s, 1H), 3.53 (d, 2H, J = 6.4 Hz), 2.61-2.56 (m, 3H), 1.90-1.42 (m, 6H), 1.36 (s, 6H), 1.23 (s, 9H). MS 529.7 (M + 1)$^+$ |

| # | Structure | Analytical data |
|---|---|---|
| 21/3 | 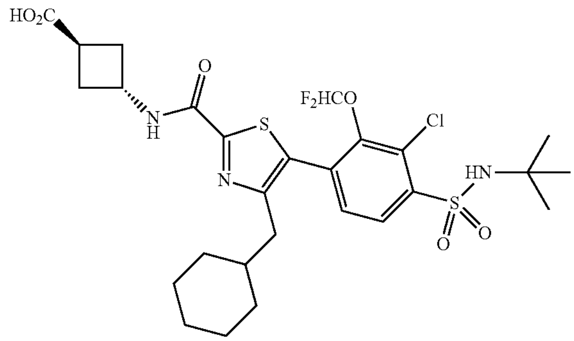 [SMILES: CC(C)(C)NS(=O)(=O)c1ccc(-c2sc(C(=O)N[C@H]3C[C@H](C(=O)O)C3)nc2CC2CCCCC2)c(OC(F)F)c1Cl] | $^1$H-NMR (400 MHz, CDCl$_3$) δ: 8.12 (d, 1H, J = 8.0 Hz), 7.52 (d, 1H, J = 7.6 Hz), 7.42 (d, 1H, J = 8.4 Hz), 6.48-6.11 (m, 1H), 5.64 (s, 1H), 4.84 (d, 1H, J = 8.0 Hz), 3.20-3.14 (m, 1H), 2.81-2.77 (m, 2H), 2.54-2.48 (m, 4H), 1.78-1.53 (m, 6H), 1.27-0.76 (m, 14H). MS 634.2 (M + 1)$^+$ |
| 21/4 | 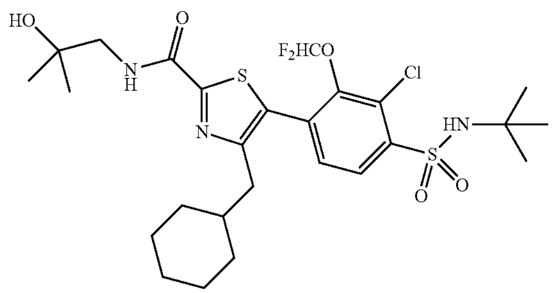 [SMILES: CC(C)(O)CNC(=O)c1nc(CC2CCCCC2)c(-c2ccc(S(=O)(=O)NC(C)(C)C)c(Cl)c2OC(F)F)s1] | $^1$H-NMR (400 MHz, CDCl$_3$) δ: 8.13 (d, 1H, J = 8.4 Hz), 7.67 (t, 1H, J = 6.0 Hz), 7.43 (d, 1H, J = 8.4 Hz), 6.50-6.13 (m, 1H), 3.51 (d, 2H, J = 6.4 Hz), 2.51-2.49 (m, 2H), 1.78-1.54 (m, 6H), 1.34 (s, 6H), 1.29 (s, 9H), 1.27-1.06 (m, 3H), 0.83-0.77 (m, 2H). MS 608.2 (M + 1)$^+$ |
| 21/5 | 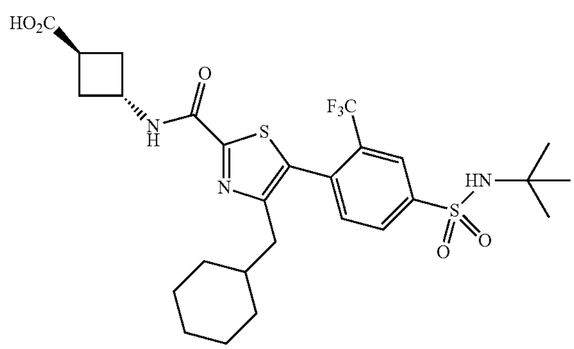 | $^1$H-NMR (400 MHz, CDCl$_3$) δ: 8.28 (s, 1H), 8.11 (d, 1H, J = 6.4 Hz), 7.34 (d, 1H, J = 8.0 Hz), 7.56 (d, 1H, J = 8.0 Hz), 4.85 (m ,1H), 4.77 (s, 1H), 3.20 (m, 1H), 2.79 (m, 2H), 2.49 (m, 4H), 1.75 (m, 1H), 1.62-1.41 (m, 5H), 1.31-1.15 (m, 12H), 0.75 (m ,2H). MS 602.2 (M + H)$^+$ |
| 21/6 | 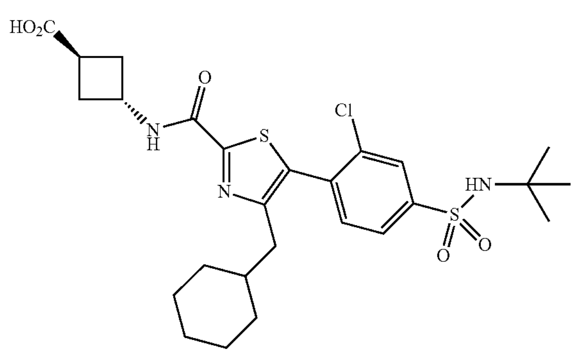 | $^1$H-NMR (400 MHz, CDCl$_3$) δ: 8.02 (s, 1H), 7.83 (d, 1H, J = 6.8 Hz), 7.44 (m, 2H), 4.80 (m, 1H), 4.59 (s, 1H), 3.20 (m, 1H), 2.80 (m, 2H), 2.51 (m, 4H), 1.74-1.51 (m, 6H), 1.31-1.04 (m, 12H), 0.71 (m, 2H). MS 568.2 (M + H)$^+$ |

-continued

| # | Structure | Analytical data |
|---|---|---|
| 21/7 | 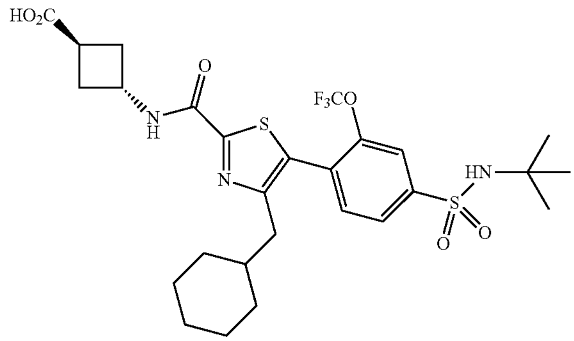 | $^1$H-NMR (400 MHz, DMSO-d$_6$) δ: 12.25 (s, 1H), 9.19 (d, 1H, J = 8.0 Hz), 7.95 (m, 3H), 7.84 (d, 1H, J = 8.0 Hz), 4.58 (m, 1H), 2.95 (m, 1H), 2.55 (m, 4H), 2.43 (m, 2H), 1.71 (m, 1H), 1.49 (m, 5H), 1.12-1.00 (m, 12H), 0.70 (m, 2H). MS 618.2 (M + H)$^+$ |
| 21/8 | 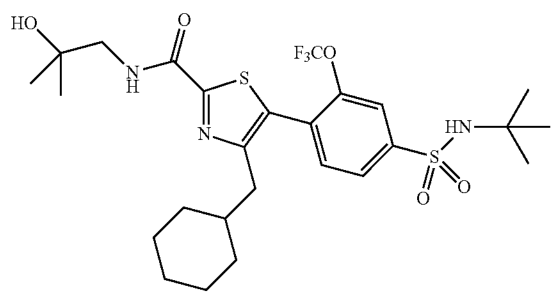 [SMILES: CC(C)(O)CNC(=O)c1nc(CC2CCCCC2)c(-c2ccc(S(=O)(=O)NC(C)(C)C)cc2OC(F)(F)F)s1] | $^1$H-NMR (400 MHz, DMSO-d$_6$) δ: 8.23 (m, 1H), 7.98-7.82 (m, 4H), 4.72 (s, 1H), 3.29 (m, 2H), 2.56-2.49 (m, 2H), 1.68 (m, 1H), 1.56-1.45 (m, 5H), 1.20-1.01 (m, 18H), 0.73 (m, 2H). MS 592.2 (M + H)$^+$ |
| 21/9 | 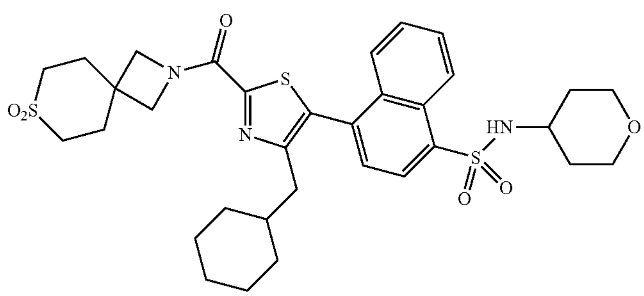 [SMILES: O=C(c1nc(CC2CCCCC2)c(-c2ccc(S(=O)(=O)NC3CCOCC3)c3ccccc23)s1)N1CC2(CCS(=O)(=O)CC2)C1] | $^1$H-NMR (400 MHz, CDCl$_3$) δ: 8.70 (d, 1H, J = 8.8 Hz), 8.34 (d, 1H, J = 7.2 Hz), 7.73 (m, 2H), 7.59 (m, 1H), 7.52 (d, 1H, J = 7.6 Hz), 4.65 (d, 1H, J = 8.0 Hz), 4.56 (s, 2H), 4.07 (s, 2H), 3.83 (m, 2H), 3.43 (m, 1H), 3.32 (m, 2H), 3.08 (m, 4H), 2.46 (m, 4H), 2.35 (m, 2H), 1.68 (m, 3H), 1.48 (m, 7H), 1.07 (m, 3H), 0.69 (m, 2H). MS 672.2 (M + H)$^+$ |
| 21/10 | 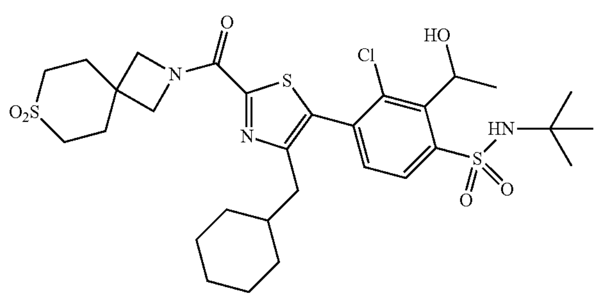 [SMILES: CC(O)c1c(S(=O)(=O)NC(C)(C)C)ccc(-c2sc(C(=O)N3CC4(CCS(=O)(=O)CC4)C3)nc2CC2CCCCC2)c1Cl] | $^1$H-NMR (400 MHz, CDCl$_3$) δ: 8.15 (d, 1H, J = 8.0 Hz), 7.34 (d, 1H, J = 8.0 Hz), 5.69 (m, 1H), 5.60 (m, 1H), 4.51 (s, 2H), 4.03 (s, 2H), 3.05 (m, 4H), 2.43 (m, 6H), 1.72 (m, 3H), 1.46 (m, 6H), 1.31 (s, 9H), 1.11 (m, 3H), 1.82 (m, 2H). MS 672.2 (M + H)$^+$ |
| 21/11 | 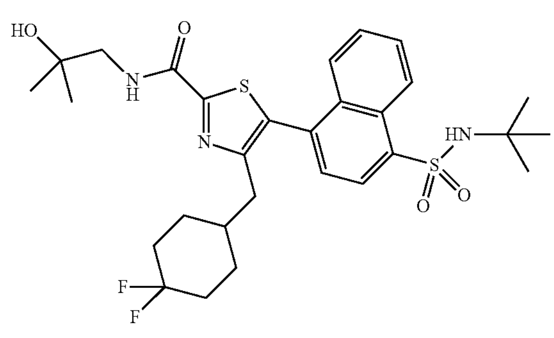 [SMILES: CC(C)(O)CNC(=O)c1nc(CC2CCC(F)(F)CC2)c(-c2ccc(S(=O)(=O)NC(C)(C)C)c3ccccc23)s1] | $^1$H-NMR (400 MHz, DMSO-d$_6$) δ: 8.82 (d, J = 8.8 Hz, 1H), 8.31-8.26 (m, 2H), 7.93 (s, 1H), 7.79-7.66 (m, 4H), 4.74 (s, 1H), 3.32 (d, J = 4.0 Hz, 2H), 2.35-2.45 (m, 2H), 1.81-1.54 (m, 7H), 1.15 (s, 6H), 1.07 (s, 9H), 0.91-0.82 (m, 2H). MS 594.3 (M + 1)$^+$ |

-continued

| # | Structure | Analytical data |
|---|---|---|
| 21/12 | 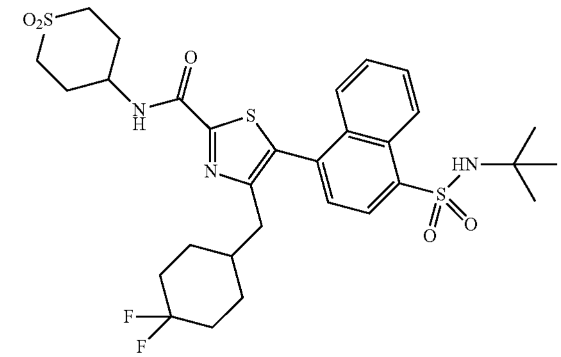 [SMILES: CC(C)(C)NS(=O)(=O)c1ccc(-c2sc(C(=O)NC3CCS(=O)(=O)CC3)nc2CC2CCC(F)(F)CC2)c2ccccc12] | $^1$H-NMR (400 MHz, DMSO-d$_6$) δ: 9.05 (d, J = 8 Hz, 1H), 8.82 (d, J = 8.8 Hz, 1H), 8.27 (d, J = 7.6 Hz, 1H), 7.93 (s, 1H), 7.79-7.66 (m, 4H), 4.27-4.24 (m, 1H), 3.41-3.32 (m, 2H), 3.13 (d, J = 12.4 Hz, 2H), 2.40-2.23 (m, 4H), 2.12 (d, J = 11.6 Hz, 2H), 1.80-1.53 (m, 7H), 1.07 (s, 9H), 0.85-0.82 (m, 2H). MS 654.3 (M + 1)$^+$ |
| 21/13 | 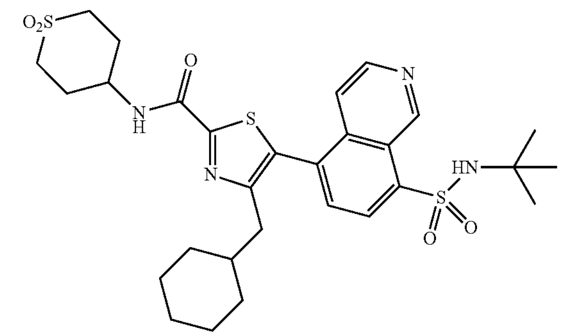 [SMILES: CC(C)(C)NS(=O)(=O)c1ccc(-c2sc(C(=O)NC3CCS(=O)(=O)CC3)nc2CC2CCCCC2)c2ccncc12] | $^1$H-NMR (400 MHz, DMSO-d$_6$) δ: 10.19 (s, 1H), 8.65 (d, 1H, J = 6.0 Hz), 8.46 (d, 1H, J = 8.0 Hz), 7.96 (d, 1H, J = 7.6 Hz), 7.69 (d, 1H, J = 6.0 Hz), 4.30 (m, 1H), 3.95 (m ,2H), 3.16 (m, 2H), 2.46-2.34 (m, 6H), 1.73 (m, 1H), 1.54 (m, 5H), 1.28 (s, 9H), 1.06 (m, 3H), 0.68 (m, 2H). MS 619.3 (M + 1)$^+$ |
| 21/14 | 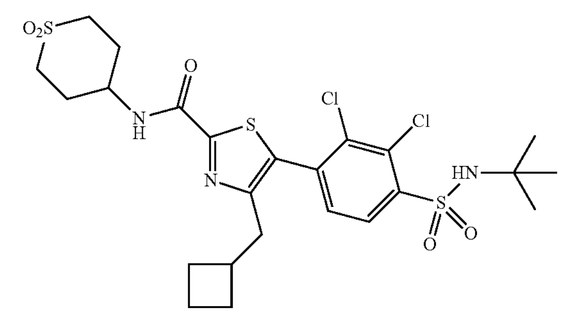 [SMILES: CC(C)(C)NS(=O)(=O)c1ccc(-c2sc(C(=O)NC3CCS(=O)(=O)CC3)nc2CC2CCC2)c(Cl)c1Cl] | $^1$H-NMR (400 MHz, DMSO-d$_6$) δ: 8.98 (d, 1H, J = 8.4 Hz), 8.11 (d, 1H, J = 8.0 Hz), 7.97 (m, 1H), 7.68 (d, 1H, J = 8.4 Hz), 4.21 (m, 1H), 3.38 (m, 2H), 3.10 (m, 2H), 2.60 (m, 3H), 2.21 (m, 2H), 2.08 (m, 2H), 1.89 (m, 2H), 1.66 (m, 2H), 1.44 (m, 2H), 1.16 (s, 9H). MS 608.2 (M + H)$^+$ |
| 21/15 | 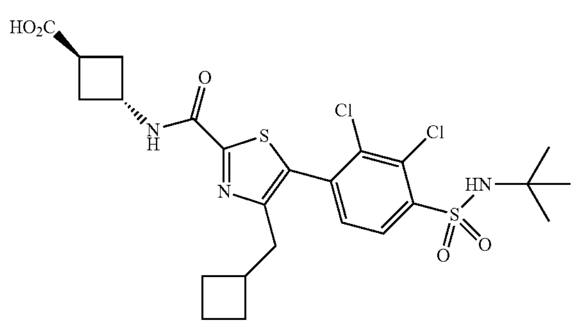 [SMILES: CC(C)(C)NS(=O)(=O)c1ccc(-c2sc(C(=O)N[C@H]3C[C@H](C(=O)O)C3)nc2CC2CCC2)c(Cl)c1Cl] | $^1$H-NMR (400 MHz, DMSO-d$_6$) δ: 12.25 (s, 1H), 9.16 (d, 1H, J = 8.0 Hz), 8.11 (d, 1H, J = 8.4 Hz), 8.04 (s, 1H), 7.69 (d, 1H, J = 8.4 Hz), 4.57 (m, 1H), 2.95 (m, 1H), 2.62 (m, 3H), 2.47-2.42 (m, 4H), 1.89 (m, 2H), 1.67 (m, 2H), 1.44 (m, 2H), 1.16 (s, 9H). MS 574.1 (M + H)$^+$ |

-continued

| # | Structure | Analytical data |
|---|---|---|
| 21/16 | 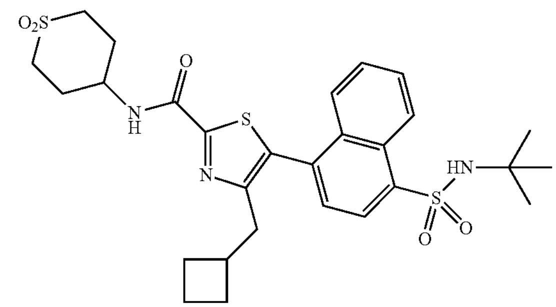 [SMILES: CC(C)(C)NS(=O)(=O)c1ccc(-c2sc(C(=O)NC3CCS(=O)(=O)CC3)nc2CC2CCC2)c2ccccc12] | ¹H-NMR (400 MHz, DMSO-$d_6$) δ: 9.01 (d, 1H, J = 8.4 Hz), 8.81 (d, 1H, J = 8.8 Hz), 8.26 (d, 1H, J = 7.6 Hz), 7.94 (s, 1H), 7.74 (m, 4H), 4.25 (m, 1H), 3.40 (m, 2H), 3.10 (m, 2H), 2.67 (m, 3H), 2.29 (m, 2H), 2.11 (m, 2H), 1.80 (m, 2H), 1.53 (m, 2H), 1.26 (m, 2H), 1.09 (s, 9H). MS 590.2 (M + H)⁺ |
| 21/17 | 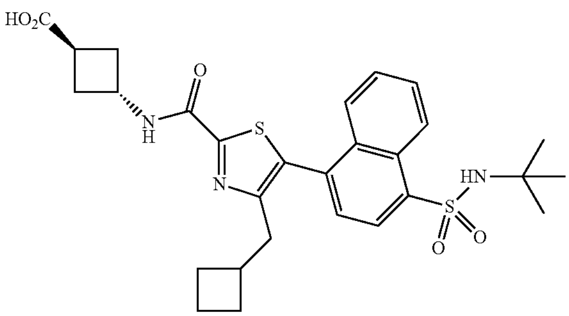 [SMILES: CC(C)(C)NS(=O)(=O)c1ccc(-c2sc(C(=O)N[C@H]3C[C@H](C(=O)O)C3)nc2CC2CCC2)c2ccccc12] | ¹H-NMR (400 MHz, DMSO-$d_6$) δ: 9.16 (d, 1H, J = 8.4 Hz), 8.81 (d, 1H, J = 8.8 Hz), 8.26 (d, 1H, J = 7.6 Hz), 7.81 (m, 2H), 7.70 (m, 3H), 4.60 (m, 1H), 2.92 (m, 1H), 2.56 (m, 3H), 2.45 (m, 4H), 1.79 (m, 2H), 1.64 (m, 2H), 1.31 (m, 2H), 1.09 (s, 9H). MS 556.2 (M + H)⁺ |
| 21/18 | 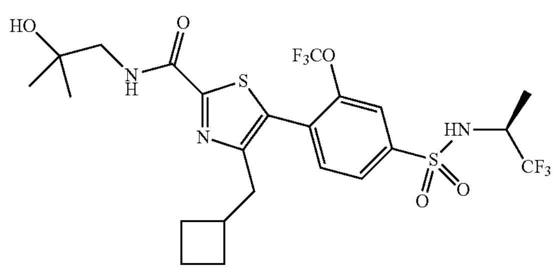 [SMILES: C[C@H](NS(=O)(=O)c1ccc(-c2sc(C(=O)NCC(C)(C)O)nc2CC2CCC2)c(OC(F)(F)F)c1)C(F)(F)F] | MS 604.1 (M + H)⁺ |
| 21/19 | 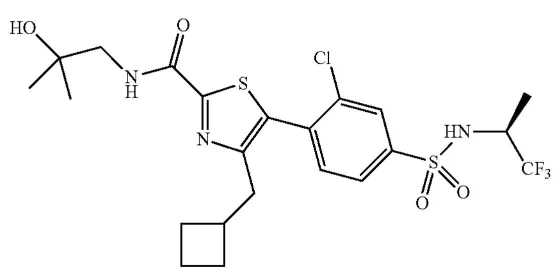 [SMILES: C[C@H](NS(=O)(=O)c1ccc(-c2sc(C(=O)NCC(C)(C)O)nc2CC2CCC2)c(Cl)c1)C(F)(F)F] | MS 554.1 (M + H)⁺ |
| 21/20 | 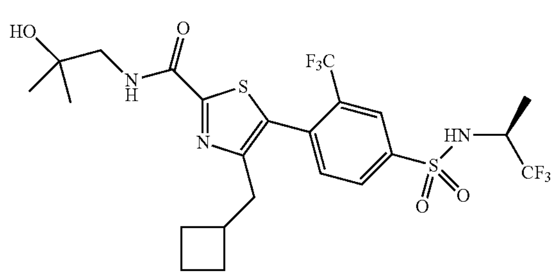 [SMILES: C[C@H](NS(=O)(=O)c1ccc(-c2sc(C(=O)NCC(C)(C)O)nc2CC2CCC2)c(C(F)(F)F)c1)C(F)(F)F] | MS 588.1 (M + H)⁺ |

| # | Structure | Analytical data |
|---|---|---|
| 21/21 | 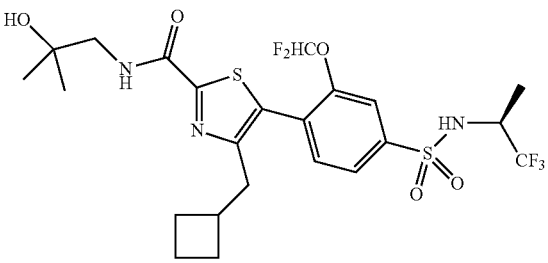 [SMILES: C[C@H](NS(=O)(=O)c1ccc(-c2sc(C(=O)NCC(C)(C)O)nc2CC2CCC2)c(OC(F)F)c1)C(F)(F)F] | MS 586.1 (M + H)+ |
| 21/22 | 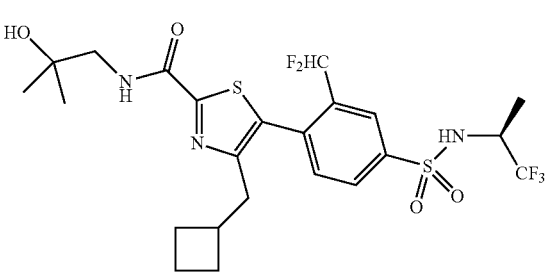 | MS 570.1 (M + H)+ |
| 21/23 | 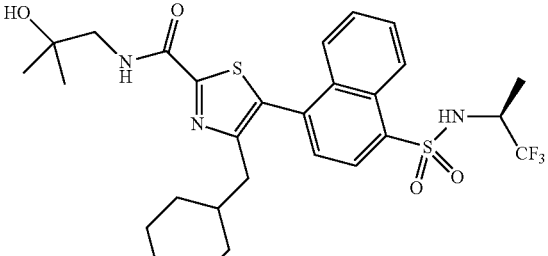 | MS 634.1 (M + H)+ |
| 21/24 | 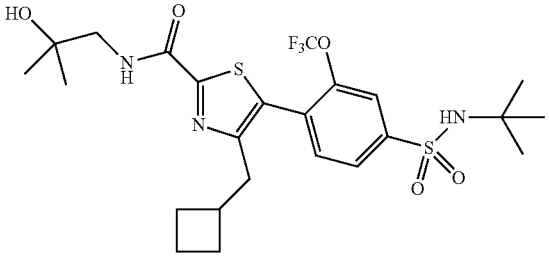 [SMILES: CC(C)(O)CNC(=O)c1nc(CC2CCC2)c(-c2ccc(S(=O)(=O)NC(C)(C)C)cc2OC(F)(F)F)s1] | $^1$H-NMR (400 MHz, DMSO-$d_6$) δ: 8.24 (m, 1H), 7.99-7.82 (m, 4H), 4.73 (s, 1H), 3.28 (m, 2H), 2.73 (m, 2H), 2.62 (m, 1H), 1.95-1.86 (m, 2H), 1.75-1.60 (m, 2H), 1.55-1.42 (m, 4H), 1.18-1.09 (m, 16H). MS 564.1 (M + H)+ |
| 21/25 | 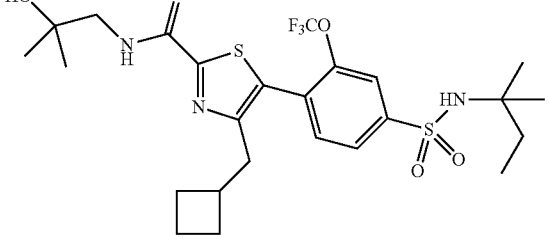 | $^1$H-NMR (400 MHz, DMSO-$d_6$) δ: 8.23 (m, 1H), 7.98-7.92 (m, 2H), 7.87-7.82 (m, 1H), 7.79 (s, 1H), 4.71 (s, 1H), 3.28 (m ,2H), 2.73 (m, 2H), 2.62 (m, 1H), 1.95-1.86 (m, 2H), 1.75-1.60 (m, 2H), 1.55-1.42 (m, 4H), 1.13 (s, 6H), 1.08 (s, 6H), 0.74 (t, J = 7.6 Hz, 3H). MS 578.1 (M + H)+ |

Example 22

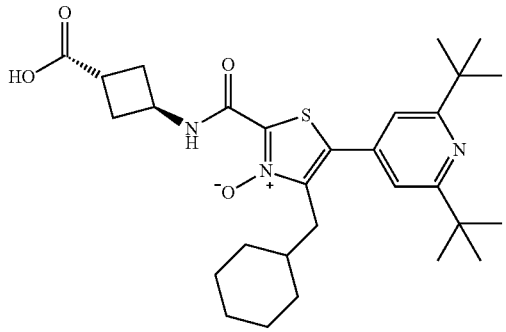

Step 1: 4-(Cyclohexylmethyl)-5-(2,6-di-tert-butylpyridin-4-yl)-2-(((trans)-3-(methoxycarbonyl)-cyclobutyl)carbamoyl)thiazole 3-oxide (22a)

To a solution of (trans)-methyl 3-(4-(cyclohexylmethyl)-5-(2,6-di-tert-butylpyridin-4-yl)thiazole-2-carboxamido)cyclobutanecarboxylate (60 mg, 0.11 mmol) in DCM (2 mL) was added m-CPBA (35 mg, 0.17 mmol) and the solution was stirred at rt overnight, washed with sat. NaHCO$_3$ and sat. aq. NaS$_2$O$_3$ consecutively, dried over Na$_2$SO$_4$, filtered, concentrated and purified by CC (PE/EA=3/1) to give compound 22a (38 mg, 62%) as a pale yellow solid.

Step 2: 2-(((trans)-3-Carboxycyclobutyl)carbamoyl)-4-(cyclohexylmethyl)-5-(2,6-di-tert-butylpyridin-4-yl)thiazole 3-oxide (22)

A solution of compound 22a (36 mg, 0.066 mmol) and LiOH.H$_2$O (6 mg, 0.1 mmol) in a mixture of MeOH (2 mL) and H$_2$O (1 mL) was stirred at rt overnight, diluted with aq. HCl to adjust the pH to ca. 5 and extracted with EA. The organic layer was washed with water and brine, dried over Na$_2$SO$_4$, filtered, concentrated and purified by CC (DCM/MeOH=10/1) to give compound 22 (22 mg, 63%) as a white solid. $^1$H-NMR (400 MHz, DMSO-d$_6$) δ: 0.83-0.89 (m, 2H), 1.04-1.06 (m, 3H), 1.35 (s, 18H), 1.52-1.55 (m, 5H), 1.75-1.78 (m, 1H), 2.40-2.45 (m, 2H), 2.50-2.53 (m, 2H), 2.76 (d, J=7.2 Hz, 2H), 2.98-3.01 (m, 1H), 4.59-4.61 (m, 1H), 7.37 (s, 2H), 10.56 (d, J=7.6 Hz, 1H), 12.32 (s, 1H). MS 528.3 (M+1)$^+$.

Example 22/1 to 22/2

The following examples were prepared similar to Example 22.

| # | Structure | Analytical data |
|---|---|---|
| 22/1 | ![structure] | $^1$H-NMR (400 MHz, DMSO-d$_6$) δ: 0.44-0.51 (m, 2H), 0.81-0.92 (m, 6H), 1.06 (s, 9H), 1.45 (s, 3H), 1.22-1.28 (m, 1H), 1.38-1.40 (m, 5H), 1.55-1.60 (m, 1H), 2.40-2.45 (m, 2H), 3.00-3.04 (m, 1H), 4.60-4.66 (m, 1H), 7.69 (t, J = 7.6 Hz, 1H), 7.77-7.82 (m, 2H), 7.90 (d, J = 8.4 Hz, 1H), 8.00 (s, 1H), 8.29 (d, J = 7.6 Hz, 1H), 8.81 (d, J = 8.8 Hz, 1H), 10.68 (d, J = 7.6 Hz, 1H), 12.34 (m, 1H). MS 600.3 (M + 1)$^+$ |
| 22/2 | ![structure] | $^1$H-NMR (300 MHz, CDCl$_3$) δ: 0.79-0.95 (m, 6H), 1.11-1.26 (m, 4H), 1.35 (s, 9H), 1.45 (s, 3H), 1.62-1.65 (m, 5H), 1.89-1.91 (m, 1H), 2.45-2.57 (m, 2H), 2.76-2.87 (m, 4H), 3.17-3.23 (m, 1H), 4.80-4.88 (m, 1H), 7.14 (s, 1H), 7.26 (s, 1H), 7.39 (s, 1H), 10.76 (d, J = 6.0 Hz, 1H). MS 525.3 (M + 1)$^+$ |

Example 23

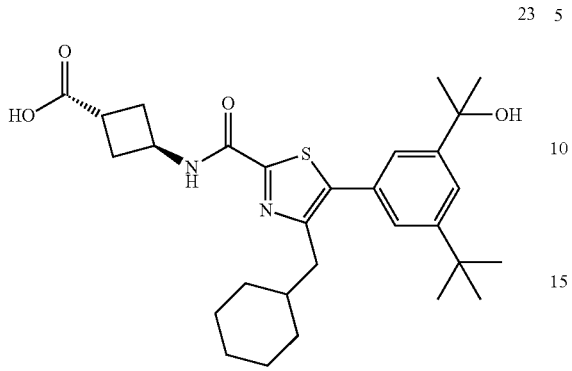

Step 1: (trans)-Methyl 3-(5-(3-acetyl-5-(tert-butyl) phenyl)-4-(cyclohexylmethyl)thiazole-2-carboxamido)cyclobutanecarboxylate (23a)

A mixture of (trans)-methyl 3-(5-bromo-4-(cyclohexylmethyl)thiazole-2-carboxamido)cyclobutanecarboxylate (415 mg, 1.00 mmol), 1-(3-(tert-butyl)-5-(4,4,5,5-tetramethyl-1,3,2-dioxaborolan-2-yl)phenyl)ethanone (362 mg, 1.20 mmol) and $K_2CO_3$ (500 mg, 3.62 mmol) in dry DMF (10 mL) was purged with $N_2$ for 10 min. Pd(dppf)Cl$_2$ (50 mg) was added and degassing with $N_2$ was continued for 10 min. The mixture was stirred at 100° C. for 14 h under $N_2$, cooled to rt, concentrated and purified by CC (PE/EA=5/1) to give compound 23a (465 mg, 91%) as a white solid.

Step 2: (trans)-Methyl 3-(5-(3-(tert-butyl)-5-(2-hydroxypropan-2-yl)phenyl)-4-(cyclohexyl-methyl)-thiazole-2-carboxamido)cyclobutanecarboxylate (23b)

To a solution of compound 23a (465 mg, 0.91 mmol) in dry THF (10 mL) was added MeMgBr (3M in Et$_2$O, 0.30 mL, 0.90 mmol) at 0° C. under $N_2$ and the solution was stirred at rt for 2.5 h, quenched with sat. NH$_4$Cl and extracted with EA. The organic layer was washed with water and brine, dried over $Na_2SO_4$, filtered, concentrated and purified by CC (PE/EA=5/1) to give compound 23b (240 mg, 50%) as a white solid.

Step 3: (trans)-3-(5-(3-(tert-Butyl)-5-(2-hydroxypropan-2-yl)phenyl)-4-(cyclohexylmethyl)-thiazole-2-carboxamido)cyclobutanecarboxylic acid (23)

To a solution of compound 23b (50 mg, 0.095 mmol) in a mixture of THF (4 mL) and water (1 mL) was added LiOH.H$_2$O (40 mg, 0.95 mmol), and the resulting mixture was stirred at rt overnight, pH-adjusted to pH=56 with 1N HCl and extracted with EA. The organic layer was washed with brine, dried over $Na_2SO_4$, filtered, concentrated and purified by prep-HPLC to give compound 23 (20 mg, 41%) as a white solid. $^1$H-NMR (300 MHz, CD$_3$OD) δ: 0.89-0.96 (m, 2H), 1.12-1.32 (m, 3H), 1.37 (s, 9H), 1.51 (s, 6H), 1.56-1.66 (m, 5H), 1.82-1.88 (m, 6H), 2.51-2.71 (m, 6H), 3.05-3.11 (m, 1H), 4.71-4.74 (m, 1H), 7.32 (s, 1H), 7.36 (s, 1H), 7.64 (s, 1H), 8.78 (d, J=8.1 Hz, 1H). MS 513.3 (M+1)$^+$.

Example 24

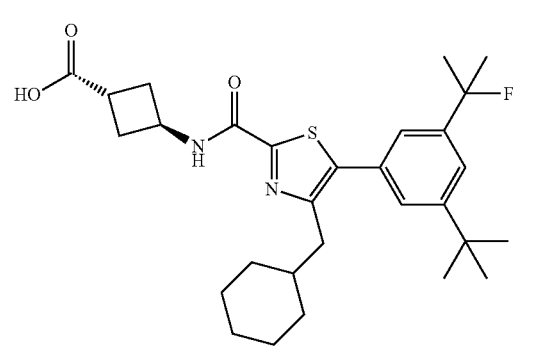

Step 1: (trans)-Methyl 3-(5-(3-(tert-butyl)-5-(2-fluoropropan-2-yl)phenyl)-4-(cyclohexylmethyl)-thiazole-2-carboxamido)cyclobutanecarboxylate (24a)

To a solution of compound 23b (180 mg, 0.34 mmol) in dry DCM (5 mL) was added DAST (165 mg, 1.03 mmol) at 0° C. under $N_2$ and the solution was stirred at this temperature for 15 h, quenched with water and extracted with EA. The organic layer was washed with water and brine, dried over $Na_2SO_4$, filtered, concentrated and purified by prep-TLC (PE/EA=5/1) to give compound 24a (90 mg, 50%) as a white solid.

Step 2: (trans)-3-(5-(3-(tert-Butyl)-5-(2-fluoropropan-2-yl)phenyl)-4-(cyclohexylmethyl)thiazole-2-carboxamido)cyclobutanecarboxylic acid (24)

A similar procedure as described for Example 23 was applied to afford compound 24 (50 mg, 52%) as a white solid. $^1$H-NMR (300 MHz, CD$_3$OD) δ: 0.89-0.96 (m, 2H), 1.12-1.32 (m, 3H), 1.37 (s, 9H), 1.58-1.70 (m, 8H), 1.72 (s, 3H), 1.81-1.88 (m, 1H), 2.47-2.70 (m, 6H), 3.04-3.12 (m, 1H), 4.70-4.75 (m, 1H), 7.27 (t, J=1.5 Hz, 1H), 7.38 (t, J=1.5 Hz, 1H), 7.51 (t, J=1.5 Hz, 1H), 8.78 (d, J=8.1 Hz, 1H). MS 515.3 (M+1)$^+$.

Example 25

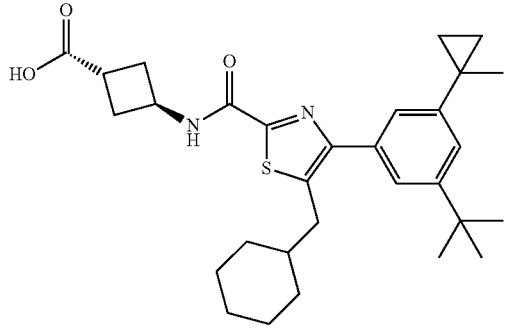

Step 1: 2,4-Dibromothiazole-5-carbaldehyde (25a)

To a solution of LDA (1M in THF, 183 mL, 183 mmol) was added a solution of 2,4-dibromothiazole (37 g, 154 mmol) in dry THF (500 mL) at −78° C. under $N_2$ and the solution was stirred under this condition for 40 min. Then DMF (13 g, 178 mmol) was added slowly at this temperature and the solution was stirred for another 1 h, warmed to rt, quenched with sat. $NH_4Cl$ and extracted with EA twice. The combined organic layers were washed with water and brine, dried over $Na_2SO_4$, filtered, concentrated and purified by CC (PE/EA=15/1) to give compound 25a (14.5 g, 35%) as a yellow solid.

Step 2: Cyclohexyl(2,4-dibromothiazol-5-yl)methanol (25b)

To a solution of compound 25a (11.2 g, 41.7 mmol) in dry THF (150 mL) was added a solution of cyclohexylmagnesium chloride (1M in THF, 45 mL, 45.0 mol) at −78° C. and the solution was stirred at this temperature for 1 h, warmed to rt, quenched with water and extracted with EA twice. The combined organic layers were washed with water and brine, dried over $Na_2SO_4$, filtered, concentrated and purified by CC (PE/EA=20/1) to give compound 25b (5.4 g, 37%) as a pale yellow solid.

Step 3: 2,4-Dibromo-5-(cyclohexylmethyl)thiazole (25c)

To a solution of compound 25b (5.4 g, 15.3 mmol) in DCM (50 mL) was added $Et_3SiH$ (17.7 g, 153 mmol) and TFA (684 mg, 30.6 mmol) and the solution was stirred at rt for overnight and quenched with water. The organic layer was washed with water and brine, dried over $Na_2SO_4$, filtered, concentrated and purified by CC (PE/EA=30/1) to give compound 25c (2.91 g, 56%) as a white solid.

Step 4: Ethyl 4-bromo-5-(cyclohexylmethyl)thiazole-2-carboxylate (25d)

To a solution of compound 25c (6.50 g, 19.1 mmol) in dry THF (60 mL) was added a solution of n-BuLi (2.5M in THF, 8.0 mL, 20.0 mmol) at −78° C. under $N_2$ and the solution was stirred at this temperature for 1 h. Then ethylchloroformate (2.36 g, 25.0 mmol) was added and the solution was stirred at −78° C. for another 1 h, quenched with water and extracted with EA twice. The combined organic layers were washed with water and brine, dried over $Na_2SO_4$, filtered, concentrated and purified by CC (PE/EA=30/1) to give compound 25d (2.54 g, 40%) as a light yellow oil.

Step 5: Ethyl 4-(3-(tert-butyl)-5-(1-methylcyclopropyl)phenyl)-5-(cyclohexylmethyl)thiazole-2-carboxylate (25e)

The suspension of compound 25d (500 mg, 1.50 mmol), $K_2CO_3$ (690 mg, 5.00 mmol), 2-(3-(tert-butyl)-5-(1-methylcyclopropyl)phenyl)-4,4,5,5-tetramethyl-1,3,2-dioxaborolane (471 mg, 1.50 mmol) and $Pd(dppf)Cl_2$ (150 mg) in DMF (10 mL) was stirred at 100° C. for overnight, cooled to rt, concentrated and purified by CC (PE/EA=15/1) to give compound 25e (299 mg, 45%) as a white solid.

Step 6: Potassium 4-(3-(tert-butyl)-5-(1-methylcyclopropyl)phenyl)-5-(cyclohexylmethyl)thiazole-2-carboxylate (25f)

To a solution of compound 25e (299 mg, 0.68 mmol) in MeOH (3.0 mL) was added KOH (50.4 mg, 0.90 mmol) and the solution was stirred at rt for overnight and concentrated to give crude compound 25f (305 mg) as a yellow solid.

Step 7: trans-3-(4-(3-(tert-Butyl)-5-(1-methylcyclopropyl)phenyl)-5-(cyclohexylmethyl)thiazole-2-carboxamido)cyclobutanecarboxylic acid (25)

The solution of compound 25f (305 mg, 0.68 mmol), trans-3-amino-cyclobutane carboxylic acid hydrochloride (106 mg, 0.70 mmol), HATU (285 mg, 0.75 mmol) and DIEA (257 mg, 2.00 mmol) in DMF (5 mL) was stirred at rt for 30 min, diluted with water and extracted by EA (3×). The combined organic layers were washed by water (3×) and brine consecutively, dried over $Na_2SO_4$, filtered, concentrated and purified by prep-HPLC and then prep-TLC to give compound 25 (37 mg, 11%) as a white solid. $^1$H-NMR (CDCl$_3$, 300 MHz) δ: 0.75-0.78 (m, 2H), 0.85-0.87 (m, 2H), 0.97-1.16 (m, 2H), 1.20-1.30 (m, 4H), 1.34 (s, 9H), 1.43 (s, 3H), 1.71-1.87 (m, 6H), 2.55-2.57 (m, 2H), 2.85-2.90 (m, 4H), 4.48-4.49 (m, 1H), 5.83 (d, J=9.0 Hz, 1H), 7.24 (s, 1H), 7.33 (s, 1H), 7.41 (s, 1H). MS 509.3 (M+1)$^+$.

Example 25/1 to 25/2

The following examples were prepared similar to Example 25.

| # | Structure | Analytical data |
|---|-----------|-----------------|
| 25/1 | 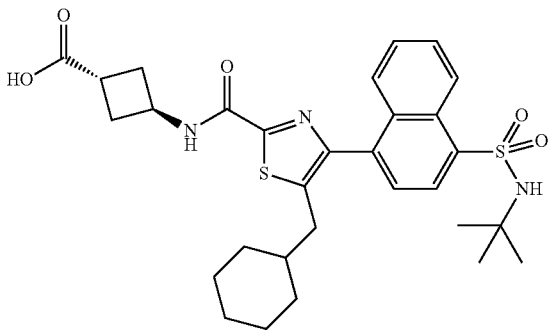 [SMILES: CC(C)(C)NS(=O)(=O)c1ccc(-c2nc(C(=O)N[C@H]3C[C@H](C(=O)O)C3)sc2CC2CCCCC2)c2ccccc12] | $^1$H-NMR (CDCl$_3$, 300 MHz) δ: 0.63-0.66 (m, 2H), 0.98-1.20 (m, 3H), 1.22 (s, 9H), 1.48-1.67 (m, 6H), 2.37 (br s, 2H), 2.53-2.57 (m, 2H), 2.84-2.86 (m, 2H), 3.20-3.21 (m, 2H), 4.67 (s, 1H), 4.81-4.83 (m, 1H), 7.48-7.51 (m, 3H), 7.70-7.75 (m, 1H), 8.36 (d, J = 10.8 Hz, 1H), 8.69 (d, J = 8.4 Hz, 1H). MS 584.2 (M + 1)$^+$ |

| # | Structure | Analytical data |
|---|---|---|
| 25/2 | 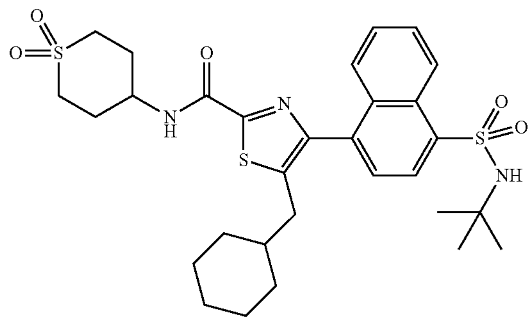 [SMILES: CC(C)(C)NS(=O)(=O)c1ccc(-c2nc(C(=O)NC3CCS(=O)(=O)CC3)sc2CC2CCCCC2)c2ccccc12] | ¹H-NMR (CDCl₃, 300 MHz) δ: 1.00-1.05 (m, 2H), 1.10-1.20 (m, 3H), 1.27 (s, 9H), 1.46-1.56 (m, 2H), 1.60-1.90 (m, 6H), 1.95-2.09 (m, 2H), 2.39-2.46 (m, 2H), 2.79-2.82 (m, 2H), 2.96 (d, J = 7.8 Hz, 2H), 3.81-3.82 (m, 1H), 4.78 (s, 1H), 5.13 (d, J = 7.8 Hz, 2H), 7.61-7.83 (m, 4H), 8.42 (d, J = 7.8 Hz, 1H), 8.75 (d, J = 8.4 Hz, 1H). MS 618.2 (M + 1)⁺ |

Additional Examples

The following compounds can be prepared in the same manner by using the procedures as described above:

| 311 -continued | 312 -continued |
|---|---|
| Structure | Structure |
| 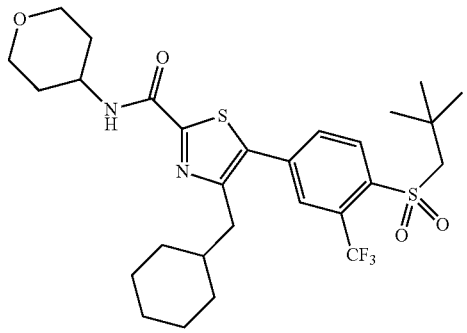 [SMILES: CC(C)(C)CS(=O)(=O)c1ccc(-c2sc(C(=O)NC3CCOCC3)nc2CC2CCCCC2)cc1C(F)(F)F] | 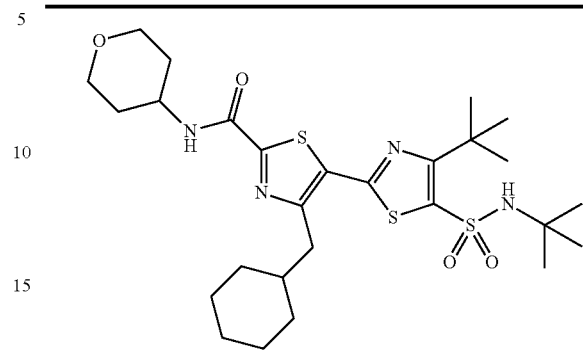 |
| 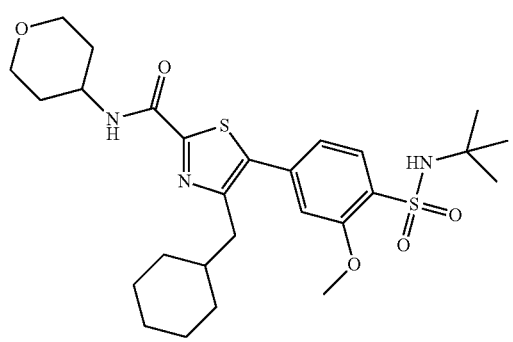 [SMILES: COc1cc(-c2sc(C(=O)NC3CCOCC3)nc2CC2CCCCC2)ccc1S(=O)(=O)NC(C)(C)C] | 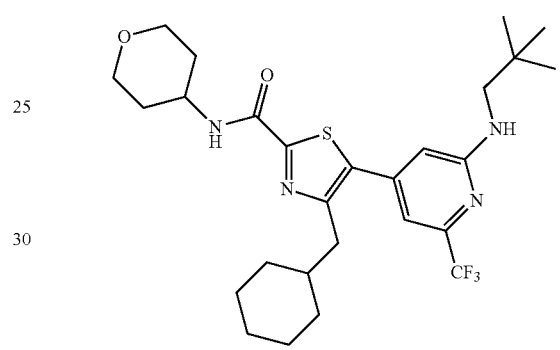 |
| 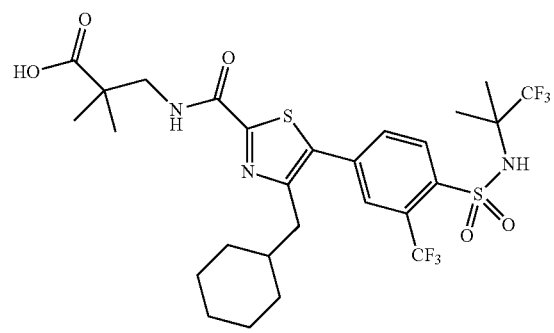 [SMILES: CC(C)(CNC(=O)c1nc(CC2CCCCC2)c(-c2ccc(S(=O)(=O)NC(C)(C)C(F)(F)F)c(C(F)(F)F)c2)s1)C(=O)O] | 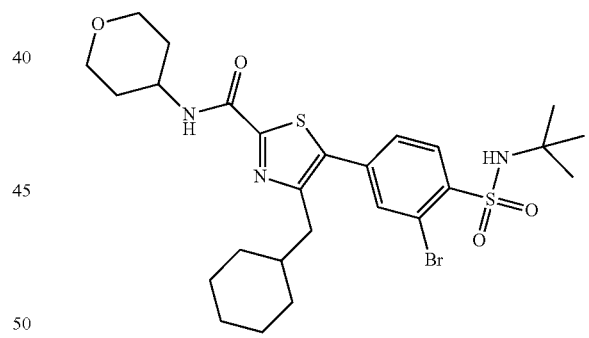 |
| 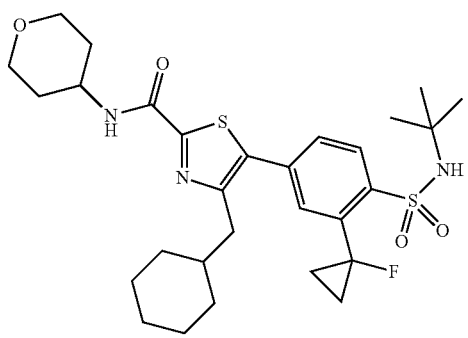 [SMILES: CC(C)(C)NS(=O)(=O)c1ccc(-c2sc(C(=O)NC3CCOCC3)nc2CC2CCCCC2)cc1C1(F)CC1] | 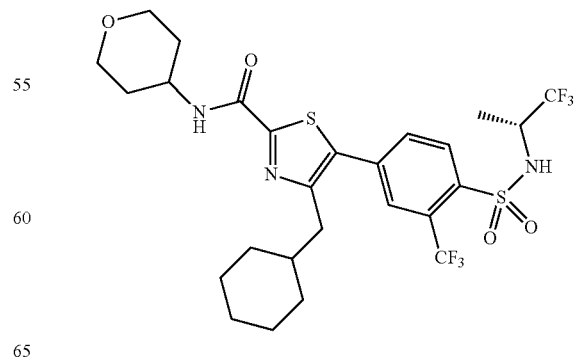 |

| 313 -continued | 314 -continued |
|---|---|
| Structure | Structure |
| 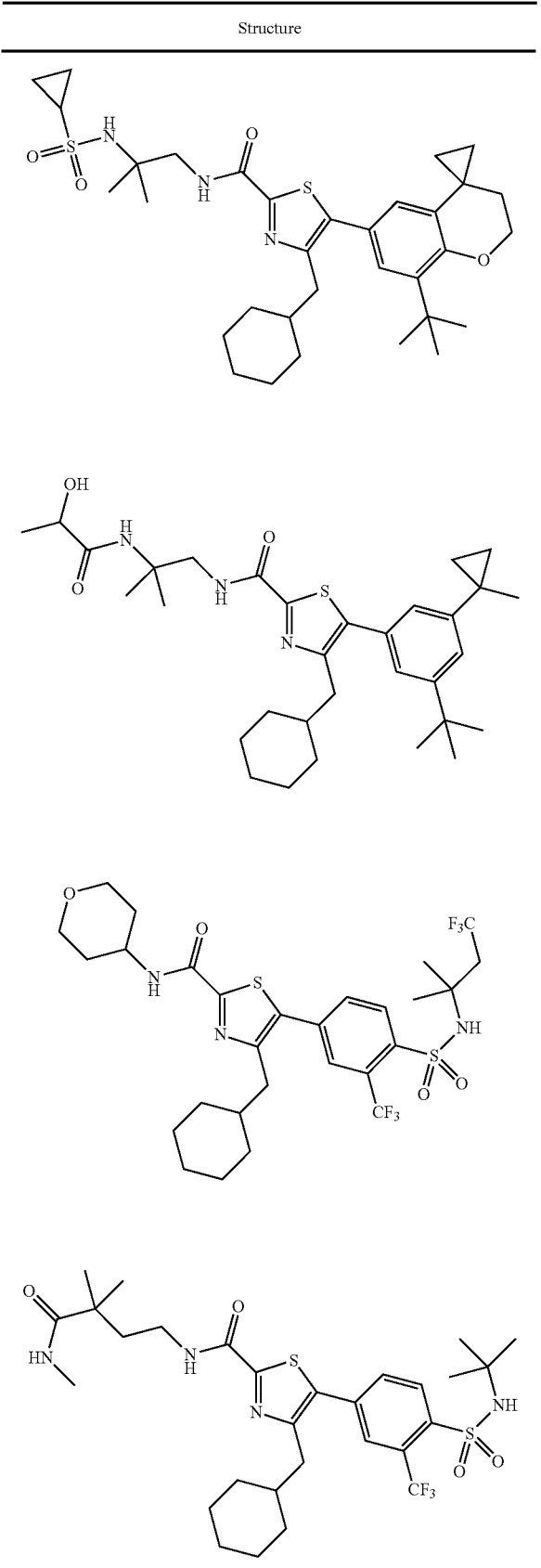 | 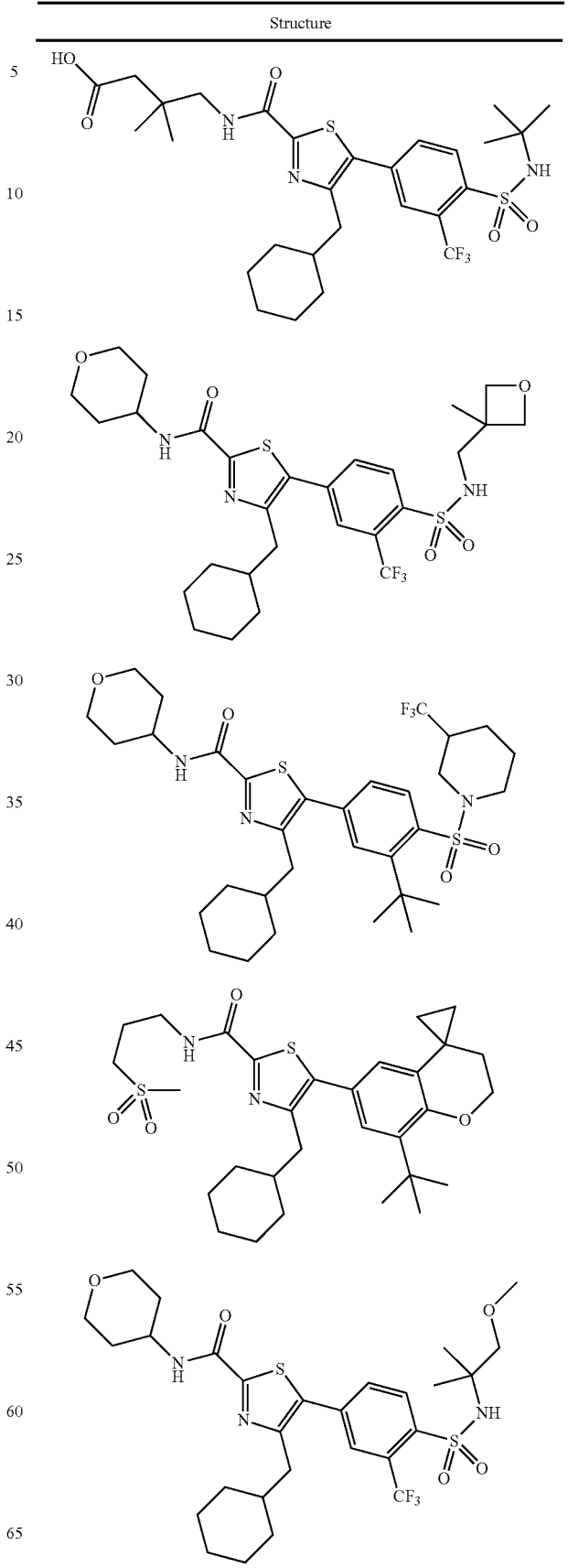 |

| 315 -continued | 316 -continued |
|---|---|
| Structure | Structure |
| 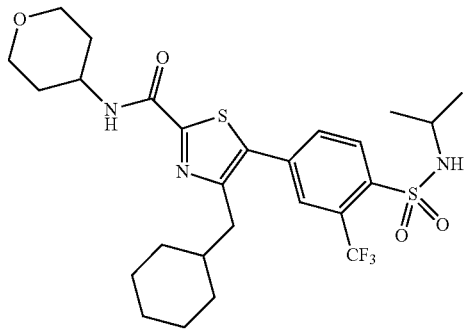 [SMILES: CC(C)NS(=O)(=O)c1ccc(-c2sc(C(=O)NC3CCOCC3)nc2CC2CCCCC2)cc1C(F)(F)F] | 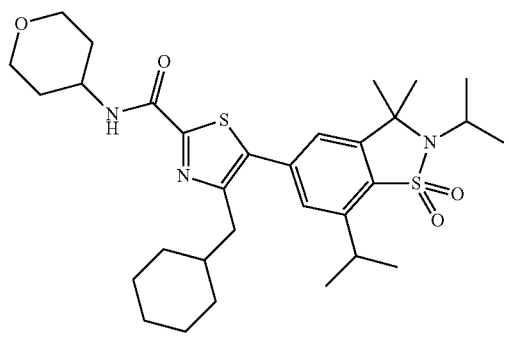 |
| 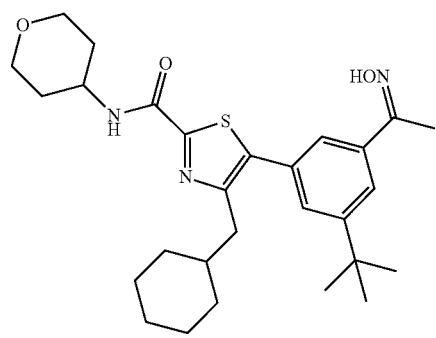 | 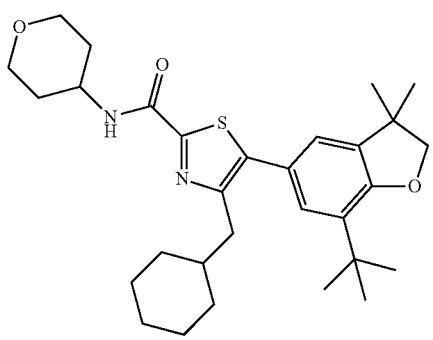 |
| 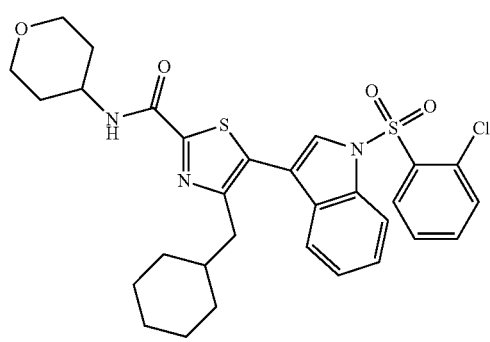 [SMILES: O=C(NC1CCOCC1)c1nc(CC2CCCCC2)c(-c2cn(S(=O)(=O)c3ccccc3Cl)c3ccccc23)s1] | 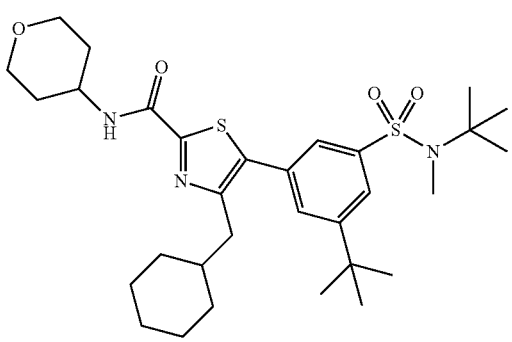 |
| 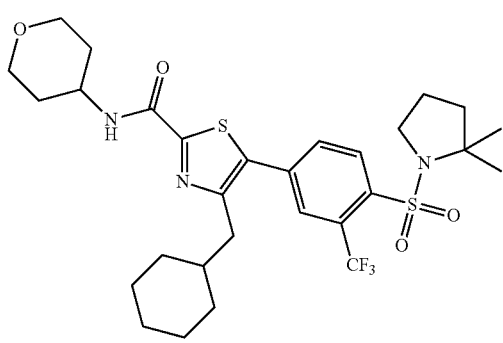 [SMILES: CC1(C)CCCN1S(=O)(=O)c1ccc(-c2sc(C(=O)NC3CCOCC3)nc2CC2CCCCC2)cc1C(F)(F)F] | 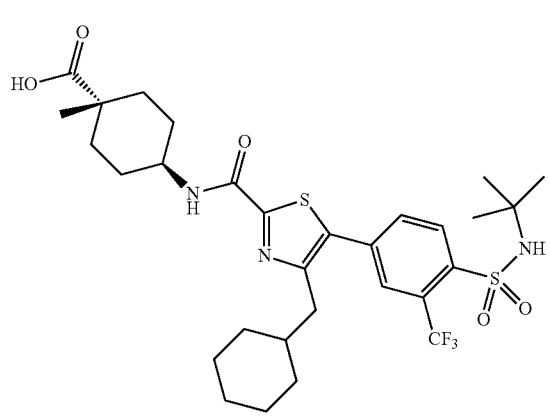 [SMILES: CC(C)(C)NS(=O)(=O)c1ccc(-c2sc(C(=O)N[C@H]3CC[C@](C)(C(=O)O)CC3)nc2CC2CCCCC2)cc1C(F)(F)F] |

| 317 -continued | 318 -continued |
|---|---|
| Structure | Structure |
| 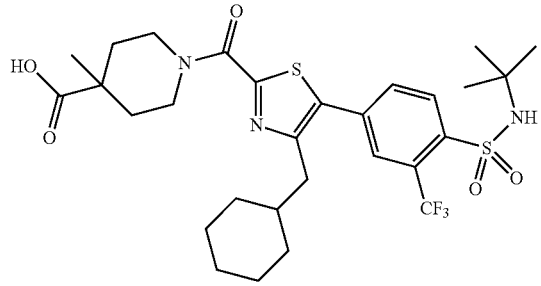 [SMILES: CC(C)(C)NS(=O)(=O)c1ccc(-c2sc(C(=O)N3CCC(C)(C(=O)O)CC3)nc2CC2CCCCC2)cc1C(F)(F)F] | 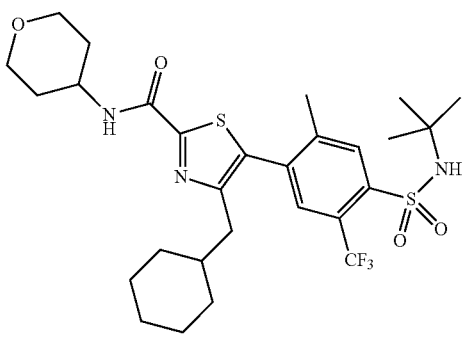 |
| 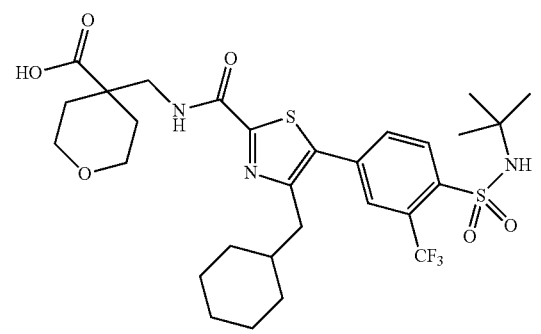 [SMILES: CC(C)(C)NS(=O)(=O)c1ccc(-c2sc(C(=O)NCC3(C(=O)O)CCOCC3)nc2CC2CCCCC2)cc1C(F)(F)F] | 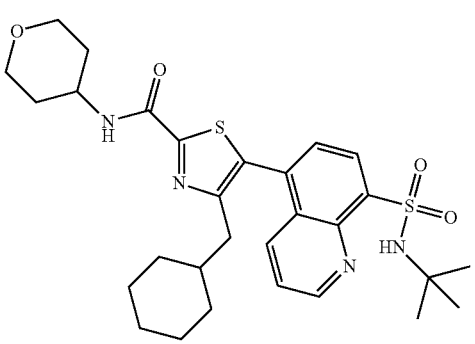 |
| 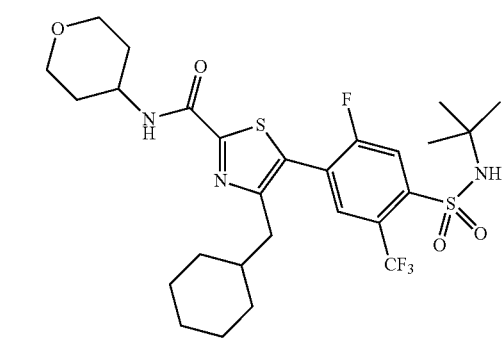 [SMILES: CC(C)(C)NS(=O)(=O)c1cc(F)c(-c2sc(C(=O)NC3CCOCC3)nc2CC2CCCCC2)cc1C(F)(F)F] | 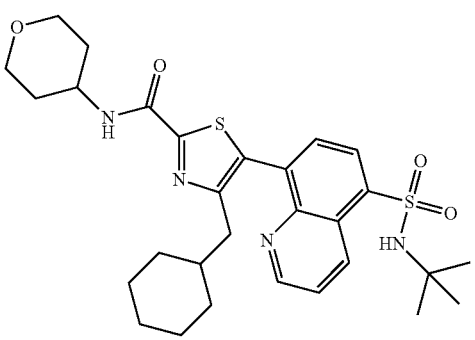 |
| 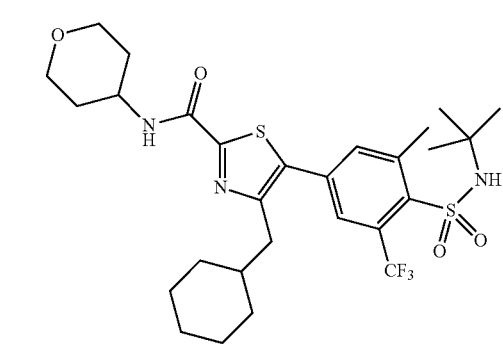 [SMILES: Cc1cc(-c2sc(C(=O)NC3CCOCC3)nc2CC2CCCCC2)cc(C(F)(F)F)c1S(=O)(=O)NC(C)(C)C] | 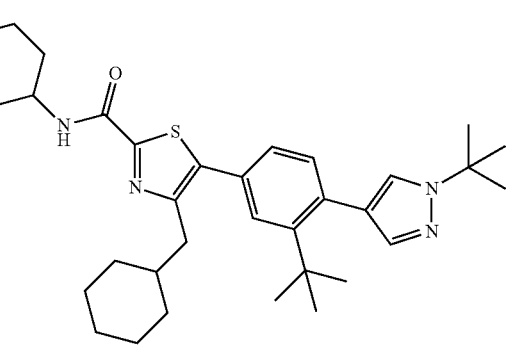 |

| 319 -continued | 320 -continued |
|---|---|
| Structure | Structure |
| 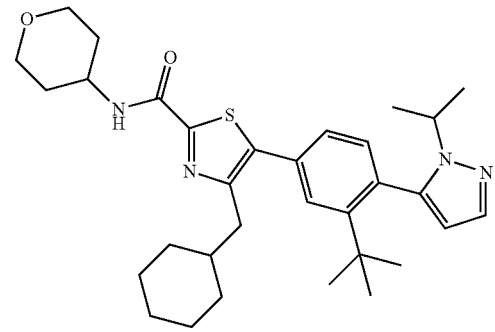 [SMILES: CC(C)n1nccc1-c1ccc(-c2sc(C(=O)NC3CCOCC3)nc2CC2CCCCC2)cc1C(C)(C)C] | 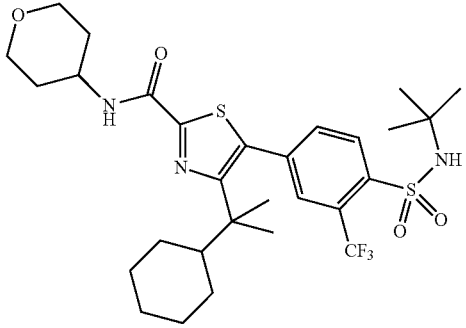 |
| 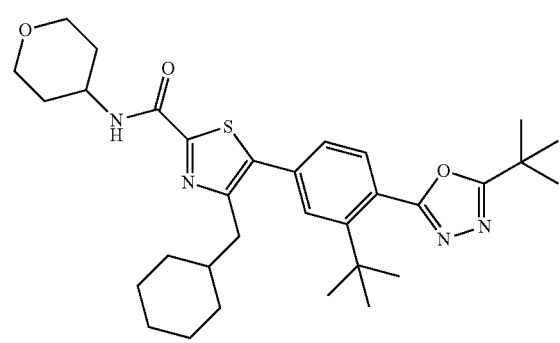 [SMILES: CC(C)(C)c1nnc(-c2ccc(-c3sc(C(=O)NC4CCOCC4)nc3CC3CCCCC3)cc2C(C)(C)C)o1] | 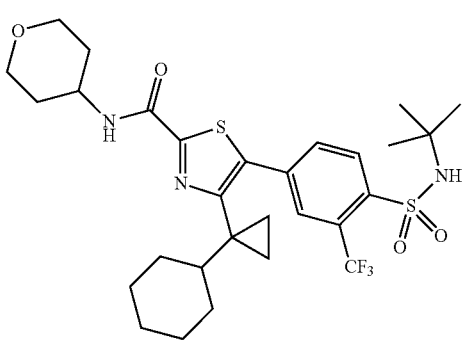 |
| 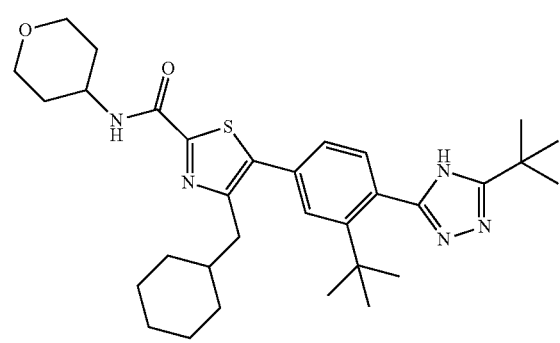 [SMILES: CC(C)(C)c1nnc(-c2ccc(-c3sc(C(=O)NC4CCOCC4)nc3CC3CCCCC3)cc2C(C)(C)C)[nH]1] | 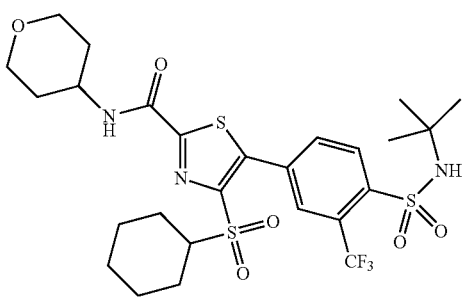 [SMILES: CC(C)(C)NS(=O)(=O)c1ccc(-c2sc(C(=O)NC3CCOCC3)nc2S(=O)(=O)C2CCCCC2)cc1C(F)(F)F] |
| | 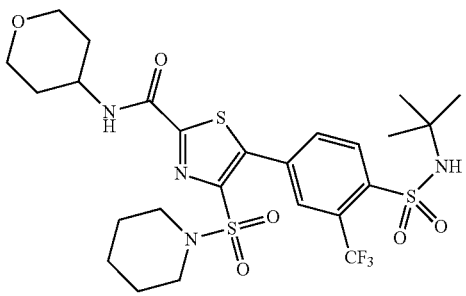 [SMILES: CC(C)(C)NS(=O)(=O)c1ccc(-c2sc(C(=O)NC3CCOCC3)nc2S(=O)(=O)N2CCCCC2)cc1C(F)(F)F] |
| 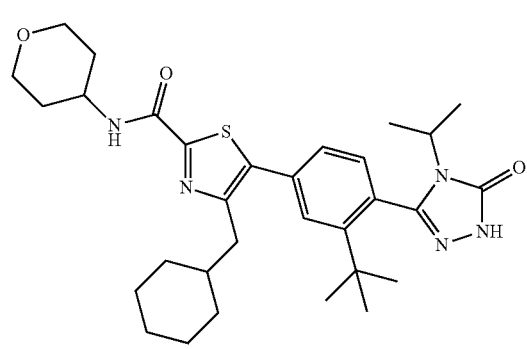 | 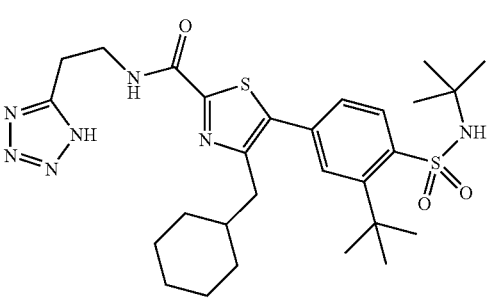 [SMILES: CC(C)(C)NS(=O)(=O)c1ccc(-c2sc(C(=O)NCCc3nnn[nH]3)nc2CC2CCCCC2)cc1C(C)(C)C] |

| 321 -continued | 322 -continued |
|---|---|
| Structure | Structure |
| 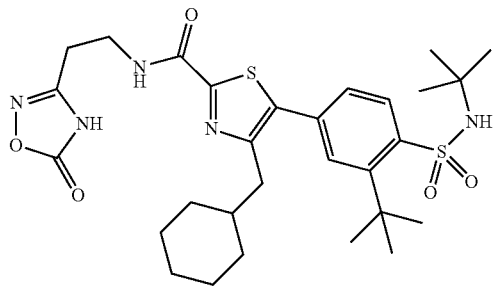 [SMILES: CC(C)(C)NS(=O)(=O)c1ccc(-c2sc(C(=O)NCCc3noc(=O)[nH]3)nc2CC2CCCCC2)cc1C(C)(C)C] | 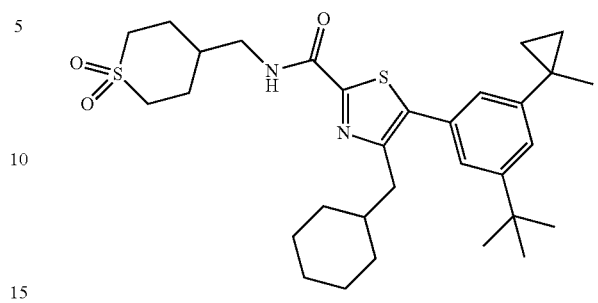 |
| 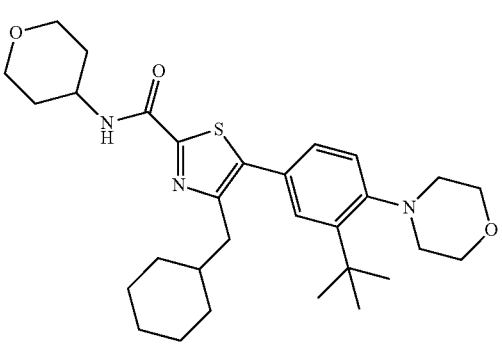 [SMILES: CC(C)(C)c1cc(-c2sc(C(=O)NC3CCOCC3)nc2CC2CCCCC2)ccc1N1CCOCC1] | 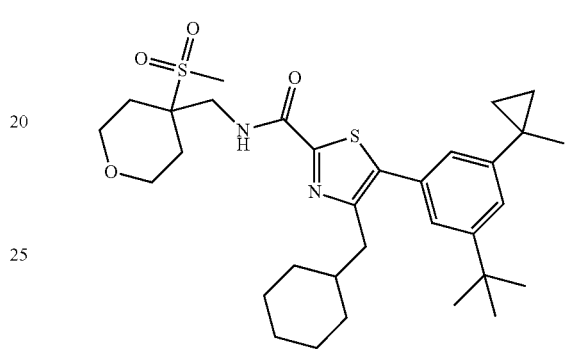 |
| 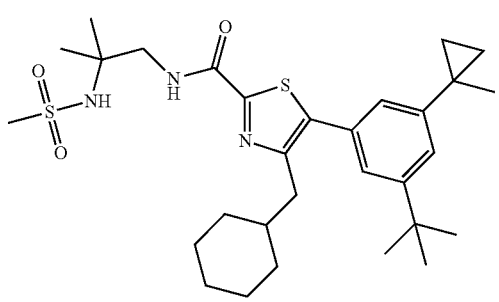 | 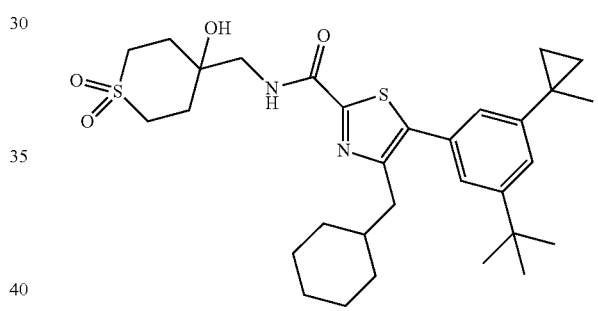 |
| 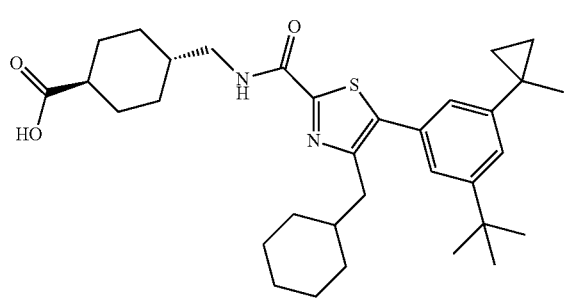 [SMILES: CC(C)(C)c1cc(-c2sc(C(=O)NC[C@H]3CC[C@H](C(=O)O)CC3)nc2CC2CCCCC2)cc(C2(C)CC2)c1] | 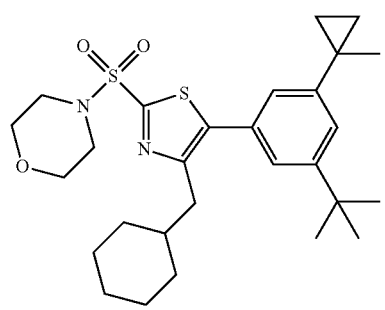 |
| 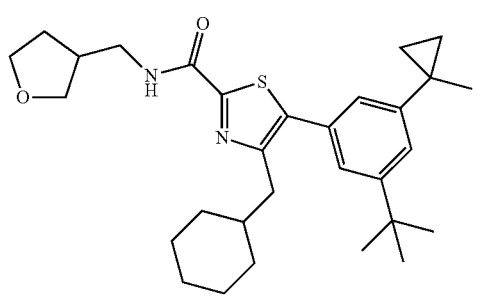 [SMILES: CC(C)(C)c1cc(-c2sc(C(=O)NCC3CCOC3)nc2CC2CCCCC2)cc(C2(C)CC2)c1] | 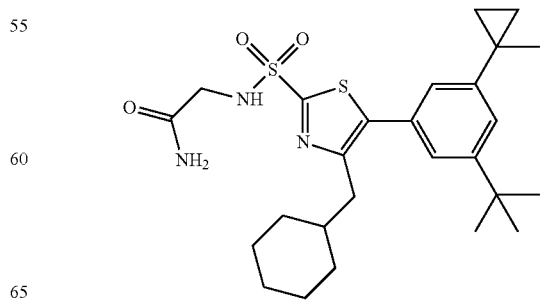 |

| 323 -continued | 324 -continued |
|---|---|
| Structure | Structure |
| 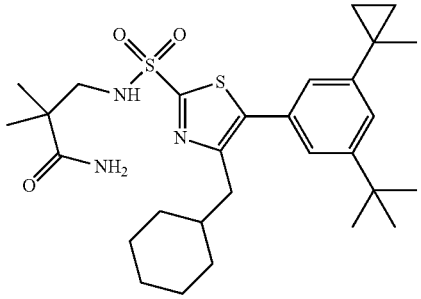 [SMILES: CC(C)(CNS(=O)(=O)c1nc(CC2CCCCC2)c(-c2cc(C(C)(C)C)cc(C3(C)CC3)c2)s1)C(N)=O] | 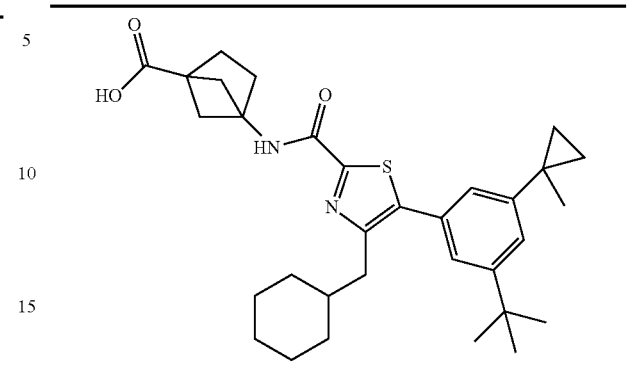 |
| 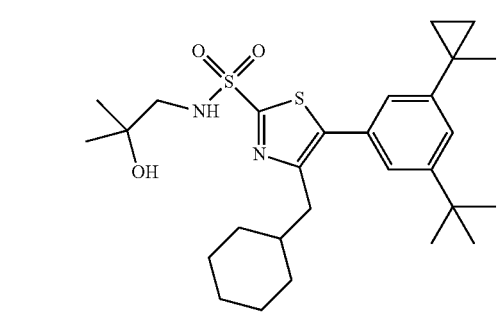 [SMILES: CC(C)(O)CNS(=O)(=O)c1nc(CC2CCCCC2)c(-c2cc(C(C)(C)C)cc(C3(C)CC3)c2)s1] | 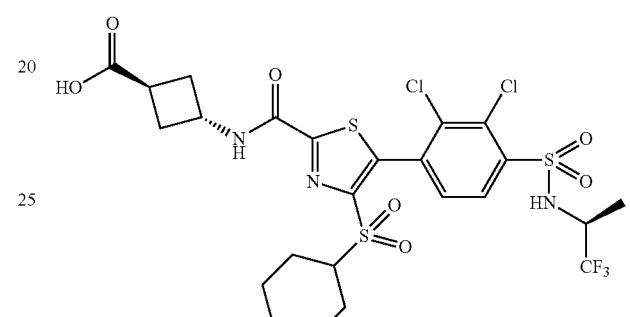 |
| 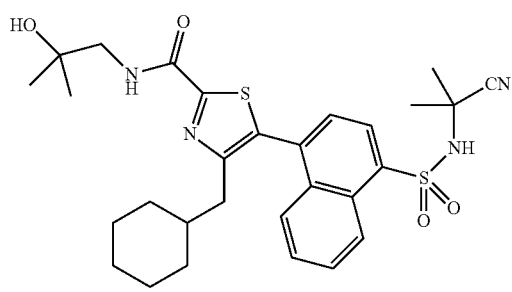 [SMILES: CC(C)(O)CNC(=O)c1nc(CC2CCCCC2)c(-c2ccc(S(=O)(=O)NC(C)(C)C#N)c3ccccc23)s1] | 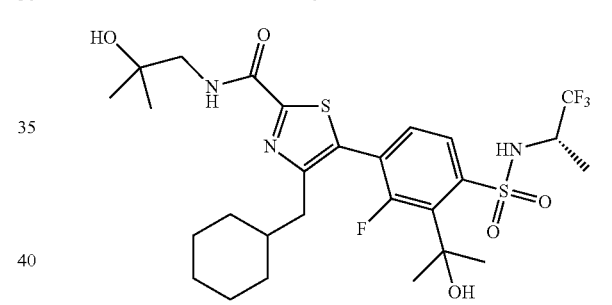 |
|  | 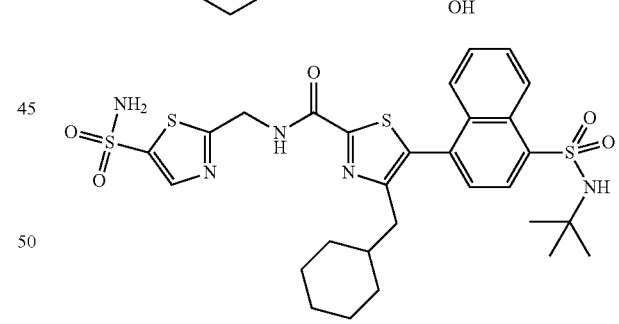 |
| 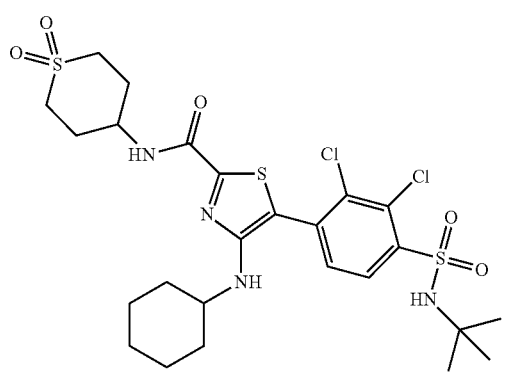 [SMILES: CC(C)(C)NS(=O)(=O)c1ccc(-c2sc(C(=O)NC3CCS(=O)(=O)CC3)nc2NC2CCCCC2)c(Cl)c1Cl] | 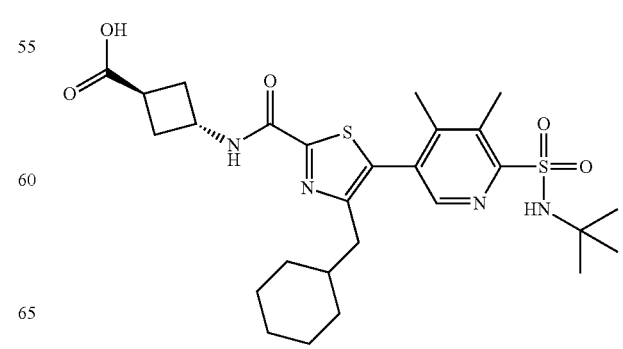 |

US 10,301,272 B2

325
-continued

| Structure |

326
-continued

| Structure |

| 327 -continued | 328 -continued |
|---|---|
| Structure | Structure |
| 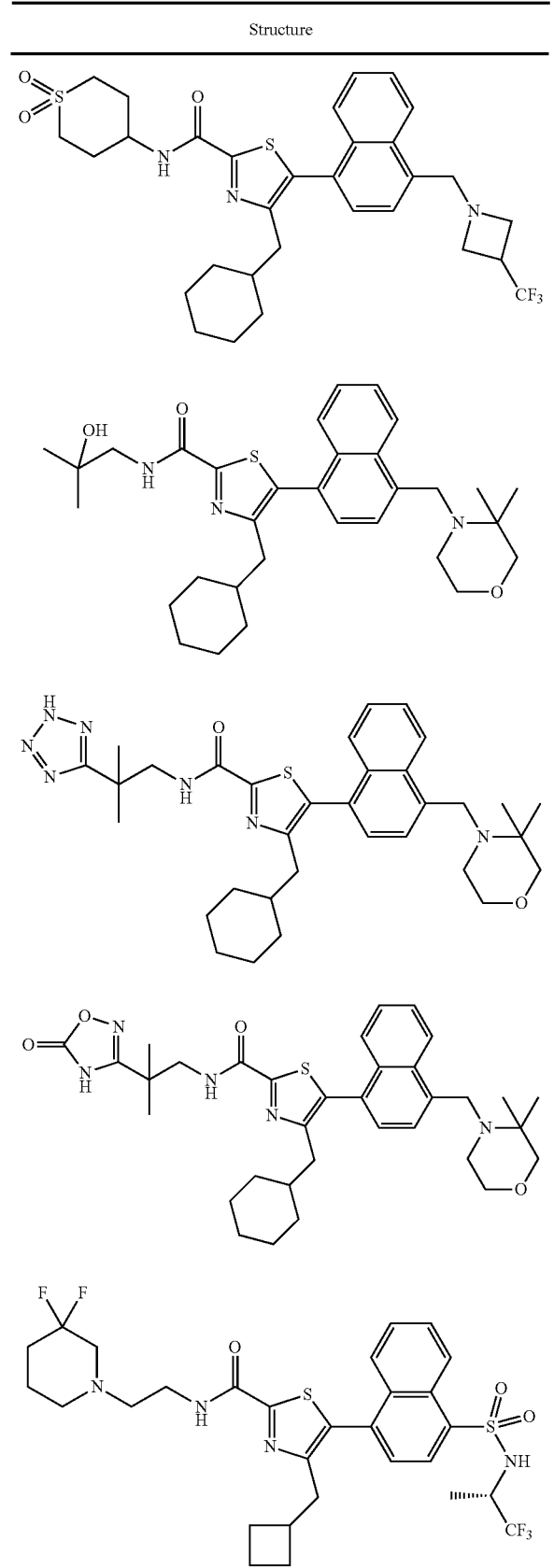 | 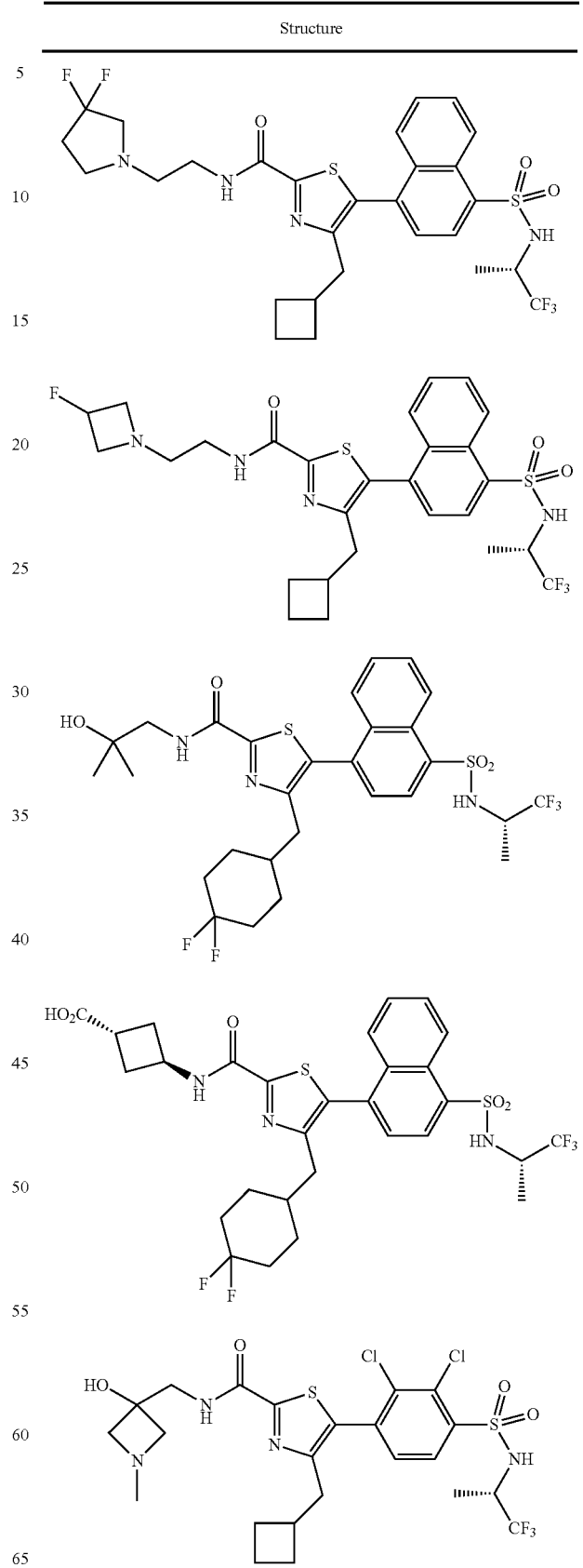 |

| 329 -continued | 330 -continued |
|---|---|
| Structure | Structure |
| 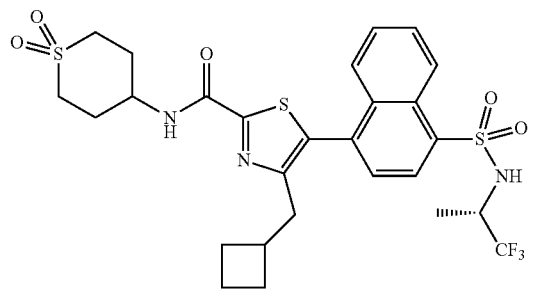 [SMILES: C[C@H](NS(=O)(=O)c1ccc(-c2sc(C(=O)NC3CCS(=O)(=O)CC3)nc2CC2CCC2)c2ccccc12)C(F)(F)F] | 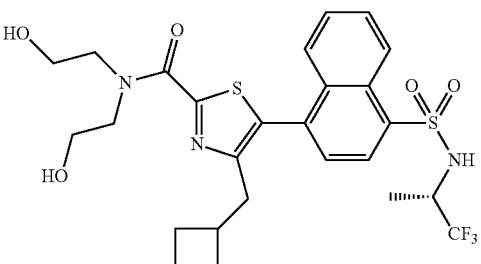 |
| 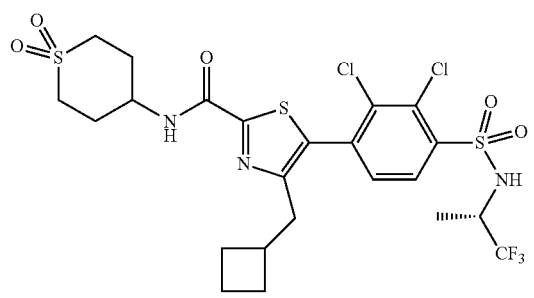 [SMILES: C[C@H](NS(=O)(=O)c1ccc(-c2sc(C(=O)NC3CCS(=O)(=O)CC3)nc2CC2CCC2)c(Cl)c1Cl)C(F)(F)F] | 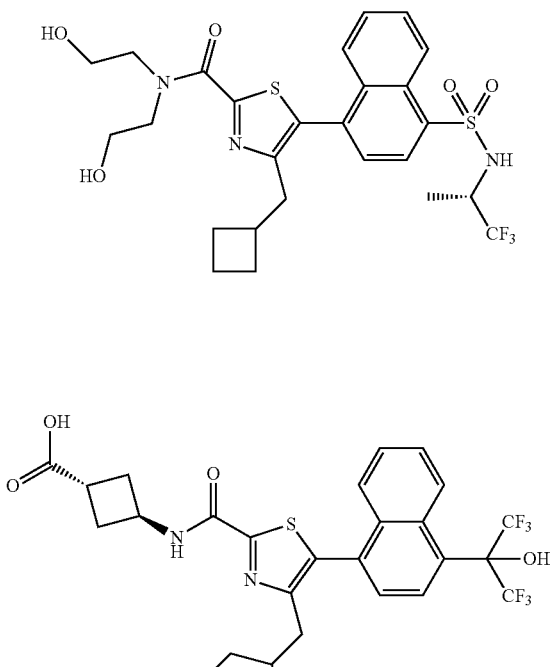 |
| 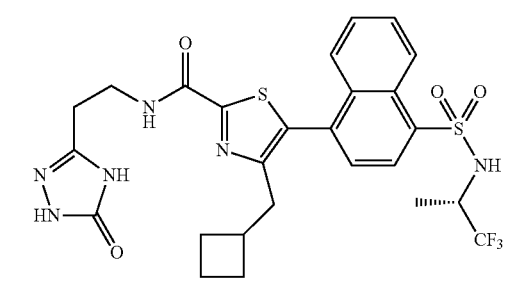 [SMILES: C[C@H](NS(=O)(=O)c1ccc(-c2sc(C(=O)NCCc3n[nH]c(=O)[nH]3)nc2CC2CCC2)c2ccccc12)C(F)(F)F] | |
| 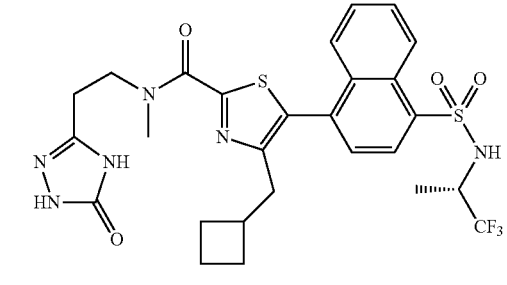 [SMILES: C[C@H](NS(=O)(=O)c1ccc(-c2sc(C(=O)N(C)CCc3n[nH]c(=O)[nH]3)nc2CC2CCC2)c2ccccc12)C(F)(F)F] | 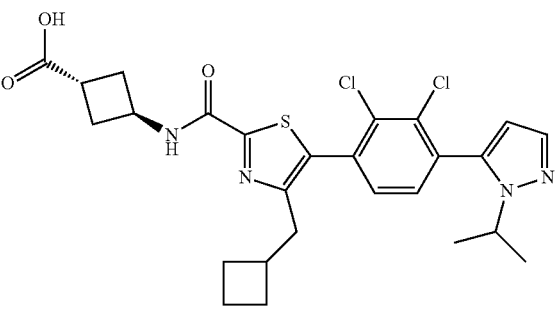 |
| 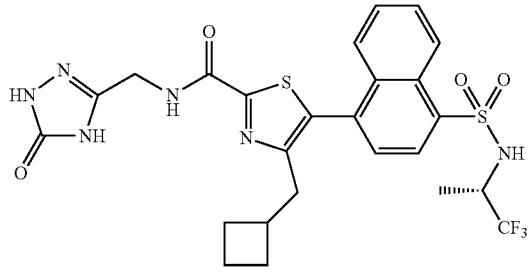 [SMILES: C[C@H](NS(=O)(=O)c1ccc(-c2sc(C(=O)NCc3n[nH]c(=O)[nH]3)nc2CC2CCC2)c2ccccc12)C(F)(F)F] | 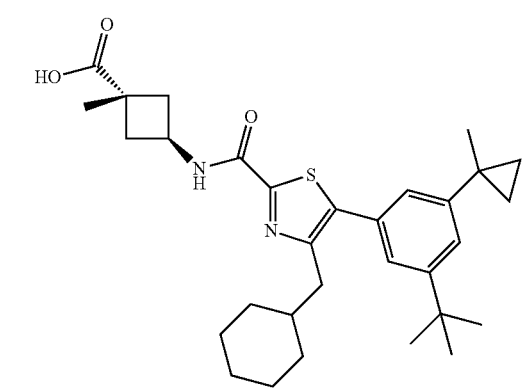 [SMILES: CC(C)(C)c1cc(-c2sc(C(=O)N[C@H]3C[C@](C)(C(=O)O)C3)nc2CC2CCCCC2)cc(C2(C)CC2)c1] |

US 10,301,272 B2
| 331 -continued | 332 -continued |
|---|---|
| Structure | Structure |
| 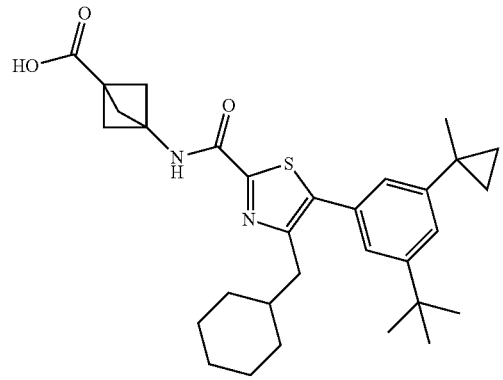 [SMILES: CC(C)(C)c1cc(-c2sc(C(=O)NC34CC(C(=O)O)(C3)C4)nc2CC2CCCCC2)cc(C2(C)CC2)c1] | 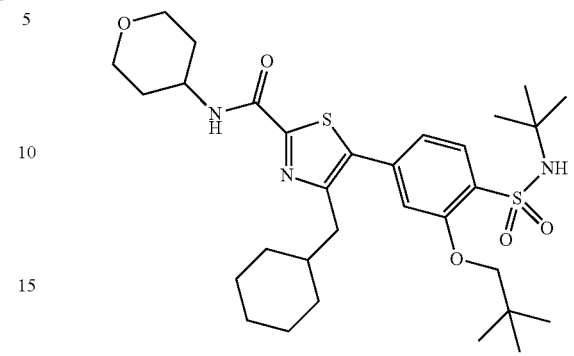 |
| 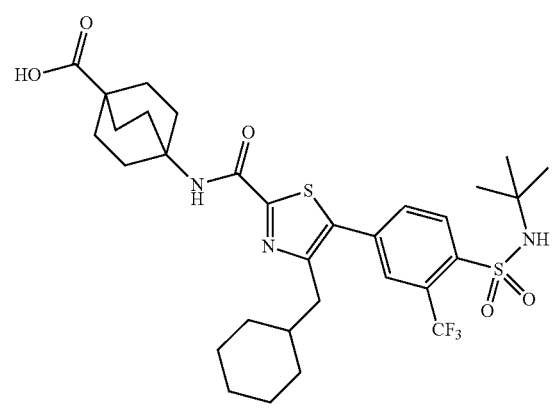 [SMILES: CC(C)(C)NS(=O)(=O)c1ccc(-c2sc(C(=O)NC34CCC(C(=O)O)(CC3)CC4)nc2CC2CCCCC2)cc1C(F)(F)F] | 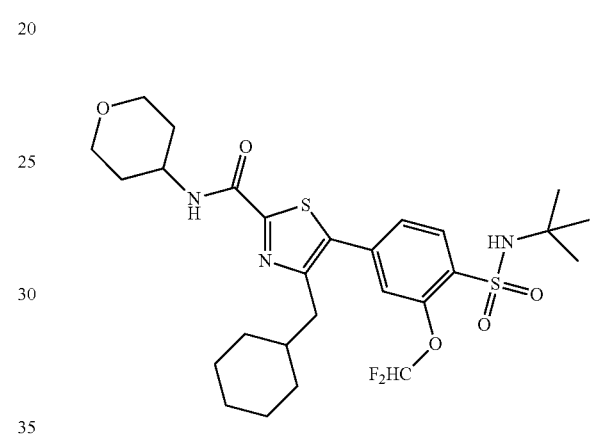 |
| 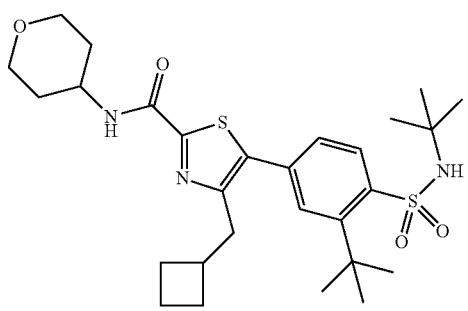 [SMILES: CC(C)(C)NS(=O)(=O)c1ccc(-c2sc(C(=O)NC3CCOCC3)nc2CC2CCC2)cc1C(C)(C)C] | 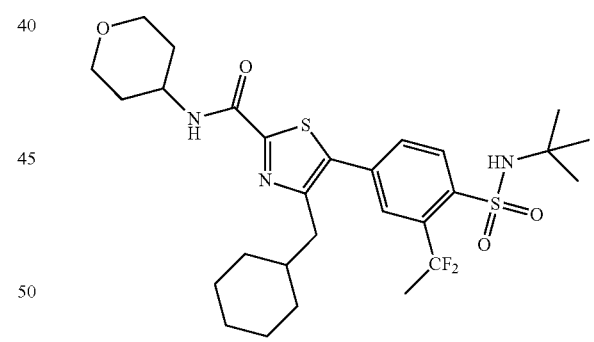 |
| 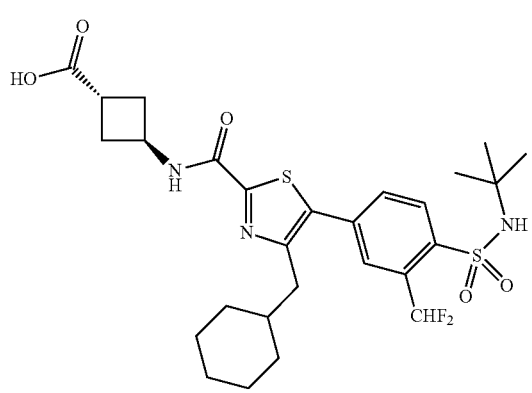 [SMILES: CC(C)(C)NS(=O)(=O)c1ccc(-c2sc(C(=O)N[C@H]3C[C@H](C(=O)O)C3)nc2CC2CCCCC2)cc1C(F)F] | 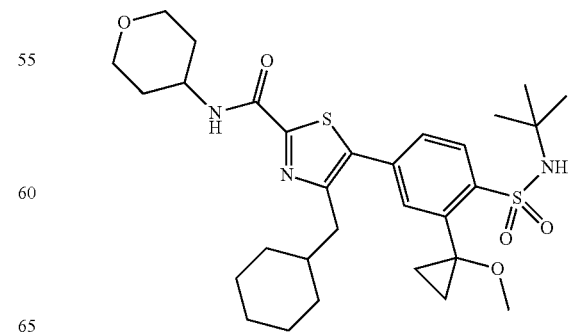 |

| 333 -continued | 334 -continued |
|---|---|
| Structure | Structure |
| 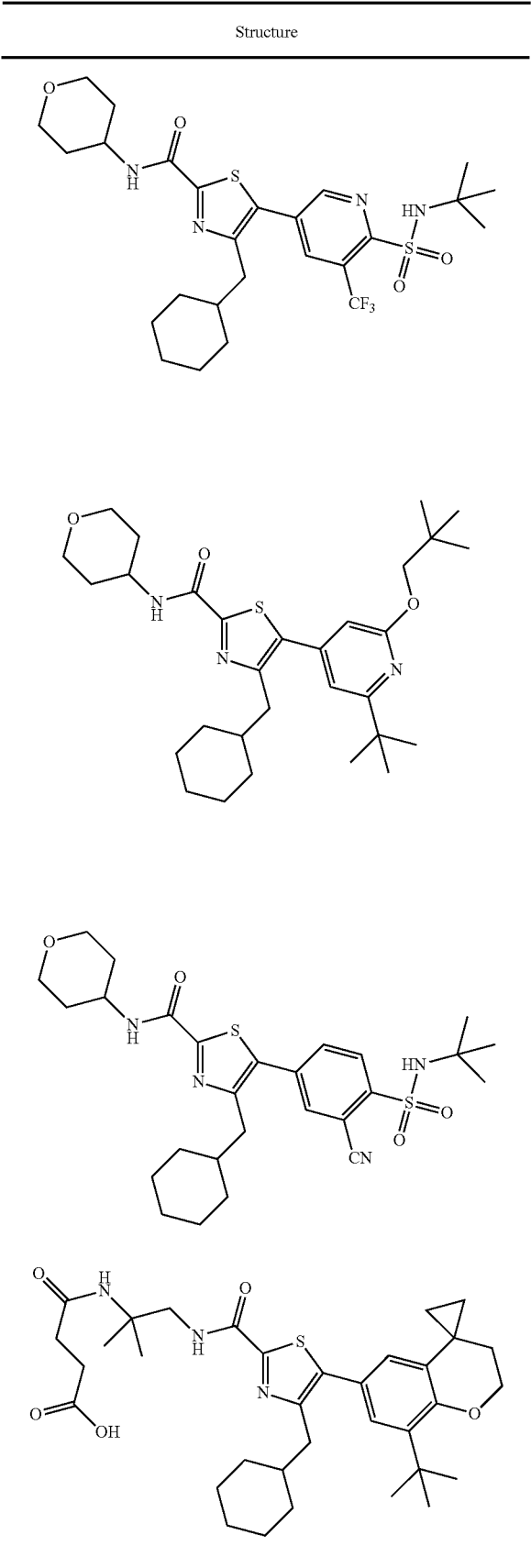 | 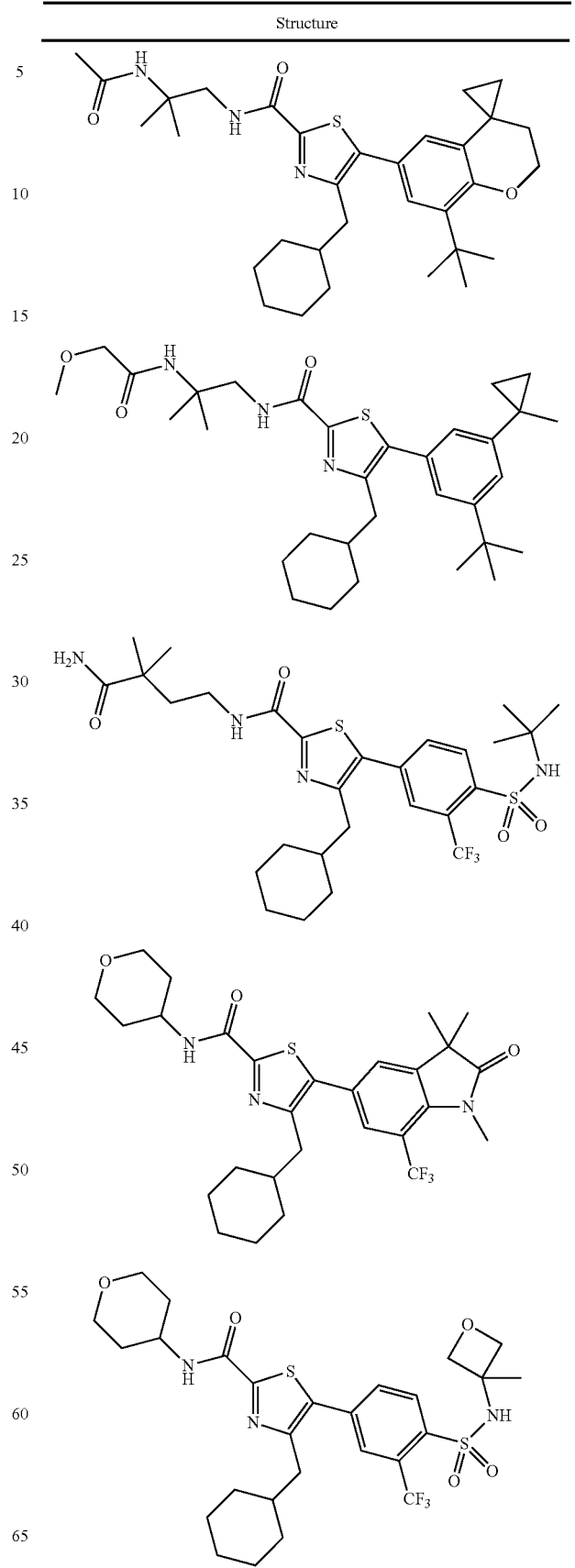 |

| 335 -continued | 336 -continued |
|---|---|
| Structure | Structure |
| 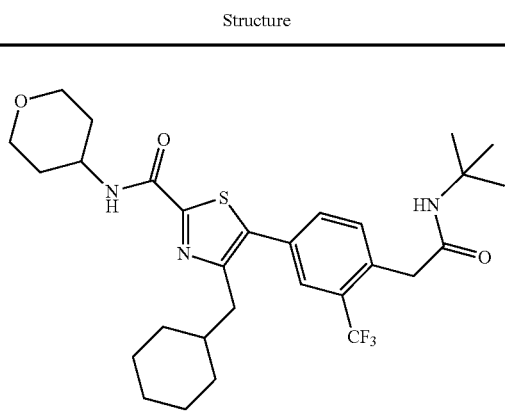 | 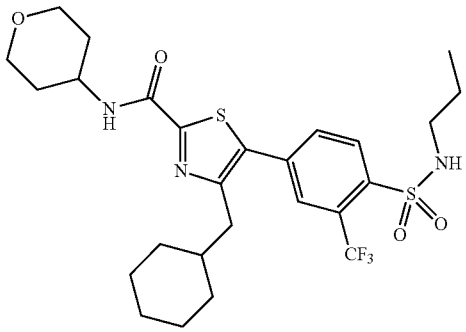 |
| 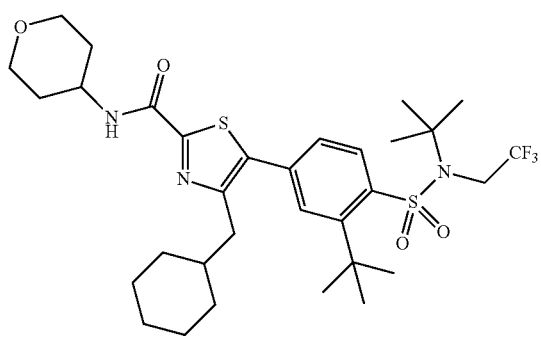 [SMILES: CC(C)(C)c1cc(-c2sc(C(=O)NC3CCOCC3)nc2CC2CCCCC2)ccc1S(=O)(=O)N(CC(F)(F)F)C(C)(C)C] | 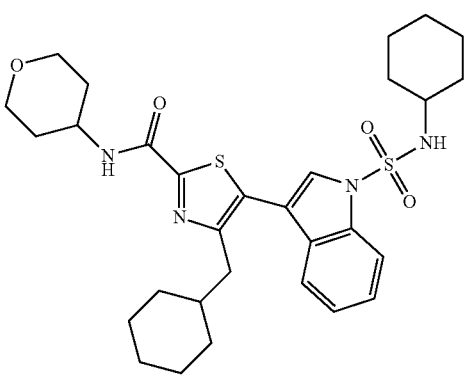 [SMILES: O=C(NC1CCOCC1)c1nc(CC2CCCCC2)c(-c2cn(S(=O)(=O)NC3CCCCC3)c3ccccc23)s1] |
| 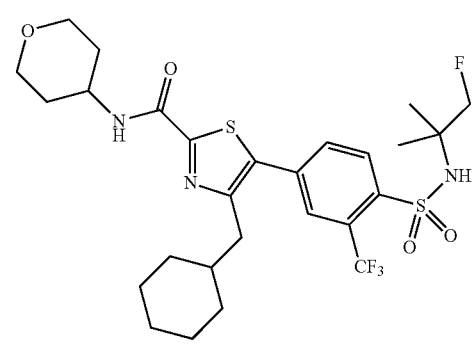 [SMILES: CCC(C)(C)NS(=O)(=O)c1ccc(-c2sc(C(=O)NC3CCOCC3)nc2CC2CCCCC2)cc1C(F)(F)F] | 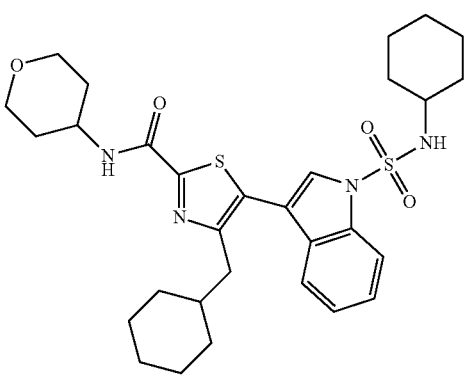 [SMILES: O=C(NC1CCOCC1)c1nc(CC2CCCCC2)c(-c2cn(S(=O)(=O)NC3CCCCC3)c3ccccc23)s1] |
| 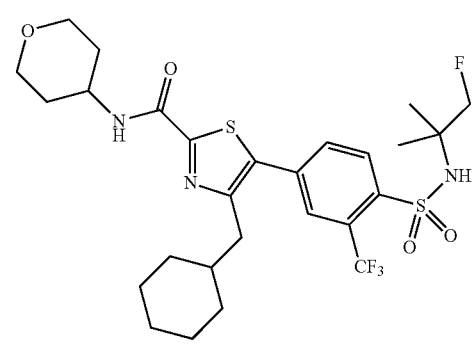 [SMILES: CCC(C)(C)NS(=O)(=O)c1ccc(-c2sc(C(=O)NC3CCOCC3)nc2CC2CCCCC2)cc1C(F)(F)F] | 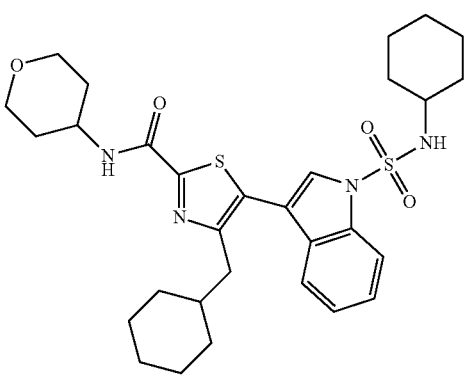 [SMILES: O=C(NC1CCOCC1)c1nc(CC2CCCCC2)c(-c2cn(S(=O)(=O)NC3CCCCC3)c3ccccc23)s1] |

| 337 -continued | 338 -continued |
|---|---|
| Structure | Structure |
| 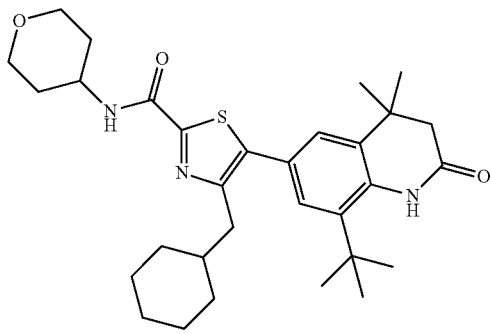 [SMILES: CC(C)(C)c1cc(-c2sc(C(=O)NC3CCOCC3)nc2CC2CCCCC2)cc2c1NC(=O)CC2(C)C] | 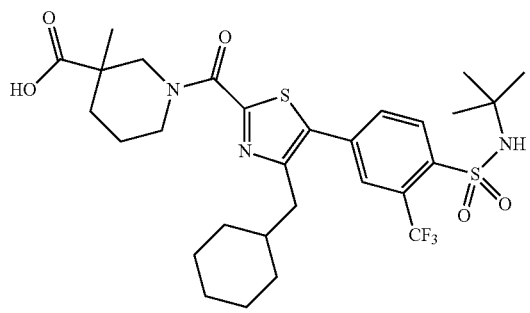 |
| 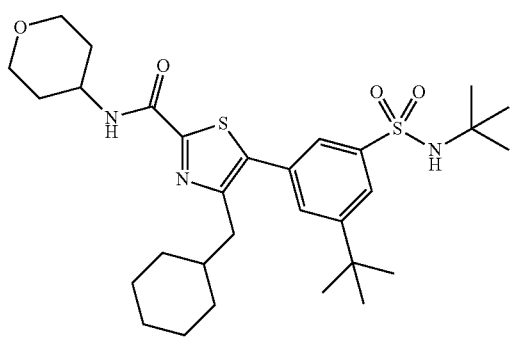 [SMILES: CC(C)(C)NS(=O)(=O)c1cc(-c2sc(C(=O)NC3CCOCC3)nc2CC2CCCCC2)cc(C(C)(C)C)c1] | 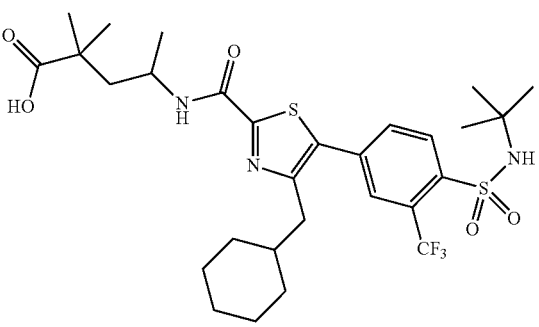 |
| 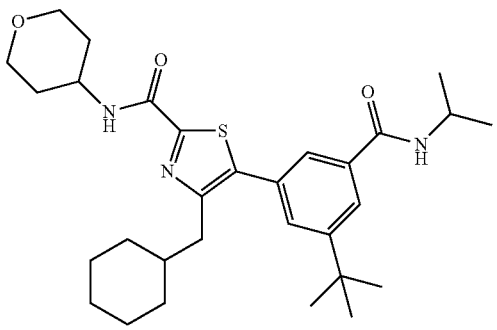 [SMILES: CC(C)NC(=O)c1cc(-c2sc(C(=O)NC3CCOCC3)nc2CC2CCCCC2)cc(C(C)(C)C)c1] | 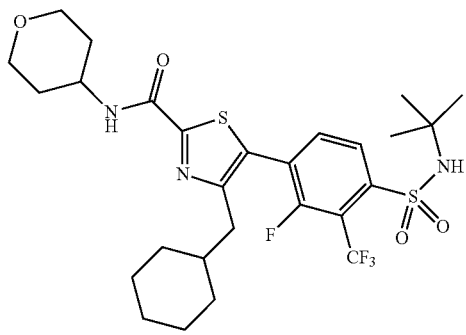 |
| 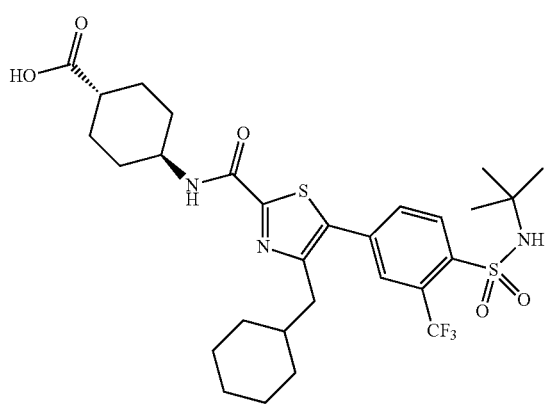 [SMILES: CC(C)(C)NS(=O)(=O)c1ccc(-c2sc(C(=O)N[C@H]3CC[C@H](C(=O)O)CC3)nc2CC2CCCCC2)cc1C(F)(F)F] | 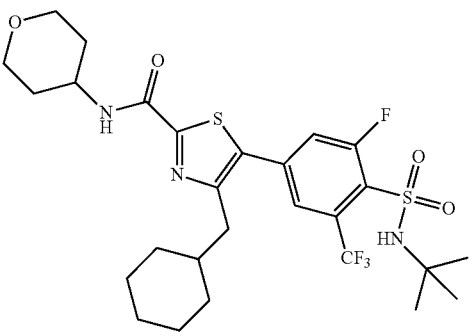 [SMILES: CC(C)(C)NS(=O)(=O)c1c(F)cc(-c2sc(C(=O)NC3CCOCC3)nc2CC2CCCCC2)cc1C(F)(F)F] |

| 339 -continued | 340 -continued |
|---|---|
| Structure | Structure |
| 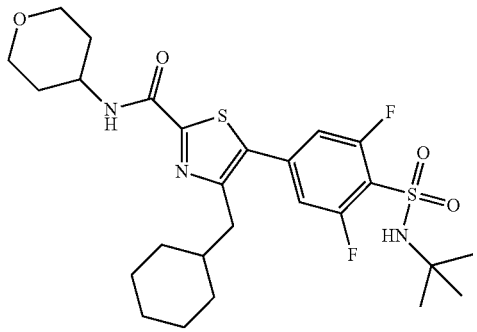 [SMILES: CC(C)(C)NS(=O)(=O)c1c(F)cc(-c2sc(C(=O)NC3CCOCC3)nc2CC2CCCCC2)cc1F] | 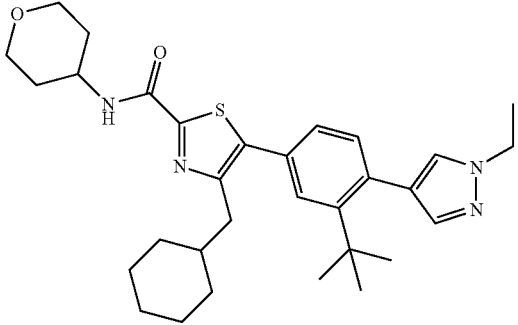 |
| 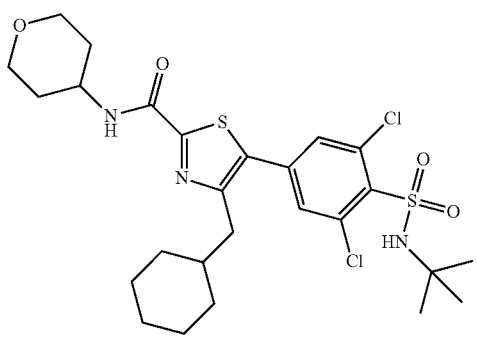 [SMILES: CC(C)(C)NS(=O)(=O)c1c(Cl)cc(-c2sc(C(=O)NC3CCOCC3)nc2CC2CCCCC2)cc1Cl] | 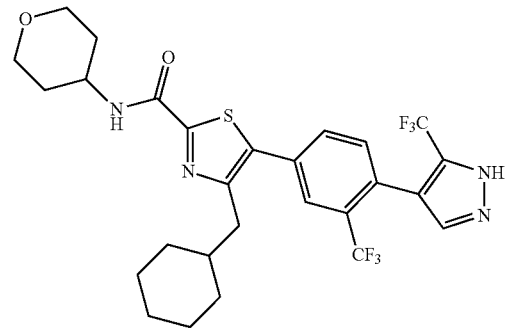 |
| 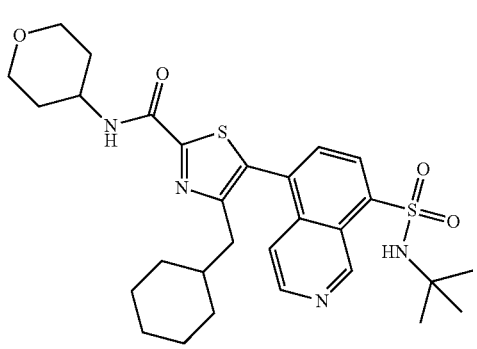 [SMILES: CC(C)(C)NS(=O)(=O)c1ccc(-c2sc(C(=O)NC3CCOCC3)nc2CC2CCCCC2)c2ccncc12] | 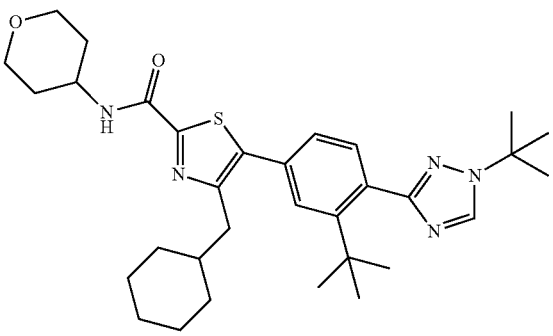 |
| 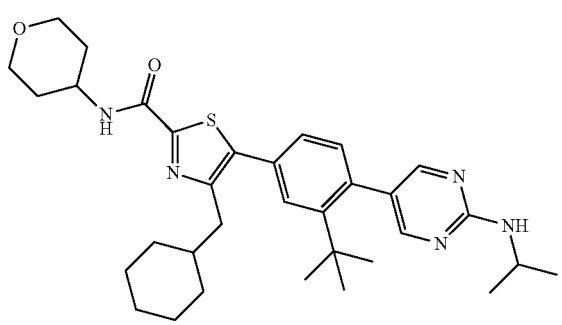 [SMILES: CC(C)Nc1ncc(-c2ccc(-c3sc(C(=O)NC4CCOCC4)nc3CC3CCCCC3)cc2C(C)(C)C)cn1] | 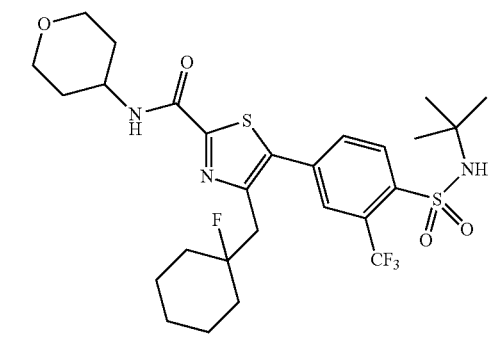 [SMILES: CC(C)(C)NS(=O)(=O)c1ccc(-c2sc(C(=O)NC3CCOCC3)nc2CC2(F)CCCCC2)cc1C(F)(F)F] |

| 341 -continued | 342 -continued |
|---|---|
| Structure | Structure |
| 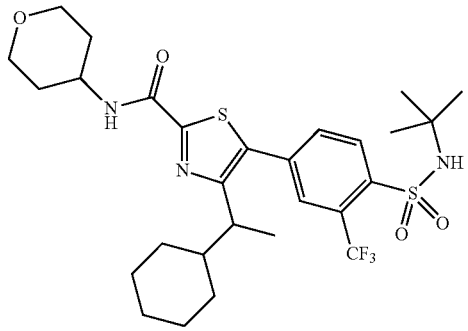 [SMILES: CC(c1nc(C(=O)NC2CCOCC2)sc1-c1ccc(S(=O)(=O)NC(C)(C)C)c(C(F)(F)F)c1)C1CCCCC1] | 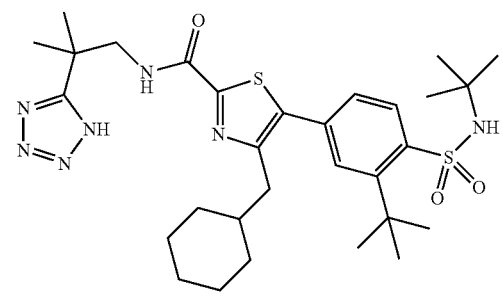 |
| 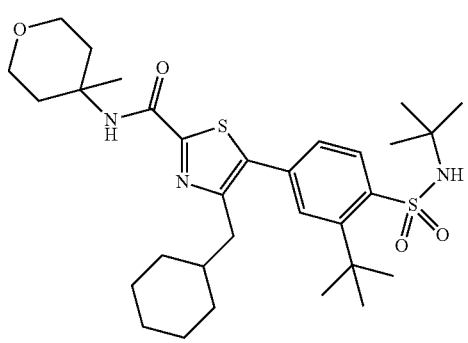 [SMILES: CC(C)(C)NS(=O)(=O)c1ccc(-c2sc(C(=O)NC3(C)CCOCC3)nc2CC2CCCCC2)cc1C(C)(C)C] | 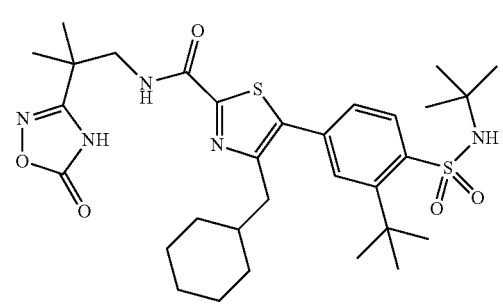 |
| 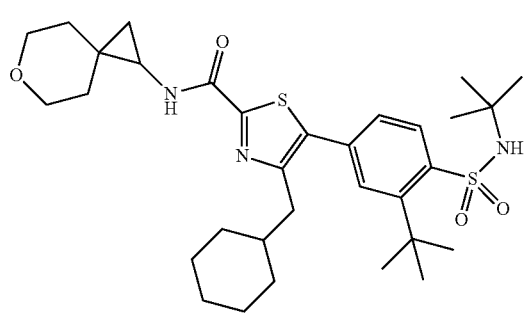 [SMILES: CC(C)(C)NS(=O)(=O)c1ccc(-c2sc(C(=O)NC3CC34CCOCC4)nc2CC2CCCCC2)cc1C(C)(C)C] | 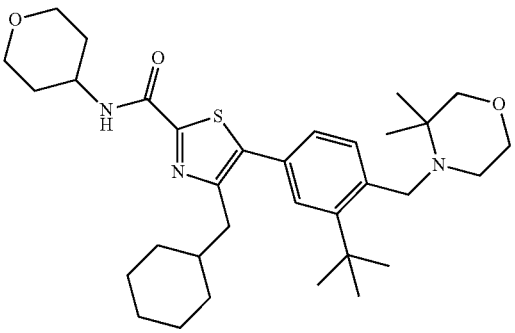 |
| 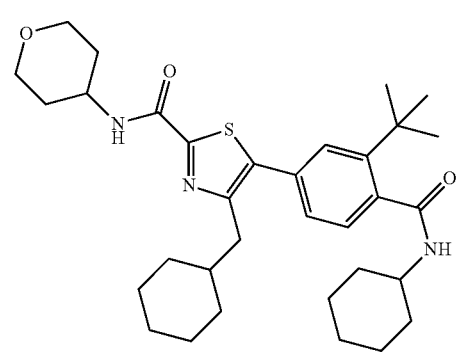 [SMILES: CC(C)(C)c1cc(-c2sc(C(=O)NC3CCOCC3)nc2CC2CCCCC2)ccc1C(=O)NC1CCCCC1] | 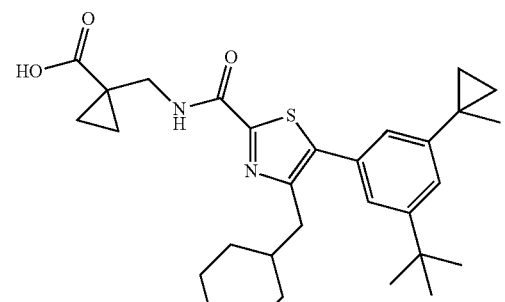 |

| 343 -continued | 344 -continued |
|---|---|
| Structure | Structure |
| 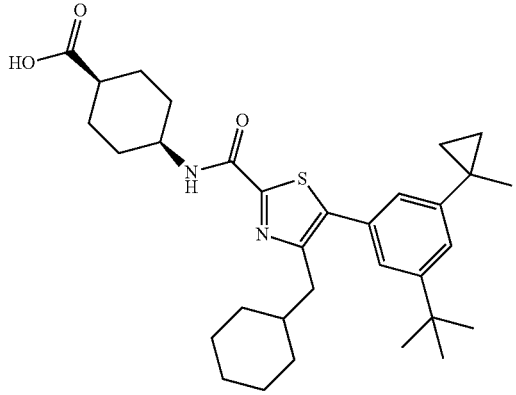 [SMILES: CC(C)(C)c1cc(-c2sc(C(=O)N[C@H]3CC[C@@H](C(=O)O)CC3)nc2CC2CCCCC2)cc(C2(C)CC2)c1] | 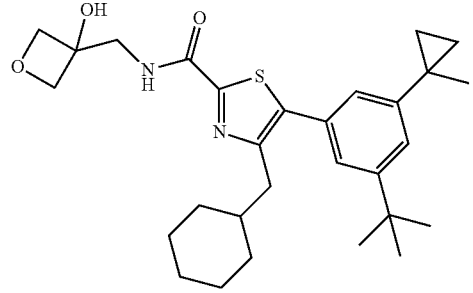 |
| 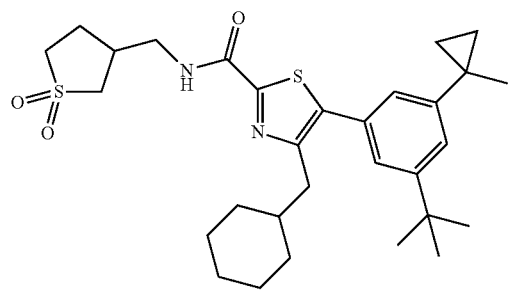 [SMILES: CC(C)(C)c1cc(-c2sc(C(=O)NCC3CCS(=O)(=O)C3)nc2CC2CCCCC2)cc(C2(C)CC2)c1] | 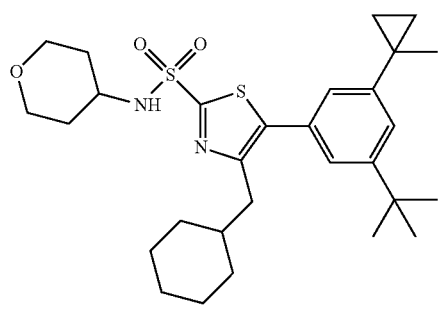 |
| 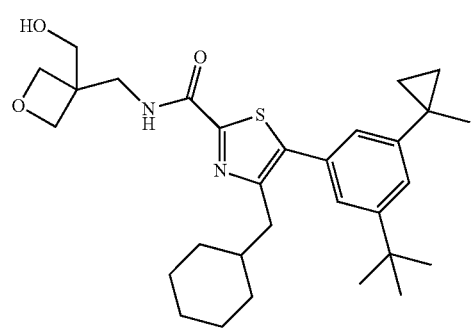 [SMILES: CC(C)(C)c1cc(-c2sc(C(=O)NCC3(CO)COC3)nc2CC2CCCCC2)cc(C2(C)CC2)c1] | 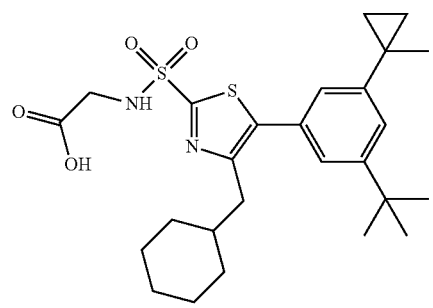 |
| 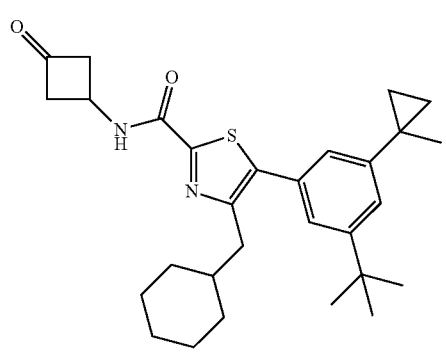 [SMILES: CC(C)(C)c1cc(-c2sc(C(=O)NC3CC(=O)C3)nc2CC2CCCCC2)cc(C2(C)CC2)c1] | 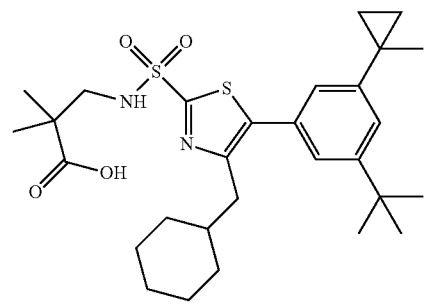 [SMILES: CC(C)(CNS(=O)(=O)c1nc(CC2CCCCC2)c(-c2cc(C(C)(C)C)cc(C3(C)CC3)c2)s1)C(=O)O] |
| | 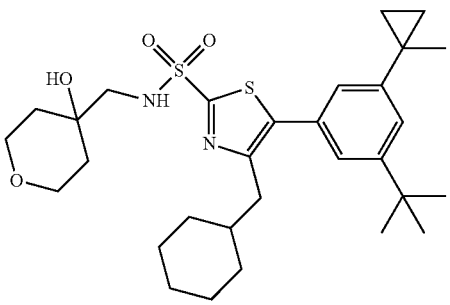 [SMILES: CC(C)(C)c1cc(-c2sc(S(=O)(=O)NCC3(O)CCOCC3)nc2CC2CCCCC2)cc(C2(C)CC2)c1] |

| 345 -continued | 346 -continued |
|---|---|
| Structure | Structure |
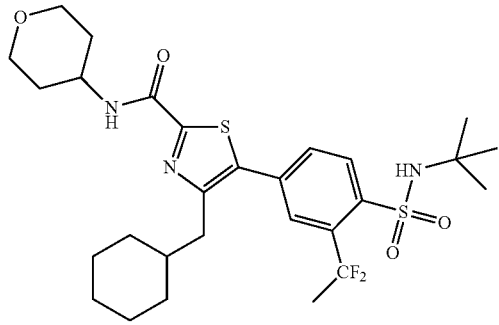 [SMILES: CC(C)(C)NS(=O)(=O)c1ccc(-c2sc(C(=O)NC3CCOCC3)nc2CC2CCCCC2)cc1C(C)(F)F]
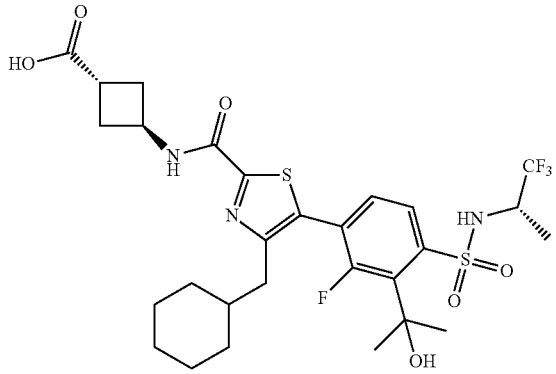 [SMILES: C[C@H](NS(=O)(=O)c1ccc(-c2sc(C(=O)N[C@H]3C[C@H](C(=O)O)C3)nc2CC2CCCCC2)c(F)c1C(C)(C)O)C(F)(F)F]
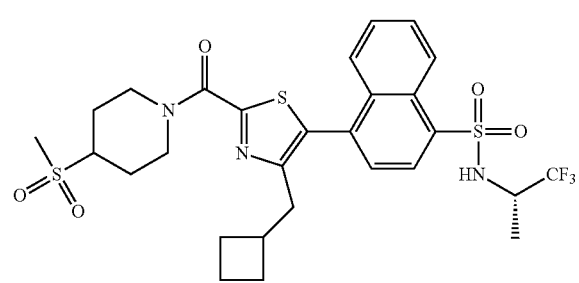 [SMILES: C[C@H](NS(=O)(=O)c1ccc(-c2sc(C(=O)N3CCC(S(C)(=O)=O)CC3)nc2CC2CCC2)c2ccccc12)C(F)(F)F]

347
-continued
Structure
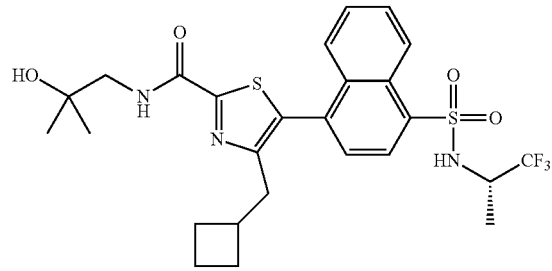 [SMILES: C[C@H](NS(=O)(=O)c1ccc(-c2sc(C(=O)NCC(C)(C)O)nc2CC2CCC2)c2ccccc12)C(F)(F)F]
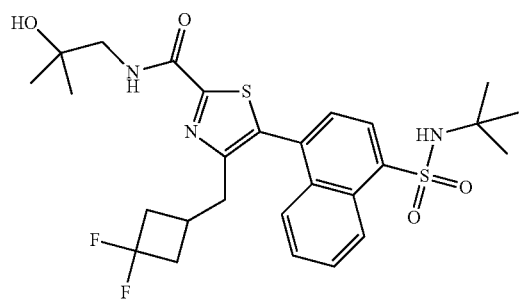 [SMILES: CC(C)(O)CNC(=O)c1nc(CC2CC(F)(F)C2)c(-c2ccc(S(=O)(=O)NC(C)(C)C)c3ccccc23)s1]
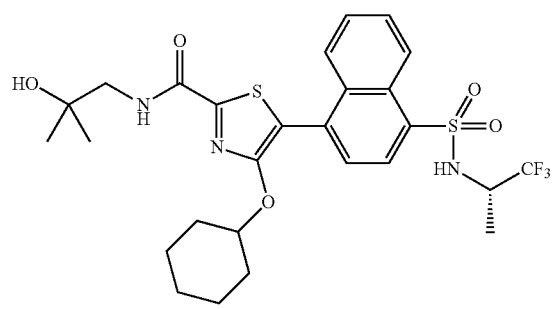 [SMILES: C[C@H](NS(=O)(=O)c1ccc(-c2sc(C(=O)NCC(C)(C)O)nc2OC2CCCCC2)c2ccccc12)C(F)(F)F]
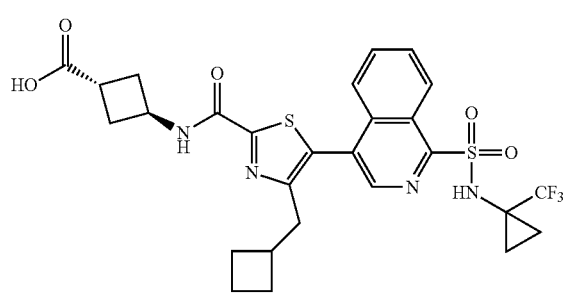 [SMILES: O=C(N[C@H]1C[C@H](C(=O)O)C1)c1nc(CC2CCC2)c(-c2cnc(S(=O)(=O)NC3(C(F)(F)F)CC3)c3ccccc23)s1]
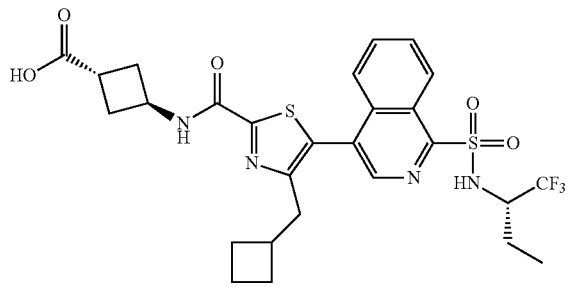
348
-continued
Structure
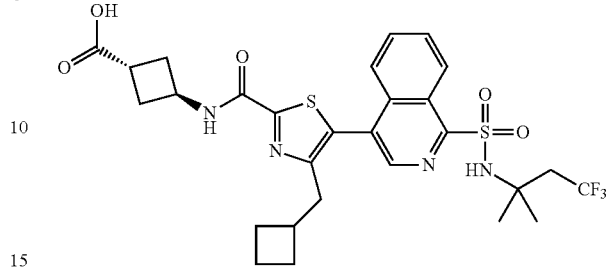
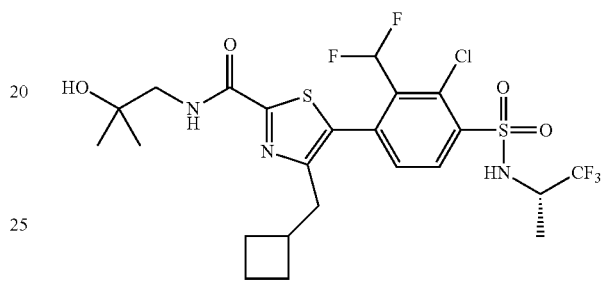
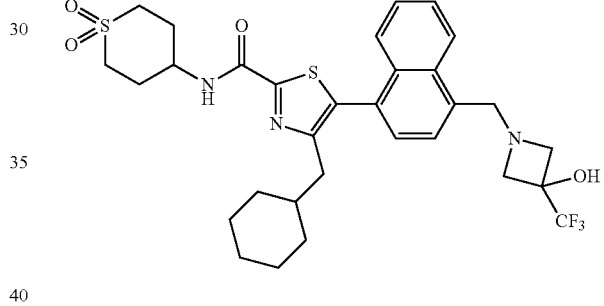
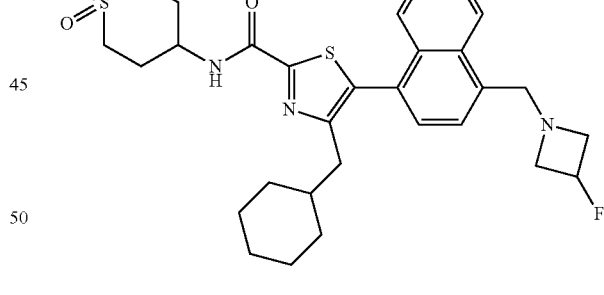
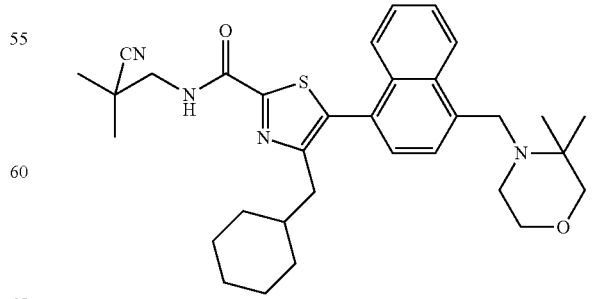

| 349 -continued | 350 -continued |
|---|---|
| Structure | Structure |
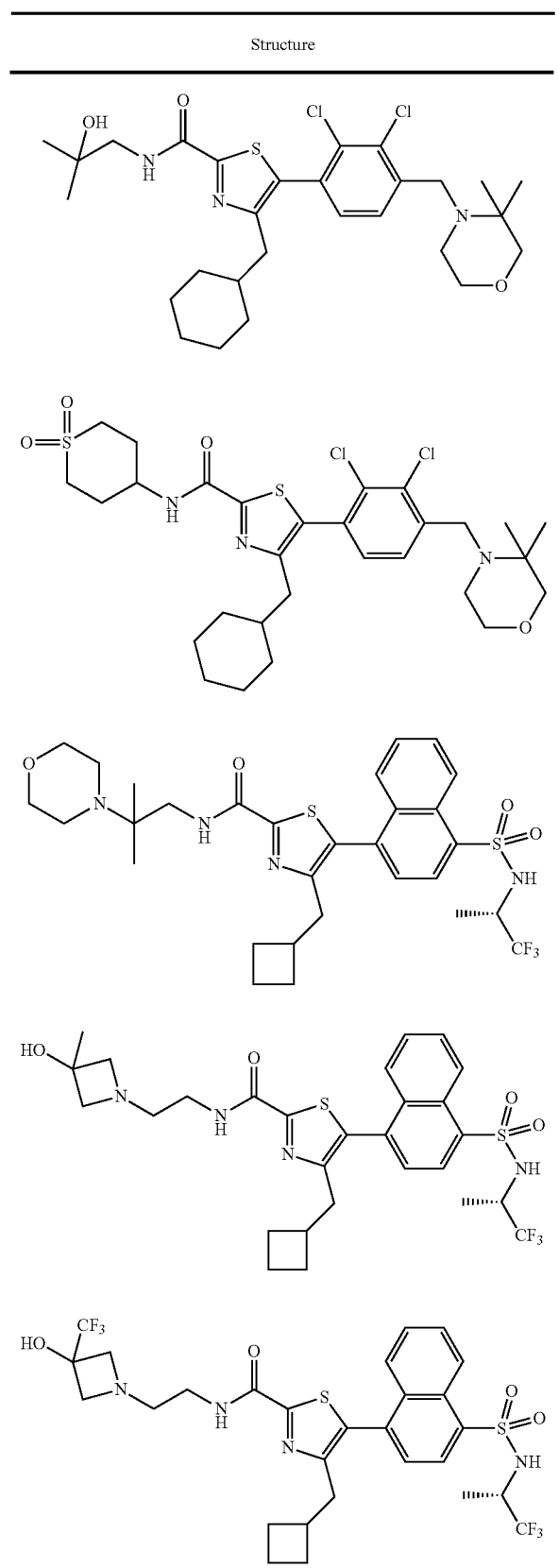
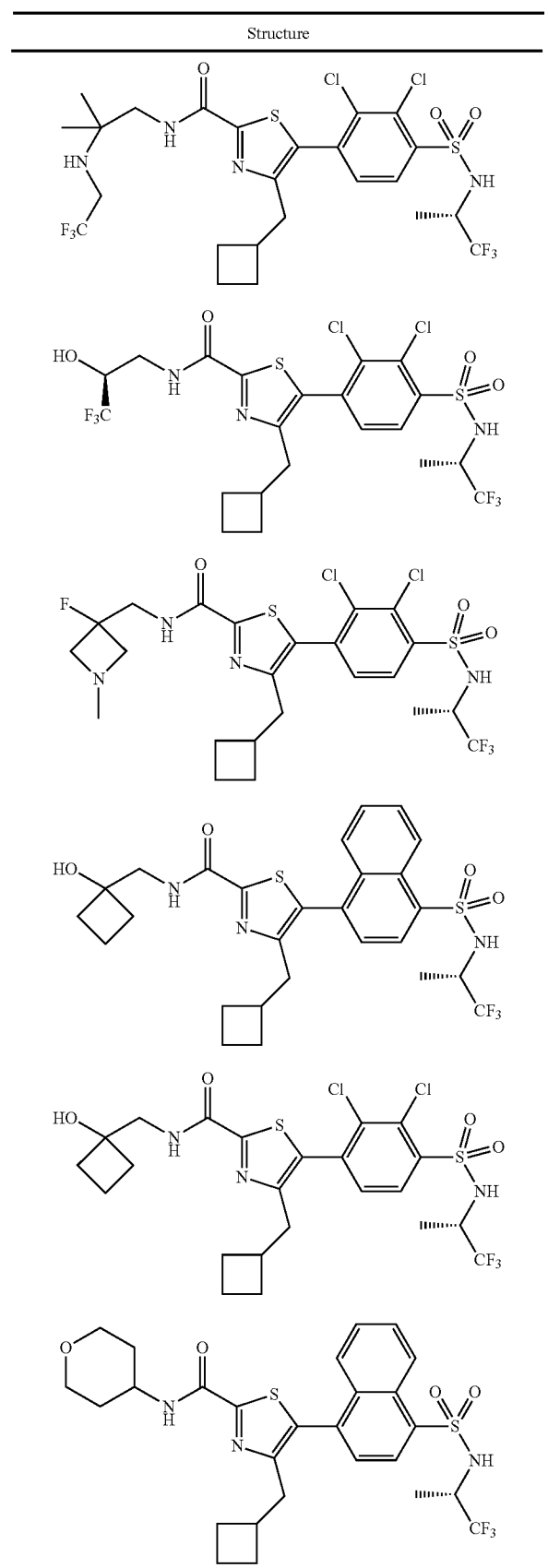

| 351 -continued | 352 -continued |
|---|---|
| Structure | Structure |
| 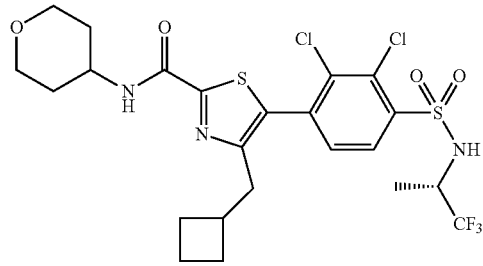 [SMILES: C[C@H](NS(=O)(=O)c1ccc(-c2sc(C(=O)NC3CCOCC3)nc2CC2CCC2)c(Cl)c1Cl)C(F)(F)F] | 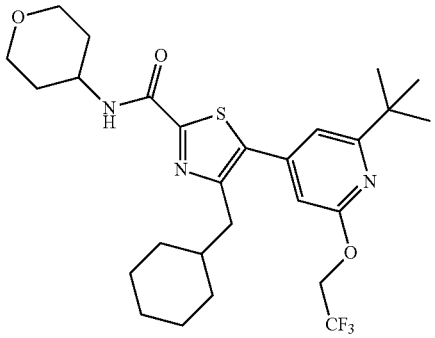 |
| 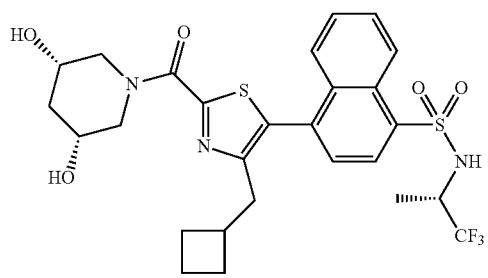 [SMILES: C[C@H](NS(=O)(=O)c1ccc(-c2sc(C(=O)N3C[C@H](O)C[C@H](O)C3)nc2CC2CCC2)c2ccccc12)C(F)(F)F] | |
| 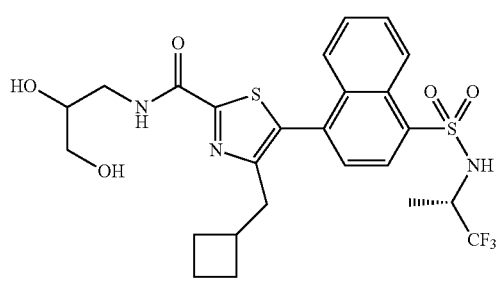 [SMILES: C[C@H](NS(=O)(=O)c1ccc(-c2sc(C(=O)NCC(O)CO)nc2CC2CCC2)c2ccccc12)C(F)(F)F] | 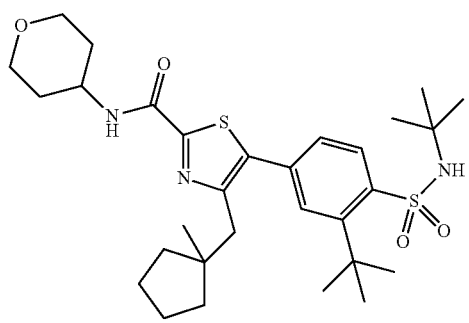 |
| 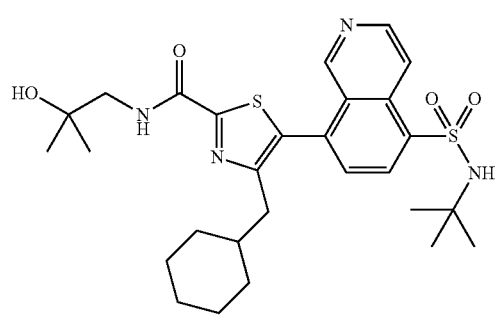 [SMILES: CC(C)(O)CNC(=O)c1nc(CC2CCCCC2)c(-c2ccc(S(=O)(=O)NC(C)(C)C)c3ccncc23)s1] | 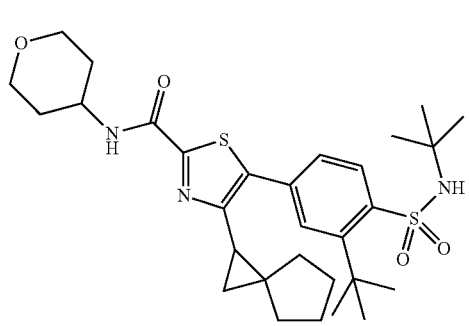 |
| 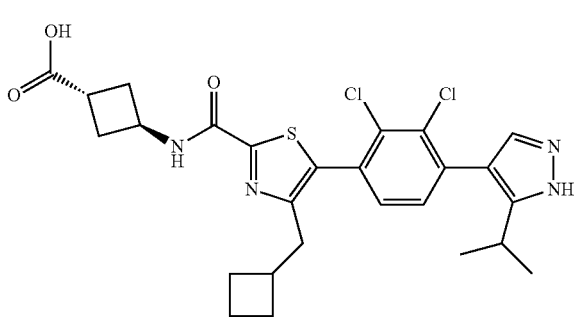 [SMILES: CC(C)c1[nH]ncc1-c1ccc(-c2sc(C(=O)N[C@H]3C[C@H](C(=O)O)C3)nc2CC2CCC2)c(Cl)c1Cl] | 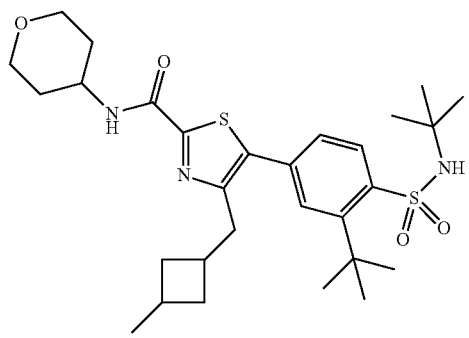 [SMILES: CC1CC(Cc2nc(C(=O)NC3CCOCC3)sc2-c2ccc(S(=O)(=O)NC(C)(C)C)c(C(C)(C)C)c2)C1] |

| 353 -continued | 354 -continued |
|---|---|
| Structure | Structure |
| 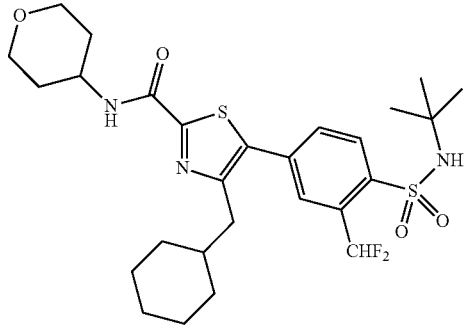 [SMILES: CC(C)(C)NS(=O)(=O)c1ccc(-c2sc(C(=O)NC3CCOCC3)nc2CC2CCCCC2)cc1C(F)F] | 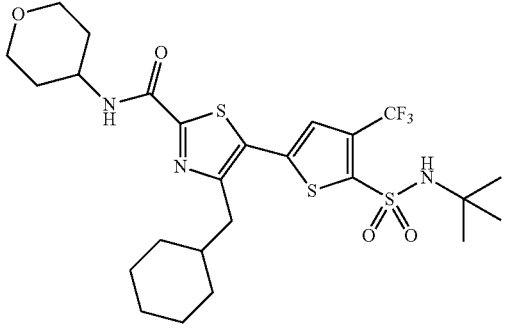 |
| 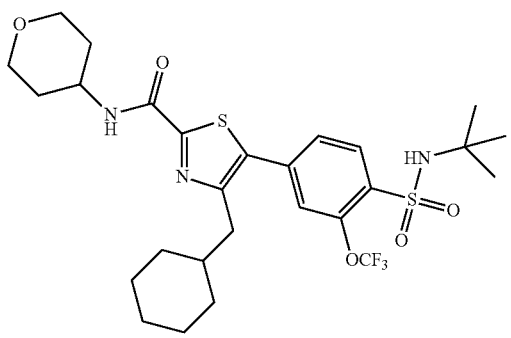 [SMILES: CC(C)(C)NS(=O)(=O)c1ccc(-c2sc(C(=O)NC3CCOCC3)nc2CC2CCCCC2)cc1OC(F)(F)F] | 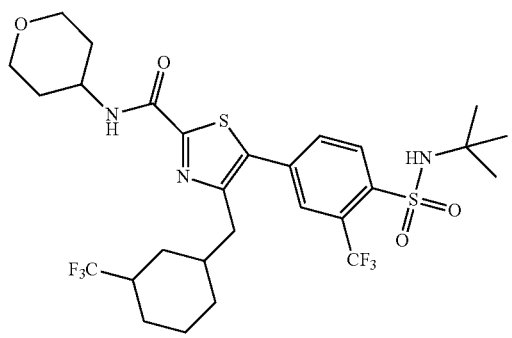 |
| 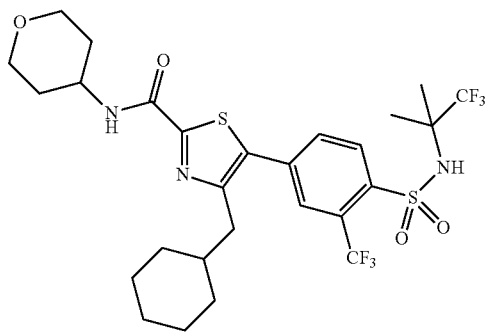 [SMILES: CC(C)(NS(=O)(=O)c1ccc(-c2sc(C(=O)NC3CCOCC3)nc2CC2CCCCC2)cc1C(F)(F)F)C(F)(F)F] | 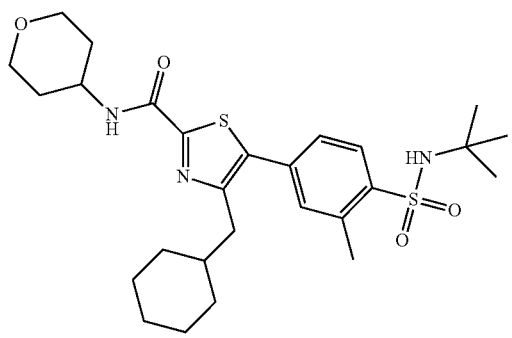 |
| 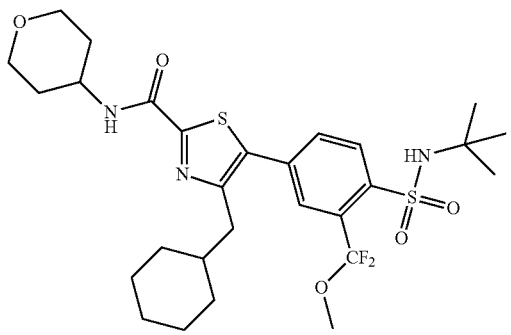 [SMILES: COC(F)(F)c1cc(-c2sc(C(=O)NC3CCOCC3)nc2CC2CCCCC2)ccc1S(=O)(=O)NC(C)(C)C] | 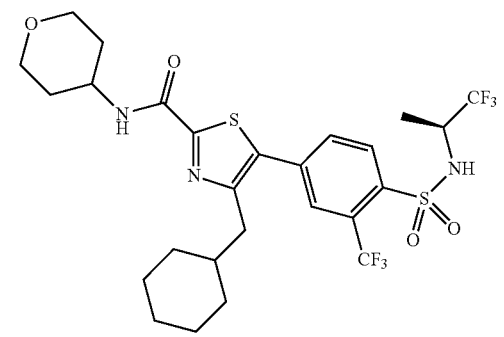 [SMILES: C[C@H](NS(=O)(=O)c1ccc(-c2sc(C(=O)NC3CCOCC3)nc2CC2CCCCC2)cc1C(F)(F)F)C(F)(F)F] |

| 355 -continued | 356 -continued |
|---|---|
| Structure | Structure |
| 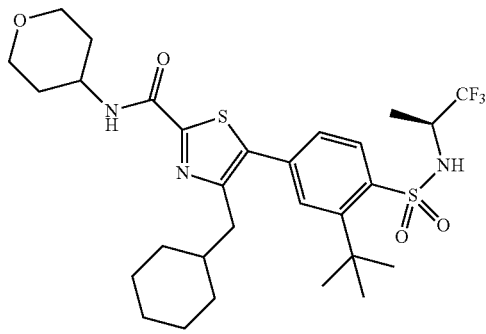 [SMILES: C[C@H](NS(=O)(=O)c1ccc(-c2sc(C(=O)NC3CCOCC3)nc2CC2CCCCC2)cc1C(C)(C)C)C(F)(F)F] | 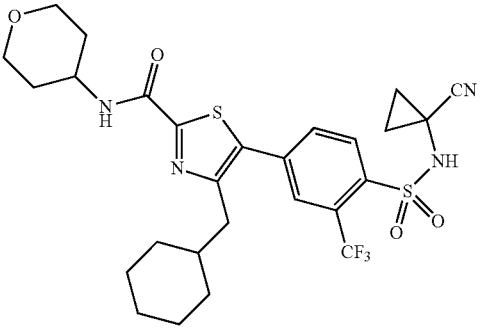 |
| 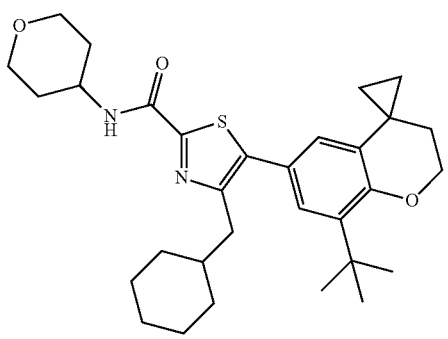 [SMILES: CC(C)(C)c1cc(-c2sc(C(=O)NC3CCOCC3)nc2CC2CCCCC2)cc2c1OCCC21CC1] | 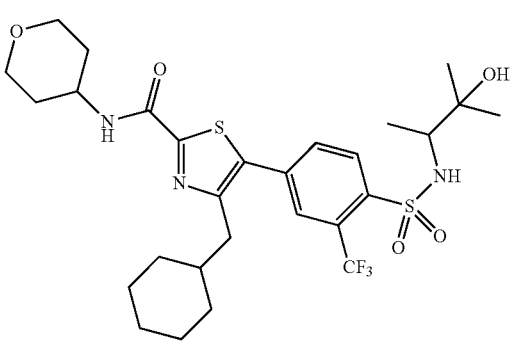 |
| 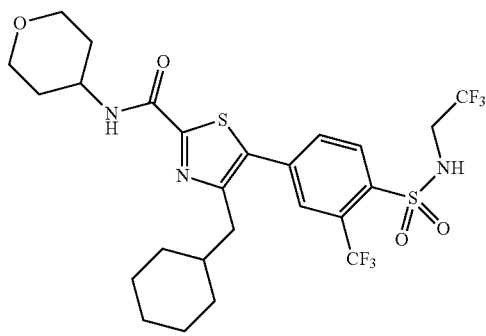 [SMILES: O=C(NC1CCOCC1)c1nc(CC2CCCCC2)c(-c2ccc(S(=O)(=O)NCC(F)(F)F)c(C(F)(F)F)c2)s1] | 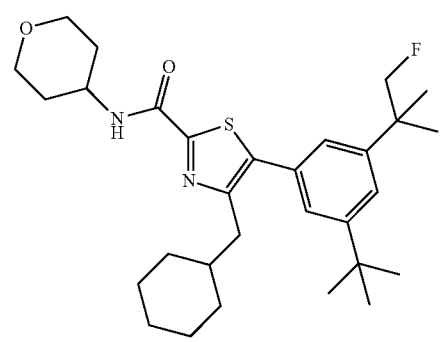 |
| 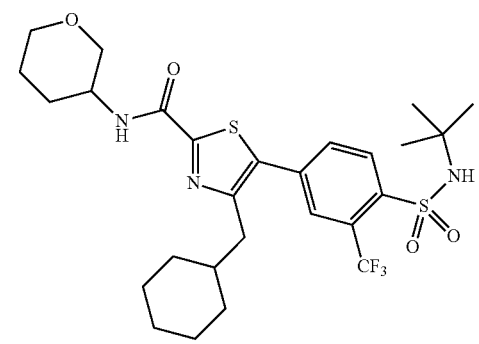 [SMILES: CC(C)(C)NS(=O)(=O)c1ccc(-c2sc(C(=O)NC3CCCOC3)nc2CC2CCCCC2)cc1C(F)(F)F] | 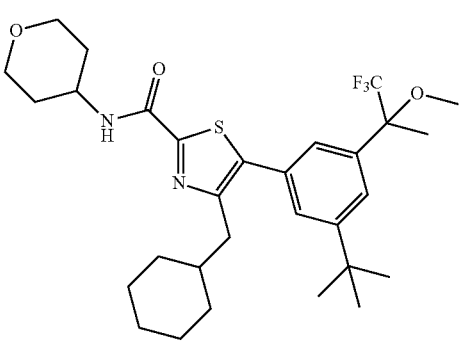 [SMILES: COC(C)(c1cc(-c2sc(C(=O)NC3CCOCC3)nc2CC2CCCCC2)cc(C(C)(C)C)c1)C(F)(F)F] |

| 357 -continued | 358 -continued |
|---|---|
| Structure | Structure |
| 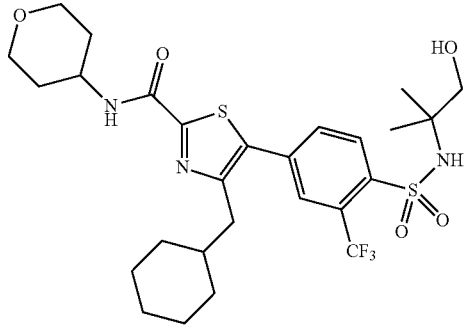 [SMILES: CC(C)(CO)NS(=O)(=O)c1ccc(-c2sc(C(=O)NC3CCOCC3)nc2CC2CCCCC2)cc1C(F)(F)F] | 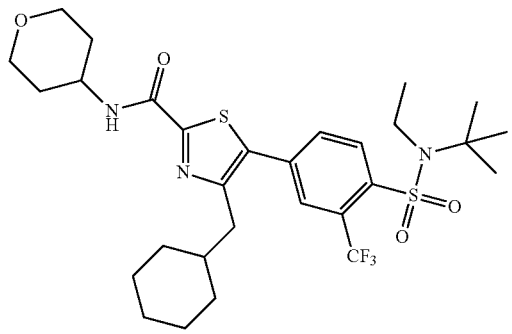 |
| 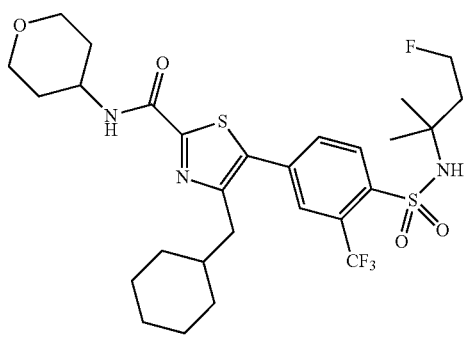 [SMILES: CC(C)(CCF)NS(=O)(=O)c1ccc(-c2sc(C(=O)NC3CCOCC3)nc2CC2CCCCC2)cc1C(F)(F)F] | 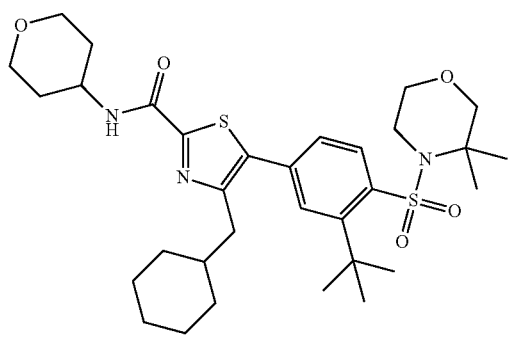 |
| 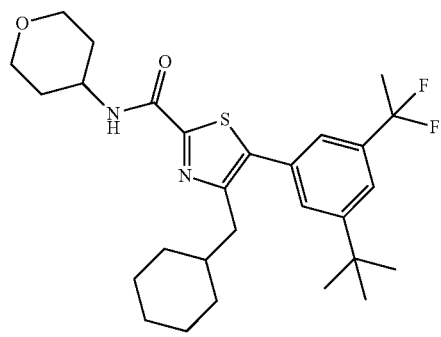 [SMILES: CC(C)(C)c1cc(-c2sc(C(=O)NC3CCOCC3)nc2CC2CCCCC2)cc(C(C)(F)F)c1] | 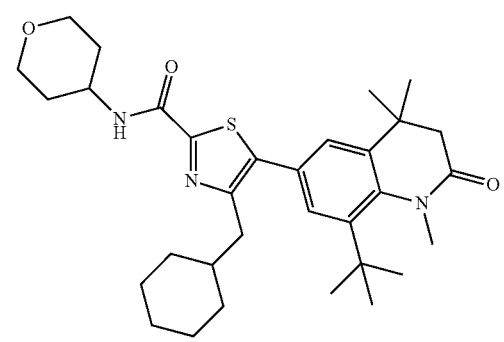 |
| 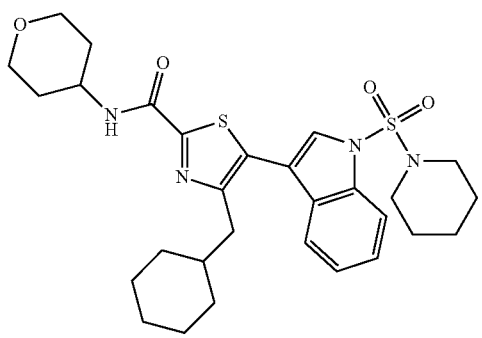 [SMILES: O=C(NC1CCOCC1)c1nc(CC2CCCCC2)c(-c2cn(S(=O)(=O)N3CCCCC3)c3ccccc23)s1] | 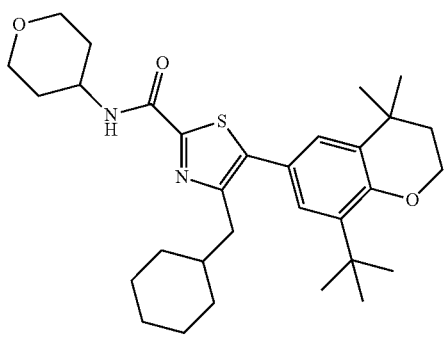 [SMILES: CC(C)(C)c1cc(-c2sc(C(=O)NC3CCOCC3)nc2CC2CCCCC2)cc2c1OCCC2(C)C] |

| 359 -continued | 360 -continued |
|---|---|
| Structure | Structure |
| 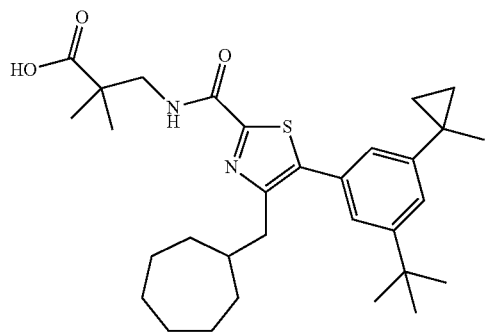 [SMILES: CC(C)(CNC(=O)c1nc(CC2CCCCCC2)c(-c2cc(C(C)(C)C)cc(C3(C)CC3)c2)s1)C(=O)O] | 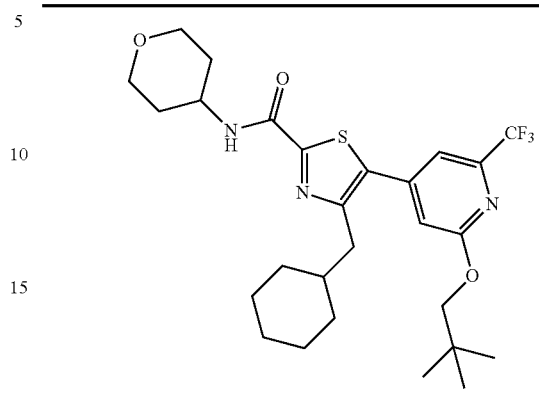 |
| 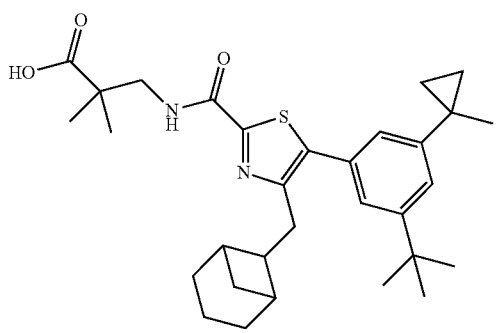 [SMILES: CC(C)(CNC(=O)c1nc(CC2C3CCCC2C3)c(-c2cc(C(C)(C)C)cc(C3(C)CC3)c2)s1)C(=O)O] | 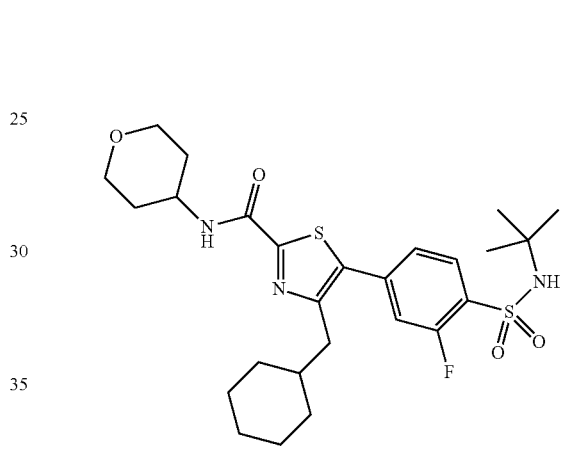 |
| 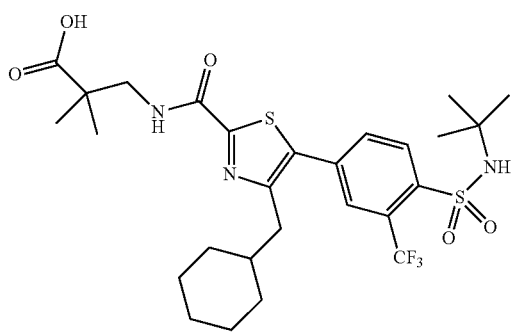 [SMILES: CC(C)(C)NS(=O)(=O)c1ccc(-c2sc(C(=O)NCC(C)(C)C(=O)O)nc2CC2CCCCC2)cc1C(F)(F)F] | 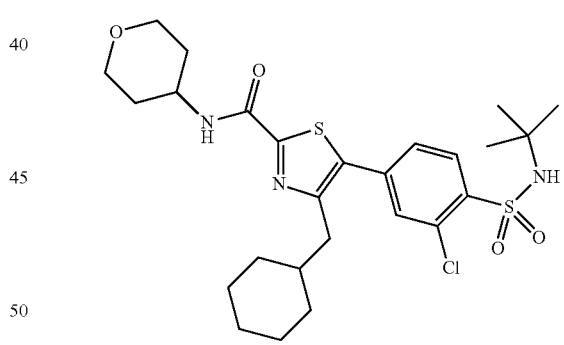 |
| 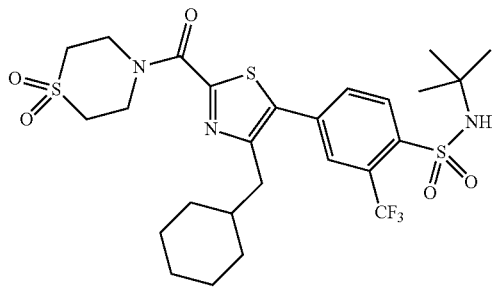 [SMILES: CC(C)(C)NS(=O)(=O)c1ccc(-c2sc(C(=O)N3CCS(=O)(=O)CC3)nc2CC2CCCCC2)cc1C(F)(F)F] | 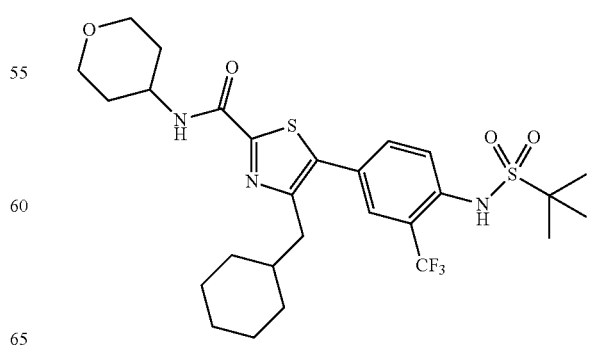 |
| 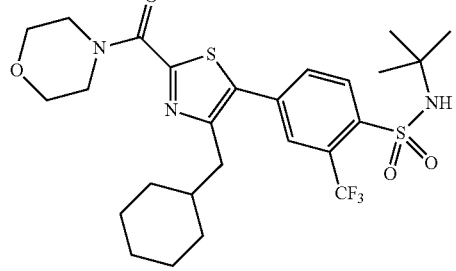 | |

| 361 -continued | 362 -continued |
|---|---|
| Structure | Structure |
| 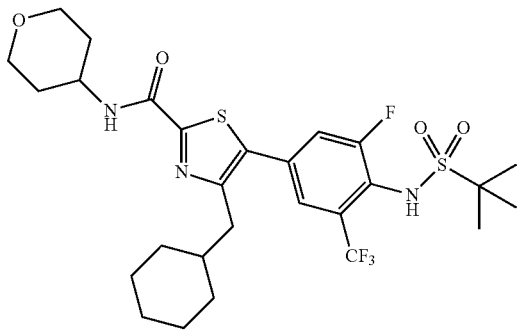 [SMILES: CC(C)(C)S(=O)(=O)Nc1c(F)cc(-c2sc(C(=O)NC3CCOCC3)nc2CC2CCCCC2)cc1C(F)(F)F] | 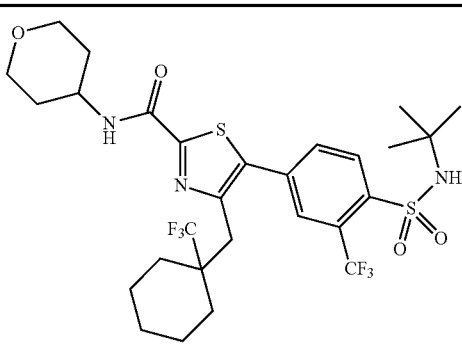 |
| 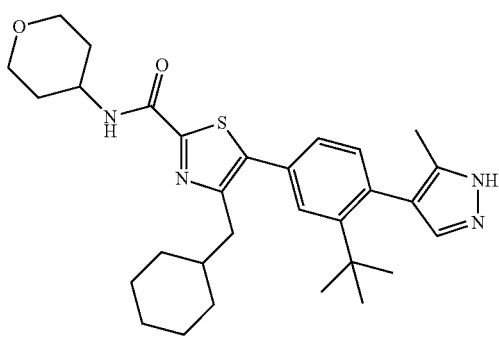 [SMILES: Cc1[nH]ncc1-c1ccc(-c2sc(C(=O)NC3CCOCC3)nc2CC2CCCCC2)cc1C(C)(C)C] | 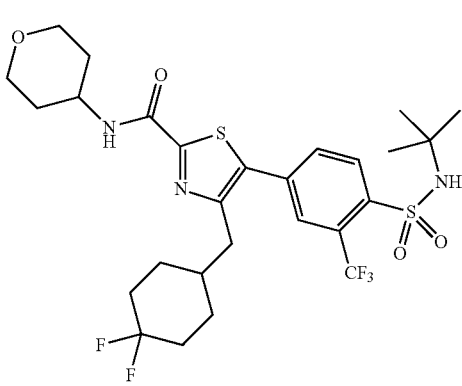 |
| 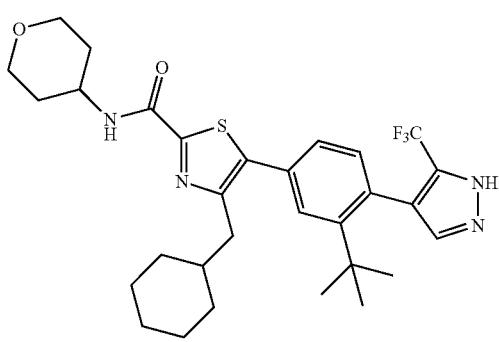 [SMILES: CC(C)(C)c1cc(-c2sc(C(=O)NC3CCOCC3)nc2CC2CCCCC2)ccc1-c1cn[nH]c1C(F)(F)F] | 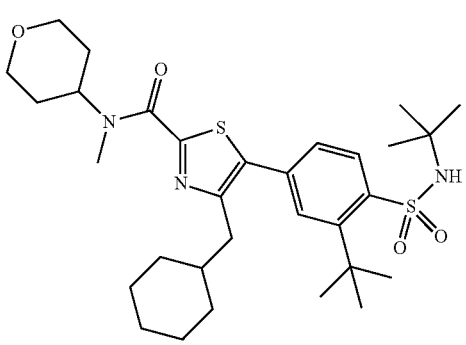 |
| 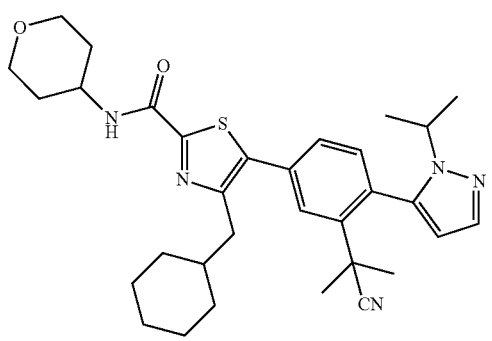 [SMILES: CC(C)n1nccc1-c1ccc(-c2sc(C(=O)NC3CCOCC3)nc2CC2CCCCC2)cc1C(C)(C)C#N] | 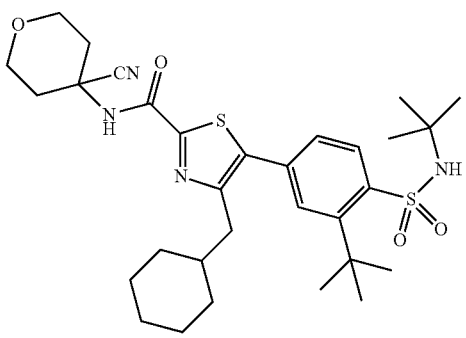 [SMILES: CC(C)(C)NS(=O)(=O)c1ccc(-c2sc(C(=O)NC3(C#N)CCOCC3)nc2CC2CCCCC2)cc1C(C)(C)C] |

| 363 -continued | 364 -continued |
|---|---|
| Structure | Structure |
| 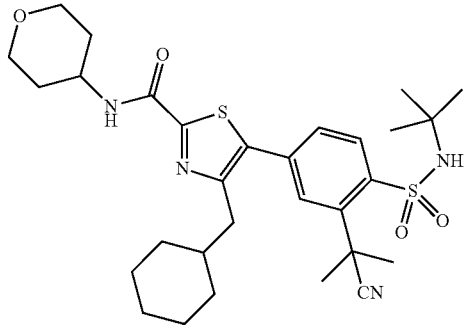 [SMILES: CC(C)(C)NS(=O)(=O)c1ccc(-c2sc(C(=O)NC3CCOCC3)nc2CC2CCCCC2)cc1C(C)(C)C#N] | 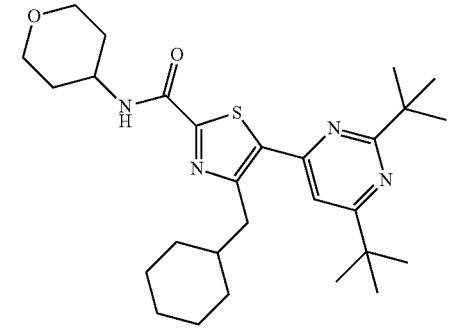 |
| 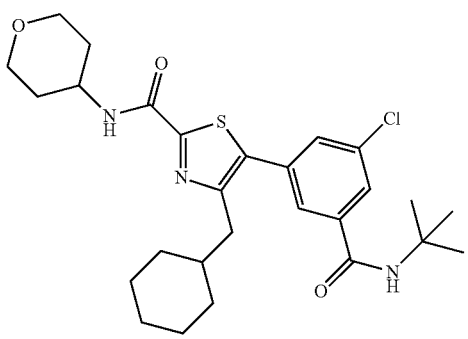 [SMILES: CC(C)(C)NC(=O)c1cc(Cl)cc(-c2sc(C(=O)NC3CCOCC3)nc2CC2CCCCC2)c1] | 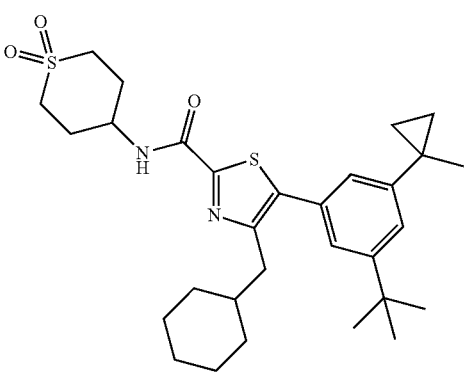 |
| 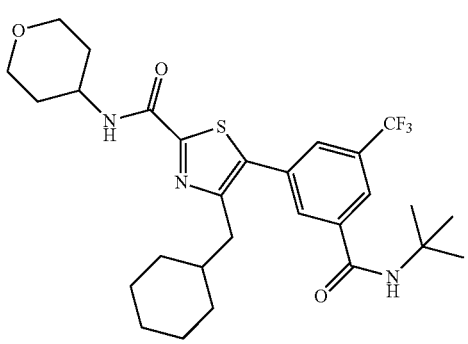 | 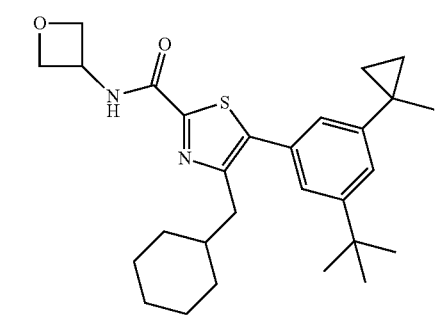 |
| 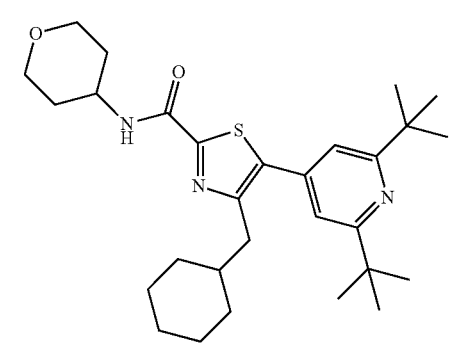 [SMILES: CC(C)(C)c1cc(-c2sc(C(=O)NC3CCOCC3)nc2CC2CCCCC2)cc(C(C)(C)C)n1] | 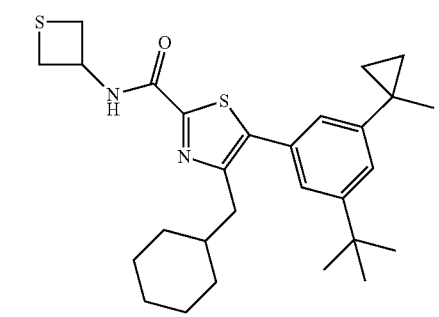 [SMILES: CC(C)(C)c1cc(-c2sc(C(=O)NC3CSC3)nc2CC2CCCCC2)cc(C2(C)CC2)c1] |

| 365-continued | 366-continued |
|---|---|
| Structure | Structure |
| 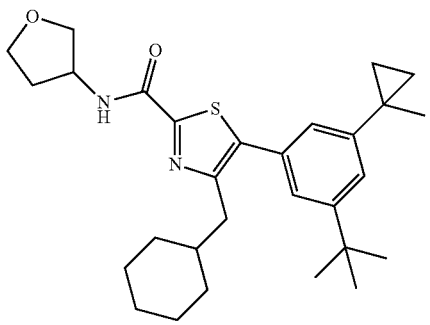 [SMILES: CC(C)(C)c1cc(-c2sc(C(=O)NC3CCOC3)nc2CC2CCCCC2)cc(C2(C)CC2)c1] | 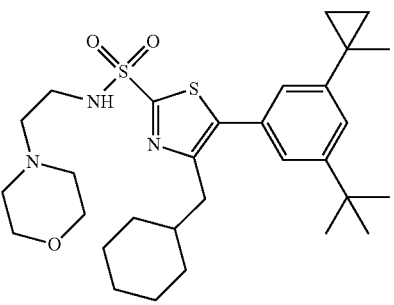 |
| 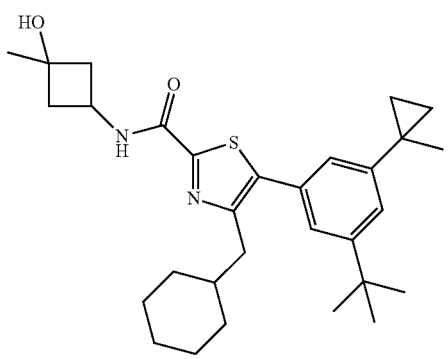 | 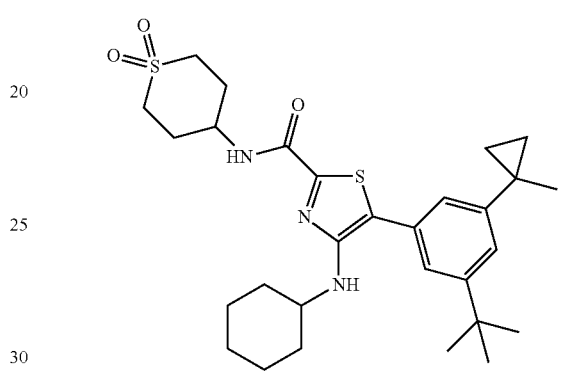 |
| 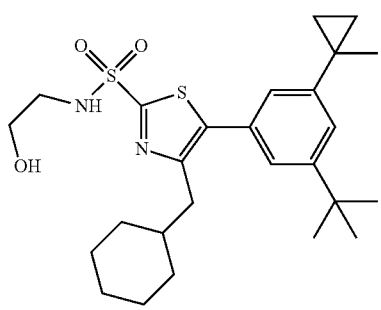 [SMILES: CC(C)(C)c1cc(-c2sc(S(=O)(=O)NCCO)nc2CC2CCCCC2)cc(C2(C)CC2)c1] | 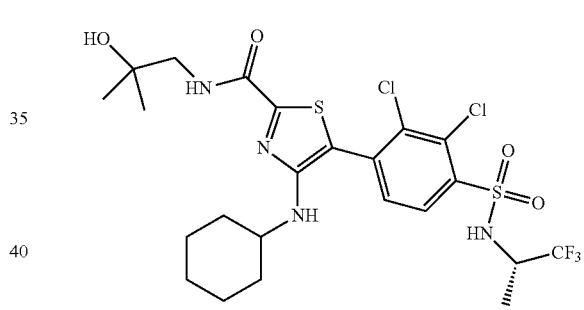 |
| 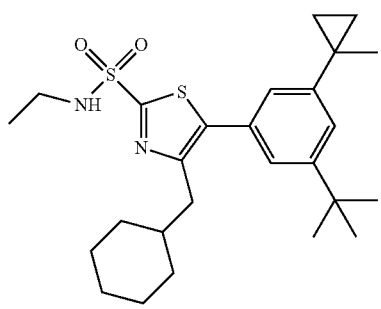 [SMILES: CCNS(=O)(=O)c1nc(CC2CCCCC2)c(-c2cc(C(C)(C)C)cc(C3(C)CC3)c2)s1] | 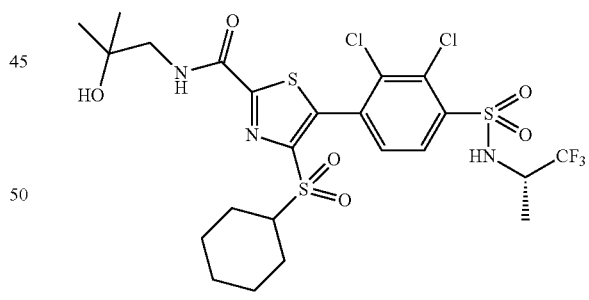 |
| 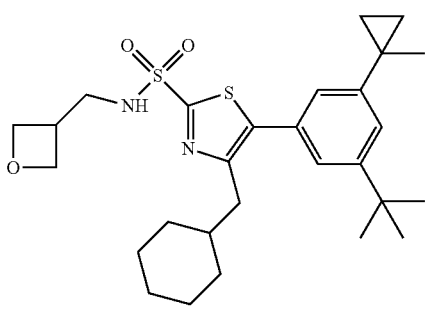 [SMILES: CC(C)(C)c1cc(-c2sc(S(=O)(=O)NCC3COC3)nc2CC2CCCCC2)cc(C2(C)CC2)c1] | 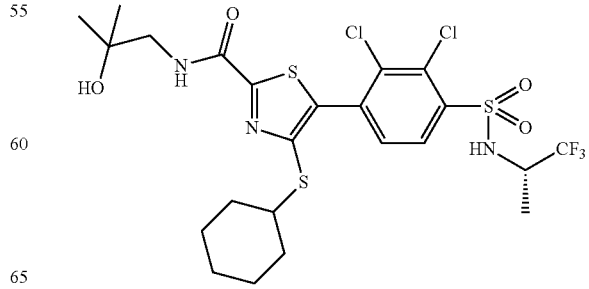 |

| 367 -continued | 368 -continued |
|---|---|
| Structure | Structure |
| 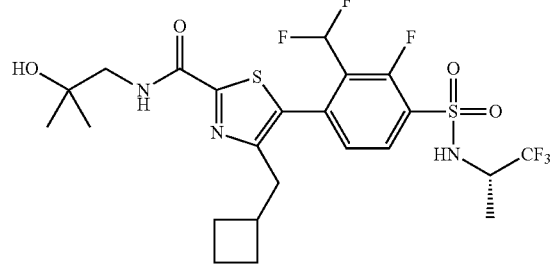 | 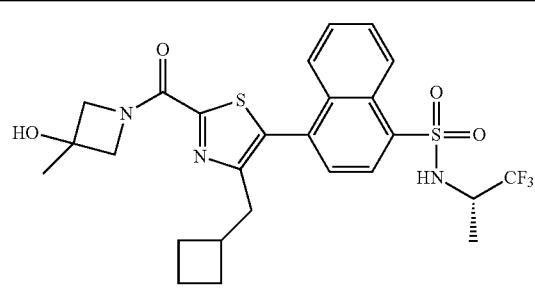 |
| 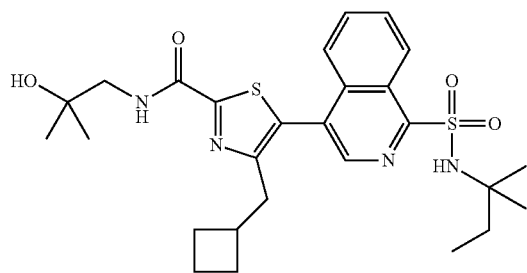 [SMILES: CCC(C)(C)NS(=O)(=O)c1ncc(-c2sc(C(=O)NCC(C)(C)O)nc2CC2CCC2)c2ccccc12] | 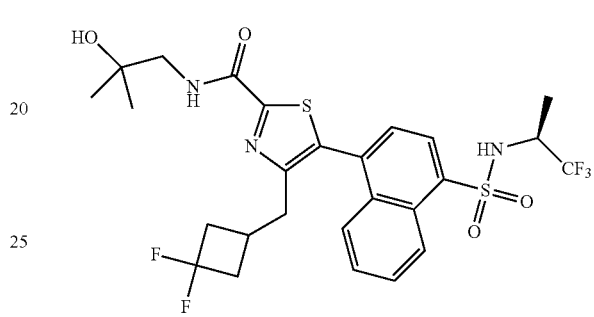 |
| 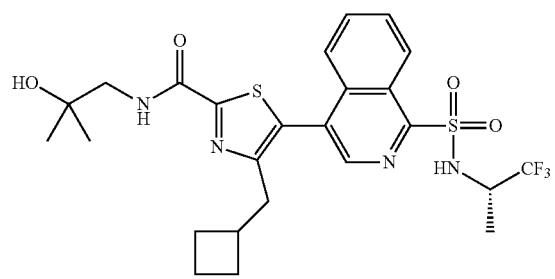 [SMILES: C[C@H](NS(=O)(=O)c1ncc(-c2sc(C(=O)NCC(C)(C)O)nc2CC2CCC2)c2ccccc12)C(F)(F)F] | 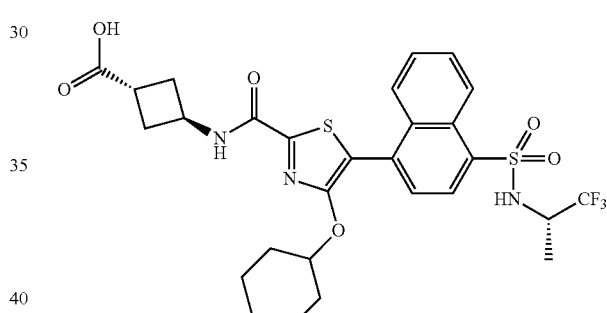 |
| 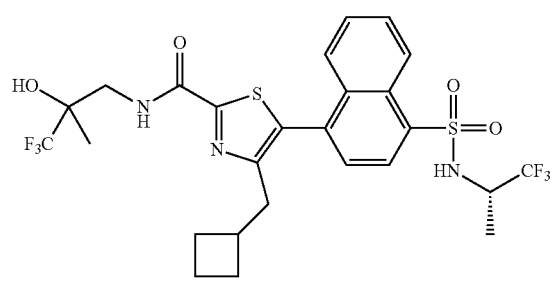 [SMILES: C[C@H](NS(=O)(=O)c1ccc(-c2sc(C(=O)NCC(C)(O)C(F)(F)F)nc2CC2CCC2)c2ccccc12)C(F)(F)F] | 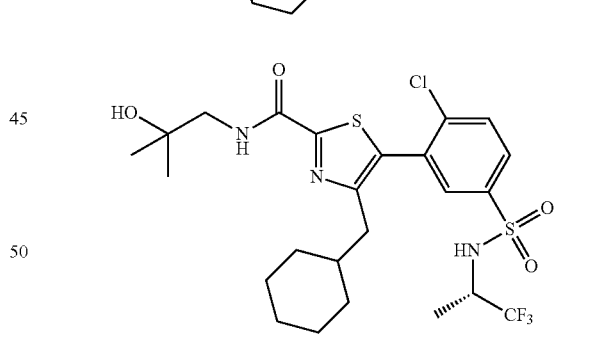 |
| 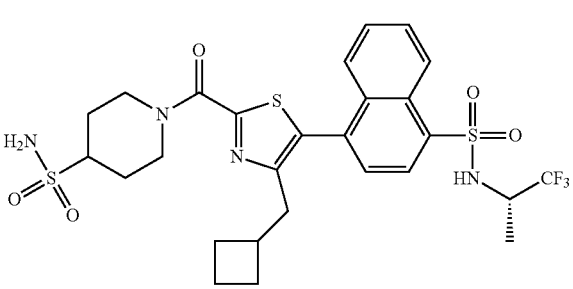 [SMILES: C[C@H](NS(=O)(=O)c1ccc(-c2sc(C(=O)N3CCC(S(N)(=O)=O)CC3)nc2CC2CCC2)c2ccccc12)C(F)(F)F] | 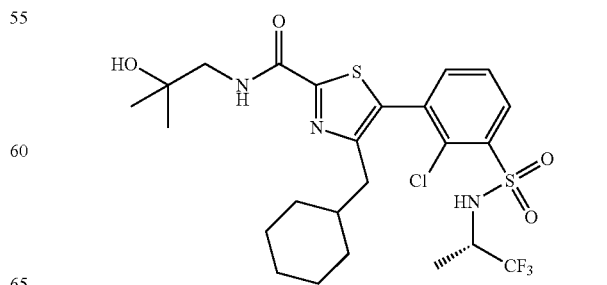 |

| 369 -continued | 370 -continued |
|---|---|
| Structure | Structure |
| 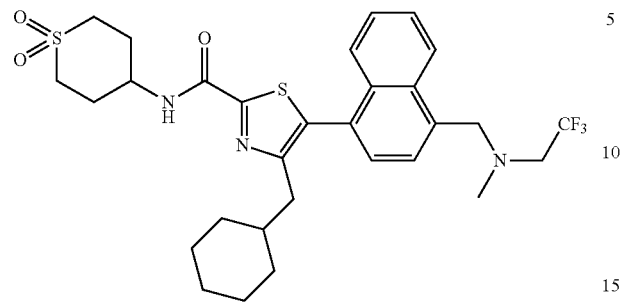 | 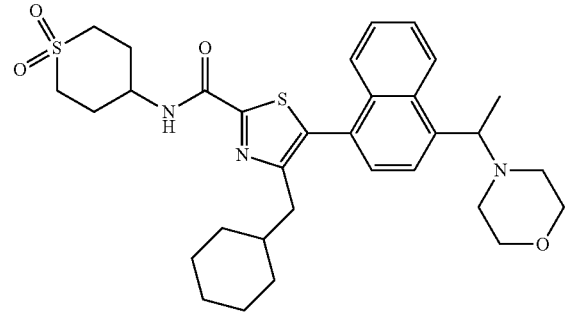 [SMILES: CC(c1ccc(-c2sc(C(=O)NC3CCS(=O)(=O)CC3)nc2CC2CCCCC2)c2ccccc12)N1CCOCC1] |
| 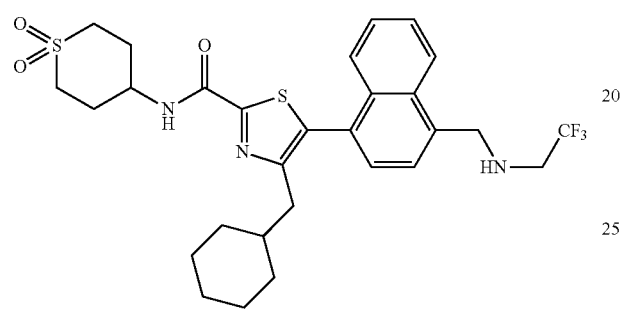 | 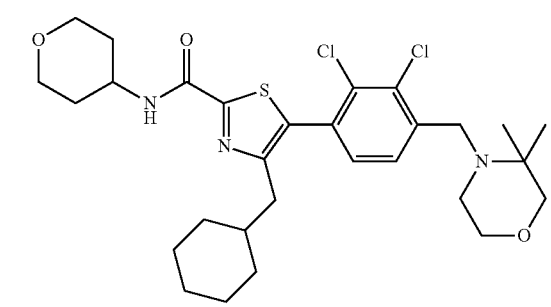 [SMILES: CC1(C)COCCN1Cc1ccc(-c2sc(C(=O)NC3CCOCC3)nc2CC2CCCCC2)c(Cl)c1Cl] |
| 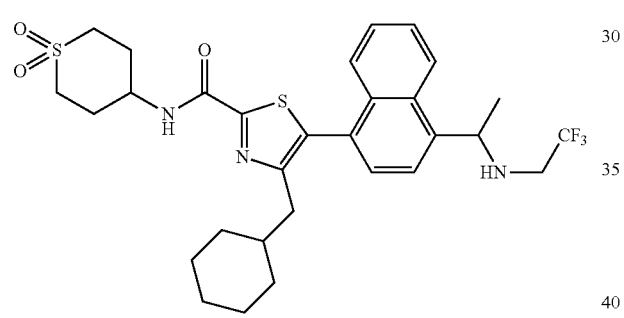 | 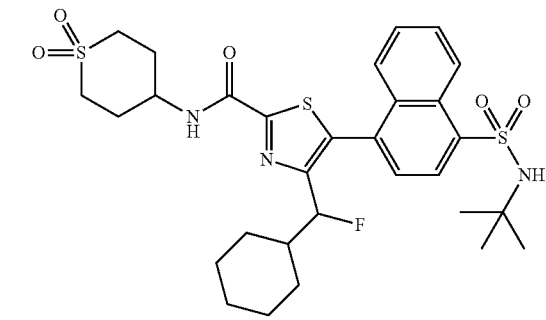 [SMILES: CC(C)(C)NS(=O)(=O)c1ccc(-c2sc(C(=O)NC3CCS(=O)(=O)CC3)nc2C(F)C2CCCCC2)c2ccccc12] |
| 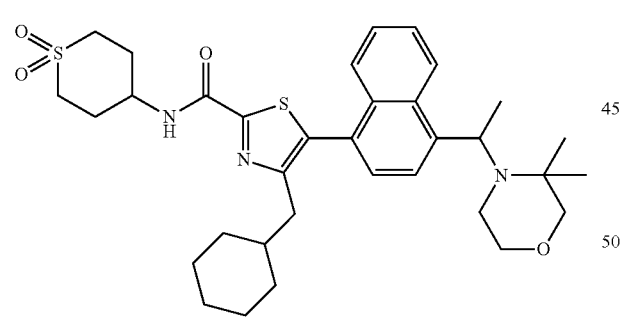 | 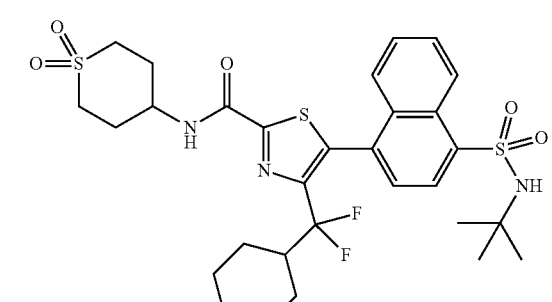 |
| 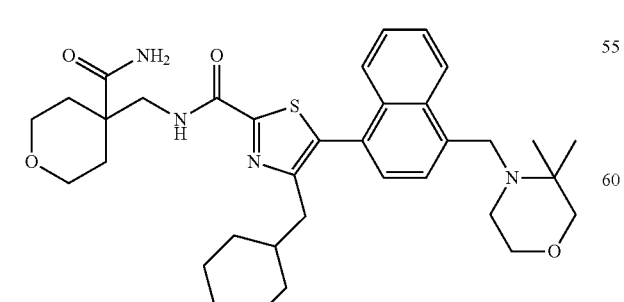 | 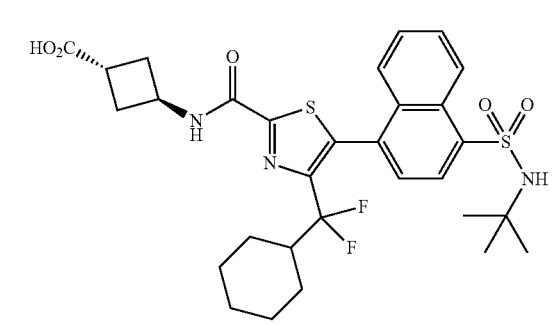 [SMILES: CC(C)(C)NS(=O)(=O)c1ccc(-c2sc(C(=O)N[C@H]3C[C@H](C(=O)O)C3)nc2C(F)(F)C2CCCCC2)c2ccccc12] |

| 371 -continued | 372 -continued |
|---|---|
| Structure | Structure |
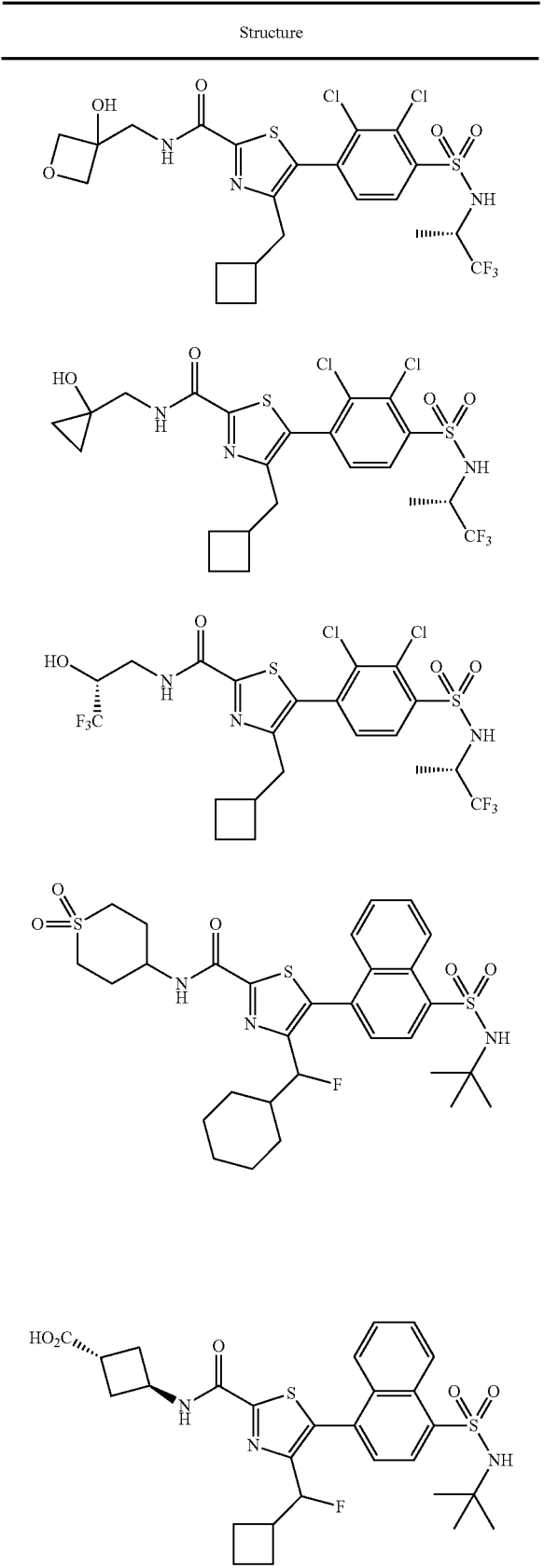
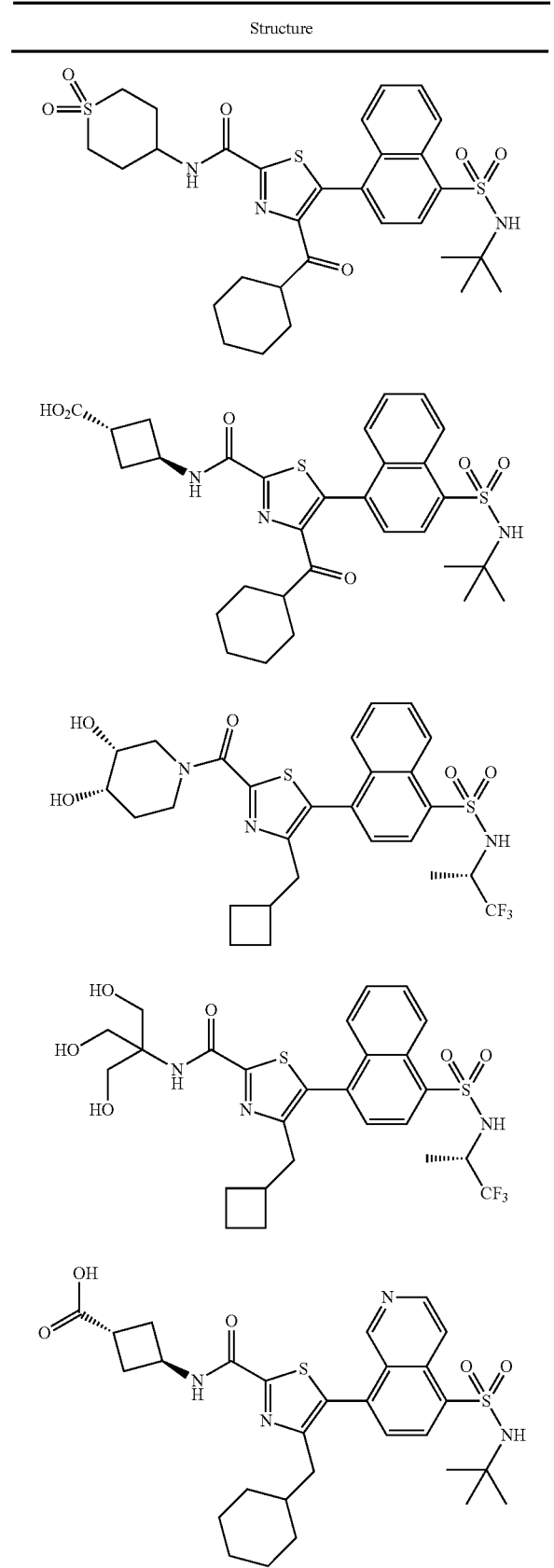

Structure

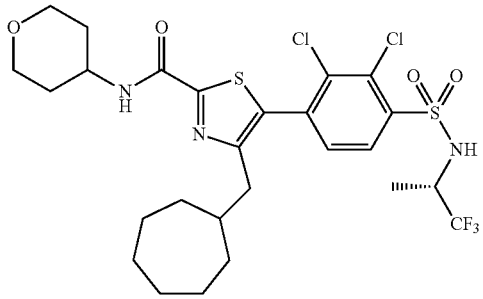 [SMILES: C[C@H](NS(=O)(=O)c1ccc(-c2sc(C(=O)NC3CCOCC3)nc2CC2CCCCCC2)c(Cl)c1Cl)C(F)(F)F]

Example 100

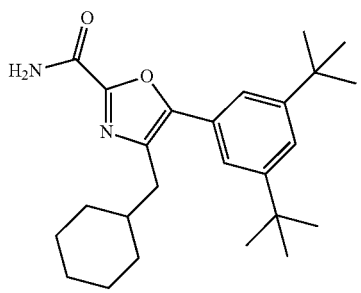

Step 1: ((2-Cyclohexyl-1-isocyanoethyl)sulfonyl)benzene (100a)

To a solution of 1-((isocyanomethyl)sulfonyl)-4-methylbenzene (8.0 g, 80 mmol) in dry DMF (180 mL) was added K$_2$CO$_3$ (11.4 g, 160 mmol), bromocyclohexylmethane (11.5 g, 160 mmol) and tetrabutylammonium iodide (1.6 g, 8.0 mmol). The reaction mixture was stirred at rt for 20 h, then heated to 5° C. for 4 h, poured into ice water and extracted with DCM (3×). The combined organic layers were washed with brine, dried over Na$_2$SO$_4$, concentrated and purified by CC (PE/EA=10/1) to give compound 100a (2.2 g, 10%) as a white solid.

Step 2: 4-(Cyclohexylmethyl)-5-(3,5-di-tert-butylphenyl)oxazole (100b)

To a solution of compound 100a (1.0 g, 3.4 mmol) in dry MeOH (20 mL) was added K$_2$CO$_3$ (1.0 g, 6.8 mmol) and 3,5-di-tert-butylbenzaldehyde (0.8 g, 3.4 mmol). The mixture was heated to reflux for 2 h, cooled to rt and diluted with water. The mixture was extracted with EA (3×). The combined organic layers were washed with brine, dried over Na$_2$SO$_4$, concentrated and purified by CC (PE/EA=15/1) to give compound 100b (0.65 g, 54%) as a white solid.

Step 3: 2-Bromo-4-(cyclohexylmethyl)-5-(3,5-di-tert-butylphenyl)oxazole (100c)

To a solution of compound 100b (0.65 g, 1.9 mmol) in dry DCM (10 mL) was added NBS (0.5 g, 3.7 mmol). The reaction mixture was stirred at rt until completion, diluted with water and extracted with DCM (3×). The combined organic layers were washed with brine, dried over Na$_2$SO$_4$, concentrated and purified by CC (PE/EA=20/1) to give compound 100c (0.5 g, 63%) as a white solid.

Step 4: Methyl 4-(cyclohexylmethyl)-5-(3,5-di-tert-butylphenyl)oxazole-2-carboxylate (100d)

To a solution of compound 100c (0.5 g, 1.2 mmol) in MeOH (30 mL) was added Pd(dppf)Cl$_2$ (50 mg) and Et$_3$N (0.6 g, 6 mmol). The reaction was stirred at 60° C. overnight under CO atmosphere (1.5 MPa), filtered, concentrated and purified by CC (PE/EA=20/1) to give compound 100d (0.3 g, 65%) as a yellow solid.

Step 5: 4-(Cyclohexylmethyl)-5-(3,5-di-tert-butylphenyl)oxazole-2-carboxylic acid (100e)

To a solution of compound 100d (300 mg, 0.7 mmol) in THF (10 mL) and H$_2$O (2 mL) was added LiOH.H$_2$O (110 mg, 2.6 mmol) and then the mixture was stirred overnight at rt, concentrated, diluted with H$_2$O, adjusted to pH 5 with 1N HCl and extracted with DCM. The organic layer was washed with brine, dried over Na$_2$SO$_4$, filtered and concentrated to give compound 100e (270 mg, 97%) as a white solid.

Step 6: 4-(Cyclohexylmethyl)-5-(3,5-di-tert-butylphenyl)oxazole-2-carboxamide (100)

To a solution of compound 100e (270 mg, 0.7 mmol) and 1 drop of DMF in DCM (10 mL) at 0° C. was added dropwise oxalyl chloride (0.15 mL, 1.5 mmol). The reaction mixture was stirred at rt for 0.5 h and concentrated. A solution of the crude carbonyl chloride in dry THF (5 mL) was added to a NH$_3$/THF solution (20 mL) and the mixture stirred at rt for 1 h, quenched with aq. NaHCO$_3$ (30 mL) and extracted with EA (3×). The combined organic layers were washed with brine, dried over Na$_2$SO$_4$, concentrated and purified by CC (PE/EA=4/1) to give the compound 100 (75 mg, 22%) as a white solid. $^1$H-NMR (CDCl$_3$, 400 MHz) δ: 1.03-1.09 (2H, m), 1.21-1.27 (3H, m), 1.36 (18H, s), 1.65-1.82 (6H, m), 2.65 (2H, d, J=6.4 Hz), 5.55 (1H, br s), 6.92 (1H, br s), 7.45 (1H, s), 7.51 (2H, s). MS 397.3 (M+H$^+$).

Example 100/1 to 100/20

The following Examples were prepared similar as described above:

| # | Structure | Analytical data |
|---|---|---|
| 100/1 | 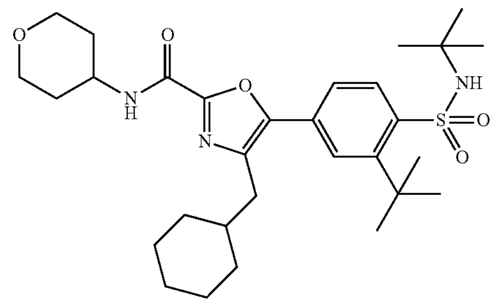 [SMILES: CC(C)(C)NS(=O)(=O)c1ccc(-c2oc(C(=O)NC3CCOCC3)nc2CC2CCCCC2)cc1C(C)(C)C] | $^1$H-NMR (300 MHz, CDCl$_3$) δ: 8.24 (d, J = 8.4 Hz, 1H), 7.93 (d, J = 1.8 Hz, 1H), 7.67 (dd, J = 8.4, 1.8 Hz, 1H), 6.95 (d, J = 7.8 Hz, 1H), 4.54 (s, 1H), 4.25-4.14 (m, 1H), 4.02 (d, J = 10.2 Hz, 2H), 3.54 (td, J = 11.7, 1.8 Hz, 2H), 2.68 (d, J = 6.6 Hz, 2H), 2.04-1.99 (m, 2H), 1.79-1.66 (m, 17H), 1.31-1.10 (m, 12H), 1.09-1.01 (m, 2H). MS 560.3 (M + 1)$^+$ |
| 100/2 | 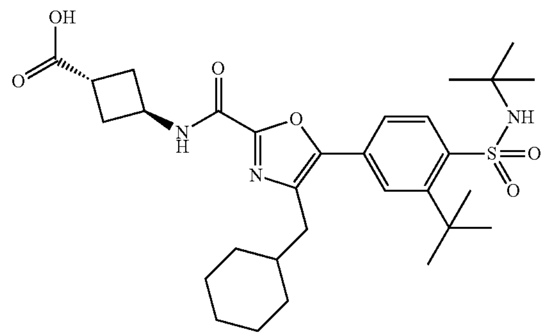 [SMILES: CC(C)(C)NS(=O)(=O)c1ccc(-c2oc(C(=O)N[C@H]3C[C@H](C(=O)O)C3)nc2CC2CCCCC2)cc1C(C)(C)C] | $^1$H-NMR (400 MHz, DMSO-d$_6$) δ: 9.23 (d, J = 7.6 Hz, 1H), 8.25 (d, J = 8.0 Hz, 1H), 7.86 (s, 2H), 7.78 (d, J = 8.0 Hz, 1H), 4.59-4.54 (m, 1H), 2.93-2.89 (m, 1H), 2.71 (d, J = 6.4 Hz, 2H), 2.49-2.43 (m, 4H), 1.80-1.64 (m, 6H), 1.58 (s, 9H), 1.20-1.15 (m, 12H), 1.03-1.00 (m, 2H). MS 574.3 (M + 1)$^+$ |
| 100/3 | 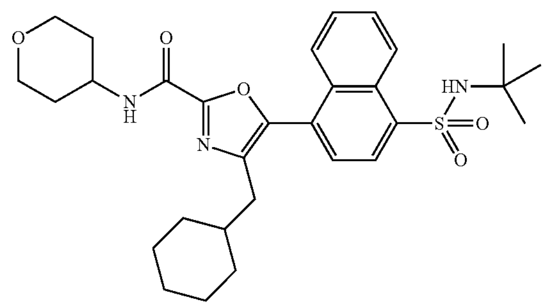 [SMILES: CC(C)(C)NS(=O)(=O)c1ccc(-c2oc(C(=O)NC3CCOCC3)nc2CC2CCCCC2)c2ccccc12] | $^1$H-NMR (400 MHz, CDCl$_3$) δ: 8.67 (d, J = 8.8 Hz, 1H), 8.37 (d, J = 7.6 Hz, 1H), 7.87 (d, J = 8.0 Hz, 1H), 7.74-7.68 (m, 1H), 7.65-7.59 (m, 2H), 7.01 (d, J = 8.4 Hz, 1H), 4.63 (s, 1H), 4.26-4.19 (m, 1H), 4.10-4.01 (m, 2H), 3.55 (m, 2H), 2.42 (d, J = 6.8 Hz, 2H), 2.07-2.01 (m, 2H), 1.75-1.01 (m, 7H), 1.30-1.20 (m, 2H), 1.18 (s, 9H), 1.15-0.99 (m, 2H), 0.81-0.71 (m, 2H). MS 552.3 (M + H)$^+$ |
| 100/4 | 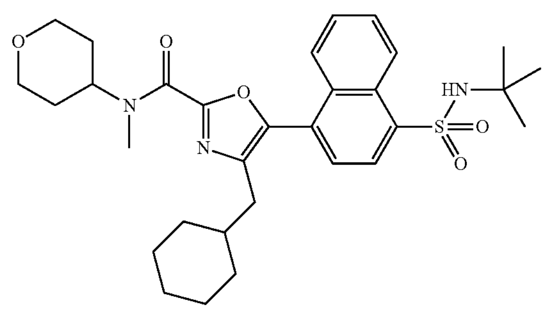 [SMILES: CN(C(=O)c1nc(CC2CCCCC2)c(-c2ccc(S(=O)(=O)NC(C)(C)C)c3ccccc23)o1)C1CCOCC1] | $^1$H-NMR (400 MHz, CDCl$_3$) δ: 8.67 (d, J = 8.0 Hz, 1H), 8.37 (d, J = 7.6 Hz, 1H), 7.96-7.93 (m, 1H), 7.4-7.69 (m, 1H), 7.65-7.60 (m, 2H), 5.12-5.04 (m, ½H), 4.86-4.79 (m, ½H), 4.15-4.05 (m, 2H), 3.60-3.43 (m, 2H), 3.38 (s, 1½H), 3.07 (s, 1½H), 2.46 (d, J = 6.8 Hz, 2H), 2.06-1.82 (m, 3H), 1.76-1.55 (m, 6H), 1.27-1.24 (m, 2H), 1.19 (s, 9H), 1.14-1.00 (m, 3H), 0.90-0.75 (m, 2H). MS 568.2 (M + 1)$^+$ |
| 100/5 | 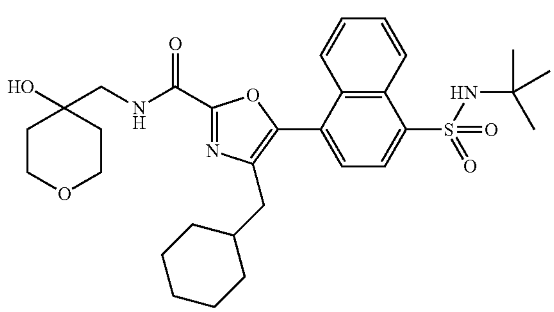 [SMILES: CC(C)(C)NS(=O)(=O)c1ccc(-c2oc(C(=O)NCC3(O)CCOCC3)nc2CC2CCCCC2)c2ccccc12] | $^1$H-NMR (CDCl$_3$, 400 MHz) δ: 0.76-0.79 (m, 2H), 1.14-1.18 (m, 3H), 1.25 (s, 9H), 1.58-1.66 (m, 9H), 1.74-1.80 (m, 2H), 2.37 (s, 1H), 2.42 (d, J = 7.6 Hz, 2H), 3.56 (d, J = 6.0 Hz, 2H), 3.81 (dd, J = 7.6 Hz, 3.2 Hz, 4H), 4.62 (s, 1H), 7.45-7.50 (m, 1H), 7.60-7.65 (m, 2H), 7.71-7.72 (m, 1H), 7.87 (d, J = 8.0 Hz, 1H), 8.37 (d, J = 7.6 Hz, 1H), 8.67 (d, J = 8.8 Hz, 1H). MS 584.3 (M + 1)$^+$ |

| # | Structure | Analytical data |
|---|---|---|
| 100/6 | 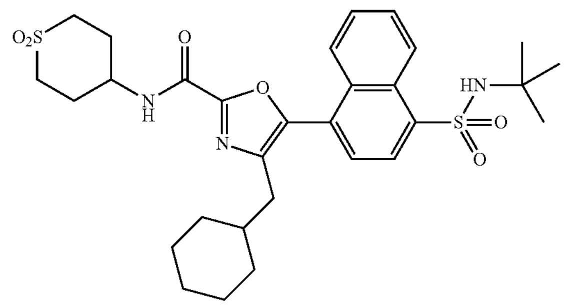 [SMILES: CC(C)(C)NS(=O)(=O)c1ccc(-c2oc(C(=O)NC3CCS(=O)(=O)CC3)nc2CC2CCCCC2)c2ccccc12] | ¹H-NMR (CDCl₃, 400 MHz) δ: 0.76-0.79 (m, 2H), 1.03-1.15 (m, 3H), 1.19 (s, 9H), 1.59-1.61 (m, 7H), 2.32-2.36 (m, 2H), 2.41-2.48 (m, 4H), 3.16-3.18 (m, 4H), 4.28-4.29 (m, 1H), 4.63 (s, 1H), 7.10 (d, J = 8.0 Hz, 1H), 7.60-7.65 (m, 2H), 7.73 (t, J = 7.2 Hz, 1H), 7.85 (d, J = 8.8 Hz, 1H), 8.37 (d, J = 8.0 Hz, 1H), 8.68 (d, J = 8.4 Hz, 1H). MS 602.3 (M + 1)⁺ |
| 100/7 | 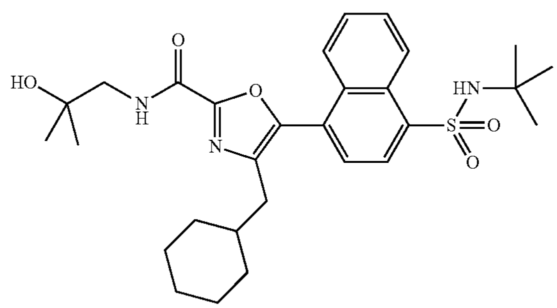 [SMILES: CC(C)(O)CNC(=O)c1nc(CC2CCCCC2)c(-c2ccc(S(=O)(=O)NC(C)(C)C)c3ccccc23)o1] | ¹H-NMR (CDCl₃, 300 MHz) δ: 0.78-0.82 (m, 2H), 0.96-1.15 (m, 3H), 1.18 (s, 9H), 1.34 (s, 6H), 1.58-1.75 (m, 6H), 1.94 (s, 1H), 2.42 (d, J = 7.2 Hz, 2H), 3.51 (d, J = 6.3 Hz, 2H), 4.61 (s, 1H), 7.45-7.52 (m, 1H), 7.60-7.72 (m, 2H), 7.75-7.80 (m, 1H), 7.85 (d, J = 8.4 Hz, 1H), 8.37 (d, J = 7.5 Hz, 1H), 8.67 (d, J = 8.7 Hz, 1H). MS 542.3 (M + 1)⁺ |
| 100/8 | 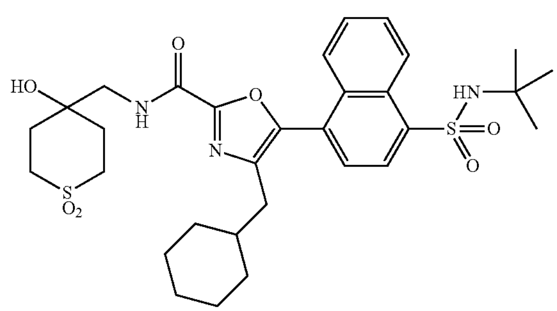 [SMILES: CC(C)(C)NS(=O)(=O)c1ccc(-c2oc(C(=O)NCC3(O)CCS(=O)(=O)CC3)nc2CC2CCCCC2)c2ccccc12] | ¹H-NMR (CDCl₃, 300 MHz) δ: 0.76-0.80 (m, 2H), 1.09-1.13 (m, 3H), 1.18 (s, 9H), 1.59-1.61 (m, 5H), 2.17-2.19 (m, 4H), 2.43 (d, J = 7.2 Hz, 2H), 2.88-2.95 (m, 4H), 3.39-3.51 (m, 2H), 3.57 (d, J = 6.0 Hz, 2H), 3.77 (s, 1H), 4.67 (s, 1H), 7.57-7.65 (m, 3H), 7.70-7.73 (m, 1H), 7.85 (d, J = 8.7 Hz, 1H), 8.37 (d, J = 7.8 Hz, 1H), 8.68 (d, J = 8.1 Hz, 1H). MS 632.2 (M + H)⁺ |
| 100/9 | 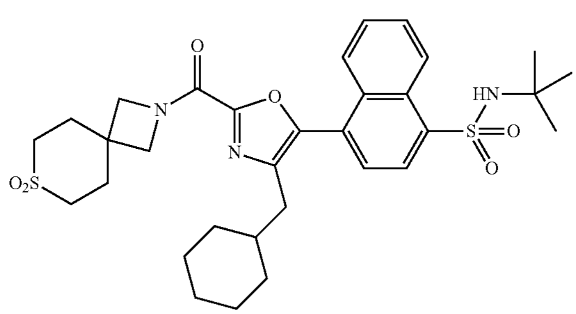 [SMILES: CC(C)(C)NS(=O)(=O)c1ccc(-c2oc(C(=O)N3CC4(CCS(=O)(=O)CC4)C3)nc2CC2CCCCC2)c2ccccc12] | ¹H-NMR (CDCl₃, 300 MHz) δ: 0.76-0.79 (m, 2H), 1.14-1.17 (m, 3H), 1.18 (s, 9H), 1.58-1.66 (m, 7H), 2.42-2.47 (m, 6H), 3.05-3.09 (m, 4H), 4.04 (s, 2H), 4.51 (s, 2H), 4.66 (s, 1H), 7.58-7.61 (m, 2H), 7.66-7.69 (m, 1H), 7.83 (d, J = 8.1 Hz, 1H), 8.36 (d, J = 7.8 Hz, 1H), 8.67 (d, J = 9.0 Hz, 1H). MS 628.2 (M + 1)⁺ |
| 100/10 | 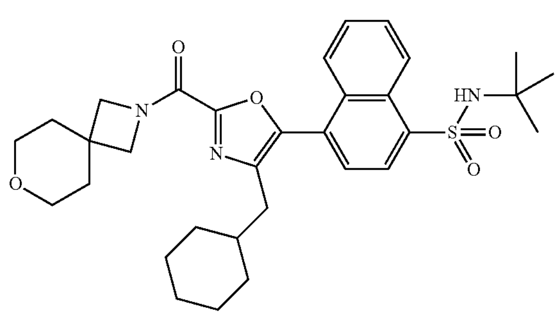 [SMILES: CC(C)(C)NS(=O)(=O)c1ccc(-c2oc(C(=O)N3CC4(CCOCC4)C3)nc2CC2CCCCC2)c2ccccc12] | H-NMR (CDCl₃, 300 MHz) δ: 0.78-0.82 (m, 2H), 0.96-1.15 (m, 3H), 1.19 (s, 9H), 1.59-1.63 (m, 6H), 1.87 (m, 4H), 2.44 (d, J = 7.2 Hz, 2H), 3.67-3.71 (m, 4H), 4.00 (s, 2H), 4.44 (s, 2H), 4.62 (s, 1H), 7.59-7.64 (m, 2H), 7.71-7.72 (m, 1H), 7.88 (d, J = 8.4 Hz, 1H), 8.37 (d, J = 7.8 Hz, 1H), 8.68 (d, J = 9.0 Hz, 1H). MS 580.3 (M + 1)⁺ |

-continued

| # | Structure | Analytical data |
|---|---|---|
| 100/11 | 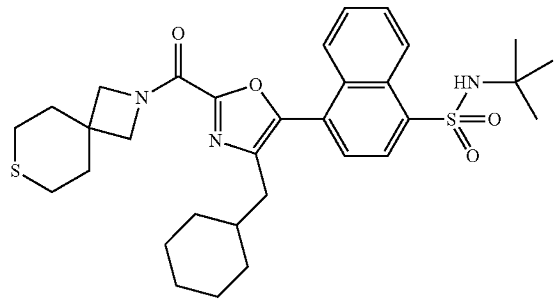 [SMILES: CC(C)(C)NS(=O)(=O)c1ccc(-c2oc(C(=O)N3CC4(CCSCC4)C3)nc2CC2CCCCC2)c2ccccc12] | $^1$H-NMR (CDCl$_3$, 300 MHz) δ: 0.76-0.83 (m, 2H), 1.14-1.17 (m, 3H), 1.19 (s, 9H), 1.58-1.66 (m, 6H), 2.09-2.11 (m, 4H), 2.43 (d, J = 6.9 Hz, 2H), 2.62-2.64 (m, 4H), 3.90 (s, 2H), 4.34 (s, 2H), 4.62 (s, 1H), 7.60-7.63 (m, 2H), 7.71 (m, 1H), 7.87 (d, J = 10.8 Hz, 1H), 8.36 (d, J = 10.2 Hz, 1H), 8.66 (d, J = 10.2 Hz, 1H). MS 596.3 (M + 1)$^+$ |
| 100/12 | 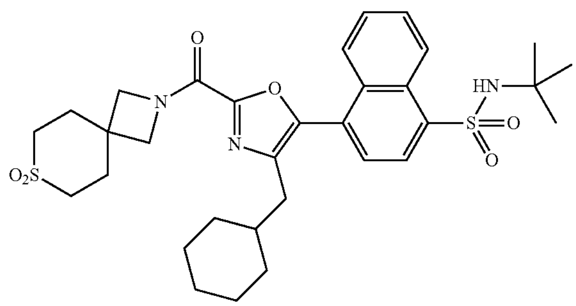 | $^1$H-NMR (CDCl$_3$, 300 MHz) δ: 0.75-0.83 (m, 2H), 0.99-1.17 (m, 3H), 1.18 (s, 9H), 1.61-1.70 (m, 6H), 2.42-2.47 (m, 6H), 3.07 (m, 4H), 4.04 (s, 2H), 4.51 (s, 2H), 4.66 (s, 1H), 7.58-7.61 (m, 2H), 7.72 (m, 1H), 7.85 (d, J = 8.4 Hz, 1H), 8.36 (d, J = 7.8 Hz, 1H), 8.67 (d, J = 9.0 Hz, 1H). MS 612.3 (M + 1)$^+$ |
| 100/13 | 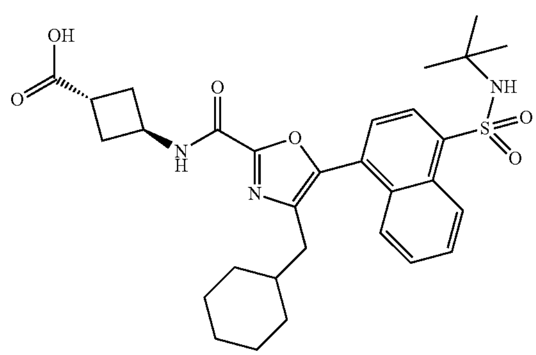 [SMILES: CC(C)(C)NS(=O)(=O)c1ccc(-c2oc(C(=O)N[C@H]3C[C@H](C(=O)O)C3)nc2CC2CCCCC2)c2ccccc12] | $^1$H-NMR (DMSO-d$_6$, 300 MHz) δ: 0.66-0.80 (m, 2H), 1.05 (s, 9H), 1.21 (br s, 2H), 1.45-1.65 (m, 4H), 1.77 (s, 4H), 2.29-2.35 (m, 4H), 2.41 (d, J = 6.9 Hz, 2H), 4.53-4.59 (m, 2H), 7.68-7.75 (m, 4H), 7.86-7.89 (m, 1H), 8.27 (d, J = 7.5 Hz, 1H), 8.78 (d, J = 8.4 Hz, 1H), 9.15 (d, J = 7.5 Hz, 1H). MS 568.3 (M + 1)$^+$ |
| 100/14 | 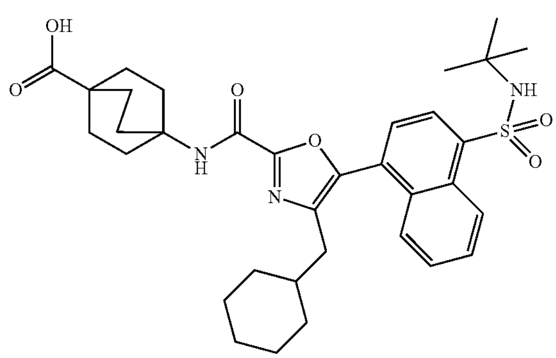 [SMILES: CC(C)(C)NS(=O)(=O)c1ccc(-c2oc(C(=O)NC34CCC(C(=O)O)(CC3)CC4)nc2CC2CCCCC2)c2ccccc12] | $^1$H-NMR (CDCl$_3$, 300 MHz) δ: 0.73-0.78 (m, 2H), 0.96-1.13 (m, 3H), 1.18 (s, 9H), 1.57-1.71 (m, 6H), 1.99-2.14 (m, 12H), 2.40 (d, J = 6.9 Hz, 2H), 4.64 (s, 1H), 6.85 (s, 1H), 7.58-7.64 (m, 3H), 7.66-7.71 (m, 1H), 7.88 (d, J = 8.1 Hz, 1H), 8.36 (d, J = 7.5 Hz, 1H), 8.66 (d, J = 8.7 Hz, 1H). MS 622.3 (M + 1)$^+$ |

-continued

| # | Structure | Analytical data |
|---|---|---|
| 100/15 | 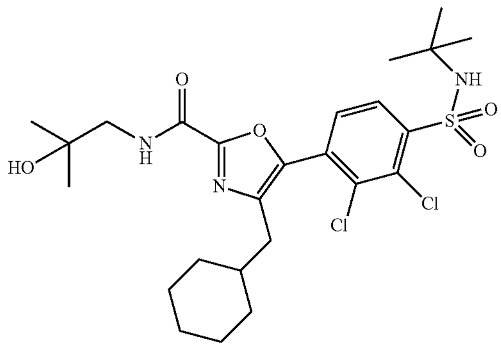 [SMILES: CC(C)(O)CNC(=O)c1nc(CC2CCCCC2)c(-c2ccc(S(=O)(=O)NC(C)(C)C)c(Cl)c2Cl)o1] | MS 560.2 (M + 1)⁺ |
| 100/16 | 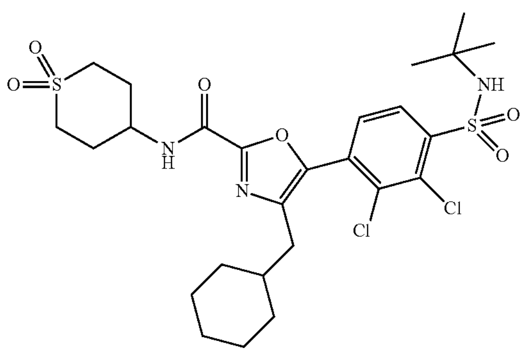 [SMILES: CC(C)(C)NS(=O)(=O)c1ccc(-c2oc(C(=O)NC3CCS(=O)(=O)CC3)nc2CC2CCCCC2)c(Cl)c1Cl] | MS 620.1 (M + 1)⁺ |
| 100/17 | 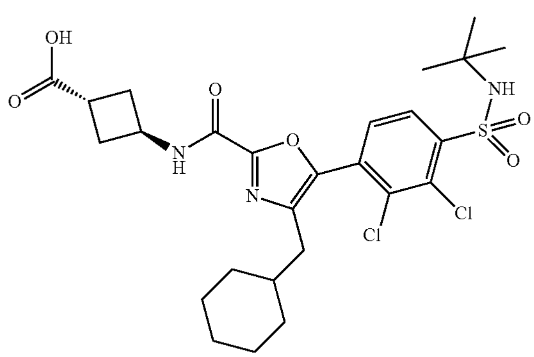 [SMILES: CC(C)(C)NS(=O)(=O)c1ccc(-c2oc(C(=O)N[C@H]3C[C@H](C(=O)O)C3)nc2CC2CCCCC2)c(Cl)c1Cl] | MS 586.2 (M + 1)⁺ |
| 100/18 | 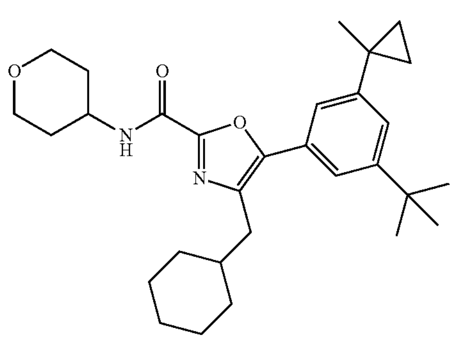 [SMILES: CC(C)(C)c1cc(-c2oc(C(=O)NC3CCOCC3)nc2CC2CCCCC2)cc(C2(C)CC2)c1] | $^1$H-NMR (400 MHz, CDCl$_3$) δ: 0.75-0.77 (m, 2H), 0.88-0.90 (m, 2H), 1.00-1.08 (m, 2H), 1.16-1.26 (m, 3H), 1.35 (s, 9H), 1.43 (s, 3H), 1.62-1.79 (m, 8H), 2.02 (dd, J = 8.4, 2.0 Hz, 2H), 2.64 (d, J = 6.8 Hz, 2H), 3.54 (td, J = 12.0, 2.0 Hz, 2H), 4.02 (dd, J = 8.4, 2.4 Hz, 2H), 4.14-4.22 (m, 1H), 6.94 (d, J = 8.4 Hz, 1H), 7.30 (t, J = 1.6 Hz, 1H), 7.42 (t, J = 1.6 Hz, 1H), 7.49 (t, J = 1.6 Hz, 1H). MS 479.3 (M + 1)⁺ |

| # | Structure | Analytical data |
|---|-----------|-----------------|
| 100/19 | 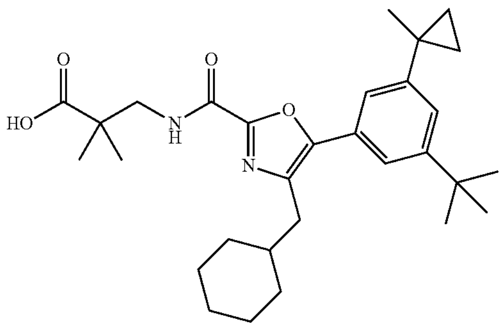 [SMILES: CC(C)(CNC(=O)c1nc(CC2CCCCC2)c(-c2cc(C(C)(C)C)cc(C3(C)CC3)c2)o1)C(=O)O] | $^1$H-NMR (400 MHz, CDCl$_3$) δ: 0.70-0.73 (m, 2H), 0.84-0.86 (m, 2H), 0.90-0.98 (m, 2H), 1.05-1.10 (m, 3H), 1.15 (s, 6H), 1.31 (s, 9H), 1.39 (s, 3H), 1.53-1.69 (m, 6H), 2.58 (d, J = 6.8 Hz, 2H), 3.49 (d, J = 6.8 Hz, 2H), 7.26 (s, 1H), 7.35 (s, 1H), 7.43 (s, 1H), 7.87 (t, J = 6.4 Hz, 1H). MS 495.3 (M + 1)$^+$ |
| 100/20 | 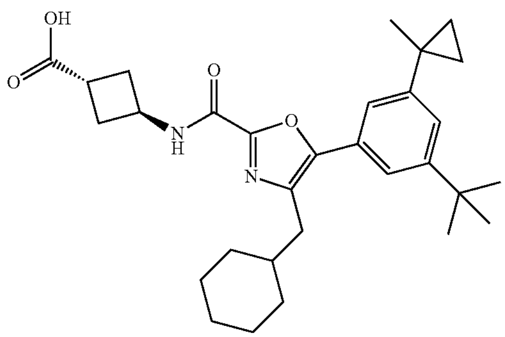 [SMILES: CC(C)(C)c1cc(-c2oc(C(=O)N[C@H]3C[C@H](C(=O)O)C3)nc2CC2CCCCC2)cc(C2(C)CC2)c1] | $^1$H-NMR (400 MHz, CDCl$_3$) δ: 0.75-0.77 (m, 2H), 0.88-0.90 (m, 2H), 1.03-1.06 (m, 2H), 1.19-1.25 (m, 3H), 1.35 (s, 9H), 1.43 (s, 3H), 1.63-1.79 (m, 6H), 2.45-2.53 (m, 2H), 2.64 (d, J = 7.2 Hz, 2H), 2.78-2.84 (m, 2H), 3.19-3.21 (m, 1H), 4.75-4.81 (m, 1H), 7.29-7.30 (m, 2H), 7.41 (t, J = 1.6 Hz, 1H), 7.48 (t, J = 1.6 Hz, 1H). MS 493.3 (M + 1)$^+$ |
| 100/21 | 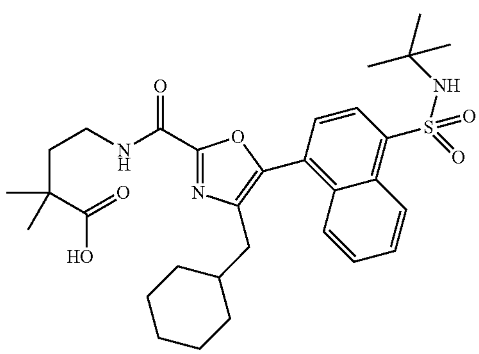 [SMILES: CC(C)(C)NS(=O)(=O)c1ccc(-c2oc(C(=O)NCCC(C)(C)C(=O)O)nc2CC2CCCCC2)c2ccccc12] | $^1$H-NMR (CDCl$_3$, 300 MHz) δ: 0.71-0.77 (m, 2H), 1.03-1.17 (m, 3H), 1.18 (s, 9H), 1.32 (s, 6H), 1.57-1.60 (m, 3H), 1.95-2.06 (m, 2H), 2.42 (d, J = 7.2 Hz, 2H), 3.45-3.56 (m, 6H), 4.69 (s, 1H), 7.58-7.72 (m, 4H), 7.84-7.87 (m, 1H), 8.35 (d, J = 7.5 Hz, 1H), 8.65 (d, J = 8.4 Hz, 1H). MS 584.3 (M + 1)$^+$ |
| 100/22 | 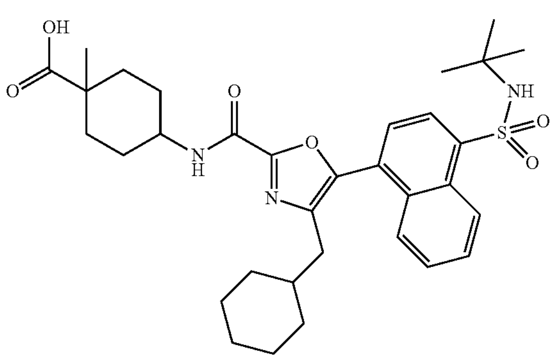 [SMILES: CC(C)(C)NS(=O)(=O)c1ccc(-c2oc(C(=O)NC3CCC(C)(C(=O)O)CC3)nc2CC2CCCCC2)c2ccccc12] | $^1$H-NMR (CDCl$_3$, 300 MHz) δ: 0.69-0.73 (m, 2H), 1.04-1.16 (m, 3H), 1.18 (s, 9H), 1.25-1.31 (m, 5H), 1.32-1.60 (m, 7H), 2.05-2.08 (m, 2H), 2.30-2.42 (m, 4H), 2.93 (s, 1H), 3.01 (s, 1H), 4.00 (br s, 1H), 4.71 (s, 1H), 7.60-7.75 (m, 3H), 7.83-7.86 (m, 1H), 8.28 (d, J = 7.2 Hz, 1H), 8.37 (d, J = 7.8 Hz, 1H), 8.66 (d, J = 8.4 Hz, 1H). MS 610.3 (M + 1)$^+$ |

| # | Structure | Analytical data |
|---|---|---|
| 100/23 | 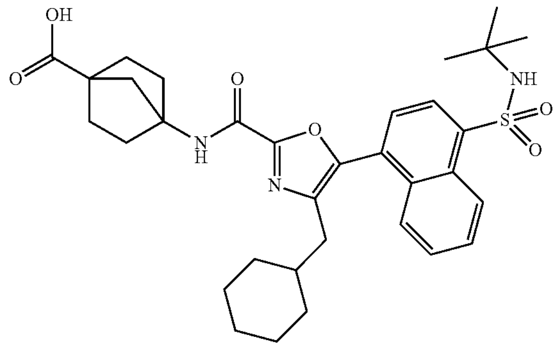 [SMILES: CC(C)(C)NS(=O)(=O)c1ccc(-c2oc(C(=O)NC34CCC(C(=O)O)(CC3)C4)nc2CC2CCCCC2)c2ccccc12] | ¹H-NMR (CDCl₃, 300 MHz) δ: 0.69-0.73 (m, 2H), 1.04-1.16 (m, 3H), 1.18 (s, 9H), 1.57-1.60 (m, 6H), 1.81-1.85 (m, 2H), 1.98-2.01 (m, 2H), 2.18-2.23 (m, 7H), 2.41 (d, J = 7.2 Hz, 2H), 4.70 (s, 1H), 7.36 (s, 1H), 7.59-7.72 (m, 3H), 7.87-7.90 (m, 1H), 8.36 (d, J = 7.5 Hz, 1H), 8.66 (d, J = 8.7 Hz, 1H). MS 608.3 (M + 1)⁺ |
| 100/24 | 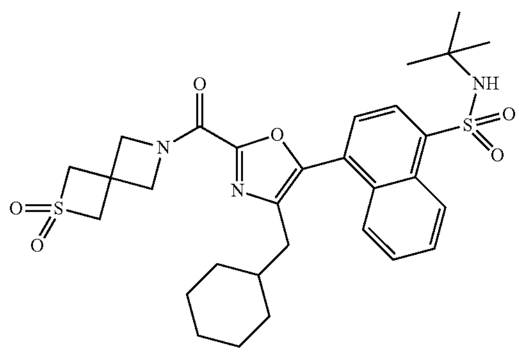 [SMILES: CC(C)(C)NS(=O)(=O)c1ccc(-c2oc(C(=O)N3CC4(C3)CS(=O)(=O)C4)nc2CC2CCCCC2)c2ccccc12] | ¹H-NMR (CDCl₃, 300 MHz) δ: 0.69-0.73 (m, 2H), 1.04-1.16 (m, 3H), 1.18 (s, 9H), 1.58-1.72 (m, 6H), 2.42 (d, J = 6.9 Hz, 2H), 4.43 (s, 4H), 4.49 (s, 2H), 4.68 (s, 1H), 4.99 (s, 2H), 7.58-7.73 (m, 3H), 7.83-7.86 (m, 1H), 8.37 (d, J = 7.2 Hz, 1H), 8.64 (d, J = 8.4 Hz, 1H). MS 600.2 (M + 1)⁺ |
| 100/25 | 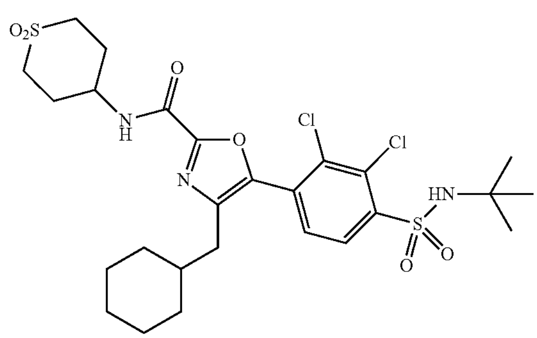 [SMILES: CC(C)(C)NS(=O)(=O)c1ccc(-c2oc(C(=O)NC3CCS(=O)(=O)CC3)nc2CC2CCCCC2)c(Cl)c1Cl] | ¹H-NMR (300 MHz, CDCl₃): δ 0.81-0.89 (m, 2H), 1.12-1.18 (m, 2H), 1.25 (s, 9H), 1.60-1.70 (m, 7H), 2.24-2.46 (m, 7H), 3.14-3.17 (m, 4H), 4.25-4.26 (m, 1H), 5.07 (s, 1H), 7.08 (d, J = 8.4 Hz, 1H), 7.45 (d, J = 8.4 Hz, 1H), 8.15 (d, J = 8.4 Hz, 1 H). MS 620.1 (M + 1)⁺. |
| 100/26 | 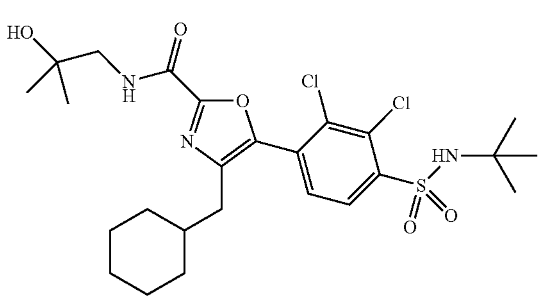 [SMILES: CC(C)(O)CNC(=O)c1nc(CC2CCCCC2)c(-c2ccc(S(=O)(=O)NC(C)(C)C)c(Cl)c2Cl)o1] | ¹H-NMR (300 MHz, CDCl₃): δ 0.81-0.88 (m, 2H), 1.11-1.21 (m, 3H), 1.25 (s, 9H), 1.32 (s, 6H), 1.61-1.70 (m, 6H), 2.40 (d, J = 7.2 Hz, 2H), 3.48 (d, J = 6.3 Hz, 2H), 5.10 (s, 1H), 7.45-7.49 (m, 2H), 8.13 (d, J = 8.4 Hz, 1H; MS 560.2 (M + 1)⁺. |

| # | Structure | Analytical data |
|---|---|---|
| 100/27 | 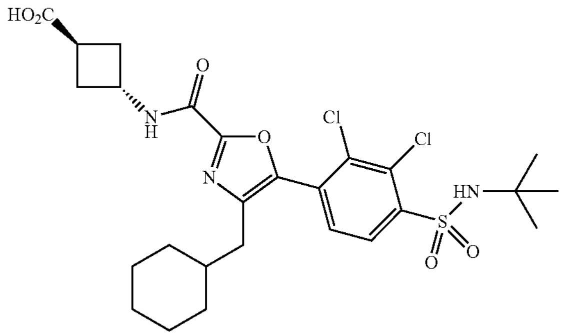 [SMILES: CC(C)(C)NS(=O)(=O)c1ccc(-c2oc(C(=O)N[C@H]3C[C@H](C(=O)O)C3)nc2CC2CCCCC2)c(Cl)c1Cl] | ¹H-NMR (400 MHz, CDCl₃): δ 0.81-0.84 (m, 2H), 1.11-1.22 (m, 3H), 1.25 (s, 9H), 1.61-1.71 (m, 6H), 2.38-2.53 (m, 4H), 2.77-2.85 (m, 2H), 3.17-3.19 (m, 1H), 4.81-4.84 (m, 1H), 5.09 (s, 1H), 7.35 (d, J = 8.1 Hz, 1H), 7.46 (d, J = 8.4 Hz, 1H), 8.14 (d, J = 8.4 Hz, 1H). MS 586.2 (M + 1)⁺. |
| 100/28 | 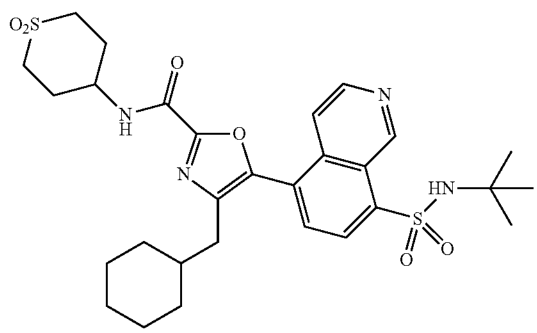 [SMILES: CC(C)(C)NS(=O)(=O)c1ccc(-c2oc(C(=O)NC3CCS(=O)(=O)CC3)nc2CC2CCCCC2)c2ccncc12] | ¹H-NMR (400 MHz, CD₃OD): δ 0.81-0.84 (m, 2H), 1.16-1.21 (m, 12H), 1.59-1.66 (m, 6H), 2.33-2.36 (m, 4H), 2.55 (d, J = 7.2 Hz, 2H), 3.15-3.18 (m, 2H), 3.33-3.36 (m, 2H), 4.29-4.33 (m, 1H), 7.94 (d, J = 6.0 Hz, 1H), 8.05 (d, J = 7.6 Hz, 1H), 8.47 (d, J = 7.6 Hz, 1H), 8.69 (d, J = 6.4 Hz, 1H), 10.19 (s, 1H); MS 603.3 (M + 1)⁺. |

Example 101

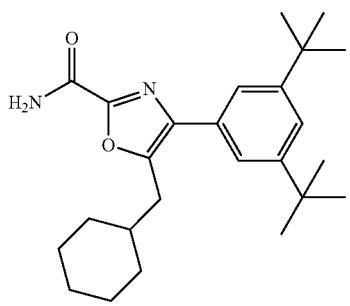

101

Step 1: 4-Methylbenzenesulfinic acid (101a)

To a mixture of sodium 4-methylbenzenesulfinate (1.0 g, 5.0 mmol) in TBME (30 mL) was added conc. HCl (2 mL) and the mixture was stirred at rt for 0.5 h. Then water (40 mL) was added. The layers were separated and the organic layer was dried over Na₂SO₄ and concentrated to give compound 101a (0.8 g, 93%) as a white solid.

Step 2: N-((3,5-Di-tert-butylphenyl)(tosyl)methyl)formamide (101b)

To a solution of 3,5-di-tert-butylbenzaldehyde (873 mg, 4 mmol) in toluene (6 mL) and MeCN (6 mL) was added formamide (540 mg, 12 mmol) and TMSCI (0.52 mL, 4.0 mmol) and the mixture was stirred at 50° C. overnight. Then compound 101a (630 mg, 4.0 mmol) was added. The resulting mixture was stirred at 50° C. overnight, then quenched with water (20 mL) and extracted with EA (20 mL). The organic layer was concentrated and the resulting solid was washed with TBME (4 mL) to give compound 101b (650 mg, 40%) as a white solid.

Step 3: 1,3-Di-tert-butyl-5-(isocyano(tosyl)methyl)benzene (101c)

To a solution of compound 101b (0.20 g, 0.49 mmol) in THF (1.5 mL) was added POCl₃ (151 mg, 1.0 mmol) and the mixture was stirred at rt for 10 min. Then the mixture was cooled to 4° C., 2,5-lutidine (321 mg, 3.0 mmol) was added over 3 min, warmed to rt, stirred for 4 h, poured into a mixture of ice and aq. NaHCO₃ (20 mL) and extracted with TBME (20 mL). The organic layer was concentrated to give compound 101c (50 mg, 26%) as an oil.

Step 4: 5-(Cyclohexylmethyl)-4-(3,5-di-tert-butylphenyl)oxazole (101d)

A solution of compound 101c (0.20 g, 0.50 mmol), 2-cyclohexylacetaldehyde (64 mg, 0.50 mmol) and K₂CO₃ (138 mg, 1.0 mmol) in DMF (3 mL) was stirred overnight at rt, poured into water and extracted with EA (20 mL×2). The combined organic layers were concentrated and purified by CC (PE/EA=100/1) to give compound 101d (80 mg, 45%) as an oil.

Step 5: Ethyl 5-(cyclohexylmethyl)-4-(3,5-di-tert-butylphenyl)oxazole-2-carboxylate (101e)

To a solution of compound 101d (0.20 g, 0.56 mmol) in dry THF (20 mL) was added LHMDS solution (1M in THF, 0.6 mL, 0.6 mmol) at −78° C. dropwise and the solution was stirred at −78° C. for 1 h. Then a solution of ethyl chloroformate (108 mg, 1.0 mmol) in dry THF (1 mL) was added. The mixture was warmed to rt, stirred for 2 h, quenched with aq. NH₄Cl and extracted with EA (20 mL×2). The combined organic layers were concentrated and purified by CC (PE/EA=100/1) to give compound 101e (60 mg, 25%) as an oil.

Step 6: 5-(Cyclohexylmethyl)-4-(3,5-di-tert-butylphenyl)oxazole-2-carboxamide (101)

A mixture of compound 101e (300 mg, 0.70 mmol) and THF/NH₃ (2M, 5 mL, 10 mmol) in a sealed tube was heated at 90° C. for 12 h, concentrated and purified by prep-HPLC to give compound 101 (70 mg, 25%) as a white solid. ¹H-NMR (CDCl₃, 300 MHz) δ: 1.06-1.30 (5H, m), 1.39 (18H, s), 1.59-1.87 (5H, m), 1.88-1.90 (1H, m), 2.80-2.83 (2H, d, J=9.9 Hz), 5.57 (1H, s), 7.01 (1H, s), 7.42 (1H, t, J=1.8 Hz), 7.48 (2H, d, J=1.8 Hz). MS 397.3 (M+1).

a white solid. ¹H-NMR (300 MHz, CDCl₃) δ: 0.73-0.81 (m, 2H), 1.05-1.10 (m, 3H), 1.18 (s, 9H), 1.57 (br s, 2H), 1.77 (br s, 4H), 1.94-1.99 (m, 6H), 2.12-2.17 (m, 6H), 2.39 (d, J=6.9 Hz, 2H), 3.30 (s, 3H), 4.68 (m, 1H), 6.86 (s, 1H), 7.58-7.74 (m, 3H), 7.85-7.93 (m, 2H), 8.36 (d, J=7.8 Hz, 1H), 8.66 (d, J=9.9 Hz, 1H). MS 699 [M+1]⁺.

Example 102/1

The following Example was prepared similar as described in Example 102 above:

| # | Structure | Analytical data |
|---|---|---|
| 102/1 | 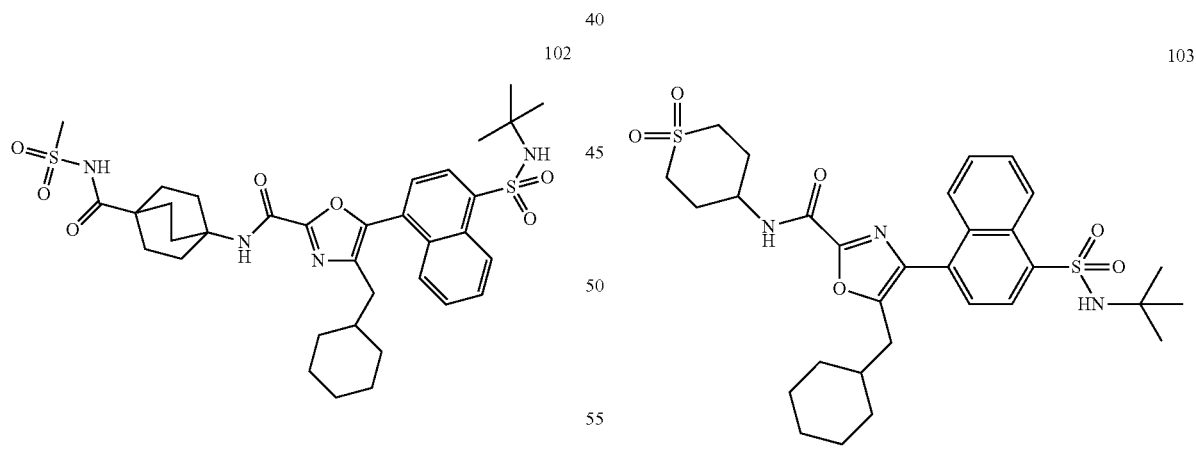 | ¹H-NMR (300 MHz, CDCl₃) δ: 0.75-0.85 (m, 2H), 1.04-1.06 (m, 3H), 1.18 (s, 9H), 1.58-1.61 (m, 7H), 2.42 (d, J = 6.9 Hz, 2H), 2.53-2.56 (m, 2H), 2.80-2.88 (m, 2H), 3.14-3.18 (m, 1H), 3.34 (s, 3H), 4.68-4.73 (m, 2H), 7.28-7.30 (m, 1H), 7.61 (d, J = 6.9 Hz, 2H), 7.70-7.75 (m, 1H), 7.85 (d, J = 7.5 Hz, 1H), 8.37 (d, J = 9.6 Hz, 1H), 8.66 (d, J = 8.4 Hz, 1H). MS 645 [M + 1]⁺ |

Example 102

5-(4-(N-(tert-Butyl)sulfamoyl)naphthalen-1-yl)-4-(cyclohexylmethyl)-N-(4-((methylsulfonyl)carbamoyl)bicyclo[2.2.2]octan-1-yl)oxazole-2-carboxamide (102)

A solution of compound 100/14 (94 mg, 0.15 mmol), EDCl (105 mg, 0.53 mmol), DMAP (110 mg, 0.85 mmol) and MeSO₂NH₂ (45 mg, 0.44 mmol) in DCM (5 mL) were stirred at 30° C. overnight, diluted with EA, washed with H₂O and brine, dried over Na₂SO₄, concentrated and purified by prep-HPLC to give compound 102 (31 mg, 30%) as Example 103

Step 1: 2-Cyclohexylacetaldehyde (103a)

To a solution of 2-cyclohexylethanol (25.6 g, 200 mmol) in DCM (500 mL) was added PCC (64.6 g, 300 mmol), and the solution was stirred at rt for 3 h, diluted with Et₂O, stirred at rt for 1 h and filtered through a pad of celite and silica gel (1/1). The filtrate was carefully concentrated to give crude compound 103a (25.2 g) as a pale yellow oil.

Step 2: 3-Cyclohexyl-2-hydroxypropanenitrile (103b)

To a stirred solution of compound 103a (25.2 g, 200 mmol) in DCM (180 mL) was added titanium isopropoxide (11.8 mL, 40.0 mmol) at 0° C. and warmed up to rt. Trimethysilyl cyanide (39.7 g, 400 mmol) was added and the solution was stirred at rt for 4 h, quenched with 1N HCl and THF at 0° C. and extracted with EA. The organic portion was washed with water and brine, dried over $Na_2SO_4$, filtered, concentrated and purified by CC (PE/EA=10/1) to give compound 103b (24.1 g, 72% over two steps) as a colorless oil.

Step 3: 1-Amino-3-cyclohexylpropan-2-ol (103c)

A solution of compound 103b (24.1 g, 144 mmol) in dry THF (250 mL) was added $LiAlH_4$ (8.2 g, 216 mmol) under stirring and the suspension was stirred at rt for 3 h. After cooling to 0 to 5° C., excess $LiAlH_4$ was neutralized by addition of $H_2O$ (8 mL), 15% aq. NaOH (8 mL) and $H_2O$ (24 mL). The suspension was stirred until all $LiAlH_4$ was neutralized and a white precipitate was formed, filtered and the precipitate was washed with $Et_2O$. The combined organic layers were dried over $Na_2SO_4$, filtered and concentrated to give compound 103c (21.6 g, 95%) as a colorless oil.

Step 4: Ethyl 2-((3-cyclohexyl-2-hydroxypropyl)amino)-2-oxoacetate (103d)

To a solution of compound 103c (21.6 g, 137 mmol) in dry DCM (200 mL) was added ethyl chloro(oxo)acetate (18.8 g, 137 mmol) followed by TEA (20.8 g, 206.1 mmol) at 0° C. and the mixture was slowly warmed to rt. After stirring overnight the mixture was concentrated, diluted with aq. $NaHCO_3$ and extracted with EA. The organic layer was washed with brine, dried over $Na_2SO_4$, filtered, concentrated and purified by CC (PE/EA=1/1) to give compound 103d (12.4 g, 35%) as a colorless oil.

Step 5: Ethyl 2-((3-cyclohexyl-2-oxopropyl)amino)-2-oxoacetate (103e)

To a stirred solution of compound 103d (12.4 g, 48.2 mmol) in dry DCM (150 mL) was added Dess-Martin periodinane (20.4 g, 48.2 mmol) at 0° C. and the solution was stirred at rt for 3 h, diluted with water at 0° C. and extracted with DCM twice. The combined organic layers were washed with water twice and brine, dried over $Na_2SO_4$, filtered, concentrated and purified by CC (PE/EA=1/1) to give compound 103e (10.1 g, 82%) as colorless solid.

Step 6: Ethyl 5-(cyclohexylmethyl)oxazole-2-carboxylate (103f)

A solution of compound 103e (10.1 g, 39.6 mmol) and $POCl_3$ (6.1 g, 39.6 mmol) in dry toluene (100 mL) was heated at reflux overnight, cooled to rt, concentrated and then partitioned between DCM and 5% aq. $Na_2CO_3$. The layers were separated and the aq. layer was extracted with DCM. The combined organic layers were dried over $Na_2SO_4$, filtered, concentrated and purified by CC (PE/EA=10/1) to give compound 103f (8.7 g, 92%) as a yellow oil.

Step 7: Ethyl 4-(4-(N-(tert-butyl)sulfamoyl)naphthalen-1-yl)-5-(cyclohexylmethyl)oxazole-2-carboxylate (103g)

The solution of compound 103f (500 mg, 2.10 mmol), 4-bromo-N-(tert-butyl)naphthalene-1-sulfonamide (791 mg, 2.30 mmol), $PPh_3$ (603 mg, 2.3 mmol) and $Pd(OAc)_2$ (95 mg, 0.40 mmol) in DMF (8 mL) was heated at 125° C. overnight, cooled to rt, partitioned between EA and water and the layers were separated. The organic layer was washed with water and brine, dried over $Na_2SO_4$, filtered, concentrated. This procedure was repeated three times and the combined residues were purified by CC (PE/EA=5/1) to give compound 103g (350 mg, 8%) as a yellow solid.

Step 8: Potassium 4-(4-(N-(tert-butyl)sulfamoyl)naphthalen-1-yl)-5-(cyclohexylmethyl)oxazole-2-carboxylate (103h)

To a solution of compound 103g (350 mg, 0.70 mmol) in a mixture of MeOH (10 mL) and $H_2O$ (1 mL) was added KOH (56 mg, 1.0 mmol) and the mixture was stirred at rt for 5 h and concentrated to give crude compound 103h (365 mg) as an off-white solid.

Step 9: 4-(4-(N-(tert-Butyl)sulfamoyl)naphthalen-1-yl)-5-(cyclohexylmethyl)-N-(1,1-dioxidotetrahydro-2H-thiopyran-4-yl)oxazole-2-carboxamide (103)

A solution of compound 103h (150 mg, 0.30 mmol), HATU (136 mg, 0.36 mmol), DIEA (90 mg, 0.70 mmol) and 1,1-dioxo-hexahydrothiopyran-4-ylamine hydrochloride salt (56 mg, 0.36 mmol) in DMF (3 mL) was stirred overnight and diluted with $H_2O$ and EA. The organic layer was washed with brine, dried over $Na_2SO_4$, filtered, concentrated and purified by prep-HPLC to give compound 103 (31 mg, 18%) as a colorless solid. $^1$H-NMR (300 MHz, DMSO-$d_6$) δ: 0.70-0.74 (m, 2H), 0.97-1.02 (m, 12H), 1.46-1.50 (m, 6H), 2.08-2.17 (m, 4H), 2.60 (d, J=7.2 Hz, 2H), 3.04-3.08 (m, 2H), 3.26-3.37 (m, 2H), 4.17-4.21 (m, 1H), 7.64-7.73 (m, 3H), 7.86 (s, 1H), 7.97 (d, J=8.4 Hz, 1H), 8.24 (d, J=8.1 Hz, 1H), 8.76 (d, J=8.4 Hz, 1H), 9.06 (d, J=8.4 Hz, 1H). MS 602.2 [M+1]$^+$.

Example 103/1 to 103/3

The following Examples were prepared similar as described in Example 103 above:

| # | Structure | Analytical data |
|---|---|---|
| 103/1 | 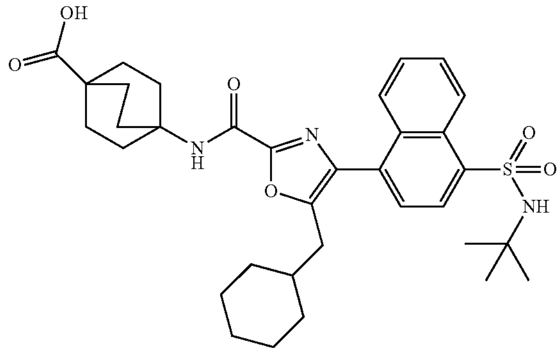 [SMILES: CC(C)(C)NS(=O)(=O)c1ccc(-c2nc(C(=O)NC34CCC(C(=O)O)(CC3)CC4)oc2CC2CCCCC2)c2ccccc12] | $^1$H-NMR (300 MHz, DMSO-d$_6$) δ: 0.69-0.73 (m, 2H), 0.96-1.05 (m, 12H), 1.42-1.47 (m, 6H), 1.74-1.79 (m, 6H), 1.92-1.97 (m, 6H), 2.57 (d, J = 6.9 Hz, 2H), 7.62-7.72 (m, 3H), 7.86 (s, 1H), 7.94-7.97 (m, 2H), 8.23 (d, J = 7.5 Hz, 1H), 8.75 (d, J = 8.4 Hz, 1H), 11.95 (br s, 1H). MS 622.3 [M + 1]$^+$ |
| 103/2 | 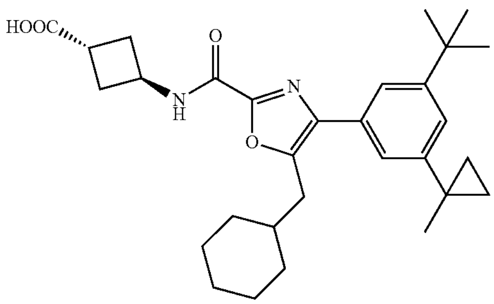 [SMILES: CC(C)(C)c1cc(-c2nc(C(=O)N[C@H]3C[C@H](C(=O)O)C3)oc2CC2CCCCC2)cc(C2(C)CC2)c1] | $^1$H-NMR (300 MHz, CDCl$_3$) δ: 0.76-0.78 (m, 2H), 0.88-0.91 (m, 2H), 1.01-1.08 (m, 2H), 1.18-1.33 (m, 3H), 1.36 (s, 9H), 1.45 (s, 3H), 1.63-1.75 (m, 5H), 1.82-1.93 (m, 1H), 2.43-2.53 (m, 2H), 2.78-2.80 (m, 4H), 3.14-3.23 (m, 1H), 4.76-4.84 (m, 1H), 7.29 (t, J = 1.8 Hz, 1H), 7.35 (t, J = 1.8 Hz, 1H), 7.44 (t, J = 1.8 Hz, 1H). MS 493.3 [M + 1]$^+$ |
| 103/3 | 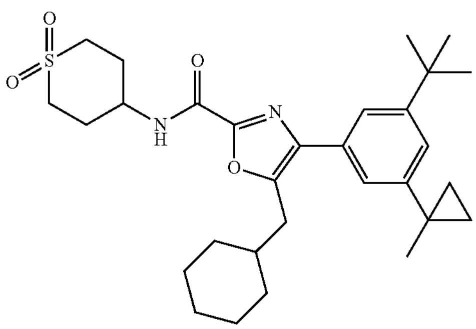 [SMILES: CC(C)(C)c1cc(-c2nc(C(=O)NC3CCS(=O)(=O)CC3)oc2CC2CCCCC2)cc(C2(C)CC2)c1] | $^1$H-NMR (300 MHz, CDCl$_3$) δ: 0.76-0.78 (m, 2H), 0.88-0.91 (m, 2H), 1.01-1.08 (m, 2H), 1.18-1.33 (m, 3H), 1.36 (s, 9H), 1.45 (s, 3H), 1.63-1.75 (m, 5H), 1.82-1.93 (m, 1H), 2.29-2.43 (m, 4H), 2.80 (d, J = 7.2 Hz, 2H), 3.13-3.17 (m, 4H), 4.23-4.28 (m, 1H), 7.09-7.12 (m, 1H), 7.29 (t, J = 1.8 Hz, 1H), 7.34 (t, J = 1.8 Hz, 1H), 7.43 (t, J = 1.8 Hz, 1H). MS 527.3 ([M + 1]$^+$ |

Example 104

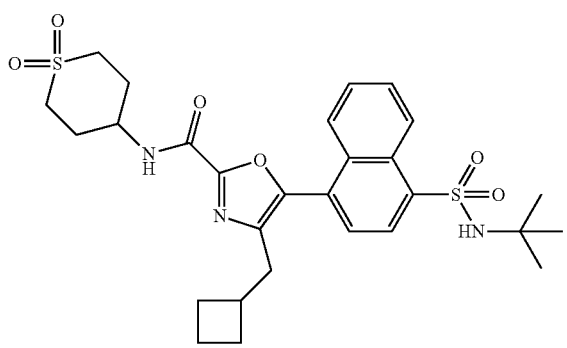

104

Step 1: Ethyl 5-(4-(N-(tert-butyl)sulfamoyl)naphthalen-1-yl)-4-(cyclobutylmethyl)oxazole-2-carboxylate (104a)

To a solution of N-(tert-butyl)-4-(4-(cyclobutylmethyl)oxazol-5-yl)naphthalene-1-sulfonamide (1.6 g, 4.0 mmol, prepared similar to intermediate 100b) in THF (20 mL) was added n-butyllithium (3.2 mL, 8.0 mmol) at −78° C. and then stirred for 30 min at this temperature. Ethyl chloroformate (6.5 g, 6.0 mmol) was added dropwise at −78° C. The solution was stirred at −78° C. for 1 h, quenched with sat. aq. NH$_4$Cl, stirred at rt for 1 h and extracted with DCM. The organic layer was dried with Na$_2$SO$_4$, filtered, concentrated and purified by CC (DCM/MeOH=60/1) to afford compound 104a (600 mg, 31%) as a white solid.

Step 2 and Step 3: 5-(4-(N-(tert-Butyl)sulfamoyl)naphthalen-1-yl)-4-(cyclobutylmethyl)-N-(1,1-dioxidotetrahydro-2H-thiopyran-4-yl)oxazole-2-carboxamide (104)

Example 104 was prepared from intermediate 104a similar as described for Example 6 from intermediate 6e. $^1$H-NMR (300 MHz, CDCl$_3$) δ: 1.10 (s, 9H), 1.40-1.45 (m, 2H), 1.56-1.68 (m, 2H), 1.81-1.85 (m, 2H), 2.20-2.25 (m, 4H), 2.56-2.63 (m, 3H), 2.74 (s, 2H), 3.01-3.06 (m, 2H), 4.20-4.21 (m, 1H), 7.60-7.71 (m, 3H), 7.81 (d, J=8.4 Hz, 1H), 8.29 (d, J=7.6 Hz, 1H), 8.76 (d, J=8.6 Hz, 1H). MS 574.3 (M+1)⁺.

Example 200

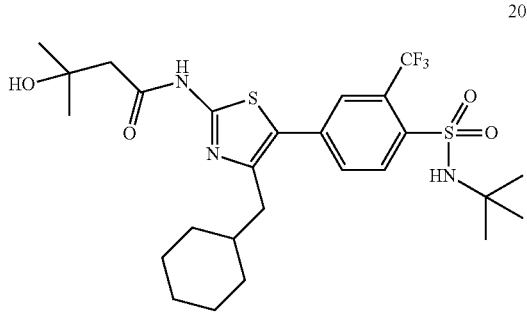

Step 1: 4-(Cyclohexylmethyl)thiazol-2-amine (200a)

A solution of 1-bromo-3-cyclohexylpropan-2-one (2.8 g, 12.8 mmol) and thiourea (1.07 g, 14.1 mmol) in EtOH (20 mL) was refluxed for 4 h, concentrated and portioned between DCM and sat. NaHCO₃. The organic layer was washed with brine, dried over Na₂SO₄, filtered, concentrated and purified by CC (PE/EA=3/1) to give compound 200a (1.1 g, 44%) as a yellow solid.

Step 2: 5-Bromo-4-(cyclohexylmethyl)thiazol-2-amine (200b)

A mixture of compound 200a (7.6 g, 38.8 mmol) and NBS (6.9 g, 38.8 mmol) in MeCN (100 mL) was stirred at 50° C. for 10 h, diluted with water (30 mL) and extracted with EA (3×100 mL). The combined organic layer was washed with brine, dried over Na₂SO₄ and evaporated to obtain compound 200b (7.5 g, 71%) as yellowish solid.

Step 3: N-(5-Bromo-4-(cyclohexylmethyl)thiazol-2-yl)-3-hydroxy-3-methylbutanamide (200c)

A mixture of compound 200b (548 mg, 2.0 mmol), DCC (412 mg, 2.0 mmol) and 3-hydroxy-3-methylbutanoic acid (236 mg, 2.0 mmol) in DMF (20 mL) was stirred at rt for 12 h, diluted with water (30 mL) and extracted with EA (3×50 mL). The combined organic layer was washed with brine, dried over Na₂SO₄ and evaporated to obtain compound 200c (220 mg, 29%) as yellowish solid.

Step 4: N-(5-(4-(N-(tert-Butyl)sulfamoyl)-3-(trifluoromethyl)phenyl)-4-(cyclohexylmethyl)thiazol-2-yl)-3-hydroxy-3-methylbutanamide (200)

A suspension of compound 200c (75 mg, 0.2 mmol), Cs₂CO₃ (130 mg, 0.4 mmol), N-(tert-butyl)-4-(4,4,5,5-tetramethyl-1,3,2-dioxaborolan-2-yl)-2-(trifluoromethyl)benzenesulfonamide (81 mg, 0.2 mmol), Pd(PPh₃)₄ (23 mg, 20 µmol) in toluene/H₂O (10:1, 10 mL) was heated overnight under N₂ at 100° C., concentrated and extracted with EA. The organic layer was washed with brine, dried over MgSO₄, filtered, evaporated and purified by prep-HPLC to give compound 200 (30 mg, 25%) as yellowish solid. ¹H-NMR (DMSO-d₆, 300 MHz) δ: 12.10 (br s, 1H), 8.24 (d, 1H, J=6.3 Hz), 7.86-7.94 (m, 3H), 2.57-2.60 (m, 4H), 1.59-1.75 (m, 6H), 1.07-1.23 (m, 18H), 0.85-0.91 (m, 2H). MS 576.2 (M+1)⁺.

Example 200/1

The following Example was prepared similar as in Example 200:

| # | Structure | Analytical data |
|---|-----------|-----------------|
| 200/1 | 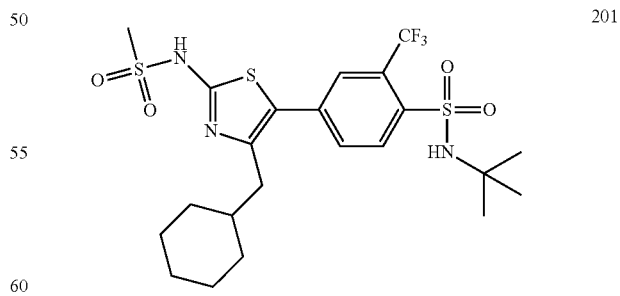 | ¹H-NMR (400 MHz, CDCl₃) δ: 8.25 (d, J = 8.4 Hz, 1H), 7.87 (d, J = 8.4 Hz, 2H), 7.79 (s, 1H), 7.61 (d, J = 8.4 Hz, 1H), 7.50 (d, J = 8.4 Hz, 2H), 4.68 (s, 1H), 3.87 (s, 2H), 3.11-3.05 (m, 2H), 2.49 (d, J = 7.2 Hz, 2H), 1.59-1.53 (m, 6H), 1.26-1.20 (m, 12H), 1.12-0.79 (m, 5H). MS 686.1 (M + 1)⁺. |

Example 201

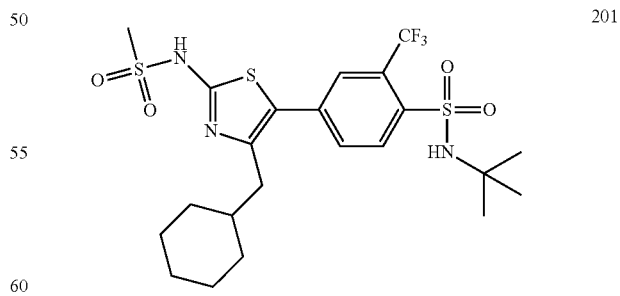

Step 1: N-(5-Bromo-4-(cyclohexylmethyl)thiazol-2-yl)methanesulfonamide (201a)

To the mixture of compound 200b (548 mg, 2.0 mmol) and TEA (404 mg, 4.0 mmol) in DCM (20 mL) at −10° C.

was added MsCl (262 mg, 2.2 mmol) for 2 h, diluted with water (30 mL) and extracted with DCM (3×50 mL). The organic layer was washed with brine, dried over $Na_2SO_4$, filtered and concentrated to give compound 201a (640 mg, 91%) as a yellow is solid.

Step 2: N-(tert-Butyl)-4-(4-(cyclohexylmethyl)-2-(methylsulfonamido)thiazol-5-yl)-2-(trifluoromethyl)benzenesulfonamide (201)

A suspension of compound 201a (90 mg, 0.25 mmol), $Cs_2CO_3$ (162 mg, 0.5 mmol), N-(tert-butyl)-4-(4,4,5,5-tetramethyl-1,3,2-dioxaborolan-2-yl)-2-(trifluoromethyl)benzenesulfonamide (101 mg, 0.25 mmol), Pd $(PPh_3)_4$ (35 mg, 0.03 mmol) in toluene/$H_2O$ (10:1, 10 mL) was heated overnight under $N_2$ at 100° C., cooed, concentrated and extracted with EA. The organic layer was washed with brine, dried over $MgSO_4$, filtered, evaporated and purified by prep-HPLC to give compound 201 (35 mg, 25%) as yellowish solid. $^1$H-NMR (DMSO-$d_6$, 300 MHz) δ: 12.73 (br s, 1H), 8.25 (d, 1H, J=6.3 Hz), 7.85-7.93 (m, 3H), 2.97 (s, 3H), 2.50-2.53 (m, 2H), 1.55-1.62 (m, 6H), 1.06-1.17 (m, 11H), 0.80-0.851 (m, 3H). MS 554.1 $(M+1)^+$.

Example 202

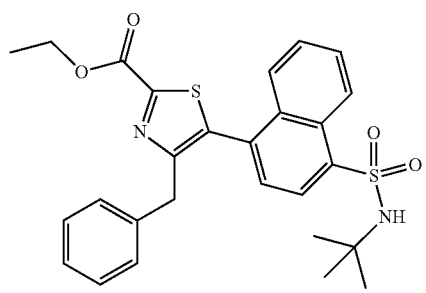

Ethyl 4-benzyl-5-(4-(N-(tert-butyl)sulfamoyl)naphthalen-1-yl)thiazole-2-carboxylate (202)

The solution of ethyl 4-benzyl-5-bromothiazole-2-carboxylate (1.50 g, 4.53 mmol), N-(tert-butyl)-4-(4,4,5,5-tetramethyl-1,3,2-dioxaborolan-2-yl)naphthalene-1-sulfonamide (2.11 g, 5.43 mmol), $Na_2CO_3$ (1.90 g, 18.0 mmol) and Pd(dppf)$Cl_2$ (331 mg, 0.45 mmol) in a mixture of toluene (30 mL), EtOH (15 mL) and water (15 mL) was heated at 70° C. for 15 h, cooled to rt, partitioned between EA and water and separated. The organic phase was washed with water and brine, dried over $Na_2SO_4$, filtered, concentrated and purified by CC (PE/EA=10/1 to 5/1) to give compound 202 (1.24 g, 53%) as a white solid. $^1$H-NMR (400 MHz, CDCl$_3$) δ: 0.56-0.66 (m, 2H), 0.93-1.14 (m, 3H), 1.22 (s, 9H), 1.45-1.49 (m, 5H), 1.52-1.58 (m, 3H), 1.74-1.79 (m, 1H), 2.39-2.43 (m, 2H), 4.53 (q, J=6.8 Hz, 2H), 4.71 (s, 1H), 7.53 (d, J=7.6 Hz, 1H), 7.57-7.61 (m, 1H), 7.71-7.74 (m, 1H), 8.36 (d, J=7.6 Hz, 1H). MS 515.2 $[M+1]^+$.

Example 203

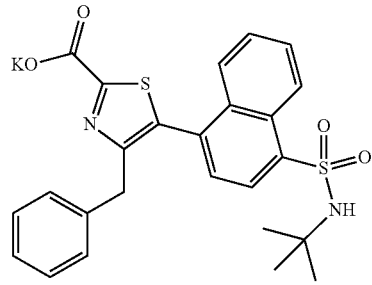

Potassium 4-benzyl-5-(4-(N-(tert-butyl)sulfamoyl)naphthalen-1-yl)thiazole-2-carboxylate (203)

To a solution of compound 202 (1.35 g, 2.63 mmol) in a solution of MeOH (20 mL) and $H_2O$ (5 mL) was added KOH (147 mg, 2.63 mmol) and then the solution was stirred for 30 min at 50° C. The resulting solution was concentrated, washed with $Et_2O$ and dried in vacuum to give compound 203 (1.32 g, 96%) as a yellow solid. $^1$H-NMR (400 MHz, CD$_3$OD) δ: 0.57-0.65 (m, 2H), 0.94-1.07 (m, 3H), 1.13 (s, 9H), 1.48 (d, J=10.0 Hz, 5H), 1.63-1.67 (m, 1H), 2.38 (br s, 2H), 7.59-7.63 (m, 2H), 7.72 (t, J=7.2 Hz, 2H), 7.79 (d, J=8.4 Hz, 1H), 8.31 (d, J=7.6 Hz, 1H), 8.81 (d, J=8.4 Hz, 1H). MS 443.2 [M-K+1]+.

Example 204

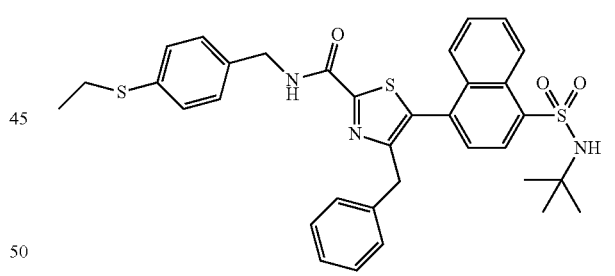

4-Benzyl-5-(4-(N-(tert-butyl)sulfamoyl)naphthalen-1-yl)-N-(4-(ethylthio)benzyl)thiazole-2-carboxamide (204)

The solution of compound 203 (200 mg, 0.38 mmol), HATU (72 mg, 0.38 mmol), DIEA (129 mg, 1.00 mmol) and (4-(ethylthio)phenyl)methanamine (72 mg, 0.41 mmol) in DMF (2 mL) was stirred for 1 h at rt, quenched with $H_2O$ and extracted with EA (3×). The combined organic layers were washed with water (3×) and brine consecutively, dried over $Na_2SO_4$, filtered, concentrated and purified by prep-HPLC to give compound 204 (117 mg, 48%) as a white powder.

Example 205

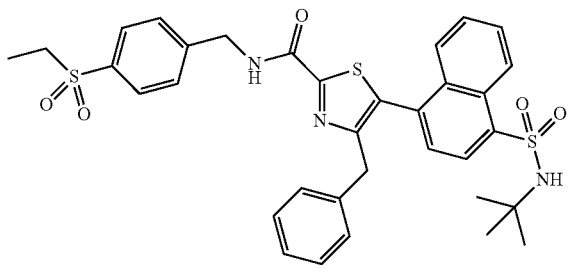

4-Benzyl-5-(4-(N-(tert-butyl)sulfamoyl)naphthalen-1-yl)-N-(4-(ethylsulfonyl)benzyl)thiazole-2-carboxamide (205)

To a solution of compound 204 (117 mg, 0.18 mmol) in DCM (5 mL) was added m-CPBA (102 mg, 0.50 mmol) and the solution was stirred at rt for 30 min, quenched with aq. $Na_2SO_3$ and extracted with EA. The organic layer was washed with water and brine, dried over $Na_2SO_4$, filtered, concentrated and purified by prep-HPLC to give compound 205 (67 mg, 56%) as a white solid. $^1$H-NMR (400 MHz, $CDCl_3$) δ: 0.60-0.69 (m, 2H), 0.83-1.11 (m, 3H), 1.20 (s, 9H), 1.23-1.32 (m, 5H), 1.48-1.56 (m, 3H), 1.65-1.68 (m, 1H), 2.34 (br s, 2H), 3.13 (q, J=7.6 Hz, 2H), 4.64 (s, 1H), 4.80 (d, J=6.4 Hz, 2H), 7.52 (d, J=7.6 Hz, 1H), 7.56-7.80 (m, 6H), 7.93 (d, J=8.4 Hz, 2H), 8.36 (d, J=7.6 Hz, 1H), 8.69 (d, J=8.0 Hz, 1H). MS 668.2 [M+1]*.

Example 206

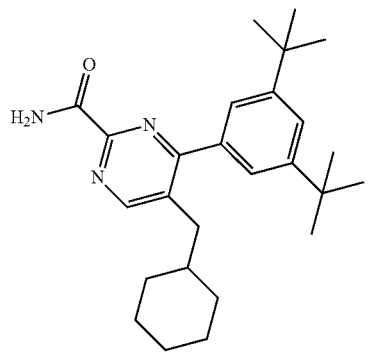

Step 1: 5-(Bromomethyl)-2,4-dichloropyrimidine (206a)

2,4-Dichloro-5-methylpyrimidine (20.0 g, 123 mmol) was dissolved in ACN (100 mL) and NBS (26.1 g, 147 mmol) and AIBN (1.01 g, 6.13 mmol) were added. The mixture was heated to 90° C. and stirred for 16 h at that temperature. The solvent was removed and purification by CC (PE/EA=99/1) afforded compound 206a (15 g, 50%) as pale yellow syrup.

Step 2: 2,4-Dichloro-5-(cyclohexylidenemethyl)pyrimidine (206b)

Triisopropylphosphite (7.28 g, 35.0 mmol) was added to compound 206a (5.0 g, 20.6 mmol) in a flask and the mixture was heated to 100° C. for 2 h, cooled to 0° C. and THF (25 mL) was added followed by cyclohexanone (2.42 g, 24.7 mmol). After 5 min, NaH (822 mg, 20.6 mmol) was added. The mixture was stirred for 15 min at 0° C., then allowed to warm up to rt and stirred for 15 min. After completion of the reaction, the mixture was diluted with sat. $NH_4Cl$ solution (25 mL) and EA (50 mL). The organic layer was separated and the aq. layer was extracted with DCM (2×25 mL). The combined organic layers were dried over $Na_2SO_4$, evaporated and purified by CC (1.5% EA in PE) to afford compound 206b (1.8 g, 36%) as an off-white solid.

Step 3: 2-Chloro-5-(cyclohexylidenemethyl)-4-(3,5-di-tert-butylphenyl)pyrimidine (206c)

A mixture of compound 206b (2.0 g, 8.26 mmol), 2-(3, 5-di-tert-butylphenyl)-4,4,5,5-tetramethyl-1,3,2-dioxaborolane (3.13 g, 9.91 mmol), $K_2CO_3$ (3.19 g, 23.1 mmol), in 1,4-dioxane (20 mL) were purged with Ar for 15 min in a sealed vial. $Pd(PPh_3)_4$ (0.477 g, 413 μmol) was added and the mixture was stirred at 140° C. for 5 h, filtered through celite and the filtrate was concentrated. Purification by CC (5% EA in PE) afforded compound 206c (1.1 g, 34%) as an off-white solid.

Step 4: 5-(Cyclohexylidenemethyl)-4-(3,5-di-tert-butylphenyl)pyrimidine-2-carbonitrile (206d)

NaCN (149 mg, 3.06 mmol) was added to a mixture of compound 206c (1.1 g, 2.78 mmol) and DABCO (31 mg, 0.28 mmol) in DMSO (20 mL). Then the mixture was heated to 40° C. and stirred for 16 h, then carefully diluted with water and extracted with DCM (3×10 mL). The combined organic layer was washed with ice cold water (3×10 mL). The organic layer was dried over $Na_2SO_4$, evaporated and purified by CC (5% EA in PE) to afford compound 206d (0.50 g, 45%) as pale yellow solid.

Step 5: 5-(cyclohexylidenemethyl)-4-(3,5-di-tert-butylphenyl)pyrimidine-2-carboxylic acid (206e)

Compound 206d (0.8 g, 2.06 mmol) was dissolved in EtOH (5 mL) and water (5 mL). Then NaOH (0.165 g, 4.13 mmol) was added and the mixture was stirred at 100° C. for 16 h, evaporated, diluted with water and extracted with $CHCl_3$ (3×10 mL). The combined organic layer was dried over $Na_2SO_4$, evaporated and purified by CC (EA/PE=1/1) to afford compound 206e (0.3 g, 36%) as pale yellow solid.

Step 6: 5-(Cyclohexylidenemethyl)-4-(3,5-di-tert-butylphenyl)pyrimidine-2-carboxamide (206f)

A mixture of compound 206e (150 mg, 369 µmol) and thionylchloride (133 µL, 1.85 mmol) was refluxed for 2 h. The thionylchloride was evaporated and NH₃ (7N in THF, 1 mL) was added at 0° C. The mixture was stirred at rt for 3 h, evaporated and dissolved in CHCl₃ (2 mL) and washed with water (2×2 mL). The organic layer was dried over Na₂SO₄, evaporated and purified by CC (30% EtOAc in PE) to afford compound 206f (0.15 g, quant.) as brown syrup.

Step 7: 5-(Cyclohexylmethyl)-4-(3,5-di-tert-butylphenyl)pyrimidine-2-carboxamide (206)

Compound 206f (0.15 g, 370 µmol) was dissolved in MeOH (5 mL) and 2N NaOH (0.1 mL) was added. Then Pd/C (20 mg) was added and the mixture was kept under hydrogen atmosphere (ballon pressure), stirred for 30 min, filtered through celite and was washed with MeOH (2 mL). The solvent was evaporated and the obtained crude product was dissolved in CHCl₃ (5 mL) and washed with water (5 mL). The organic layer was dried over Na₂SO₄, evaporated and purified by CC (PE/EA=1/1) to afford compound 206 (70 mg, 50%) as white solid. $^1$H-NMR (CDCl₃, 400 MHz) δ: 0.83-1.51 (m, 11H), 1.37 (s, 18H), 2.61 (d, 2H), 5.69 (br s, 1H), 7.26-7.30 (m, 2H), 7.54-7.55 (m, 1H), 7.84 (br s, 1H), 8.74 (s, 1H). MS 408.6 (M+1)⁺.

Example 207

Step 1: 5-(Cyclohexylidenemethyl)-4-(3,5-di-tert-butylphenyl)-N-(oxetan-3-yl)pyrimidine-2-carboxamide (207a)

Compound 206e (0.15 g, 369 µmol) was dissolved in DCM (5 mL) and TEA (74 mg, 770 µmol) was added followed by an excess of propylphosphonic acid anhydride and oxetan-3-amine (32 mg, 443 µmol). The mixture was stirred for 16 h at rt and diluted with water. The organic layer was separated, dried over Na₂SO₄ and evaporated to afford crude compound 207a (0.15 g, 88%).

Step 2: 5-(Cyclohexylmethyl)-4-(3,5-di-tert-butylphenyl)-N-(oxetan-3-yl)pyrimidine-2-carboxamide (207)

Compound 207a (0.15 g, 325 µmol) was dissolved in MeOH (5 mL) and 2N NaOH (0.1 mL) was added. Then Pd/C (20 mg) was added and the mixture was kept under hydrogen atmosphere (ballon pressure). After completion the mixture was filtered through celite and the celite was washed with MeOH (2 mL). The solvent was evaporated and the obtained crude product was dissolved in CHCl₃ (5 mL). The organic layer was washed with water (5 mL), dried over Na₂SO₄, evaporated and purified by CC (PE/EA=1/1) to afford compound 207 (65 mg, 50%) as colorless solid. $^1$H-NMR (CDCl₃, 400 MHz) δ: 0.80-1.60 (m, 11H), 1.35 (s, 18H), 2.58-2.60 (d, 2H), 4.64 (t, 2H), 5.01 (t, 2H), 5.34 (m, 1H), 7.31 (m, 2H), 7.57 (m, 1H), 8.57 (m, 1H), 8.73 (s, 1H). MS 464.6 (M+1)⁺.

Example 207/1

The following Example was prepared similar as described in Example 207.

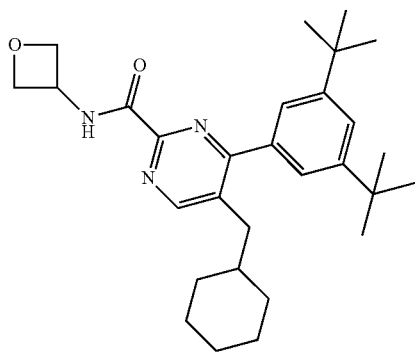

207

| # | Structure | Analytical data |
|---|---|---|
| 207/1 | 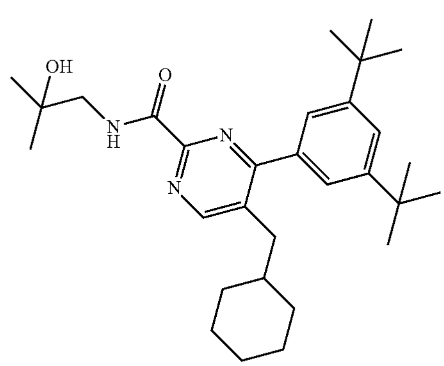 [SMILES: CC(C)(O)CNC(=O)c1ncc(CC2CCCCC2)c(-c2cc(C(C)(C)C)cc(C(C)(C)C)c2)n1] | $^1$H-NMR (CDCl₃, 400 MHz) δ: 0.80-1.60 (m, 11H), 1.12 (s, 6H), 1.35 (s, 18H), 2.60 (d, 2H), 3.29 (m, 2H), 4.66 (s, 1H), 7.37 (m, 2H), 7.54 (m, 1H), 8.50 (m, 1H), 8.83 (s, 1H). MS 480.6 (M + 1)⁺ |

Example 208

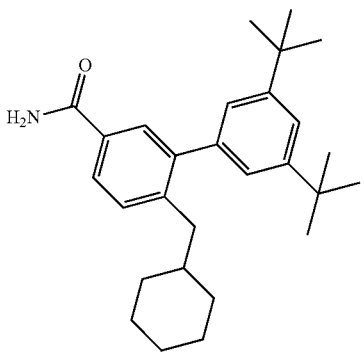

Step 1: Methyl 3-bromo-4-(bromomethyl)benzoate (208a)

AIBN (71 mg, 440 μmol) was added to a solution of methyl 3-bromo-4-methylbenzoate (2.0 g, 8.73 mmol) and NBS (1.87 g, 10.5 mmol) in ACN (10 mL). The mixture was refluxed for 48 h, cooled to rt, evaporated and purified by CC (5% EA in PE) to afford compound 208a (1.07 g, 40%).

Step 2: 3-Bromo-4-(cyclohexylidenemethyl)benzoic acid (208b)

A mixture of compound 208a (0.50 g, 2.18 mmol) and triethyl phosphite (0.62 g, 3.71 mmol) in THF (10 mL) was refluxed for 3 h, cooled to 0° C. and then NaH (52 mg, 2.18 mmol) was added followed by THF. The mixture was stirred at rt for 15 min, followed by addition of cyclohexanone (0.26 g, 2.62 mmol) at 0° C. The mixture was stirred at rt for 16 h, diluted with aq. $NH_4Cl$ and EA. The organic layer was separated and aq. layer was acidified with 2N HCl at 0° C. and extracted with DCM (3×10 mL). The combined organic layer was dried over $Na_2SO_4$ and evaporated to obtain crude product 208b.

Step 3: 3',5'-Di-tert-butyl-6-(cyclohexylidenemethyl)-[1,1'-biphenyl]-3-carboxylic acid (208c)

A mixture of compound 208b (0.5 g, 1.69 mmol), 2-(3,5-di-tert-butylphenyl)-4,4,5,5-tetramethyl-1,3,2-dioxaborolane (0.64 g, 2.03 mmol), $Na_2CO_3$ (0.50 g, 4.74 mmol) in 1,4-dioxane and water was purged with Ar for 15 min. Then $Pd(PPh_3)_4$ (97 mg, 85 mmol) was added and the mixture was stirred at 90° C. for 14 h, filtered through celite and the filtrate was concentrated and purified by CC (25% EA in PE) to afford compound 208c (342 mg, 50% over two steps).

Step 4: 3',5'-Di-tert-butyl-6-(cyclohexylmethyl)-[1,1'-biphenyl]-3-carboxylic acid (208d)

Pd/C (10 mg) was added to a solution of compound 208c (100 mg, 247 mmol) in MeOH and the reaction was performed under 60 psi hydrogen pressure at rt for 16 h. The mixture was filtered through celite and the filtrate was evaporated. The obtained crude product was partitioned between water and 10% MeOH/DCM. The organic layer was separated and dried over $Na_2SO_4$ and evaporated. The obtained crude product was triturated with $Et_2O$ and the solid was filtered off and dried under vacuum to afford compound 208d (45 mg, 45%) as pale yellow solid.

Step 5: 3',5'-Di-tert-butyl-6-(cyclohexylmethyl)-[1,1'-biphenyl]-3-carboxamide (208)

CDI (79 mg, 0.49 mmol) of was added to a solution of compound 208d (100 mg, 0.25 mmol) in THF (5 mL) and the mixture was stirred at rt for 16 h. Then a 2M solution of $NH_3$ (5 mL) in THF was added at 0° C. and the mixture was stirred at rt for 1 h, evaporated and the obtained crude product was partitioned between EA and water. The organic layer was separated, dried over $Na_2SO_4$ and evaporated. The obtained crude product was triturated with ACN and dried under vacuum to afford compound 208 (60 mg, 60%). $^1$H-NMR (DMSO-$d_6$, 400 MHz) δ: 0.70-1.55 (m, 11H), 1.30 (s, 18H), 2.45 (d, 2H), 7.08 (m, 2H), 7.24 (m, 1H), 7.33 (br s, 1H), 7.40 (m, 1H), 7.72-7.77 (m, 2H), 7.96 (br s, 1H). MS 406.5 $(M+1)^+$.

Example 209

The following Example was prepared using similar procedures as that described in Example 208.

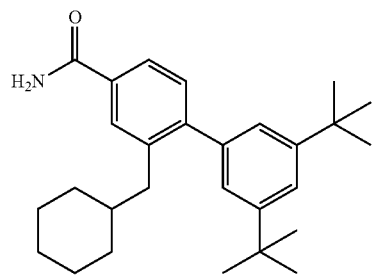

$^1$H-NMR (DMSO-$d_6$, 400 MHz) δ: 0.69-1.57 (m, 11H), 1.32 (s, 18H), 2.45 (d, 2H), 7.08 (m, 2H), 7.26-7.32 (m, 2H), 7.40 (m, 1H), 7.68 (m, 1H), 7.78 (m, 1H), 7.94 (br s, 1H). MS 406.5 $(M+1)^+$.

Example 210 and Example 211

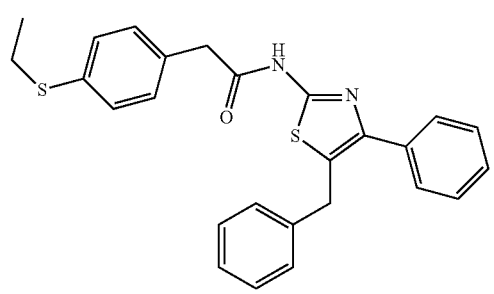

-continued

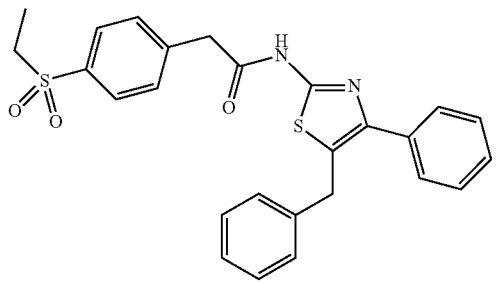

211

Step 1: 5-Benzyl-4-phenylthiazol-2-amine (210a)

(2-Amino-4-phenylthiazol-5-yl)(phenyl)methanone (prepared similar as described in WO02012/028100) was reduced with NaBH$_4$ and the obtained alcohol was treated with Et$_3$SiH and TFA to afford compound 210a.

Step 2: N-(5-Benzyl-4-phenylthiazol-2-yl)-2-(4-(ethylthio)phenyl)acetamide (210)

Compound 210a was coupled with 2-(4-(ethylthio)phenyl)acetic acid similar as described in WO2012/028100 to afford compound 210.

Step 3: N-(5-Benzyl-4-phenylthiazol-2-yl)-2-(4-(ethylsulfonyl)phenyl)acetamide (211)

Compound 210 was oxidized with meta-chloroperoxybenzoic acid to afford compound 211 as a colorless solid. $^1$H-NMR (CDCl$_3$, 300 MHz) δ: 1.28 (q, J=7.8 Hz, 3H), 3.08 (q, J=7.8 Hz, 2H), 4.23 (s, 1H), 7.12 (d, J=8.1 Hz, 2H), 7.21-7.34 (m, 5H), 7.38-7.48 (m, 3H), 7.64 (dd, J=6.0, 7.5 Hz, 2H), 7.78 (d, J=8.1 Hz, 2H), 11.84 (br s, 1H). MS 477.1 (M+1)$^+$.

Example 300

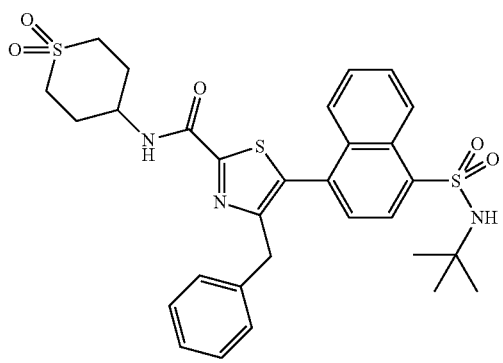

300

Step 1: 1-Bromo-3-phenylpropan-2-one (300a)

To a solution of 1-phenylpropan-2-one (6.1 g, 45.5 mmol) in AcOH (15 mL) were added a solution of HBr in AcOH (48%, 10 mL) and a solution of Br$_2$ (5.0 mL, 97.0 mmol) in AcOH (30 mL) and the resulting mixture was stirred at rt for 6 h, diluted with acetone (100 mL), stirred for a further 16 h, concentrated and extracted with DCM. The organic layer was dried over Na$_2$SO$_4$, filtered, concentrated and purified by CC (PE/EA=20/1) to give compound 300a (3.6 g, 37%) as a brown oil.

Step 2: Ethyl 4-benzylthiazole-2-carboxylate (300b)

A solution of compound 300a (3.60 g, 16.9 mmol) and ethylthioxamate (2.37 g, 18.0 mmol) in ethanol (50 mL) was heated at 80° C. for 6 h, cooled to 0° C., diluted with water and EA, then neutralized to pH=7 using NH$_4$OH. and extracted with EA (3×). The combined organic layers were dried over Na$_2$SO$_4$, filtered, concentrated and purified by CC (PE/EA=20/1) to give compound 300b (2.5 g, 60%) as a yellow oil.

Step 3: Ethyl 4-benzyl-5-(4-(N-(tert-butyl)sulfamoyl)naphthalen-1-yl)thiazole-2-carboxylate (300c)

A solution of compound 300b (250 mg, 1.1 mmol), compound P1/2 (409 mg, 1.2 mmol), Pd(OAc)$_2$ (56 mg) and PPh$_3$ (118 mg, 0.45 mmol) in DMF (10 mL) was bubbled with N$_2$ for 5 min and then stirred at 110° C. for overnight, cooled to rt, concentrated and purified by CC (PE/EA=15/1) to give compound 300c (200 mg, 36%) as a pale yellow solid.

Step 4: Potassium 4-benzyl-5-(4-(N-(tert-butyl)sulfamoyl)naphthalen-1-yl)thiazole-2-carboxylate (300d)

A solution of compound 300c (200 mg, 0.39 mmol) and KOH (28 mg, 0.5 mmol) in MeOH (5 mL) was stirred at rt for 4 h, concentrated and washed with Et$_2$O to give crude compound 300d (210 mg) as an off-white solid.

Step 5: 4-Benzyl-5-(4-(N-(tert-butyl)sulfamoyl)naphthalen-1-yl)-N-(1,1-dioxidotetrahydro-2H-thiopyran-4-yl)thiazole-2-carboxamide (300)

A solution of crude compound 300d (200 mg, 0.39 mmol), 1,1-dioxo-hexahydro-1-thiopyran-4-ylamine (148 mg, 0.80 mmol), DIEA (206 mg, 1.6 mmol) and HATU (304 mg, 0.80 mmol) in DMF (5 mL) was stirred overnight at rt, diluted with water and extracted with EA (3×). The combined organic layers were washed with water (3×) and brine consecutively, dried over Na$_2$SO$_4$, filtered, concentrated and purified by prep-HPLC to give compound 300 (57 mg, 24% over two steps) as a white solid. $^1$H-NMR (300 MHz, CDCl$_3$) δ: 1.23 (s, 9H), 2.31-2.48 (m, 4H), 3.15-3.16 (m, 4H), 3.86 (s, 2H), 4.23-4.27 (m, 1H), 4.63 (s, 1H), 6.91-6.94 (m, 2H), 7.14-7.17 (m, 3H), 7.27-7.29 (m, 1H), 7.46 (d, J=7.5 Hz, 1H), 7.50-7.57 (m, 1H), 7.68-7.71 (m, 2H), 8.31 (d, J=7.5 Hz, 1H), 8.69 (d, J=13.2 Hz, 1H). MS 612.2 [M+1]$^+$.

Example 300/1 to 300/18

The following Example was prepared similar as described in Example 300.

| # | Structure | Analytical data |
|---|---|---|
| 300/1 | 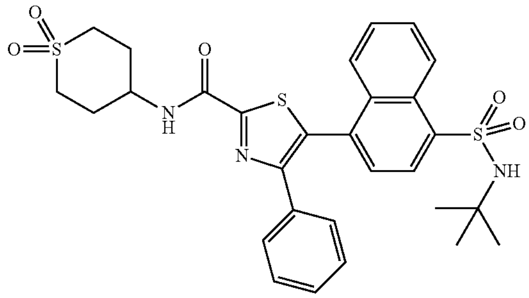 [SMILES: CC(C)(C)NS(=O)(=O)c1ccc(-c2sc(C(=O)NC3CCS(=O)(=O)CC3)nc2-c2ccccc2)c2ccccc12] | $^1$H-NMR (300 MHz, CDCl$_3$) δ: 1.20 (s, 9H), 2.34-2.52 (m, 4H), 3.17-3.20 (m, 4H), 4.29-4.33 (m, 1H), 4.65 (s, 1H), 7.10-7.20 (m, 3H), 7.31-7.34 (m, 2H), 7.41-7.52 (m, 2H), 7.55 (d, J = 7.5 Hz, 1H), 7.65-7.7.70 (m, 1H), 7.78-7.81 (m, 1H), 8.32 (d, J = 7.5 Hz, 1H), 8.68 (d, J = 8.7 Hz, 1H). MS 598.4 [M + 1]$^+$ |
| 300/2 | 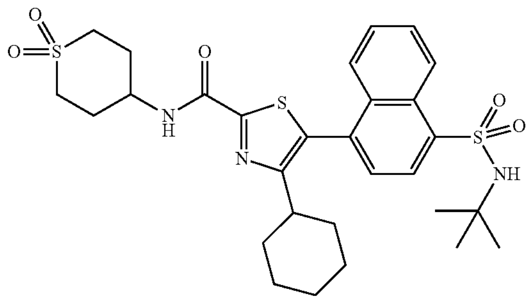 [SMILES: CC(C)(C)NS(=O)(=O)c1ccc(-c2sc(C(=O)NC3CCS(=O)(=O)CC3)nc2C2CCCCC2)c2ccccc12] | $^1$H-NMR (300 MHz, CDCl$_3$) δ: 0.90-1.16 (m, 2H), 1.23 (s, 9H), 1.66-1.72 (m, 8H), 2.25-2.51 (m, 5H), 3.16-3.21 (m, 4H), 4.28-4.30 (m, 1H), 4.63 (s, 1H), 7.31 (d, J = 8.1 Hz, 1H), 7.49 (d, J = 7.5 Hz, 1H), 7.54-7.59 (m, 1H), 7.69-7.74 (m, 2H), 8.35 (d, J = 7.5 Hz, 1H), 8.69 (d, J = 9.3 Hz, 1H). MS 604.3 [M + 1]$^+$ |
| 300/3 | 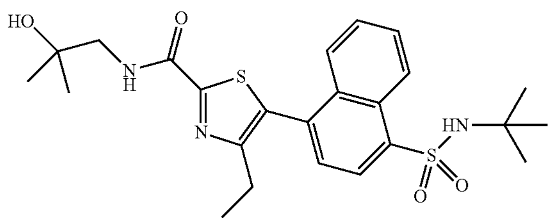 [SMILES: CCc1nc(C(=O)NCC(C)(C)O)sc1-c1ccc(S(=O)(=O)NC(C)(C)C)c2ccccc12] | $^1$H-NMR (400 MHz, CDCl$_3$) δ: 8.80 (d, 1H, J = 8.4 Hz), 8.35 (m, 1H), 8.25 (m, 1H), 7.95 (s, 1H), 7.75 (m, 4H), 3.32 (d, 2H, J = 6.4 Hz), 2.48 (m, 2H), 1.11 (m, 18H). MS 489.7 (M + 1)$^+$ |
| 300/4 | 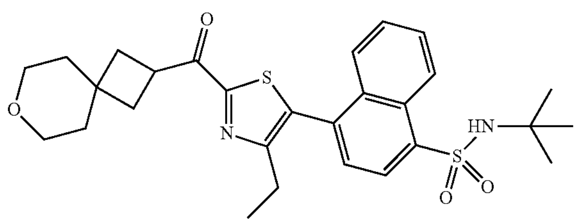 [SMILES: CCc1nc(C(=O)C2CC3(CCOCC3)C2)sc1-c1ccc(S(=O)(=O)NC(C)(C)C)c2ccccc12] | $^1$H-NMR (400 MHz, CDCl$_3$) δ: 8.70 (d, 1H, J = 8.8 Hz), 8.35 (d, 1H, J = 7.6 Hz), 7.76 (m, 2H), 7.57 (m, 2H), 4.76 (s, 1H), 4.52 (s, 2H), 4.01 (s, 2H), 3.71 (m, 4H), 2.50 (m, 2H), 1.89 (m, 4H), 1.23 (s, 9H), 1.17 (m, 3H). MS 528.2 (M + 1)$^+$ |
| 300/5 | 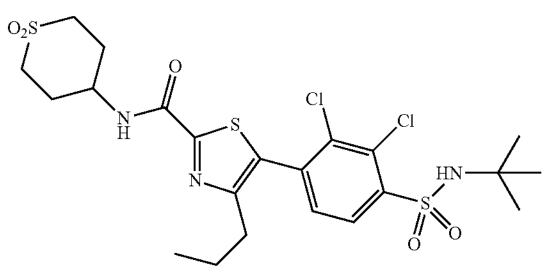 [SMILES: CCCc1nc(C(=O)NC2CCS(=O)(=O)CC2)sc1-c1ccc(S(=O)(=O)NC(C)(C)C)c(Cl)c1Cl] | $^1$H-NMR (400 MHz, CDCl$_3$) δ: 8.13 (d, 1H, J = 8.0 Hz), 7.39 (d, 1H, J = 8.4 Hz), 7.26 (s, 1H), 5.10 (s, 1H), 4.26 (m, 1H), 3.17 (m, 4H), 2.39 (m, 6H), 1.68 (m, 2H), 1.29 (s, 9H), 0.86 (t, 3H, J = 7.2 Hz). MS 582.2 (M + H)$^+$ |
| 300/6 | 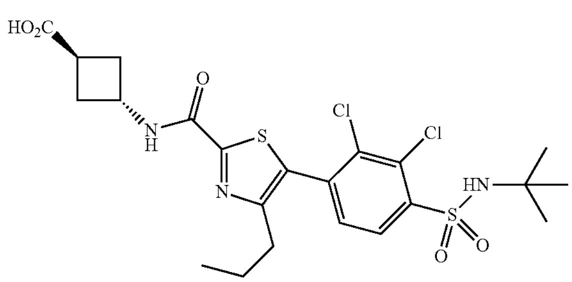 [SMILES: CCCc1nc(C(=O)N[C@H]2C[C@H](C(=O)O)C2)sc1-c1ccc(S(=O)(=O)NC(C)(C)C)c(Cl)c1Cl] | $^1$H-NMR (400 MHz, CDCl$_3$) δ: 8.13 (d, 1H, J = 8.0 Hz), 7.50 (d, 1H, J = 8.0 Hz), 7.39 (d, 1H, J = 8.0 Hz), 5.10 (s, 1H), 4.82 (m, 1H), 3.20 (m, 1H), 2.82 (m, 2H), 2.51 (m, 4H), 1.67 (m, 2H), 1.29 (s, 9H), 0.86 (t, 3H, J = 7.6 Hz). MS 548.2 (M + H)$^+$ |

| # | Structure | Analytical data |
|---|---|---|
| 300/7 | 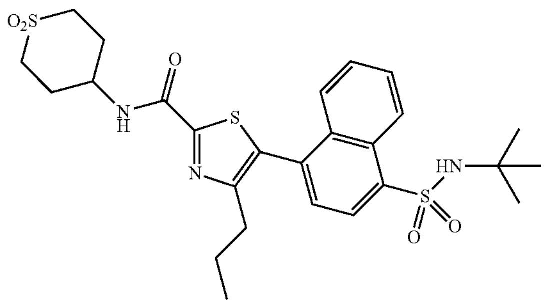 [SMILES: CCCc1nc(C(=O)NC2CCS(=O)(=O)CC2)sc1-c1ccc(S(=O)(=O)NC(C)(C)C)c2ccccc12] | $^1$H-NMR (400 MHz, CDCl$_3$) δ: 8.71 (d, 1H, J = 8.0 Hz), 8.35 (d, 1H, J = 7.2 Hz), 7.72 (m, 2H), 7.58 (m, 2H), 7.36 (d, 1H, J = 8.0 Hz), 4.86 (s, 1H), 4.29 (m, 1H), 3.19 (m, 4H), 2.40 (m, 6H), 1.62 (m, 2H), 1.24 (s, 9H), 0.76 (t, 3H, J = 7.6 Hz). MS 564.2 (M + H)$^+$ |
| 300/8 | 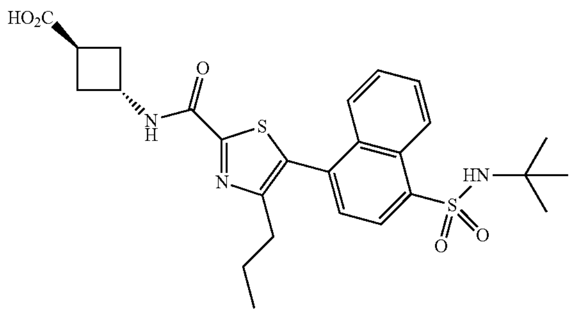 [SMILES: CCCc1nc(C(=O)N[C@H]2C[C@H](C(=O)O)C2)sc1-c1ccc(S(=O)(=O)NC(C)(C)C)c2ccccc12] | $^1$H-NMR (400 MHz, DMSO-d$_6$) δ: 9.20 (d, 1H, J = 8.4 Hz), 8.80 (d, 1H, J = 8.8 Hz), 8.26 (d, 1H, J = 7.6 Hz), 7.92-7.66 (m, 5H), 4.61 (m, 1H), 2.95 (m, 1H), 2.56 (m, 2H), 2.45 (m, 4H), 1.57 (m, 2H), 1.11 (s, 9H), 0.67 (t, 3H, J = 7.6 Hz). MS 530.2 (M + H)$^+$ |
| 300/9 | 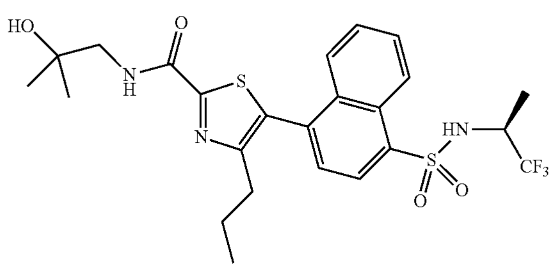 [SMILES: CCCc1nc(C(=O)NCC(C)(C)O)sc1-c1ccc(S(=O)(=O)N[C@@H](C)C(F)(F)F)c2ccccc12] | MS 544.1 (M + H)$^+$ |
| 300/10 | 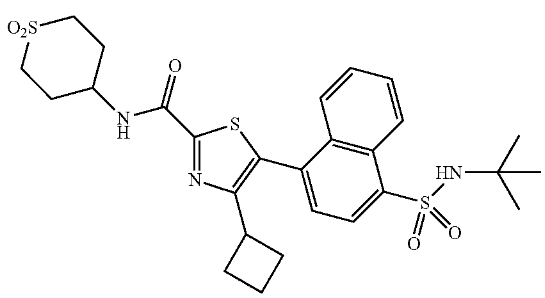 [SMILES: CC(C)(C)NS(=O)(=O)c1ccc(-c2sc(C(=O)NC3CCS(=O)(=O)CC3)nc2C2CCC2)c2ccccc12] | MS 576.1 (M + H)$^+$ |
| 300/11 | 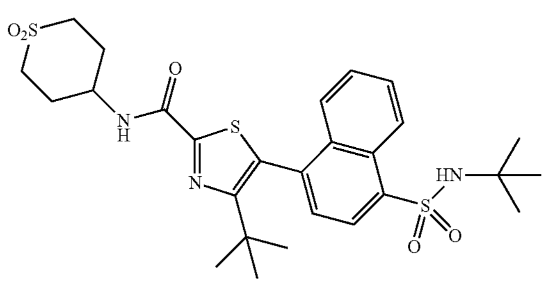 [SMILES: CC(C)(C)NS(=O)(=O)c1ccc(-c2sc(C(=O)NC3CCS(=O)(=O)CC3)nc2C(C)(C)C)c2ccccc12] | MS 578.2 (M + H)$^+$ |

-continued

| # | Structure | Analytical data |
|---|---|---|
| 300/12 | 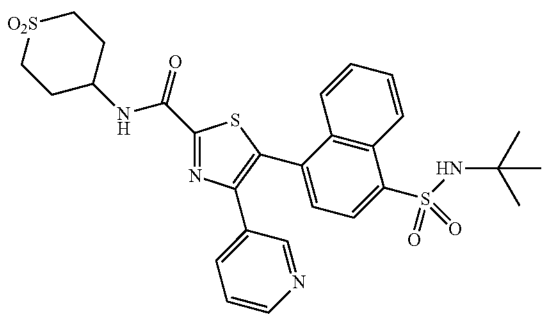 [SMILES: CC(C)(C)NS(=O)(=O)c1ccc(-c2sc(C(=O)NC3CCS(=O)(=O)CC3)nc2-c2cccnc2)c2ccccc12] | MS 599.1 (M + H)+ |
| 300/13 | 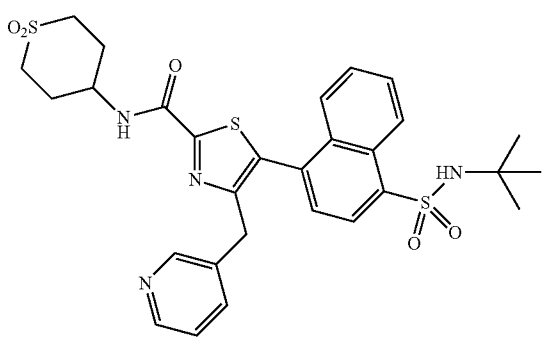 [SMILES: CC(C)(C)NS(=O)(=O)c1ccc(-c2sc(C(=O)NC3CCS(=O)(=O)CC3)nc2Cc2cccnc2)c2ccccc12] | MS 613.1 (M + H)+ |
| 300/14 | 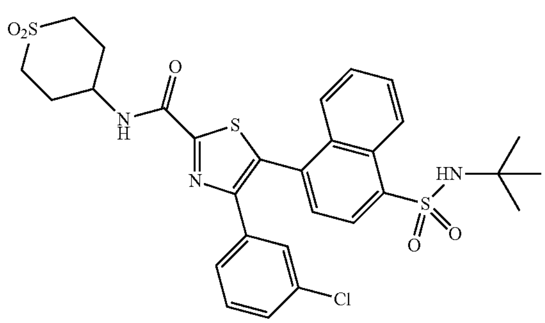 [SMILES: CC(C)(C)NS(=O)(=O)c1ccc(-c2sc(C(=O)NC3CCS(=O)(=O)CC3)nc2-c2cccc(Cl)c2)c2ccccc12] | MS 632.1 (M + H)+ |
| 300/15 | 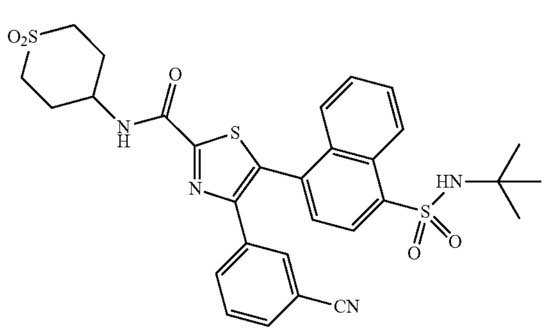 | MS 567.1 (M − tBu + H)+, 623.2 (M + H)+ |

-continued
| # | Structure | Analytical data |
|---|---|---|
| 300/16 | 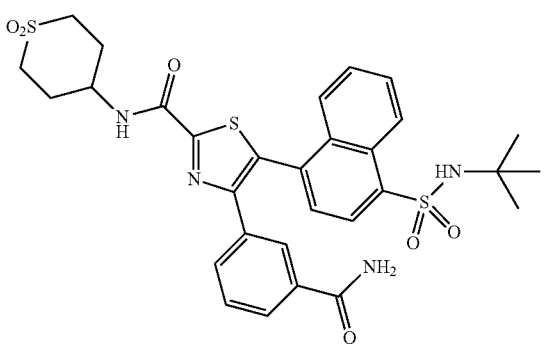 [SMILES: CC(C)(C)NS(=O)(=O)c1ccc(-c2sc(C(=O)NC3CCS(=O)(=O)CC3)nc2-c2cccc(C(N)=O)c2)c2ccccc12] | MS 585.1 (M − tBu + H)+, 641.2 (M + H)+ |
| 300/17 | 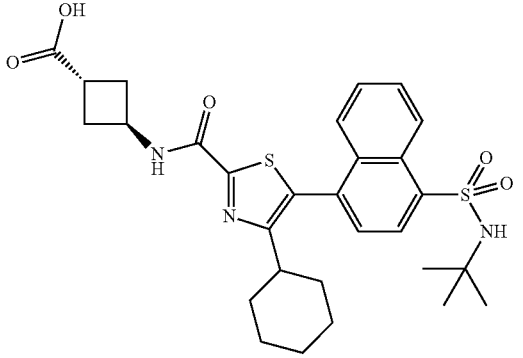 [SMILES: CC(C)(C)NS(=O)(=O)c1ccc(-c2sc(C(=O)N[C@H]3C[C@H](C(=O)O)C3)nc2C2CCCCC2)c2ccccc12] | MS 570.2 (M + H)+ |
| 300/18 | 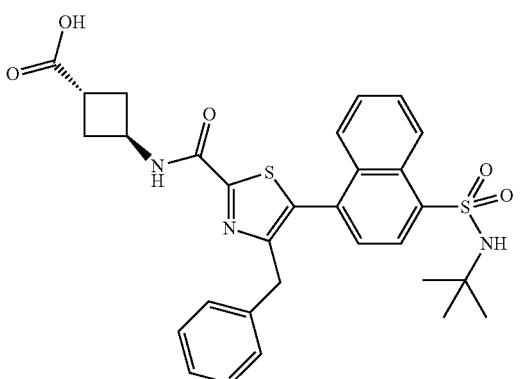 | MS 5MS78.2 (M + H)+ |

Example 301

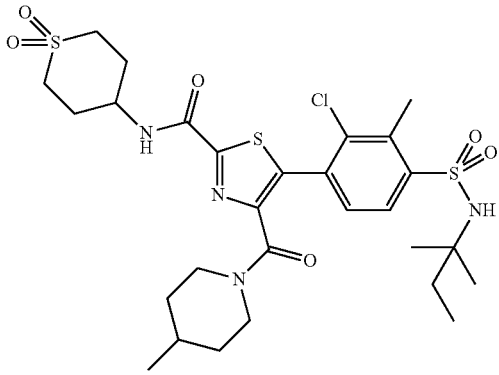

Step 1: 2-(Ethoxycarbonyl)thiazole-4-carboxylic acid (301a)

The solution of ethyl 2-amino-2-thioxoacetate (6.0 g, 45 mmol) and 3-bromo-2-oxo-propionic acid (7.5 g, 45 mmol) in dioxane (200 mL) was heated at 50° C. for 3 h, cooled to rt and concentrated to give compound 301a (11 g, crude) as a brown solid.

Step 2: Ethyl 4-(4-methylpiperidine-1-carbonyl)thiazole-2-carboxylate (301b)

A solution of compound 301a (11.0 g, 55 mmol), HATU (20.8 g, 55 mmol), DIEA (28.2 g, 219 mmol) and 4-methylpiperidine (5.4 g, 55 mmol) in DMF (110 mL) was stirred for 4 h, quenched with $H_2O$ and extracted with EA. The organic layer was washed with brine, dried over $Na_2SO_4$, filtered, concentrated and purified by CC (PE/EA=4/1) to give compound 301b (4.2 g, 27% over two steps) as a brown oil.

Step 3: Ethyl 5-(2-chloro-3-methyl-4-(N-(tert-pentyl)sulfamoyl)phenyl)-4-(4-methylpiperidine-1-carbonyl)thiazole-2-carboxylate (301c)

A solution of compound 301b (200 mg, 0.71 mmol), 4-bromo-3-chloro-2-methyl-N-(tert-pentyl)benzenesulfonamide (301 mg, 0.85 mmol), KOAc (139 mg, 1.42 mmol), $PPh_3$ (205 mg, 0.78 mmol) and $Pd(OAc)_2$ (16 mg, 0.071 mmol) in DMF (8 mL) was heated at 120° C. overnight, cooled to rt, diluted with water and extracted with EA. The organic phase was washed with water and brine, dried over $Na_2SO_4$, filtered, concentrated and purified by CC (PE/EA=4/1) to give compound 301c (110 mg, 28%) as a yellow solid.

Step 4: 5-(2-Chloro-3-methyl-4-(N-(tert-pentyl)sulfamoyl)phenyl)-4-(4-methylpiperidine-1-carbonyl)thiazole-2-carboxylic acid (301d)

To a solution of compound 301c (1.1 g, 1.98 mmol) in a solution of THF (20 mL) and $H_2O$ (4 mL) was added KOH (332 mg, 5.94 mmol) and then the solution was stirred at rt for 4 h, concentrated, diluted with water, adjusted to pH=5 with 1N HCl and extracted with EA. The organic phase was washed with water and brine, dried over $Na_2SO_4$, filtered and concentrated to give compound 301d (0.9 g, 90%) as a pale yellow solid.

Step 5: 5-(2-Chloro-3-methyl-4-(N-(tert-pentyl)sulfamoyl)phenyl)-N-(1,1-dioxidotetrahydro-2H-thiopyran-4-yl)-4-(4-methylpiperidine-1-carbonyl)thiazole-2-carboxamide (301)

A solution of compound 301d (120 mg, 0.23 mmol), HATU (86 mg, 0.23 mmol), DIEA (117 mg, 0.91 mmol) and 1,1-dioxo-hexahydrothiopyran-4-ylamine HCl salt (51 mg, 0.27 mmol) in DCM (5 mL) was stirred for overnight, quenched with $H_2O$ and diluted with DCM. The organic layer was washed with brine, dried over $Na_2SO_4$, filtered, concentrated and purified by prep-HPLC to give compound 301 (40 mg, 27%) as white solid. $^1$H-NMR (300 MHz, $CDCl_3$) δ: 0.56-0.62 (m, 1H), 0.84-0.90 (m, 7H), 0.93-0.98 (m, 1H), 1.20 (s, 6H), 1.49-1.50 (m, 2H), 1.56-1.57 (m, 2H), 2.26-2.33 (m, 2H), 2.40-2.42 (m, 2H), 2.54-2.62 (m, 1H), 2.74-2.79 (m, 4H), 3.14-3.15 (m, 4H), 3.47-3.53 (m, 1H), 4.22-4.26 (m, 1H), 4.50-4.55 (m, 2H), 7.32 (d, J=8.1 Hz, 1H), 7.44 (d, J=8.1 Hz, 1H), 8.03 (d, J=8.7 Hz, 1H). MS 659.2 [M+1]$^+$.

Example 301/1 to 301/4

The following Example was prepared similar as described in Example 301.

| # | Structure | Analytical data |
|---|-----------|-----------------|
| 301/1 | ![structure] | $^1$H-NMR (300 MHz, $CDCl_3$) δ: 0.63-0.69 (m, 1H), 0.84-0.93 (m, 7H), 0.93-0.98 (m, 1H), 1.19 (s, 6H), 1.30 (s, 6H), 1.46-1.50 (m, 2H), 1.68-1.71 (m, 2H), 2.28 (s, 1H), 2.53-2.59 (m, 1H), 2.76-2.82 (m, 4H), 3.48 (d, J = 6.3 Hz, 2H), 3.52-3.57 (m, 1H), 4.49-4.54 (m, 1H), 4.59 (s, 1 H), 7.45 (d, J = 8.1 Hz, 1H), 7.67 (t, J = 6.5 Hz, 1H), 8.02 (d, J = 8.4 Hz, 1H). MS 599.2 [M + 1]$^+$ |

-continued

| # | Structure | Analytical data |
|---|---|---|
| 301/2 | 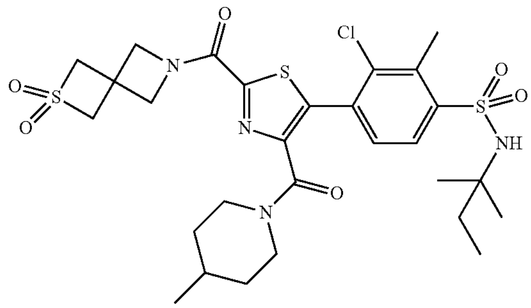 [SMILES: CCC(C)(C)NS(=O)(=O)c1ccc(-c2sc(C(=O)N3CC4(C3)CS(=O)(=O)C4)nc2C(=O)N2CCC(C)CC2)c(Cl)c1C] | ¹H-NMR (300 MHz, CDCl₃) δ: 0.69-0.72 (m, 1H), 0.86-0.98 (m, 7H), 1.01-1.02 (m, 1H), 1.20 (s, 6H), 1.49-1.54 (m, 2H), 1.63-1.69 (m, 2H), 2.63-2.65 (m, 1H), 2.76 (s, 3H), 2.80-2.84 (m, 1H), 3.56-2.61 (m, 1H), 4.39-4.46 (m, 5H), 4.48-4.53 (m, 3H), 4.99 (s, 2H), 7.44 (d, J = 8.1 Hz, 1H), 8.03 (d, J = 8.4 Hz, 1H). MS 657.2 [M + 1]⁺ |
| 301/3 | 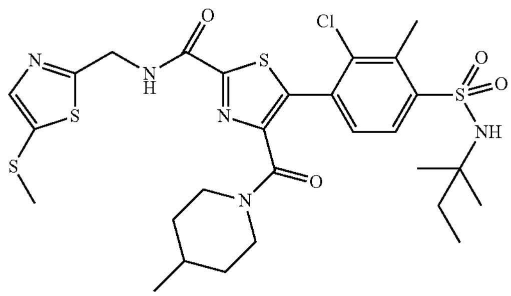 [SMILES: CCC(C)(C)NS(=O)(=O)c1ccc(-c2sc(C(=O)NCc3ncc(SC)s3)nc2C(=O)N2CCC(C)CC2)c(Cl)c1C] | n.t. |
| 301/4 | 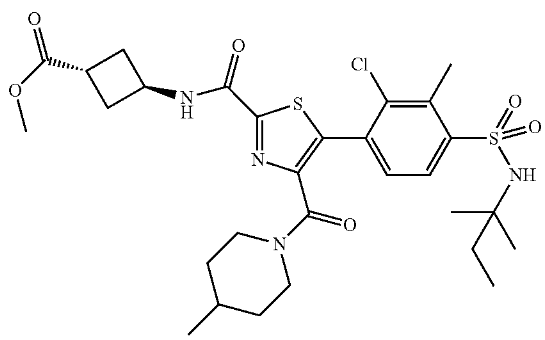 [SMILES: CCC(C)(C)NS(=O)(=O)c1ccc(-c2sc(C(=O)N[C@H]3C[C@H](C(=O)OC)C3)nc2C(=O)N2CCC(C)CC2)c(Cl)c1C] | n.t. |

Example 302 trans-3-(5-(2-Chloro-3-methyl-4-(N-(tert-pentyl)sulfamoyl)phenyl)-4-(4-methylpiperidine-1-carbonyl)thiazole-2-carboxamido)cyclobutanecarboxylic acid (302)

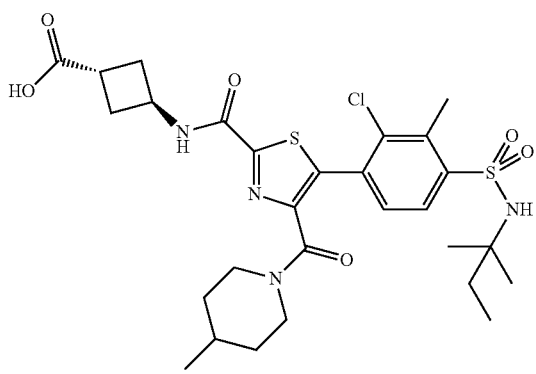

To a solution of compound 301/4 (60 mg, 94 μmol) in a mixture of THF (5 mL) and H₂O (1 mL) was added LiOH—H₂O (39 mg, 940 μmol), and then the solution was stirred at rt for 1 h, diluted with water, adjusted to pH=5 with 1N HCl and extracted with EA. The organic phase was washed with water and brine, dried over Na₂SO₄, filtered, concentrated and purified by prep-TLC (DCM/MeOH=15/1) to give compound 302 (40 mg, 68%) as a white solid. ¹H-NMR (300 MHz, CDCl₃) δ: 0.56-0.61 (m, 1H), 0.84-0.91 (m, 7H), 1.20 (s, 6H), 1.44-1.48 (m, 2H), 1.55-1.63 (m, 3H), 2.43-2.46 (m, 2H), 2.58-2.63 (m, 1H), 2.71-2.82 (m, 6H), 3.15-3.16 (m, 1H), 3.49-3.53 (m, 1H), 4.50-4.58 (m, 2H), 4.76-4.84 (m, 1H), 7.45 (d, J=8.1 Hz, 1H), 7.53 (d, J=7.8 Hz, 1H), 8.02 (d, J=8.4 Hz, 1H). MS 625.2 [M+1]⁺.

Example 303

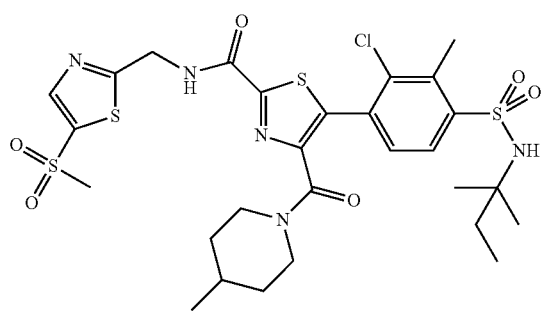

5-(2-Chloro-3-methyl-4-(N-(tert-pentyl)sulfamoyl) phenyl)-4-(4-methylpiperidine-1-carbonyl)-N-((5-(methylsulfonyl)thiazol-2-yl)methyl)thiazole-2-carboxamide (303)

A solution of compound 301/3 (125 mg, 0.19 mmol) and m-CPBA (80 mg, 0.47 mmol) in DCM (5 mL) was stirred for 2 h, quenched with $H_2O$ and diluted with DCM. The organic layer was washed with brine, dried over $Na_2SO_4$, filtered, concentrated and purified by prep-HPLC to give compound 303 (70 mg, 53%) as a white solid. $^1$H-NMR (300 MHz, $CDCl_3$) δ: 0.66-0.67 (m, 1H), 0.85-0.99 (m, 8H), 1.20 (s, 6H), 1.47-1.53 (m, 2H), 1.68-1.80 (m, 2H), 2.54-2.64 (m, 1H), 2.76-2.83 (m, 4H), 3.22 (s, 3H), 3.51-3.57 (m, 1H), 4.50-4.53 (m, 2H), 4.99 (d, J=6.3 Hz, 2H), 7.46 (d, J=8.4 Hz, 1H), 8.04 (d, J=8.1 Hz, 1H), 8.24 (s, 1H). MS 702.2 $[M+1]^+$.

Example 304

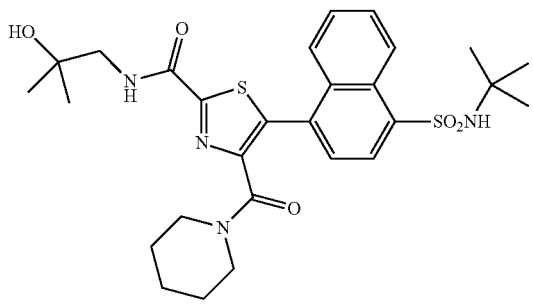

Step 1: Ethyl 4-(hydroxymethyl)thiazole-2-carboxylate (304a)

A mixture of ethyl 1-bromo-3-hydroxypropan-2-one (129 mg, 0.85 mmol) in 10 mL dry dioxane was treated with 2-amino-2-thioxoacetate (113 mg, 0.85 mmol) for 1.2 h at 50° C. and concentrated at 50° C. under vacuum to yield a dry yellow solid. The crude product was dissolved in saturated $Na_2CO_3$ (15 mL) and water (15 mL), and extracted with EA (6×20 mL). The aq. layer was then acidified to pH=2 with conc. HCl, resulting in the formation of a precipitate. This suspension was extracted with EA. The extracts were pooled, dried with $Na_2SO_4$, filtered and concentrated to give compound 304a as a red-brown solid (115 mg, 73%).

Step 2: N-(2-hydroxy-2-methylpropyl)-4-(hydroxymethyl)thiazole-2-carboxamide (304b)

To a stirred solution of 304a (115 mg, 0.62 mmol) in 5.5 mL toluene was added 1-amino-2-methylpropan-2-ol (66 mg, 0.74 mmol). The mixture was stirred at 100° C. overnight. Water was added and the mixture was extracted with EA. The organic phase was washed with water and brine, dried over $Na_2SO_4$, filtered, concentrated purified by CC (PE/EA=10/1 to 5/1) to give compound 304b (104 mg, 73%) as a white solid.

Step 3: 5-(4-(N-(tert-butyl)sulfamoyl)naphthalen-1-yl)-N-(2-hydroxy-2-methylpropyl)-4-(hydroxymethyl)thiazole-2-carboxamide (304c)

A solution of 304b (103 mg, 0.45 mmol), 4-bromo-N-tert-butylnaphthalene-1-sulfonamide (153 mg, 0.45 mmol), $K_2CO_3$ (124 mg, 0.9 mmol), $Pd(OAc)_2$ (5 mg, 0.01 mmol), $PCy_3 \cdot HBF_4$ (10 mg, 0.02 mmol) and PivOH (14 mg, 0.14 mmol) in a solution of DMA (6 mL) was heated under argon at 100° C. overnight, cooled to rt and partitioned between EA and water. The organic phase was washed with water and brine, dried over $Na_2SO_4$, filtered, concentrated and purified by CC (PE/EA=10/1 to 5/1) to give compound 304c (128 mg, 58%) as a white solid.

Step 4: 5-(4-(N-(tert-butyl)sulfamoyl)naphthalen-1-yl)-2-((2-hydroxy-2-methylpropyl)carbamoyl)thiazole-4-carboxylic acid (304d)

To a solution of 304c (128 mg, 0.26 mmol) in MeCN (30 mL) was added iodobenzene diacetate (341 mg, 1.06 mmol) and TEMPO (40 mg, 0.26 mmol). The mixture was stirred for 1 h, concentrated and extracted with EA (20 mL×2). The organic layer was washed by saturated $NaHCO_3$ and brine, dried with $Na_2SO_4$, evaporated and purified by CC (PE/EA=20/1 to 10/1) to give compound 304d (95 mg, 73%) as a white solid.

Step 5: 5-(4-(N-(tert-butyl)sulfamoyl)naphthalen-1-yl)-N-(2-hydroxy-2-methylpropyl)-4-(piperidine-1-carbonyl)thiazole-2-carboxamide (304)

To a solution of 304d (47 mg, 0.09 mmol) in 3.0 mL DMF was added HATU (13 mg, 0.13 mmol) and DIPEA (35 mg, 0.27 mmol). The mixture was stirred for 60 min and then piperidine (10 mg, 0.11 mmol) was added, stirred overnight, quenched with water and extracted with EA. The organic layer was separated, washed with brine and dried over $Na_2SO_4$. After filtration, the filtrate was evaporated and purified by prep-HPLC to give compound 304 (34 mg, 64%) as a white solid. $^1$H-NMR (400 MHz, $d_6$-DMSO) δ: 8.78 (d, 1H, J=8.0 Hz), 8.52 (t, 1H, J=6.4 Hz), 8.24 (d, 1H, J=7.6 Hz), 8.00-7.97 (m, 1H), 7.79-7.65 (m, 3H), 3.32-3.28 (m, 4H), 3.16 (s, 2H), 1.32 (s, 2H), 1.15 (s, 6H), 1.09 (s, 9H), 0.87-0.86 (m, 2H). MS 573.3 $(M+1)^+$.

Example 304/1 to 304/27

The following examples were prepared similar to Example 304.

| # | Structure | Analytical data |
|---|---|---|
| 304/1 | 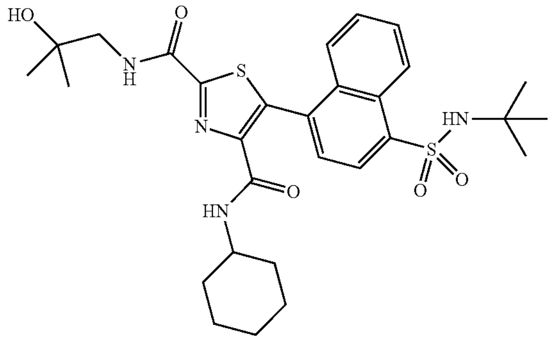 [SMILES: CC(C)(O)CNC(=O)c1nc(C(=O)NC2CCCCC2)c(-c2ccc(S(=O)(=O)NC(C)(C)C)c3ccccc23)s1] | ¹H-NMR (400 MHz, d₆-DMSO) δ: 8.79-8.74 (m, 2H), 8.33 (d, 1H, J = 8.4 Hz), 8.19 (d, 1H, J = 7.2 Hz), 7.92 (s, 1H), 7.73-7.66 (m, 3H), 7.59 (t, 1H, J = 8.0 Hz), 3.46 (s, 1H), 1.66-1.53 (m, 5H), 1.27-1.06 (m, 20H). MS 587.3 (M + 1)⁺ |
| 304/2 | 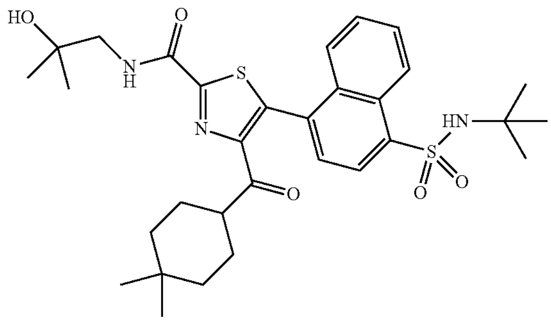 [SMILES: CC(C)(O)CNC(=O)c1nc(C(=O)C2CCC(C)(C)CC2)c(-c2ccc(S(=O)(=O)NC(C)(C)C)c3ccccc23)s1] | ¹H-NMR (400 MHz, CDCl₃) δ: 8.71 (d, 1H, J = 8.8 Hz), 8.34 (d, 1H, J = 7.6 Hz), 8.00 (d, 1H, J = 8.4 Hz), 7.76 (m, 2H), 7.64 (m, 2H), 4.71 (br s, 1H), 3.53 (m, 2H), 3.28 (m, 4H), 1.27 (s, 6H), 1.19 (s, 9H), 0.99 (m, 2H), 0.68 (m, 8H). MS 601.3 (M + 1)⁺ |
| 304/3 | 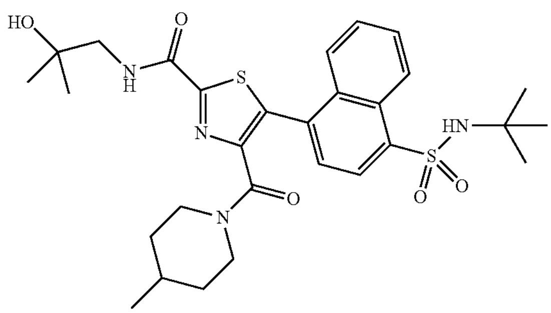 [SMILES: CC1CCN(C(=O)c2nc(C(=O)NCC(C)(C)O)sc2-c2ccc(S(=O)(=O)NC(C)(C)C)c3ccccc23)CC1] | ¹H-NMR (400 MHz, CDCl₃) δ: 8.71 (d, 1H, J = 8.4 Hz), 8.34 (d, 1H, J = 7.6 Hz), 8.02 (d, 1H, J = 8.8 Hz), 7.75 (m, 2H), 7.64 (m, 2H), 4.82 (s, 1H), 4.39 (m, 1H), 3.50 (m, 3H), 2.59 (m, 1H), 2.42 (m, 1H), 1.49 (m, 1H), 1.23 (m, 17H), 0.70 (m, 4H), 0.22 (m, 1H). MS 587.3 (M + 1)⁺ |
| 304/4 | 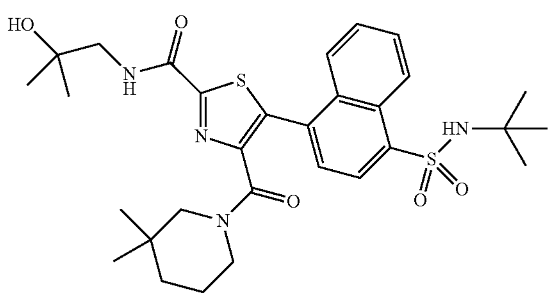 [SMILES: CC(C)(O)CNC(=O)c1nc(C(=O)N2CCCC(C)(C)C2)c(-c2ccc(S(=O)(=O)NC(C)(C)C)c3ccccc23)s1] | ¹H-NMR (400 MHz, CDCl₃) δ: 8.70 (d, 1H, J = 8.4 Hz), 8.33 (d, 1H, J = 7.6 Hz), 8.00 (m, 1H), 7.75 (m, 4H), 4.78 (s, 1H), 3.52 (d, 2H, J = 6.4 Hz), 3.30 (m, 4H), 1.27 (m, 16H), 1.12 (m, 3H), 0.80 (m, 6H). MS 601.3 (M + 1)⁺ |
| 304/5 | 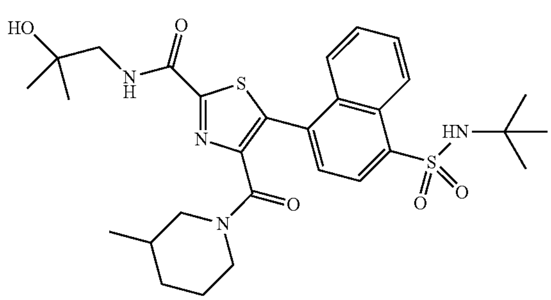 [SMILES: CC1CCCN(C(=O)c2nc(C(=O)NCC(C)(C)O)sc2-c2ccc(S(=O)(=O)NC(C)(C)C)c3ccccc23)C1] | ¹H-NMR (400 MHz, CDCl₃) δ: 8.72 (d, 1H, J = 8.4 Hz), 8.33 (d, 1H, J = 7.6 Hz), 8.05 (m, 1H), 7.70 (m, 4H), 4.89 (s, 1H), 4.25 (m, 2H), 3.52 (d, 2H, J = 6.0 Hz), 3.40 (m, 1H), 2.60 (m, 1H), 2.20 (m, 1H), 1.49 (m, 2H), 1.33 (s, 6H), 1.22 (s, 9H), 0.75 (m, 6H). MS 587.3 (M + 1)⁺ |

| # | Structure | Analytical data |
|---|---|---|
| 304/6 | 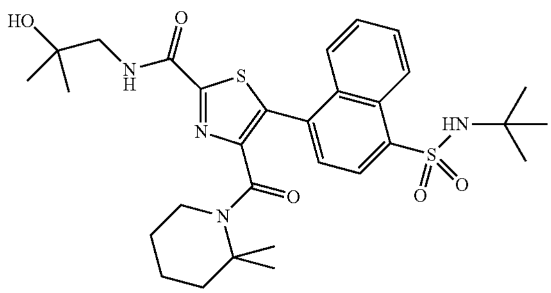 [SMILES: CC(C)(O)CNC(=O)c1nc(C(=O)N2CCCCC2(C)C)c(-c2ccc(S(=O)(=O)NC(C)(C)C)c3ccccc23)s1] | $^1$H-NMR (400 MHz, CDCl$_3$) δ: 8.70 (d, 1H, J = 8.4 Hz), 8.34 (d, 1H, J = 7.6 Hz), 8.01 (d, 1H, J = 8.4 Hz), 7.75 (m, 4H), 4.73 (s, 1H), 3.52 (d, 2H, J = 6.0 Hz), 3.05 (m, 2H), 1.33 (m, 8H), 1.25 (m, 17H), 0.95 (m, 2H). MS 601.3 (M + 1)$^+$ |
| 304/7 | 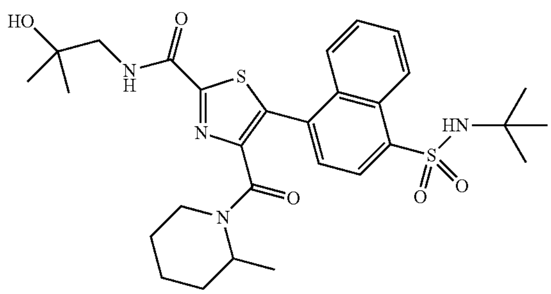 [SMILES: CC1CCCCN1C(=O)c1nc(C(=O)NCC(C)(C)O)sc1-c1ccc(S(=O)(=O)NC(C)(C)C)c2ccccc12] | $^1$H-NMR (400 MHz, DMSO-d$_6$) δ: 8.78 (d, 1H, J = 8.4 Hz), 8.50 (m, 1H), 8.24 (d, 1H, J = 7.6 Hz), 7.99 (m, 1H), 7.77 (m, 3H), 4.40 (m, 2H), 3.37 (m, 3H), 2.68 (m, 1H), 1.46 (m, 3H), 1.25 (s, 6H), 1.11 (s, 9H), 0.90 (m, 5H). MS 587.3 (M + 1)$^+$ |
| 304/8 | 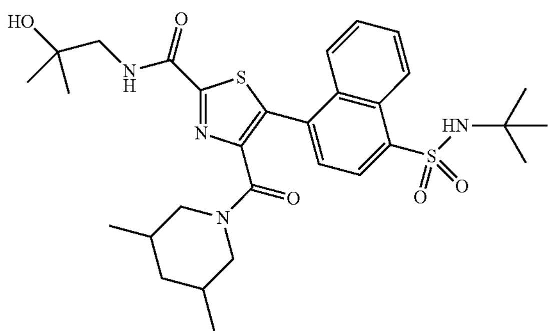 [SMILES: CC1CC(C)CN(C(=O)c2nc(C(=O)NCC(C)(C)O)sc2-c2ccc(S(=O)(=O)NC(C)(C)C)c3ccccc23)C1] | $^1$H-NMR (400 MHz, CDCl$_3$) δ: 8.70 (d, 1H, J = 8.4 Hz), 8.34 (d, 1H, J = 7.6 Hz), 8.06 (d, 1H, J = 8.4 Hz), 7.77 (m, 2H), 7.64 (m, 2H), 4.78 (s, 1H), 4.45 (m, 1H), 3.52 (d, 2H, J = 6.8 Hz), 3.35 (m, 1H), 2.08 (m, 2H), 1.88 (m, 1H), 1.45 (m, 1H), 1.34 (s, 6H), 1.22 (s, 9H), 1.08 (m, 1H), 0.76 (m, 3H), 0.50 (m, 4H). MS 601.3 (M + 1)$^+$ |
| 304/9 | 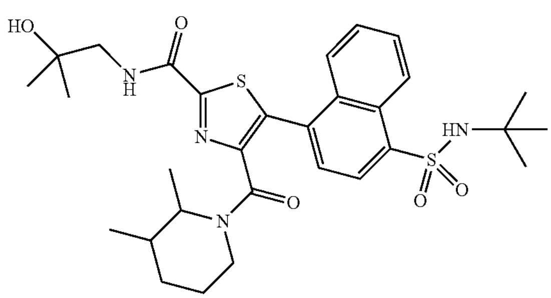 [SMILES: CC1CCCN(C(=O)c2nc(C(=O)NCC(C)(C)O)sc2-c2ccc(S(=O)(=O)NC(C)(C)C)c3ccccc23)C1C] | $^1$H-NMR (400 MHz, CDCl$_3$) δ: 8.72 (m, 1H), 8.34 (m, 1H), 8.05 (m, 1H), 7.73 (m, 4H), 4.86 (s, 1H), 4.40 (m, 1H), 3.55 (m, 3H), 2.58 (m, 1H), 1.54 (m, 1H), 1.34 (s, 6H), 1.22 (m, 10H), 0.76 (m, 9H). MS 601.3 (M + 1)$^+$ |
| 304/10 | 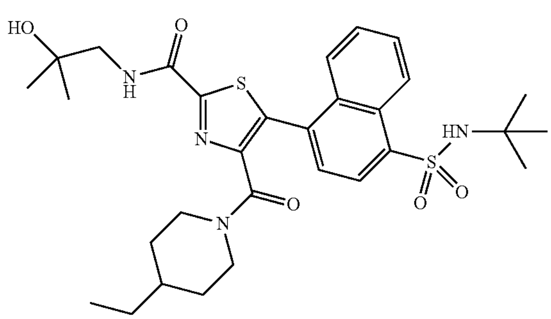 | $^1$H-NMR (400 MHz, CDCl$_3$) δ: 8.70 (d, 1H, J = 8.4 Hz), 8.34 (d, 1H, J = 7.6 Hz), 8.03 (d, 1H, J = 8.4 Hz), 7.77 (m, 4H), 4.80 (s, 1H), 4.39 (m, 1H), 3.52 (m, 3H), 2.56 (m, 1H), 1.55 (m, 1H), 1.33 (m, 20H), 0.70 (m, 4H), 0.22 (m, 1H). MS 601.2 (M + 1)$^+$ |

-continued

| # | Structure | Analytical data |
|---|---|---|
| 304/11 | 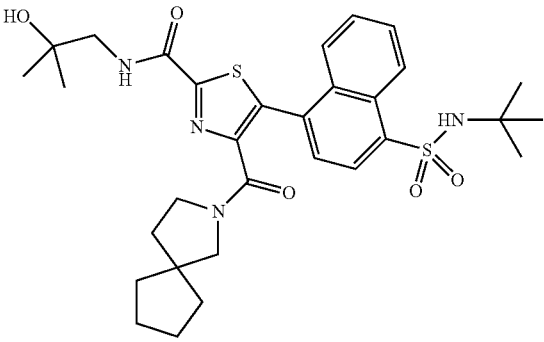 [SMILES: CC(C)(O)CNC(=O)c1nc(C(=O)N2CCC3(CCCC3)C2)c(-c2ccc(S(=O)(=O)NC(C)(C)C)c3ccccc23)s1] | $^1$H-NMR (400 MHz, CDCl$_3$) δ: 8.72 (d, 1H, J = 8.8 Hz), 8.34 (d, 1H, J = 7.6 Hz), 7.99 (d, 1H, J = 8.4 Hz), 7.86 (s, 1H), 7.71 (m, 3H), 4.60 (m, 4H), 3.52 (m, 2H), 3.11 (m, 3H), 1.60 (m, 4H), 1.24 (m, 19H). MS 613.3 (M + 1)$^+$ |
| 304/12 | 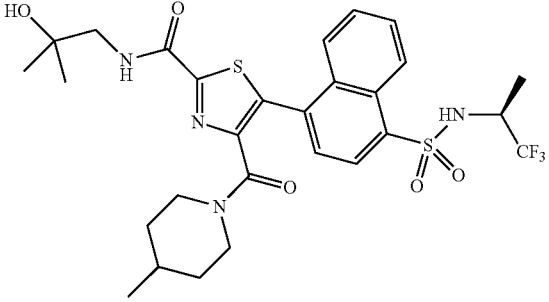 [SMILES: CC1CCN(C(=O)c2nc(C(=O)NCC(C)(C)O)sc2-c2ccc(S(=O)(=O)N[C@@H](C)C(F)(F)F)c3ccccc23)CC1] | $^1$H-NMR (400 MHz, CDCl$_3$) δ: 8.66 (d, 1H, J = 8.4 Hz), 8.31 (d, 1H, J = 7.6 Hz), 8.01 (m, 1H), 7.75 (m, 1H), 7.65 (m, 1H), 5.30 (d, 1H, J = 9.2 Hz), 4.37 (m, 1H), 4.01 (m, 1H), 3.50 (m, 3H), 2.60 (m, 1H), 2.40 (m, 1H), 1.50 (m, 1H), 1.30 (m, 11H), 0.70 (m, 4H), 0.33 (m, 1H). MS 627.2 (M + 1)$^+$ |
| 304/13 | 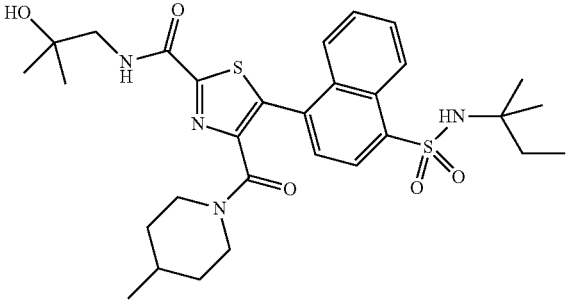 [SMILES: CCC(C)(C)NS(=O)(=O)c1ccc(-c2sc(C(=O)NCC(C)(C)O)nc2C(=O)N2CCC(C)CC2)c2ccccc12] | $^1$H-NMR (400 MHz, CDCl$_3$) δ: 8.71 (d, 1H, J = 8.4 Hz), 8.33 (d, 1H, J = 7.6 Hz), 8.02 (d, 1H, J = 8.0 Hz), 7.77-7.58 (m, 4H), 4.71 (s, 1H), 4.39-4.34 (m, 1H), 3.53-3.43 (m, 3H), 2.55 (m, 2H), 1.56-1.49 (m, 3H), 1.36-1.15 (m, 14H), 0.78 (t, J = 8.0 Hz, 3H), 0.66 (m, 4H), 0.25 (m, 1H). MS 601.3 (M + 1)$^+$ |
| 304/14 | 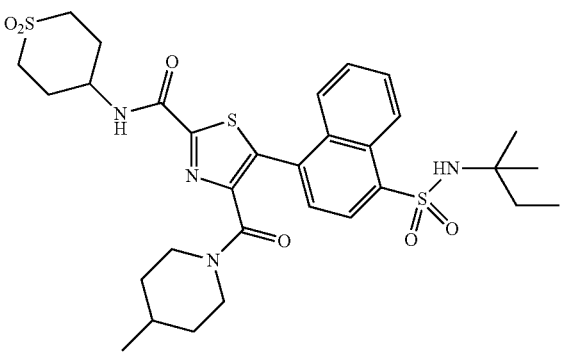 [SMILES: CCC(C)(C)NS(=O)(=O)c1ccc(-c2sc(C(=O)NC3CCS(=O)(=O)CC3)nc2C(=O)N2CCC(C)CC2)c2ccccc12] | $^1$H-NMR (400 MHz, CDCl$_3$) δ: 8.71 (d, 1H, J = 8.8 Hz), 8.33 (d, 1H, J = 7.6 Hz), 8.02 (d, 1H, J = 8.0 Hz), 7.75 (m, 1H), 7.63 (m, 2H), 7.39 (d, 1H, J = 8.0 Hz), 4.70 (s, 1H), 4.38 (m, 1H), 4.28 (m, 1H), 3.42 (m, 1H), 3.20 (m, 4H), 2.43 (m, 6H), 1.55 (m, 3H), 1.35 (m, 1H), 1.15 (m, 7H), 0.78 (t, J = 8.0 Hz, 3H), 0.66 (m, 4H), 0.16 (m, 1H). MS 661.2 (M + 1)$^+$ |

-continued

| # | Structure | Analytical data |
|---|---|---|
| 304/15 | 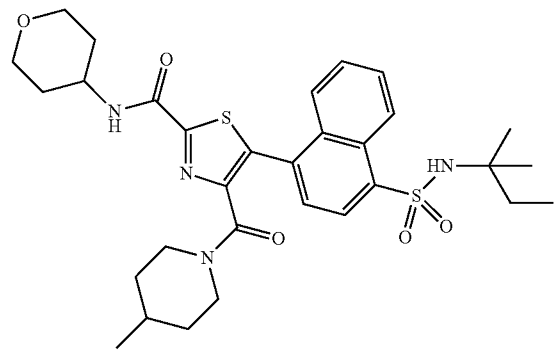 [SMILES: CCC(C)(C)NS(=O)(=O)c1ccc(-c2sc(C(=O)NC3CCOCC3)nc2C(=O)N2CCC(C)CC2)c2ccccc12] | $^1$H-NMR (400 MHz, CDCl$_3$) δ: 8.71 (d, 1H, J = 8.4 Hz), 8.33 (d, 1H, J = 7.6 Hz), 8.02 (d, 1H, J = 8.4 Hz), 7.72 (m, 3H), 7.26 (m, 1H), 4.63 (s, 1H), 4.39 (m, 1H), 4.20 (m, 1H), 4.04 (m, 2H), 3.58 (m, 2H), 3.41 (m, 1H), 2.40 (m, 2H), 1.65 (m, 5H), 1.31 (m, 1H), 1.15 (m, 7H), 0.77 (t, J = 8.0 Hz, 3H), 0.66 (m, 4H), 0.18 (m, 1H). MS 613.3 (M + 1)$^+$ |
| 304/16 | 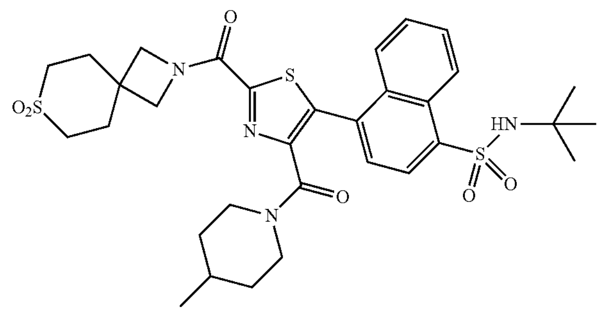 [SMILES: CC1CCN(C(=O)c2nc(C(=O)N3CC4(CCS(=O)(=O)CC4)C3)sc2-c2ccc(S(=O)(=O)NC(C)(C)C)c3ccccc23)CC1] | MS 673.2 (M + 1)$^+$ |
| 304/17 | 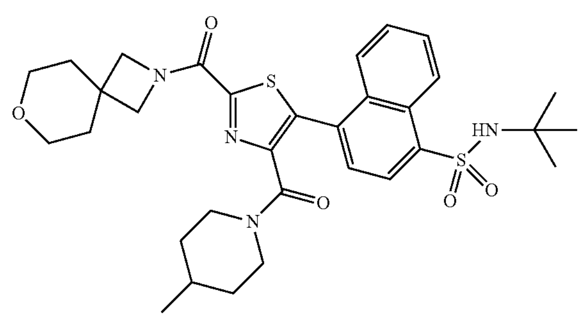 [SMILES: CC1CCN(C(=O)c2nc(C(=O)N3CC4(CCOCC4)C3)sc2-c2ccc(S(=O)(=O)NC(C)(C)C)c3ccccc23)CC1] | $^1$H-NMR (400 MHz, CDCl$_3$) δ: 8.69 (d, J = 8.4 Hz, 1H), 8.33 (d, J = 8.8 Hz, 1H), 7.98 (d, J = 8.0 Hz, 1H), 7.75-7.58 (m, 3H), 4.68 (s, 1H), 4.53 (s, 2H), 4.37 (m, 2H), 4.02 (s, 2H), 3.71-3.65 (m, 4H), 3.52 (m, 1H), 2.65 (m, 1H), 2.45 (m, 1H), 1.87 (m, 4H), 1.51 (m, 1H), 1.40-1.20 (m, 11H), 0.80-0.65 (m, 4H), 0.25 (m, 1H). MS 625.2 (M + 1)$^+$ |
| 304/18 | 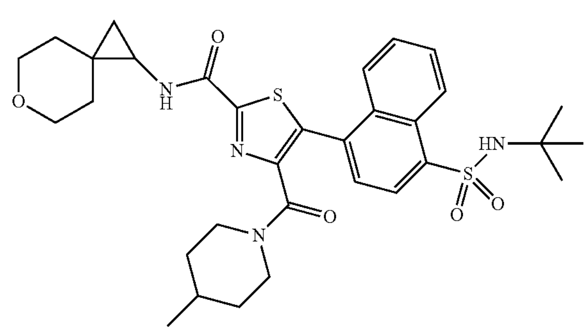 [SMILES: CC1CCN(C(=O)c2nc(C(=O)NC3CC34CCOCC4)sc2-c2ccc(S(=O)(=O)NC(C)(C)C)c3ccccc23)CC1] | $^1$H-NMR (400 MHz, CDCl$_3$) δ: 8.69 (d, J = 8.4 Hz, 1H), 8.33 (d, J = 8.8 Hz, 1H), 7.98 (d, J = 8.0 Hz, 1H), 7.75-7.57 (m, 3H), 7.33 (m, 1H), 4.75 (s, 1H), 4.36 (m, 1H), 3.95-3.68 (m, 4H), 3.45 (m, 1H), 2.86 (m, 1H), 2.55 (m, 1H), 2.38 (m, 1H), 1.65-1.40 (m, 4H), 1.39-1.20 (m, 12H), 1.01 (m, 1H), 0.75-0.62 (m, 5H), 0.20 (m, 1H). MS 625.2 (M + 1)$^+$ |

| # | Structure | Analytical data |
|---|---|---|
| 304/19 | 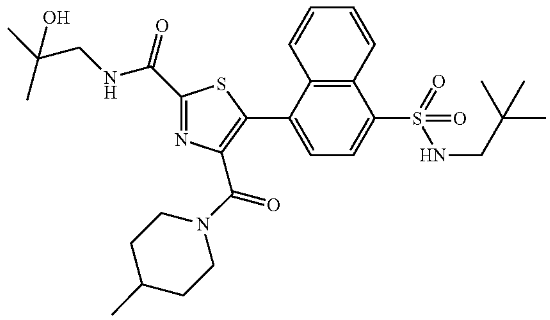 [SMILES: CC1CCN(C(=O)c2nc(C(=O)NCC(C)(C)O)sc2-c2ccc(S(=O)(=O)NCC(C)(C)C)c3ccccc23)CC1] | ¹H-NMR (400 MHz, DMSO-d₆) δ: 8.81 (d, J = 8.8 Hz, 1H), 8.51 (m, 1H), 8.14 (d, J = 8.0 Hz, 1H), 8.10 (m, 1H), 7.98 (d, J = 8.4 Hz, 1H), 7.81-7.66 (m, 3H), 4.13 (m, 1H), 3.59 (m, 1H), 3.32 (m, 2H), 2.80 (m, 1H), 2.64 (m, 2H), 2.43 (m, 1H), 1.46-1.39 (m, 3H), 1.26 (s, 6H), 0.80 (s, 9H), 0.68 (d, J = 6.4 Hz, 3H), 0.43 (m, 1H), 0.23 (m, 1H). MS 601.2 (M + 1)⁺ |
| 304/20 | 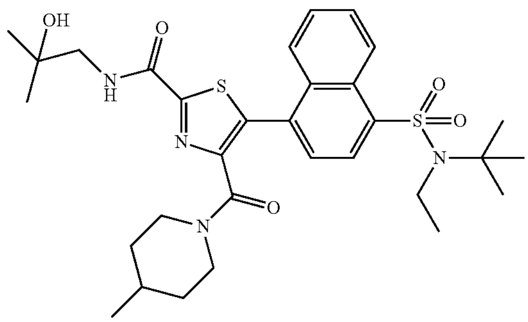 [SMILES: CCN(C(C)(C)C)S(=O)(=O)c1ccc(-c2sc(C(=O)NCC(C)(C)O)nc2C(=O)N2CCC(C)CC2)c2ccccc12] | ¹H-NMR (400 MHz, CDCl₃) δ: 8.87 (d, J = 8.4 Hz, 1H), 8.00 (d, J = 8.0 Hz, 1H), 7.96 (d, J = 7.6 Hz, 1H), 7.73-7.69 (m, 2H), 7.64-7.59 (m, 2H), 4.40 (m, 1H), 3.64 (m, 2H), 3.50 (m, 2H), 3.40 (m, 1H), 2.62 (m, 1H), 2.44 (m, 1H), 1.51-1.33 (m, 20H), 1.20 (m, 1H), 0.69 (d, J = 6.4 Hz, 3H), 0.63 (m, 1H), 0.05 (m, 1H). MS 615.2 (M + 1)⁺ |
| 304/21 | 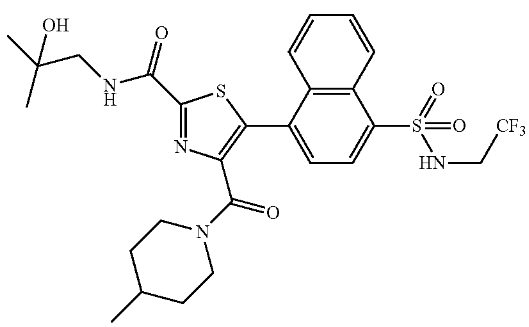 [SMILES: CC1CCN(C(=O)c2nc(C(=O)NCC(C)(C)O)sc2-c2ccc(S(=O)(=O)NCC(F)(F)F)c3ccccc23)CC1] | ¹H-NMR (400 MHz, CDCl₃) δ: 8.67 (d, J = 8.4 Hz, 1H), 8.30 (d, J = 7.6 Hz, 1H), 8.03 (d, J = 8.4 Hz, 1H), 7.78-7.64 (m, 4H), 5.28 (m, 1H), 4.38 (m, 1H), 3.71 (m, 2H), 3.51 (m, 3H), 2.65 (m, 1H), 2.43 (m, 1H), 1.40-1.26 (m, 9H), 0.76-0.72 (m, 4H), 0.38 (m, 1H). MS 613.1 (M + 1)⁺ |
| 304/22 | 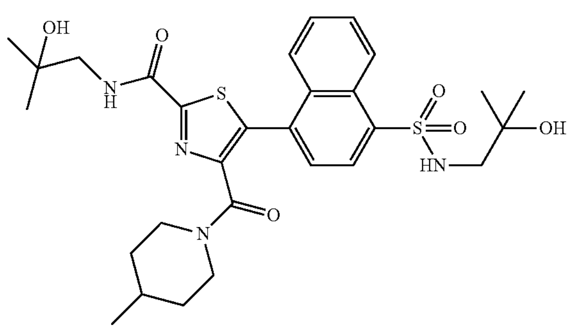 [SMILES: CC1CCN(C(=O)c2nc(C(=O)NCC(C)(C)O)sc2-c2ccc(S(=O)(=O)NCC(C)(C)O)c3ccccc23)CC1] | ¹H-NMR (400 MHz, CDCl₃) δ: 8.77 (d, J = 7.6 Hz, 1H), 8.26 (d, J = 7.6 Hz, 1H), 7.98 (d, J = 8.4 Hz, 1H), 7.84 (m, 1H), 7.74 (m, 1H), 7.65-7.61 (m, 2H), 5.44 (br s, 1H), 4.34 (br s, 1H), 3.52 (m, 3H), 2.92 (m, 2H), 2.67-2.48 (m, 2H), 1.53-1.20 (m, 15H), 0.76-0.74 (m, 4H), 0.32 (m, 1H). MS 603.2 (M + 1)⁺ |

-continued

| # | Structure | Analytical data |
|---|---|---|
| 304/23 | 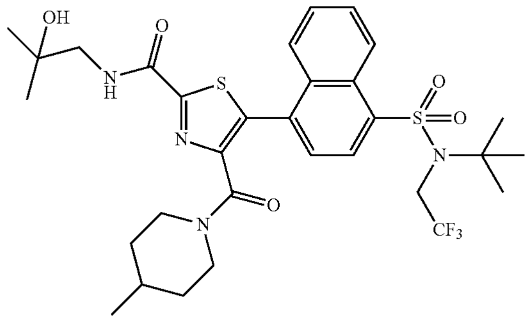 [SMILES: CC1CCN(C(=O)c2nc(C(=O)NCC(C)(C)O)sc2-c2ccc(S(=O)(=O)N(CC(F)(F)F)C(C)(C)C)c3ccccc23)CC1] | ¹H-NMR (400 MHz, DMSO-d₆) δ: 8.81 (d, J = 8.8 Hz, 1H), 8.70 (m, 1H), 8.26 (d, J = 8.0 Hz, 1H), 8.19 (d, J = 7.6 Hz, 1H), 8.02-7.86 (m, 3H), 4.90 (s, 1H), 4.67 (m, 1H), 4.31 (m, 1H), 3.73 (m, 1H), 3.49-3.47 (m, 2H), 2.96 (m, 1H), 2.61 (m, 1H), 1.63-1.47 (m, 11H), 1.36-1.32 (m, 7H), 0.80 (m, 3H), 0.49 (m, 1H), 0.13 (m, 1H). MS 669.2 (M + 1)⁺ |
| 304/24 | 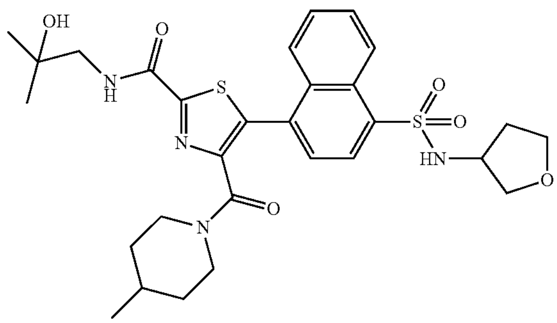 [SMILES: CC1CCN(C(=O)c2nc(C(=O)NCC(C)(C)O)sc2-c2ccc(S(=O)(=O)NC3CCOC3)c3ccccc23)CC1] | ¹H-NMR (400 MHz, CDCl₃) δ: 8.72 (d, J = 8.4 Hz, 1H), 8.32 (d, J = 7.2 Hz, 1H), 8.01 (d, J = 8.4 Hz, 1H), 7.82-7.63 (m, 4H), 5.21 (br s, 1H), 4.34 (br s, 1H), 3.99-3.81 (m, 3H), 3.71-3.62 (m, 2H), 3.53 (m, 3H), 2.75-2.40 (m, 2H), 2.06 (m, 1H), 1.73 (m, 1H), 1.39-1.34 (m, 9H), 0.76-0.74 (m, 4H), 0.29 (m, 1H). MS 601.2 (M + 1)⁺ |
| 304/25 | 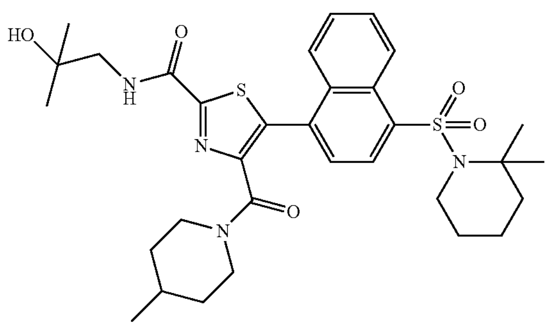 [SMILES: CC1CCN(C(=O)c2nc(C(=O)NCC(C)(C)O)sc2-c2ccc(S(=O)(=O)N3CCCCC3(C)C)c3ccccc23)CC1] | ¹H-NMR (400 MHz, DMSO-d₆) δ: 8.73 (d, J = 8.8 Hz, 1H), 8.52 (m, 1H), 8.17 (d, J = 7.6 Hz, 1H), 8.00 (d, J = 8.0 Hz, 1H), 7.83-7.67 (m, 3H), 4.13 (m, 1H), 3.59 (m, 1H), 3.32 (m, 2H), 3.15 (m, 2H), 2.87-2.77 (m, 3H), 2.45 (m, 1H), 1.59 (m, 2H), 1.-46-1.40 (m, 2H), 1.27-1.24 (m, 3H), 1.15 (s, 6H), 0.67 (d, J = 6.4 Hz, 3H), 0.39 (m, 1H), 0.20 (m, 1H). MS 627.2 (M + 1)⁺ |
| 304/26 | 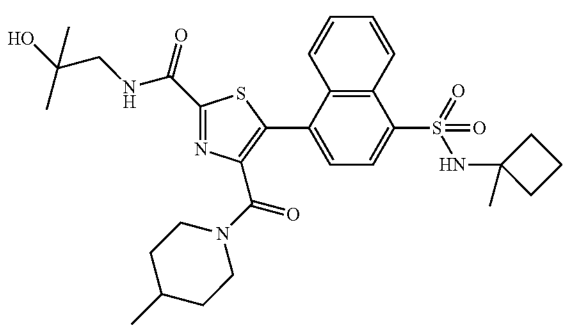 [SMILES: CC1CCN(C(=O)c2nc(C(=O)NCC(C)(C)O)sc2-c2ccc(S(=O)(=O)NC3(C)CCC3)c3ccccc23)CC1] | ¹H-NMR (400 MHz, DMSO-d₆) δ: 8.77 (d, J = 8.8 Hz, 1H), 8.52 (m, 1H), 8.31 (s, 1H), 8.20 (d, J = 7.6 Hz, 1H), 7.98 (d, J = 8.0 Hz, 1H), 7.81-7.66 (m, 3H), 4.10 (m, 1H), 3.57 (m, 1H), 3.32 (m, 2H), 2.77 (m, 1H), 2.41 (m, 1H), 2.14 (m, 1H), 1.69-1.15 (m, 16H), 0.66 (d, J = 6.4 Hz, 3H), 0.43 (m, 1H), 0.23 (m, 1H). MS 599.2 (M + 1)⁺ |

| # | Structure | Analytical data |
|---|---|---|
| 304/27 | 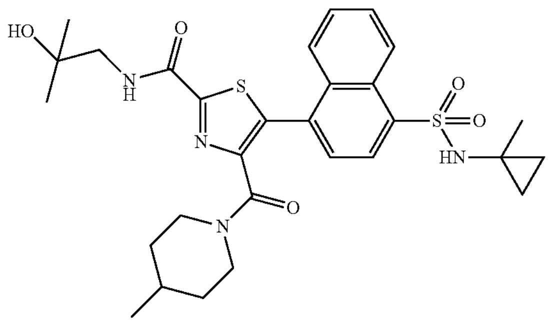 [SMILES: CC1CCN(C(=O)c2nc(C(=O)NCC(C)(C)O)sc2-c2ccc(S(=O)(=O)NC3(C)CC3)c3ccccc23)CC1] | $^1$H-NMR (400 MHz, DMSO-$d_6$) δ: 8.68 (d, J = 8.4 Hz, 1H), 8.52 (m, 1H), 8.23 (d, J = 7.2 Hz, 1H), 7.98 (d, J = 8.0 Hz, 1H), 7.79-7.65 (m, 3H), 4.72 (s, 1H), 4.12 (m, 1H), 3.58 (m, 1H), 3.33 (m, 2H), 2.76 (m, 1H), 2.46 (m, 1H), 1.50-1.15 (m, 9H), 1.06 (s, 3H), 0.52-0.24 (m, 6H). MS 585.2 (M + 1)$^+$ |

Example 305

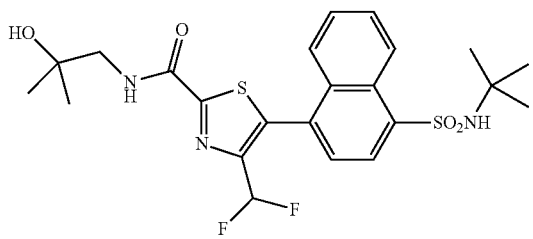

Step 1: Ethyl 5-(4-(N-(tert-butyl)sulfamoyl)naphthalen-1-yl)-4-formylthiazole-2-carboxylate (305a)

A solution of ethyl 5-(4-(N-(tert-butyl)sulfamoyl)naphthalen-1-yl)-4-(hydroxymethyl)thiazole-2-carboxylate (1.2 g, 2.7 mmol) in DCM (50 mL) was added MnO$_2$ (0.49 g, 5.4 mmol). The mixture was stirred at rt overnight. Water (20 mL) was added, the aq. phase was extracted with EA (20 mL×3). The combined organic layers were washed with brine, dried over Na$_2$SO$_4$, concentrated and purified by CC (EA/PE=1/2) to give compound 305a (1.1 g, 92%) as a brown solid.

Step 2: Ethyl 5-(4-(N-(tert-butyl)sulfamoyl)naphthalen-1-yl)-4-(difluoromethyl)thiazole-2-carboxylate (305b)

To a solution of compound 305a (1.1 g, 2.5 mmol) in dry DCM (50 mL) at 0° C. was added DAST (0.81 g, 5 mmol) dropwise over 30 min. The mixture was stirred at 0° C. for 0.5 h and at rt for 3 h, poured into ice-water and extracted with EA (40 mL×3). The combined organic layers were washed with brine, dried over Na$_2$SO$_4$, concentrated and purified by CC (PE/EA=15/1) to afford compound 305b (655 mg, 56%) as a colorless oil.

Step 3: 5-(4-(N-(tert-butyl)sulfamoyl)naphthalen-1-yl)-4-(difluoromethyl)-N-(2-hydroxy-2-methylpropyl)thiazole-2-carboxamide (305)

To a solution of compound 305b (0.66 g, 1.2 mmol) and 1-amino-2-methylpropan-2-ol (0.21 g, 2.4 mmol) in toluene (20 mL) was heated to 95° C. overnight, poured into water (40 mL) and extracted with EA (30 mL×3). The combined organic layers were washed with brine, dried over Na$_2$SO$_4$, concentrated and purified by prep-TLC to afford compound 305 (0.5 g, 82%) as a white solid. $^1$H-NMR (400 MHz, CDCl$_3$) δ: 8.72 (d, 1H, J=8.8 Hz), 8.38 (d, 1H, J=7.6 Hz), 7.77 (m, 3H), 7.61 (m, 2H), 6.40 (m, 1H), 4.70 (s, 1H), 3.53 (d, 1H, J=6.4 Hz), 1.35 (s, 6H), 1.21 (s, 9H). MS 511.7 (M+1)$^+$.

Example 305/1

The following example was prepared similar to Example 305.

| # | Structure | Analytical data |
|---|---|---|
| 305/1 | 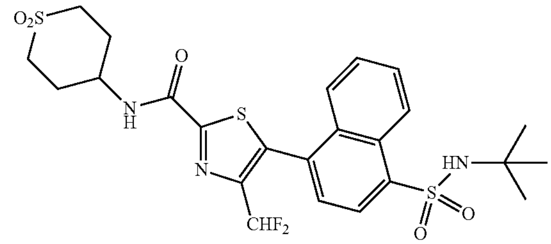 [SMILES: CC(C)(C)NS(=O)(=O)c1ccc(-c2sc(C(=O)NC3CCS(=O)(=O)CC3)nc2C(F)F)c2ccccc12] | $^1$H-NMR (400 MHz, CDCl$_3$) δ: 8.73 (d, 1H, J = 8.8 Hz), 8.38 (d, 1H, J = 7.2 Hz), 7.75 (m, 4H), 7.37 (d, 1H, J = 8.0 Hz), 6.40 (t, J = 53.2 Hz, 1H), 4.67 (s, 1H), 4.28 (m, 1H), 3.18 (m, 4H), 2.40 (m, 4H), 1.21 (s, 9H). MS 572.1 (M + 1)$^+$ |

Example 306

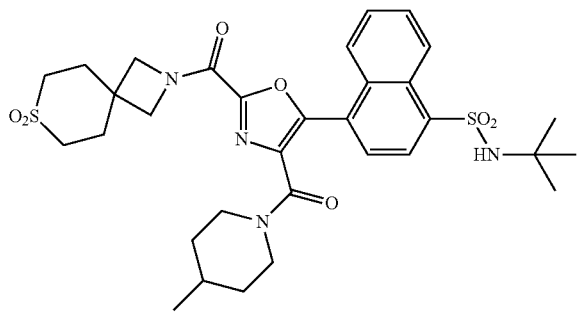

Step 1: Methyl 4-(N-(tert-butyl)sulfamoyl)-1-naphthoate (306a)

A solution of 4-bromo-N-(tert-butyl)naphthalene-1-sulfonamide (300 mg, 0.88 mmol), Pd(AcO)$_2$ (19.7 mg, 88 μmol), DPPP (54.4 mg, 0.132 mmol) and NEt$_3$ (266.6 mg, 2.64 mmol) in CH$_3$OH (10 mL) in an autoclave under CO (3.0 MPa pressure) was stirred at 80° C. overnight, concentrated and purified by CC (PE/EA=5/1) to give compound 306a (160 mg, 57%) as a white solid.

Step 2: 4-(N-(tert-Butyl)sulfamoyl)-1-naphthoic acid (306b)

A solution of compound 306a (2.4 g, 7.4 mmol) in CH$_3$OH/H$_2$O (10:1, 50 mL) was added LiOH.H$_2$O (0.94 g, 22.4 mmol) and the solution was stirred at rt overnight, concentrated and dissolved in H$_2$O. The pH was adjusted to ~5 with 2N HCl under cooling with an ice bath and then the aq. phase was extracted with EA. The combined organic layers were washed with water and brine, dried over Na$_2$SO$_4$, filtered and concentrated to give compound 306b (2.2 g, 95%) as a pale white solid.

Step 3: 4-(N-(tert-Butyl)sulfamoyl)-1-naphthoyl chloride (306c)

To a solution of compound 306b (307 mg, 1.0 mmol) in dry DCM (5 mL) was added oxalyl chloride (189 mg, 1.5 mmol) slowly and the mixture was stirred at rt for 3 hr and concentrated to give crude compound 306c as pale yellow oil.

Step 4: Ethyl 5-(4-(N-(tert-butyl)sulfamoyl)naphthalen-1-yl)oxazole-4-carboxylate (306d)

To a solution of ethyl 2-isocyanoacetate (124 mg, 1.1 mmol) and compound 306c (1.0 mmol) in dry THF (5.0 mL) was added NEt$_3$ (400 mg, 4.0 mmol) slowly and the solution was stirred at rt overnight, diluted with EA, washed with sat. NH$_4$Cl and brine, dried over Na$_2$SO$_4$, filtered, concentrated and purified by CC (PE/EA=3/1) to give compound 306d (190 mg, 47%) as a yellow solid.

Step 5: 5-(4-(N-(tert-Butyl)sulfamoyl)naphthalen-1-yl)oxazole-4-carboxylic acid (306e)

To a solution of compound 306d (220 mg, 0.55 mmol) in EtOH (5.0 mL) was added NaOH (65 mg, 1.64 mmol) and the solution was stirred at rt overnight, concentrated and dissolved in H$_2$O. The pH was adjusted to 5 with 2N HCl under cooling with an ice bath and then the aq. phase was extracted with EA. The organic layer was washed with water and brine, dried over Na$_2$SO$_4$, filtered and concentrated to give compound 306e (130 mg, 65%) as a pale white solid.

Step 6: N-(tert-Butyl)-4-(4-(4-methylpiperidine-1-carbonyl)oxazol-5-yl)naphthalene-1-sulfonamide (306f)

A mixture of compound 306e (750 mg, 2.0 mmol), 4-methylpiperidine (300 mg, 3.0 mmol), HATU (1.14 g, 3.0 mmol) and DIPEA (0.77 g, 6.0 mmol) in DMF (10 mL) was stirred overnight at rt, poured into water and extracted with EA. The organic layer was washed with water and brine, dried over Na$_2$SO$_4$, filtered, concentrated and purified by CC gel (DCM/MeOH=100/1 to 50/1) to afford compound 306f (820 mg, 90%) as a white solid.

Step 7: Methyl 5-(4-(N-(tert-butyl)sulfamoyl)naphthalen-1-yl)-4-(4-methylpiperidine-1-carbonyl)oxazole-2-carboxylate (306c)

To a solution of compound 306f (199 mg, 0.44 mmol) in dry THF (3 mL) was added n-butyllithium (2.5M in hexane, 0.53 mL, 1.32 mmol) at −78° C. under argon and the solution was stirred for 2 h at −78° C. Then methyl chloroformate (124 mg, 1.32 mmol) was added and the solution was stirred for 1 h, quenched with sat. NH$_4$Cl, extracted with EA, washed with brine, dried over Na$_2$SO$_4$, filtered, concentrated and purified by CC (DCM/MeOH=100/1) to give compound 306g (65 mg, 29%) as a white solid.

Step 8: 5-(4-(N-(tert-Butyl)sulfamoyl)naphthalen-1-yl)-4-(4-methylpiperidine-1-carbonyl)oxazole-2-carboxylic acid (306h)

To a solution of compound 306g (65 mg, 0.13 mmol) in THF/H$_2$O (3/1, 5 mL) was added LiOH.H$_2$O (11 mg, 0.26 mmol) and the solution was stirred for 15 min at rt, adjusted to pH 3-4 with 2N HCl under cooling with an ice bath and then extracted with DCM. The organic layer was washed with water and brine, dried over Na$_2$SO$_4$, filtered and this DCM solution was used for the next reaction without further purification.

Step 9: N-(tert-Butyl)-4-(2-(7,7-dioxido-7-thia-2-azaspiro[3.5]nonane-2-carbonyl)-4-(4-methyl-piperidine-1-carbonyl)oxazol-5-yl)naphthalene-1-sulfonamide (306)

A solution of compound 306h (65 mg, 0.13 mmol, th.), 7-thia-2-azaspiro[3.5]nonane-7,7-dione hemi-oxalate (35 mg, 0.13 mmol), HATU (74 mg, 0.2 mmol) and DIPEA (25 mg, 0.2 mmol) in DCM (2 mL) was stirred overnight at rt, washed with water and brine, dried over Na$_2$SO$_4$, filtered, concentrated and purified by prep-HPLC to give compound 306 (24 mg, 28% over two steps) as a white solid. $^1$H-NMR (400 MHz, CD$_3$OD) δ: 0.46-0.53 (m, 1H), 0.76-0.85 (m, 1H), 0.79 (d, J=6.4 Hz, 3H), 1.16 (s, 9H), 1.36-1.39 (m, 1H), 1.48-1.55 (m, 1H), 1.60-1.64 (m, 1H), 2.40 (t, J=5.6 Hz, 4H), 2.66 (t, J=12.0 Hz, 1H), 2.91 (t, J=8.0 Hz, 4H), 3.11-3.20 (m, 4H), 3.88 (d, J=12.8 Hz, 1H), 4.06 (s, 2H), 4.42 (d, J=12.8 Hz, 1H), 4.58 (s, 2H), 7.68-7.72 (m, 1H), 7.76-7.80 (m, 1H), 7.85 (d, J=8.0 Hz, 1H), 8.06 (d, J=8.4 Hz, 1H), 8.36 (d, J=7.6 Hz, 1H), 8.84 (d, J=8.8 Hz, 1H). MS 657.3 (M+1)⁺.

Example 307

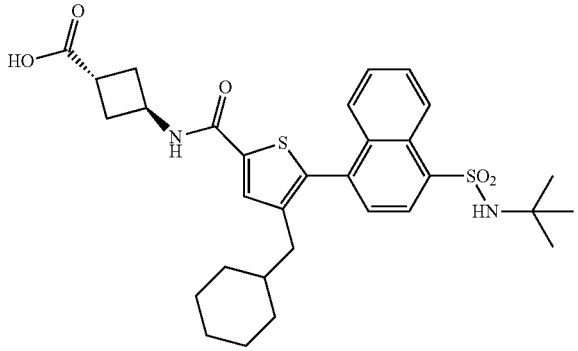

Step 1: Cyclohexyl(thiophen-3-yl)methanol (307a)

To a solution of thiophene-3-carbaldehyde (15.0 g, 134 mmol) in Et₂O (200 mL) was added cyclohexylmagnesium chloride (1M in THF, 160 mL, 160 mmol) dropwise at 0° C. and the mixture was stirred at rt for 3 h, quenched with sat. NH₄Cl at 0° C. and extracted with EA. The organic layer was washed with water and brine, dried over Na₂SO₄, filtered, concentrated and purified by CC (PE/EA=10/1) to give compound 307a (22.1 g, 84%) as a pale yellow oil.

Step 2: Cyclohexyl(thiophen-3-yl)methyl methanesulfonate (307b)

To a solution of compound 307a (18.8 g, 95.9 mmol) and Et₃N (11.6 g, 115 mmol) in DCM (200 mL) was added MsCl (13.1 g, 115 mmol) dropwise at 0° C. and the mixture was stirred at 0° C. for 30 min, then at rt overnight, concentrated and diluted with a mixture of PE and EA (100 mL/50 mL). The suspension was filtered to remove salt. After concentration at rt, crude compound 307b (22.0 g) was used for the next step without further purification.

Step 3: 3-(Cyclohexylmethyl)thiophene (307c)

To a solution of compound 307b (22.0 g, 80.3 mmol) in EA (250 mL) was added 10% Pd/C (4.5 g) and the suspension was stirred under H₂ (50 psi) at 60° C. for 24 h, filtered and the filtrate was concentrated and purified by CC (PE/EA=50/1) to give compound 307c (6.8 g, 37.8 mmol) as a colorless oil.

Step 4: 2-Bromo-3-(cyclohexylmethyl)thiophene (307d)

To a solution of compound 307c (6.80 g, 37.8 mmol) in AcOH (40 mL) was added NBS (7.40 g, 41.6 mmol) portionwise and the solution was stirred at 30° C. for 7 hr, poured into ice-water and extracted with EA. The organic layer was washed with water and brine and dried over Na₂SO₄, filtered, concentrated and purified by CC (PE/EA=50/1) to give compound 307d (5.00 g, 51%) as a red oil.

Step 5: Methyl 5-bromo-4-(cyclohexylmethyl)thiophene-2-carboxylate (307e)

To a solution of LDA (1M in THF, 21.5 mL, 21.5 mmol) was added a solution of compound 307d (5.00 g, 19.6 mmol) in dry THF (50 mL) dropwise at −78° C. under N₂ and the solution was stirred at −78° C. for 45 min. Then a solution of ethyl chloroformate (2.32 g, 21.5 mmol) in dry THF (3 mL) was added dropwise at −78° C., kept stirring for 2 h at −78° C., then quenched with sat. NH₄Cl at −78° C. and then warmed to rt. After extraction with EA (3×), the combined organic layers were washed with water and brine consecutively, dried over Na₂SO₄, filtered, concentrated and purified by CC (PE/EA=10/1) to give compound 307e (4.50 g, 70%) as a white solid.

Step 6: Methyl 5-(4-(N-(tert-butyl)sulfamoyl)naphthalen-1-yl)-4-(cyclohexylmethyl)thiophene-2-carboxylate (307f)

A mixture of compound 307e (800 mg, 2.42 mmol), compound P1/2 (1.04 g, 2.67 mmol) Pd(dppf)Cl₂ (297 mg, 0.36 mmol) and Na₂CO₃ (771 mg, 7.27 mmol) in dry DME (40 mL) was bubbled with N₂ for 10 min and then refluxed overnight under N₂. The mixture was cooled to rt, diluted with EA and then filtered. The filtrate was concentrated and purified by prep-HPLC to give compound 307f (480 mg, 39%) as a white solid.

Step 7: 5-(4-(N-(tert-Butyl)sulfamoyl)naphthalen-1-yl)-4-(cyclohexylmethyl)thiophene-2-carboxylic acid (307g)

To a solution of compound 307f (220 mg, 0.428 mmol) in a mixture of MeOH and H₂O (10 mL/1 mL) was added LiOH.H₂O (36 mg, 0.86 mmol) and the solution was stirred overnight at rt, adjusted pH to 4-5 with 2N HCl, concentrated and dissolved with DCM. The organic layer was dried with Na₂SO₄, filtered and concentrated to give crude compound 307g (224 mg) as a pale yellow solid.

Step 8: trans-3-(5-(4-(N-(tert-Butyl)sulfamoyl)naphthalen-1-yl)-4-(cyclohexylmethyl)thiophene-2-carboxamido)cyclobutanecarboxylic acid (307)

A mixture of compound 307g (114 mg, 0.24 mmol), trans 3-aminocyclobutanecarboxylic acid hydrochloride (58 mg, 0.35 mmol), HATU (134 mg, 0.35 mmol) and DIEA (91 mg, 0.71 mmol) in dry DMF (8 mL) was stirred at 30° C. overnight, diluted with water, adjusted pH to 5 with 1N HCl and extracted with EA twice. The combined organic layers were concentrated and purified by prep-HPLC to give compound 307 (30 mg, 21%) as a white solid. ¹H-NMR (400 MHz, CDOD₃) δ: 0.48-0.58 (m, 2H), 0.91-0.98 (m, 3H), 1.04 (s, 9H), 1.19-1.23 (m, 2H), 1.30 (m, 1H), 1.37-1.50 (m, 5H), 2.32-2.38 (m, 2H), 2.55-2.58 (m, 2H), 2.98-3.00 (m, 1H), 4.58-4.62 (m, 1H), 7.47-7.53 (m, 2H), 7.62-7.68 (m, 3H), 8.20-8.24 (m, 1H), 8.70-8.75 (m, 1H). MS 583.3 [M+1]⁺.

Example 307/1

The following example was prepared similar to Example 307.

| # | Structure | Analytical data |
|---|---|---|
| 307/1 | 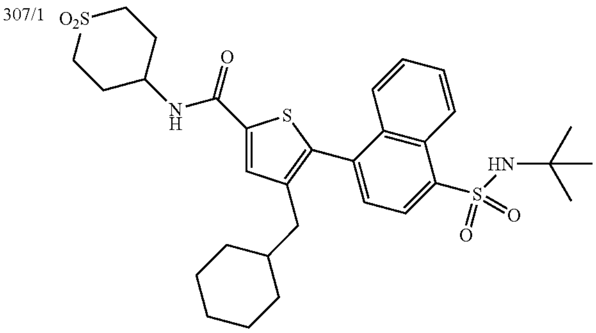 | $^1$H-NMR (400 MHz, DMSO-$d_6$) δ: 0.53-0.56 (m, 2H), 0.92-1.03 (m, 3H), 1.06 (s, 9H), 1.32-1.46 (m, 7H), 2.06-2.17 (m, 5H), 3.11-3.15 (m, 2H), 3.30-3.38 (m, 2H), 4.17-4.24 (m, 1H), 7.61-7.67 (m, 2H), 7.70-7.76 (m, 2H), 7.84 (s, 1H), 7.90 (s, 1H), 8.24 (d, J = 7.6 Hz, 1H), 8.50 (d, J = 7.6 Hz, 1H), 8.78 (d, J = 9.2 Hz, 1H). MS 617.3 [M + 1]$^+$ |

Example 308

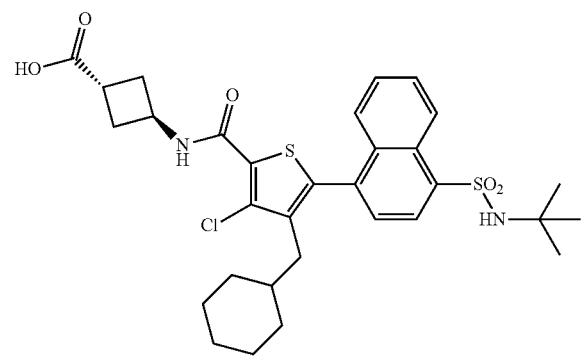

308

Step 1: Methyl 4,5-dibromo-3-chlorothiophene-2-carboxylate (308a)

To a solution of methyl 3-chlorothiophene-2-carboxylate (5.0 g, 28.3 mmol) and AcONa (17.4 g, 212 mmol) in AcOH (80 mL) was added Br$_2$ (13.2 mL, 255 mmol) dropwise at rt and the mixture was stirred at 75° C. for 3 d, cooled to rt, quenched with sat. Na$_2$S$_2$O$_3$, basified to pH=8 with sat. NaHCO$_3$ and extracted with Et$_2$O. The organic layer was washed with water and brine, dried over Na$_2$SO$_4$, filtered, concentrated and washed with a mixture of PE and EA (20 mL, 20/1) to give compound 308a (4.0 g, 42%) as pale red solid.

Step 2: Methyl 4-bromo-3-chlorothiophene-2-carboxylate (308b)

To a solution of compound 308a (1.0 g, 3.0 mmol) in THF (30 mL) was added n-BuLi (2.5 M in THF, 1.2 mL, 3.0 mmol) dropwise at −100° C. and the mixture was stirred at −100° C. for 5 min, quenched with water and extracted with EA. The organic layer was washed with water and brine, dried over Na$_2$SO$_4$, filtered, concentrated and purified by CC (PE/EA=100/1) to give compound 308b (500 mg, 65%) as a white solid.

Step 3: Methyl 3-chloro-4-(cyclohexylmethyl)thiophene-2-carboxylate (308c)

To a suspension of compound 308b (500 mg, 2.0 mmol) and Pd(dppf)Cl$_2$ (156 mg, 0.2 mmol) in THF (10 mL) was added cyclohexylmethyl zinc bromide (0.5M in THF, 19.6 mL, 9.8 mmol) at rt under N$_2$ and the suspension was stirred at reflux for 6 h, cooled to rt, quenched with water and extracted with EA. The organic layer was washed with water and brine, dried over Na$_2$SO$_4$, filtered, concentrated and purified by CC (PE/EA=100/1) to give compound 308c (500 mg, 92%) as a colorless oil.

Step 4: Methyl 5-bromo-3-chloro-4-(cyclohexylmethyl)thiophene-2-carboxylate (308d)

To a solution of compound 308c (200 mg, 0.7 mmol) and AcONa (451 mg, 5.5 mmol) in AcOH (10 mL) was added Br$_2$ (0.2 mL, 3.7 mmol) dropwise at 75° C. and the solution was stirred at 75° C. overnight, cooled to rt, quenched with sat. Na$_2$S$_2$O$_3$, adjusted pH=8 with sat. NaHCO$_3$ and extracted with EA. The organic layer was washed with water and brine, dried over Na$_2$SO$_4$, filtered, concentrated and purified by prep-HPLC to give compound 308d (40 mg, 16%) as a pale brown solid.

Step 5: trans-3-(5-(4-(N-(tert-Butyl)sulfamoyl)naphthalen-1-yl)-3-chloro-4-(cyclohexylmethyl)thiophene-2-carboxamido)cyclobutanecarboxylic acid (308)

If one were to treat compound 308d similar as described in Example 307, Step 6 to 8 one would obtain compound 308.

Example 309

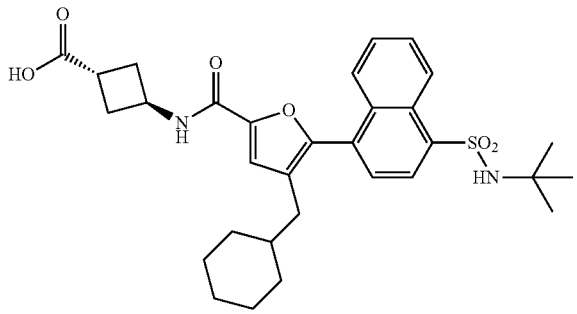

Step 1: Methyl 4,5-dibromo-3-methylfuran-2-carboxylate (309a)

To a suspension of AlCl$_3$ (2.28 g, 17.1 mmol) in dry DCM (25 mL) was added solution methyl 3-methylfuran-2-carboxylate (1.2 g, 8.57 mmol) in dry DCM (5.0 mL) slowly at 0° C. over 30 min. To this solution, Br$_2$ (4.11 g, 25.7 mmol) was added under the same condition over 1 h. The suspension was stirred at rt overnight, poured into ice-water and then diluted with EA. The aqueous layer was extracted with EA twice. The combine organic layers were washed with sat. Na$_2$SO$_3$ twice and brine consecutively, dried over Na$_2$SO$_4$, filtered, concentrated and purified by CC (PE/EA=20/1) to give compound 309a (1.0 g, 39%) as a white solid.

Step 2: Methyl 4-bromo-3-methylfuran-2-carboxylate (309b)

The solution of compound 309a (350 mg, 1.17 mmol) in THF (30 mL) was added n-BuLi (2.5M in THF, 0.47 mL, 1.18 mmol) dropwise at −78° C. under N$_2$ and the solution was stirred at this temperature for 10 min, quenched with sat. NH$_4$Cl and extracted with EA (3×). The combined organic layers were washed with water and brine, dried over Na$_2$SO$_4$, filtered, concentrated and purified by prep-HPLC to give compound 309b (50 mg, 19%) as a white solid.

Step 3: Methyl 4-(cyclohexylmethyl)-3-methylfuran-2-carboxylate (309c)

A solution of compound 309b (150 mg, 0.69 mmol), cyclohexylmethylzinc bromide (0.5M in THF, 7.0 mL, 3.5 mmol) and Pd(dppf)Cl$_2$ (50 mg, 0.069 mmol) in THF (5.0 mL) was refluxed under N$_2$ at 85° C. for 6 h, evaporated and purified by CC (PE/EA=20/1) to give compound 309c (140 mg, 86%) as white solid.

Step 4: Methyl 5-bromo-4-(cyclohexylmethyl)-3-methylfuran-2-carboxylate (309d)

To the solution of compound 309c (100 mg, 0.42 mol) in DCM (10.0 mL) was added Br$_2$ (200 mg, 1.26 mmol) slowly at 0° C. and the solution was stirred at rt overnight, diluted with EA and quenched with sat. Na$_2$SO$_3$. The aqueous layer was extracted with EA twice. The combined organic layers were washed with water and brine, dried over Na$_2$SO$_4$, filtered, concentrated and purified by CC (PE/EA=15/1) to give compound 309d (105 mg, 80%) as a yellow solid.

Step 5: Methyl 5-(4-(N-(tert-butyl)sulfamoyl)naphthalen-1-yl)-4-(cyclohexylmethyl)-3-methylfuran-2-carboxylate (309e)

The suspension of compound 309d (105 mg, 0.333 mmol), K$_2$CO$_3$ (138 mg, 1.0 mmol), compound P1/2 (130 mg, 0.333 mmol) and Pd(dppf)Cl$_2$ (20 mg) in DMF (5 mL) was stirred at 100° C. overnight, cooled to rt, concentrated and purified by CC (PE/EA=15/1) to give compound 309e (81 mg, 49%) as a white solid.

Step 6: 5-(4-(N-(tert-Butyl)sulfamoyl)naphthalen-1-yl)-4-(cyclohexylmethyl)-3-methylfuran-2-carboxylic acid (309f)

To a solution of compound 309e (81 mg, 0.16 mmol) in MeOH (2 mL) was added NaOH (20 mg, 5.0 mmol) and the solution was stirred at rt overnight, concentrated, diluted with water, adjusted pH to 5 with 1N HCl and extracted with EA. The organic layer was washed with water and brine, dried over Na$_2$SO$_4$, filtered and concentrated to give compound 309f (69 mg, 89%) as a yellow solid.

Step 7: trans-3-(5-(4-(N-(tert-Butyl)sulfamoyl)naphthalen-1-yl)-4-(cyclohexylmethyl)furan-2-carboxamido)cyclobutanecarboxylic acid (309)

If one were to treat compound 309f similar as described in Example 307, Step 8 one would obtain compound 309.

Additional Examples

The following compounds can be prepared in the same manner by using the procedures as described above:

| Structure |
| --- |
| 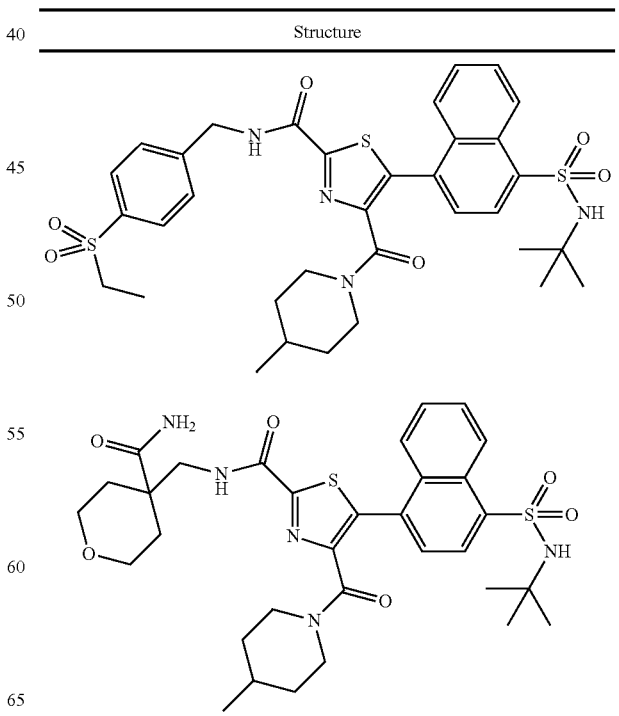 |

| 443 -continued | 444 -continued |
|---|---|
| Structure | Structure |
| 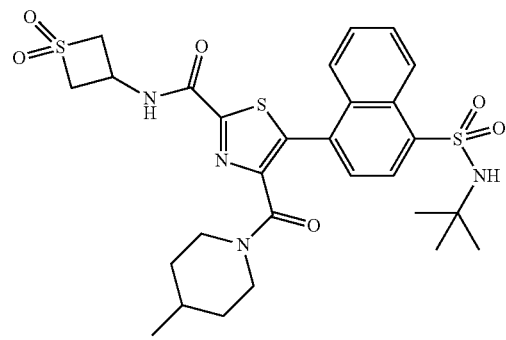 [SMILES: CC1CCN(C(=O)c2nc(C(=O)NC3CS(=O)(=O)C3)sc2-c2ccc(S(=O)(=O)NC(C)(C)C)c3ccccc23)CC1] | 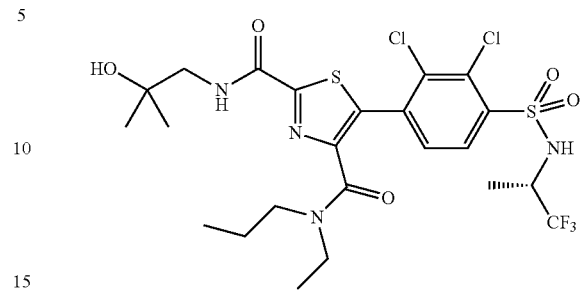 |
| 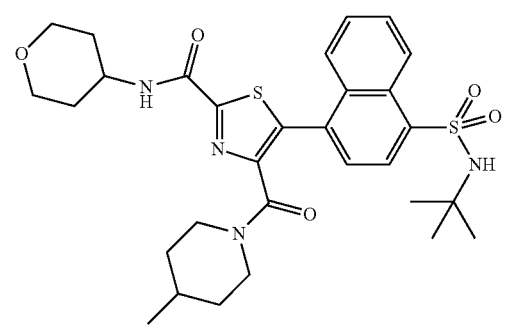 [SMILES: CC1CCN(C(=O)c2nc(C(=O)NC3CCOCC3)sc2-c2ccc(S(=O)(=O)NC(C)(C)C)c3ccccc23)CC1] | 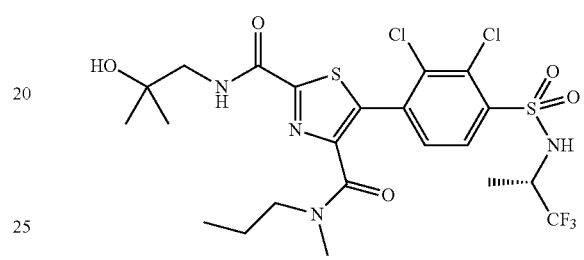 |
| 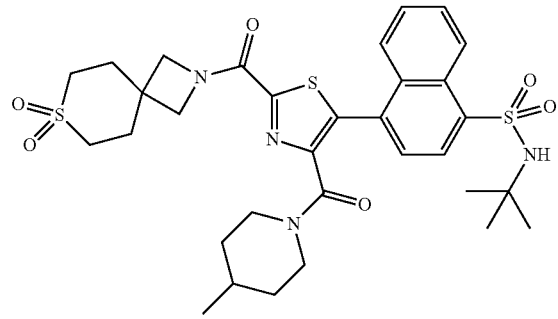 [SMILES: CC1CCN(C(=O)c2nc(C(=O)N3CC4(CCS(=O)(=O)CC4)C3)sc2-c2ccc(S(=O)(=O)NC(C)(C)C)c3ccccc23)CC1] | 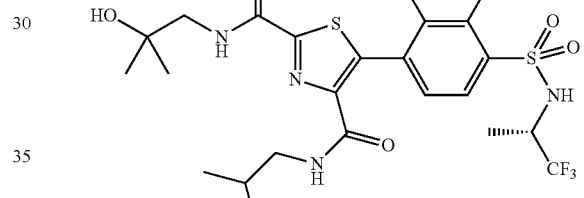 |
| 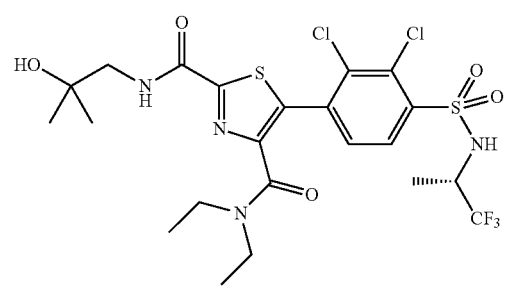 [SMILES: CCN(CC)C(=O)c1nc(C(=O)NCC(C)(C)O)sc1-c1ccc(S(=O)(=O)N[C@@H](C)C(F)(F)F)c(Cl)c1Cl] | 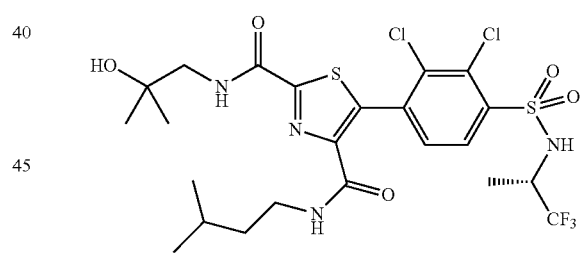 |
| 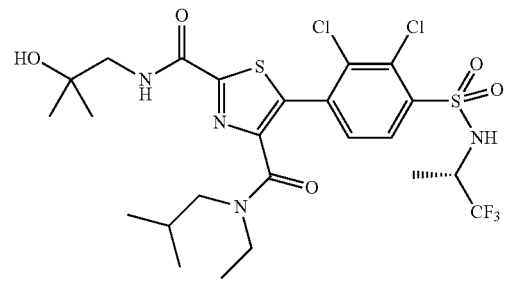 [SMILES: CCN(CC(C)C)C(=O)c1nc(C(=O)NCC(C)(C)O)sc1-c1ccc(S(=O)(=O)N[C@@H](C)C(F)(F)F)c(Cl)c1Cl] | 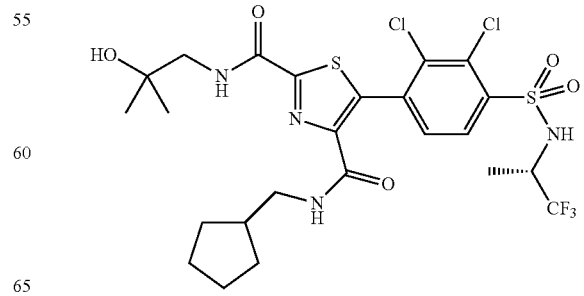 |

| 445 -continued | 446 -continued |
|---|---|
| Structure | Structure |
| 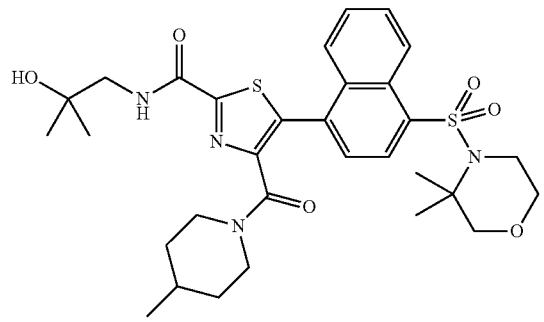 [SMILES: CC1CCN(C(=O)c2nc(C(=O)NCC(C)(C)O)sc2-c2ccc(S(=O)(=O)N3CCOCC3(C)C)c3ccccc23)CC1] | 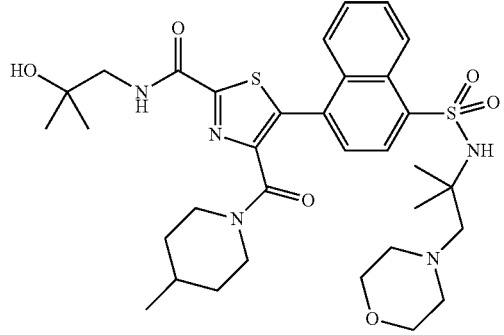 |
| 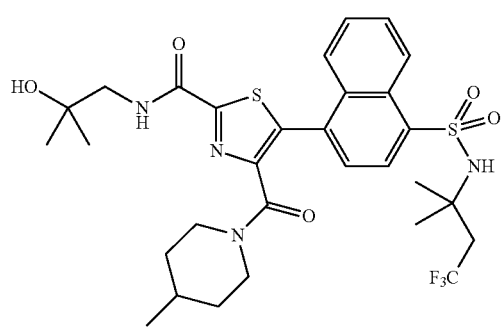 [SMILES: CC1CCN(C(=O)c2nc(C(=O)NCC(C)(C)O)sc2-c2ccc(S(=O)(=O)NC(C)(C)CC(F)(F)F)c3ccccc23)CC1] | 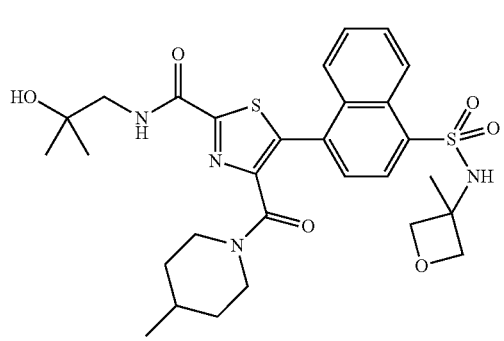 |
| 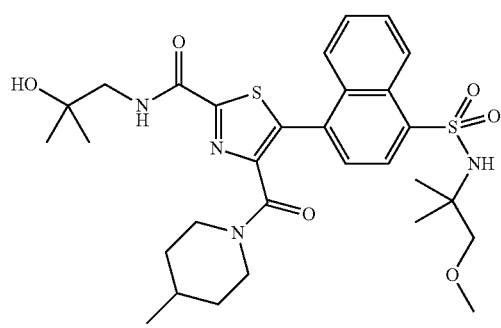 [SMILES: COCC(C)(C)NS(=O)(=O)c1ccc(-c2sc(C(=O)NCC(C)(C)O)nc2C(=O)N2CCC(C)CC2)c2ccccc12] | 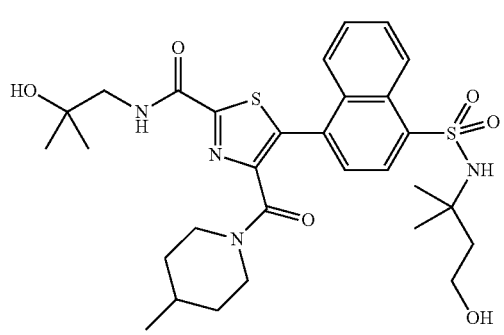 |
| 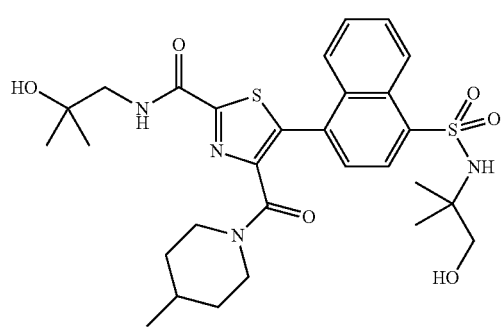 [SMILES: CC1CCN(C(=O)c2nc(C(=O)NCC(C)(C)O)sc2-c2ccc(S(=O)(=O)NC(C)(C)CO)c3ccccc23)CC1] | 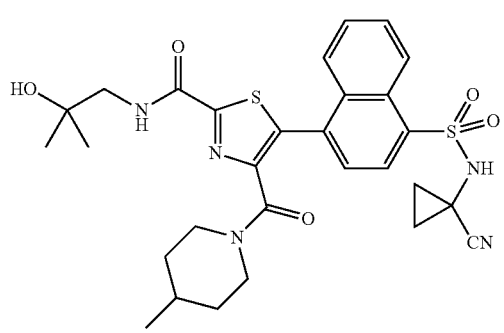 [SMILES: CC1CCN(C(=O)c2nc(C(=O)NCC(C)(C)O)sc2-c2ccc(S(=O)(=O)NC3(C#N)CC3)c3ccccc23)CC1] |

447
-continued
| Structure |
|---|
| 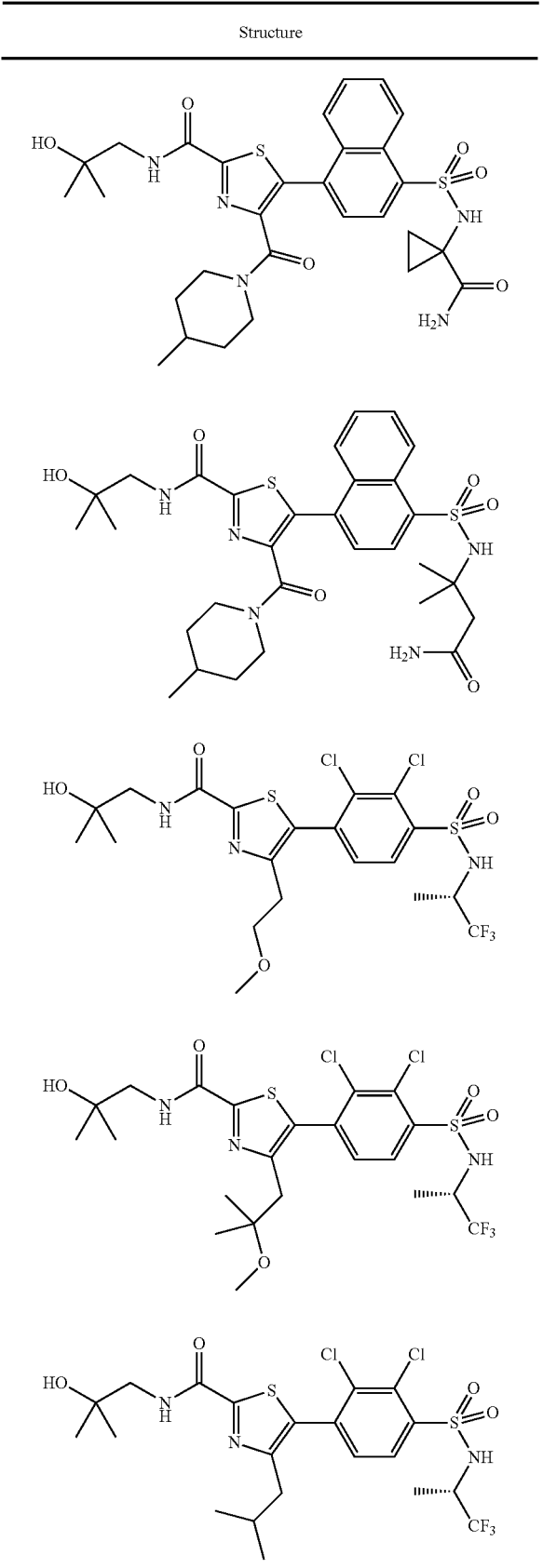 |
448
-continued
| Structure |
|---|
| 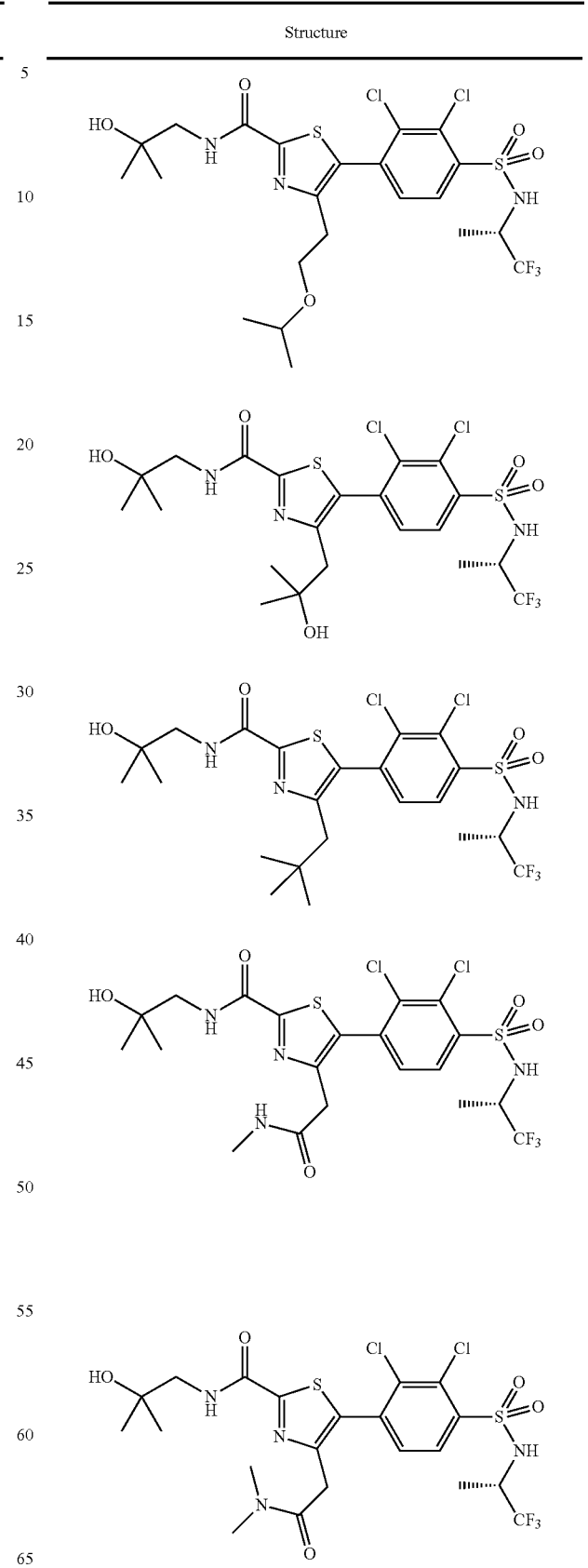 |

| 449 -continued | 450 -continued |
|---|---|
| Structure | Structure |
| 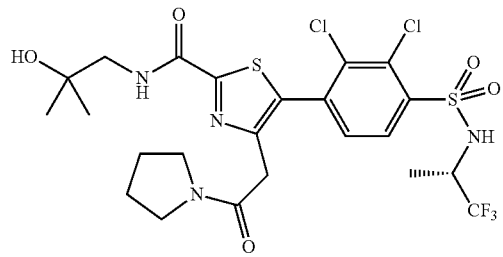 [SMILES: C[C@H](NS(=O)(=O)c1ccc(-c2sc(C(=O)NCC(C)(C)O)nc2CC(=O)N2CCCC2)c(Cl)c1Cl)C(F)(F)F] | 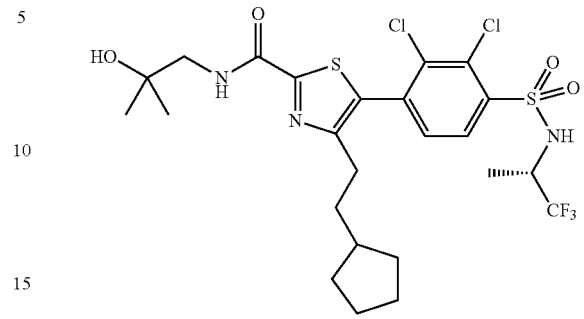 |
| 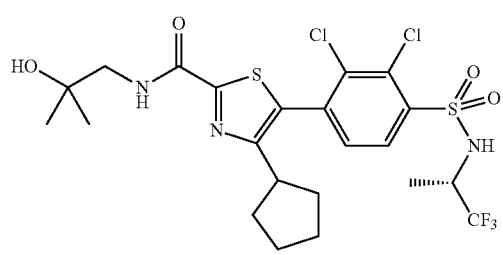 [SMILES: C[C@H](NS(=O)(=O)c1ccc(-c2sc(C(=O)NCC(C)(C)O)nc2C2CCCC2)c(Cl)c1Cl)C(F)(F)F] | 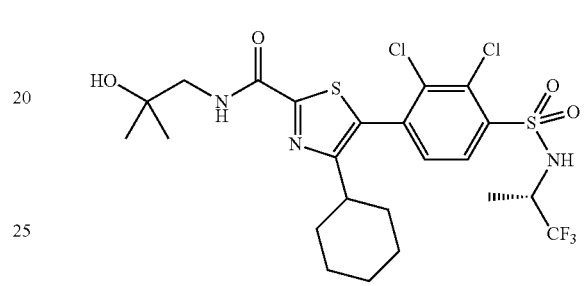 |
| 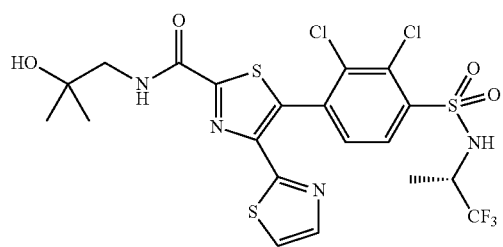 [SMILES: C[C@H](NS(=O)(=O)c1ccc(-c2sc(C(=O)NCC(C)(C)O)nc2-c2nccs2)c(Cl)c1Cl)C(F)(F)F] | 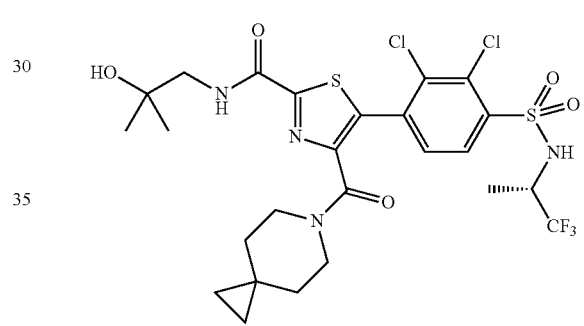 |
| 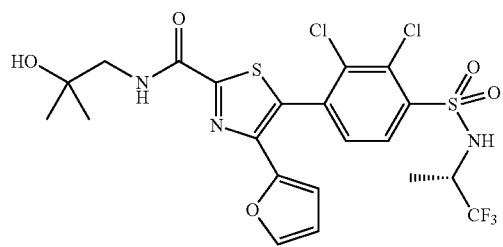 [SMILES: C[C@H](NS(=O)(=O)c1ccc(-c2sc(C(=O)NCC(C)(C)O)nc2-c2ccco2)c(Cl)c1Cl)C(F)(F)F] | 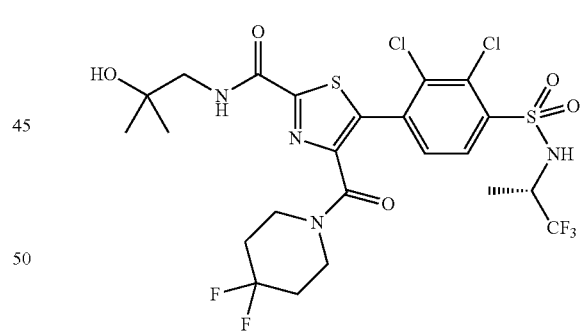 |
| 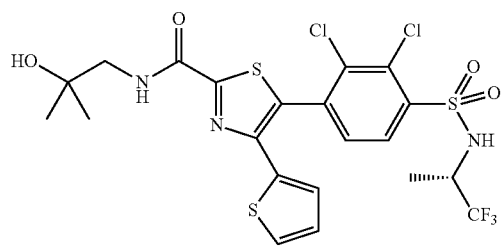 [SMILES: C[C@H](NS(=O)(=O)c1ccc(-c2sc(C(=O)NCC(C)(C)O)nc2-c2cccs2)c(Cl)c1Cl)C(F)(F)F] | 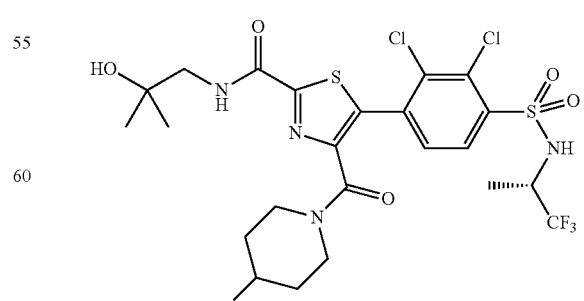 |
| 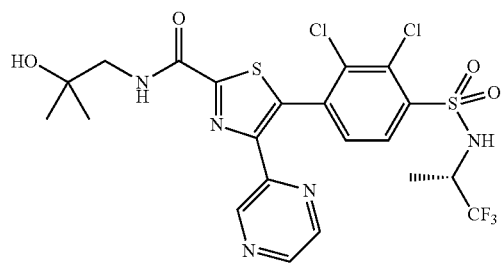 [SMILES: C[C@H](NS(=O)(=O)c1ccc(-c2sc(C(=O)NCC(C)(C)O)nc2-c2cnccn2)c(Cl)c1Cl)C(F)(F)F] | |

| 451 -continued | 452 -continued |
|---|---|
| Structure | Structure |
| 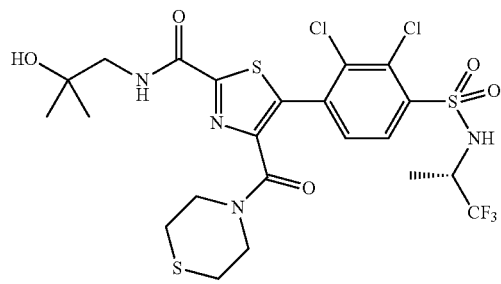 [SMILES: C[C@H](NS(=O)(=O)c1ccc(-c2sc(C(=O)NCC(C)(C)O)nc2C(=O)N2CCSCC2)c(Cl)c1Cl)C(F)(F)F] | 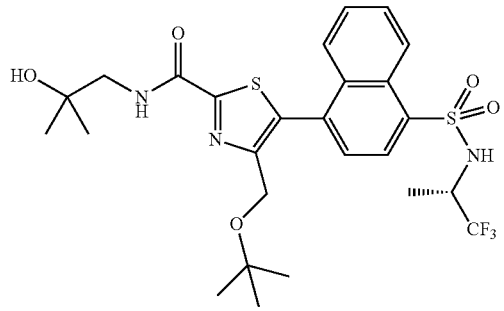 |
| 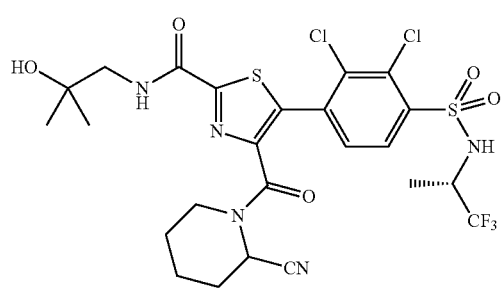 [SMILES: C[C@H](NS(=O)(=O)c1ccc(-c2sc(C(=O)NCC(C)(C)O)nc2C(=O)N2CCCCC2C#N)c(Cl)c1Cl)C(F)(F)F] | 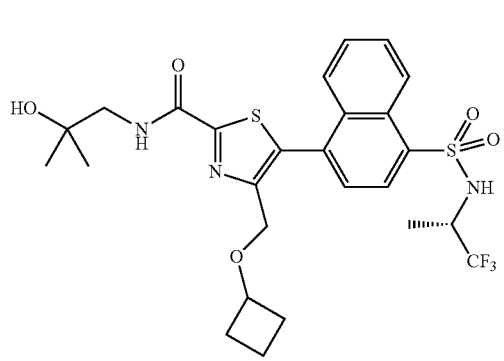 |
| 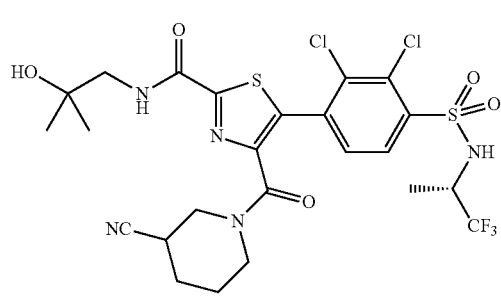 [SMILES: C[C@H](NS(=O)(=O)c1ccc(-c2sc(C(=O)NCC(C)(C)O)nc2C(=O)N2CCCC(C#N)C2)c(Cl)c1Cl)C(F)(F)F] | 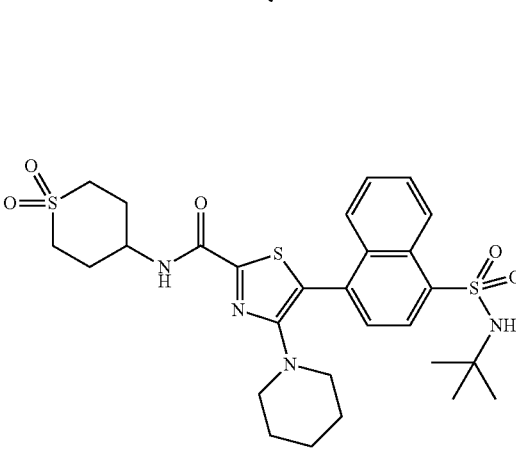 |
| 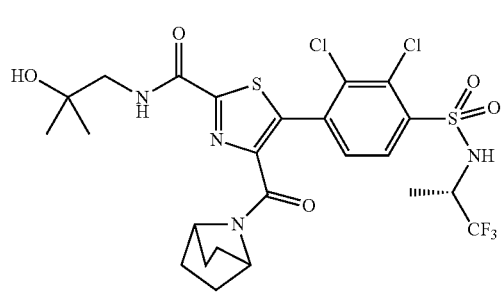 [SMILES: C[C@H](NS(=O)(=O)c1ccc(-c2sc(C(=O)NCC(C)(C)O)nc2C(=O)N2C3CCC2CC3)c(Cl)c1Cl)C(F)(F)F] | 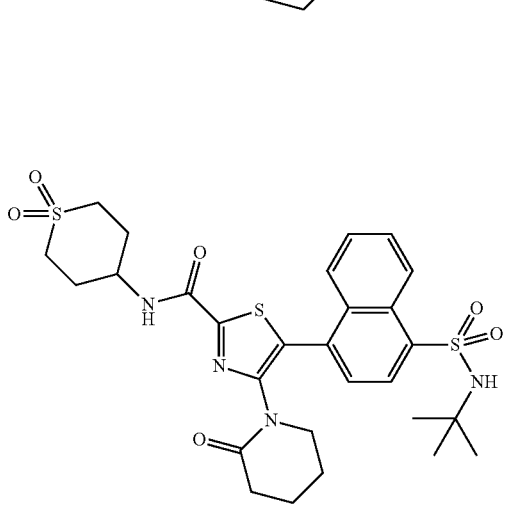 |
| 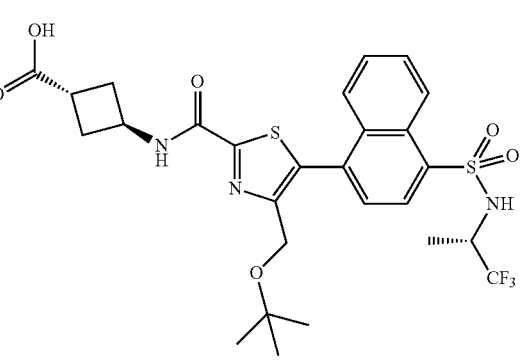 | |

| Structure |
|---|
| 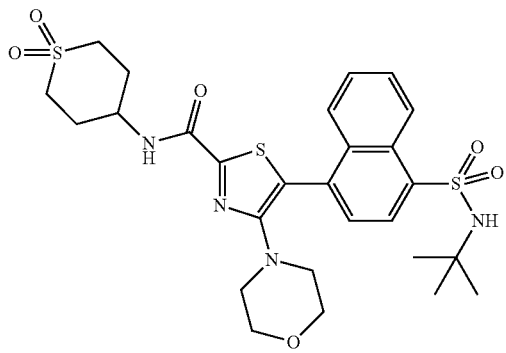 [SMILES: CC(C)(C)NS(=O)(=O)c1ccc(-c2sc(C(=O)NC3CCS(=O)(=O)CC3)nc2N2CCOCC2)c2ccccc12] |

Protein Expression and Purification

Protein expression and purification was done as described in WO2010/049144.

TR-FRET Activity Assay

This method measures the ability of putative ligands to modulate the interaction between the purified bacterial expressed RORγ ligand binding domain (LBD) and synthetic N-terminally biotinylated peptides which are derived from nuclear receptor coactivator proteins such as but not limited to SRC1 (NcoA1), SRC2 (NcoA2,TIF2), SRC3 (NcoA3), PGC1α, PGC1β, CBP, GRIP1, TRAP220, RIP140. The peptides used are listed in Table 1 below:

TABLE 1

| Peptide Name (aa range) | DB entry Protein | DB entry DNA | Sequence |
|---|---|---|---|
| SRC1(676-700) | NP_003734 | NM_003743.4 | $NH_2$-CPSSHSSLTERHKILHRLLQEGSPS-COOH |
| TRAP220(631-655) | NP_004765 | NM_004774.3 | $NH_2$-PVSSMAGNTKNHPMLMNLLKDNPAQ-COOH |
| TIF2(628-651) | NP_006531 | NM_006540.2 | $NH_2$-GQSRLHDSKGQTKLLQLLTTKSDQ-COOH |

The ligand-binding domain (LBD) of RORγ was expressed as fusion protein with GST in BL-21 (BL3) cells using the vector pDEST15. Cells were lysed by lysozyme-treatment and sonication, and the fusion proteins purified over glutathione sepharose (Pharmacia) according to the manufacturers instructions. For screening of compounds for their influence on the RORγ-peptide interaction, the LANCE technology (Perkin Elmer) was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection assays were done in a final volume of 25 μL in a 384 well plate, in a Tris-based buffer system (20 mM Tris-HCl pH 6.8; 60 mM KCl, 1 mM DTT; 5 mM $MgCl_2$; 35 ng/μL BSA), containing 20-60 ng/well recombinantly expressed RORγ-LBD fused to GST, 200-600 nM N-terminally biotinylated peptide, 200 ng/well Streptavidin-xlAPC conjugate (Prozyme) and 6-10 ng/well Eu W1024-antiGST (Perkin Elmer). DMSO content of the samples was kept at 1%.

After generation of the Tris-based buffer system, the potentially RORγ modulating ligands were diluted. After his step, protein, peptide and fluorescent acceptor and donor solutions were mixed in the Tris-based buffer system and have been added to the compound dilutions, after this addition of 'detection mix', the assay was equilibrated for one hour in the dark at rt in FIA-plates black 384 well (Corning). The LANCE signal was detected by a Perkin Elmer EnVision™ Multilabel Counter. The results were visualized by plotting the ratio between the emitted light at 665 nm and 615 nm. A basal level of RORγ-peptide formation is observed in the absence of added ligand. Ligands that promote the complex formation induce a concentration-dependent increase in time-resolved fluorescent signal. Compounds which bind equally well to both monomeric RORγ and to the RORγ-peptide complex would be expected to give no change in signal, whereas ligands, which bind preferentially to the monomeric receptor would be expected to induce a concentration-dependent decrease in the observed signal.

To assess the antagonistic potential of the compounds, $IC_{50}$ values were determined using a Ligand Sensing Assay based on Time-resolved Fluorescence Energy Transfer (TR-FRET) as described above. The normalised TR-FRET assay values, using the following equation: 1000*665 nm measurement value/615 nm measurement value, were transferred to the program GraphPad Prism to generate graphs and dose response curves using the following equation:

Equation: Sigmoidal dose-response (variable slope)

$$Y = \text{Bottom} + (\text{Top} - \text{Bottom})/(1 + 10\hat{\,}((\text{Log } EC50 - X) * \text{HillSlope}))$$

X is the logarithm of the concentration. Y is the response. Y starts at Bottom and goes to Top with a sigmoidal shape.

This is identical to the "four parameter logistic equation". The $IC_{50}$ values are calculated using this equation. Examples listed below do reduce the signal in the TR-FRET assay in a dose dependent manner. The Examples of the present invention usually have an inhibition activity ($IC_{50}$ FRET) ranging from below 100 nM to about 20 μM. The RORγ modulating compounds of the invention desirably have an inhibition in the TR-FRET Activity Assay ranging from below 100 nM to about 1 μM. Table 3 lists the $pIC_{50}$-value of compounds of the invention. Is is understood that the data illustrated below may have reasonable variation depending on the specific conditions and procedures used by the person conducting the test.

RORγ Gal4 Reporter Gene Assay

Determination of a ligand mediated Gal4 promoter driven transactivation to quantify ligand binding to RORγ was performed as follows: DNA encoding three different RORγ protein fragments was cloned into vector pCMV-BD (Stratagene). Expression was under control of a CMV promoter and as fusion to the DNA-binding domain of the yeast protein GAL4. The amino acid boundaries of the three proteins and the respective database entries are listed in Table 2. Other vectors used were pFR-Luc (Stratagene) as regulated reporter plasmid. pFR-Luc contains a synthetic promoter with five tandem repeats of the yeast GAL4 binding sites that control expression of the Photinus pyralis (American firefly) luciferase gene. In order to improve experimental accuracy the plasmid pRL-CMV was cotransfected. pRL-CMV contains the constitutive CMV promoter, controlling the expression of the *Renilla reniformis* luciferase.

TABLE 2

| construct name | aa borders (RefSeq) | Ref sequence ID |
|---|---|---|
| hRORg-LBD | aa259-518 | NP_005051.2 |
| hRORgt | aa1-497 | NP_001001523 (RORg, t isoform, 497aa) |
| mRORg-LBD | aa264-516 | NP_035411 |

All Gal4 reporter gene assays were done in 293T cells (DSMZ (German Collection of Microorganisms and Cell Cultures), Braunschweig, Germany, ACC635) grown in Minimum Essential Medium (MEM) with Phenol Red. The medium is supplemented with 10% fetal bovine serum, 0.1 mM nonessential amino acids, 1 mM sodium pyruvate, 1% Glutamax and 100 units Penicilin/Streptavidin per mL at 37° C. in 5% $CO_2$.

For the assay, $5\times10^5$ cells were plated per well in 96 well plates in 100 µL per well, incubated over night at 37° C. in 5% $CO_2$. The following day, medium was discarded and the cells were transiently transfected using 20 µL per well of a OptiMEM—PEI-based transfection-reagent (Sigma-Aldrich, 408727) including the three plasmids described above. About 4 h after addition of the transfection solution, fresh Minimal Essential Medium (MEM, same composition as used for plating cells, but without serum) was added. Then compound stocks, prediluted in MEM (same composition as used for plating cells) were added (final vehicle concentration not exceeding 0.1%).

Cells were incubated for additional 16 h before firefly (FF) and renilla (REN) luciferase activities were measured sequentially in the same cell extract using a Dual-Light-Luciferase-Assay system (Dyer et al., Anal. Biochem. 2000, 282:158). All experiments were done at least in triplicates.

Applying the Gal4 reporter gene assay as described above, the Examples of the present invention usually have an inhibition activity ($IC_{50}$ FF resp. $IC_{50}$ RENnorm) ranging from below 10 nM to about 20 µM, and typically, from about 10 nM to about 1 µM. The RORγ modulating compounds of the invention desirably have an inhibition in the Gal4 reporter gene assay ranging from below 10 nM to about 1 µM. Table 3 list the $pIC_{50}$-value of typical examples of compounds of the invention that have an RORγ activity in the Gal4 reporter gene assay for firefly (FF) and renilla normalised (RENnorm) luciferase measurements (nt=not tested). It is understood that the data illustrated below may have reasonable variation depending on the specific conditions and procedures used by the person conducting the test. The efficacy was determined in comparison to the RORγt inhibitor T0901317 (equals 100%) and the $pIC_{50}$-value is underlined, when the efficacy of the compound is below 50% of the reference.

TABLE 3

Table 3

| Ex. # | $pIC_{50}$ (FRET/FF/REN) | Ex. # | $pIC_{50}$ (FRET/FF/REN) | Ex. # | $pIC_{50}$ (FRET/FF/REN) |
|---|---|---|---|---|---|
| 1 | 6.5/5.8/5.8 | 2 | 5.9/<u>6.1</u>/<u>6.0</u> | 3 | 5.1/<4.7/<4.7 |
| 4 | 6.8/6.4/6.4 | 5 | 6.7/6.3/6.1 | 6 | 6.7/6.2/6.3 |
| 6/1 | 6.5/7.5/7.7 | 6/2 | 7.0/7.5/7.7 | 6/3 | 6.5/8.5/8.7 |
| 6/4 | 6.7/8.7/8.7 | 6/5 | 6.6/8.5/8.7 | 6/6 | 6.7/9.0/9.0 |
| 6/7 | 6.7/7.9/8.0 | 6/8 | 6.3/8.2/8.2 | 6/9 | 6.4/6.7/6.4 |
| 6/10 | 7.0/8.7/8.7 | 6/11 | 7.2/9.0/9.0 | 6/12 | 6.9/8.7/8.7 |
| 6/13 | 6.5/8.0/8.0 | 6/14 | 6.8/8.7/8.7 | 6/15 | 5.9/7.5/7.6 |
| 6/16 | 5.9/7.2/<u>7.6</u> | 6/17 | 6.2/8.0/8.0 | 6/18 | 7.0/8.5/8.7 |
| 6/19 | 6.8/8.5/8.5 | 6/20 | 6.9/8.7/8.7 | 6/21 | 6.8/8.7/8.7 |
| 6/22 | 6.8/7.7/7.7 | 6/23 | 6.6/7.5/7.6 | 6/24 | 7.3/7.9/8.0 |
| 6/25 | 5.8/6.7/6.7 | 6/26 | 6.6/7.7/7.8 | 6/27 | 6.7/7.7/7.7 |
| 6/28 | 6.1/7.7/7.7 | 6/29 | 7.2/9.0/9.0 | 6/30 | 7.2/8.7/8.7 |
| 6/31 | 7.3/8.0/8.0 | 6/32 | 6.9/8.0/8.2 | 6/33 | 6.6/7.9/8.0 |
| 6/34 | 7.2/8.5/8.5 | 6/35 | 7.0/7.5/7.5 | 6/36 | 6.3/7.4/7.4 |
| 6/37 | 6.1/6.9/6.9 | 6/38 | 6.8/7.8/7.9 | 6/39 | 6.4/8.2/8.2 |
| 6/40 | 7.0/8.2/8.3 | 6/41 | 7.3/8.0/8.2 | 6/42 | 7.2/8.2/8.4 |
| 6/43 | 7.0/8.7/8.7 | 6/44 | 7.4/7.8/8.0 | 6/45 | 7.1/7.9/8.0 |
| 6/46 | nt/8.1/8.1 | 6/47 | nt/8.2/8.2 | 6/48 | nt/8.1/8.1 |
| 6/49 | 5.7/7.3/7.4 | 6/50 | nt/7.6/7.7 | 6/51 | 6.3/8.4/8.4 |
| 6/52 | nt/6.9/6.9 | 6/53 | 6.6/7.1/7.4 | 6/54 | 6.3/6.8/6.9 |
| 6/55 | nt/8.0/8.2 | 6/56 | nt/8.1/8.2 | 6/57 | nt/7.9/8.2 |
| 6/58 | nt/8.7/8.7 | 6/59 | nt/7.6/7.8 | 6/60 | nt/8.5/8.7 |
| 6/61 | nt/8.3/8.3 | 6/62 | nt/7.5/7.5 | 6/63 | nt/9.2/8.9 |
| 6/64 | nt/8.9/9.0 | | | 7 | 6.3/7.0/7.0 |
| 7/1 | 6.1/6.8/6.9 | 7/2 | 6.2/7.5/7.6 | 7/3 | 6.4/7.2/7.3 |
| 7/4 | 6.6/9.0/9.0 | 7/5 | 6.3/7.0/7.1 | 7/6 | 6.2/7.1/7.2 |
| 7/7 | 6.9/8.7/8.7 | 7/8 | 6.6/9.0/9.0 | 7/9 | 6.3/8.7/9.0 |
| 7/10 | 6.3/8.5/8.7 | 7/11 | 5.9/7.4/7.4 | 7/12 | 6.2/8.0/8.2 |
| 7/13 | 6.5/8.4/8.4 | 7/14 | 5.8/8.5/8.7 | 7/15 | 6.7/8.7/8.5 |
| 7/16 | 6.5/8.5/8.5 | 7/17 | 6.5/8.0/8.0 | 7/18 | 6.4/7.4/7.4 |
| 7/19 | nt/7.7/7.9 | 7/20 | <4.7/6.6/6.6 | 7/21 | 5.7/6.9/6.9 |
| 7/22 | <4.7/6.5/6.2 | 7/23 | <4.7/6.8/6.7 | 7/24 | 5.7/6.3/6.2 |
| 7/25 | <u>6.2</u>/6.6/6.5 | 7/26 | 6.8/7.7/7.9 | 7/27 | 6.5/6.9/6.9 |
| 8 | 7.0/7.3/7.5 | 8/1 | 7.0/7.8/7.9 | 8/2 | 6.7/7.4/7.7 |
| 8/3 | 6.4/7.5/7.6 | 8/4 | 6.5/8.2/8.4 | 8/5 | 6.4/8.5/8.7 |
| 8/6 | 7.0/8.2/8.3 | 8/7 | 6.3/8.7/9.0 | 8/8 | 6.3/7.2/7.1 |
| 8/9 | 6.1/6.9/6.9 | 8/10 | 6.2/6.8/6.8 | 8/11 | nt/9.0/9.0 |
| 8/12 | nt/8.9/8.9 | | | 9 | 7.2/8.0/8.3 |

TABLE 3-continued

Table 3

| Ex. # | pIC$_{50}$ (FRET/FF/REN) | Ex. # | pIC$_{50}$ (FRET/FF/REN) | Ex. # | pIC$_{50}$ (FRET/FF/REN) |
|---|---|---|---|---|---|
| 9/1 | 6.5/7.4/7.4 | 9/2 | 6.9/8.0/8.0 | 9/3 | 6.4/7.2/7.4 |
| 9/4 | 6.5/7.1/7.1 | 9/5 | 6.7/7.8/7.9 | 9/6 | 6.1/7.5/7.5 |
| 9/7 | 6.2/7.4/7.5 | 9/8 | 6.5/7.1/7.1 | 9/9 | 5.4/6.9/7.0 |
| 9/10 | 6.3/7.2/7.2 | 9/11 | 6.6/8.5/8.5 | | |
| | | 10 | 5.9/6.9/7.0 | 10/1 | 6.2/7.0/7.1 |
| 10/2 | 6.6/7.3/7.4 | 10/3 | nt/7.9/8.0 | 10/4 | nt/7.9/7.9 |
| 12 | 5.5/<4.7/<4.7 | 13 | 7.0/6.5/6.7 | 13/1 | 6.3/6.6/6.6 |
| 13/2 | 6.5/6.7/6.8 | 13/3 | 6.6/7.5/7.7 | 14 | 6.7/7.6/7.7 |
| 14/1 | 6.2/7.1/7.1 | 14/2 | 6.5/7.4/7.4 | 14/3 | 6.6/6.4/6.4 |
| 14/4 | 6.2/6.4/6.3 | 14/5 | 6.3/6.6/6.6 | 14/6 | nt/9.0/9.0 |
| 14/7 | nt/7.6/7.7 | | | | |
| 15 | 6.6/8.3/8.4 | 15/1 | 6.7/8.0/8.0 | 15/2 | 6.6/7.3/7.3 |
| 15/3 | 6.9/7.9/7.9 | 15/4 | 7.3/8.7/9.0 | 15/5 | 6.9/8.5/8.4 |
| 15/6 | 7.3/8.1/8.2 | 15/7 | 7.2/8.3/8.4 | 15/8 | nt/8.3/8.4 |
| 15/9 | 6.4/7.8/7.9 | | | | |
| 16 | 7.2/8.5/8.5 | 17 | 5.0/<4.7/<4.7 | 17/1 | 5.6/6.1/6.5 |
| 17/2 | nt/5.7/5.9 | 18 | 6.9/8.1/8.0 | 19 | 5.4/6.4/6.6 |
| 19/1 | 6.1/6.7/6.7 | 19/2 | 6.1/7.0/7.0 | 19/3 | 6.8/7.1/7.1 |
| 19/4 | 6.0/7.3/7.2 | 19/5 | 6.4/7.8/8.0 | 19/6 | 6.4/7.7/7.7 |
| 19/7 | 5.8/6.8/6.8 | 19/8 | 7.0/7.7/7.8 | 19/9 | 6.3/7.0/7.1 |
| 19/10 | 6.7/8.4/8.5 | 19/11 | nt/7.6/7.7 | 19/12 | 6.1/6.8/6.7 |
| 19/13 | 6.5/6.9/6.9 | 19/14 | 6.4/6.8/6.9 | | |
| 20 | nt/8.7/8.9 | 21 | 7.0/8.1/8.2 | 21/1 | 6.6/7.5/7.4 |
| 21/2 | 6.8/8.4/8.5 | 21/3 | 6.4/8.0/8.3 | 21/4 | 6.9/8.2/8.4 |
| 21/5 | 6.0/7.8/7.8 | 21/6 | 6.3/7.6/7.8 | 21/7 | nt/8.0/8.2 |
| 21/8 | nt/7.7/7.8 | 21/9 | 6.2/7.3/7.4 | 21/10 | 5.9/6.7/6.7 |
| 21/11 | nt/8.0/8.2 | 21/12 | nt/8.0/8.2 | 21/13 | 6.3/7.9/7.9 |
| 21/14 | nt/8.3/8.4 | 21/15 | nt/7.7/7.7 | 21/16 | nt/8.4/8.4 |
| 21/17 | nt/8.1/8.2 | 21/18 | nt/8.0/8.1 | 21/19 | nt/7.9/7.9 |
| 21/20 | nt/7.7/7.7 | 21/21 | nt/7.7/7.8 | 21/22 | nt/7.5/7.6 |
| 21/23 | nt/8.7/8.6 | 21/24 | nt/7.5/7.6 | 21/25 | nt/7.7/7.8 |
| 22 | 6.4/7.1/7.1 | 22/1 | 6.4/7.5/7.5 | 22/2 | 6.4/7.5/7.6 |
| 23 | 6.2/8.2/8.2 | 24 | 6.5/7.5/7.5 | 25 | nt/6.1/6.1 |
| 25/1 | nt/8.9/8.8 | 25/2 | nt/9.0/9.0 | | |
| 100 | 6.6/5.8/5.8 | 100/1 | 5.9/6.3/6.3 | 100/2 | 5.5/6.4/6.3 |
| 100/3 | 6.7/7.8/7.9 | 100/4 | 6.6/7.1/7.3 | 100/5 | 6.3/8.1/8.2 |
| 100/6 | 6.4/8.5/8.4 | 100/7 | 6.6/7.7/7.9 | 100/8 | 6.5/8.0/8.2 |
| 100/9 | 6.3/8.5/8.5 | 100/10 | 6.4/7.2/7.4 | 100/11 | 6.8/7.1/7.3 |
| 100/12 | 4.8/5.9/6.1 | 100/13 | 6.1/7.0/7.1 | 100/14 | 5.8/7.9/7.9 |
| 100/15 | 6.4/7.4/7.5 | 100/16 | 6.6/8.4/8.2 | 100/17 | 6.1/7.1/7.0 |
| 100/18 | 6.9/6.9/6.9 | 100/19 | 5.9/6.6/6.6 | 100/20 | 6.0/6.8/7.0 |
| 100/21 | nt/7.2/7.1 | 100/22 | 5.9/6.8/7.0 | 100/23 | 6.1/8.3/8.4 |
| 100/24 | nt/7.5/7.7 | 100/25 | 6.6/8.4/8.2 | 100/26 | 6.4/7.4/7.5 |
| 100/27 | 6.1/7.1/7.0 | 100/28 | nt/7.1/7.2 | | |
| 101 | 6.0/<4.7/<4.7 | 102 | 6.0/7.3/7.4 | 102/1 | 6.1/6.7/6.7 |
| 103 | 6.3/7.2/7.3 | 103/1 | 6.2/7.4/7.4 | 103/2 | nt/6.4/6.6 |
| 103/3 | nt/6.6/6.6 | 104 | 6.6/7.5/7.9 | | |
| 200 | 6.6/7.5/7.8 | 200/1 | 7.1/7.4/7.8 | 201 | 6.0/6.5/6.6 |
| 202 | 7.2/7.9/8.0 | 203 | 6.1/<4.7/<4.7 | | |
| 205 | 7.0/8.7/8.7 | 206 | 5.9/6.3/6.2 | 207 | 5.4/6.4/6.5 |
| 207/1 | 6.0/6.2/6.1 | 208 | 6.5/6.3/6.3 | 209 | 6.4/6.2/6.2 |
| 211 | 5.8/6.3/6.4 | | | | |
| 300 | 7.1/8.2/8.4 | 300/1 | 7.2/7.8/7.9 | 300/2 | 6.9/8.2/8.2 |
| 300/3 | 6.2/6.7/6.9 | 300/4 | 5.9/6.8/6.9 | 300/5 | 7.0/7.4/7.5 |
| 300/6 | 6.7/6.9/6.8 | 300/7 | nt/7.7/7.9 | 300/8 | nt/7.1/7.2 |
| 300/9 | nt/7.9/7.9 | 300/10 | nt/7.2/7.3 | 300/11 | nt/8.0/8.2 |
| 300/12 | nt/6.1/6.2 | 300/13 | nt/6.4/6.6 | 300/14 | nt/8.2/8.2 |
| 300/15 | nt/7.3/7.4 | 300/16 | nt/6.0/6.1 | 300/17 | nt/8.0/8.0 |
| 300/18 | nt/7.5/7.6 | | | | |
| 301 | nt/7.8/7.9 | 301/1 | nt/8.5/8.5 | 301/2 | nt/7.7/7.8 |
| 302 | nt/7.3/7.5 | 303 | nt/7.7/7.7 | 304 | 6.0/7.1/7.2 |
| 304/1 | 5.8/6.6/6.9 | 304/2 | 5.9/7.6/7.5 | 304/3 | 5.9/7.6/7.5 |
| 304/4 | 5.8/7.4/7.3 | 304/5 | 5.9/7.4/7.3 | 304/6 | nt/6.6/6.8 |
| 304/7 | 6.1/7.3/7.3 | 304/8 | 6.0/6.9/6.9 | 304/9 | nt/7.3/7.4 |
| 304/10 | nt/7.5/7.5 | 304/11 | 5.9/7.2/7.3 | 304/12 | nt/7.7/7.7 |
| 304/13 | nt/7.6/7.7 | 304/14 | nt/7.5/7.6 | 304/15 | nt/7.6/7.7 |
| 304/16 | nt/6.6/6.6 | 304/17 | nt/7.2/7.2 | 304/18 | nt/7.5/7.7 |
| 304/19 | nt/7.4/7.5 | 304/20 | nt/7.4/7.7 | 304/21 | nt/7.4/7.4 |
| 304/22 | nt/5.8/5.8 | 304/23 | nt/7.5/7.7 | 304/24 | nt/6.6/6.7 |
| 304/25 | nt/8.0/7.6 | 304/26 | nt/8.0/7.9 | 304/27 | nt/7.6/7.5 |
| 305 | nt/6.6/7.2 | 304/1 | nt/6.5/6.6 | 306 | nt/5.6/5.6 |
| 307 | nt/8.2/8.3 | 307/1 | nt/8.4/8.5 | | |

The invention claimed is:
1. A compound represented by Formula (200) and Formula (200'):

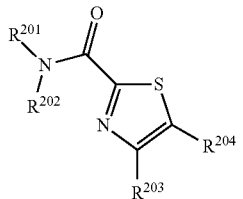
(200)

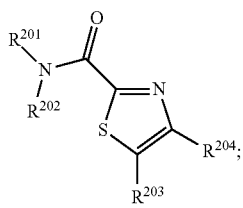
(200')

or an enantiomer, diastereomer, tautomer, N-oxide, solvate, formulation or pharmaceutically acceptable salt thereof,
wherein:
$R^{201}$ and $R^{202}$ are independently selected from H, $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl), $C_{1-10}$-alkylene-(6-membered heteroaryl), $SO_2$—$C_{1-10}$-alkyl, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, $OR^{211}$, O—$C_{2-6}$-alkylene-$OR^{211}$, $C_{1-6}$-alkyl, halo-$C_{1-6}$-alkyl, halogen, $CO_2R^{211}$, $CONR^{211}R^{212}$, $CONR^{211}SO_2R^{211}$, $COR^{211}$, $SO_xR^{211}$, $SO_3H$, $SO_2NR^{211}R^{212}$, $NR^{211}COR^{211}$, $NR^{211}SO_2R^{211}$, $NR^{211}$—CO—$NR^{211}R^{212}$, $NR^{211}$—$SO_2$—$NR^{211}R^{212}$, $C_{3-10}$-cycloalkyl, O—$C_{3-10}$-cycloalkyl, $C_{3-10}$-heterocycloalkyl, O—$C_{3-10}$-heterocycloalkyl and $NR^{211}R^{212}$;
or $R^{201}$ and $R^{202}$ when taken together with the nitrogen to which they are attached complete a 3- to 8-membered ring containing carbon atoms and optionally containing 1 or 2 heteroatoms selected from 0, S or N, wherein the ring is unsubstituted or substituted with 1 to 4 substitutents independently selected from the group consisting of halogen, oxo, CN, $OR^{211}$, $SO_xR^{211}$, $SO_3H$, $NR^{211}SO_2R^{211}$, $SO_2NR^{211}R^{212}$, $C_{0-6}$-alkylene-$CO_2R^{211}$, $CONR^{211}R^{212}$, $CONR^{211}SO_2R^{211}$, $COR^{211}$, $NR^{211}$—CO—$R^{211}$, $NR^{211}$—CO—$NR^{211}R^{212}$, $NR^{211}$—$SO_2$—$NR^{211}R^{212}$, $NR^{211}R^{212}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl,
wherein cycloalkyl and heterocycloalkyl are unsubstituted or substituted with 1 to 4 substitutents independently selected from the group consisting of halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;
$R^{203}$ is selected from $C_{1-10}$-alkyl, fluoro-$C_{1-10}$-alkyl, $C_{1-6}$-alkylene-$C_{3-10}$-cycloalkyl, $C_{1-6}$-alkylene-$C_{3-10}$-heterocycloalkyl, $C_{1-6}$-alkylene-(6- to 10-membered aryl), and $C_{1-6}$-alkylene-(5- to 10-membered heteroaryl),
wherein alkyl, alkylene, cycloalkyl, heterocycloalkyl, aryl and heteroaryl is unsubstituted or substituted with 1 to 6 substituents independently selected from the group consisting of oxo, halogen, CN, $C_{1-6}$-alkyl, halo-$C_{1-6}$-alkyl, $C_{3-6}$-cycloalkyl, $C_{3-6}$-heterocycloalkyl, $OR^{212}$, $CO_2R^{212}$, $CONR^{212}R^{212}$ and $COR^{212}$; and
wherein optionally one $CH_2$ unit in alkyl or alkylene can be replaced by O, $SO_x$, NH or N($C_{1-3}$-alkyl);
$R^{204}$ is

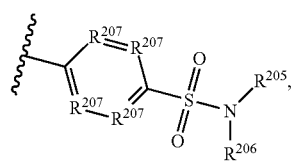

wherein:
$R^{205}$ and $R^{206}$ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cycloalkyl, heterocycloalkyl, aryl and heteroaryl are unsubstituted or substituted with 1 to 6 substituents independently selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl, $NR^{211}R^{212}$, $CO_2R^{212}$ and $CONR^{211}R^{212}$;
and optionally wherein $R^{205}$ and $R^{206}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, $C_{1-4}$-alkyl and halo-$C_{1-4}$-alkyl;
$R^{207}$ is independently selected from N and $CR^{208}$; or
two adjacent $R^{207}$ form a 5- or 6-membered unsaturated or partially saturated ring containing carbon atoms and optionally containing 1 or 2 heteroatoms selected from O, S or N, wherein the ring is unsubstituted or substituted with 1 to 4 substituents independently selected from the group consisting of halogen, OH, oxo, $C_{1-4}$-alkyl and fluoro-$C_{1-4}$-alkyl;
$R^{208}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl and $C_{3-10}$-cycloalkyl,
wherein alkylene is unsubstituted or substituted with 1 to 3 substituents selected from F and cycloalkyl is unsubstituted or substituted with 1 to 3 substituents independently selected from the group consisting of F, $C_{1-3}$-alkyl and fluoro-$C_{1-3}$-alkyl;
$R^{211}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl,
wherein alkyl, alkylene, cycloalkyl and heterocycloalkyl is unsubstituted or substituted with 1 to 6 substituents independently selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, $NH(C_{1-3}$-alkyl), $N(C_{1-3}$-alkyl)$_2$, $C_{3-6}$-heterocycloalkyl, $C_{3-6}$-cycloalkyl and $SO_2$—$C_{1-3}$-alkyl, wherein cycloalkyl and heterocycloalkyl is unsubstituted or substituted with 1 to 3 substituents independently selected from the group consisting of F, OH, oxo, $CH_3$ and $CF_3$;

$R^{212}$ is independently selected from H, $C_{1-6}$-alkyl, halo-$C_{1-6}$-alkyl and $C_{3-6}$-cycloalkyl; and x is independently selected from 0, 1 and 2.

2. The compound according to claim 1 wherein:

$R^{201}$ is selected from H, $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl), $C_{1-10}$-alkylene-(6-membered heteroaryl) and $SO_2$—$C_{1-10}$-alkyl, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, $OR^{211}$, O—$C_{2-6}$-alkylene-$OR^{211}$, $C_{1-6}$-alkyl, halo-$C_{1-6}$-alkyl, halogen, $CO_2R^{211}$, $CONR^{211}R^{212}$, $CONR^{211}SO_2R^{211}$, $COR^{211}$, $SO_xR^{211}$, $SO_3H$, $SO_2NR^{211}R^{212}$, $NR^{211}COR^{211}$, $NR^{211}SO_2R^{211}$, $NR^{211}$—CO—$NR^{211}R^{212}$, $NR^{211}$—$SO_2$—$NR^{211}R^{212}$, $C_{3-10}$-cycloalkyl, O—$C_{3-10}$-cycloalkyl, $C_{3-10}$-heterocycloalkyl, O—$C_{3-10}$-heterocycloalkyl and $NR^{211}R^{212}$;

$R^{202}$ is selected from H, $C_{1-6}$-alkyl, halo-$C_{1-6}$-alkyl and hydroxy-$C_{1-6}$-alkyl;

or $R^{201}$ and $R^{202}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of halogen, oxo, CN, $OR^{211}$, $SO_xR^{211}$, $SO_3H$, $NR^{211}SO_2R^{211}$, $SO_2NR^{211}R^{212}$, $C_{0-6}$-alkylene-$CO_2R^{211}$, $CONR^{211}R^{212}$, $CONR^{211}SO_2R^{211}$, $COR^{211}$, $NR^{211}$—CO—$R^{211}$, $NR^{211}$—CO—$NR^{211}R^{212}$, $NR^{211}$—$SO_2$—$NR^{211}R^{212}$, $NR^{211}R^{212}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substitutents independently selected from the group consisting of halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo.

3. The compound according to claim 1 wherein $NR^{201}R^{202}$ is selected from:

NHMe, NHEt, NH$^i$Pr, NH$^t$Bu, NHCH$_2$CONH$_2$, NHCH$_2$CONMe$_2$, NHCH$_2$CH$_2$OH, NHCH$_2$CH$_2$OMe, NHCH$_2$CH$_2$SO$_2$Me, NHCH$_2$CH$_2$SO$_2$NH$_2$, NH(CH$_2$)$_3$OH, NH(CH$_2$)$_3$OMe, NH(CH$_2$)$_4$OH, NH(CH$_2$)$_4$OMe, NH(CH$_2$)$_5$OH, NH(CH$_2$)$_2$CO$_2$H, NH(CH$_2$)$_3$CO$_2$H, NH(CH$_2$)$_4$CO$_2$H, NH(CH$_2$)$_5$CO$_2$H, NHCH$_2$CH(CF$_3$)OH, NHCH$_2$C(Me)(CF$_3$)OH, NHCH$_2$CMe$_2$OH, NHCH$_2$CH$_2$CMe$_2$OH, NHCH$_2$CMe$_2$NHCH$_2$CF$_3$, NHCH(Me)CMe$_2$OH, NHCH$_2$CMe$_2$OMe, NHCH$_2$CMe$_2$CO$_2$H, NHCH$_2$CMe$_2$CONHMe, NHCH$_2$CMe$_2$CONMe$_2$, NHCH$_2$CMe$_2$NHSO$_2$Me, NH(CH$_2$)$_3$SOMe, NH(CH$_2$)$_5$SO$_2$Me, NH(CH$_2$)$_5$SO$_2$NH$_2$, NH(CH$_2$)$_3$NHSO$_2$Me, NH(CH$_2$)$_2$O(CH$_2$)$_2$OH, NHCH$_2$CHMeOH, NH(CH$_2$)$_5$SOMe, NH(CH$_2$)$_3$SO$_2$Me, NHC(CH$_2$OH)$_3$, NHCH$_2$CH(OH)CH$_2$OH, N(CH$_2$CH$_2$OH)$_2$,

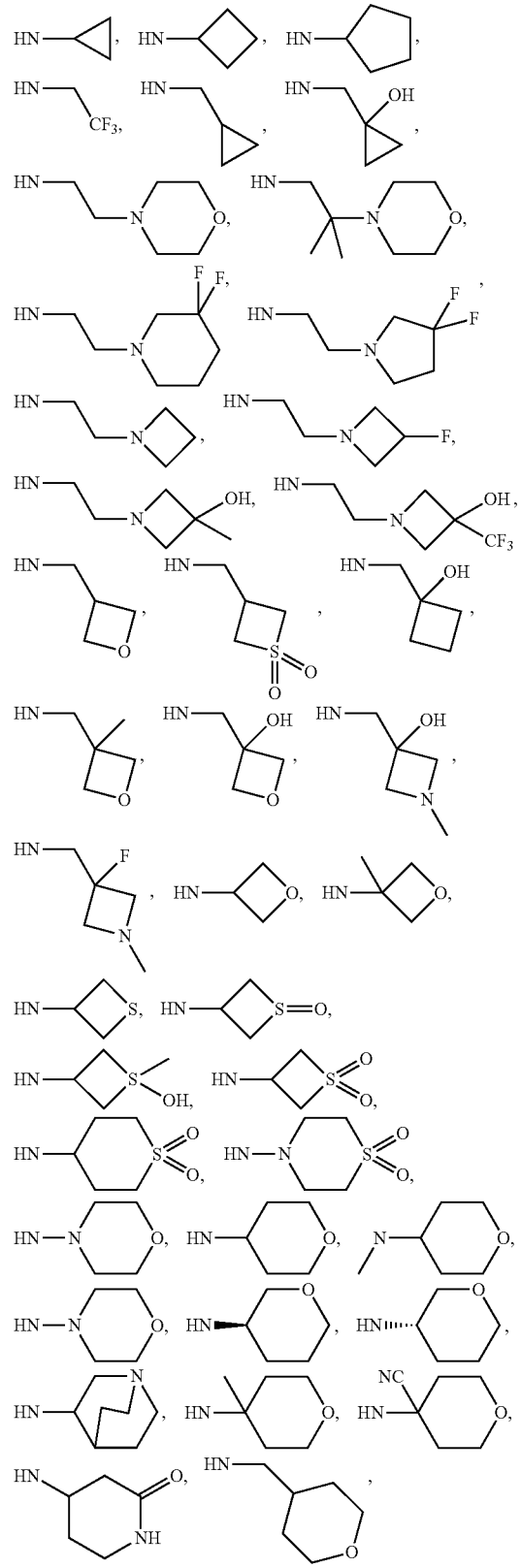

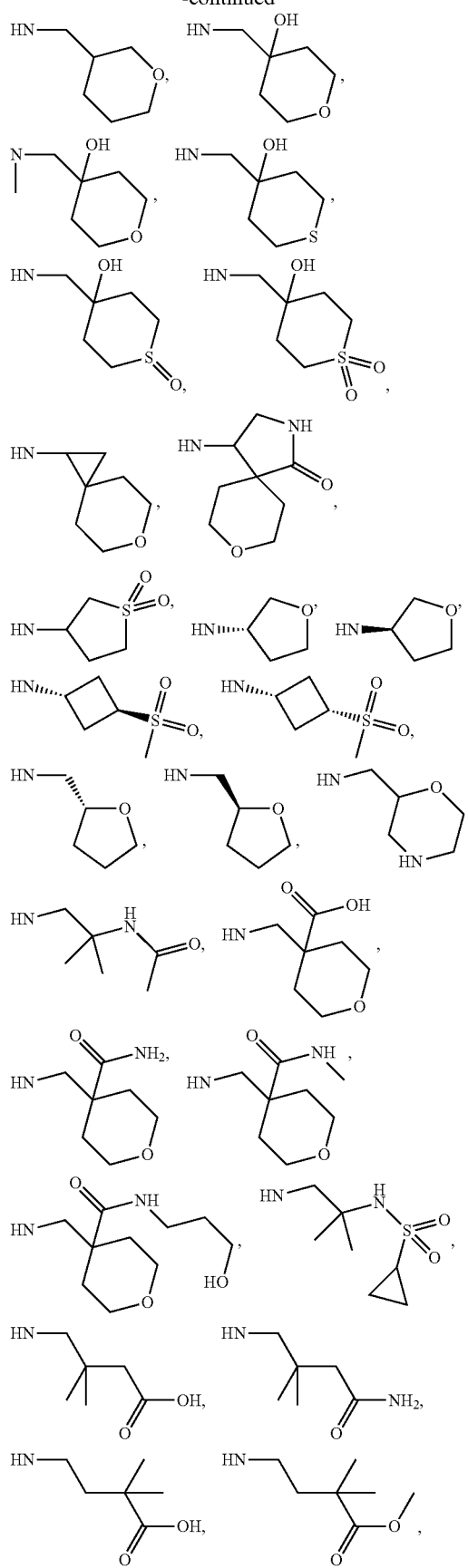
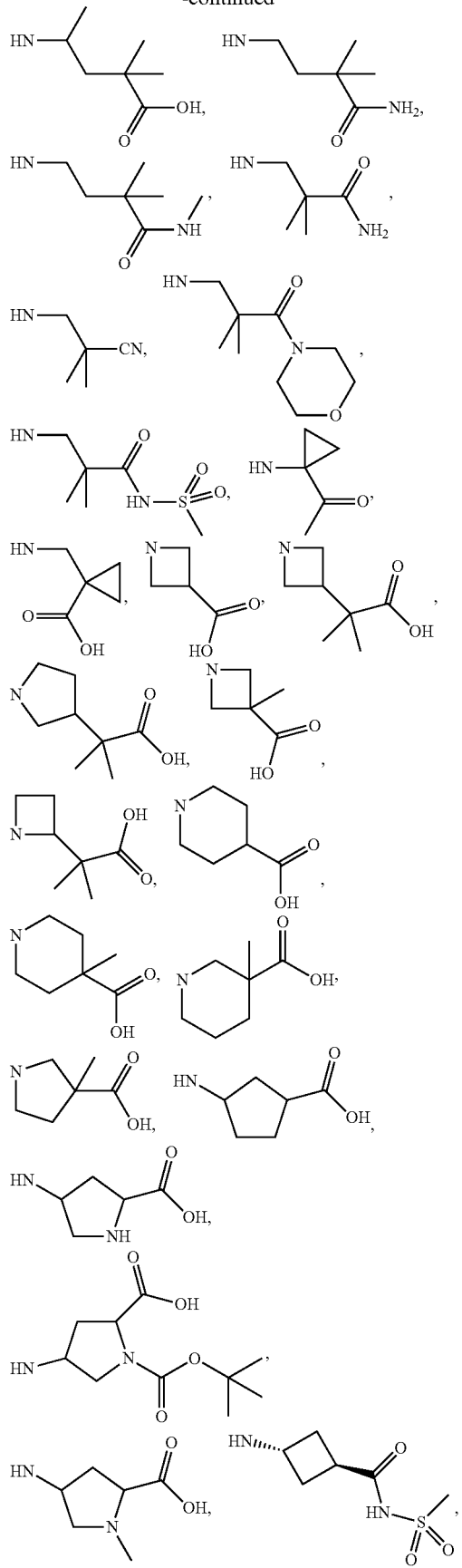

465
-continued
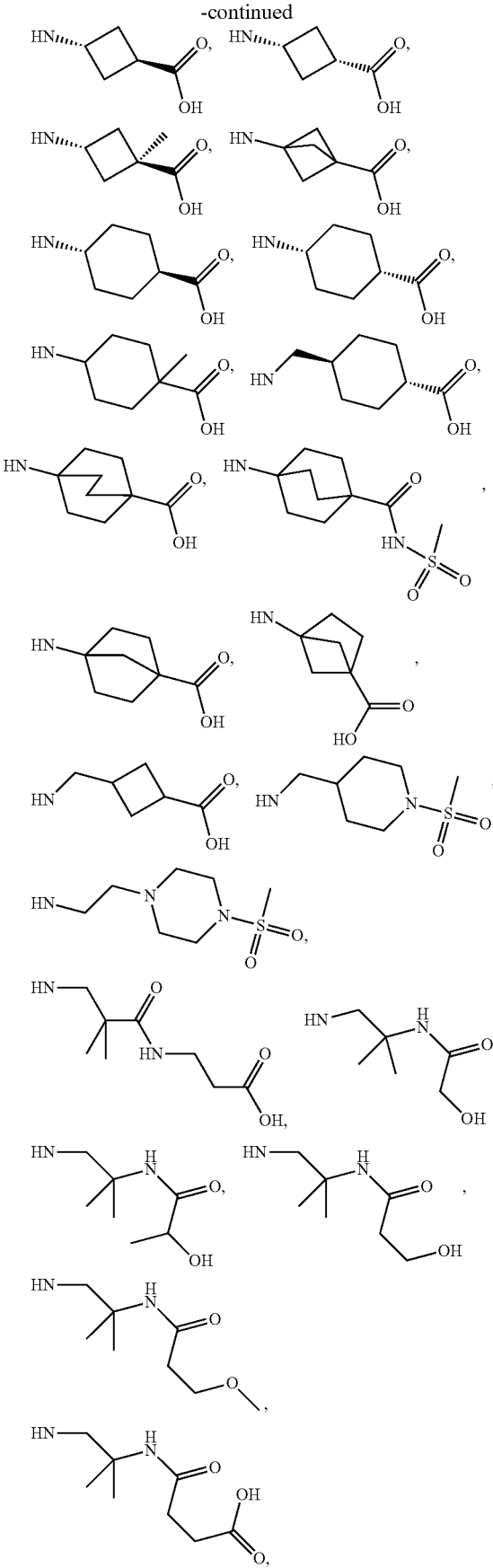
466
-continued
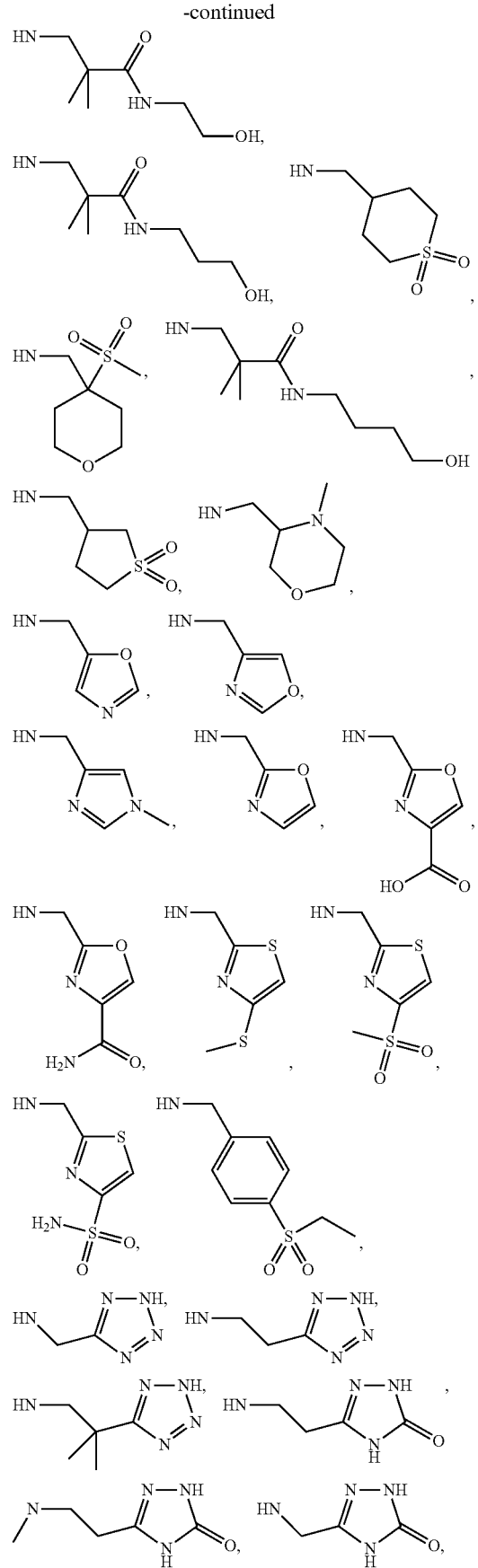

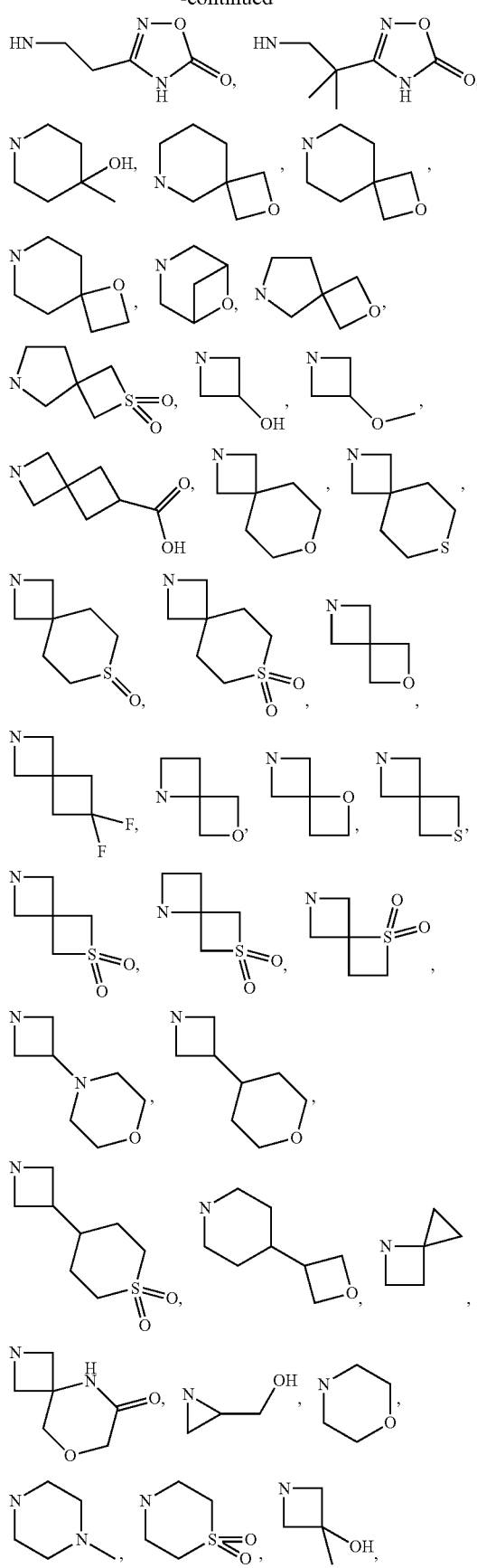
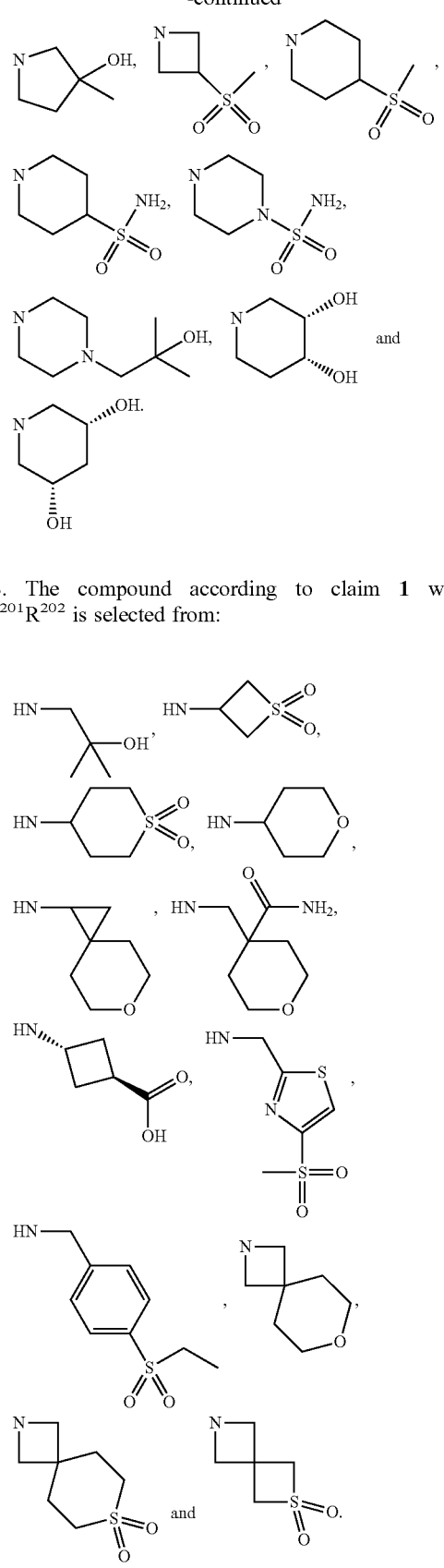
4. The compound according to claim 1 wherein $NR^{201}R^{202}$ is selected from:

5. The compound according to claim 1 wherein $R^{204}$ is selected from:

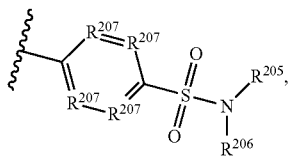

wherein all $R^{207}$ are $CR^{208}$ or one $R^{207}$ is N and the three other $R^{207}$ are $CR^{208}$; or wherein

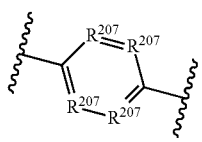

is selected from:

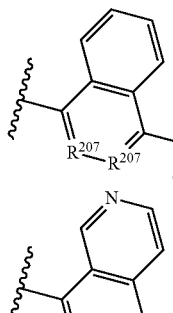 , 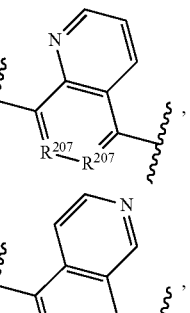 ,

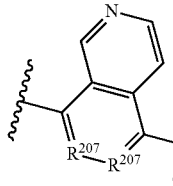 , 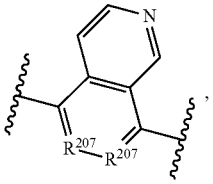 ,

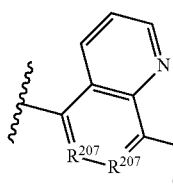 , 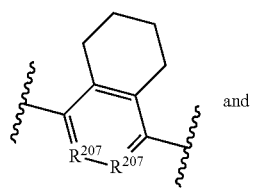 and

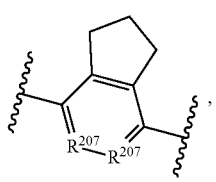 , wherein the additional ring is unsubstituted or substituted with 1 to 4 substitutents independently selected from the group consisting of halogen, OH, oxo, $C_{1-4}$-alkyl and fluoro-$C_{1-4}$-alkyl.

6. The compound according to claim 1 wherein $R^{204}$ is selected from:

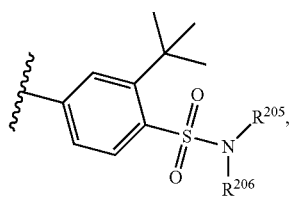

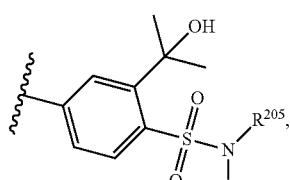

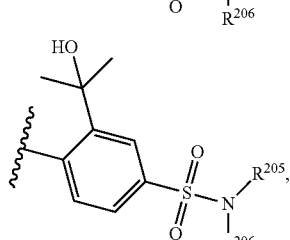

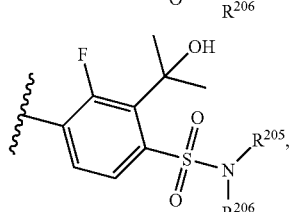

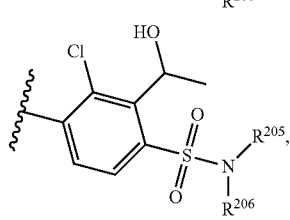

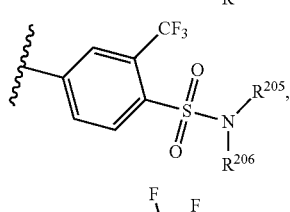

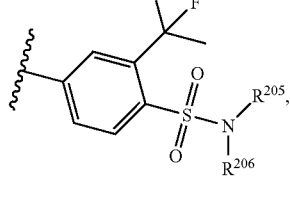

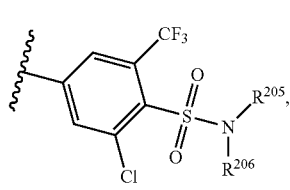

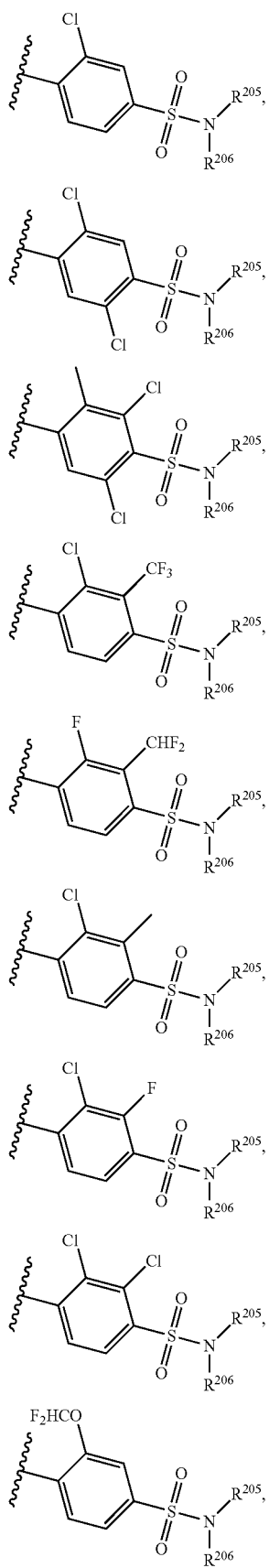
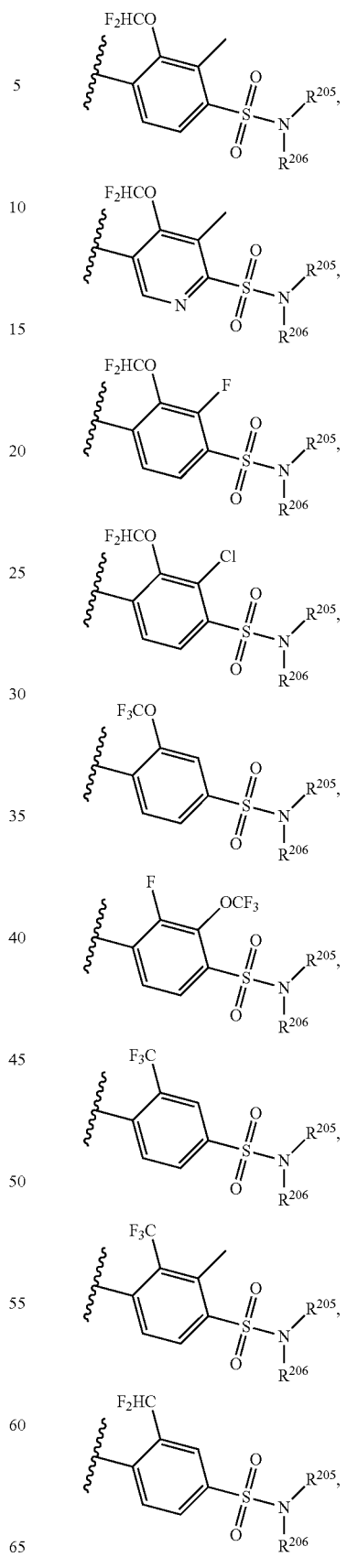

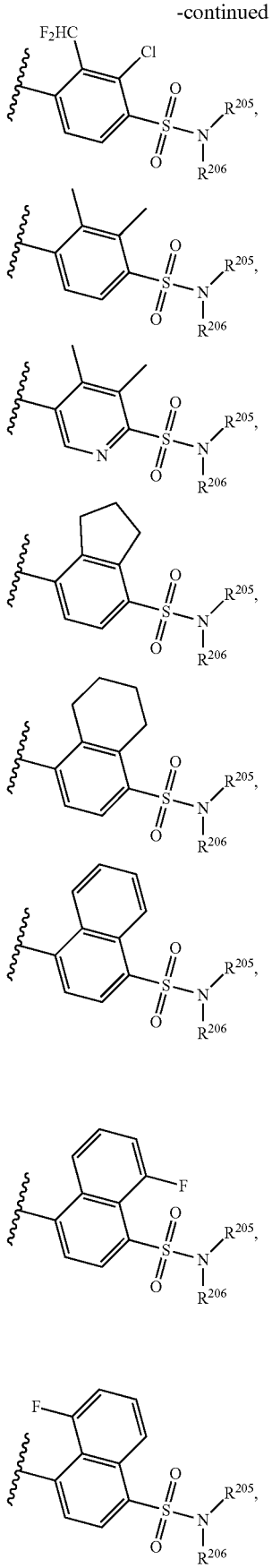

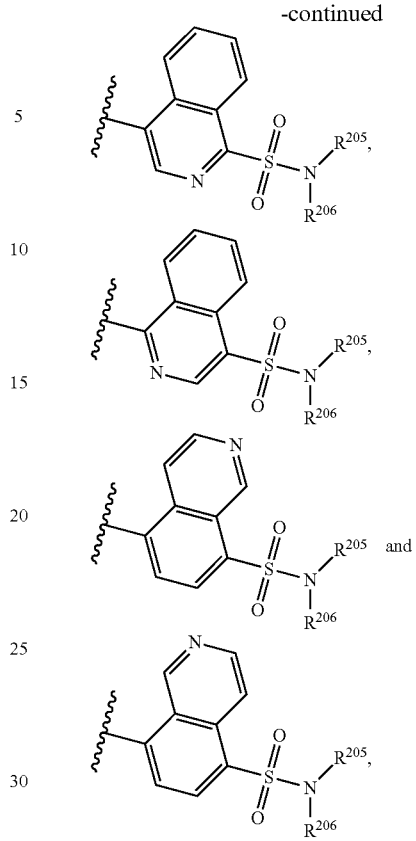

wherein:
R²⁰⁵ and R²⁰⁶ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cycloalkyl, heterocycloalkyl, aryl and heteroaryl are unsubstituted or substituted with 1 to 6 substituents independently selected from the group consisting of halogen, CN, OH, oxo, $C_{1-3}$-alkyl, halo-$C_{1-3}$-alkyl, O—$C_{1-3}$-alkyl, C-halo-$C_{1-3}$-alkyl, $SO_2$—$C_{1-3}$-alkyl, $NR^{211}R^{212}$, $CO_2R^{212}$ and $CONR^{211}R^{212}$;
and optionally wherein R²⁰⁵ and R²⁰⁶ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, $C_{1-4}$-alkyl and halo-$C_{1-4}$-alkyl.

7. The compound according to claim 1 wherein $NR^{205}R^{206}$ is selected from:

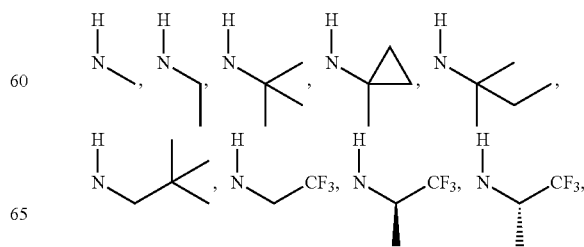

-continued

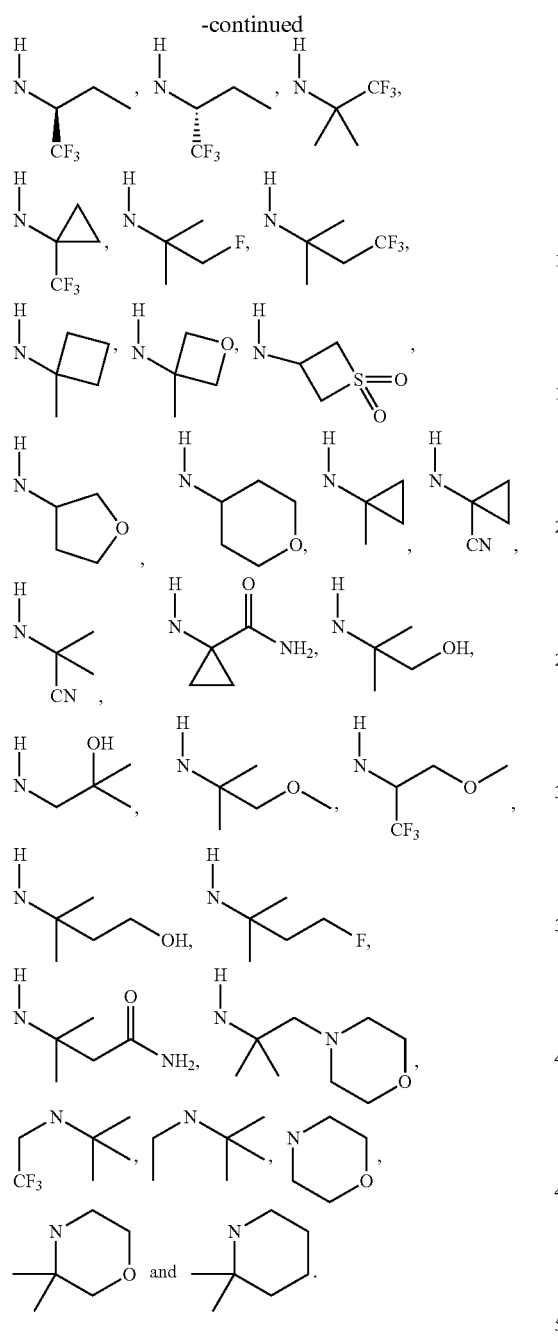

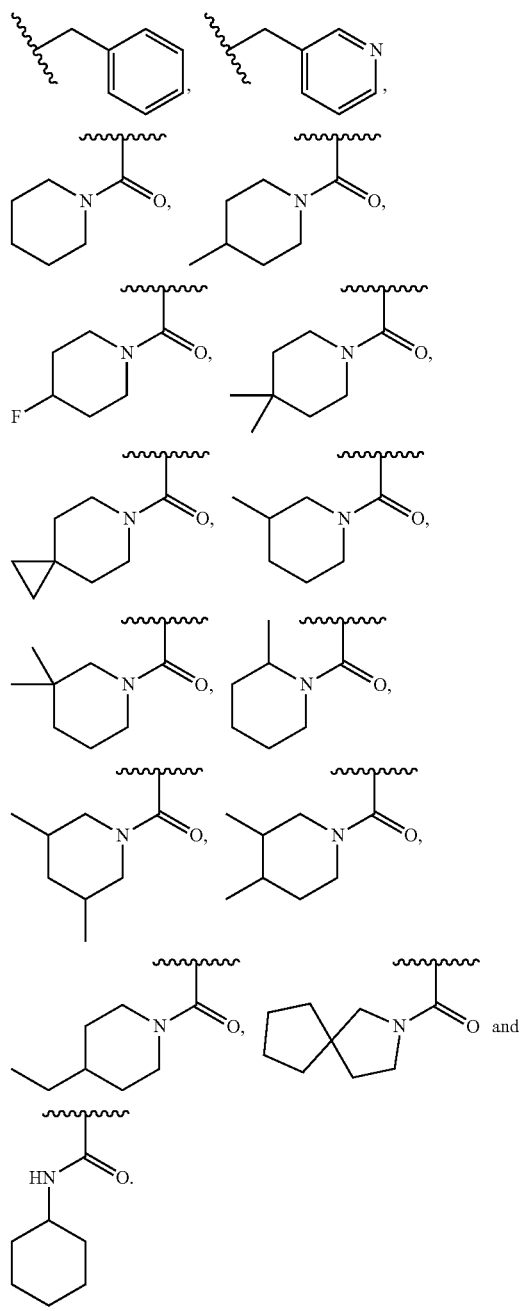

8. The compound according to claim 1 wherein:

R$^{203}$ is selected from C$_{1-8}$-alkyl, fluoro-C$_{1-8}$-alkyl, C$_{1-2}$-alkylene-C$_{3-8}$-cycloalkyl, C$_{1-2}$-alkylene-C$_{3-8}$-heterocycloalkyl, C$_{1-2}$-alkylene-(6- to 10-membered aryl) and C$_{1-2}$-alkylene-(5- to 10-membered heteroaryl), wherein alkyl, alkylene, cycloalkyl, heterocycloalkyl, aryl and heteroaryl is unsubstituted or substituted with 1 to 6 substituents independently selected from the group consisting of oxo, fluoro, chloro, CN, CONH$_2$, C$_{1-3}$-alkyl, fluoro-C$_{1-3}$-alkyl, C$_{3-8}$-cycloalkyl, C$_{3-8}$-heterocycloalkyl and OC$_{1-4}$-alkyl.

9. The compound according to claim 1 wherein:

R$^{203}$ is selected from CHF$_2$, CH$_2$CH$_3$, CH$_2$CH$_2$CH$_3$, C(CH$_3$)$_3$, CH$_2$OC(CH$_3$)$_3$,

10. A compound represented by Formula (100) and Formula (100')

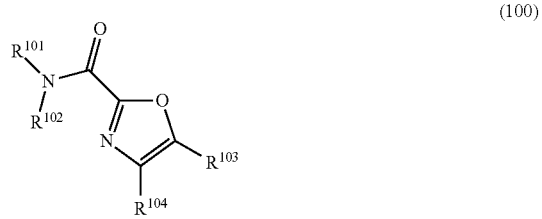

(100)

-continued

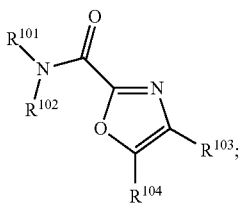

(100')

or an enantiomer, diastereomer, tautomer, N-oxide, solvate, formulation or pharmaceutically acceptable salt thereof,
wherein:
$R^{101}$ and $R^{102}$ are independently selected from H, $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl), $C_{1-10}$-alkylene-(6-membered heteroaryl), and $SO_2$—$C_{1-10}$-alkyl, wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, $OR^{111}$, O—$C_{2-6}$-alkylene-$OR^{111}$, $C_{1-6}$-alkyl, halo-$C_{1-6}$-alkyl, halogen, $CO_2R^{111}$ $CONR^{111}R^{112}$, $CONR^{111}SO_2R^{111}$, $COR^{111}$, $SO_xR^{111}$, $SO_3H$, $SO_2NR^{111}R^{112}$, $NR^{111}COR^{111}$, $NR^{111}SO_2R^{111}$, $NR^{111}$—CO—$NR^{111}R^{112}$, $NR^{111}$—$SO_2$—$NR^{111}R^{112}$, $C_{3-10}$-cycloalkyl, O—$C_{3-10}$-cycloalkyl, $C_{3-10}$-heterocycloalkyl, O—$C_{3-10}$-heterocycloalkyl and $NR^{111}R^{112}$;
or $R^{101}$ and $R^{102}$ when taken together with the nitrogen to which they are attached complete a 3- to 8-membered ring containing carbon atoms and optionally containing 1 or 2 heteroatoms selected from 0, S or N, wherein the ring is unsubstituted or substituted with 1 to 4 substitutents independently selected from the group consisting of halogen, oxo, CN, $OR^{111}$, $SO_xR^{111}$, $SO_3H$, $NR^{111}SO_2R^{111}$, $SO_2NR^{111}R^{112}$, $C_{0-6}$-alkylene-$CO_2R^{111}$, $CONR^{111}R^{112}$, $CONR^{111}SO_2R^{111}$, $COR^{111}$, $NR^{111}$—CO—$R^{111}$, $NR^{111}$—CO—$NR^{111}R^{112}$, $NR^{112}$—$SO_2$—$NR^{111}R^{112}$, $NR^{111}R^{112}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl,
wherein cycloalkyl and heterocycloalkyl are unsubstituted or substituted with 1 to 4 substitutents independently selected from the group consisting of halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;
$R^{103}$ is a 6-10 membered mono- or bicyclic aryl or a 5-14 membered mono-, bi- or tricyclic heteroaryl containing 1 to 5 heteroatoms independently selected from the group consisting of N, O and S,
wherein aryl and heteroaryl is optionally substituted with 1 to 5 substituents independently selected from the group consisting of halogen, $C_{1-6}$-alkyl, $C_{1-6}$-alkenyl, $C_{1-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered heteroaryl), $C_{1-6}$-alkylene-O—$R^{131}$, $C_{0-6}$-alkylene-CN, $C_{0-6}$-alkylene-N($R^{131}$)$_2$, O—$C_{3-10}$-cycloalkyl, O—$C_{1-6}$-alkylene-O—$R^{131}$, O—$C_{3-10}$-heterocycloalkyl, $C_{0-6}$-alkylene-$COOR^{131}$, $C_{0-6}$-alkylene-C(O)$R^{131}$, $C_{0-6}$-alkylene-C(O)N($R^{131}$)$_2$, $C_{0-6}$-alkylene-N($R^{131}$)C(O)$R^{131}$, $C_{0-6}$-alkylene-SO—$R^{131}$, $C_{0-6}$-alkylene-$SO_2$—$R^{131}$, $C_{0-6}$-alkylene-$SO_2$—N($R^{131}$)$_2$, $C_{0-6}$-alkylene-N($R^{131}$)$SO_2$—$R^{131}$, $C_{0-6}$-alkylene-$SO_2$—$C_{3-10}$-heterocycloalkyl and $C_{0-6}$-alkylene-$SO_2$—$C_{3-10}$-heterocycloalkyl,
wherein alkylene, cycloalkyl, heterocycloalkyl and the 5- or 6-membered heteroaryl is optionally substituted by 1 to 4 substituents independently selected from the group consisting of halogen, CN, $C_{1-3}$-alkyl, halo-$C_{1-3}$-alkyl, OH, oxo, =N—$OR^{132}$, O—$C_{1-3}$-alkyl and O-halo-$C_{1-3}$-alkyl,
or wherein two adjacent substituents complete a 3- to 8-membered saturated or partially unsaturated ring containing carbon atoms and optionally containing 1 to 3 heteroatoms selected from O, S or N, wherein the ring is unsubstituted or substituted with 1 to 7 substituents independently selected from the group consisting of halogen, $C_{1-6}$-alkyl, halo-$C_{1-6}$-alkyl, $C_{3-6}$-cycloalkyl, $C_{3-6}$-heterocycloalkyl, oxo, =N—$OR^{132}$, OH, O—$C_{1-6}$-alkyl and O-halo-$C_{1-6}$-alkyl;
$R^{104}$ is selected from ($CR^{108}R^{109}$)$R^{140}$, (C=O)$R^{140}$, $OR^{140}$, $SO_y$—$R^{107}$ and $C_{3-6}$-cycloalkyl, which is spirocyclic fused with $R^{140}$,
wherein cycloalkyl is unsubstituted or substituted with 1 to 4 substituents independently selected from the group consisting of F, $CH_3$ and $CF_3$;
$R^{107}$ is selected from $C_{3-10}$-cycloalkyl and $C_{3-10}$-heterocycloalkyl,
wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$alkyl, $C_{1-6}$-alkyl, halo-$C_{1-6}$alkyl, cycloalkyl and heterocycloalkyl;
$R^{108}$ is selected from H, F, halo-$C_{1-3}$-alkyl, OH, O—$C_{1-3}$-alkyl and O-halo-$C_{1-3}$-alkyl;
$R^{109}$ is selected from H, F, $C_{1-3}$-alkyl and halo-$C_{1-3}$-alkyl;
$R^{111}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl,
wherein alkyl, alkylene, cycloalkyl and heterocycloalkyl is unsubstituted or substituted with 1 to 6 substituents selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, NH($C_{1-3}$-alkyl), N($C_{1-3}$-alkyl)$_2$, $C_{3-6}$-heterocycloalkyl, $C_{3-6}$-cycloalkyl and $SO_2$—$C_{1-3}$-alkyl,
wherein cycloalkyl and heterocycloalkyl is unsubstituted or substituted with 1 to 3 substituents independently selected from the group consisting of F, OH, oxo, $CH_3$ and $CF_3$;
$R^{112}$ is independently selected from H, $C_{1-6}$-alkyl, halo-$C_{1-6}$-alkyl and $C_{3-6}$-cycloalkyl;
$R^{131}$ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from the group consisting of halogen, CN, OH, oxo, =N—$OR^{132}$, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

and optionally wherein two R[131] when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of fluoro, OH, oxo, $C_{1-4}$-alkyl and halo-$C_{1-4}$-alkyl;

R[132] is independently selected from H, $C_{1-6}$-alkyl, halo-$C_{1-6}$-alkyl and $C_{3-6}$-cycloalkyl;

R[140] is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-8}$-cycloalkyl and $C_{3-8}$-heterocycloalkyl; and x and y are independently selected from 0, 1 and 2.

11. The compound according to claim 10 wherein:

R[101] is selected from H, $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $C_{1-10}$-alkylene-(6-membered aryl) and $C_{1-10}$-alkylene-(6-membered heteroaryl), wherein alkyl, alkenyl, alkynyl, alkylene, cycloalkyl, heterocycloalkyl, aryl and heteroaryl is unsubstituted or substituted with 1 to 7 substituents independently selected from the group consisting of oxo, CN, OR[111], O—$C_{2-6}$-alkylene-OR[111], $C_{1-6}$-alkyl, halo-$C_{1-6}$-alkyl, halogen, $CO_2R^{111}$, CONR[111]R[112], CONR[111]SO$_2$R[111], COR[111], SO$_x$R[111], SO$_3$H, SO$_2$NR[111]R[112], NR[111]COR[111], NR[111]SO$_2$R[111], NR[111]—CO—NR[111]R[112], NR[111]—SO$_2$—NR[111]R[112], $C_{3-8}$-cycloalkyl, O—$C_{3-8}$-cycloalkyl, $C_{3-8}$-heterocycloalkyl, O—$C_{3-8}$-heterocycloalkyl and NR[111]R[112]; and R[102] is selected from H, $C_{1-3}$-alkyl, fluoro-$C_{1-3}$-alkyl and hydroxy-$C_{1-3}$-alkyl;

or R[101] and R[102] when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of halogen, oxo, CN, OR[111], SO$_x$R[111], SO$_3$H, NR[111]SO$_2$R[111], SO$_2$NR[111]R[112], $C_{0-6}$-alkylene-CO$_2$R[111], CONR[111]R[112], CONR[111]SO$_2$R[111], COR[111], NR[111]—CO—R[111], NR[111]—CO—NR[111]R[112], NR[111]—SO$_2$—NR[111]R[112], NR[111]R[112], $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substituents independently selected from the group consisting of halogen, $C_{1-3}$-alkyl, halo-$C_{1-3}$-alkyl, OH, O—$C_{1-3}$-alkyl, O-halo-$C_{1-3}$-alkyl, SO$_2$—$C_{1-3}$-alkyl, COOH and oxo.

12. The compound according to claim 10 wherein NR[101]R[102] is selected from

NHMe, NHEt, NH$^i$Pr, NH$^t$Bu, NHCH$_2$CONH$_2$, NHCH$_2$CONMe$_2$, NHCH$_2$CH$_2$OH, NHCH$_2$CH$_2$OMe, NHCH$_2$CH$_2$SO$_2$Me, NHCH$_2$CH$_2$SO$_2$NH$_2$, NH(CH$_2$)$_3$OH, NH(CH$_2$)$_3$OMe, NH(CH$_2$)$_4$OH, NH(CH$_2$)$_4$OMe, NH(CH$_2$)$_5$OH, NH(CH$_2$)$_2$CO$_2$H, NH(CH$_2$)$_3$CO$_2$H, NH(CH$_2$)$_4$CO$_2$H, NH(CH$_2$)$_5$CO$_2$H, NHCH$_2$CH(CF$_3$)OH, NHCH$_2$C(Me)(CF$_3$)OH, NHCH$_2$CMe$_2$OH, NHCH$_2$CH$_2$CMe$_2$OH, NHCH$_2$CMe$_2$NHCH$_2$CF$_3$, NHCH(Me)CMe$_2$OH, NHCH$_2$CMe$_2$OMe, NHCH$_2$CMe$_2$CO$_2$H, NHCH$_2$CMe$_2$CONHMe, NHCH$_2$CMe$_2$CONMe$_2$, NHCH$_2$CMe$_2$NHSO$_2$Me, NH(CH$_2$)$_3$SOMe, NH(CH$_2$)$_5$SO$_2$Me, NH(CH$_2$)$_5$SO$_2$NH$_2$, NH(CH$_2$)$_3$NHSO$_2$Me, NH(CH$_2$)$_2$O(CH$_2$)$_2$OH, NHCH$_2$CHMeOH, NH(CH$_2$)$_5$SOMe, NH(CH$_2$)$_3$SO$_2$Me, NHC(CH$_2$OH)$_3$, NHCH$_2$CH(OH)CH$_2$OH, N(CH$_2$CH$_2$OH)$_2$,

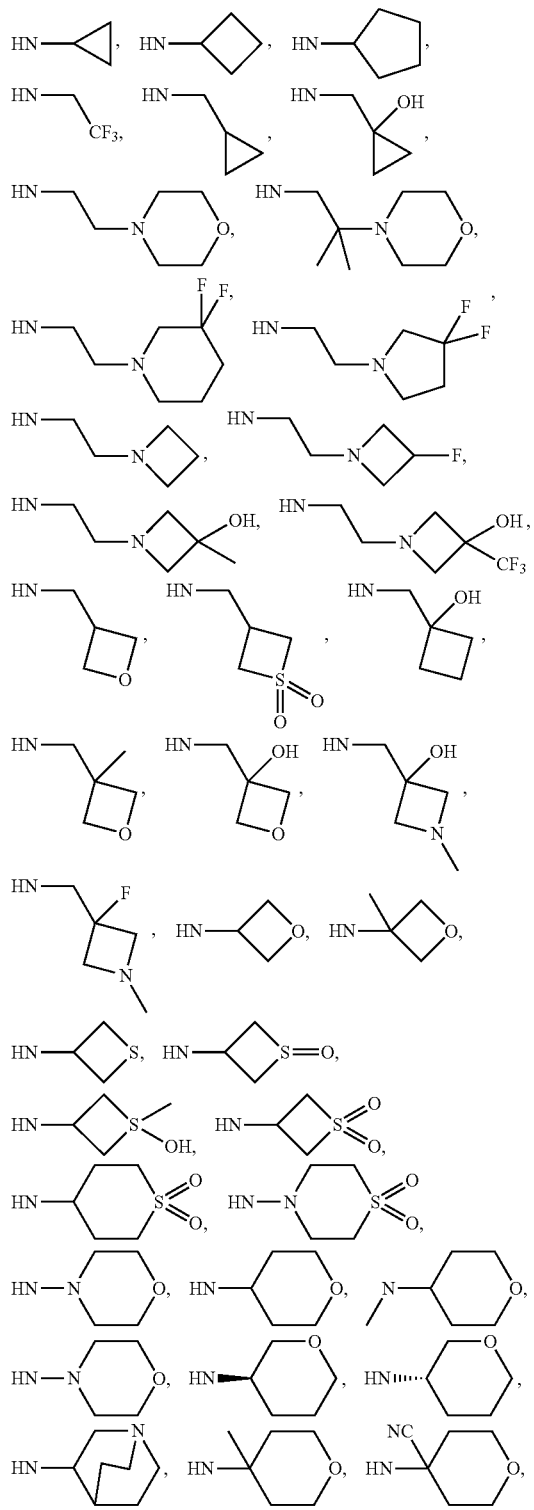

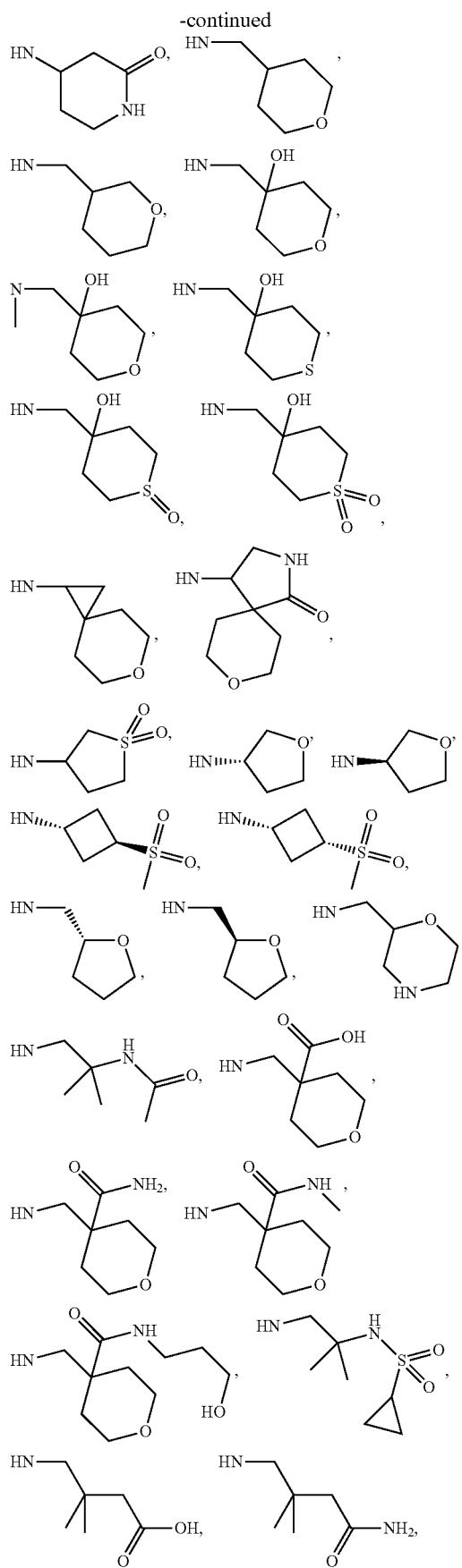
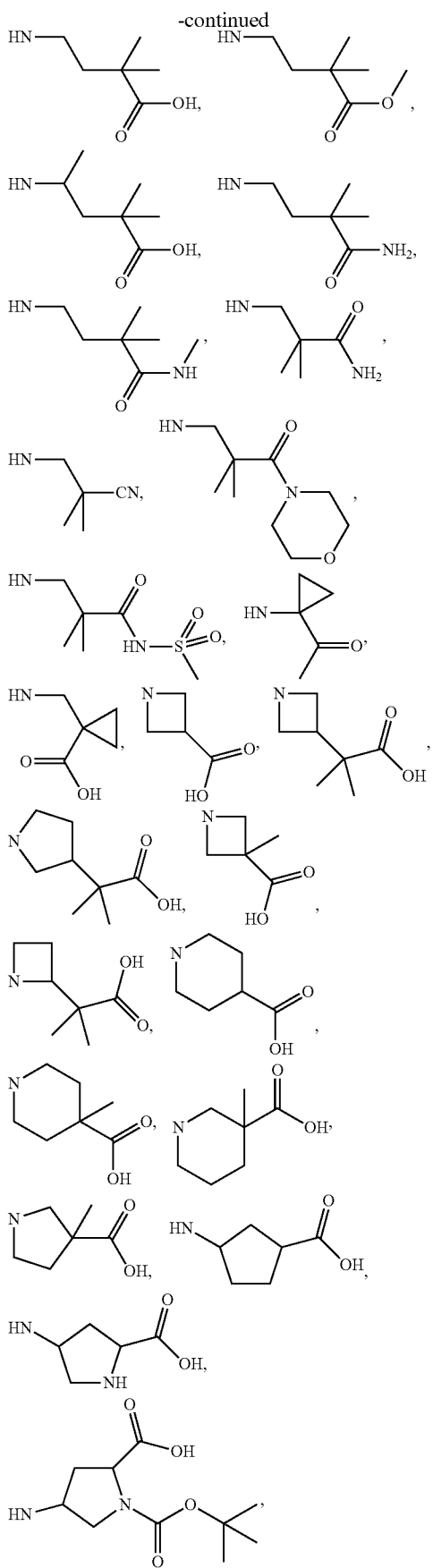

483
-continued
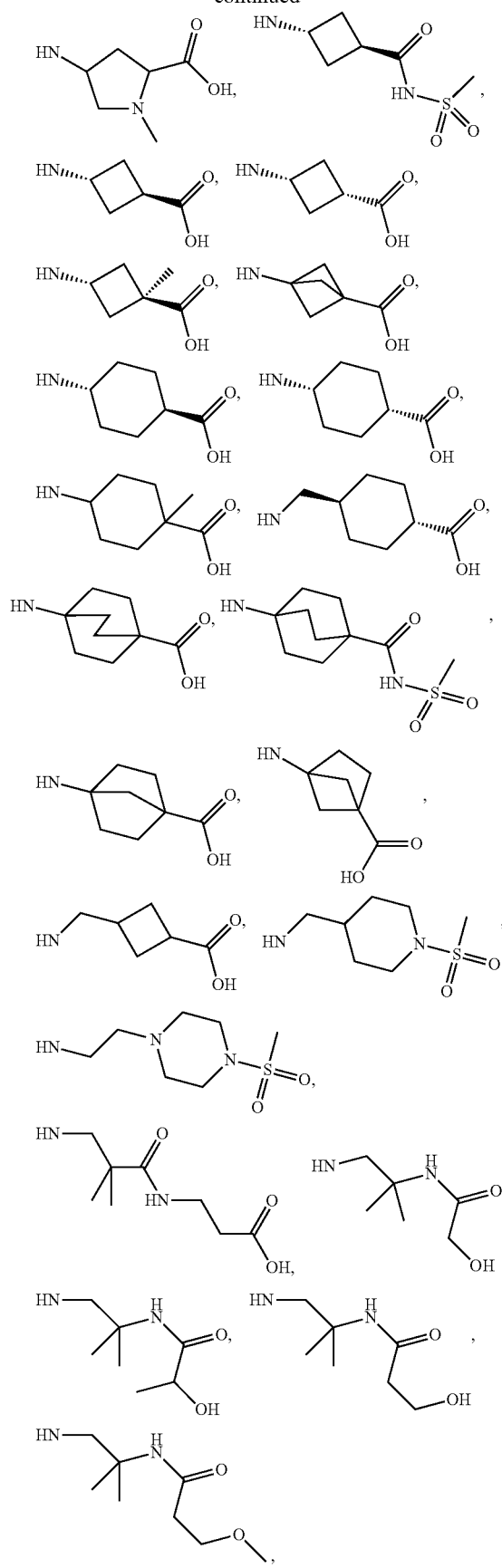
484
-continued
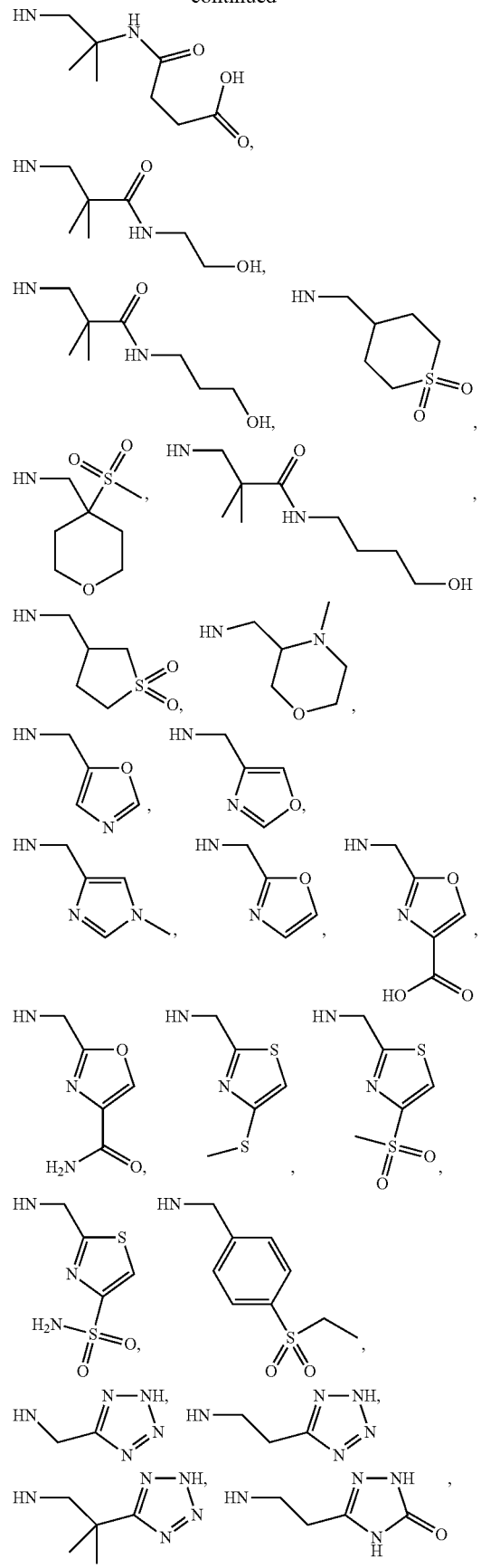

13. The compound according to claim 10 wherein:
R$^{103}$ is selected from
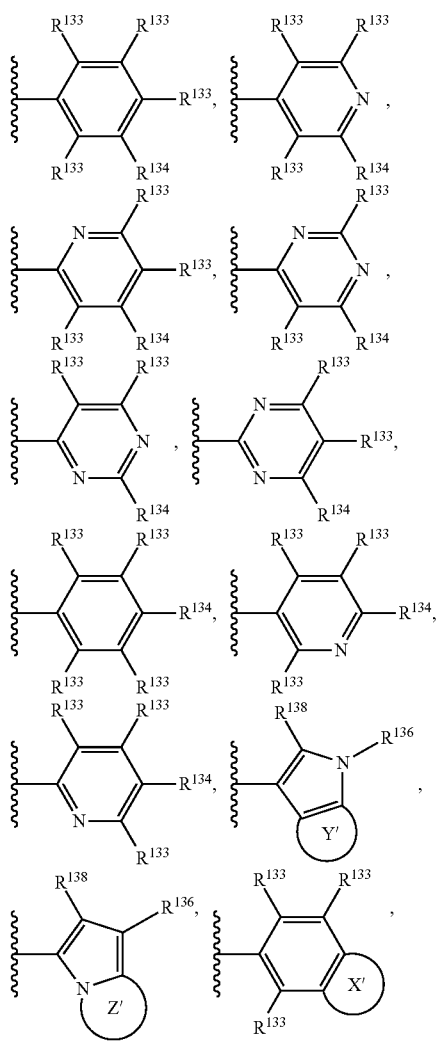

-continued

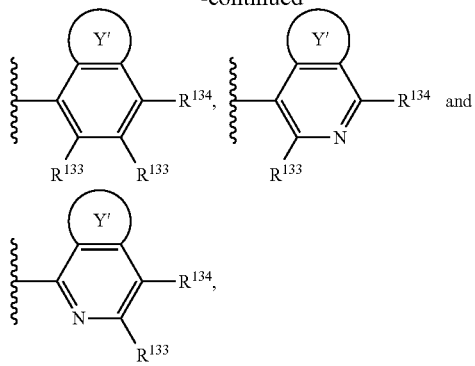

wherein:
R$^{133}$ is independently selected from H, halogen, CN, C$_{1-6}$-alkyl, fluoro-C$_{1-6}$-alkyl, C$_{1-4}$-alkylene-OH, C$_{1-4}$-alkylene-O—C$_{1-3}$-alkyl, C$_{1-4}$-alkylene-O-fluoro-C$_{1-3}$-alkyl, OH, O—C$_{1-6}$-alkyl, O-fluoro-C$_{1-6}$-alkyl, NH—C$_{1-6}$-alkyl, NH-fluoro-C$_{1-6}$-alkyl and C$_{3-10}$-cycloalkyl,
wherein alkylene is unsubstituted or substituted with 1 to 3 substituents selected from F and cycloalkyl is unsubstituted or substituted with 1 to 3 substituents independently selected from the group consisting of F, C$_{1-3}$-alkyl and fluoro-C$_{1-3}$-alkyl;
R$^{134}$ is independently selected from H, halogen, CN, C$_{1-6}$-alkyl, fluoro-C$_{1-6}$-alkyl, C$_{1-4}$-alkylene-OH, C$_{1-4}$-alkylene-O—C$_{1-3}$-alkyl, C$_{1-4}$-alkylene-O-fluoro-C$_{1-3}$-alkyl, OH, O—C$_{1-6}$-alkyl, O-fluoro-C$_{1-6}$-alkyl, NH—C$_{1-6}$-alkyl, NH-fluoro-C$_{1-6}$-alkyl, C$_{3-10}$-cycloalkyl, C$_{0-6}$-alkylene-C$_{3-10}$-heterocycloalkyl, 5-membered heteroaryl, 6-membered heteroaryl, C(O)N(R$^{137}$)$_2$ and SO$_2$N(R$^{137}$)$_2$,
wherein alkylene is unsubstituted or substituted with 1 to 3 substituents selected from F and cycloalkyl, heterocycloalkyl and heteroaryl is unsubstituted or substituted with 1 to 3 substituents independently selected from F, C$_{1-3}$-alkyl, fluoro-C$_{1-3}$-alkyl, OH, O—C$_{1-3}$-alkyl and fluoro-O—C$_{1-3}$-alkyl;
R$^{135}$ is selected from halogen, C$_{1-6}$-alkyl, halo-C$_{1-6}$-alkyl, C$_{3-6}$-cycloalkyl, C$_{3-6}$-heterocycloalkyl, oxo, =N—OR$^{132}$, OH, O—C$_{1-6}$-alkyl and O-halo-C$_{1-6}$-alkyl;
R$^{136}$ is selected from C$_{1-6}$-alkyl, fluoro-C$_{1-6}$-alkyl, C(O)N(R$^{137}$)$_2$ and SO$_2$N(R$^{137}$)$_2$;
R$^{137}$ is independently selected from H, C$_{1-6}$-alkyl, halo-C$_{1-6}$-alkyl, C$_{0-4}$-alkylene-C$_{3-6}$-cycloalkyl and C$_{0-4}$-alkylene-C$_{3-6}$-heterocycloalkyl, wherein alkyl and alkylene is unsubstituted or substituted with 1 to 4 substituents selected from the group consisting of halogen, OH, O—C$_{1-3}$-alkyl and CN; and cycloalkyl or heterocycloalkyl is unsubstituted or substituted with 1 to 3 substituents independently selected from the group consisting of F, CN, OH, oxo, C$_{1-3}$-alkyl and fluoro-C$_{1-3}$-alkyl;
or wherein two R$^{137}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of fluoro, OH, oxo, C$_{1-4}$-alkyl and halo-C$_{1-4}$-alkyl;

R$^{138}$ is selected from H, C$_{1-3}$-alkyl and fluoro-C$_{1-3}$-alkyl;
X' is an annelated saturated heterocycle selected from the group consisting of

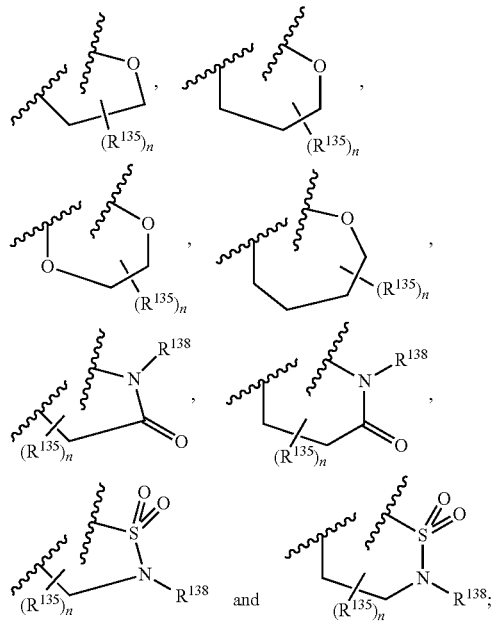

Y' is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from the group consisting of fluoro, C$_{1-3}$-alkyl and fluoro-C$_{1-3}$-alkyl;
Z' is an annelated 6-membered cycle forming a heteroaryl containing 1 to 2 nitrogen atoms, wherein the heteroaryl is unsubstituted or substituted with 1 to 3 substituents selected from fluoro, C$_{1-3}$-alkyl and fluoro-C$_{1-3}$-alkyl; and
n is selected from 1 to 4.

14. The compound according to claim 10 wherein R$^{103}$ is selected from

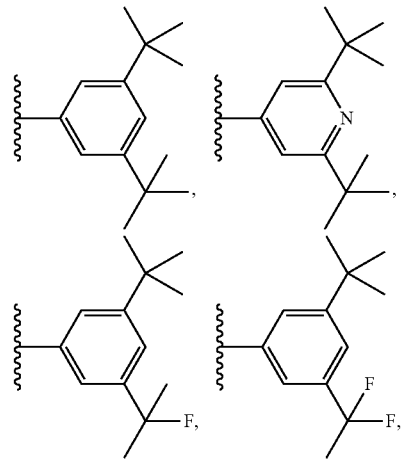

489
-continued
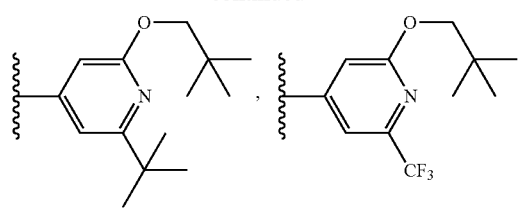
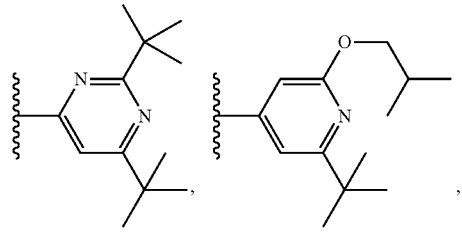
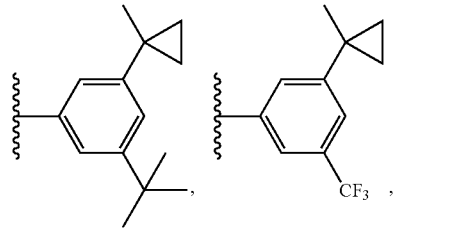
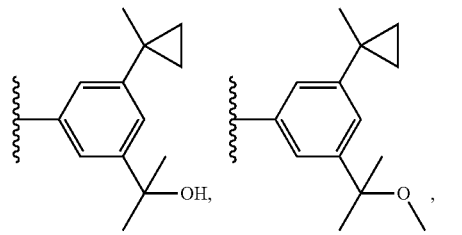
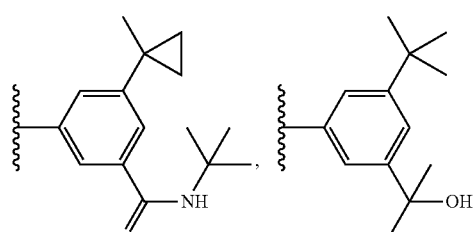
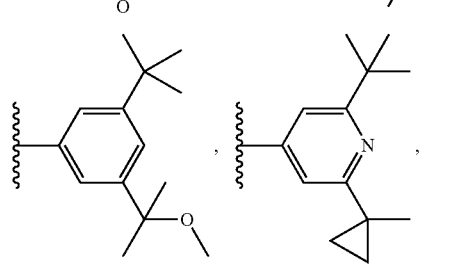
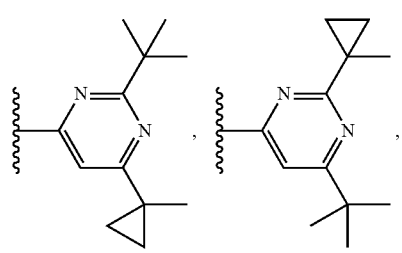
490
-continued
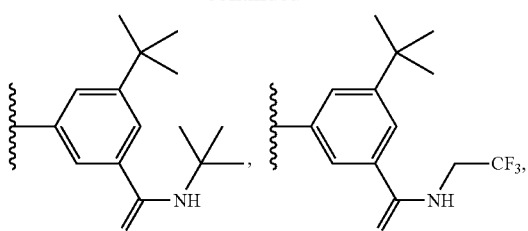
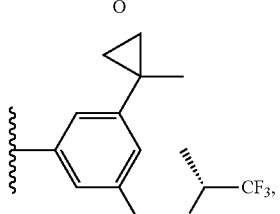
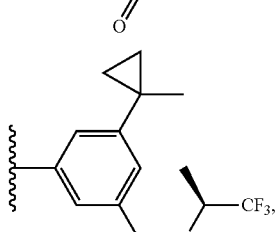
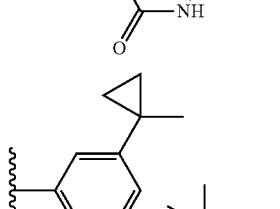
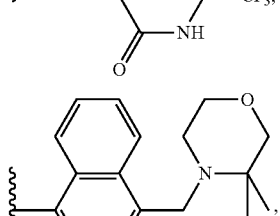
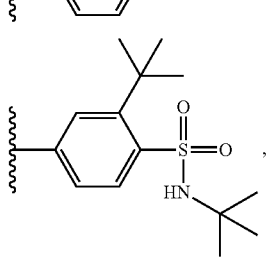
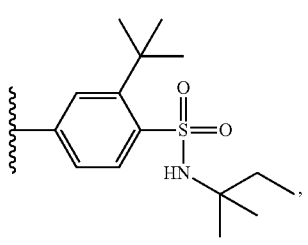

491
-continued
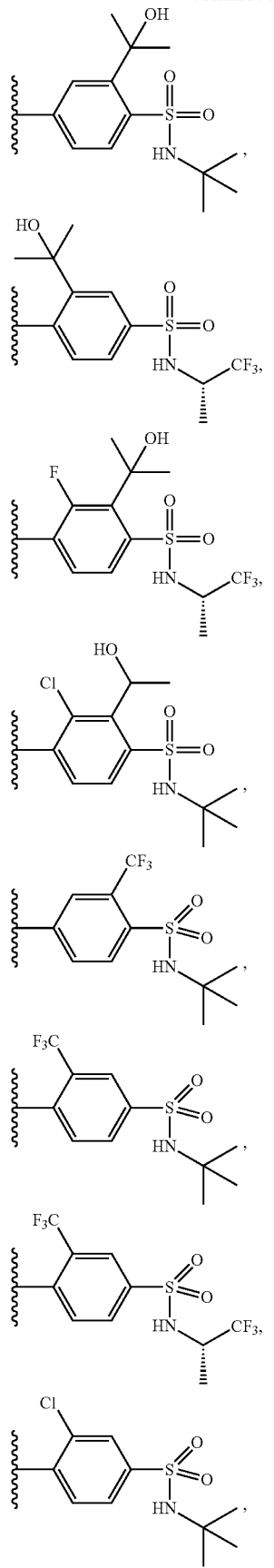
492
-continued
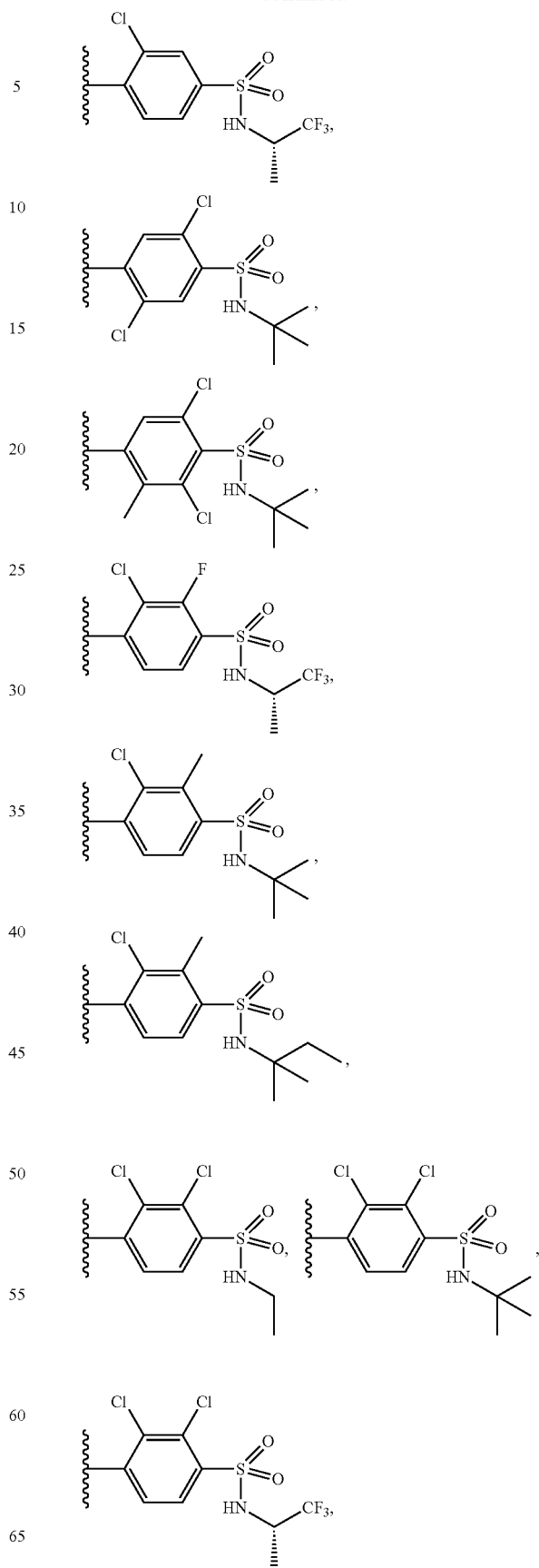

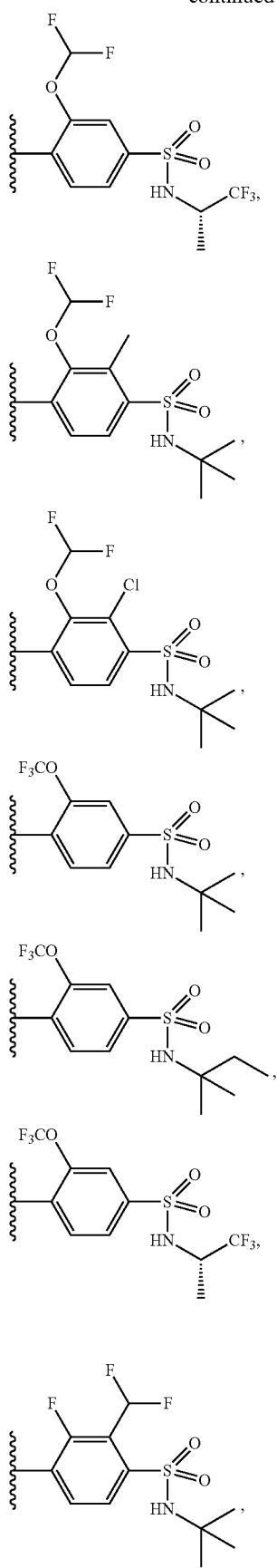
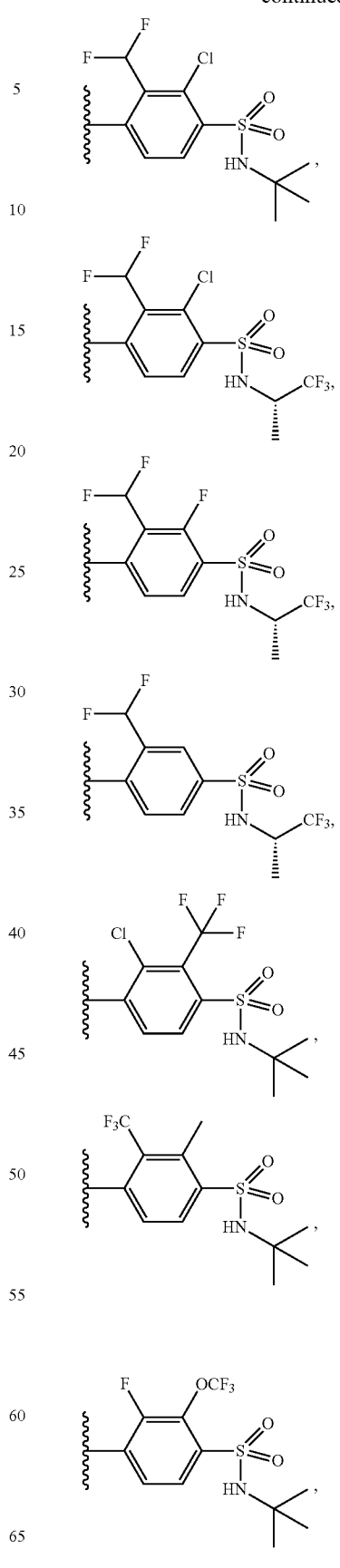

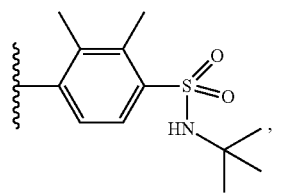
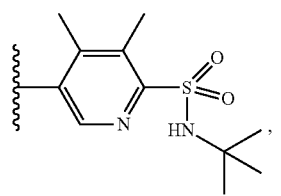
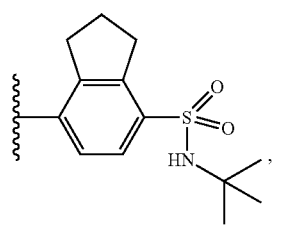
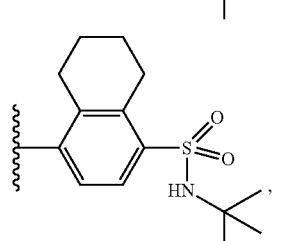
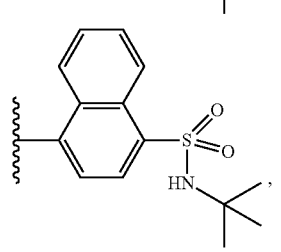
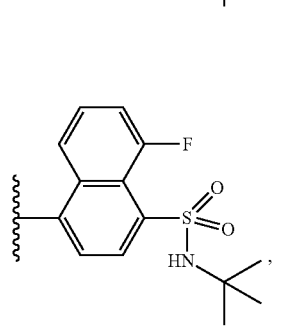
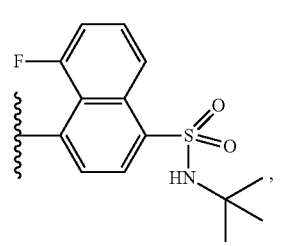
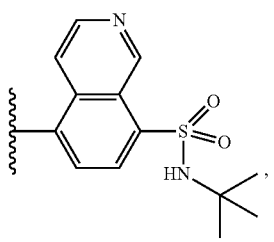
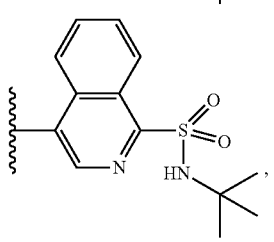
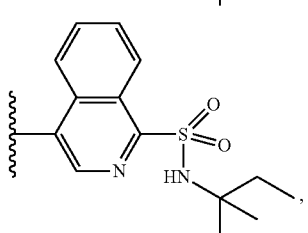
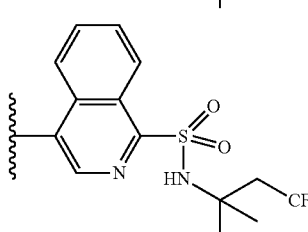
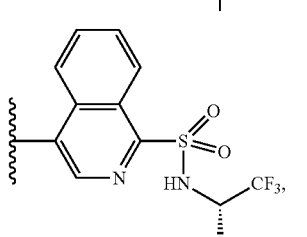
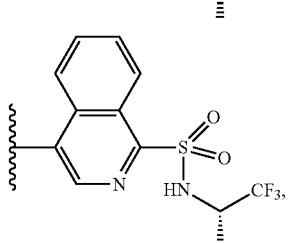
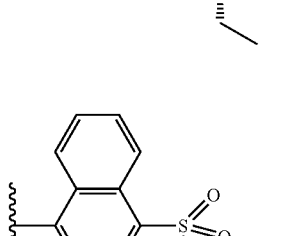
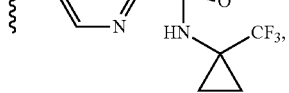

-continued

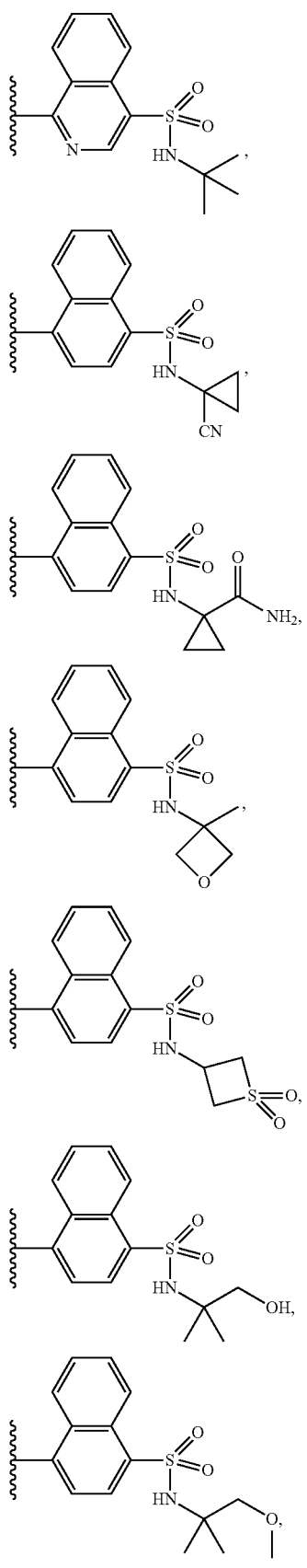

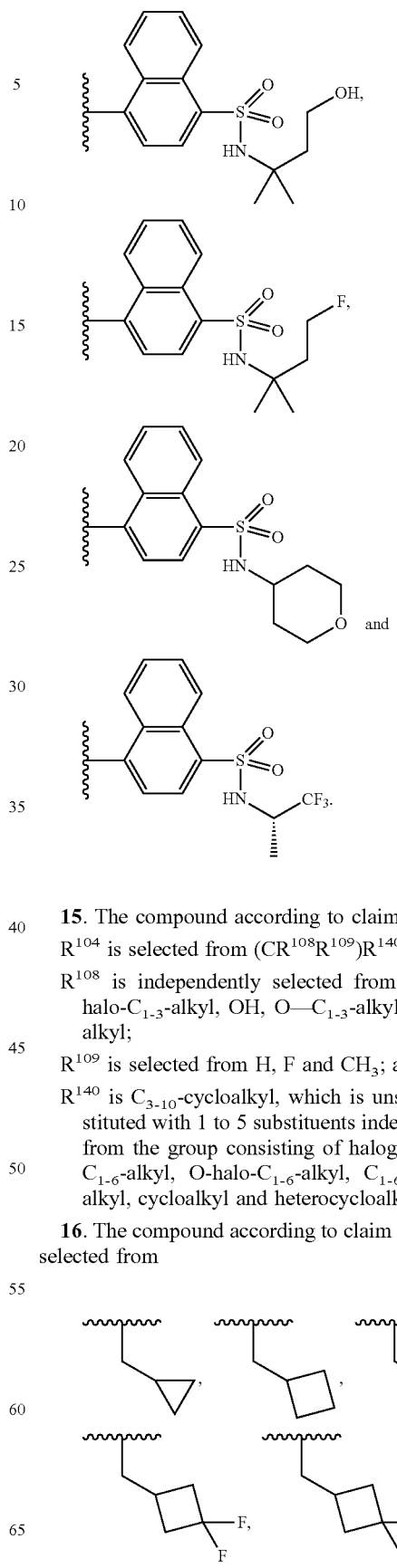

15. The compound according to claim 10 wherein:
R$^{104}$ is selected from (CR$^{108}$R$^{109}$)R$^{140}$ and (C=O)R$^{140}$;
R$^{108}$ is independently selected from H, F, C$_{1-3}$-alkyl, halo-C$_{1-3}$-alkyl, OH, O—C$_{1-3}$-alkyl and O-halo-C$_{1-3}$-alkyl;
R$^{109}$ is selected from H, F and CH$_3$; and
R$^{140}$ is C$_{3-10}$-cycloalkyl, which is unsubstituted or substituted with 1 to 5 substituents independently selected from the group consisting of halogen, OH, oxo, O—C$_{1-6}$-alkyl, O-halo-C$_{1-6}$-alkyl, C$_{1-6}$-alkyl, halo-C$_{1-6}$-alkyl, cycloalkyl and heterocycloalkyl.

16. The compound according to claim 10 wherein R$^{104}$ is selected from

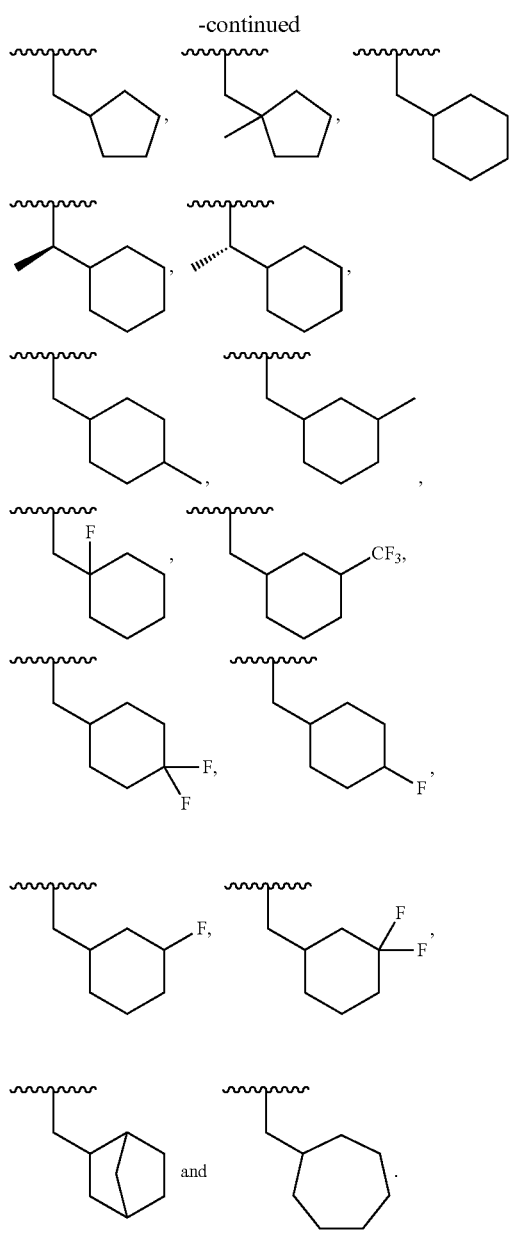
17. The compound of claim 10 selected from the group consisting of
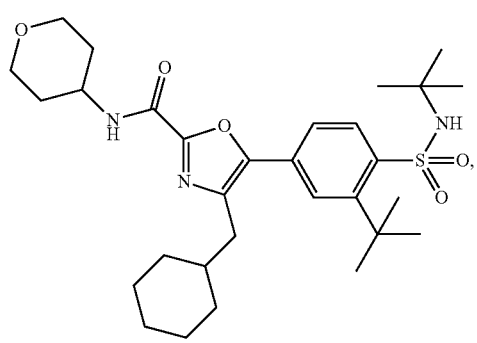
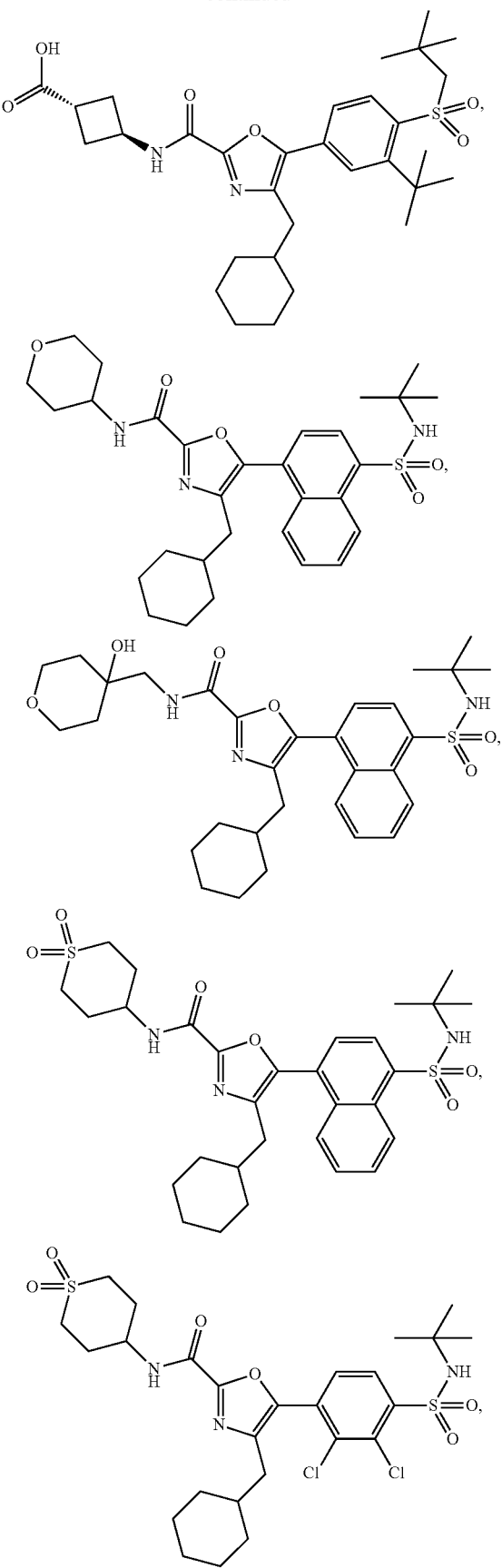

501
-continued
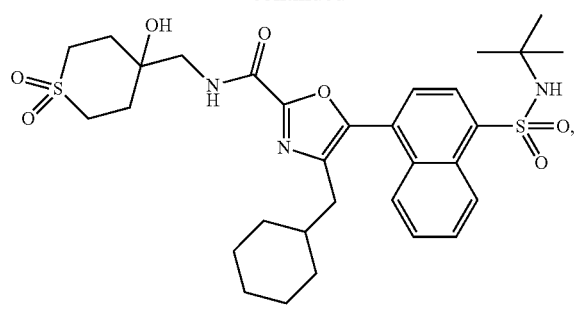
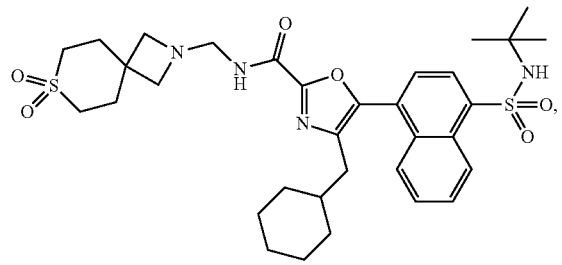
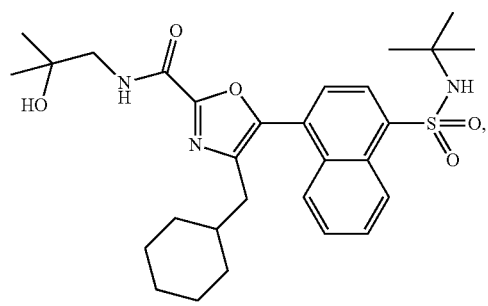
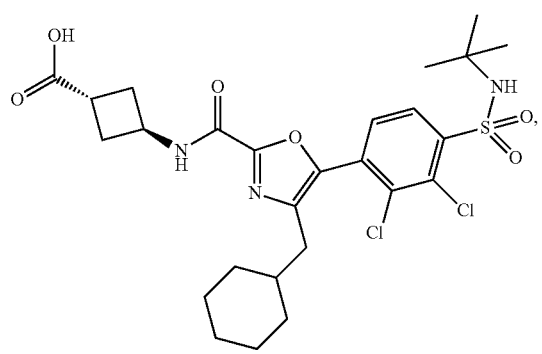
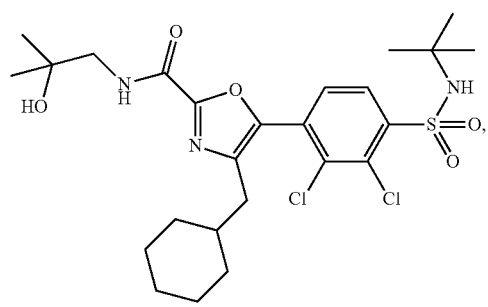
502
-continued
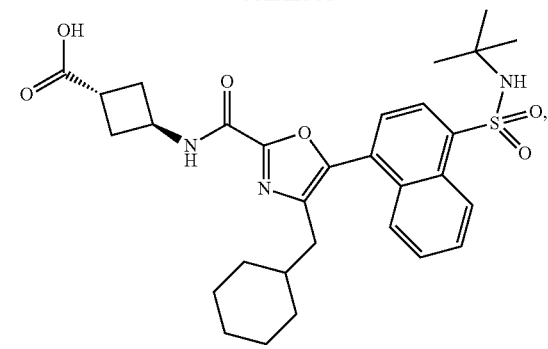
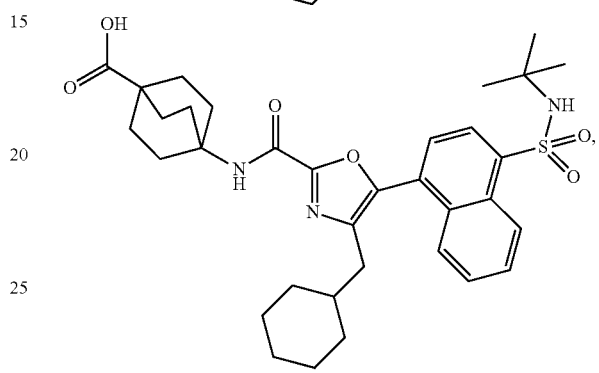
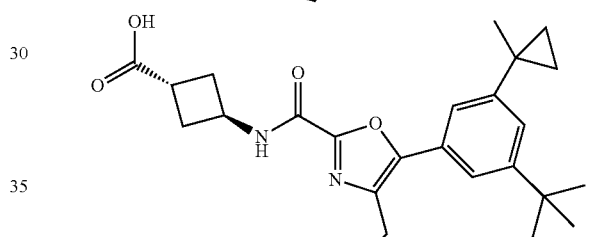
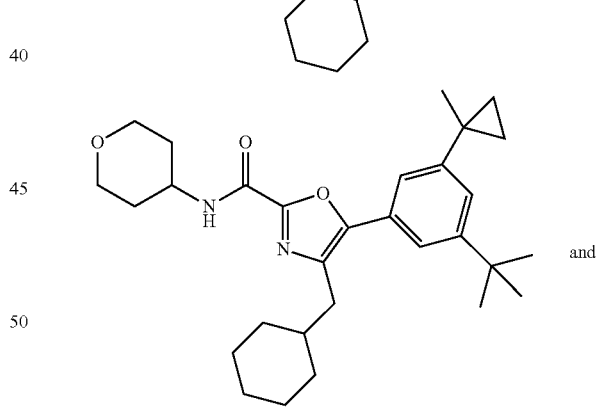
and
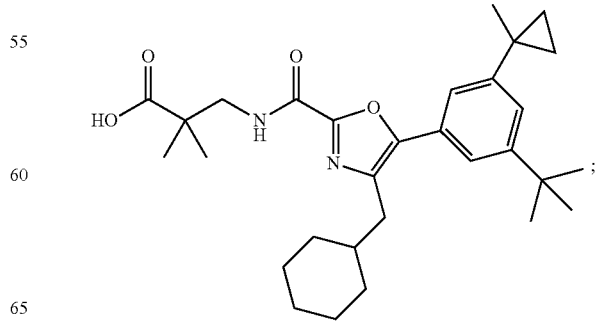
;

or an enantiomer, diastereomer, tautomer, N-oxide, solvate or pharmaceutically acceptable salt thereof.

18. A compound represented by Formula (1) or Formula (1'):

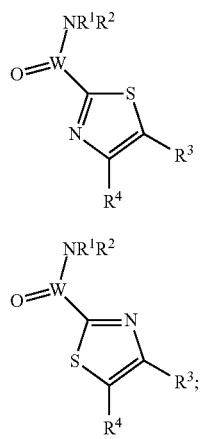

(1)

(1')

or an enantiomer, diastereomer, tautomer, N-oxide, solvate, formulation or pharmaceutically acceptable salt thereof, wherein:

$R^1$ and $R^2$ are independently selected from H, $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl) and $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from the group consisting of oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$; $CONR^{11}SO_2R^{11}$, $COR^{11}$, $NR^{11}$—CO—$R^{11}$, $NR^{11}$—CO—$NR^{11}R^{12}$; $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substitutents independently selected from the group consisting of halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;

$R^3$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl is unsubstituted or substituted with 1 to 5 substituents independently selected from the group consisting of halogen, $C_{1-6}$-alkyl, $C_{1-6}$-alkenyl, $C_{1-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered heteroaryl), $C_{1-6}$-alkylene-O—$R^{31}$, $C_{0-6}$-alkylene-CN, $C_{0-6}$-alkylene-N($R^{31}$)$_2$, $C_{0-6}$-alkylene-O—$C_{3-10}$-cycloalkyl, O—$C_{1-6}$-alkylene-O—$R^{31}$, $C_{0-6}$-alkylene-O—$C_{3-10}$-heterocycloalkyl, $C_{0-6}$-alkylene-COOR$^{31}$, $C_{0-6}$-alkylene-C(O)R$^{31}$, $C_{0-6}$-alkylene-C(O)N($R^{31}$)$_2$, $C_{0-6}$-alkylene-N($R^{31}$)C(O)R$^{31}$, $C_{0-6}$-alkylene-SO—$R^{31}$, $C_{0-6}$-alkylene-$SO_2$—$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$C_{3-10}$-heterocycloalkyl and $C_{0-6}$-alkylene-$SO_2$—$C_{3-10}$-heterocycloalkyl, wherein alkyl, alkenyl, alkynyl, alkylene, cycloalkyl, heterocycloalkyl and the 5- or 6-membered heteroaryl is optionally substituted by 1 to 4 substituents independently selected from the group consisting of halogen, CN, $C_{1-3}$-alkyl, halo-$C_{1-3}$-alkyl, OH, oxo, =N—$OR^{32}$, O—$C_{1-6}$-alkyl, O-halo-$C_{1-3}$-alkyl, N($R^{31}$)$_2$, COOH, CON($R^{31}$)$_2$, $NR^{31}$—COR$^{31}$, $C_{3-10}$-cycloalkyl, $C_{3-10}$-heterocycloalkyl, 6-10-membered mono- or bicyclic aryl and 6-10-membered mono- or bicyclic heteroaryl, or wherein two adjacent substituents complete a 3- to 8-membered saturated or partially unsaturated ring containing carbon atoms and optionally containing 1 to 3 heteroatoms selected from O, S, N, SO, $SO_2$ or $NR^{31}$, wherein the ring is unsubstituted or substituted with 1 to 7 substituents independently selected from the group consisting of halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl;

$R^4$ is selected from $(CR^8R^9)R^{40}$, (C=O)$R^{40}$, $OR^{40}$, $NR^{41}R^{40}$, $SO_y$—$R^7$ and $C_{3-6}$-cycloalkyl substituted with $R^{40}$, wherein the connection between the $C_{3-6}$-cycloalkyl and the $R^{40}$ substituent is a spirocyclic fused connection, and wherein cycloalkyl is unsubstituted or substituted with 1 to 4 substituents independently selected from the group consisting of F, $CH_3$ and $CF_3$;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ and $R^9$ are independently selected from H, F, $C_{1-3}$-alkyl, halo-$C_{1-3}$-alkyl, OH, O—$C_{1-3}$-alkyl and O-halo-$C_{1-3}$-alkyl;

$R^{11}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, NH($C_{1-3}$-alkyl), N($C_{1-3}$-alkyl)$_2$, $C_{3-6}$-heterocycloalkyl, $C_{3-6}$-cycloalkyl and $SO_2$—$C_{1-3}$-alkyl, wherein cycloalkyl and heterocycloalkyl is unsubstituted or substituted with 1 to 3 substituents independently selected from the group consisting of F, OH, oxo, $CH_3$ and $CF_3$;

$R^{12}$ is independently selected from H, $C_{1-6}$-alkyl, halo-$C_{1-6}$-alkyl and $C_{3-6}$-cycloalkyl;

$R^{31}$ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from the group consisting of halogen, CN, OH, oxo, =N—$OR^{32}$, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

and optionally wherein two $R^{31}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of fluoro, OH, oxo, $C_{1-4}$-alkyl and halo-$C_{1-4}$-alkyl;

$R^{32}$ is independently selected from H, $C_{1-6}$-alkyl, halo-$C_{1-6}$-alkyl and $C_{3-6}$-cycloalkyl;

$R^{40}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-8}$-cycloalkyl and $C_{3-8}$-heterocycloalkyl;

$R^{41}$ is selected from H, $C_{1-6}$-alkyl, $C_{3-6}$-cycloalkyl and $C_{3-6}$-heterocycloalkyl,
wherein alkyl, cycloalkyl and heterocycloalkyl is unsubstituted or substituted with 1 to 3 substituents selected from the group consisting of OH, oxo, CN, halogen, O—$C_{1-6}$-alkyl, O-halo-$C_{1-6}$-alkyl, $C_{3-6}$-heterocycloalkyl and $C_{3-6}$-cycloalkyl;

x and y are independently selected from 0, 1 and 2; and
W is selected from C or S=O;
with the proviso that for $R^3$ the 5-14 membered mono-, bi- or tricyclic heteroaryl containing ring is not

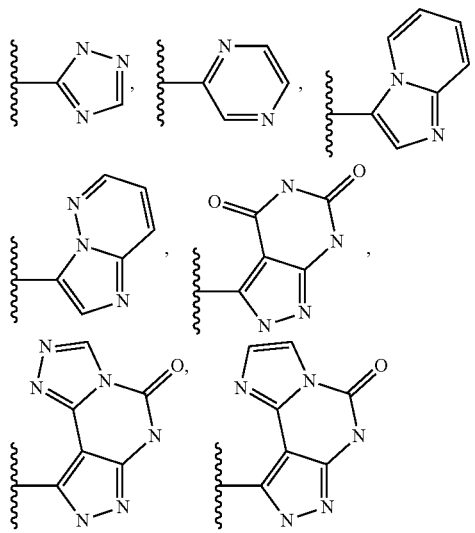

or a 5-membered aromatic heterocyclic group containing at least one oxygen atom.

19. The compound according to claim 18 wherein W is C.
20. The compound according to claim 18 wherein
$R^4$ is selected from $(CR^8R^9)R^{40}$, $(C=O)R^{40}$ and $OR^{40}$;
$R^8$ is selected from H, F, $CH_3$, $CF_3$ and O—$CH_3$;
$R^9$ is selected from H, F and $CH_3$; and
$R^{40}$ is $C_{3-8}$-cycloalkyl, which is unsubstituted or substituted with 1 to 3 substituents independently selected from the group consisting of fluoro, $CH_3$ and $CF_3$.

21. The compound according to claim 18 wherein:
$R^1$ is selected from H, $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl and $C_{1-10}$-alkylene-(5-membered heteroaryl), wherein alkyl, alkenyl, alkynyl, alkylene, cycloalkyl and heterocycloalkyl is unsubstituted or substituted with 1 to 7 substituents independently selected from the group consisting of oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$; and
$R^2$ is selected from H, $C_{1-6}$-alkyl, halo-$C_{1-6}$-alkyl and hydroxy-$C_{1-6}$-alkyl;
or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from the group consisting of halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $CONR^{11}SO_2R^{11}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl,
wherein cycloalkyl and heterocycloalkyl are unsubstituted or substituted with 1 to 4 substitutents independently selected from the group consisting of halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo.

22. The compound according to claim 18 wherein $NR^1R^2$ is selected from
NHMe, NHEt, $NH^iPr$, $NH^tBu$, $NHCH_2CONH_2$, $NHCH_2CONMe_2$, $NHCH_2CH_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CH(CF_3)OH$, $NHCH_2C(Me)(CF_3)OH$, $NHCH_2CMe_2OH$, $NHCH_2CH_2CMe_2OH$, $NHCH_2CMe_2NHCH_2CF_3$, $NHCH(Me)CMe_2OH$, $NHCH_2CMe_2OMe$, $NHCH_2CMe_2CO_2H$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_5SO_2NH_2$, $NH(CH_2)_3NHSO_2Me$, $NH(CH_2)_2O(CH_2)_2OH$, $NHCH_2CHMeOH$, $NH(CH_2)_5SOMe$, $NH(CH_2)_3SO_2Me$, $NHC(CH_2OH)_3$, $NHCH_2CH(OH)CH_2OH$, $N(CH_2CH_2OH)_2$,

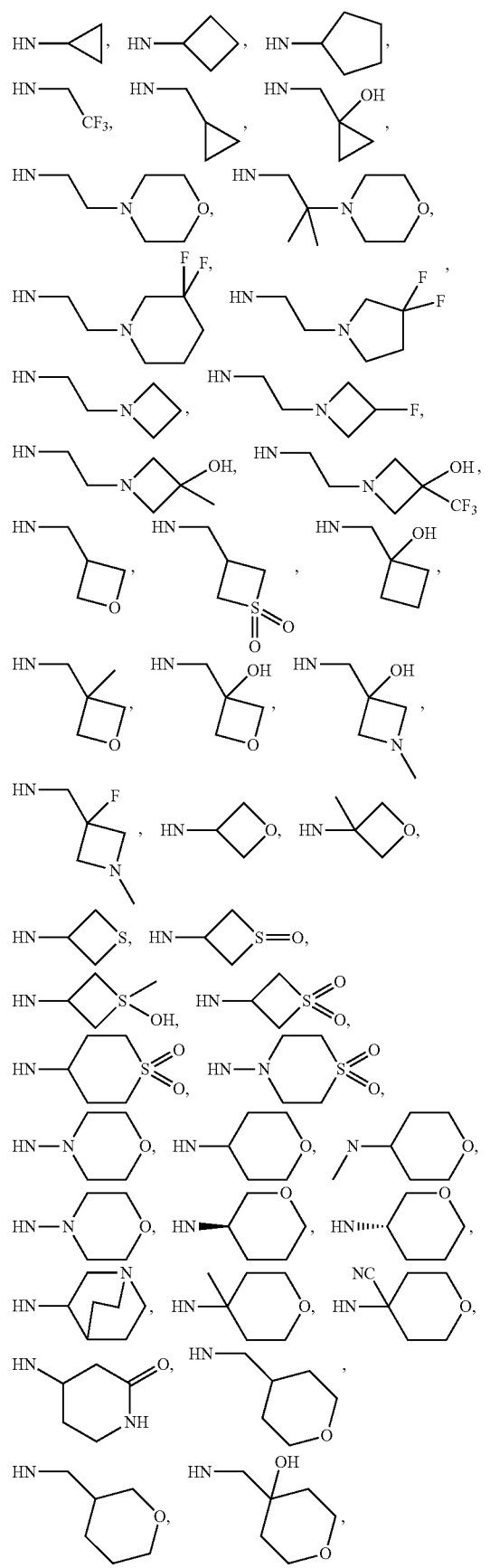
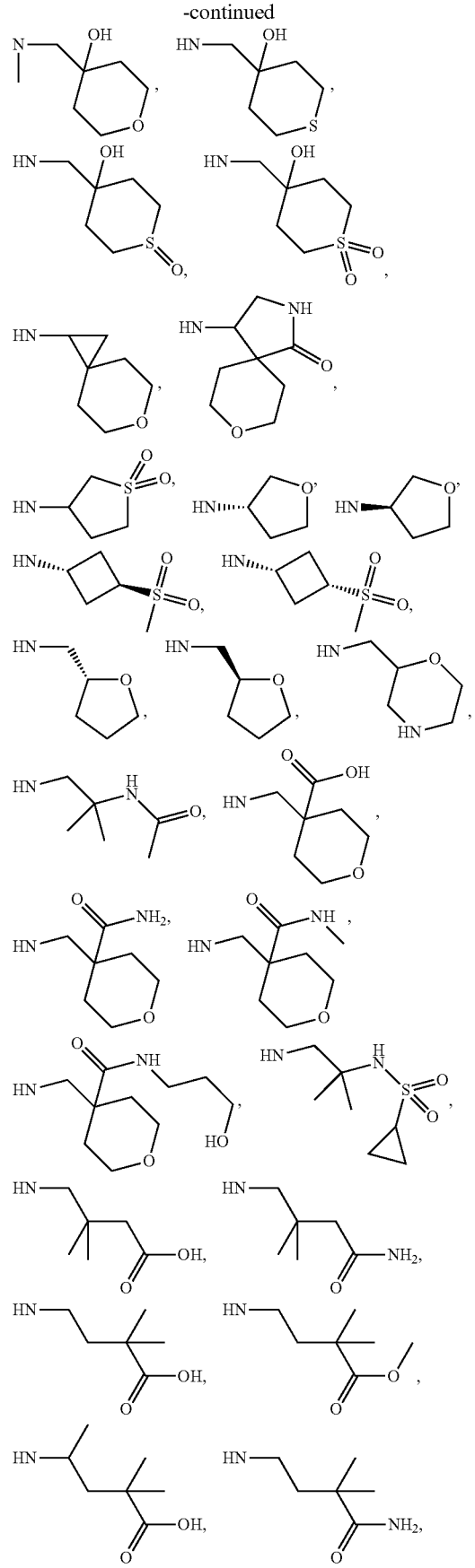
-continued

509
-continued
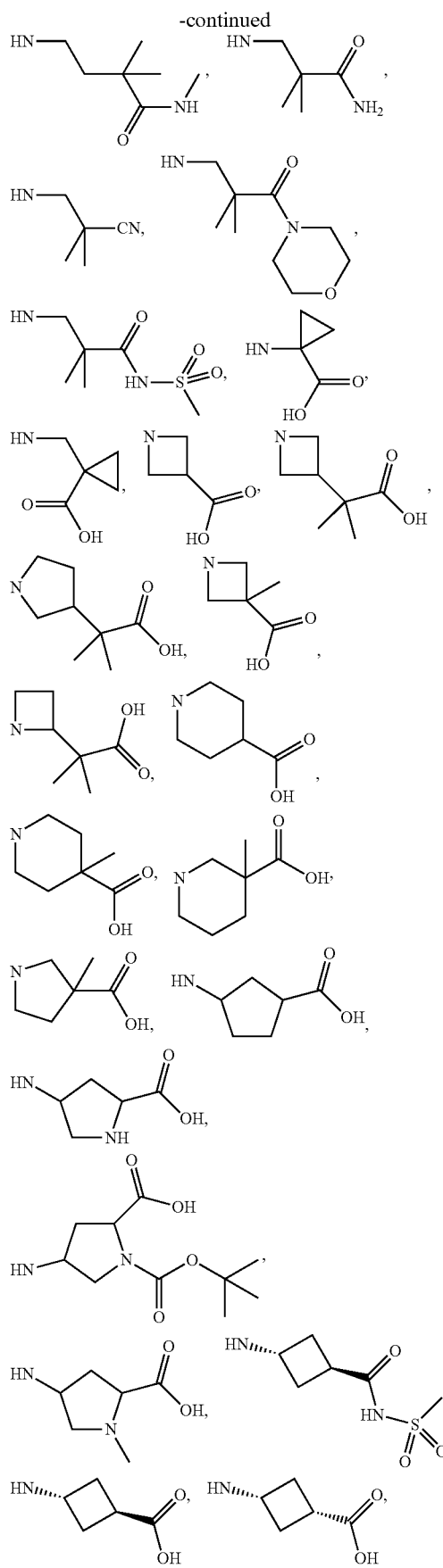
510
-continued
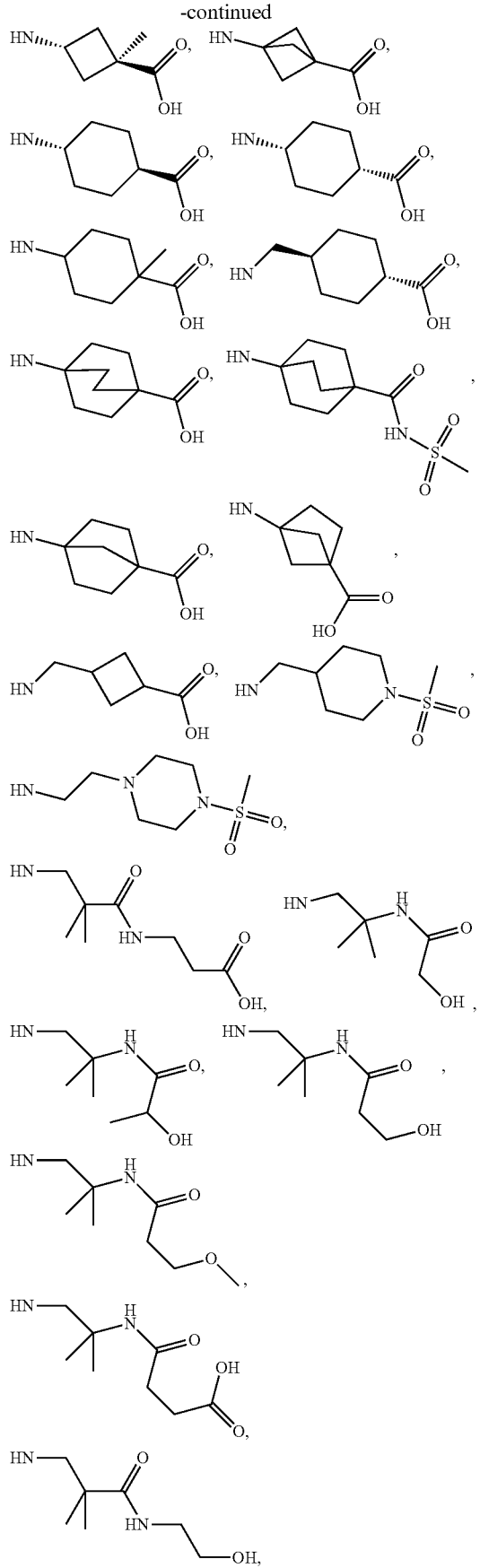

511
-continued
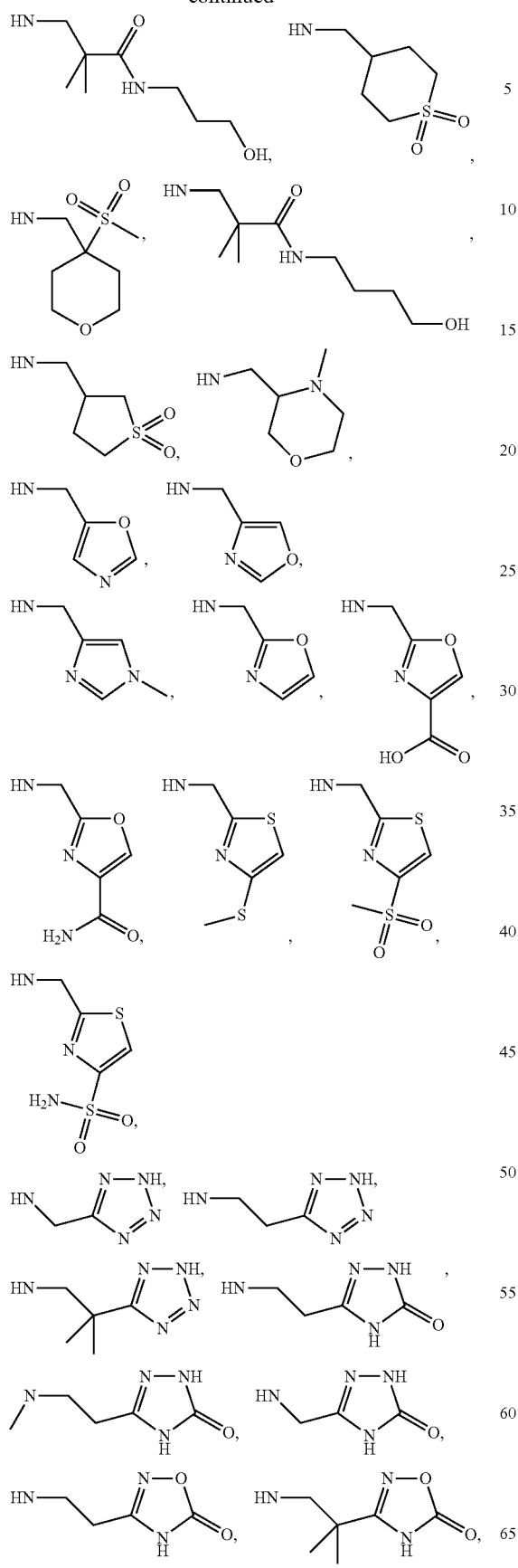
512
-continued
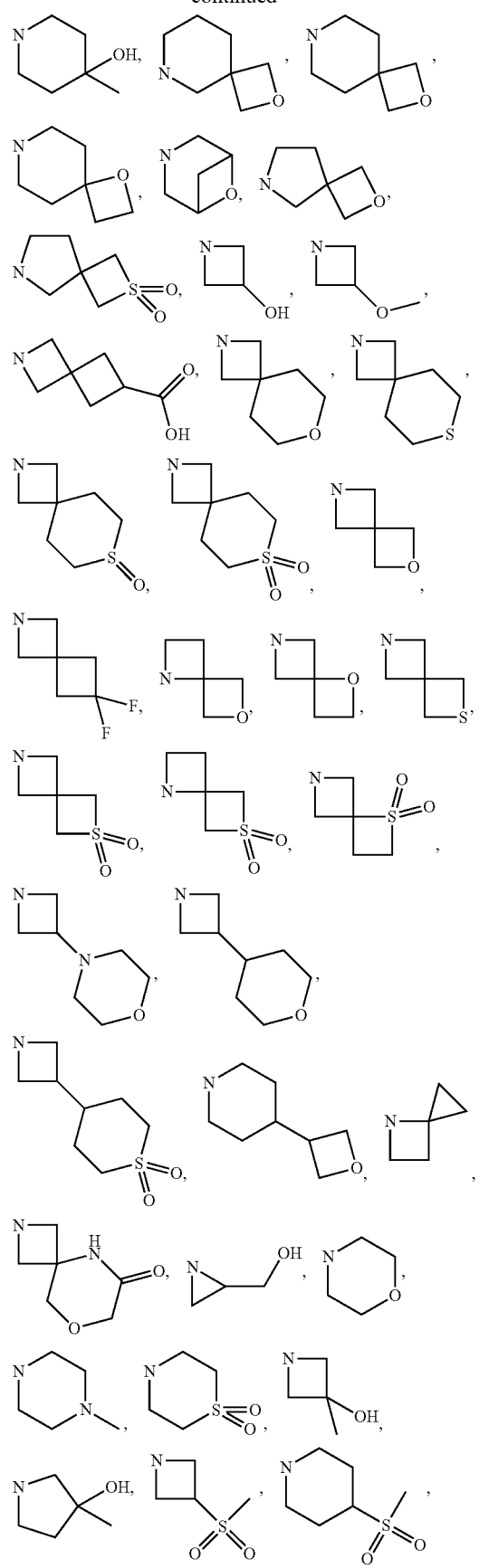

23. The compound according to claim 18 wherein:

R³ is a 6-10 membered mono- or bicyclic aryl or a 5-10 membered mono- or bicyclic heteroaryl containing 1 to 4 heteroatoms independently selected from the group consisting of N, O and S wherein aryl and heteroaryl are unsubstituted or substituted with 1 to 5 substituents independently selected from the group consisting of halogen, CN, $C_{1-6}$-alkyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-COOR³¹, $C_{0-6}$-alkylene-C(O)R³¹, $C_{0-6}$-alkylene-C(O)N(R³¹)₂, $C_{0-6}$-alkylene-SO₂—N(R³¹)₂, $C_{0-6}$-alkylene-SO₂—R³¹, $C_{0-6}$-alkylene-(5-membered heteroaryl), $C_{0-6}$-alkylene-(6-membered heteroaryl), wherein alkyl, alkylene, cycloalkyl, heterocycloalkyl and heteroaryl are unsubstituted or substituted by 1 to 3 substituents independently selected from the group consisting of halogen, OH, oxo, =N—OR³², N(R³¹)₂, O—$C_{1-6}$-alkyl; COOH, CON(R³¹)₂, CN, NR³¹—COR³¹, $C_{3-10}$-cycloalkyl, $C_{3-10}$-heterocycloalkyl, 6-10-membered mono- or bicyclic aryl and 6-10-membered mono- or bicyclic heteroaryl, or wherein two adjacent substituents may complete a 3- to 8-membered saturated or partially unsaturated ring containing carbon atoms and optionally containing 1 to 3 members selected from O, S, SO, SO₂ or NR³¹, wherein the ring is unsubstituted or substituted with 1 to 4 substituents independently selected from halogen, oxo, =N—OR³², OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl.

24. The compound according to claim 18 wherein R³ is selected from

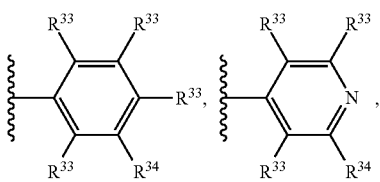

wherein:
R³³ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH-fluoro-$C_{1-6}$-alkyl, $C_{3-10}$-cycloalkyl, wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;

R³⁴ are independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH-fluoro-$C_{1-6}$-alkyl, $C_{3-10}$-cycloalkyl, $C_{0-6}$-alkylene-$C_{3-10}$-heterocycloalkyl, 5-membered heteroaryl, 6-membered heteroaryl, C(O)N(R³⁷)₂ and SO₂N(R³⁷)₂, wherein alkylene is unsubstituted or substituted with 1 to 3 substituents selected from F and cycloalkyl, heterocycloalkyl and heteroaryl is unsubstituted or substituted with 1 to 3 substituents independently selected from F, $C_{1-3}$-alkyl, fluoro-$C_{1-3}$-alkyl, OH, O—$C_{1-3}$-alkyl, fluoro-O—$C_{1-3}$-alkyl;

$R^{35}$ is selected from halogen, $C_{1-6}$-alkyl, halo-$C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl;

$R^{36}$ is selected from $C_{1-6}$-alkyl, fluoro-$C_{1-6}$-alkyl, C(O)N($R^{37}$)$_2$, SO$_2$N($R^{37}$)$_2$;

$R^{37}$ is independently selected from H, $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl, wherein alkyl and alkylene is unsubstituted or substituted with 1 to 4 substituents selected from halogen, OH, O—$C_{1-3}$-alkyl, CN, CONH$_2$; and cycloalkyl or heterocycloalkyl is unsubstituted or substituted with 1 to 3 substituents independently selected from F, CN, OH, oxo, $C_{1-3}$-alkyl and fluoro-$C_{1-3}$-alkyl;

or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{14}$-alkyl and halo-$C_{14}$-alkyl;

$R^{38}$ is selected from H, $C_{1-3}$-alkyl and fluoro-$C_{1-3}$-alkyl;

X is an annelated saturated heterocycle selected from the group consisting of

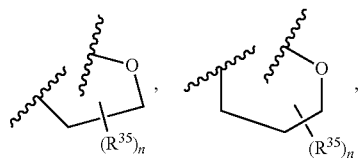

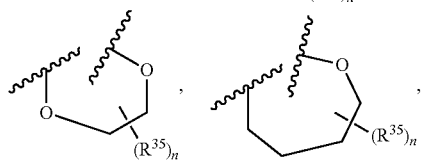

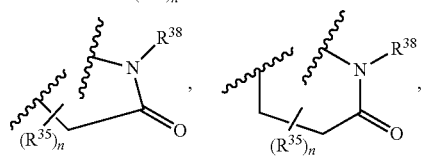

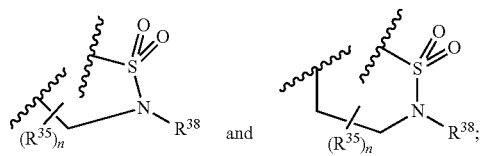

Y is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from halogen, $C_{1-3}$-alkyl and fluoro-$C_{1-3}$-alkyl;

Z is an annelated 6-membered cycle forming a heteroaryl containing 1 to 2 nitrogen atoms, wherein the heteroaryl is unsubstituted or substituted with 1 to 3 substituents selected from fluoro, $C_{1-3}$-alkyl and fluoro-$C_{1-3}$-alkyl; and n is selected from 1 to 4.

25. The compound according to claim 18 wherein $R^3$ is selected from

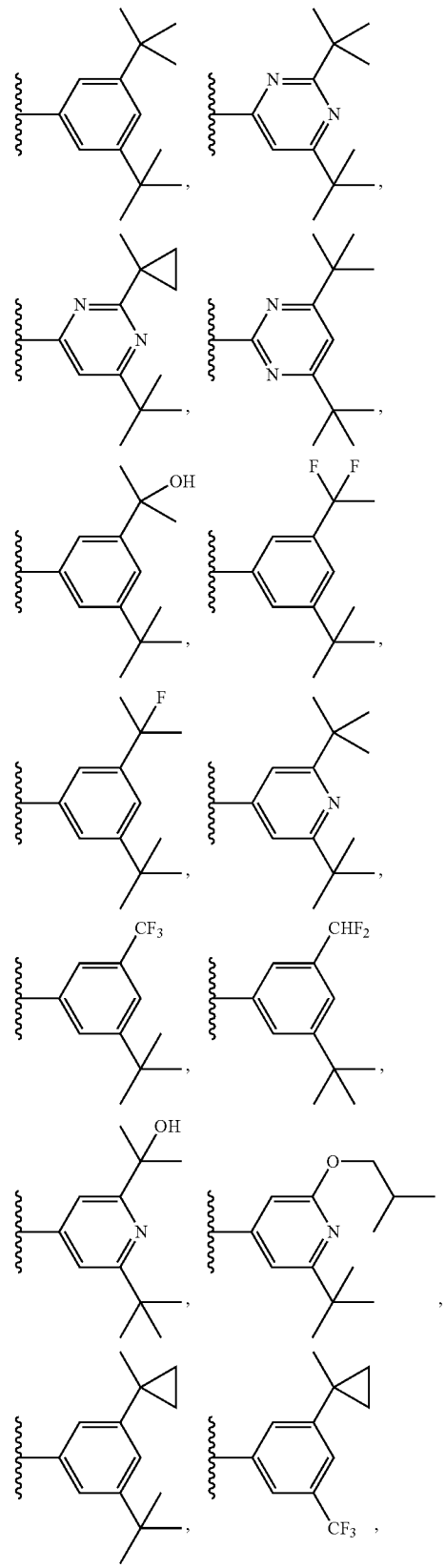

517
-continued
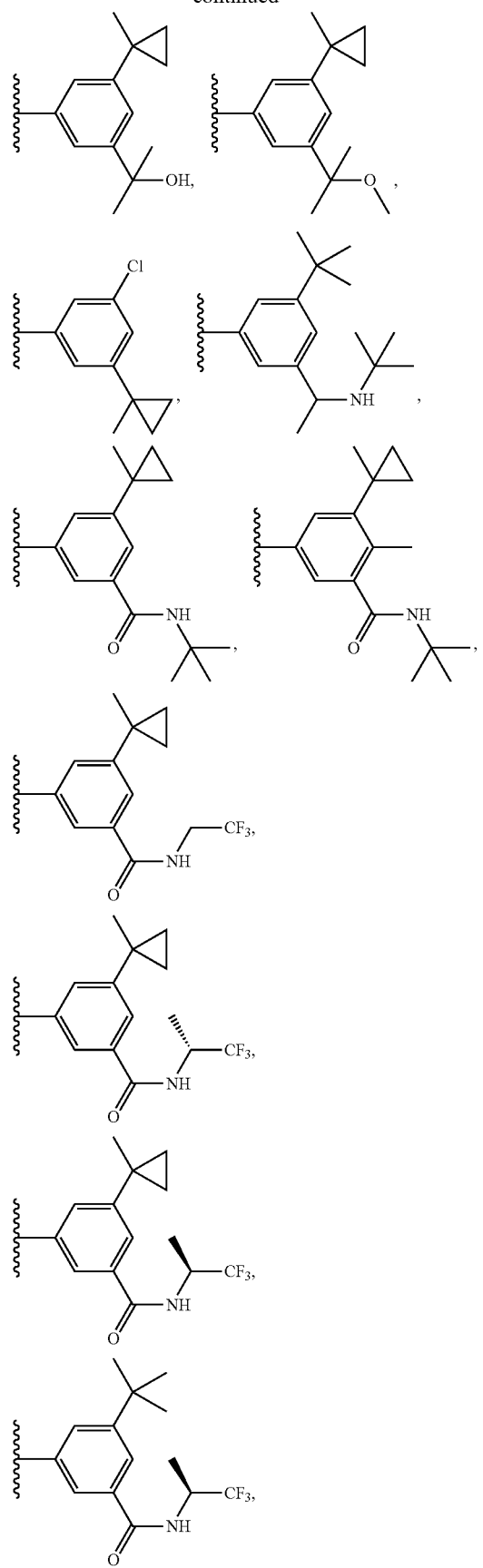
518
-continued
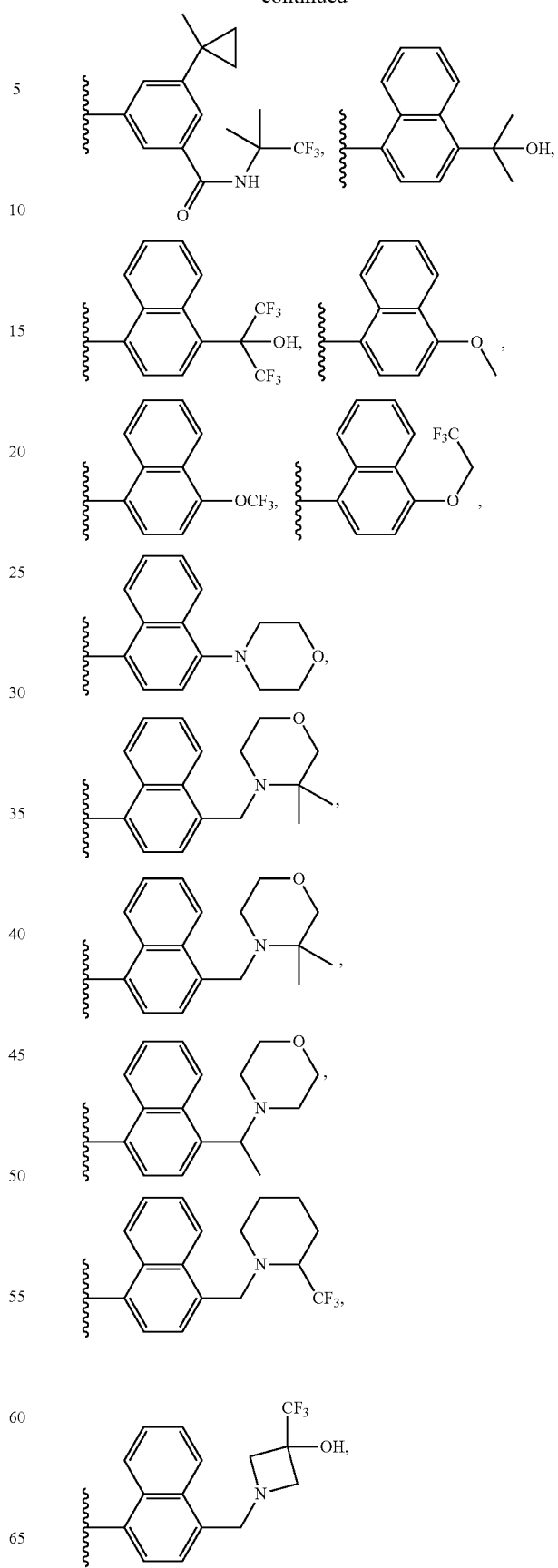

-continued
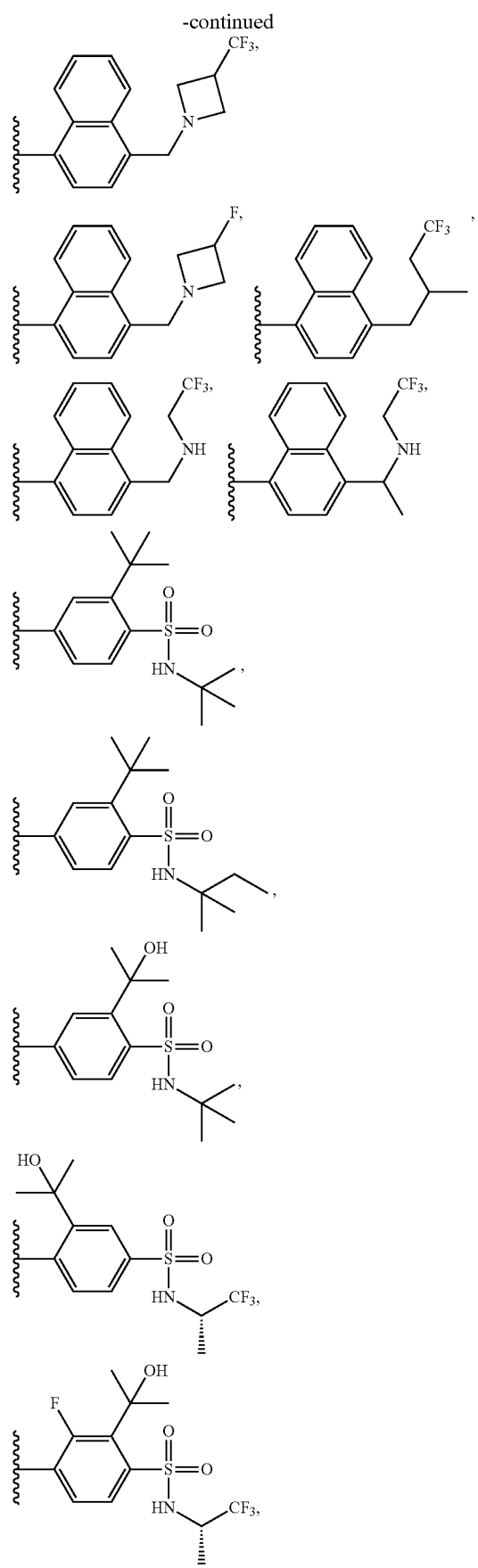
-continued
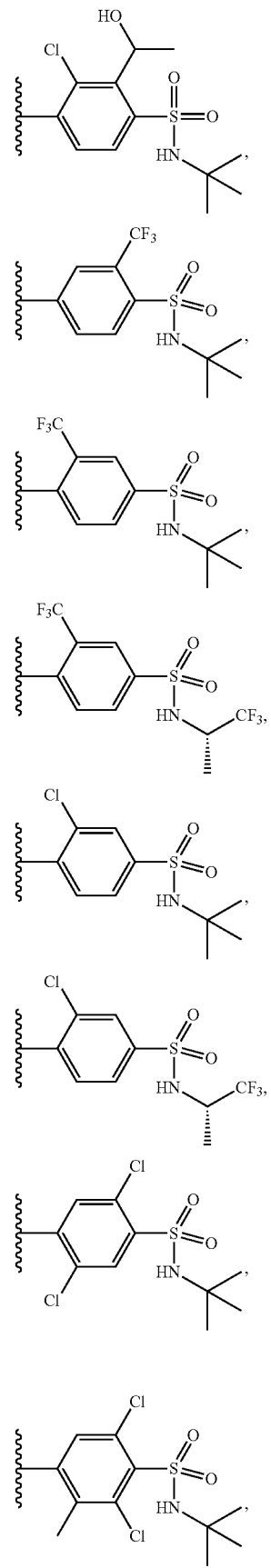

521
-continued
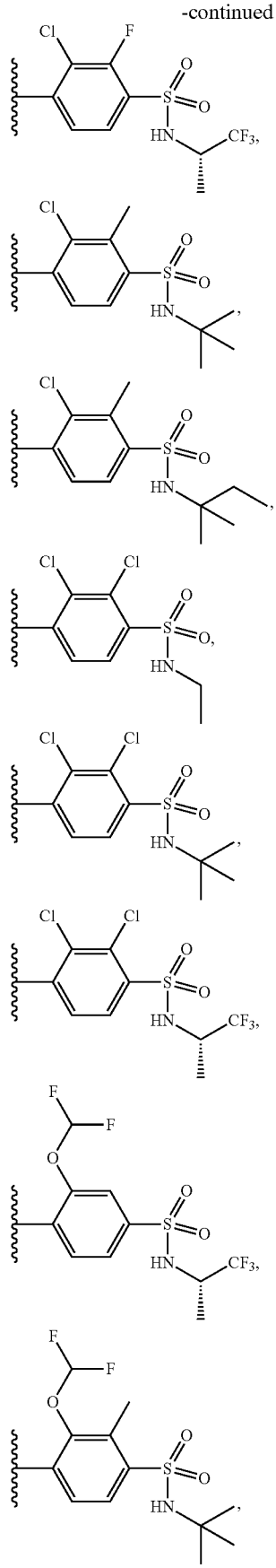
522
-continued
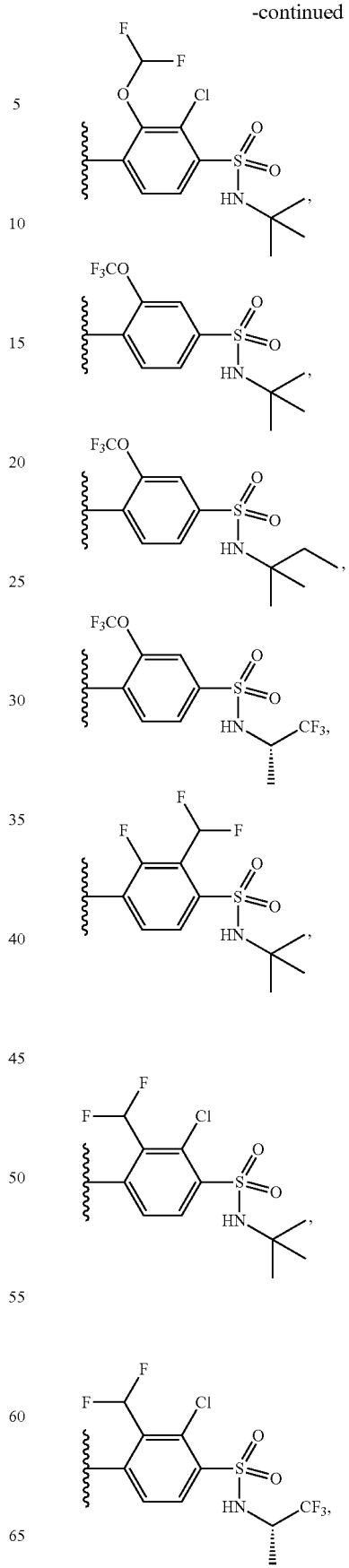

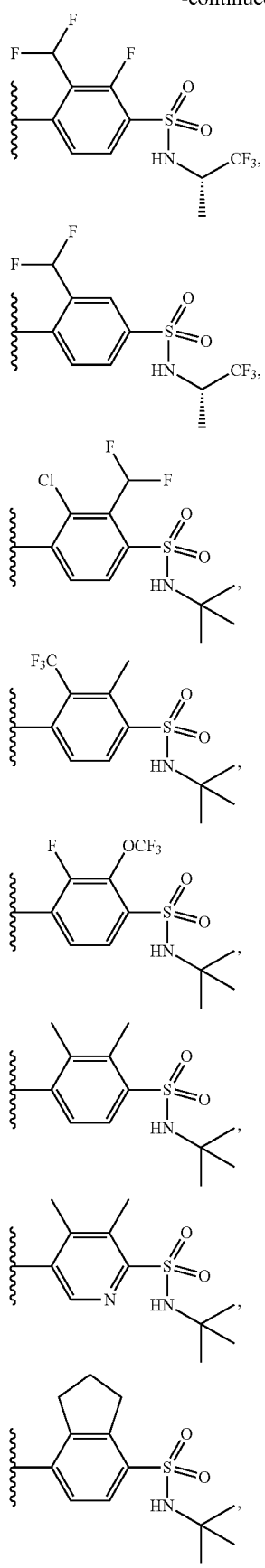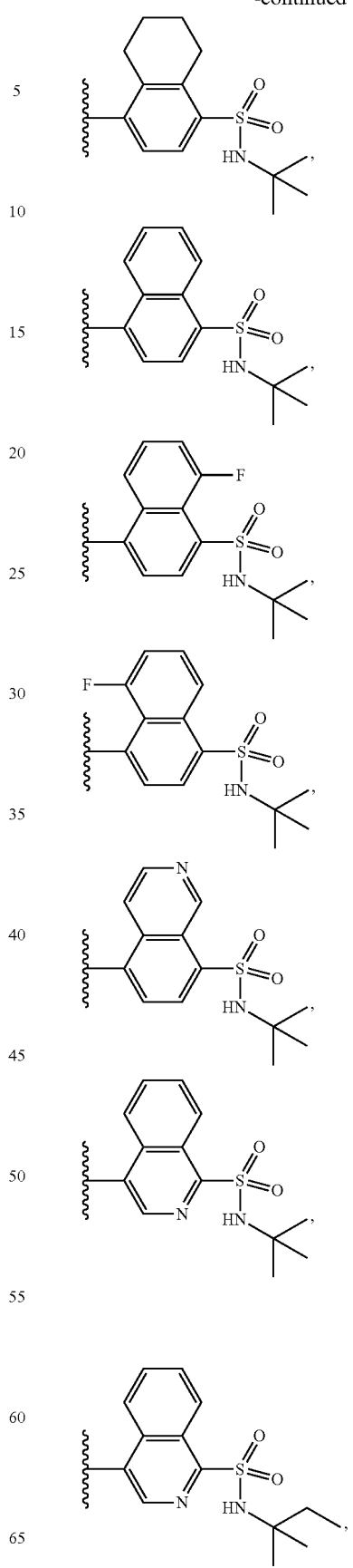

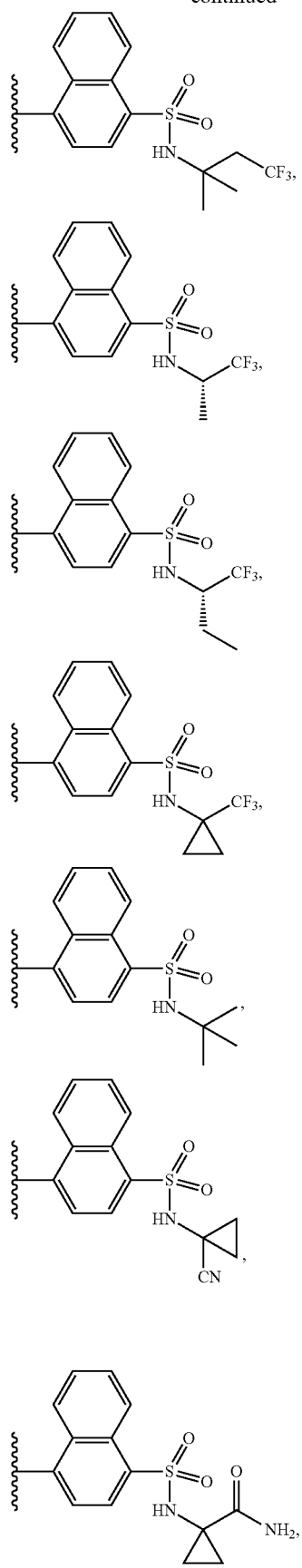
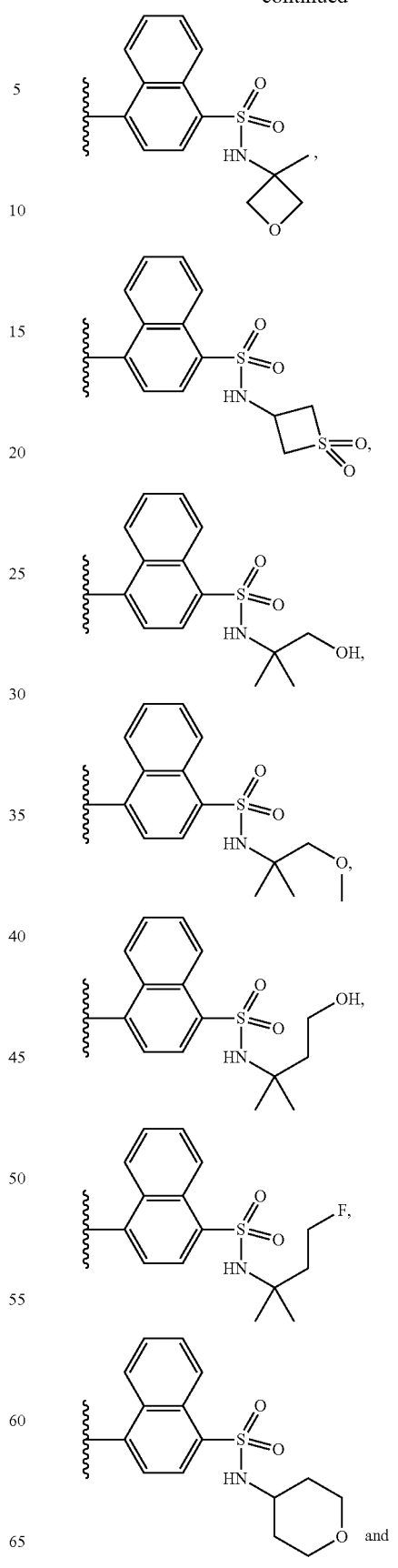

527
-continued
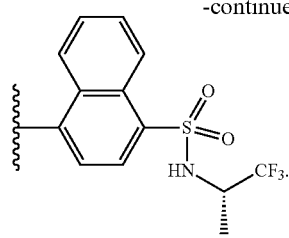
26. The compound according to claim 18 represented by Formula (1).
27. The compound according to claim 18, wherein the compound is selected from
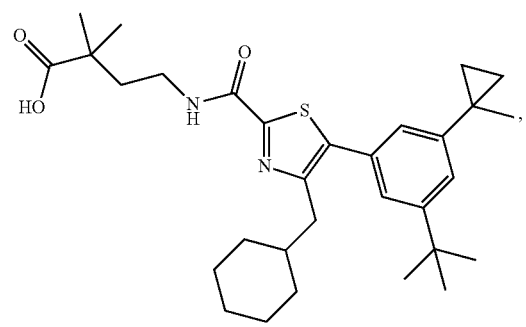
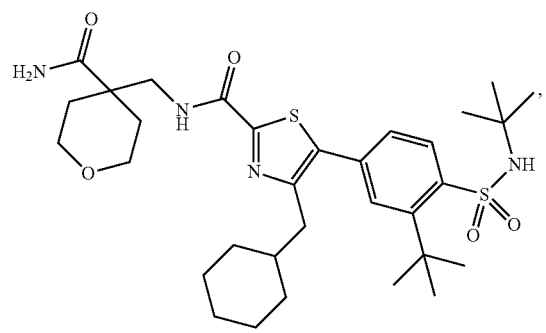
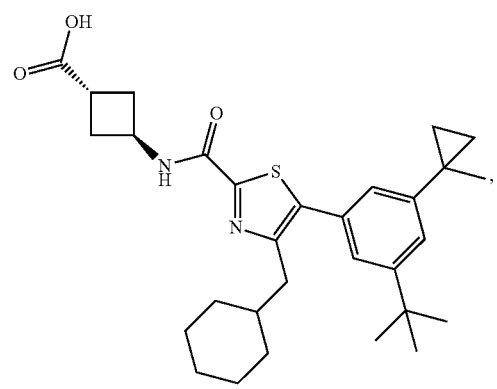
528
-continued
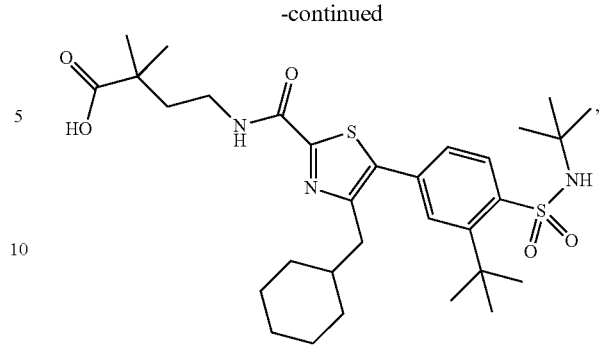
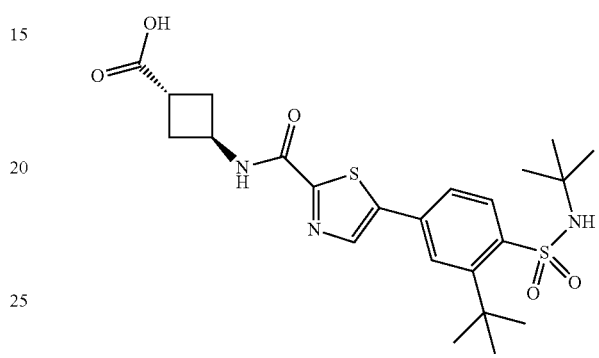
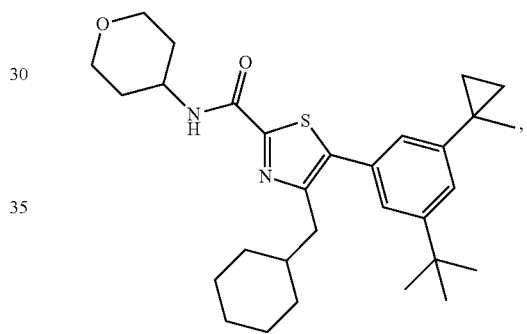
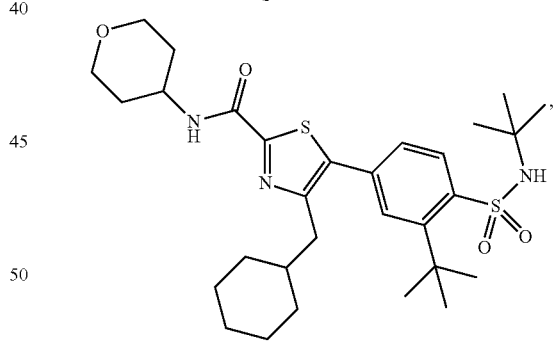
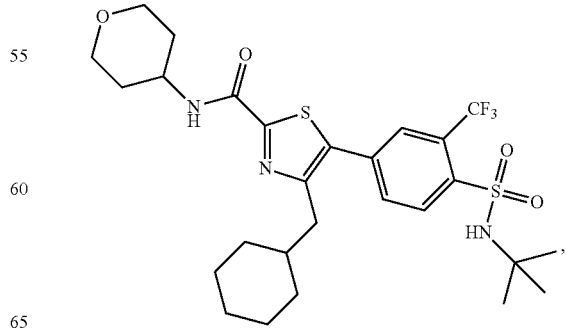

529
-continued
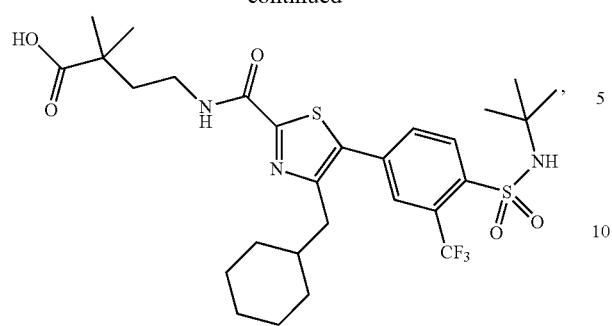
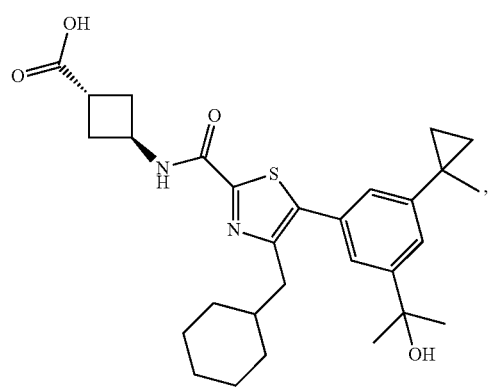
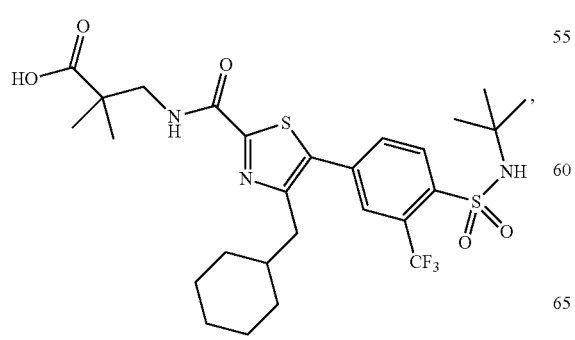
530
-continued
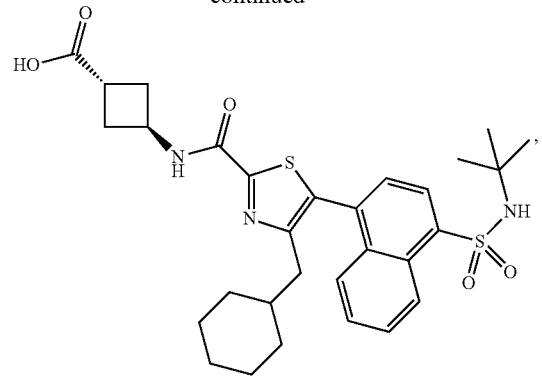
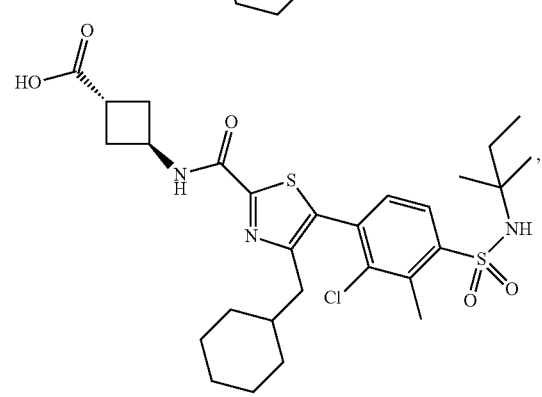
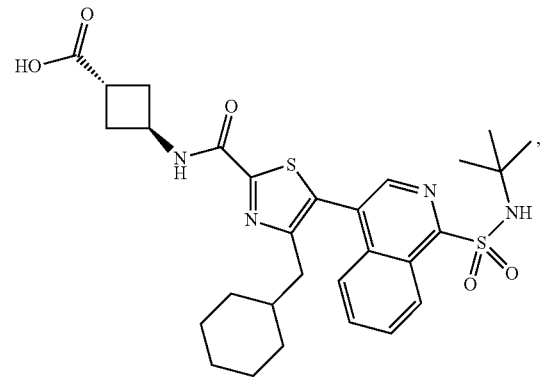
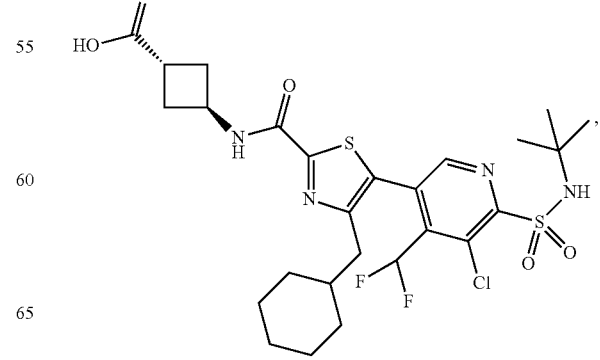

531
-continued
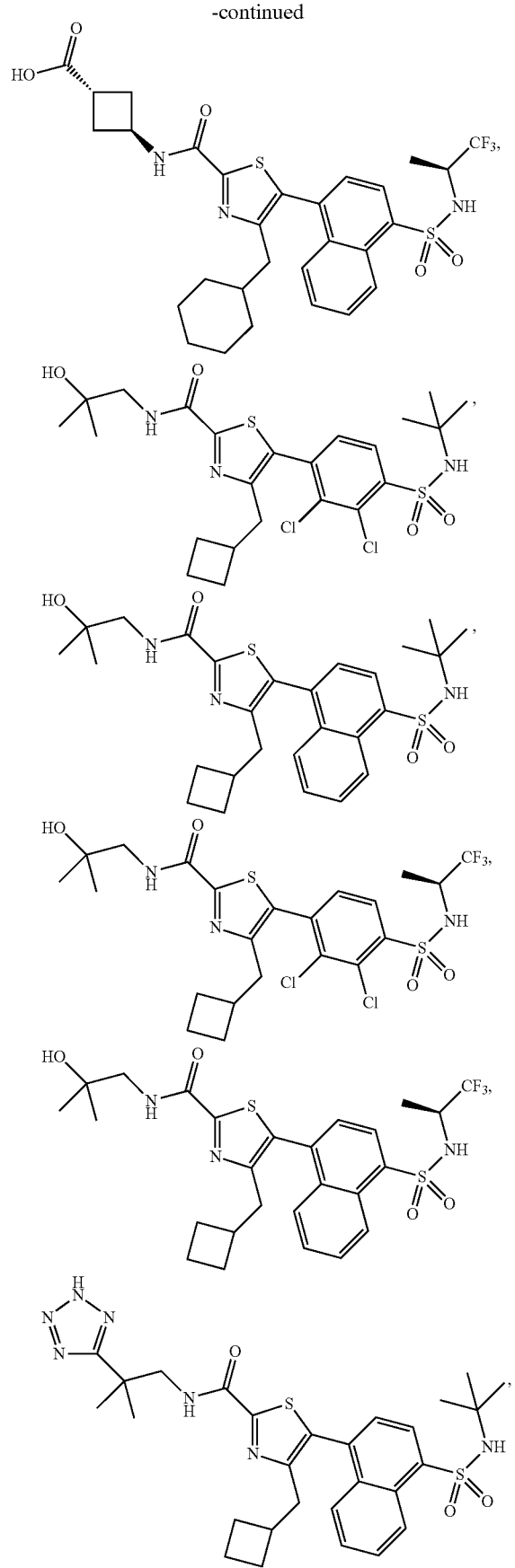
532
-continued
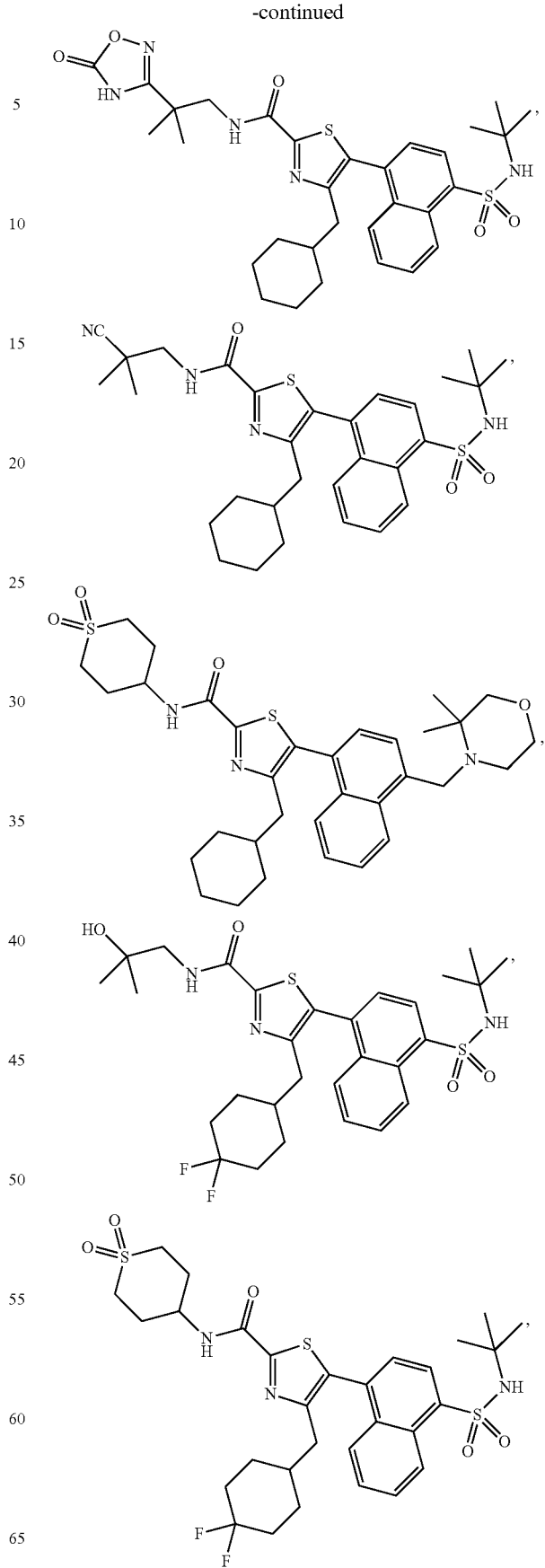

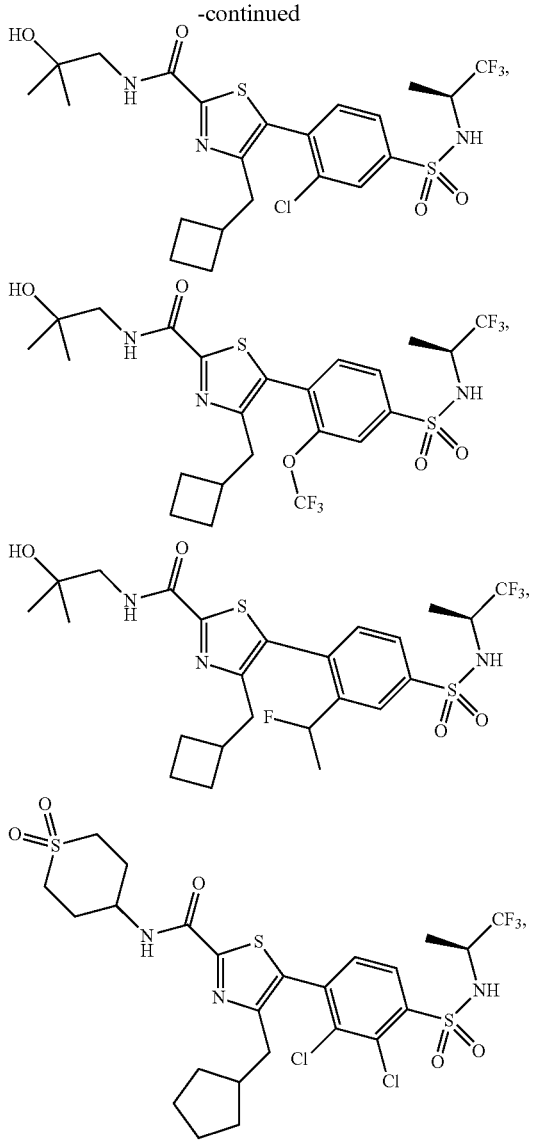

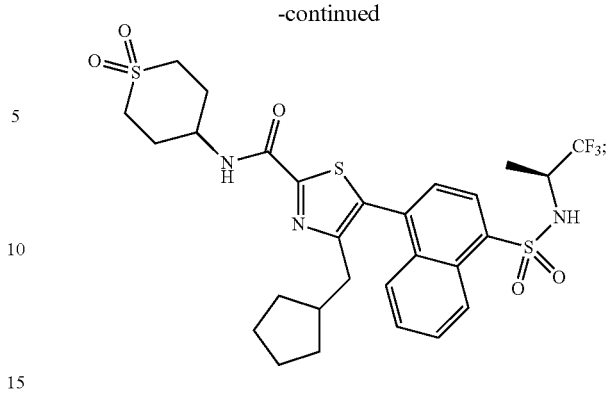

and an enantiomer, diastereomer, tautomer, N-oxide, solvate and pharmaceutically acceptable salt thereof.

28. A method for the treatment of a disease or disorder associated with the inhibition or activation of the RORγ receptor, wherein the method comprises administering to a mammal an effective amount of a compound according to claim 1, or an enantiomer, diastereomer, tautomer, solvate, formulation or pharmaceutically acceptable salt thereof and wherein the disease or disorder is selected from the group consisting of psoriasis, multiple sclerosis, psoriatic arthritis, ankylosing spondylitis, type 1 diabetes, rheumatoid arthritis, asthma, lupus erythematosus, atopic eczema and chronic obstructive pulmonary disease.

29. A pharmaceutical composition comprising a compound according to claim 1, or an enantiomer, diastereomer, tautomer, solvate, formulation or pharmaceutically acceptable salt thereof, and a pharmaceutically acceptable carrier or excipient.

30. A method for the treatment of a disease or disorder in a mammal associated with the inhibition or activation of the RORγ receptor, wherein the method comprises administering to the mammal an effective amount of a pharmaceutical composition according to claim 29 and wherein the disease or disorder is selected from the group consisting of psoriasis, multiple sclerosis, psoriatic arthritis, ankylosing spondylitis, type 1 diabetes, rheumatoid arthritis, asthma, lupus erythematosus, atopic eczema and chronic obstructive pulmonary disease.

\* \* \* \* \*